US012414982B2

(12) United States Patent
Sinclair et al.

(10) Patent No.: US 12,414,982 B2
(45) Date of Patent: *Sep. 16, 2025

(54) CELLULAR REPROGRAMMING TO REVERSE AGING AND PROMOTE ORGAN AND TISSUE REGENERATION

(71) Applicant: President and Fellows of Harvard College, Cambridge, MA (US)

(72) Inventors: David A. Sinclair, Cambridge, MA (US); Yuancheng Lu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/583,147

(22) Filed: Feb. 21, 2024

(65) Prior Publication Data

US 2024/0316148 A1    Sep. 26, 2024

Related U.S. Application Data

(63) Continuation of application No. 18/318,566, filed on May 16, 2023, which is a continuation of application No. 17/280,384, filed as application No. PCT/US2019/053545 on Sep. 27, 2019, now Pat. No. 12,274,733.

(60) Provisional application No. 62/880,488, filed on Jul. 30, 2019, provisional application No. 62/865,877, filed on Jun. 24, 2019, provisional application No. 62/792,283, filed on Jan. 14, 2019, provisional application No. 62/738,922, filed on Sep. 28, 2018.

(51) Int. Cl.
*A61K 38/17* (2006.01)
*A61K 31/65* (2006.01)
*C12N 15/86* (2006.01)

(52) U.S. Cl.
CPC .......... *A61K 38/1709* (2013.01); *A61K 31/65* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,589,362 A | 12/1996 | Bujard et al. |
| 5,641,515 A | 6/1997 | Ramtoola |
| 5,650,298 A | 7/1997 | Bujard et al. |
| 5,738,868 A | 4/1998 | Shinkarenko |
| 5,741,516 A | 4/1998 | Webb et al. |
| 5,795,587 A | 8/1998 | Gao et al. |
| 5,928,941 A | 7/1999 | Lee et al. |
| 6,750,015 B2 | 6/2004 | Horwitz et al. |
| 7,541,446 B2 | 6/2009 | Hillen et al. |
| 8,080,647 B2 | 12/2011 | Gordon-Kamm et al. |
| 8,158,415 B2 | 4/2012 | Jo et al. |
| 8,278,104 B2 | 10/2012 | Yamanaka et al. |
| 8,326,547 B2 | 12/2012 | Liu et al. |
| 8,383,364 B2 | 2/2013 | Berkhout et al. |

(Continued)

FOREIGN PATENT DOCUMENTS

| | | |
|---|---|---|
| AU | 746850 B2 | 5/2002 |
| CN | 101302553 A | 11/2008 |
| CN | 103562376 A | 2/2014 |
| CN | 104837862 A | 8/2015 |
| CN | 104919048 A | 9/2015 |
| DE | 19851415 A1 | 5/2000 |
| EP | 1071776 A2 | 1/2001 |
| EP | 1358349 A2 | 11/2003 |
| EP | 1394274 A2 | 3/2004 |
| EP | 1572987 A2 | 9/2005 |
| EP | 1578367 A2 | 9/2005 |
| EP | 1578996 A2 | 9/2005 |
| EP | 1888627 A2 | 2/2008 |
| EP | 2021499 A2 | 2/2009 |

(Continued)

OTHER PUBLICATIONS

Bekris, et al. (2010) "The Genetics of Parkinson's Disease", Journal of Geriatiric Psychiatry, 23(4): 228-42. (Year: 2010).*

(Continued)

*Primary Examiner* — Robert M Kelly
(74) *Attorney, Agent, or Firm* — Wolf, Greenfield & Sacks, P.C.

(57) ABSTRACT

Provided herein are engineered nucleic acids (e.g., expression vectors, including viral vectors, such as lentiviral vectors, adenoviral vectors, AAV vectors, herpes viral vectors, and retroviral vectors) that encode OCT4; KLF4; SOX2; or any combination thereof that are useful, for example, in inducing cellular reprogramming, tissue repair, tissue regeneration, organ regeneration, reversing aging, or any combination thereof. Also provided herein are recombinant viruses (e.g., lentiviruses, alphaviruses, vaccinia viruses, adenoviruses, herpes viruses, retroviruses, or AAVs) comprising the engineered nucleic acids (e.g., engineered nucleic acids), engineered cells, compositions comprising the engineered nucleic acids, the recombinant viruses, engineered cells, engineered proteins, chemical agents that are capable of activating expression of OCT4; KLF4; SOX2; or any combination thereof, an engineered protein selected from the group consisting of OCT4; KLF4; SOX2; or any combination thereof, an antibody capable of activating expression of OCT4; KLF4; SOX2; or any combination thereof, and methods of treating a (e.g., ocular disease), preventing a disease (e.g., ocular disease), regulating (e.g., inducing or inducing and then stopping) cellular reprogramming, regulating tissue repair, regulating tissue regeneration, or any combination thereof).

23 Claims, 154 Drawing Sheets

Specification includes a Sequence Listing.

(56) References Cited

U.S. PATENT DOCUMENTS

| | | |
|---|---|---|
| 8,609,373 B2 | 12/2013 | Liu et al. |
| 8,716,465 B2 | 5/2014 | Rossi et al. |
| 8,883,506 B2 | 11/2014 | Rossi et al. |
| 8,957,037 B2 | 2/2015 | Collard et al. |
| 9,127,283 B2 | 9/2015 | Bisgrove et al. |
| 9,175,311 B2 | 11/2015 | Townes et al. |
| 9,228,204 B2 | 1/2016 | Pulst et al. |
| 9,580,689 B2 | 2/2017 | Kikyo et al. |
| 9,644,184 B2* | 5/2017 | Mack ............... C12N 15/85 |
| 9,862,926 B2 | 1/2018 | Chin et al. |
| 9,862,930 B2 | 1/2018 | Dowdy et al. |
| 9,920,333 B2 | 3/2018 | Pulst et al. |
| 11,058,729 B2 | 7/2021 | Tomarev et al. |
| 11,525,119 B2 | 12/2022 | Vo et al. |
| RE49,583 E | 7/2023 | Berkhout et al. |
| 11,692,029 B2 | 7/2023 | Min et al. |
| 12,274,733 B2 | 4/2025 | Sinclair et al. |
| 2002/0165180 A1 | 11/2002 | Weaver |
| 2003/0065157 A1 | 4/2003 | Lasek |
| 2003/0138772 A1 | 7/2003 | Gao et al. |
| 2003/0138799 A1 | 7/2003 | Ruppert et al. |
| 2003/0165921 A1 | 9/2003 | Tang et al. |
| 2003/0186281 A1 | 10/2003 | Hillen |
| 2004/0038249 A1 | 2/2004 | Darteil et al. |
| 2004/0219579 A1 | 11/2004 | Aziz et al. |
| 2004/0235073 A1 | 11/2004 | Ruppert et al. |
| 2005/0064454 A1 | 3/2005 | Young et al. |
| 2005/0208496 A1 | 9/2005 | Ohtani et al. |
| 2006/0263774 A1 | 11/2006 | Clark et al. |
| 2007/0042392 A1 | 2/2007 | Tang et al. |
| 2007/0048301 A1 | 3/2007 | Bodary-Winter et al. |
| 2007/0060743 A1 | 3/2007 | Tang et al. |
| 2007/0072175 A1 | 3/2007 | Cooper et al. |
| 2007/0161031 A1 | 7/2007 | Trinklein et al. |
| 2008/0050379 A1 | 2/2008 | Young et al. |
| 2008/0050393 A1 | 2/2008 | Tang et al. |
| 2008/0233648 A1 | 9/2008 | Sugaya et al. |
| 2009/0047263 A1 | 2/2009 | Yamanaka et al. |
| 2010/0040649 A1 | 2/2010 | Berkhout et al. |
| 2010/0048678 A1 | 2/2010 | Smit et al. |
| 2010/0074864 A1 | 3/2010 | Achiron et al. |
| 2010/0099144 A1 | 4/2010 | Jo et al. |
| 2010/0150889 A1 | 6/2010 | Townes et al. |
| 2010/0190250 A1 | 7/2010 | Hu et al. |
| 2010/0273220 A1 | 10/2010 | Yanik et al. |
| 2010/0285589 A1 | 11/2010 | Lowry et al. |
| 2011/0002940 A1 | 1/2011 | Piek et al. |
| 2011/0081708 A1 | 4/2011 | Liu et al. |
| 2012/0064048 A1 | 3/2012 | Collard et al. |
| 2012/0095188 A1 | 4/2012 | Jo et al. |
| 2012/0129254 A1 | 5/2012 | Bisgrove et al. |
| 2012/0196328 A1 | 8/2012 | Liu et al. |
| 2012/0208278 A1 | 8/2012 | Yanik et al. |
| 2012/0225076 A1 | 9/2012 | Peeper et al. |
| 2012/0322864 A1 | 12/2012 | Rossi et al. |
| 2012/0322865 A1 | 12/2012 | Rossi et al. |
| 2013/0017596 A1 | 1/2013 | Townes et al. |
| 2013/0059752 A1 | 3/2013 | Bodary-Winter et al. |
| 2013/0065791 A1 | 3/2013 | Rosenthal et al. |
| 2013/0130387 A1 | 5/2013 | Itskovitz-Eldor et al. |
| 2014/0093486 A1 | 4/2014 | Chiou et al. |
| 2014/0107190 A1 | 4/2014 | Molina et al. |
| 2014/0128277 A1 | 5/2014 | Moller et al. |
| 2014/0170752 A1 | 6/2014 | Pulst et al. |
| 2015/0159143 A1 | 6/2015 | Dowdy et al. |
| 2015/0299701 A1 | 10/2015 | Collard et al. |
| 2016/0032393 A1 | 2/2016 | Achiron et al. |
| 2016/0076000 A1 | 3/2016 | Townes et al. |
| 2016/0102127 A1 | 4/2016 | Thepen et al. |
| 2016/0143951 A1 | 5/2016 | Lawrence et al. |
| 2017/0073639 A1 | 3/2017 | Eilertsen et al. |
| 2018/0155789 A1 | 6/2018 | Maeder et al. |
| 2018/0161358 A1 | 6/2018 | Arber et al. |
| 2018/0195047 A1 | 7/2018 | Jo |
| 2018/0216079 A1 | 8/2018 | Dowdy et al. |
| 2018/0299430 A1 | 10/2018 | Kuo et al. |
| 2018/0305689 A1 | 10/2018 | Sætrom et al. |
| 2019/0055518 A1 | 2/2019 | Young-Ae |
| 2019/0292250 A1 | 9/2019 | Hinderer et al. |
| 2021/0324414 A1 | 10/2021 | Weiss et al. |
| 2021/0403923 A1 | 12/2021 | Sinclair et al. |
| 2023/0048010 A1 | 2/2023 | Sinclair et al. |
| 2023/0338468 A1 | 10/2023 | Sinclair et al. |
| 2024/0261370 A1 | 8/2024 | Sinclair et al. |

FOREIGN PATENT DOCUMENTS

| | | |
|---|---|---|
| EP | 2126135 A2 | 12/2009 |
| EP | 2132225 A1 | 12/2009 |
| EP | 2191018 A2 | 6/2010 |
| EP | 2191840 A1 | 6/2010 |
| EP | 2388336 A1 | 11/2011 |
| EP | 2407488 A2 | 1/2012 |
| EP | 2421563 A1 | 2/2012 |
| EP | 2432881 A2 | 3/2012 |
| EP | 2478101 A1 | 7/2012 |
| EP | 2572000 A2 | 3/2013 |
| EP | 2638163 A1 | 9/2013 |
| EP | 2655621 A1 | 10/2013 |
| EP | 2675903 A1 | 12/2013 |
| EP | 2852671 A2 | 4/2015 |
| EP | 2931914 A1 | 10/2015 |
| EP | 3060237 A1 | 8/2016 |
| EP | 3194623 A1 | 7/2017 |
| EP | 2643459 B1 | 9/2017 |
| EP | 3334755 A1 | 6/2018 |
| EP | 3385373 A1 | 10/2018 |
| JP | 2014-500022 A | 1/2014 |
| WO | WO 9954460 A2 | 10/1999 |
| WO | WO 2000/069450 A1 | 11/2000 |
| WO | WO 2001/094629 A2 | 12/2001 |
| WO | WO 2004/073657 A2 | 9/2004 |
| WO | WO 2005/052164 A1 | 6/2006 |
| WO | WO 2006/123930 A2 | 11/2006 |
| WO | WO 2007/058527 A2 | 5/2007 |
| WO | WO 2007/078599 A2 | 7/2007 |
| WO | WO 2008/051854 A2 | 5/2008 |
| WO | WO 2008/081435 A2 | 7/2008 |
| WO | WO 2009/028945 A2 | 3/2009 |
| WO | WO 2009/061442 A1 | 5/2009 |
| WO | WO 2010/104357 A2 | 9/2010 |
| WO | WO 2010/123501 A1 | 10/2010 |
| WO | WO 2010/135329 A2 | 11/2010 |
| WO | WO 2010/138263 A2 | 12/2010 |
| WO | WO 2011/017910 A1 | 2/2011 |
| WO | WO 2011/034421 A1 | 3/2011 |
| WO | WO 2011/144718 A2 | 11/2011 |
| WO | WO 2012/014207 A2 | 2/2012 |
| WO | WO 2012/065143 A1 | 5/2012 |
| WO | WO 2012/071549 A2 | 5/2012 |
| WO | WO 2012/087983 A1 | 6/2012 |
| WO | WO 2012/120026 A1 | 9/2012 |
| WO | WO 2012/136841 A1 | 10/2012 |
| WO | WO 2013/177133 A2 | 11/2013 |
| WO | WO 2014/053082 A1 | 4/2014 |
| WO | WO 2014/152607 A2 | 9/2014 |
| WO | WO 2014/191391 A1 | 12/2014 |
| WO | WO 2016/170348 A2 | 10/2016 |
| WO | WO 2017/026776 A1 | 2/2017 |
| WO | WO 2017/173354 A2 | 10/2017 |
| WO | WO 2017/180587 A2 | 10/2017 |
| WO | WO 2018/041959 A1 | 3/2018 |
| WO | WO 2018/204764 A1 | 11/2018 |
| WO | WO 2019/023680 A1 | 1/2019 |
| WO | WO 2019/094778 A1 | 5/2019 |
| WO | WO 2019/099552 A2 | 5/2019 |
| WO | WO 2020/012164 A1 | 1/2020 |
| WO | WO 2020/069339 A1 | 4/2020 |
| WO | WO 2020/069373 A1 | 4/2020 |
| WO | WO 2021/183825 A1 | 9/2021 |
| WO | WO 2021/183946 A2 | 9/2021 |

(56) References Cited

FOREIGN PATENT DOCUMENTS

| WO | WO 2022/232327 A2 | 11/2022 |
|---|---|---|
| WO | WO 2023/004367 A2 | 1/2023 |

OTHER PUBLICATIONS

Brennan, et al. (2017) "Ocular Salvage and Vision Preservation Using a Topotecan-Based Regimen for advanced Intraocular Retinoblastoma" Journal of Clinical Oncology, 35(1): 72-80. (Year: 2017).*
International Search Report and Written Opinion for Application No. PCT/US2019/053545, mailed Dec. 19, 2019.
International Preliminary Report on Patentability for Application No. PCT/US2019/053545, mailed Apr. 8, 2021.
International Search Report and Written Opinion for Application No. PCT/US2019/053492, mailed Feb. 2, 2020.
International Preliminary Report on Patentability for Application No. PCT/US2019/053492, mailed Apr. 8, 2021.
International Search Report and Written Opinion for Application No. PCT/US2023/065374, mailed Jun. 6, 2023.
Aasen et al., Efficient and rapid generation of induced pluripotent stem cells from human keratinocytes. Nat Biotechnol. Nov. 2008;26(11):1276-84. doi: 10.1038/nbt.1503. Epub Oct. 17, 2008.
Agha-Mohammadi et al., Second-generation tetracycline-regulatable promoter: repositioned tet operator elements optimize transactivator synergy while shorter minimal promoter offers tight basal leakiness. J Gene Med. Jul. 2004;6(7):817-28. doi: 10.1002/jgm.566.
Agrawal et al., Generation of recombinant skin in vitro by adeno-associated virus type 2 vector transduction. Tissue Eng. Nov.-Dec. 2004;10(11-12):1707-15. doi: 10.1089/ten.2004.10.1707.
Aida et al., Cloning-free CRISPR/Cas system facilitates functional cassette knock-in in mice. Genome Biol. Apr. 29, 2015;16(1):87. doi: 10.1186/s13059-015-0653-x.
Alaei et al., An improved reprogrammable mouse model harbouring the reverse tetracycline- controlled transcriptional transactivator 3. Stem Cell Res. Jul. 2016;17(1):49-53. doi: 10.1016/j.scr.2016.05.008. Epub May 25, 2016.
Anokye-Danso et al., Highly efficient miRNA-mediated reprogramming of mouse and human somatic cells to pluripotency. Cell Stem Cell. Apr. 8, 2011;8(4):376-88. doi: 10.1016/j.stem.2011.03.001.
Azte et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.
Bar-Nur et al., Small molecules facilitate rapid and synchronous iPSC generation. Nat Methods. Nov. 2014;11(11):1170-6. doi: 10.1038/nmeth.3142. Epub Sep. 24, 2014.
Baron et al., Tet repressor-based system for regulated gene expression in eukaryotic cells: principles and advances. Methods Enzymol. 2000;327:401-21. doi: 10.1016/s0076- 6879(00)27292-3.
Behr et al., Gene transfer with synthetic cationic amphiphiles: prospects for gene therapy. Bioconjugate Chem. Sep.-Oct. 1994;5(5):382-9. doi: 10.1021/bc00029a002.
Belin et al., Injury-induced decline of intrinsic regenerative ability revealed by quantitative proteomics. Neuron. May 20, 2015;86(4):1000-1014. doi: 10.1016/j.neuron.2015.03.060. Epub Apr. 30, 2015.
Blackmore et al., Krüppel-like Factor 7 engineered for transcriptional activation promotes axon regeneration in the adult corticospinal tract. Proc Natl Acad Sci USA. May 8, 2012;109(19):7517-22. doi: 10.1073/pnas.1120684109. Epub Apr. 23, 2012.
Blanchard et al., Replacing reprogramming factors with antibodies selected from combinatorial antibody libraries. Nat Biotechnol. Oct. 2017;35(10):960-968. doi: 10.1038/nbt.3963. Epub Sep. 11, 2017.
Borkent et al., A Serial shRNA Screen for Roadblocks to Reprogramming Identifies the Protein Modifier SUMO2. Stem Cell Reports. May 10, 2016;6(5):704-716. doi: 10.1016/j.stemcr.2016.02.004. Epub Mar. 3, 2016.

Brumbaugh et al., Nudt21 Controls Cell Fate by Connecting Alternative Polyadenylation to Chromatin Signaling. Cell. Jan. 11, 2018;172(1-2):106-120.e21. doi: 10.1016/j.cell.2017.11.023. Epub Dec. 14, 2017.
Bussian et al., Clearance of senescent glial cells prevents tau-dependent pathology and cognitive decline. Nature. Oct. 2018;562(7728):578-582. doi: 10.1038/s41586-018-0543-y. Epub Sep. 19, 2018.
Carey et al., Reprogramming of murine and human somatic cells using a single polycistronic vector. Proc Natl Acad Sci U S A. Jan. 6, 2009;106(1):157-62. doi: 10.1073/pnas.0811426106. Epub Dec. 24, 2008.
Cheloufi et al., The histone chaperone CAF-1 safeguards somatic cell identity. Nature. Dec. 10, 2015;528(7581):218-24. doi: 10.1038/nature15749.
Chen et al., Reprogramming adipose tissue-derived mesenchymal stem cells into pluripotent stem cells by a mutant adeno-associated viral vector. Hum Gene Ther Methods. Feb. 2014;25(1):72-82. doi: 10.1089/hgtb.2013.011. Epub Dec. 28, 2013.
Chen et al., Targeting oncogenic Myc as a strategy for cancer treatment. Signal Transduct Target Ther. Feb. 23, 2018;3:5. doi: 10.1038/s41392-018-0008-7. eCollection 2018.
Cho et al., Generation of transgenic mice. Curr Protoc Cell Biol. Mar. 2009;Chapter 19:Unit 19.11. doi: 10.1002/0471143030.cb1911s42.
Chtarto et al., A regulatable AAV vector mediating GDNF biological effects at clinically-approved sub-antimicrobial doxycycline doses. Mol Ther Methods Clin Dev. Mar. 30, 2016;5:16027. doi: 10.1038/mtm.2016.27. eCollection 2016.
Cieślar-Pobuda et al., Transdifferentiation and reprogramming: Overview of the processes, their similarities and differences. Biochim Biophys Acta Mol Cell Res. Jul. 2017;1864(7):1359-1369. doi: 10.1016/j.bbamcr.2017.04.017. Epub Apr. 28, 2017.
Crudele et al., Cas9 immunity creates challenges for CRISPR gene editing therapies. Nat Commun. Aug. 29, 2018;9(1):3497. doi: 10.1038/s41467-018-05843-9.
Cyranoski, 'Reprogrammed' stem cells approved to mend human hearts for the first time. Nature. May 2018;557(7707):619-620. doi: 10.1038/d41586-018-05278-8.
Danke et al., Adjusting transgene expression levels in lymphocytes with a set of inducible promoters. J Gene Med. Jun. 2010;12(6):501-15. doi: 10.1002/jgm.1461.
Das et al., Selecting the optimal Tet-On system for doxycycline-inducible gene expression in transiently transfected and stably transduced mammalian cells. Biotechnol J. Jan. 2016;11(1):71-9. doi: 10.1002/biot.201500236. Epub Sep. 24, 2015.
Das et al., Tet-On Systems For Doxycycline-inducible Gene Expression. Curr Gene Ther. 2016;16(3):156-67. doi: 10.2174/1566523216666160524144041.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Doench et al., Optimized sgRNA design to maximize activity and minimize off-target effects of CRISPR-Cas9. Nat Biotechnol. Feb. 2016;34(2):184-191. doi: 10.1038/nbt.3437. Epub Jan. 18, 2016.
Dong et al., Poly(glycoamidoamine) Brushes Formulated Nanomaterials for Systemic siRNA and mRNA Delivery in Vivo. Nano Lett. Feb. 10, 2016;16(2):842-8. doi: 10.1021/acs.nanolett.5b02428. Epub Jan. 13, 2016.
Dugan et al., Non-Arteritic Anterior Ischemic Optic Neuropathy (NAION). American Academy of Ophthalmology Eyewiki. Apr. 7, 2023. 6 pages.
Eguchi et al., Reprogramming cell fate with a genome-scale library of artificial transcription factors. Proc Natl Acad Sci USA. Dec. 20, 2016;113(51):E8257-E8266. doi: 10.1073/pnas.1611142114. Epub Dec. 5, 2016.
Encinas et al., Sequential treatment of SH-SY5Y cells with retinoic acid and brain-derived neurotrophic factor gives rise to fully differentiated, neurotrophic factor-dependent, human neuron-like cells. J Neurochem. Sep. 2000;75(3):991-1003. doi: 10.1046/j.1471-4159.2000.0750991.x.

(56) References Cited

OTHER PUBLICATIONS

Erahimi, Reprogramming barriers and enhancers: strategies to enhance the efficiency and kinetics of induced pluripotency. Cell Regen. Nov. 11, 2015;4:10. doi: 10.1186/s13619-015-0024-9. eCollection 2015.
Gao et al., Replacement of Oct4 by Tet1 during iPSC induction reveals an important role of DNA methylation and hydroxymethylation in reprogramming. Cell Stem Cell. Apr. 4, 2013;12(4):453-69. doi: 10.1016/j.stem.2013.02.005. Epub Mar. 14, 2013.
GENBANK Submission; NCBI, Accession No. NM_001040400.2; Mus musculus tet methylcytosine dioxygenase 2 (Tet2), transcript variant 1, mRNA. Yang et al.; Sep. 23, 2018.
GENBANK Submission; NCBI, Accession No. NM_001127208.2; Homo sapiens Kruppel like factor 4 (KLF4), transcript variant 2, mRNA. Yang et al.; Sep. 23, 2018.
GENBANK Submission; NCBI, Accession No. NM_001130823.2; Homo sapiens Kruppel like factor 4 (KLF4), transcript variant 2, mRNA. Yang et al.; Sep. 24, 2018.
GENBANK Submission; NCBI, Accession No. NM_001173531. Homo sapiens POU class 5 homeobox 1 (POU5F1), transcript variant 3, mRNA. Jul. 31, 2023. 4 pages.
GENBANK Submission; NCBI, Accession No. NM_001173531.2; Homo sapiens POU class 5 homeobox 1 (POU5F1), transcript variant 3, mRNA. Miyoshi et al.; Sep. 23, 2018.
GENBANK Submission; NCBI, Accession No. NM_001207055.1; Homo sapiens DNA methyltransferase 3 beta (DNMT3B), transcript variant 7, mRNA. Nunes et al.; Sep. 23, 2018.
GENBANK Submission; NCBI, Accession No. NM_001207056.1; Homo sapiens DNA methyltransferase 3 beta (DNMT3B), transcript variant 8, mRNA. Nunes et al.; Sep. 23, 2018.
GENBANK Submission; NCBI, Accession No. NM_001253857.2; Mus musculus tet methylcytosine dioxygenase 1 (Tet1), transcript variant 1, mRNA. SanMiguel et al.; Jul. 15, 2018.
GENBANK Submission; NCBI, Accession No. NM_001285986. Homo sapiens POU class 5 homeobox 1 (POU5F1), transcript variant 4, mRNA. Jul. 31, 2023. 4 pages.
GENBANK Submission; NCBI, Accession No. NM_001285986.1; Homo sapiens POU class 5 homeobox 1 (POU5F1), transcript variant 4, mRNA. Miyoshi et al.; Sep. 23, 2018.
GENBANK Submission; NCBI, Accession No. NM_001285987. Homo sapiens POU class 5 homeobox 1 (POU5F1), transcript variant 5, mRNA, 4 pages. Jul. 31, 2023.
GENBANK Submission; NCBI, Accession No. NM_001285987.1; Homo sapiens POU class 5 homeobox 1 (POU5F1), transcript variant 5, mRNA. Miyoshi et al.; Sep. 23, 2018.
GENBANK Submission; NCBI, Accession No. NM_001314052.1; Homo sapiens Kruppel like factor 4 (KLF4), transcript variant 1, mRNA. Feng et al.; Sep. 24, 2018.
GENBANK Submission; NCBI, Accession No. NM_001314052.1; Homo sapiens Kruppel like factor 4 (KLF4), transcript variant 1, mRNA. May 28, 2019. 5 pages.
GENBANK Submission; NCBI, Accession No. NM_001318730.1; Homo sapiens DNA methyltransferase 1 (DNMT1), transcript variant 3, mRNA. Yang et al.; Sep. 24, 2018.
GENBANK Submission; NCBI, Accession No. NM_001318731.1; Homo sapiens DNA methyltransferase 1 (DNMT1), transcript variant 4, mRNA. Yang et al.; Sep. 24, 2018.
GENBANK Submission; NCBI, Accession No. NM_001320892.1; Homo sapiens DNA methyltransferase 3 alpha (DNMT3A), transcript variant 5, mRNA. Liang et al.; Sep. 2, 2018.
GENBANK Submission; NCBI, Accession No. NM_001320893.1; Homo sapiens DNA methyltransferase 3 alpha (DNMT3A), transcript variant 6, mRNA. Wozniak et al.; Jun. 13, 2021.
GENBANK Submission; NCBI, Accession No. NM_001346736.1; Mus musculus tet methylcytosine dioxygenase 2 (Tet2), transcript variant 2, mRNA. Li et al.; May 16, 2021.
GENBANK Submission; NCBI, Accession No. NM_001354870.1. Homo sapiens MYC proto-oncogene, bHLH transcription factor (MYC), transcript variant 2, mRNA. Jul. 31, 2023. 7 pages.
GENBANK Submission; NCBI, Accession No. NM_001354870.1; Homo sapiens MYC proto-oncogene, bHLH transcription factor (MYC), transcript variant 2, mRNA. Gong et al.; Sep. 2, 2018.
GENBANK Submission; NCBI, Accession No. NM_001379.3; Homo sapiens DNA methyltransferase 1 (DNMT1), transcript variant 2, mRNA. Yang et al.; Sep. 24, 2018.
GENBANK Submission; NCBI, Accession No. NM_002467.5; Homo sapiens MYC proto-oncogene, bHLH transcription factor (MYC), transcript variant 1, mRNA. Gong et al.; Sep. 2, 2018.
GENBANK Submission; NCBI, Accession No. NM_002467.5; Homo sapiens MYC proto-oncogene, bHLH transcription factor (MYC), transcript variant 1, mRNA. Dec. 30, 2018. 5 pages.
GENBANK Submission; NCBI, Accession No. NM_002701. Homo sapiens POU class 5 homeobox 1 (POU5F1), transcript variant 1, mRNA. Jul. 31, 2023. 5 pages.
GENBANK Submission; NCBI, Accession No. NM_002701.5; Homo sapiens POU class 5 homeobox 1 (POU5F1), transcript variant 1, mRNA. Miyoshi et al.; Sep. 23, 2018.
GENBANK Submission; NCBI, Accession No. NM_003106.3; Homo sapiens SRY-box transcription factor 2 (SOX2), mRNA. Chen et al.; Sep. 22, 2018.
GENBANK Submission; NCBI, Accession No. NM_003106.4. Homo sapiens SRY-box transcription factor 2 (SOX2), mRNA. Jul. 31, 2023. 4 pages.
GENBANK Submission; NCBI, Accession No. NM_004235.5; Homo sapiens Kruppel like factor 4 (KLF4), transcript variant 2, mRNA. Feng et al.; Sep. 24, 2018.
GENBANK Submission; NCBI, Accession No. NM_004235.5; Homo sapiens Kruppel like factor 4 (KLF4), transcript variant 2, mRNA. Nov. 18, 2018. 4 pages.
GENBANK Submission; NCBI, Accession No. NM_006892.3; Homo sapiens DNA methyltransferase 3 beta (DNMT3B), transcript variant 1, mRNA. Nunes et al.; Sep. 23, 2018.
GENBANK Submission; NCBI, Accession No. NM_011443.4. Mus musculus SRY (sex determining region Y)-box 2 (Sox2), mRNA. Aug. 1, 2023. 4 pages.
GENBANK Submission; NCBI, Accession No. NM_011443.4; Mus musculus SRY (sex determining region Y)-box 2 (Sox2), mRNA. Bernardo et al.; Sep. 24, 2018.
GENBANK Submission; NCBI, Accession No. NM_013369.3; Homo sapiens DNA methyltransferase 3 like (DNMT3L), transcript variant 1, mRNA. Lu et al.; Sep. 22, 2018.
GENBANK Submission; NCBI, Accession No. NM_017628.4; Homo sapiens tet methylcytosine dioxygenase 2 (TET2), transcript variant 2, mRNA. Yang et al.; Sep. 23, 2018.
GENBANK Submission; NCBI, Accession No. NM_022552.4; Homo sapiens DNA methyltransferase 3 alpha (DNMT3A), transcript variant 3, mRNA. Zhang et al.; Sep. 23, 2018.
GENBANK Submission; NCBI, Accession No. NM_030625.3; Homo sapiens tet methylcytosine dioxygenase 1 (TET1), mRNA. Li et al.; Sep. 16, 2018.
GENBANK Submission; NCBI, Accession No. NM_153759.3; Homo sapiens DNA methyltransferase 3 alpha (DNMT3A), transcript variant 2, mRNA. Zhang et al.; Sep. 23, 2018.
GENBANK Submission; NCBI, Accession No. NM_175629.2; Homo sapiens DNA methyltransferase 3 alpha (DNMT3A), transcript variant 1, mRNA. Zhang et al.; Sep. 23, 2018.
GENBANK Submission; NCBI, Accession No. NM_175630.1; Homo sapiens DNA methyltransferase 3 alpha (DNMT3A), transcript variant 4, mRNA. Zhang et al.; Sep. 23, 2018.
GENBANK Submission; NCBI, Accession No. NM_175848.1; Homo sapiens DNA methyltransferase 3 beta (DNMT3B), transcript variant 2, mRNA. Nunes et al.; Sep. 23, 2018.
GENBANK Submission; NCBI, Accession No. NM_175849.1; Homo sapiens DNA methyltransferase 3 beta (DNMT3B), transcript variant 3, mRNA. Nunes et al.; Sep. 23, 2018.
GENBANK Submission; NCBI, Accession No. NM_175850.2; Homo sapiens DNA methyltransferase 3 beta (DNMT3B), transcript variant 6, mRNA. Nunes et al.; Sep. 23, 2018.
GENBANK Submission; NCBI, Accession No. NM_175867.2; Homo sapiens DNA methyltransferase 3 like (DNMT3L), transcript variant 2, mRNA. Lu et al.; Sep. 23, 2018.

(56) References Cited

OTHER PUBLICATIONS

GENBANK Submission; NCBI, Accession No. NM_203289. *Homo sapiens* POU class 5 homeobox 1 (POU5F1), transcript variant 2, mRNA. Jul. 31, 2023. 4 pages.
GENBANK Submission; NCBI, Accession No. NM_203289.5; *Homo sapiens* POU class 5 homeobox 1 (POU5F1), transcript variant 2, mRNA. Miyoshi et al.; Sep. 23, 2018.
GENBANK Submission; NCBI, Accession No. NP 002458.2. myc proto-oncogene protein isoform 1 [*Homo sapiens*]. Jul. 31, 2023. 5 pages.
GENBANK Submission; NCBI, Accession No. NP_001035490.2; methylcytosine dioxygenase TET2 isoform 1 [Mus musculus]. Yang et al.; Sep. 23, 2018.
GENBANK Submission; NCBI, Accession No. NP_001120680.1; methylcytosine dioxygenase TET2 isoform a [Homo sapiens]. Yang et al.; Sep. 23, 2018.
GENBANK Submission; NCBI, Accession No. NP_001124295.1; DNA (cytosine-5)-methyltransferase 1 isoform a [*Homo sapiens*]. Yang et al.; Sep. 24, 2018.
GENBANK Submission; NCBI, Accession No. NP_001167002.1. POU domain, class 5, transcription factor 1 isoform 2 [*Homo sapiens*]. Jul. 31, 2023. 3 pages.
GENBANK Submission; NCBI, Accession No. NP_001193984.1; DNA (cytosine-5)-methyltransferase 3B isoform 7 [*Homo sapiens*]. Nunes et al.; Sep. 23, 2018.
GENBANK Submission; NCBI, Accession No. NP_001193985.1; DNA (cytosine-5)- methyltransferase 3B isoform 8 [*Homo sapiens*]. Nunes et al.; Sep. 23, 2018.
GENBANK Submission; NCBI, Accession No. NP_001240786.1; methylcytosine dioxygenase TET1 isoform 1 [Mus musculus]. SanMiguel et al.; Jul. 15, 2018.
GENBANK Submission; NCBI, Accession No. NP_001272915.1. POU domain, class 5, transcription factor 1 isoform 4 [*Homo sapiens*]. Jul. 31, 2023. 3 pages.
GENBANK Submission; NCBI, Accession No. NP_001272916.1. POU domain, class 5, transcription factor 1 isoform 3 [*Homo sapiens*]. Jul. 31, 2023. 3 pages.
GENBANK Submission; NCBI, Accession No. NP_001274420.1; methylcytosine dioxygenase TET3 isoform 1 [*Homo sapiens*]. Lasho et al.; Sep. 20, 2018.
GENBANK Submission; NCBI, Accession No. NP_001300981.1; Krueppel-like factor 4 isoform 1 [*Homo sapiens*]. Feng et al.; Sep. 24, 2018.
GENBANK Submission; NCBI, Accession No. NP_001305659.1; DNA (cytosine-5)- methyltransferase 1 isoform c [*Homo sapiens*]. Yang et al.; Sep. 24, 2018.
GENBANK Submission; NCBI, Accession No. NP_001305660.1; DNA (cytosine-5)- methyltransferase 1 isoform d [*Homo sapiens*]. Yang et al.; Sep. 24, 2018.
GENBANK Submission; NCBI, Accession No. NP_001307821.1; DNA (cytosine-5)-methyltransferase 3A isoform c [*Homo sapiens*]. Liang et al.; Sep. 2, 2018.
GENBANK Submission; NCBI, Accession No. NP_001307822.1; DNA (cytosine-5)-methyltransferase 3A isoform d [*Homo sapiens*]. Liang et al.; Sep. 2, 2018.
GENBANK Submission; NCBI, Accession No. NP_001333665.1; methylcytosine dioxygenase TET2 isoform 2 [Mus musculus]. Reizel et al.; Jul. 29, 2018.
GENBANK Submission; NCBI, Accession No. NP_001334242.1; methylcytosine dioxygenase TET3 isoform 1 [Mus musculus]. Reizel et al.; Jul. 28, 2018.
GENBANK Submission; NCBI, Accession No. NP_001341799.1. myc proto-oncogene protein isoform 2 [*Homo sapiens*]. Jul. 31, 2023. 5 pages.
GENBANK Submission; NCBI, Accession No. NP_001341799.1; myc proto-oncogene protein isoform 2 [*Homo sapiens*]. Gong et al.; Sep. 2, 2018.
GENBANK Submission; NCBI, Accession No. NP_001352951.1; methylcytosine dioxygenase TET3 isoform 2 [*Homo sapiens*]. Lasho et al.; Sep. 20, 2018.
GENBANK Submission; NCBI, Accession No. NP_001370.1; DNA (cytosine-5)-methyltransferase 1 isoform b [*Homo sapiens*]. Yang et al.; Sep. 24, 2018.
GENBANK Submission; NCBI, Accession No. NP_002458.2; myc proto-oncogene protein isoform 1 [*Homo sapiens*]. Gong et al.; Sep. 2, 2018.
GENBANK Submission; NCBI, Accession No. NP_002692.2; POU domain, class 5, transcription factor 1 isoform 1 [*Homo sapiens*]. Sep. 23, 2018.
GENBANK Submission; NCBI, Accession No. NP_003097.1. transcription factor SOX-2 [*Homo sapiens*]. Jul. 31, 2023. 3 pages.
GENBANK Submission; NCBI, Accession No. NP_003097.1; transcription factor SOX-2 [*Homo sapiens*]. Wu et al.; Sep. 22, 2018.
GENBANK Submission; NCBI, Accession No. NP_004226.3. Krueppel-like factor 4 isoform 2 [*Homo sapiens*]. Jul. 13, 2023. 4 pages.
GENBANK Submission; NCBI, Accession No. NP_004226.3; Krueppel-like factor 4 isoform 2 [*Homo sapiens*]. Feng et al.; Sep. 24, 2018.
GENBANK Submission; NCBI, Accession No. NP_008823.1; DNA (cytosine-5)-methyltransferase 3B isoform 1 [*Homo sapiens*]. Nunes et al.; Sep. 23, 2018.
GENBANK Submission; NCBI, Accession No. NP_037501.2; DNA (cytosine-5)-methyltransferase 3-like isoform 1 [*Homo sapiens*]. Lu et al.; Sep. 22, 2018.
GENBANK Submission; NCBI, Accession No. NP_060098.3; methylcytosine dioxygenase TET2 isoform b [*Homo sapiens*]. Yang et al.; Sep. 23, 2018.
GENBANK Submission; NCBI, Accession No. NP_072046.2; DNA (cytosine-5)-methyltransferase 3A isoform a [*Homo sapiens*]. Zhang et al.; Sep. 23, 2018.
GENBANK Submission; NCBI, Accession No. NP_085128.2; methylcytosine dioxygenase TET1 [*Homo sapiens*]. Li et al.; Sep. 16, 2018.
GENBANK Submission; NCBI, Accession No. NP_715640.2; DNA (cytosine-5)-methyltransferase 3A isoform b [*Homo sapiens*]. Zhang et al.; Sep. 23, 2018.
GENBANK Submission; NCBI, Accession No. NP_783328.1; DNA (cytosine-5)-methyltransferase 3A isoform a [*Homo sapiens*]. Zhang et al.; Sep. 23, 2018.
GENBANK Submission; NCBI, Accession No. NP_783329.1; DNA (cytosine-5)-methyltransferase 3A isoform c [*Homo sapiens*]. Zhang et al.; Sep. 23, 2018.
GENBANK Submission; NCBI, Accession No. NP_787044.1; DNA (cytosine-5)-methyltransferase 3B isoform 2 [*Homo sapiens*]. Nunes et al.; Sep. 23, 2018.
GENBANK Submission; NCBI, Accession No. NP_787045.1; DNA (cytosine-5)-methyltransferase 3B isoform 3 [*Homo sapiens*]. Nunes et al.; Sep. 23, 2018.
GENBANK Submission; NCBI, Accession No. NP_787046.1; DNA (cytosine-5)-methyltransferase 3B isoform 6 [*Homo sapiens*]. Nunes et al.; Sep. 23, 2018.
GENBANK Submission; NCBI, Accession No. NP_787063.1; DNA (cytosine-5)-methyltransferase 3-like isoform 2 [*Homo sapiens*]. Lu et al.; Sep. 23, 2018.
GENBANK Submission; NCBI, Accession No. NP_898961.2; methylcytosine dioxygenase TET3 isoform 2 [Mus musculus]. Reizel et al.; Jul. 28, 2018.
GENBANK Submission; NCBI, Accession No. NP_976034.4. POU domain, class 5, transcription factor 1 isoform 2 [*Homo sapiens*]. Jul. 31, 2023. 3 pages.
GENBANK Submission; NCBI, Accession No. NP_001300981.1. Krueppel-like factor 4 isoform 1 [*Homo sapiens*]. Jul. 13, 2023. 4 pages.
Geoffroy et al., Evidence for an Age-Dependent Decline in Axon Regeneration in the Adult Mammalian Central Nervous System. Cell Rep. Apr. 12, 2016;15(2):238-46. doi: 10.1016/j.celrep.2016.03.028. Epub Mar. 31, 2016.
Gill et al., Multi-omic rejuvenation of human cells by maturation phase transient reprogramming. Elife. Apr. 8, 2022:11:e71624. doi: 10.7554/eLife.71624.
Goldberg et al., Amacrine-signaled loss of intrinsic axon growth ability by retinal ganglion cells. Science. Jun. 7, 2002;296(5574):1860-4. doi: 10.1126/science.1068428.

(56) References Cited

OTHER PUBLICATIONS

Gomes et al., Induced pluripotent stem cells reprogramming: Epigenetics and applications in the regenerative medicine. Rev Assoc Med Bras (1992). Feb. 2017;63(2):180-189. doi: 10.1590/1806-9282.63.02.180.

Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.

Gossen et al., Transcriptional activation by tetracyclines in mammalian cells. Science. Jun. 23, 1995;268(5218):1766-9. doi: 10.1126/science.7792603.

Guo et al., Hydroxylation of 5-methylcytosine by TET1 promotes active DNA demethylation in the adult brain. Cell. Apr. 29, 2011;145(3):423-34. doi: 10.1016/j.cell.2011.03.022. Epub Apr. 14, 2011.

Heinz et al., Retroviral and transposon-based tet-regulated all-in-one vectors with reduced background expression and improved dynamic range. Hum Gene Ther. Feb. 2011;22(2):166-76. doi: 10.1089/hum.2010.099. Epub Dec. 19, 2010.

Heng et al., The nuclear receptor Nr5a2 can replace Oct4 in the reprogramming of murine somatic cells to pluripotent cells. Cell Stem Cell. Feb. 5, 2010;6(2):167-74. doi: 10.1016/j.stem.2009.12.009. Epub Jan. 21, 2010.

Hishida et al., In vivo partial cellular reprogramming enhances liver plasticity and regeneration. Cell Rep. Apr. 26, 2022;39(4):110730. doi: 10.1016/j.celrep.2022.110730.

Horvath et al., DNA methylation-based biomarkers and the epigenetic clock theory of ageing. Nat Rev Genet. Jun. 2018;19(6):371-384. doi: 10.1038/s41576-018-0004-3.

Horvath, DNA methylation age of human tissues and cell types. Genome Biol. 2013;14(10):R115. doi: 10.1186/GB-2013-14-10-r115.

Hosoda et al., Development of a tightly-regulated tetracycline-dependent transcriptional activator and repressor co-expression system for the strong induction of transgene expression. Cytotechnology. May 2011;63(3):211-6. doi: 10.1007/s10616-011-9335-z. Epub Feb. 20, 2011.

Hou et al., Pluripotent Stem Cells Induced from Mouse Somatic Cells by Small-Molecule Compounds. Science. Aug. 9, 2013;341(6146):651-4. doi: 10.1126/science.1239278. Epub Jul. 18, 2013.

Hrit et al., OGT binds a conserved C-terminal domain of TET1 to regulate TET1 activity and function in development. Elife. Oct. 16, 2018;7:e34870. doi: 10.7554/eLife.34870.

Hsu et al., Development and applications of CRISPR-Cas9 for genome engineering. Cell. Jun. 5, 2014;157(6):1262-1278. doi: 10.1016/j.cell.2014.05.010.

Jiang et al., Tetracycline-regulated gene expression mediated by a novel chimeric repressor that recruits histone deacetylases in mammalian cells. J Biol Chem. Nov. 30, 2001;276(48):45168-74.

Karg et al., Sustained vision recovery by OSK gene therapy in a mouse model of glaucoma. Cell Reprogram. Dec. 2023;25(6):288-299. doi: 10.1089/cell.2023.0074. Epub Dec. 7, 2023.

Kaplun et al., Kaiso Gene Knockout Promotes Somatic Cell Reprogramming. Biochemistry (Mosc). Mar. 2019;84(3):283-290. doi: 10.1134/S0006297919030106.

Koch et al., ROCK2 is a major regulator of axonal degeneration, neuronal death and axonal regeneration in the CNS. Cell Death Dis. May 15, 2014;5(5):e1225. doi: 10.1038/cddis.2014.191.

Koch et al., Viral vector-mediated downregulation of RhoA increases survival and axonal regeneration of retinal ganglion cells. Front Cell Neurosci. Sep. 5, 2014;8:273. doi: 10.3389/fncel.2014.00273. eCollection 2014.

Lamartina et al., Construction of an rtTA2(s)-m2/tts(kid)-based transcription regulatory switch that displays No. basal activity, good inducibility, and high responsiveness to doxycycline in mice and non-human primates. Mol Ther. Feb. 2003;7(2):271-80. doi: 10.1016/s1525-0016(02)00051-5.

Lavars, Japan moves to fast-track innovative stem cell therapy with first trials on human hearts. New Atlas. Jun. 1, 2018. https://newatlas.com/japan-stem-cell-therapy-hearts/54866/.

Lawther et al., Blood-brain barrier. Continuing Education in Anaesthesia, Critical Care & Pain. 2011; 11(4): 128-32.

Levine et al., An epigenetic biomarker of aging for lifespan and healthspan. Aging (Albany NY). Apr. 18, 2018;10(4):573-591. doi: 10.18632/aging.101414.

Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.

Li et al., Reprogramming induced pluripotent stem cells in the absence of c-Myc for differentiation into hepatocyte-like cells. Biomaterials. Sep. 2011;32(26):5994-6005. doi: 10.1016/j.biomaterials.2011.05.009. Epub Jun. 11, 2011.

Li et al., Small-Molecule-Driven Direct Reprogramming of Mouse Fibroblasts into Functional Neurons. Cell Stem Cell. Aug. 6, 2015;17(2):195-203. doi: 10.1016/j.stem.2015.06.003.

Liao et al., In Vivo Target Gene Activation via CRISPR/Cas9-Mediated Trans-epigenetic Modulation. Cell. Dec. 14, 2017;171(7):1495-1507.e15. doi: 10.1016/j.cell.2017.10.025. Epub Dec. 7, 2017.

Lim et al., Neural activity promotes long-distance, target-specific regeneration of adult retinal axons. Nat Neurosci. Aug. 2016;19(8):1073-84. doi: 10.1038/nn.4340. Epub Jul. 11, 2016.

Liu et al., A Sensitized IGF1 Treatment Restores Corticospinal Axon-Dependent Functions. Neuron. Aug. 16, 2017;95(4):817-833.e4. doi: 10.1016/j.neuron.2017.07.037.

Liu et al., CRISPR-Based Chromatin Remodeling of the Endogenous Oct4 or Sox2 Locus Enables Reprogramming to Pluripotency. Cell Stem Cell. Feb. 1, 2018;22(2):252-261.e4. doi: 10.1016/j.stem.2017.12.001. Epub Jan. 18, 2018.

Liu et al., Systematic comparison of 2A peptides for cloning multi-genes in a polycistronic vector. Sci Rep. May 19, 2017;7(1):2193. doi: 10.1038/s41598-017-02460-2.

Loew et al., Improved Tet-responsive promoters with minimized background expression. BMC Biotechnol. Nov. 24, 2010:10:81. doi: 10.1186/1472-6750-10-81.

Long et al., Bromodeoxyuridine promotes full-chemical induction of mouse pluripotent stem cells. Cell Res. Oct. 2015;25(10):1171-4. doi: 10.1038/cr.2015.96. Epub Aug. 7, 2015.

Lozano-Torres et al., An Off-On Two-Photon Fluorescent Probe for Tracking Cell Senescence in Vivo. J Am Chem Soc. Jul. 5, 2017;139(26):8808-8811. doi: 10.1021/jacs.7b04985. Epub Jun. 23, 2017.

Lu et al., In Vivo Cellular Reprogramming for Tissue Regeneration and Age Reversal. Innov Aging. Nov. 2018; 2(Suppl 1): 883. Published online Nov. 16, 2018. doi: 10.1093/geroni/igy031.3294.

Lu et al., Reprogramming to recover youthful epigenetic information and restore vision. Nature. Dec. 2020;588(7836):124-129. doi: 10.1038/s41586-020-2975-4. Epub Dec. 2, 2020.

Lu et al., Reprogramming to recover youthful epigenetic information and restore vision. Nature. Dec. 2020;588(7836):124-129. doi: 10.1038/s41586-020-2975-4. Epub Dec. 2, 2020. with Supplementary Information. 35 pages.

Lu et al., Reversal of ageing- and injury-induced vision loss by Tet-dependent epigenetic reprogramming. BioRXiv. Jul. 2019; 1-51. doi https://doi.org/10.1101/710210.

Macip et al., Gene Therapy-Mediated Partial Reprogramming Extends Lifespan and Reverses Age-Related Changes in Aged Mice. Cellular Reprogram. Feb. 2024;26(1):24-32. doi: 10.1089/cell.2023.0072.

Mahmoudi et al., Illuminating microbial species-specific effects on organic matter remineralization in marine sediments. Environ Microbiol. May 2020;22(5):1734-1747. doi: 10.1111/1462-2920.14871. Epub Dec. 10, 2019.

Mai et al., NKX3-1 is required for induced pluripotent stem cell reprogramming and can replace OCT4 in mouse and human iPSC induction. Nat Cell Biol. Aug. 2018;20(8):900-908. doi: 10.1038/s41556-018-0136-x. Epub Jul. 16, 2018.

(56) References Cited

OTHER PUBLICATIONS

Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Manukyan et al., Epigenome rejuvenation: HP1ß mobility as a measure of pluripotent and senescent chromatin ground states. Sci Rep. Apr. 25, 2014;4:4789. doi: 10.1038/srep04789.
Matsui et al., Avian adeno-associated virus vector efficiently transduces neurons in the embryonic and post-embryonic chicken brain. PLoS One. 2012;7(11):e48730. doi: 10.1371/journal.pone.0048730. Epub Nov. 7, 2012.
McDermott et al., Gamma Band Neural Stimulation in Humans and the Promise of a New Modality to Prevent and Treat Alzheimer's Disease. J Alzheimers Dis. 2018;65(2):363-392. doi: 10.3233/JAD-180391.
Meer et al., A whole lifespan mouse multi-tissue DNA methylation clock. Elife. Nov. 14, 2018;7:e40675. doi: 10.7554/eLife.40675.
Michalon et al., Inducible and neuron-specific gene expression in the adult mouse brain with the rtTA2S-M2 system. Genesis. Dec. 2005;43(4):205-12. doi: 10.1002/gene.20175.
Miyoshi et al., Reprogramming of mouse and human cells to pluripotency using mature microRNAs. Cell Stem Cell. Jun. 3, 2011;8(6):633-8. doi: 10.1016/j.stem.2011.05.001.
Mohit et al., Cellular Reprogramming, Transdifferentiation and Alleviation of the Aging Pathology. Res J Biotech. 2024; 19(2): 127-139.
Montana et al., Reprogramming of adult rod photoreceptors prevents retinal degeneration. Proc Natl Acad Sci USA. Jan. 29, 2013;110(5):1732-7. doi: 10.1073/pnas.1214387110. Epub Jan. 14, 2013.
Moore et al., KLF family members regulate intrinsic axon regeneration ability. Science. Oct. 9, 2009;326(5950):298-301. doi: 10.1126/science.1175737.
Mor et al., Neutralizing Gatad2a-Chd4-Mbd3/NuRD Complex Facilitates Deterministic Induction of Naive Pluripotency. Cell Stem Cell. Sep. 6, 2018;23(3):412-425.e10. doi: 10.1016/j.stem.2018.07.004. Epub Aug. 16, 2018.
Moreira et al., Assessing Executive Dysfunction in Neurodegenerative Disorders: A Critical Review of Brief Neuropsychological Tools. Front Aging Neurosci. Nov. 9, 2017;9:369. doi: 10.3389/fnagi.2017.00369. eCollection 2017.
Mosteiro et al., Tissue damage and senescence provide critical signals for cellular reprogramming in vivo. Science. Nov. 25, 2016;354(6315):aaf4445. doi: 10.1126/science.aaf4445.
Nehlin et al., The Werner syndrome. A model for the study of human aging. Ann N Y Acad Sci. Jun. 2000;908:167-79. doi: 10.1111/j.1749-6632.2000.tb06645.x.
No Author Listed, Tet-On® 3G Inducible Expression System. Clontech Laboratories, Inc. 8 pages.
No Author Listed, Tet-On® 3G Inducible Expression Systems User Manual. Clonetech Laboratories, Inc. 2014. 24 pages. Published online at takarabio.com.
No Author Listed, Tet-One technology overview. Takara Bio USA, Inc. Accessed at: https://www.takarabio.com/learning-centers/gene-function/inducible-systems/tet-inducible-systems/tet-one-technology-overview. Last accessed: May 15, 2024. 3 pages.
Norsworthy et al., Sox11 Expression Promotes Regeneration of Some Retinal Ganglion Cell Types but Kills Others. Neuron. Jun. 21, 2017;94(6):1112-1120.e4. doi: 10.1016/j.neuron.2017.05.035.
O'Connor et al., Genetic medicines: treatment strategies for hereditary disorders. Nat Rev Genet. Apr. 2006;7(4):261-76. doi: 10.1038/nrg1829.
Oberdoerffer et al., SIRT1 redistribution on chromatin promotes genomic stability but alters gene expression during aging. Cell. Nov. 28, 2008;135(5):907-18. doi: 10.1016/j.cell.2008.10.025.
Oberdoerffer et al., The role of nuclear architecture in genomic instability and ageing. Nat Rev Mol Cell Biol. Sep. 2007;8(9):692-702. doi: 10.1038/nrm2238.
Ocampo et al., In Vivo Amelioration of Age-Associated Hallmarks by Partial Reprogramming. Cell. Dec. 15, 2016;167(7):1719-1733.e12. doi: 10.1016/j.cell.2016.11.052.
O'Donovan et al., B-RAF kinase drives developmental axon growth and promotes axon regeneration in the injured mature CNS. J Exp Med. May 5, 2014;211(5):801-14. doi: 10.1084/jem.20131780. Epub Apr. 14, 2014.
Otake, Japan Times. Jun. 14, 2017. Accessed at: https://www.japantimes.co.jp/news/2017/06/14/national/science-health/transplants-using-ips-cells-put-riken-specialist-forefront-regenerative-medicine-research/#.W6UF5y-ZOfQ.
Park et al., Promoting axon regeneration in the adult CNS by modulation of the PTEN/mTOR pathway. Science. Nov. 7, 2008;322(5903):963-6. doi: 10.1126/science.1161566.
Paska et al., Aberrant methylation patterns in cancer: a clinical view. Biochem Med (Zagreb). Jun. 5, 2015;25(2):161-76. doi: 10.11613/BM.2015.017. eCollection 2015.
Patel et al., Inhaled Nanoformulated mRNA Polyplexes for Protein Production in Lung Epithelium. Adv Mater. Feb. 2019;31(8):e1805116. doi: 10.1002/adma.201805116. Epub Jan. 4, 2019.
Pico et al., Comparative analysis of mouse strains for in vivo reprogramming. bioRxiv. Mar. 8, 2024. 32 pages. https://doi.org/10.1101/2024.03.08.584074.
Puri et al., Epigenetic rejuvenation by partial reprogramming. Bioessays. Apr. 2023;45(4):e2200208. doi: 10.1002/bies.202200208. Epub Mar. 4, 2023.
Ramamoorth et al., Non viral vectors in gene therapy—an overview. J Clin Diagn Res. Jan. 2015;9(1):GE01-6. doi: 10.7860/JCDR/2015/10443.5394. Epub Jan. 1, 2015.
Randolph et al., An all-in-one, Tet-On 3G inducible PiggyBac system for human pluripotent stem cells and derivatives. Sci Rep. May 8, 2017;7(1):1549. doi: 10.1038/s41598-017-01684-6.
Redmer et al., E-cadherin is crucial for embryonic stem cell pluripotency and can replace OCT4 during somatic cell reprogramming. EMBO Rep. Jul. 1, 2011;12(7):720-6. doi: 10.1038/embor.2011.88.
Ribas et al., Gene Manipulation Strategies to Identify Molecular Regulators of Axon Regeneration in the Central Nervous System. Front Cell Neurosci. Aug. 7, 2017;11:231. doi: 10.3389/fncel.2017.00231. eCollection 2017.
Rodda et al., Transcriptional Regulation of Nanog by OCT4 and SOX2. J Biol Chem. Jul. 1, 2005;280(26):24731-7. doi: 10.1074/jbc.M502573200. Epub Apr. 27, 2005.
Roney et al., Improvement of the reverse tetracycline transactivator by single amino acid substitutions that reduce leaky target gene expression to undetectable levels. Sci Rep. Jun. 21, 2016;6:27697. doi: 10.1038/srep27697.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sarin et al., Inhibition of acquired immunodeficiency syndrome virus by oligodeoxynucleoside methylphosphonates. Proc Natl Acad Sci USA. Oct. 1988;85(20):7448-51. Doi 10.1073/pnas.85.20.7448.
Sarkar et al., Transient non-integrative nuclear reprogramming promotes multifaceted reversal of aging in human cells. Nat Commun. Mar. 24, 2020;11(1):1545. doi: 10.1038/s41467-020-15174-3.
Senis et al., AAV vector-mediated in vivo reprogramming into pluripotency. Nat Commun. Jul. 9, 2018;9(1):2651. doi: 10.1038/s41467-018-05059-x.
Sheng et al., Generation and characterization of a Tet-On (rtTA-M2) transgenic rat. BMC Dev Biol. Feb. 16, 2010:10:17. doi: 10.1186/1471-213X-10-17.
Shipley et al., Differentiation of the SH-SY5Y Human Neuroblastoma Cell Line. J Vis Exp. Feb. 17, 2016;(108):53193. doi: 10.3791/53193.
Shu et al., Induction of pluripotency in mouse somatic cells with lineage specifiers. Cell. May 23, 2013;153(6):963-75. doi: 10.1016/j.cell.2013.05.001.
Sichani et al., Partial Reprogramming as a Method for Regenerating Neural Tissues in Aged Organisms. Cell Reprogram. Feb. 2024;26(1):10-23. doi: 10.1089/cell.2023.0123.

(56) References Cited

OTHER PUBLICATIONS

Singh et al., Age reprogramming: cell rejuvenation by partial reprogramming. Development. Nov. 15, 2022;149(22):dev200755. doi: 10.1242/dev.200755. Epub Nov. 16, 2022.

Smalley, First AAV gene therapy poised for landmark approval. Nat Biotechnol. Nov. 9, 2017;35(11):998-999. doi: 10.1038/nbt1117-998.

Smith et al., SOCS3 deletion promotes optic nerve regeneration in vivo. Neuron. Dec. 10, 2009;64(5):617-23. doi: 10.1016/j.neuron.2009.11.021.

Takahashi et al., Induction of pluripotent stem cells from adult human fibroblasts by defined factors. Cell. Nov. 30, 2007;131(5):861-72. doi: 10.1016/j.cell.2007.11.019.

Tammam et al., Nuclear delivery of recombinant OCT4 by chitosan nanoparticles for transgene-free generation of protein-induced pluripotent stem cells. Oncotarget. Jun. 21, 2016;7(25):37728-37739. doi: 10.18632/oncotarget.9276.

Tan et al., Inhibition of transforming growth factor β (TGF-β) signaling can substitute for Oct4 protein in reprogramming and maintain pluripotency. J Biol Chem. Feb. 13, 2015;290(7):4500-11. doi: 10.1074/jbc.M114.609016. Epub Dec. 29, 2014.

Thompson et al., A multi-tissue full lifespan epigenetic clock for mice. Aging (Albany NY). Oct. 21, 2018;10(10):2832-2854. doi: 10.18632/aging.101590.

Tyner et al., p53 mutant mice that display early ageing-associated phenotypes. Nature. Jan. 3, 2002;415(6867):45-53. doi: 10.1038/415045a.

Uchida et al., Tight regulation of transgene expression by tetracycline-dependent activator and repressor in brain. Genes Brain Behav. Feb. 2006;5(1):96-106. doi: 10.1111/j.1601-183X.2005.00139.x.

Urlinger et al., Exploring the sequence space for tetracycline-dependent transcriptional activators: novel mutations yield expanded range and sensitivity. Proc Natl Acad Sci U S A. Jul. 5, 2000;97(14):7963-8. doi: 10.1073/pnas.130192197.

Wang et al., Lin28 Signaling Supports Mammalian PNS and CNS Axon Regeneration. Cell Rep. Sep. 4, 2018;24(10):2540-2552.e6. doi: 10.1016/j.celrep.2018.07.105.

Wang et al., Ribosomal DNA harbors an evolutionarily conserved clock of biological aging. Genome Res. Mar. 2019;29(3):325-333. doi: 10.1101/gr.241745.118. Epub Feb. 14, 2019.

Wang et al., Spatiotemporal control of gene expression by a light-switchable transgene system. Nat Methods. Feb. 12, 2012;9(3):266-9. doi: 10.1038/nmeth.1892.

Wang et al., The lysine demethylase LSD1 (KDM1) is required for maintenance of global DNA methylation. Nat Genet. Jan. 2009;41(1):125-9. doi: 10.1038/ng.268. Epub Dec. 21, 2008.

Warren et al., Highly Efficient Reprogramming to Pluripotency and Directed Differentiation of Human Cells with Synthetic Modified mRNA. Cell Stem Cell. Nov. 5, 2010;7(5):618-30. doi: 10.1016/j.stem.2010.08.012. Epub Sep. 30, 2010.

Weltner et al., Human pluripotent reprogramming with CRISPR activators. Nat Commun. Jul. 6, 2018;9(1):2643. doi: 10.1038/s41467-018-05067-x.

Weng et al., An Intrinsic Epigenetic Barrier for Functional Axon Regeneration. Neuron. Apr. 19, 2017;94(2):337-346.e6. doi: 10.1016/j.neuron.2017.03.034.

Wright et al., Identification of factors that contribute to recombinant AAV2 particle aggregation and methods to prevent its occurrence during vector purification and formulation. Mol Ther. Jul. 2005;12(1):171-8. doi: 10.1016/j.ymthe.2005.02.021.

Wu et al. Induced pluripotent stem cells Cellular research progress in ophthalmic diseases Exhibition. International Journal of Ophthalmology. 2013; 13(2): 295-298.

Xiao et al., Endogenous Reprogramming of Alpha Cells into Beta Cells, Induced by Viral Gene Therapy, Reverses Autoimmune Diabetes. Cell Stem Cell. Jan. 4, 2018;22(1):78-90.e4. doi: 10.1016/j.stem.2017.11.020.

Yang et al., Induced pluripotent stem cell lines derived from human somatic cells. Science. Dec. 21, 2007;318(5858):1917-20. doi: 10.1126/science.1151526. Epub Nov. 20, 2007.

Yao et al., Restoration of vision after de novo genesis of rod photoreceptors in mammalian retinas. Nature. Aug. 2018;560(7719):484-488. doi: 10.1038/s41586-018-0425-3. Epub Aug. 15, 2018.

Yao et al., Systemic and localized reversible regulation of transgene expression by tetracycline with tetR-mediated transcription repression switch. J Surg Res. Apr. 2007;138(2):267-74. doi: 10.1016/j.jss.2006.05.007. Epub Jan. 24, 2007.

Yilmazer et al., In vivo cell reprogramming towards pluripotency by virus-free overexpression of defined factors. PLoS One. 2013;8(1):e54754. doi: 10.1371/journal.pone.0054754. Epub Jan. 23, 2013.

Yu et al., Tet3 regulates synaptic transmission and homeostatic plasticity via DNA oxidation and repair. Nat Neurosci. Jun. 2015;18(6):836-43. doi: 10.1038/nn.4008. Epub Apr. 27, 2015.

Yuan et al., Brief report: combined chemical treatment enables Oct4-induced reprogramming from mouse embryonic fibroblasts. Stem Cells. Mar. 2011;29(3):549-53. doi: 10.1002/stem.594.

Zahid et al., Protein transduction domains: applications for molecular medicine. Curr Gene Ther. Oct. 2012; 12(5):374-80. doi: 10.2174/156652312802762527.

Zhang et al., Reducing Background Expression of Target Gene with tTS/rtTA System in Cell Model. Journal of Sun Yat-Sen University (Medical Sciences). Jul. 30, 2006; 27(4): 361-364.

Zhao et al., A coumermycin/novobiocin-regulated gene expression system. Hum Gene Ther. Nov. 20, 2003;14(17):1619-29. doi: 10.1089/104303403322542266.

Zhao et al., A XEN-like State Bridges Somatic Cells to Pluripotency during Chemical Reprogramming. Cell. Dec. 17, 2015;163(7):1678-91. doi: 10.1016/j.cell.2015.11.017. Epub Dec. 10, 2015.

Zhou et al., Generation of induced pluripotent stem cells using recombinant proteins. Cell Stem Cell. May 8, 2009;4(5):381-4. doi: 10.1016/j.stem.2009.04.005. Epub Apr. 23, 2009.

Zhou et al., Optimization of the Tet-On system for regulated gene expression through viral evolution. Gene Ther. Oct. 2006;13(19):1382-90. doi: 10.1038/sj.gt.3302780. Epub May 25, 2006.

Zhu et al., Silencing and un-silencing of tetracycline-controlled genes in neurons. PLoS One. Jun. 20, 2007;2(6):e533. doi: 10.1371/journal.pone.0000533.

International Preliminary Report on Patentability for Application No. PCT/US2023/065374, mailed Oct. 17, 2024.

[No Author Listed], *Homo sapiens* tet methylcytosine dioxygenase 3 (TET3), transcript variant 2, mRNA. NCBI Ref Seq No. NM_001366022.1. Sep. 20, 2018. Accessible at https://www.ncbi.nlm.nih.gov/nuccore/1478050930?sat=47&satkey=7913.

Bareyre et al., In vivo imaging reveals a phase-specific role of STAT3 during central and peripheral nervous system axon regeneration. Proc Natl Acad Sci USA. Apr. 12, 2011;108(15):6282-7. doi: 10.1073/pnas.1015239108. Epub Mar. 29, 2011.

Cameron et al., Optic Nerve Crush in Mice to Study Retinal Ganglion Cell Survival and Regeneration. Bio Protoc. Mar. 20, 2020;10(6):e3559. doi: 10.21769/BioProtoc.3559.

Chan et al., Engineered AAVs for efficient noninvasive gene delivery to the central and peripheral nervous systems. Nat Neurosci. Author manuscript; available in PMC: Dec. 26, 2017. Published in final edited form as: Nat Neurosci. Jun. 26, 2017;20(8):1172-1179. doi: 10.1038/nn.4593.

Choi et al., Optimization of AAV expression cassettes to improve packaging capacity and transgene expression in neurons. Mol Brain. Mar. 11, 2014;7:17. doi: 10.1186/1756-6606-7-17.

Chtarto et al., Tetracycline-inducible transgene expression mediated by a single AAV vector. Gene Ther. Jan. 2003;10(1):84-94. doi: 10.1038/sj.gt.3301838.

Fan et al., Transient, Inducible, Placenta-Specific Gene Expression in Mice. Endocrinology. Nov. 2012;153(11):5637-44. doi: 10.1210/en.2012-1556. Epub Sep. 25, 2012.

Gjoneska et al., Conserved epigenomic signals in mice and humans reveal immune basis of Alzheimer's disease. Nature. Feb. 19, 2015;518(7539):365-9. doi: 10.1038/nature14252.

Goertsen et al., AAV capsid variants with brain-wide transgene expression and decreased liver targeting after intravenous delivery in mouse and marmoset. Nat Neurosci. Jan. 2022;25(1):106-115. doi: 10.1038/s41593-021-00969-4. Epub Dec. 9, 2021.

(56) References Cited

OTHER PUBLICATIONS

Hager et al., An internal polyadenylation signal substantially increases expression levels of lentivirus-delivered transgenes but has the potential to reduce viral titer in a promoter-dependent manner. Hum Gene Ther. Aug. 2008;19(8):840-50. doi: 10.1089/hum.2007.165.
Khalilpour et al., Ischemic optic neuropathy as a model of neurodegenerative disorder: A review of pathogenic mechanism of axonal degeneration and the role of neuroprotection. J Neurol Sci. Apr. 15, 2017:375:430-441. doi: 10.1016/j.jns.2016.12.044. Epub Dec. 26, 2016.
Krolak et al., A High-Efficiency AAV for Endothelial Cell Transduction Throughout the Central Nervous System. Nat Cardiovasc Res. Author manuscript; available in PMC: Oct. 13, 2022. Published in final edited form as: Nat Cardiovasc Res. Apr. 13, 2022;1(4):389-400. doi: 10.1038/s44161-022-00046-4.
Lambert et al., Towards A Microbead Occlusion Model of Glaucoma for a Non-Human Primate. Sci Rep. Aug. 9, 2019;9(1):11572. doi: 10.1038/s41598-019-48054-y.
Li et al., Epigenetics and Common Ophthalmic Diseases. Yale J Biol Med. Dec. 23, 2016;89(4):597-600. eCollection Dec. 2016.
Li et al., Production of Lentiviral Vectors for Transducing Cells from the Central Nervous System. J Vis Exp. May 24, 2012:(63):e4031. doi: 10.3791/4031.
Mahmoudi et al., Old fibroblasts secrete inflammatory cytokines that drive variability in reprogramming efficiency and may affect wound healing between old individuals. Biorxiv. Oct. 19, 2018. doi: https://doi.org/10.1101/448431.
Mathiesen et al., CNS Transduction Benefits of AAV-PHP.eB over AAV9 are Dependent on Administration Route and Mouse Strain. Mol Ther Methods Clin Dev. Oct. 20, 2020:19:447-458. doi: 10.1016/j.omtm.2020.10.011. eCollection Dec. 11, 2020.
Mertens et al., Directly Reprogrammed Human Neurons Retain Aging-Associated Transcriptomic Signatures and Reveal Age-Related Nucleocytoplasmic Defects. Cell Stem Cell. Dec. 3, 2015;17(6):705-718. doi: 10.1016/j.stem.2015.09.001. Epub Oct. 8, 2015.
Nakagawa et al., Generation of induced pluripotent stem cells without Myc from mouse and human fibroblasts. Nat Biotechnol. Jan. 2008;26(1):101-6. doi: 10.1038/nbt1374. Epub Nov. 30, 2007.
No Author Listed, Optic Nerve Crush. EYECRO. 2024. Accessed at: https://eyecro.com/models/optic-nerve-crush/. [last accessed: Sep. 18, 2024].
Olova et al., Partial reprogramming induces a steady decline in epigenetic age before loss of somatic identity. Aging Cell. Feb. 2019;18(1):e12877. doi: 10.1111/acel.12877. Epub Nov. 18, 2018.
Reichmuth et al., mRNA vaccine delivery using lipid nanoparticles. Ther Deliv. 2016;7(5):319-34. doi: 10.4155/tde-2016-0006.
Shannon, A Mathematical Theory of Communication. The Bell System Technical Journal. 1948; 1: 379-423. https://doi.org/10.1002/j.1538-7305.1948.tb01338.x.
Wang et al., 2A self-cleaving peptide-based multi-gene expression system in the silkworm *Bombyx mori*. Sci Rep. Nov. 5, 2015:5:16273. doi: 10.1038/srep16273.
Abad et al., Reprogramming in vivo produces teratomas and iPS cells with totipotency features. Nature. Oct. 17, 2013;502(7471):340-5. doi: 10.1038/nature12586. Epub Sep. 11, 2013.
Buganim et al., Mechanisms and models of somatic cell reprogramming. Nat Rev Genet. Jun. 2013;14(6):427-39. doi: 10.1038/nrg3473.
Buganim et al., Single-cell expression analyses during cellular reprogramming reveal an early stochastic and a late hierarchic phase. Cell. Sep. 14, 2012;150(6):1209-22. doi: 10.1016/j.cell.2012.08.023.
Coukos et al., Key genes and convergent pathogenic mechanisms in Parkinson disease. Nat Rev Neurosci. Jun. 2024;25(6):393-413. doi: 10.1038/s41583-024-00812-2. Epub Apr. 10, 2024.
Ellis et al., A survey of ex vivo/in vitro transduction efficiency of mammalian primary cells and cell lines with Nine natural adeno-associated virus (AAV1-9) and one engineered adeno-associated virus serotype. Virol J. Mar. 6, 2013:10:74. doi: 10.1186/1743-422X-10-74.
Fardi et al., Epigenetic mechanisms as a new approach in cancer treatment: An updated review. Genes Dis. Jun. 18, 2018;5(4):304-311. doi: 10.1016/j.gendis.2018.06.003. eCollection Dec. 2018.
Gurdon, Adult frogs derived from the nuclei of single somatic cells. Dev Biol. Apr. 1962:4:256-73. doi: 10.1016/0012-1606(62)90043-x.
Hansson et al., Highly coordinated proteome dynamics during reprogramming of somatic cells to pluripotency. Cell Rep. Dec. 27, 2012;2(6):1579-92. doi: 10.1016/j.celrep.2012.10.014.
Horvath et al., Cognitive rejuvenation in old rats by hippocampal OSKM gene therapy. bioRxiv. Jun. 14, 2023. DOI: 10.1101/2023.06.13.544719.
Horvath et al., Cognitive rejuvenation in old rats by hippocampal OSKM gene therapy. Geroscience. Feb. 2025;47(1):809-823. doi: 10.1007/s11357-024-01269-y. Epub Jul. 22, 2024.
Karg et al., In vivo epigenetic reprogramming reverses the age-induced morphological decline of retinal pigment epithelial cells. Investigative Ophthalmology & Visual Science. Jun. 2021; 62(8): 3283. ARVO Annual Meeting Abstract.
Karg et al., Partial epigenetic reprogramming of RPE cells reverses age and rejuvenates mitochondrial metabolism. Investigative Ophthalmology & Visual Science. Jun. 2023; 64(8): 2966. ARVO Annual Meeting Abstract.
Ksander et al., Epigenetic reprogramming—A novel gene therapy that restores vision loss in a nonhuman primate model of NAION. Investigative Ophthalmology & Visual Science. Jun. 2023; 64(8): 474. ARVO Annual Meeting Abstract.
Kurian et al., Conversion of human fibroblasts to angioblast-like progenitor cells. Nat Methods. Jan. 2013;10(1):77-83. doi: 10.1038/nmeth.2255. Epub Dec. 2, 2012.
Ohnishi et al., Premature termination of reprogramming in vivo leads to cancer development through altered epigenetic regulation. Cell. Feb. 13, 2014;156(4):663-77. doi: 10.1016/j.cell.2014.01.005.
Polo et al., A molecular roadmap of reprogramming somatic cells into iPS cells. Cell. Dec. 21, 2012;151(7):1617-32. doi: 10.1016/j.cell.2012.11.039.
Rodríguez-Matellán et al., In vivo reprogramming ameliorates aging features in dentate gyrus cells and improves memory in mice. Stem Cell Reports. Nov. 10, 2020;15(5):1056-1066. doi: 10.1016/j.stemcr.2020.09.010. Epub Oct. 22, 2020.
Roux et al., Diverse partial reprogramming strategies restore youthful gene expression and transiently suppress cell identity. Cell Syst. Jul. 20, 2022;13(7):574-587.e11. doi: 10.1016/j.cels.2022.05.002. Epub Jun. 10, 2022.
Roux et al., Partial reprogramming restores youthful gene expression through transient suppression of cell identity. bioRxiv. May 23, 2021. DOI: 10.1101/2021.05.21.444556.
Sahu et al., Targeted partial reprogramming of age-associated cell states improves markers of health in mouse models of aging. Sci Transl Med. Sep. 11, 2024; 16(764): eadg1777. doi: 10.1126/scitranslmed.adg1777. Epub Sep. 11, 2024.
Takahashi et al., Induction of pluripotent stem cells from mouse embryonic and adult fibroblast cultures by defined factors. Cell. Aug. 25, 2006;126(4):663-76. doi: 10.1016/j.cell.2006.07.024. Epub Aug. 10, 2006.
Thier et al., Direct conversion of fibroblasts into stably expandable neural stem cells. Cell Stem Cell. Apr. 6, 2012;10(4):473-9. doi: 10.1016/j.stem.2012.03.003. Epub Mar. 22, 2012.
Vivien et al., Non-viral expression of mouse Oct4, Sox2, and Klf4 transcription factors efficiently reprograms tadpole muscle fibers in vivo. J Biol Chem. Mar. 2, 2012;287(10):7427-35. doi: 10.1074/jbc.M111.324368. Epub Jan. 9, 2012.
Wallen et al., Metagenomics of Parkinson's disease implicates the gut microbiome in multiple disease mechanisms. Nat Commun. Nov. 15, 2022;13(1):6958. doi: 10.1038/s41467-022-34667-x.
Benskey et al., Targeted gene delivery to the enteric nervous system using AAV: a comparison across serotypes and capsid mutants. Mol Ther. Mar. 2015;23(3):488-500. doi: 10.1038/mt.2015.7. Epub Jan. 16, 2015.

(56) References Cited

OTHER PUBLICATIONS

Hjelm et al., Mifepristone-inducible transgene expression in neural progenitor cells in vitro and in vivo. Gene Ther. May 2016;23(5):424-37. doi: 10.1038/gt.2016.13. Epub Feb. 10, 2016.

Sun et al., Tetracycline-inducible expression systems: new strategies and practices in the transgenic mouse modeling. Acta Biochim Biophys Sin (Shanghai). Apr. 2007;39(4):235-46. doi: 10.1111/j.1745-7270.2007.00258.x.

\* cited by examiner

```
5' ... TTATGCAGTGCTGCCATAACCATGAGTGATAACACTGCGGCCAACTTACTTCTGACAACGATCGGAGGACCGAAGGAGCTAACCG       85
       ++++++++++++++++++++++++++++++++++++++++++++++++++++++++++++++++++++++++++++++++++++
3'     AATACGTCACGACGGTATTGGTACTCACTATTGTGACGCCGGTTGAATGAAGACTGTTGCTAGCCTCCTGGCTTCCTCGATTGGC
```
RYBxO8mRbwMFOFCf7oNIW1BYMn0.1515186099985.7
Extracted region from pAAV-TRE3G-OSK-WPRE3-SV40pA

```
       CTTTTTTGCACAACATGGGGATCATGTAACTCGCCTTGATCGTTGGGAACCGGAGCTGAATGAAGCCATACCAAACGACGAGCG       170
       ++++++++++++++++++++++++++++++++++++++++++++++++++++++++++++++++++++++++++++++++++++
       GAAAAAACGTGTTGTACCCCCTAGTACATTGAGCGGAACTAGCAACCCTTGGCCTCGACTTACTTCGGTATGGTTTGCTGCTCGC
```
RYBxO8mRbwMFOFCf7oNIW1BYMn0.1515186099985.7
Extracted region from pAAV-TRE3G-OSK-WPRE3-SV40pA

```
       TGACACCACGATGCCTGTAGTAATGGTAACAACGTTGCGCAAACTATTAACTGGCGAACTACTTACTCTAGCTTCCCGGCAACAA       255
       ++++++++++++++++++++++++++++++++++++++++++++++++++++++++++++++++++++++++++++++++++++
       ACTGTGGTGCTACGGACATCATTACCATTGTTGCAACGCGTTTGATAATTGACCGCTTGATGAATGAGATCGAAGGGCCGTTGTT
```
RYBxO8mRbwMFOFCf7oNIW1BYMn0.1515186099985.7
Extracted region from pAAV-TRE3G-OSK-WPRE3-SV40pA

```
       TTAATAGACTGGATGGAGGCGGATAAAGTTGCAGGACCACTTCTGCGCTCGGCCCTTCCGGCTGGCTGGTTTATTGCTGATAAAT       340
       ++++++++++++++++++++++++++++++++++++++++++++++++++++++++++++++++++++++++++++++++++++
       AATTATCTGACCTACCTCCGCCTATTTCAACGTCCTGGTGAAGACGCGAGCCGGGAAGGCCGACCGACCAAATAACGACTATTTA
```
RYBxO8mRbwMFOFCf7oNIW1BYMn0.1515186099985.7
Extracted region from pAAV-TRE3G-OSK-WPRE3-SV40pA

```
                                    BsrDI
                                      |
       CTGGAGCCGGTGAGCGTGGGTCTCGCGGTATCATTGCAGCACTGGGGCCAGATGGTAAGCCCTCCCGTATCGTAGTTATCTACAC       425
       ++++++++++++++++++++++++++++++++++++++++++++++++++++++++++++++++++++++++++++++++++++
       GACCTCGGCCACTCGCACCCAGAGCGCCATAGTAACGTCGTGACCCCGGTCTACCATTCGGGAGGGCATAGCATCAATAGATGTG
```
RYBxO8mRbwMFOFCf7oNIW1BYMn0.1515186099985.7
Extracted region from pAAV-TRE3G-OSK-WPRE3-SV40pA

```
       GACGGGGAGTCAGGCAACTATGGATGAACGAAATAGACAGATCGCTGAGATAGGTGCCTCACTGATTAAGCATTGGTAACTGTCA       510
       ++++++++++++++++++++++++++++++++++++++++++++++++++++++++++++++++++++++++++++++++++++
       CTGCCCCTCAGTCCGTTGATACCTACTTGCTTTATCTGTCTAGCGACTCTATCCACGGAGTGACTAATTCGTAACCATTGACAGT
```
RYBxO8mRbwMFOFCf7oNIW1BYMn0.1515186099985.7
Extracted region from pAAV-TRE3G-OSK-WPRE3-SV40pA

FIG. 4A

```
GACCAAGTTTACTCATATATACTTTAGATTGATTTAAAACTTCATTTTTAATTTAAAAGGATCTAGGTGAAGATCCTTTTTGATA
++++++++++++++++++++++++++++++++++++++++++++++++++++++++++++++++++++++++++++++++++++    595
CTGGTTCAAATGAGTATATATGAAATCTAACTAAATTTTGAAGTAAAAATTAAATTTTCCTAGATCCACTTCTAGGAAAAACTAT
```
▷ RYBxO8mRbwMFOFCf7oNIW1BYMn0.1515186099985.7
▷ Extracted region from pAAV-TRE3G-OSK-WPRE3-SV40pA

```
ATCTCATGACCAAAATCCCTTAACGTGAGTTTTCGTTCCACTGAGCGTCAGACCCCGTAGAAAAGATCAAAGGATCTTCTTGAGA
++++++++++++++++++++++++++++++++++++++++++++++++++++++++++++++++++++++++++++++++++++    680
TAGAGTACTGGTTTTAGGGAATTGCACTCAAAAGCAAGGTGACTCGCAGTCTGGGGCATCTTTTCTAGTTTCCTAGAAGAACTCT
```
▷ RYBxO8mRbwMFOFCf7oNIW1BYMn0.1515186099985.7
▷ Extracted region from pAAV-TRE3G-OSK-WPRE3-SV40pA
▷ pBR322_origin

```
TCCTTTTTTTCTGCGCGTAATCTGCTGCTTGCAAACAAAAAAACCACCGCTACCAGCGGTGGTTTGTTTGCCGGATCAAGAGCTA
++++++++++++++++++++++++++++++++++++++++++++++++++++++++++++++++++++++++++++++++++++    765
AGGAAAAAAAGACGCGCATTAGACGACGAACGTTTGTTTTTTTGGTGGCGATGGTCGCCACCAAACAAACGGCCTAGTTCTCGAT
```
▷ RYBxO8mRbwMFOFCf7oNIW1BYMn0.1515186099985.7
▷ Extracted region from pAAV-TRE3G-OSK-WPRE3-SV40pA
▷ pBR322_origin

```
CCAACTCTTTTTCCGAAGGTAACTGGCTTCAGCAGAGCGCAGATACCAAATACTGTCCTTCTAGTGTAGCCGTAGTTAGGCCACC
++++++++++++++++++++++++++++++++++++++++++++++++++++++++++++++++++++++++++++++++++++    850
GGTTGAGAAAAAGGCTTCCATTGACCGAAGTCGTCTCGCGTCTATGGTTTATGACAGGAAGATCACATCGGCATCAATCCGGTGG
```
▷ RYBxO8mRbwMFOFCf7oNIW1BYMn0.1515186099985.7
▷ Extracted region from pAAV-TRE3G-OSK-WPRE3-SV40pA
▷ pBR322_origin

```
ACTTCAAGAACTCTGTAGCACCGCCTACATACCTCGCTCTGCTAATCCTGTTACCAGTGGCTGCTGCCAGTGGCGATAAGTCGTG
++++++++++++++++++++++++++++++++++++++++++++++++++++++++++++++++++++++++++++++++++++    935
TGAAGTTCTTGAGACATCGTGGCGGATGTATGGAGCGAGACGATTAGGACAATGGTCACCGACGACGGTCACCGCTATTCAGCAC
```
▷ RYBxO8mRbwMFOFCf7oNIW1BYMn0.1515186099985.7
▷ Extracted region from pAAV-TRE3G-OSK-WPRE3-SV40pA
▷ pBR322_origin

FIG. 4B

TCTTACCGGGTTGGACTCAAGACGATAGTTACCGGATAAGGCGCAGCGGTCGGGCTGAACGGGGGGTTCGTGCACACAGCCCAGC
AGAATGGCCCAACCTGAGTTCTGCTATCAATGGCCTATTCCGCGTCGCCAGCCCGACTTGCCCCCCAAGCACGTGTGTCGGGTCG

1020

RYBxO8mRbwMFOFCf7oNIW1BYMn0.1515186099985.7
Extracted region from pAAV-TRE3G-OSK-WPRE3-SV40pA
pBR322_origin TTGGAGCGAACGACCTACACCGAACTGAGATACCTACAGCGTGAGCTATGAGAAAGCGCCACGCTTCCCGAAGGGAGAAAGGCGG
AACCTCGCTTGCTGGATGTGGCTTGACTCTATGGATGTCGCACTCGATACTCTTTCGCGGTGCGAAGGGCTTCCCTCTTTCCGCC

1105

RYBxO8mRbwMFOFCf7oNIW1BYMn0.1515186099985.7
Extracted region from pAAV-TRE3G-OSK-WPRE3-SV40pA
pBR322_origin ACAGGTATCCGGTAAGCGGCAGGGTCGGAACAGGAGAGCGCACGAGGGAGCTTCCAGGGGGAAACGCCTGGTATCTTTATAGTCC
TGTCCATAGGCCATTCGCCGTCCCAGCCTTGTCCTCTCGCGTGCTCCCTCGAAGGTCCCCCTTTGCGGACCATAGAAATATCAGG

1190

RYBxO8mRbwMFOFCf7oNIW1BYMn0.1515186099985.7
Extracted region from pAAV-TRE3G-OSK-WPRE3-SV40pA
pBR322_origin TGTCGGGTTTCGCCACCTCTGACTTGAGCGTCGATTTTTGTGATGCTCGTCAGGGGGGCGGAGCCTATGGAAAAACGCCAGCAAC
ACAGCCCAAAGCGGTGGAGACTGAACTCGCAGCTAAAAACACTACGAGCAGTCCCCCGCCTCGGATACCTTTTGCGGTCGTTG

1275

RYBxO8mRbwMFOFCf7oNIW1BYMn0.1515186099985.7
Extracted region from pAAV-TRE3G-OSK-WPRE3-SV40pA
pBR322_origin GCGGCCTTTTTACGGTTCCTGGCCTTTTGCTGGCCTTTTGCTCACATGTTCTTTCCTGCGTTATCCCCTGATTCTGTGGATAACC
CGCCGGAAAAATGCCAAGGACCGGAAAACGACCGGAAAACGAGTGTACAAGAAAGGACGCAATAGGGGACTAAGACACCTATTGG

1360

RYBxO8mRbwMFOFCf7oNIW1BYMn0.1515186099985.7
Extracted region from pAAV-TRE3G-OSK-WPRE3-SV40pA

 pBR322_origin     CGG

AGTTTACTCCCTATCAGTGATAGAGAACGTATCTACAGTTTACTCCCTATCAGTGATAGAGAACGTATATCCAGTTTACTCCCTA
TCAAATGAGGGATAGTCACTATCTCTTGCATAGATGTCAAATGAGGGATAGTCACTATCTCTTGCATATAGGTCAAATGAGGGAT

2125

- Digestion of pAAV-TRE3G-OSK-WPRE3-SV40pA - Frag...
- RYBxO8mRbwMFOFCf7oNIW1BYMn0.1513097172637.1
- RYBxO8mRbwMFOFCf7oNIW1BYMn0.1515186099985.7
- RYBxO8mRbwMFOFCf7oNIW1BYMn0.1520442556735.1
- RYBxO8mRbwMFOFCf7oNIW1BYMn0.1520442825019.17
- RYBxO8mRbwMFOFCf7oNIW1BYMn0.1515185884933.5
- RYBxO8mRbwMFOFCf7oNIW1BYMn0.1499881982184.9
- GTACACGCCTACCTCGACCCATCAAGTGCCACCTGACGTCTCCCTAT...
- RYBxO8mRbwMFOFCf7oNIW1BYMn0.1515186141081.10
- Extracted region from pTRE3G
- TRE3G\Promoter
- qPCR-fwd-TRE3G
- tetO
- tetO
- tetO FIG. 4F
Continued TCAGTGATAGAGAACGTATAAGCTTTAGGCGTGTACGGTGGGCGCCTATAAAAGCAGAGCTCGTTTAGTGAACCGTCAGATCGCC
AGTCACTATCTCTTGCATATTCGAAATCCGCACATGCCACCCGCGGATATTTTCGTCTCGAGCAAATCACTTGGCAGTCTAGCGG

2210

Digestion of pAAV-TRE3G-OSK-WPRE3-SV40pA - Frag...
RYBxO8mRbwMFOFCf7oNIW1BYMn0.1513097172637.1

RYBxO8mRbwMFOFCf7oNIW1BYMn0.1515186099985.7
RYBxO8mRbwMFOFCf7oNIW1BYMn0.1520442556735.1
RYBxO8mRbwMFOFCf7oNIW1BYMn0.1520442825019.17
RYBxO8mRbwMFOFCf7oNIW1BYMn0.1515185884933.5
RYBxO8mRbwMFOFCf7oNIW1BYMn0.1499881982184.9
GTACACGCCTACCTCGACCCATCAAGTGCCACCTGACGTCTCCCTAT...
RYBxO8mRbwMFOFCf7oNIW1BYMn0.1515186141081.10
Extracted region from pTRE3G
TRE3G\Promoter
tetO | Modified Minimal CMV Promoter

```
CCCGCATACGAGTTCTGCGGAGGGATGGCATACTGTGGACCTCAGGTTGGACTGGGCCTAGTCCCCAAGTTGGCGTGGAGACTT
GGGCGTATGCTCAAGACGCCTCCCTACCGTATGACACCTGGAGTCCAACCTGACCCGGATCAGGGGGTTCAACCGCACCTCTGAA
```
2550

Pro Ala Tyr Glu Phe Cys Gly Gly Met Ala Tyr Cys Gly Pro Gln Val Gly Leu Gly Leu Val Pro Gln Val Gly Val Glu Thr

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| RYBxO8mRbwMFOFCf7oNIW1BYMn0.1520442556735.1 |
| RYBxO8mRbwMFOFCf7oNIW1BYMn0.1520442825019.17 |
| Oct4 |

```
TGCAGCCTGAGGGCCAGGCAGGAGCACGAGTGGAAAGCAACTCAGAGGGAACCTCCTCTGAGCCCTGTGCCGACCGCCCCAATGC
ACGTCGGACTCCCGGTCCGTCCTCGTGCTCACCTTTCGTTGAGTCTCCCTTGGAGGAGACTCGGGACACGGCTGGCGGGGTTACG
```
2635

Leu Gln Pro Glu Gly Gln Ala Gly Ala Arg Val Glu Ser Asn Ser Glu Gly Thr Ser Ser Glu Pro Cys Ala Asp Arg Pro Asn Ala

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| RYBxO8mRbwMFOFCf7oNIW1BYMn0.1520442556735.1 |
| RYBxO8mRbwMFOFCf7oNIW1BYMn0.1520442825019.17 |
| Oct4 |

FIG. 4I

```
CGTGAAGTTGGAGAAGGTGGAACCAACTCCGGAGGAGTCCAGGACATGAAAGCCCTGCAGAAGGAGCTAGAACAGTTTGCCAAG
GCACTTCAACCTCTTCCACCTTGGTTGAGGCCTCCTCAGGTCCTGTACTTTCGGGACGTCTTCCTCGATCTTGTCAAACGGTTC
```
2720

Val Lys Leu Glu Lys Val Glu Pro Thr Pro Glu Glu Ser Gln Asp Met Lys Ala Leu Gln Lys Glu Leu Glu Gln Phe Ala Lys

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- RYBxO8mRbwMFOFCf7oNIW1BYMn0.1520442556735.1
- RYBxO8mRbwMFOFCf7oNIW1BYMn0.1520442825019.17
- Oct4

```
CTGCTGAAGCAGAAGAGGATCACCTTGGGGTACACCCAGGCCGACGTGGGGCTCACCCTGGGCGTTCTCTTTGGAAAGGTGTTCA
GACGACTTCGTCTTCTCCTAGTGGAACCCCATGTGGGTCCGGCTGCACCCCGAGTGGGACCCGCAAGAGAAACCTTTCCACAAGT
```
2805

Leu Leu Lys Gln Lys Arg Ile Thr Leu Gly Tyr Thr Gln Ala Asp Val Gly Leu Thr Leu Gly Val Leu Phe Gly Lys Val Phe

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- RYBxO8mRbwMFOFCf7oNIW1BYMn0.1520442556735.1
- RYBxO8mRbwMFOFCf7oNIW1BYMn0.1520442825019.17
- Oct4

FIG. 4J

```
                                        AflII
GCCAGACCACCATCTCTCGCTTCGAGGCCTTGCAGCTCAGCCTTAAGAACATGTGTAAGCTGCGGCCCCTGCTGGAGAAGTGGGT
++++++++++++++++++++++++++++++++++++++++++++++++++++++++++++++++++++++++++++++++++++    2890
CGGTCTGGTGGTAGAGAGCGAAGCTCCGGAACGTCGAGTCGGAATTCTTGTACACATTCGACGCCGGGGACGACCTCTTCACCCA
   |    |    |    |    |    |    |    |    |    |    |
   175      180      185      190      195      200
Ser Gln Thr Thr Ile Cys Arg Phe Glu Ala Leu Gln Leu Ser Leu Lys Asn Met Cys Lys Leu Arg Pro Leu Leu Glu Lys Trp Val
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| RYBxO8mRbwMFOFCf7oNIW1BYMn0.1520442556735.1 | > |
| RYBxO8mRbwMFOFCf7oNIW1BYMn0.1520442825019.17 | > |
| Oct4 | > |

```
GGAGGAAGCCGACAACAATGAGAACCTTCAGGAGATATGCAAATCGGAGACCCTGGTGCAGGCCCGGAAGAGAAAGCGAACTAGC
++++++++++++++++++++++++++++++++++++++++++++++++++++++++++++++++++++++++++++++++++++    2975
CCTCCTTCGGCTGTTGTTACTCTTGGAAGTCCTCTATACGTTTAGCCTCTGGGACCACGTCCGGGCCTTCTCTTTCGCTTGATCG
   |    |    |    |    |    |
   205      210      215      220      225
Glu Glu Ala Asp Asn Asn Glu Asn Leu Gln Glu Ile Cys Lys Ser Glu Thr Leu Val Gln Ala Arg Lys Arg Lys Arg Thr Ser
```

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| RYBxO8mRbwMFOFCf7oNIW1BYMn0.1520442556735.1 | > |
| RYBxO8mRbwMFOFCf7oNIW1BYMn0.1520442825019.17 | > |
| Oct4 | > |

NheI   BmtI
CTGCTCTGGGCTCTCCCATGCATTCAAACGCTAGCGGCAGCGGCGCCACGAACTTCTCTCTGTTAAAGCAAGCAGGAGATGTTGA
++++++++++++++++++++++++++++++++++++++++++++++++++++++++++++++++++++++++++++++++++++  3400
GACGAGACCCGAGAGGGTACGTAAGTTTGCGATCGCCGTCGCCGCGGTGCTTGAAGAGAGACAATTTCGTTCGTCCTCTACAACT
   345       350       355       360       365       370
Thr Ala Leu Gly Ser Pro Met His Ser Asn Ala Ser Gly Ser Gly Ala Thr Asn Phe Ser Leu Leu Lys Gln Ala Gly Asp Val Glu

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
RYBxO8mRbwMFOFCf7oNIW1BYMn0.1520442556735.1
RYBxO8mRbwMFOFCf7oNIW1BYMn0.1520442825019.17
Oct4                                          P2A AGAAAACCCCGGGCCTGCATGCATGTATAACATGATGGAGACGGAGCTGAAGCCGCCGGGCCCGCAGCAAGCTTCGGGGGGCGGC
++++++++++++++++++++++++++++++++++++++++++++++++++++++++++++++++++++++++++++++++++++  3485
TCTTTTGGGGCCCGGACGTACGTACATATTGTACTACCTCTGCCTCGACTTCGGCGGCCCGGGCGTCGTTCGAAGCCCCCCGCCG
      375       380       385       390       395
Glu Asn Pro Gly Pro Ala Cys Met Tyr Asn Met Met Glu Thr Glu Leu Lys Pro Pro Gly Pro Gln Gln Ala Ser Gly Gly Gly ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
RYBxO...            Sox2
RYBxO...   RYBxO8mRbwMFOFCf7oNIW1BYMn0.1520442556787.2
           RYBxO8mRbwMFOFCf7oNIW1BYMn0.1520442825053.18
P2A

FIG. 4N

```
TCATGGTATGGTCCCGGGGGCAGCGGCGTAAGATGGCCCAGGAGAACCCCAAGATGCACAACTCGGAGATCAGCAAGCGCCTGGG
AGTACCATACCAGGGCCCCCGTCGCCGCATTCTACCGGGTCCTCTTGGGGTTCTACGTGTTGAGCCTCTAGTCGTTCGCGGACCC
       430       435       440       445       450       455
Phe Met Val Trp Ser Arg Gly Gln Arg Arg Lys Met Ala Gln Glu Asn Pro Lys Met His Asn Ser Glu Ile Ser Lys Arg Leu Gly
```
3655

- ORF frame 3
- RYBxO8mRbwMFOFCf7oNIW1BYMn0.1513097172637.1
- RYBxO8mRbwMFOFCf7oNIW1BYMn0.1515186099932.6
- Extracted region from pAAV-TRE3G-OSK-WPRE3-SV40pA
- RYBxO8mRbwMFOFCf7oNIW1BYMn0.1499881537908.1
- Digestion of pAAV-TRE3G-OSK-WPRE3-SV40pA - Frag...
- RYBxO8mRbwMFOFCf7oNIW1BYMn0.1515186141043.9
- RYBxO8mRbwMFOFCf7oNIW1BYMn0.1515185884753.3
- Sox2
- RYBxO8mRb... | RYBxO8mRbwMFOFCf7oNIW1BYMn0.1520442556822.3
- RYBxO8mRb... | RYBxO8mRbwMFOFCf7oNIW1BYMn0.1520442825077.19

FIG. 4O
Continued

CGCGGAGTGGAAACTTTTGTCCGAGACCGAGAAGCGGCCGTTCATCGACGAGGCCAAGCGGCTGCGCGCTCTGCACATGAAGGAG
GCGCCTCACCTTTGAAAACAGGCTCTGGCTCTTCGCCGGCAAGTAGCTGCTCCGGTTCGCCGACGCGCGAGACGTGTACTTCCTC
460 465 470 475 480

Ala Glu Trp Lys Leu Leu Ser Glu Thr Glu Lys Arg Pro Phe Ile Asp Glu Ala Lys Arg Leu Arg Ala Leu His Met Lys Glu

3740

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Sox2 |
| RYBxO8mRbwMFOFCf7oNIW1BYMn0.1520442556822.3 |
| RYBxO8mRbwMFOFCf7oNIW1BYMn0.1520442825077.19 |

SacII
CACCCGGATTATAAATACCGGCCGGGCGGAAAACCAAGACGCTCATGAAGAAGGATAAGTACACGCTTCCCGGAGGCTTGCTGG
GTGGGCCTAATATTTATGGCCGGCCCGCCTTTTGGTTCTGCGAGTACTTCTTCCTATTCATGTGCGAAGGGCCTCCGAACGACC
485 490 495 500 505 510

His Pro Asp Tyr Lys Tyr Arg Pro Arg Arg Lys Thr Lys Thr Leu Met Lys Lys Asp Lys Tyr Thr Leu Pro Gly Gly Leu Leu

3825

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Sox2 |
| RYBxO8mRbwMFOFCf7oNIW1BYMn0.1520442556822.3 |
| RYBxO8mRbwMFOFCf7oNIW1BYMn0.1520442825077.19 |

```
                                                                      BclI*
CGAGGCCAGCTCCAGCCCCCCGTGGTTACCTCTTCCTCCCACTCCAGGGCGCCCTGCCAGGCCGGGGACCTCCGGGACATGATC
++++++++++++++++++++++++++++++++++++++++++++++++++++++++++++++++++++++++++++++++++++   4250
GCTCCGGTCGAGGTCGGGGGGGCACCAATGGAGAAGGAGGGTGAGGTCCCGCGGGACGGTCCGGCCCCTGGAGGCCCTGTACTAG
     630       635       640       645       650
```
Glu Ala Ser Ser Ser Pro Pro Val Val Thr Ser Ser Ser His Ser Arg Ala Pro Cys Gln Ala Gly Asp Leu Arg Asp Met Ile

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Sox2 |
| RYBxO8mRbwMFOFCf7oNIW1BYMn0.1520442556899.4 |
| RYBxO8mRbwMFOFCf7oNIW1BYMn0.1520442825096.20 |

TGGCGGAGCTGGTGCAGCTTGCAGCAGTAACAACCCGGCCCTCCTAGCCCGGAGGGAGACCGAGGAGTTCAACGACCTCCTGGAC
ACCGCCTCGACCACGTCGAACGTCGTCATTGTTGGGCCGGGAGGATCGGGCCTCCCTCTGGCTCCTCAAGTTGCTGGAGGACCTG 800 805 810 815 820

Gly Gly Ala Gly Ala Ala Cys Ser Ser Asn Asn Pro Ala Leu Leu Ala Arg Arg Glu Thr Glu Glu Phe Asn Asp Leu Leu Asp

4760

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
Klf4
RYBxO8mRbwMFOFCf7oNIW1BYMn0.1520442556899.4
RYBxO8mRbwMFOFCf7oNIW1BYMn0.1520442825096.20

CTAGACTTTATCCTTTCCAACTCGCTAACCCACCAGGAATGGTGGCCGCCACCGTGACCACCTCGGCGTCAGTTCATCCTCGT
GATCTGAAATAGGAAAGGTTGAGCGATTGGGTGGTCCTTAGCCACCGGCGGTGGCACTGGTGGAGCCGCAGTCGAAGTAGGAGCA 825 830 835 840 845 850

Leu Asp Phe Ile Leu Ser Asn Ser Leu Thr His Gln Glu Ser Val Ala Ala Thr Val Thr Thr Ser Ala Ser Ala Ser Ser Ser

4845

ORF frame 3
RYBxO8mRbwMFOFCf7oNIW1BYMn0.1513097172637.1
RYBxO8mRbwMFOFCf7oNIW1BYMn0.1515186099932.6
Extracted region from pAAV-TRE3G-OSK-WPRE3-SV40pA
RYBxO8mRbwMFOFCf7oNIW1BYMn0.1499881537908.1
Digestion of pAAV-TRE3G-OSK-WPRE3-SV40pA - Frag...
RYBxO8mRbwMFOFCf7oNIW1BYMn0.1515186141043.9
RYBxO8mRbwMFOFCf7oNIW1BYMn0.1515185884753.3
Klf4
RYBxO8mRbwMFOFCf7oNIW1BYMn0.1520442556899.4
RYBxO8mRbwMFOFCf7oNIW1BYMn0.1520442825096.20

FIG. 4V

```
CTTCCCCAGCGAGCAGCGGCCCTGCCAGCGCGCCCTCCACCTGCAGCTTCAGCTATCCGATCCGGGCCGGGGGTGACCCGGGCGT
GAAGGGGTCGCTCGTCGCCGGGACGGTCGCGCGGGAGGTGGACGTCGAAGTCGATAGGCTAGGCCCGGCCCCCACTGGGCCCGCA
         855       860       865       870       875       880
Ser Ser Pro Ala Ser Ser Gly Pro Ala Ser Ala Pro Ser Thr Cys Ser Phe Ser Tyr Pro Ile Arg Ala Gly Gly Asp Pro Gly Val
```
4930

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Klf4 |
| RYBxO8mRbwMFOFCf7oNIW1BYMn0.1520442556899.4 | RYB... |
| RYBxO8mRbwMFOFCf7oNIW1BYMn0.1520442825096.20 | RYB... |
| Klf4-mid-fwd |

FIG. 4W

```
GGCTGCCAGCAACACAGGTGGAGGGCTCCTCTACAGCCGAGAATCTGCGCCACCTCCCACGGCCCCCTTCAACCTGGCGGACATC
++++++++++++++++++++++++++++++++++++++++++++++++++++++++++++++++++++++++++++++++++++
CCGACGGTCGTTGTGTCCACCTCCCGAGGAGATGTCGGCTCTTAGACGCGGTGGAGGGTGCCGGGGAAGTTGGACCGCCTGTAG
```
    |    885    |    890    |    895    |    900    |    905    |                                                                        5015

Ala Ala Ser Asn Thr Gly Gly Gly Leu Leu Tyr Ser Arg Glu Ser Ala Pro Pro Pro Thr Ala Pro Phe Asn Leu Ala Asp Ile

| ORF frame 3 | >
| RYBxO8mRbwMFOFCf7oNIW1BYMn0.1513097172637.1 | >
| RYBxO8mRbwMFOFCf7oNIW1BYMn0.1515186099932.6 | >
| Extracted region from pAAV-TRE3G-OSK-WPRE3-SV40pA | >
| RYBxO8mRbwMFOFCf7oNIW1BYMn0.1499881537908.1 | >
| Digestion of pAAV-TRE3G-OSK-WPRE3-SV40pA - Frag... | >
| RYBxO8mRbwMFOFCf7oNIW1BYMn0.1515186141043.9 | >
| RYBxO8mRbwMFOFCf7oNIW1BYMn0.1515185884753.3 | >
| Klf4 | >
| RYBxO8mRbwMFOFCf7oNIW1BYMn0.1520442556934.5 | >
| RYBxO8mRbwMFOFCf7oNIW1BYMn0.1520442825118.21 | >

Klf4-mid-fwd

```
CATCAGTGTTAGCAAAGGAAGCCCAGACGGCAGCCACCCCGTGGTAGTGGCGCCCTACAGCGGTGGCCCGCCGCGCATGTGCCCC
++++++++++++++++++++++++++++++++++++++++++++++++++++++++++++++++++++++++++++++++++++   5270
GTAGTCACAATCGTTTCCTTCGGGTCTGCCGTCGGTGGGGCACCATCACCGCGGGATGTCGCCACCGGGCGGCGCGTACACGGGG
       970       975       980       985       990
 Ile Ser Val Ser Lys Gly Ser Pro Asp Gly Ser His Pro Val Val Val Ala Pro Tyr Ser Gly Gly Pro Pro Arg Met Cys Pro
```

ORF frame 3

RYBxO8mRbwMFOFCf7oNIW1BYMn0.1513097172637.1

RYBxO8mRbwMFOFCf7oNIW1BYMn0.1515186099932.6

Extracted region from pAAV-TRE3G-OSK-WPRE3-SV40pA

RYBxO8mRbwMFOFCf7oNIW1BYMn0.1499881537908.1

Digestion of pAAV-TRE3G-OSK-WPRE3-SV40pA - Frag...

RYBxO8mRbwMFOFCf7oNIW1BYMn0.1515186141043.9

RYBxO8mRbwMFOFCf7oNIW1BYMn0.1515185884753.3

Klf4

RYBxO8mRbwMFOFCf7oNIW1BYMn0.1520442556934.5

RYBxO8mRbwMFOFCf7oNIW1BYMn0.1520442825118.21

FIG. 4Y

```
                                                            AfeI
AAGATTAAGCAAGAGGCGGTCCCGTCCTGCACGGTCAGCCGGTCCCTAGAGGCCCATTTGAGCGCTGGACCCCAGCTCAGCAACG  5355
++++++++++++++++++++++++++++++++++++++++++++++++++++++++++++++++++++++++++++++++++++
TTCTAATTCGTTCTCCGCCAGGGCAGGACGTGCCAGTCGGCCAGGGATCTCCGGGTAAACTCGCGACCTGGGGTCGAGTCGTTGC
    995      1000      1005      1010      1015      1020
Lys Ile Lys Gln Glu Ala Val Pro Ser Cys Thr Val Ser Arg Ser Leu Glu Ala His Leu Ser Ala Gly Pro Gln Leu Ser Asn
```

| ORF frame 3 |
| RYBxO8mRbwMFOFCf7oNlW1BYMn0.1513097172637.1 |
| RYBxO8mRbwMFOFCf7oNlW1BYMn0.1515186099932.6 |
| Extracted region from pAAV-TRE3G-OSK-WPRE3-SV40pA |
| RYBxO8mRbwMFOFCf7oNlW1BYMn0.1499881537908.1 |
| Digestion of pAAV-TRE3G-OSK-WPRE3-SV40pA - Frag... |
| RYBxO8mRbwMFOFCf7oNlW1BYMn0.1515186141043.9 |
| RYBxO8mRbwMFOFCf7oNlW1BYMn0.1515185884753.3 |
| Klf4 |
| RYBxO8mRbwMFOFCf7oNlW1BYMn0.1520442556934.5 |
| RYBxO8mRbwMFOFCf7oNlW1BYMn0.1520442825118.21 |

FIG. 4Y
Continued

```
GCCACCGGCCAACACACGACTTCCCCCTGGGGCGGCAGCTCCCCACCAGGACTACCCCTACACTGAGTCCCGAGGAACTGCT
CGGTGGCCGGGTTGTGTGTGCTGAAGGGGGACCCCGCCGTCGAGGGGTGGTCCTGATGGGGATGTGACTCAGGGCTCCTTGACGA
     1025      1030      1035      1040      1045      1050
 Gly His Arg Pro Asn Thr His Asp Phe Pro Leu Gly Arg Gln Leu Pro Thr Arg Thr Thr Pro Thr Leu Ser Pro Glu Glu Leu Leu
```
5440

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

```
GAACAGCAGGGACTGTCACCCTGGCCTGCCTCTTCCCCCAGGATTCCATCCCCATCCGGGGCCCAACTACCCTCCTTTCCTGCCA
CTTGTCGTCCCTGACAGTGGGACCGGACGGAGAAGGGGGTCCTAAGGTAGGGGTAGGCCCCGGGTTGATGGGAGGAAAGGACGGT
     1055      1060      1065      1070      1075
 Asn Ser Arg Asp Cys His Pro Gly Leu Pro Leu Pro Pro Gly Phe His Pro His Pro Gly Pro Asn Tyr Pro Pro Phe Leu Pro
```
5525

| ORF frame 3 | > |
| RYBxO8mRbwMFOFCf7oNIW1BYMn0.1513097172637.1 | > |
| RYBxO8mRbwMFOFCf7oNIW1BYMn0.1515186099932.6 | > |
| Extracted region from pAAV-TRE3G-OSK-WPRE3-SV40pA | > |
| RYBxO8mRbwMFOFCf7oNIW1BYMn0.1499881537908.1 | > |
| Digestion of pAAV-TRE3G-OSK-WPRE3-SV40pA - Frag... | > |
| RYBxO8mRbwMFOFCf7oNIW1BYMn0.1515186141043.9 | > |
| RYBxO8mRbwMFOFCf7oNIW1BYMn0.1515185884753.3 | > |
| Klf4 | > |
| RYBxO8mRbwMFOFCf7oNIW1BYMn0.1520442556934.5 | > |
| RYBxO8mRbwMFOFCf7oNIW1BYMn0.1520442825118.21 | > |

FIG. 4Z

GACCAGATGCAGTCACAAGTCCCCTCTCTCCATTATCAAGAGCTCATGCCACCGGGTTCCTGCCTGCCAGAGGAGCCCAAGCCAA
CTGGTCTACGTCAGTGTTCAGGGGAGAGAGGTAATAGTTCTCGAGTACGGTGGCCCAAGGACGGACGGTCTCCTCGGGTTCGGTT

5610

1080 1085 1090 1095 1100 1105

Asp Gln Met Gln Ser Gln Val Pro Ser Leu His Tyr Gln Glu Leu Met Pro Pro Gly Ser Cys Leu Pro Glu Glu Pro Lys Pro

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Klf4 |
| RYBxO8mRbwMFOFCf7oNIW1BYMn0.1520442556934.5 |
| RYBxO8mRbwMFOFCf7oNIW1BYMn0.1520442825118.21 |

AleI

AGAGGGAAGAAGGTCGTGGCCCCGGAAAAGAACAGCCACCCACACTTGTGACTATGCAGGCTGTGGCAAAACCTATACCAAGAG
TCTCCCCTTCTTCCAGCACCGGGGCCTTTTCTTGTCGGTGGGTGTGAACACTGATACGTCCGACACCGTTTTGGATATGGTTCTC

5695

1110 1115 1120 1125 1130 1135

Lys Arg Gly Arg Arg Ser Trp Pro Arg Lys Arg Thr Ala Thr His Thr Cys Asp Tyr Ala Gly Cys Gly Lys Thr Tyr Thr Lys Ser

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Klf4 |
| RYBxO8mRbwMFOFCf7oNIW1BYMn0.1520442556934.5 |
| RYBxO8mRbwMFOFCf7oNIW1BYMn0.1520442825118.21 |

FIG. 4AA

TTCTCATCTCAAGGCACACCTGCCAACTCACACAGGCGAGAAACCTTACCACTGTGACTGGGACGGCTGTGGGTGGAAATTCGCC
AAGAGTAGAGTTCCGTGTGGACGCTTGAGTGTGTCCGCTCTTTGGAATGGTGACACTGACCCTGCCGACACCCACCTTTAAGCGG
5780

1140 1145 1150 1155 1160

Ser His Leu Lys Ala His Leu Arg Thr His Thr Gly Glu Lys Pro Tyr His Cys Asp Trp Asp Gly Cys Gly Trp Lys Phe Ala

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Klf4 |
| RYBxO8mRbwMFOFCf7oNIW1BYMn0.1520442556934.5 |
| RYBxO8mRbwMFOFCf7oNIW1BYMn0.1520442825118.21 |

CGCTCCGATGAACTGACCAGGCACTACCGCAAACACACAGGGCACCGGCCCTTTCAGTGCCAGAAGTGCGACAGGGCCTTTTCCA
GCGAGGCTACTTGACTGGTCCGTGATGGCGTTTGTGTGTCCCGTGGCCGGGAAAGTCACGGTCTTCACGCTGTCCCGGAAAAGGT
5865

1165 1170 1175 1180 1185 1190

Arg Ser Asp Glu Leu Thr Arg His Tyr Arg Lys His Thr Gly His Arg Pro Phe Gln Cys Gln Lys Cys Asp Arg Ala Phe Ser

| ORF frame 3 |
| RYBxO8mRbwMFOFCf7oNIW1BYMn0.1513097172637.1 |
| RYBxO8mRbwMFOFCf7oNIW1BYMn0.1515186099932.6 |
| Extracted region from pAAV-TRE3G-OSK-WPRE3-SV40pA |
| RYBxO8mRbwMFOFCf7oNIW1BYMn0.1499881537908.1 |
| Digestion of pAAV-TRE3G-OSK-WPRE3-SV40pA - Frag... |
| RYBxO8mRbwMFOFCf7oNIW1BYMn0.1515186141043.9 |
| RYBxO8mRbwMFOFCf7oNIW1BYMn0.1515185884753.3 |
| Klf4 |
| RYBxO8mRbwMFOFCf7oNIW1BYMn0.1520442556934.5 |
| RYBxO8mRbwMFOFCf7oNIW1BYMn0.1520442825118.21 |

FIG. 4AB

```
AGCTTATAATGGTTACAAATAAAGCAATAGCATCACAAATTTCACAAATAAAGCATTTTTTTCACTGCATTCTAGTTGTGGTTTG
++++++++++++++++++++++++++++++++++++++++++++++++++++++++++++++++++++++++++++++++++++++
TCGAATATTACCAATGTTTATTTCGTTATCGTAGTGTTTAAAGTGTTTATTTCGTAAAAAAAGTGACGTAAGATCAACACCAAAC
```
6035

RYBxO8mRbwMFOFCf7oNIW1BYMn0.1515186099985.7

RYBxO8mRbwMFOFCf7oNIW1BYMn0.1520442556934.5

RYBxO8mRbwMFOFCf7oNIW1BYMn0.1520442825118.21

CGCGCAGCGGCCGACCATGGCCCAACTTGTTTATTGCAGCTTATAAT...

Digestion of SV40pA from pAAV lacZ - Fragment 2...

Extracted region from SV40pA from pAAV lacZ

FIG. 4AC
Continued

CGTAGATAAGTAGCATGCGGGTTAATCATTAACTACAAGGAACCCCTAGTGATGGAGTTGGCCACTCCCTCTCTGCGCGCTCGC
GCATCTATTCATCGTACCGCCCAATTAGTAATTGATGTTCCTTGGGGATCACTACCTCAACCGGTGAGGGAGAGACGCGCGAGCG

6205

RYBxO8mRbwMFOFCf7oNIW1BYMn0.1515186099985.7

Digestion of pAAV-TRE3G-OSK-WPRE3-SV40pA - Frag...

RYBxO8mRbwMFOFCf7oNIW1BYMn0.1515185884933.5

RYBxO8mRbwMFOFCf7oNIW1BYMn0.1515186099985.7

RYBxO8mRbwMFOFCf7oNIW1BYMn0.1515186141081.10

RYBxO8mRbwMFOFCf7oNIW1BYMn0.1515186313796.12

RYBxO8mRbwMFOFCf7oNIW1BYMn0.1492697902333.2

RYBxO8mRbwMFOFCf7oNIW1BYMn0.1513097172637.1

Extracted region from pAAV-Ubc-EGFP-WPRE3-SV40L...

RYBxO8mRbwMFOFCf7oNIW1BYMn0.1520442556934.5

RYBxO8mRbwMFOFCf7oNIW1BYMn0.1520442825118.21

ITR 3'

TTAATTAACCTAATTCACTGGCCGTCGTTTTACAACGTCGTGACTGGGAAAACCCTGGCGTTACCCAACTTAATCGCCTTGCAGC 6375
AATTAATTGGATTAAGTGACCGGCAGCAAAATGTTGCAGCACTGACCCTTTTGGGACCGCAATGGGTTGAATTAGCGGAACGTCG

RYBxO8mRbwMFOFCf7oNIW1BYMn0.1515186099985.7

Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...

ITR 3'

ACATCCCCCTTTCGCCAGCTGGCGTAATAGCGAAGAGGCCCGCACCGATCGCCCTTCCCAACAGTTGCGCAGCCTGAATGGCGAA 6460
TGTAGGGGGAAAGCGGTCGACCGCATTATCGCTTCTCCGGGCGTGGCTAGCGGGAAGGGTTGTCAACGCGTCGGACTTACCGCTT

RYBxO8mRbwMFOFCf7oNIW1BYMn0.1515186099985.7

Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...

FIG. 4AF

TGGGACGCGCCCTGTAGCGGCGCATTAAGCGCGGCGGGTGTGGTGGTTACGGCGCAGCGTGACCGCTACACTTGCCAGCGCCCTAG
ACCCTGCGCGGGACATCGCCGCGTAATTCGCGCCGCCCACACCACCAATGCCGCGTCGCACTGGCGATGTGAACGGTCGCGGGATC
6545

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin CGCCCGCTCCTTTCGCTTTCTTCCCTTCCTTTCTCGCCACGTTCGCCGGCTTTCCCCGTCAAGCTCTAAATCGGGGGCTCCCTTT
GCGGGCGAGGAAAGCGAAAGAAGGGAAGGAAAGAGCGGTGCAAGCGGCCGAAAGGGGCAGTTCGAGATTAGCCCCGAGGGAAA
6630

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin

FIG. 4AG

AGGGTTCCGATTTAGTGCTTTACGGCACCTCGACCCCAAAAAACTTGATTAGGGTGATGGTTCACGTAGTGGGCCATCGCCCTGA 6715
TCCCAAGGCTAAATCACGAAATGCCGTGGAGCTGGGGTTTTTTGAACTAATCCCACTACCAAGTGCATCACCCGGTAGCGGGACT a

RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin TAGACGGTTTTTCGCCCTTTGACGTTGGAGTCCACGTTCTTTAATAGTGGACTCTTGTTCCAAACTGGAACAACACTCAACCCTA 6800
ATCTGCCAAAAAGCGGGAAACTGCAACCTCAGGTGCAAGAAATTATCACCTGAGAACAAGGTTTGACCTTGTTGTGAGTTGGGAT RYBxO8mRbwMFOFCf7oNIW1BYMn0.1515186099985.7
Digestion of pAAV-TRE3G-OSK-WPRE3-SV40pA - Frag...
RYBxO8mRbwMFOFCf7oNIW1BYMn0.1515185884933.5
RYBxO8mRbwMFOFCf7oNIW1BYMn0.1515186099985.7
RYBxO8mRbwMFOFCf7oNIW1BYMn0.1515186141081.10
RYBxO8mRbwMFOFCf7oNIW1BYMn0.1515186313796.12
RYBxO8mRbwMFOFCf7oNIW1BYMn0.1492697902333.2
RYBxO8mRbwMFOFCf7oNIW1BYMn0.1513097172637.1
RYBxO8mRbwMFOFCf7oNIW1BYMn0.1520442557010.7
RYBxO8mRbwMFOFCf7oNIW1BYMn0.1520442825190.23
Extracted region from pAAV-Ubc-EGFP-WPRE3-SV40L...
f1_origin

FIG. 4AH

TCTCGGTCTATTCTTTTGATTTATAAGGGATTTTGCCGATTTCGGCCTATTGGTTAAAAAATGAGCTGATTTAACAAAAATTTAA 6885
AGAGCCAGATAAGAAAACTAAATATTCCCTAAAACGGCTAAAGCCGGATAACCAATTTTTTACTCGACTAAATTGTTTTTAAATT

RYBxO8mRbwMFOFCf7oNlW1BYMn0.1515186099985.7
Digestion of pAAV-TRE3G-OSK-WPRE3-SV40pA - Frag...
RYBxO8mRbwMFOFCf7oNlW1BYMn0.1515185884933.5
RYBxO8mRbwMFOFCf7oNlW1BYMn0.1515186099985.7
RYBxO8mRbwMFOFCf7oNlW1BYMn0.1515186141081.10
RYBxO8mRbwMFOFCf7oNlW1BYMn0.1515186313796.12
RYBxO8mRbwMFOFCf7oNlW1BYMn0.1492697902333.2
RYBxO8mRbwMFOFCf7oNlW1BYMn0.1513097172637.1
RYBxO8mRbwMFOFCf7oNlW1BYMn0.1520442557010.7
RYBxO8mRbwMFOFCf7oNlW1BYMn0.1520442825190.23
Extracted region from pAAV-Ubc-EGFP-WPRE3-SV40L...

CCCGAATTTTAACAAAATATTAACGTTTATAATTTCAGGTGGCATCTTTCGGGGAAATGTGCGCGGAACCCCTATTTGTTTATTT 6970
GGGCTTAAAATTGTTTTATAATTGCAAATATTAAAGTCCACCGTAGAAAGCCCCTTTACACGCGCCTTGGGGATAAACAAATAAA

RYBxO8mRbwMFOFCf7oNlW1BYMn0.1515186099985.7
Digestion of pAAV-TRE3G-OSK-WPRE3-SV40pA - Frag...
RYBxO8mRbwMFOFCf7oNlW1BYMn0.1515185884933.5
RYBxO8mRbwMFOFCf7oNlW1BYMn0.1515186099985.7
RYBxO8mRbwMFOFCf7oNlW1BYMn0.1515186141081.10
RYBxO8mRbwMFOFCf7oNlW1BYMn0.1515186313796.12
RYBxO8mRbwMFOFCf7oNlW1BYMn0.1492697902333.2
RYBxO8mRbwMFOFCf7oNlW1BYMn0.1513097172637.1
RYBxO8mRbwMFOFCf7oNlW1BYMn0.1520442557010.7
RYBxO8mRbwMFOFCf7oNlW1BYMn0.1520442825190.23
Extracted region from pAAV-Ubc-EGFP-WPRE3-SV40L...

AGTAAAAGATGCTGAAGATCAGTTGGGTGCACGAGTGGGTTACATCGAACTGGATCTCAATAGTGGTAAGATCCTTGAGAGTTTT
TCATTTTCTACGACTTCTAGTCAACCCACGTGCTCACCCAATGTAGCTTGACCTAGAGTTATCACCATTCTAGGAACTCTCAAAA
7225

RYBxO8mRbwMFOFCf7oNIW1BYMn0.1515186099985.7

| Digestion of pAAV-TRE3G-OSK-WPRE3-SV40pA - Frag... |
| RYBxO8mRbwMFOFCf7oNIW1BYMn0.1515185884933.5 |
| RYBxO8mRbwMFOFCf7oNIW1BYMn0.1515186099985.7 |
| RYBxO8mRbwMFOFCf7oNIW1BYMn0.1515186141081.10 |
| RYBxO8mRbwMFOFCf7oNIW1BYMn0.1515186313796.12 |
| RYBxO8mRbwMFOFCf7oNIW1BYMn0.1492697902333.2 |
| RYBxO8mRbwMFOFCf7oNIW1BYMn0.1513097172637.1 |
| RYBxO8mRbwMFOFCf7oNIW1BYMn0.1520442557010.7 |
| RYBxO8mRbwMFOFCf7oNIW1BYMn0.1520442825190.23 |
| Extracted region from pAAV-Ubc-EGFP-WPRE3-SV40L... |
| AmpR |

CGCCCCGAAGAACGTTTTCCAATGATGAGCACTTTTAAAGTTCTGCTATGTGGCGCGGTATTATCCCGTATTGACGCCGGGCAAG
GCGGGGCTTCTTGCAAAAGGTTACTACTCGTGAAAATTTCAAGACGATACACCGCGCCATAATAGGGCATAACTGCGGCCCGTTC
7310

RYBxO8mRbwMFOFCf7oNIW1BYMn0.1515186099985.7

| Digestion of pAAV-TRE3G-OSK-WPRE3-SV40pA - Frag... |
| RYBxO8mRbwMFOFCf7oNIW1BYMn0.1515185884933.5 |
| RYBxO8mRbwMFOFCf7oNIW1BYMn0.1515186099985.7 |
| RYBxO8mRbwMFOFCf7oNIW1BYMn0.1515186141081.10 |
| RYBxO8mRbwMFOFCf7oNIW1BYMn0.1515186313796.12 |
| RYBxO8mRbwMFOFCf7oNIW1BYMn0.1492697902333.2 |
| RYBxO8mRbwMFOFCf7oNIW1BYMn0.1513097172637.1 |
| RYBxO8mRbwMFOFCf7oNIW1BYMn0.1520442557010.7 |
| RYBxO8mRbwMFOFCf7oNIW1BYMn0.1520442825190.23 |
| Extracted region from pAAV-Ubc-EGFP-WPRE3-SV40L... |
| AmpR |

| Feature | Location | Size | | | Type |
|---|---|---|---|---|---|
| ✓ Extracted region from pAAV-TRE3... | 1 .. 1893 | 1893 bp | | → | misc_feature |
| ✓ pBR322_origin | 659 .. 1278 | 620 bp | | → | rep_origin |
| /direction | = RIGHT | | | | |
| ✓ CGG | 1308 .. 1310 | 3 bp | | ⊢⊣ | misc_feature |
| ✓ ITR | 1692 .. 1832 | 141 bp | | → | repeat_region |
| ✓ RYBxO8mRbwMFOFCf7oNIW1BY... | 1734 .. 1744 | 11 bp | | → | misc_feature |
| ✓ RYBxO8mRbwMFOFCf7oNIW1BY... | 1734 .. 1744 | 11 bp | | → | misc_feature |
| ✓ RYBxO8mRbwMFOFCf7oNIW1BY... | 1745 .. 3410 | 1666 bp | | → | misc_feature |
| ✓ RYBxO8mRbwMFOFCf7oNIW1BY... | 1745 .. 3410 | 1666 bp | | → | misc_feature |
| ✓ EcoRI site | 1893 .. 1897 | 5 bp | | → | misc_feature |
| ✓ RYBxO8mRbwMFOFCf7oNIW1BY... | 1893 .. 1897 | 5 bp | | → | misc_feature |
| ✓ RYBxO8mRbwMFOFCf7oNIW1BY... | 1893 .. 1897 | 5 bp | | → | misc_feature |
| ✓ RYBxO8mRbwMFOFCf7oNIW1BY... | 1893 .. 1893 | 1 bp | | → | misc_feature |
| ✓ Digestion of pAAV-TRE3G-OSK-W... | 1894 .. 5911 | 4018 bp | | → | misc_feature |
| ✓ RYBxO8mRbwMFOFCf7oNIW1BY... | 1894 .. 5907 | 4014 bp | | → | misc_feature |
| ✓ RYBxO8mRbwMFOFCf7oNIW1BY... | 1894 .. 2375 | 482 bp | | → | misc_feature |
| ✓ RYBxO8mRbwMFOFCf7oNIW1BY... | 1894 .. 2282 | 389 bp | | → | misc_feature |
| ✓ GTACACGCCTACCTCGACCCATCAA... | 1894 .. 2279 | 386 bp | | ⊢⊣ | misc_feature |
| ✓ RYBxO8mRbwMFOFCf7oNIW1BY... | 1894 .. 2276 | 383 bp | | → | misc_feature |
| ✓ EcoRI site | 1894 .. 1898 | 5 bp | | → | misc_feature |
| ✓ Extracted region from pAAV-TRE-E... | 1894 .. 1898 | 5 bp | | → | misc_feature |
| ✓ RYBxO8mRbwMFOFCf7oNIW1BY... | 1894 .. 1898 | 5 bp | | → | misc_feature |
| ✓ RYBxO8mRbwMFOFCf7oNIW1BY... | 1894 .. 1898 | 5 bp | | → | misc_feature |
| ✓ Ligation | 1894 .. 1897 | 4 bp | | ⊢⊣ | misc_feature |
| ✓ Extracted region from pTRE3G | 1899 .. 2274 | 376 bp | | → | misc_feature |
| ✓ TRE3G\Promoter | 1899 .. 2274 | 376 bp | | → | misc_feature |

FIG. 5A

| | | | | | | |
|---|---|---|---|---|---|---|
| ✓ tetO | 1904 .. 1922 | 19 bp | | → | regulatory |
| ✓ tetO | 1940 .. 1958 | 19 bp | | → | regulatory |
| ✓ tetO | 1976 .. 1994 | 19 bp | | → | regulatory |
| ✓ tetO | 2012 .. 2030 | 19 bp | | → | regulatory |
| ✓ tetO | 2048 .. 2066 | 19 bp | | → | regulatory |
| ✓ qPCR-fwd-TRE3G | 2066 .. 2091 | 26 bp | | → | primer_bind |
| ✓ tetO | 2084 .. 2102 | 19 bp | | → | regulatory |
| ✓ tetO | 2120 .. 2138 | 19 bp | | → | regulatory |
| ✓ Modified Minimal CMV Promoter | 2147 .. 2214 | 68 bp | | → | promoter |
| ✓ qPCR-rev-TRE3G | 2246 .. 2266 | 21 bp | | → | primer_bind |
| ✓ NotI site | 2275 .. 2282 | 8 bp | | → | misc_feature |
| ✓ Extracted region from pAAV-TRE-E... | 2275 .. 2276 | 2 bp | | → | misc_feature |
| ✓ RYBxO8mRbwMFOFCf7oNIW1BY... | 2275 .. 2276 | 2 bp | | → | misc_feature |
| ✓ RYBxO8mRbwMFOFCf7oNIW1BY... | 2275 .. 2276 | 2 bp | | → | misc_feature |
| ✓ RYBxO8mRbwMFOFCf7oNIW1BY... | 2277 .. 5907 | 3631 bp | | → | misc_feature |
| ✓ RYBxO8mRbwMFOFCf7oNIW1BY... | 2277 .. 2375 | 99 bp | | → | misc_feature |
| ✓ Extracted region from pAAV-CAG-... | 2277 .. 2282 | 6 bp | | → | misc_feature |
| ✓ RYBxO8mRbwMFOFCf7oNIW1BY... | 2277 .. 2280 | 4 bp | | → | misc_feature |
| ✓ RYBxO8mRbwMFOFCf7oNIW1BY... | 2277 .. 2280 | 4 bp | | → | misc_feature |
| ✓ Extracted region from pAAV-TRE3... | 2283 .. 5907 | 3625 bp | | → | misc_feature |
| ✓ RYBxO8mRbwMFOFCf7oNIW1BY... | 2283 .. 5907 | 3625 bp | | → | misc_feature |

FIG. 5B

| Feature | Location | Size | | | Type |
|---|---|---|---|---|---|
| ✓ ORF frame 3 | 2292 .. 5901 | 3610 bp | | → | CDS |
| ✓ Oct4 | 2292 .. 3344 | 1053 bp | | → | exon |
| ✓ Oct reverse | 2349 .. 2382 | 34 bp | | ← | misc_feature |
| ✓ RYBx08mRbwMFOFCf7oNIW1BY... | 2376 .. 5911 | 3536 bp | | → | misc_feature |
| ✓ RYBx08mRbwMFOFCf7oNIW1BY... | 2376 .. 5907 | 3532 bp | | → | misc_feature |
| ✓ p2a | 2414 .. 2422 | 9 bp | | ← | modified_base |
| ✓ Oct4-fwd | 3268 .. 3289 | 22 bp | | → | primer_bind |
| ✓ P2A | 3360 .. 3417 | 58 bp | | → | intron |
| ✓ RYBx08mRbwMFOFCf7oNIW1BY... | 3411 .. 3585 | 175 bp | | → | misc_feature |
| ✓ RYBx08mRbwMFOFCf7oNIW1BY... | 3411 .. 3585 | 175 bp | | → | misc_feature |
| ✓ Sox2 | 3423 .. 4379 | 957 bp | | → | exon |
| ✓ Sox2-reverse | 3512 .. 3535 | 24 bp | | ← | misc_feature |
| ✓ RYBx08mRbwMFOFCf7oNIW1BY... | 3586 .. 3979 | 394 bp | | → | misc_feature |
| ✓ RYBx08mRbwMFOFCf7oNIW1BY... | 3586 .. 3979 | 394 bp | | → | misc_feature |
| ✓ RYBx08mRbwMFOFCf7oNIW1BY... | 3980 .. 4924 | 945 bp | | → | misc_feature |
| ✓ RYBx08mRbwMFOFCf7oNIW1BY... | 3980 .. 4924 | 945 bp | | → | misc_feature |
| ✓ sox2-fwd | 4306 .. 4329 | 24 bp | | → | primer_bind |
| ✓ Klf4 | 4455 .. 5901 | 1447 bp | | → | exon |
| ✓ Klf4-rev | 4517 .. 4540 | 24 bp | | ← | misc_feature |
| ✓ Klf4-mid-fwd | 4914 .. 4937 | 24 bp | | → | primer_bind |
| ✓ RYBx08mRbwMFOFCf7oNIW1BY... | 4925 .. 6246 | 1322 bp | | → | misc_feature |
| ✓ RYBx08mRbwMFOFCf7oNIW1BY... | 4925 .. 6246 | 1322 bp | | → | misc_feature |
| ✓ Stop codon | 5901 .. 5903 | 3 bp | | → | terminator |
| ✓ TTCTCGAGGGCTCGGGCCAGTGTAC... | 5902 .. 5908 | 7 bp | | ↔ | misc_feature |
| ✓ RYBx08mRbwMFOFCf7oNIW1BY... | 5908 .. 2276 | 3777 bp | | → | misc_feature |
| ▸ 2 segments | | | | | |
| ✓ CGCGCAGCGGCCGACCATGGCCCA... | 5908 .. 6084 | 177 bp | | ↔ | misc_feature |

FIG. 5C

| Feature | Location | Size | | | Type |
|---|---|---|---|---|---|
| Digestion of SV40pA from pAAV la... | 5908 .. 6084 | 177 bp | | → | misc_feature |
| Extracted region from SV40pA fro... | 5908 .. 6080 | 173 bp | | → | misc_feature |
| Ligation | 5908 .. 5911 | 4 bp | | ⊢⊣ | misc_feature |
| Digestion of pAAV-TRE3G-OSK-W... | 6081 .. 9305 | 3225 bp | | → | misc_feature |
| RYBxO8mRbwMFOFCf7oNIW1BY... | 6081 .. 9305 | 3225 bp | | → | misc_feature |
| RYBxO8mRbwMFOFCf7oNIW1BY... | 6081 .. 9305 | 3225 bp | | → | misc_feature |
| RYBxO8mRbwMFOFCf7oNIW1BY... | 6081 .. 9305 | 3225 bp | | → | misc_feature |
| RYBxO8mRbwMFOFCf7oNIW1BY... | 6081 .. 9301 | 3221 bp | | → | misc_feature |
| RYBxO8mRbwMFOFCf7oNIW1BY... | 6081 .. 9300 | 3220 bp | | → | misc_feature |
| Extracted region from pAAV-Ubc-E... | 6081 .. 7408 | 1328 bp | | → | misc_feature |
| RYBxO8mRbwMFOFCf7oNIW1BY... | 6081 .. 6098 | 18 bp | | → | misc_feature |
| Ligation | 6081 .. 6084 | 4 bp | | ⊢⊣ | misc_feature |
| RYBxO8mRbwMFOFCf7oNIW1BY... | 6099 .. 9305 | 3207 bp | | → | misc_feature |
| ITR 3' | 6159 .. 6298 | 140 bp | | → | misc_feature |
| RYBxO8mRbwMFOFCf7oNIW1BY... | 6247 .. 6257 | 11 bp | | → | misc_feature |
| RYBxO8mRbwMFOFCf7oNIW1BY... | 6247 .. 6257 | 11 bp | | → | misc_feature |
| RYBxO8mRbwMFOFCf7oNIW1BY... | 6259 .. 9141 | 2884 bp | | → | misc_feature |
| RYBxO8mRbwMFOFCf7oNIW1BY... | 6259 .. 9141 | 2884 bp | | → | misc_feature |
| f1_origin | 6482 .. 6788 | 307 bp | | → | rep_origin |
| /direction | = RIGHT | | | | |
| AmpR | 7052 .. 7912 | 861 bp | | → | misc_feature |

FIG. 5D

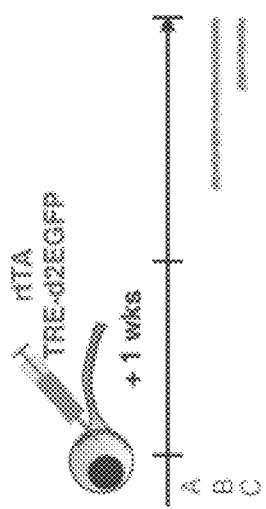
FIG. 11C
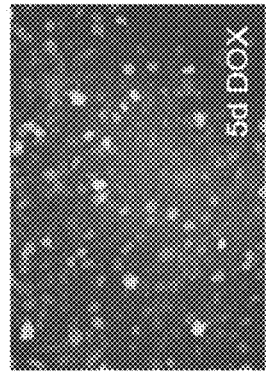
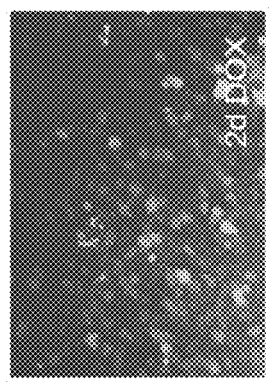
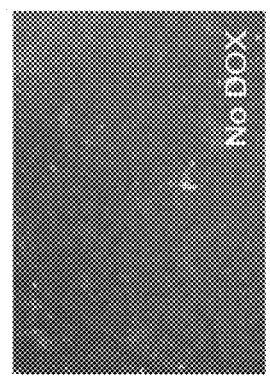
FIG. 11D

rtTA4 TRE-OSK no DOX
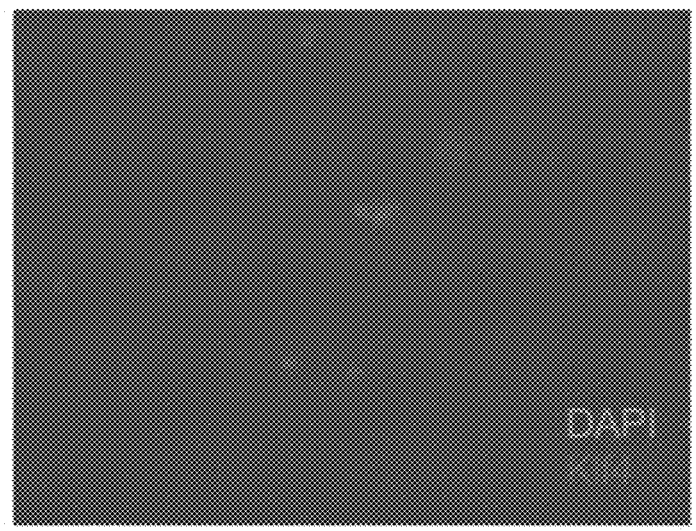
rtTA4 TRE-OSK with DOX
FIG. 13A

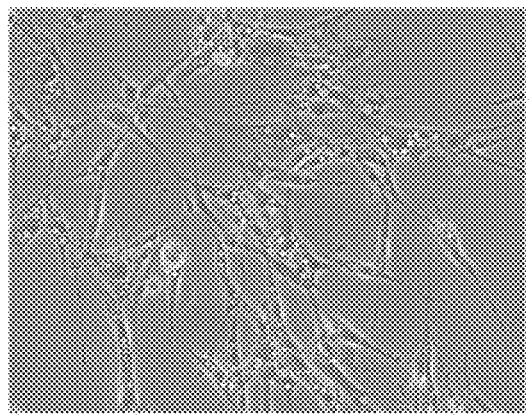 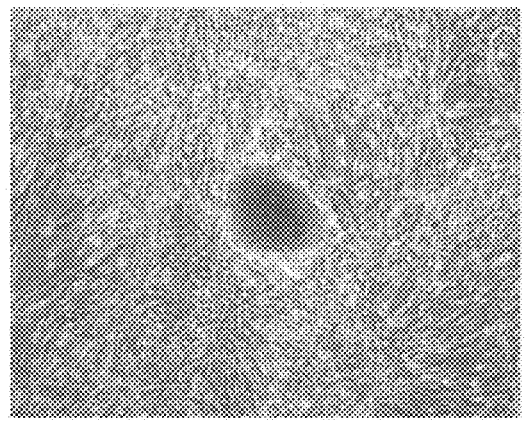
30m FBs after 3d treatment    WT MEFs after 23d treatment
FIG. 21

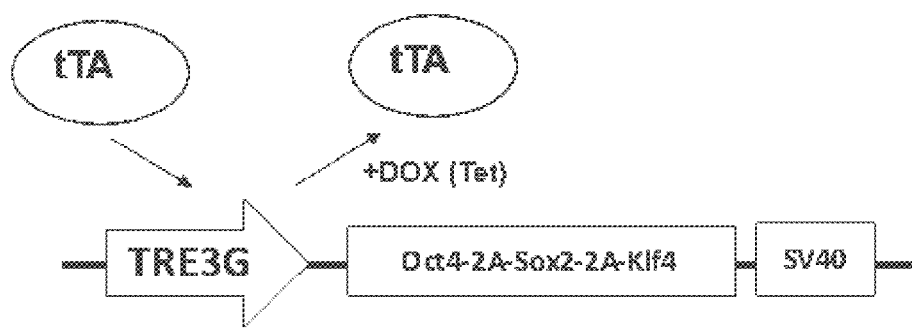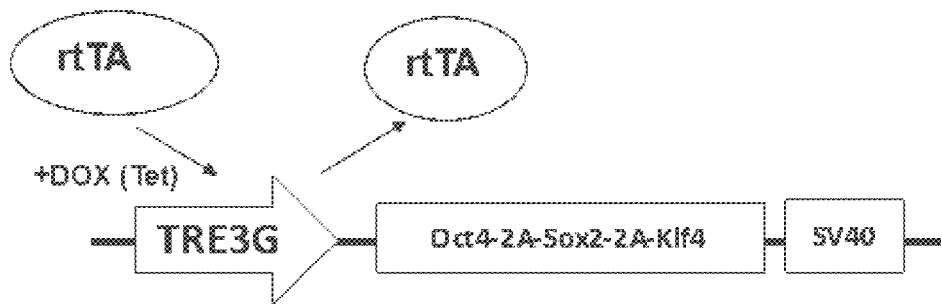
FIG. 22

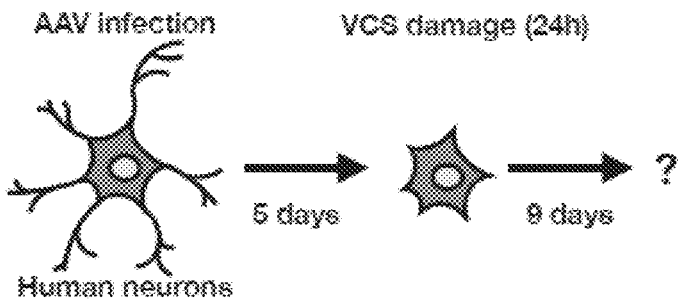
FIG. 33G
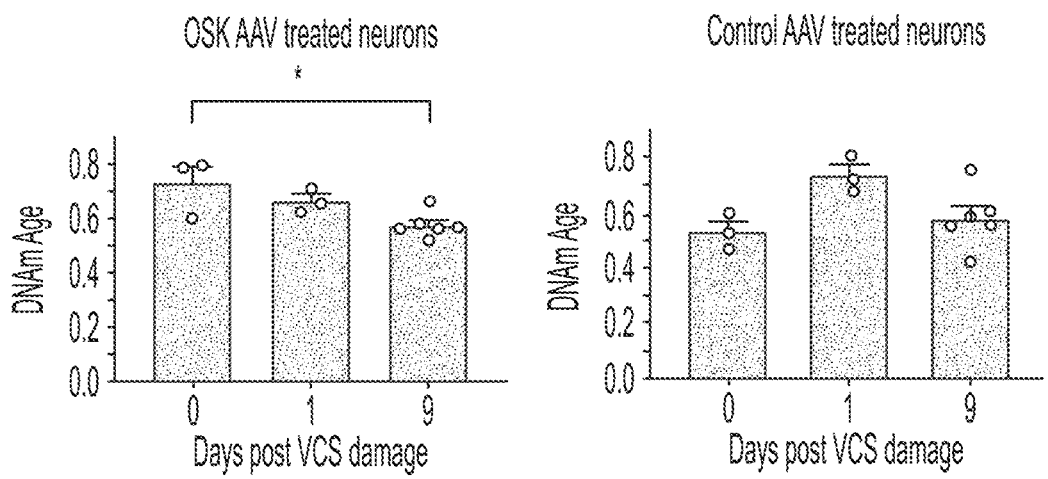
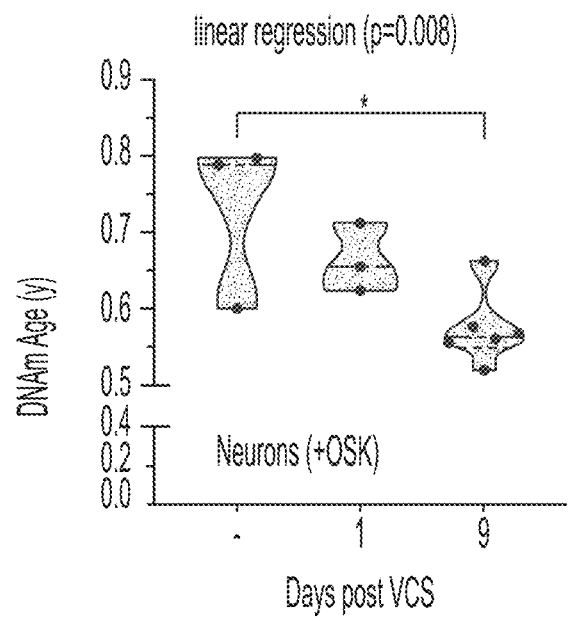
FIG. 33H

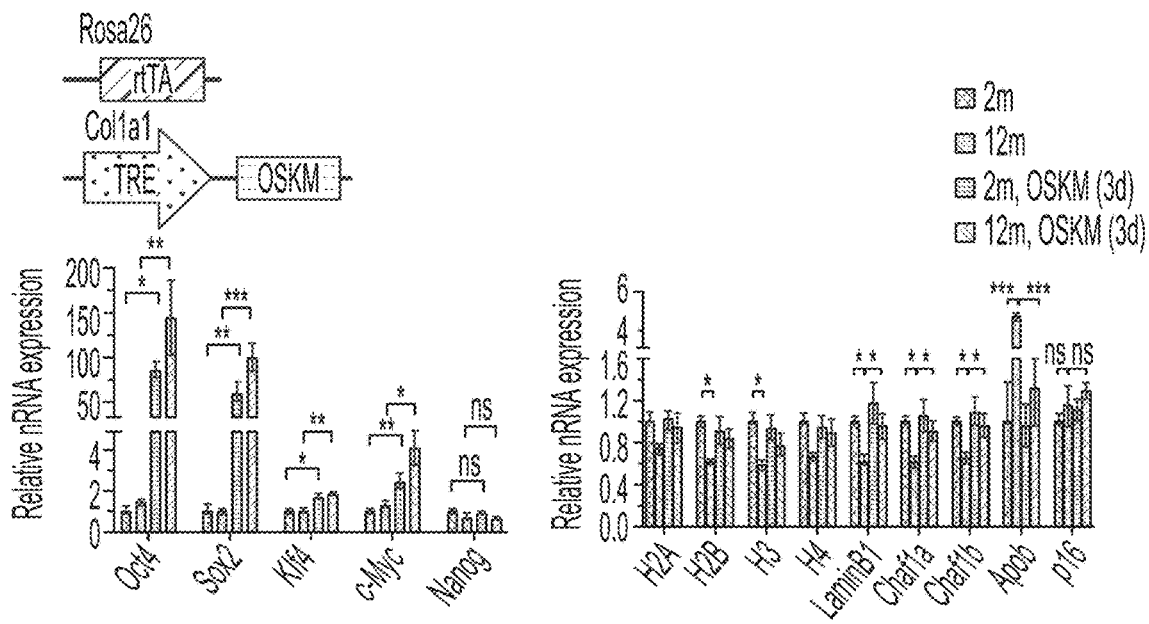
FIG. 36B
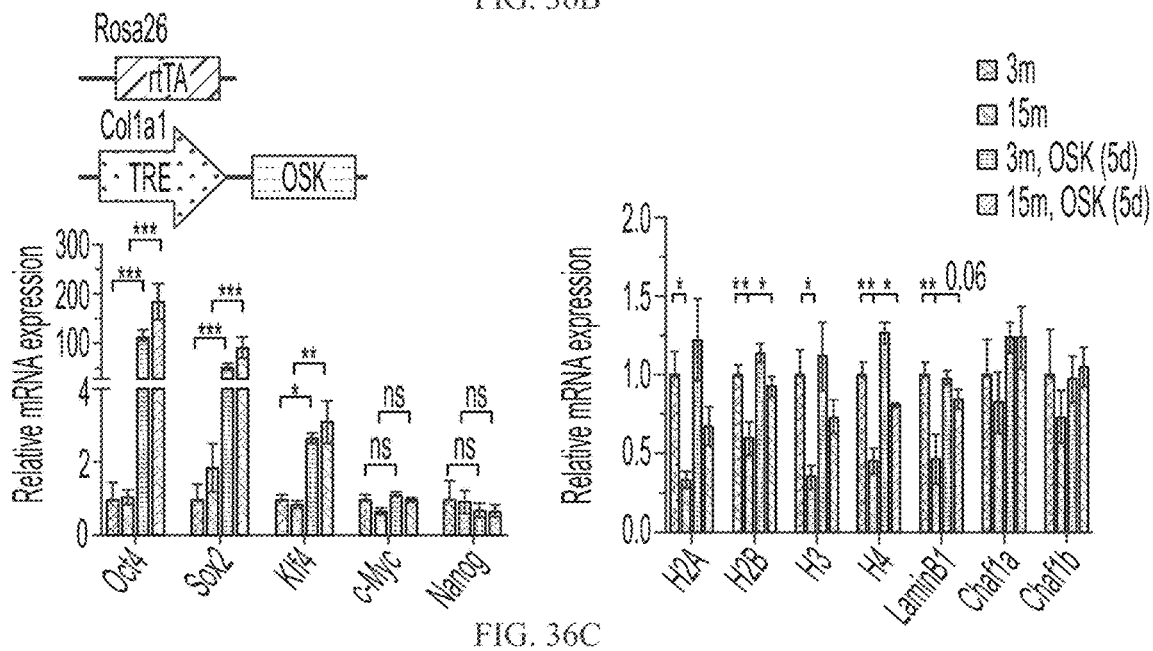
FIG. 36C
FIG. 36D

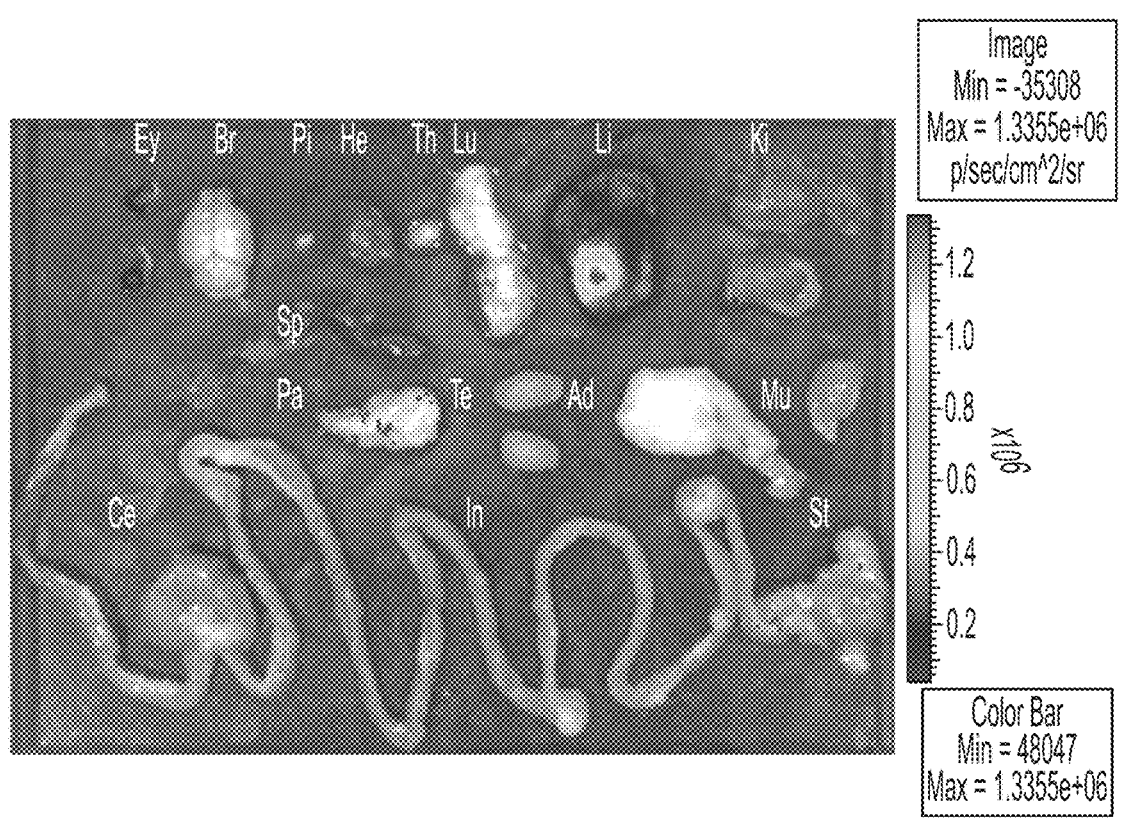
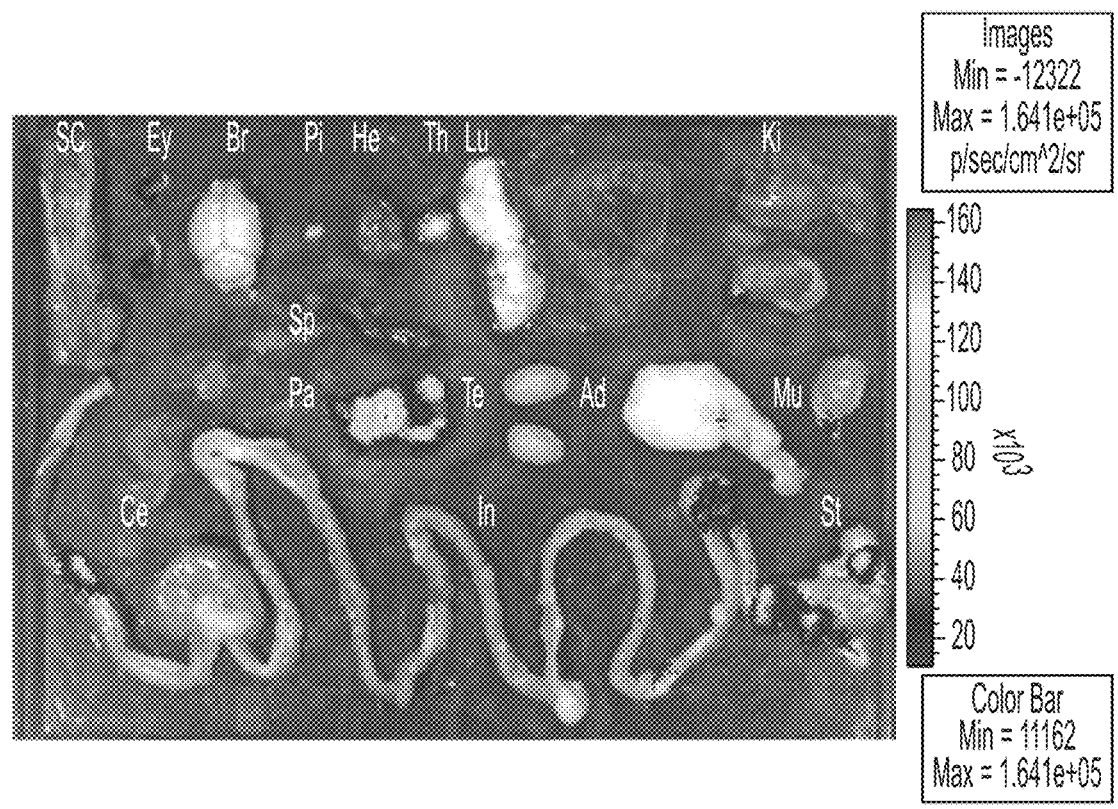
FIG. 36H

CELLULAR REPROGRAMMING TO REVERSE AGING AND PROMOTE ORGAN AND TISSUE REGENERATION

RELATED APPLICATIONS

This application is a continuation of and claims priority under 35 U.S.C. § 120 to U.S. patent application U.S. Ser. No. 18/318,566, filed May 16, 2023, which is a continuation of and claims priority under 35 U.S.C. § 120 to U.S. patent application U.S. Ser. No. 17/280,384, filed Mar. 26, 2021, which is a national stage filing under 35 U.S.C. § 371 of international PCT application number PCT/US2019/053545, filed Sep. 27, 2019, which claims priority under 35 U.S.C. § 119(e) of U.S. provisional application No. 62/738,922, filed Sep. 28, 2018, U.S. provisional application No. 62/792,283, filed Jan. 14, 2019, U.S. provisional application No. 62/865,877, filed Jun. 24, 2019, and U.S. provisional application No. 62/880,488, filed Jul. 30, 2019, each of which is incorporated by reference herein in its entirety.

GOVERNMENT SUPPORT

This invention was made with government support under DK100263 and AG019719 awarded by the National Institutes of Health. The government has certain rights in the invention.

REFERENCE TO AN ELECTRONIC SEQUENCE LISTING

The contents of the electronic sequence listing (H082470296US07-SEQ-FL.xml; Size: 251,743 bytes; and Date of Creation: Feb. 12, 2024) is herein incorporated by reference in its entirety.

BACKGROUND OF THE INVENTION

In many animals, including vertebrates, vital organs have a limited intrinsic capacity for regeneration and repair. Acute injury and chronic disorders can damage vital organs and tissues, including the heart, pancreas, brain, kidney, muscles, skin and neuronal tissue, among others. Mature somatic cells, however, often cannot survive these insults, and even if they do, they are unable to self-renew and transdifferentiate to replace damaged cells. Furthermore, cells that are capable of self-renewal can be limited in quantity, have limited capacity and are susceptible to damage, especially with age. In contrast to somatic cells from adults, cells from individuals that are chronologically closer to fertilization, such as those from embryos and infants, display cellular youthfulness and have a greater capacity to resist injury and stress, to heal, renew, and regenerate organs and tissues. Thus, compositions and methods directed at rejuvenating cells, thereby restoring them from an aged, mature state to a younger, more vital state, have long been sought to treat certain injuries and diseases, as well as generally reverse and prevent aging in entire organisms.

There are two types of information in the body: digital and analog. DNA is digital information and the epigenome is analog information. Analog information never lasts as long as digital, nor can analog information be copied with high fidelity compared to digital information. This has consequences for how long organisms live and thrive. Aging was once thought of as a process driven by mutations in the genetic material of a cell. This has largely been abandoned as an explanation. A major cause of aging is now thought to be due to epigenetic changes that cause cells to transcribe the wrong genes at the wrong time for optimal function, a process that becomes more dysfunctional over time, leading to diseases, an inability to heal and eventually to death. The Yamanaka factors (OCT4, SOX2, c-Myc, and KLF4) have previously been shown to induce pluripotency in vitro (Takahashi et al., Cell. 2006 Aug. 25; 126(4):663-76) and reverse the DNA methlylation clock of aging (Horvath, Genome Biol. 2013). Nanog and Lin28 can help induce pluoripotency together with Yamanaka factors. And Tet1, NR5A-2, Sall4, NKX3-1 can replace Oct4 (Gao et al., Cell Stem Cell 12, 1-17, Apr. 4, 2013 and Mai et al., Nature Cell Biology 20, 900-908, 2018). Expression of original four transcription factors in transgenic mice, however, induce teratomas in vivo, along with other acute toxicities like dysplasia in the intestinal epithelium, that can kill an animal in a few days (Abad et al., Nature. 2013 Oct. 17; 502(7471): 340-5). Therefore, non-toxic and efficient methods of cellular reprogramming are needed.

SUMMARY OF THE INVENTION

The cellular aging process has been postulated to be caused by the loss of both genetic and epigenetic information. While previous studies have hypothesized that aging is caused primarily by the loss of genetic information (most commonly in the form of genetic mutations such as substitutions, and deletions in an organism's genome), the compositions and methods of the present disclosure are informed by the unexpected finding that aging is primarily driven by a loss in the particular epigenetic information that is established closer to fertilization and final differentiation of particular cells. Epigenetic information, which commonly takes the form of covalent modifications to DNA, such as 5-methylcytosine(5mC), hydroxymethylcytosine (5hmeC), 5-formylcytosine (fC), and 5-carboxylcytosine (caC) and adenine methylation, and to certain proteins, such as lysine acetylation, lysine and arginine methylation, serine and threonine phosphorylation, and lysine ubiquitination and sumoylation of histone proteins, is sometimes referred to as the "analog" information of the cell. The loss of this analog information can result in dysregulation of vital cellular processes, such as the processes that maintain cell identity, causing cells to exhibit traits that are typically associated with aging such as senescence.

The methods, compositions, and kits of the present disclosure rejuvenate cells by preventing and reversing the cellular causes of aging. Without being bound by a particular theory, more specifically, the methods, compositions and kits of the present disclosure rejuvenate cells by restoring epigenetic information that has been lost due to the aging process, injury or disease. The methods compositions and kits of the present disclosure comprise the transcription factors OCT4, SOX2 and KLF4. OCT4, SOX2 and KLF4 are three of the four "Yamanaka Factors", with the fourth being c-Myc. The Yamanaka Factors have traditionally been used to reprogram cells to a pluripotent state. However, the induction of expression of the four transcription factors in transgenic mice resulted in the formation of teratomas in vivo, along with other acute toxicities like dysplasia in the intestinal epithelium, which can kill the animal in a few days. Moreover, the fact that the four Yamanaka Factors are typically used to reprogram cells to a completely pluripotent state, wherein the cell loses its pre-established cellular identity, can be dangerous for in vivo applications where the cellular identity of target cells must be maintained for tissue and/or organ integrity. In contrast, in some embodiments, the methods described herein, allow incomplete reprogramming and do not result in global changes in demethylation. In some embodiments, the methods described herein do not require complete de-differentiation of cells. For example, while expression of OCT4, SOX2, and KLF4 promoted regeneration following injury in young and old mice and following vincristine-induced injury in human neurons, expression of OCT4, SOX2, and KLF4 did not induce a global reduction of DNA methylation (see e.g., FIGS. 45B-45C).

In some embodiments, the results disclosed herein suggest that expression of OCT4, SOX2, and KLF4 can allow diseased cells to revert to a healthier state without inducing complete reprogramming. Without being bound by a particular theory, the results disclosed herein suggest that cells maintain a backup epigenome that can be restored using the methods described herein.

The methods, compositions and kits of the present disclosure are in part informed by the surprising and unexpected discovery that the spatially and temporally specific induction of OCT4, SOX2, and KLF4 expression in the absence of the induction of c-Myc expression can rejuvenate a cell without reprogramming the cell to a pluripotent state. Using inducible promoters, the expression of OCT4, SOX2 and KLF4 can be carefully controlled to decrease and reverse epigenetic marks associated with aging, increase the epigenetic marks associated with cellular youthfulness, decrease the expression of aging related proteins, increase the expression of proteins associated with a youthful cellular state, restore the balance between euchromatin and heterochromatin, prevent loss of cellular identity, restore cellular identity, reversing the aging related changes in DNA methylation, thereby rejuvenating the cell without reprogramming the cell to a pluripotent state.

Thus, in various embodiments the methods of the invention rejuvenates a cell by restoring the cellular identity of the cell by reversing the effects of or preventing of one or more dysregulated developmental pathways. For example, the methods:

(i) increase the abundance of at least one of histone H2A, histone H2B, histone H3, histone H4, or any combination thereof in the cell;
(ii) increase the abundance of at least one of CHAF1a, CHAF1b, HP1α, NuRD or any combination thereof in the cell;
(iii) increase at least one heterochromatin mark in the cell such as for example H3K9me3, H3K27me3 or any combination thereof; or decrease one heterochromatin mark such as H4K20me3 or euchromatin mark H3K4me3;
(iv) increase/decrease DNA methylation of at least one age-related CpG site in the cell towards young level;
(v) increase the abundance of lamin B1 in the cell;
(vi) increase acetylation of histone H3 at lysine 27 (H3K27ac), increase acetylation of histone H3 at lysine 56 (H3K56ac) or any combination thereof in the cell;
(vii) decrease acetylation of histone H3 at lysine 122 (H3K122Ac) or histone H4 at lysine 16 (H4K16ac), or any combination thereof in the cell
(viii) decrease the abundance of IL6, Ccl2, Ccl20, Apob, p16, LINE-1 repeats, Sat III repeats, Alu elements, IAP or any combination thereof;
(ix) restores the balance between euchromatin epigenetic marks such as H3K4me3 and heterochromatin epigenetic marks such as for example H3K9me3 or H3K27me3
(x) induces the formation of euchromatin;
(xi) restores youthful levels of at least one repressive heterochromatin epigenetic mark; and/or
(xii) restores the expression of at least one of the genes recited in Table 5 to youthful levels.

The present disclosure stems from the unexpected discovery that, in some embodiments, precise expression of OCT4, SOX2, and KLF4 in the absence of exogenous c-Myc expression can be used to promote reprogramming and tissue regeneration in vivo without acute toxicity. The expression vectors provided herein, in certain embodiments, allow for precise control of OCT4, SOX2, and KLF4 (OSK) expression, incorporation into viruses (e.g., adeno-associated virus (AAV) at a high viral titer (e.g., more than $2\times10^{12}$ particles per preparation, $1\times10^{13}$ particles per mL), reversing aging, treating diseases, including ocular diseases, and/or tissue regeneration (e.g. optic nerve regeneration) in vivo following damage.

As shown in FIG. 14, mice with inducible transgene expression of OCT4, SOX2, and KLF4 (OSK) died two days after induction of OSK expression, due to generalized cytological and architectural dysplasia in the intestinal epithelium. A similar finding has been reported in mice with transgene of OCT4, SOX2, and KLF4 µlus c-Myc (Abad et al., Nature. 2013 Oct. 17; 502(7471):340-5; Ocampo et al., Cell. 2016 Dec. 16; 167:1719-33). Surprisingly, in some embodiments as shown in FIG. 14, expression of OCT4, SOX2, and KLF4 did not cause toxicity or cancer in vivo. Continuous expression (e.g., induction by doxycycline administration) of OCT4, SOX2, and KLF4 through AAV9 delivery (TRE–OSK with UBC–rtTA4) did not result in teratoma formation in vivo. No teratoma or body weight loss was detected for three months when AAV9 viruses encoding these three transcription factors were delivered to the entire body of mice (FIG. 14).

Accordingly, provided herein, in certain embodiments, are nucleic acids (e.g., engineered nucleic acid) capable of inducing expression of OCT4, KLF4, inducing agent, and/or SOX2 and/or recombinant viruses (e.g., lentivirus, adenovirus, alphavirus, vaccinia virus, retrovirus, herpes virus, or AAV) comprising the same. The nucleic acids may encode OCT4, KLF4, and/or SOX2. The nucleic acids may encode a transcription factor selected from the group consisting of OCT4; KLF4; SOX2; and any combinations thereof. In certain embodiments, a nucleic encodes two or more transcription factors selected from the group consisting of OCT4, KLF4, and SOX2. In certain embodiments, a nucleic acid encodes OCT4 and SOX2, OCT4 and KLF4. In certain embodiments, a nucleic acid encodes SOX2 and KLF4. In certain embodiments, a nucleic acid encodes OCT4, KLF4, and SOX2. In certain embodiments, a nucleic acid encodes four or more transcription factors (e.g., OCT4, SOX2, KLF4, and another transcription factor). In some embodiments, the present disclosure provides nucleic acids encoding an inducing agent (e.g., an inducing agent that is capable of inducing expression of OCT4, KLF4, SOX2, or a combination thereof). In some embodiments, the nucleic acids encode a Cas9 fusion protein (CRISPR activator) and a guide RNA sequence targeting a promoter or enhancer at the endogenous locus of OCT4, KLF4, and/or SOX2. In some embodiments, the nucleic acids encode a Cas9 fusion protein (CRISPR activator) and a guide RNA sequence targeting a promoter or enhancer at the endogenous locus of OCT4, SOX2, KLF4, or any combination thereof.

Aspects of the present disclosure also provide methods of regulating cellular reprogramming, promoting tissue repair, promoting tissue survival, promoting tissue regeneration, promoting tissue growth, regulating tissue function, promoting organ regeneration, promoting organ survival, regulating organ function, treating and/or preventing disease, or any combination thereof. Regulating may comprise inducing cellular reprogramming, reversing aging, improving tissue function, improving organ function, tissue repair, tissue survival, tissue regeneration, tissue growth, promoting angiogenesis, reducing scar formation, reducing the appearance of aging, promoting organ regeneration, promoting organ survival, altering the taste and quality of agricultural products derived from animals, treating a disease, or any combination thereof, in vivo or in vitro. The methods may comprise administering any of the nucleic acids described herein (e.g., DNA and/or RNA), any of the engineered proteins encoding KLF4, OCT4, an inducing agent, and/or SOX2, any of the chemical agents activating (e.g., inducing expression of) OCT4, KLF4, an inducing agent, and/or SOX2, antibodies activating (e.g., inducing expression of) OCT4, KLF4, an inducing agent, and/or SOX2, and/or any of the recombinant viruses described herein. The methods may comprise administering any of the nucleic acids described herein (e.g., DNA and/or RNA), any of the engineered proteins encoding KLF4, SOX2, OCT4, or any combination thereof, any of the chemical agents activating (e.g., inducing expression of) OCT4; KLF4; SOX2; or any combination thereof, antibodies activating (e.g., inducing expression of) OCT4; KLF4; SOX2; or any combination thereof and/or any of the recombinant viruses described herein. In certain embodiments, the engineered nucleic acids comprise DNA and/or RNA. The engineered nucleic acid may be an expression vector or not an expression vector. For example, the engineered nucleic acid may be mRNA or plasmid DNA. In certain embodiments, the method further comprises administering a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent. For example, the engineered nucleic acid may be mRNA or plasmid DNA.

One aspect of the present disclosure provide vectors (e.g., expression vectors) comprising a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, alone or in combination and in the absence of an exogenous nucleic acid (e.g., engineered nucleic acid) capable of expressing c-Myc. In certain embodiments, a vector (e.g., expression vector) comprising a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, or any combination thereof. In certain embodiments, the first, second, and third nucleic acids (e.g., engineered nucleic acids) are present on separate expression vectors. In certain embodiments, two of the first, second, and third nucleic acids (e.g., engineered nucleic acids) are present on the same expression vector. In some embodiments, all three nucleic acids (e.g., engineered nucleic acids) are present on the same expression vector. In certain embodiments, the sequence encoding OCT4 is at least 70% (e.g., at least 75%, 80%, 85%, 90%, 95%, 98%, 99%, or 100%) identical to SEQ ID NO: 2 or 41. In certain embodiments, the sequence encoding SOX2 is at least 70% (e.g., at least 75%, 80%, 85%, 90%, 95%, 98%, 99%, or 100%) identical to SEQ ID NO: 4 or 43. In certain embodiments, the sequence encoding KLF4 is at least 70% identical to SEQ ID NO: 6 or 45. In certain embodiments, OCT4, SOX2, KLF4, or any combination thereof is a human protein. In certain embodiments, OCT4, SOX2, KLF4, or any combination thereof is a non-human protein (for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). If two or more of OCT4, SOX2, and KLF4 are on one vector, they may be in any order. The words "first," "second," and "third" are not meant to imply an order of the genes on the vector.

An expression vector of the present disclosure may further comprise an inducible promoter. An expression vector may only have one inducible promoter. In such instances, the expression of OCT4, SOX2, and KLF4 are under the control of the same inducible promoter. In some instances, an expression vector comprises more than one inducible promoter. The inducible promoter may comprise a tetracycline-responsive element (TRE) (e.g., a TRE3G promoter, a TRE2 promoter, or a P tight promoter), mifepristone-responsive promoters (e.g., GAL4-Elb promoter), or a coumermycin-responsive). As an example, a TRE (e.g., TRE3G) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 7. As an example, a TRE (e.g., TRE2) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 23. As an example, a TRE (e.g., P tight) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 24. See, e.g., U.S. Provisional Application, U.S. Ser. No. 62/738,894, entitled MUTANT REVERSE TETRACYCLINE TRANSACTIVATORS FOR EXPRESSION OF GENES, which was filed on Sep. 28, 2018, and the International Patent Application, PCT/US2019/053492, titled MUTANT REVERSE TETRACYCLINE TRANSACTIVATORS FOR EXPRESSION OF GENES, which was filed on the same day as the instant application, each of which is herein incorporated by reference in its entirety.

In certain embodiments, an inducing agent is capable of inducing expression of the first (e.g., OCT4), second (e.g., SOX2), third (e.g., KLF4) nucleic acids (e.g., engineered nucleic acids), or any combination thereof from the inducible promoter in the presence of a tetracycline (e.g., doxycycline). In certain embodiments, the inducing agent is reverse tetracycline-controlled transactivator (rtTA) (e.g., M2-rtTA, rtTA3 or rtTA4). In certain embodiments, the rtTA is rtTA3 comprising an amino acid sequence that is at least 70% (e.g., at least 75%, 80%, 85%, 90%, 95%, 98%, 99%, or 100%) identical to SEQ ID NO: 11. In certain embodiments, the rtTA is rtTA4 and comprises a sequence that is at least 70% (e.g., at least 75%, 80%, 85%, 90%, 95%, 98%, 99%, or 100%) identical to SEQ ID NO: 13. In certain embodiments, the rtTA is M2-rtTA and comprises a sequence that is at least 70% % (e.g., at least 75%, 80%, 85%, 90%, 95%, 98%, 99%, or 100%) identical to SEQ ID NO: 15.

In certain embodiments, an inducing agent is capable of inducing expression of expression of the first nucleic acid (e.g., engineered nucleic acid) (e.g., OCT4), second nucleic acid (e.g., engineered nucleic acid) (e.g., SOX2), third nucleic (e.g., KLF4), or any combination thereof from the inducible promoter in the absence of tetracycline (e.g., doxycycline). In certain embodiments, the inducing agent is tetracycline-controlled transactivator (tTA).

In certain embodiments, an expression vector of the present disclosure comprises a constitutive promoter (e.g., CP1, CMV, EF1 alpha, SV40, PGK1, Ubc, human beta actin, CAG, Ac5, polyhedrin, TEF1, GDS, CaM3 5S, Ubi, H1, and U6 promoter). A constitutive promoter may be operably linked to nucleic acid (e.g., engineered nucleic acid) sequences encoding OCT4, KLF4, SOX2, an inducing agent, or a combination thereof. In some embodiments, an expression vector comprises one constitutive promoter. In some embodiments, an expression vector comprises more than one constitutive promoter.

In certain embodiments, an expression vector of the present disclosure comprises an SV40-derived terminator sequence. In certain embodiments, the SV40-derived sequence is at least 70% (e.g., at least 75%, 80%, 85%, 90%, 95%, 98%, 99%, or 100%) identical to SEQ ID NO: 8.

In certain embodiments, an expression vector of the present disclosure comprises a separator sequence, which may be useful in producing two separate amino acid sequences from one transcript. The separator sequence may encode a self-cleaving peptide (e.g., 2A peptide, including a 2A peptide sequence that is at least 70% (e.g., at least 75%, 80%, 85%, 90%, 95%, 98%, 99%, or 100%) identical to SEQ ID NO: 9). In certain embodiments, the separator sequence is an Internal Ribosome Entry Site (IRES).

In certain embodiments, the expression vector is a viral vector (e.g., a lentiviral, a retroviral, or an adeno-associated virus (AAV) vector) (e.g., FIGS. 2-3). An AAV vector of the present disclosure generally comprises inverted terminal repeats (ITRs) flanking a transgene of interest (e.g., a nucleic acid (e.g., engineered nucleic acid) encoding OCT4, SOX2, KLF4, an inducing agent, or a combination thereof). In some embodiments, the distance between two inverted terminal repeats is less than 5.0 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb).

In certain embodiments, an expression vector (e.g., an expression vector encoding OCT4, KLF4, SOX2, an inducing agent, or a combination thereof) of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In some embodiments, the expression vector (e.g., viral vector) encoding OCT4, KLF4, and SOX2 comprises the sequence provided in SEQ ID NO: 16, SEQ ID NO: 105, or SEQ ID NO: 121. In some embodiments, the expression vector encoding OCT4, KLF4, and SOX2 comprise the elements depicted in FIG. 2, FIG. 3, FIGS. 4A-4AL, FIGS. 5A-5D, or a combination thereof. Viral vectors include adeno-associated virus (AAV) vectors, retroviral vectors, lentiviral vectors, and herpes viral vectors.

In another aspect, the present disclosure provides recombinant viruses (e.g., lentivirus, adenovirus, retrovirus, herpes virus, alphavirus, vaccinia virus or adeno-associated virus (AAV)) comprising any of the expression vectors described herein. In certain embodiments, a recombinant virus encodes a transcription factor selected from OCT4; KLF4; SOX2; and any combinations thereof. In certain embodiments, a recombinant virus encodes two or more transcription factors selected from the group consisting of OCT4, KLF4, and SOX2. In certain embodiments, a recombinant virus encodes OCT4 and SOX2, OCT4 and KLF4, OCT4, KLF4, and SOX2, or SOX2 and KLF4. In certain embodiments, a recombinant virus encodes OCT4, KLF4, and SOX2. In certain embodiments, a four or more transcription factors encodes four or more transcription factors (e.g., OCT4, SOX2, KLF4, and another transcription factor).

In yet another aspect, the present disclosure provides methods of regulating (e.g., inducing) cellular reprogramming, tissue repair, tissue regeneration, organ regeneration, reversing aging, or any combination thereof comprising administering to a cell a first nucleic acid (e.g., engineered nucleic acid) encoding OCT4, a second nucleic acid (e.g., engineered nucleic acid) encoding SOX2, and a third nucleic acid (e.g., engineered nucleic acid) encoding KLF4 in the absence of an exogenous nucleic acid (e.g., engineered nucleic acid) capable of expressing c-Myc. In certain embodiments, the first nucleic acid (e.g., engineered nucleic acid) encoding OCT4, the second nucleic acid (e.g., engineered nucleic acid) encoding SOX2, and the third nucleic acid (e.g., engineered nucleic acid) encoding KLF4 is administered to a subject. The subject may be human or non-human. Non-human subjects include, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the three nucleic acids (e.g., engineered nucleic acids) are administered simultaneously. In certain embodiments, the three nucleic acids (e.g., engineered nucleic acids) are administered simultaneously on the same vector.

In yet another aspect, the present disclosure provides methods of regulating (e.g., inducing) cellular reprogramming, tissue repair, tissue regeneration, organ regeneration, reversing aging, or any combination thereof comprising administering to a cell a first nucleic acid (e.g., engineered nucleic acid) encoding OCT4, a second nucleic acid (e.g., engineered nucleic acid) encoding SOX2, a third nucleic acid (e.g., engineered nucleic acid) encoding KLF4, or any combination thereof. In certain embodiments, the first nucleic acid (e.g., engineered nucleic acid) encoding OCT4, the second nucleic acid (e.g., engineered nucleic acid) encoding SOX2, the third nucleic acid (e.g., engineered nucleic acid) encoding KLF4, or any combination thereof is administered to a subject.

The expression vector comprising one or more of the first, second, and third nucleic acids (e.g., engineered nucleic acids) may be any of the expression vectors described above and herein. In some embodiments, the first nucleic acid, the second nucleic acid, the third nucleic acid, or any combination thereof are present on separate expression vectors. In certain embodiments, two of the first nucleic acid, the second nucleic acid, the third nucleic acid, or any combination thereof are present on the same expression vector. In certain embodiments, all three nucleic acids (e.g., engineered nucleic acids) are present on the same expression vector. In certain embodiments, at least two of the first, second, or third nucleic acids (e.g., engineered nucleic acids) are operably linked to the same promoter. In certain embodiments, all three of the first, second, and third nucleic acids (e.g., engineered nucleic acids) are operably linked to the same promoter.

In some embodiments, the expression vector (e.g., viral expression vector, including lentiviral, retroviral, adeno-associated viral vectors) comprises an inducible promoter (e.g., a promoter comprising a tetracycline-responsive element (TRE) including a TRE3G sequence, a TRE2 sequence, or a P tight sequence), and the method further comprises administering an inducing agent (e.g., a chemical agent, a nucleic acid (e.g., engineered nucleic acid) (e.g., nucleic acid (e.g., engineered nucleic acid) encoding an inducing agent), a protein, light, or temperature). In some embodiments, a pH is used to induce expression of a nucleic acid operably linked to a promoter. In certain embodiments, a chemical agent capable of modulating the activity of an inducing agent is tetracycline (e.g., doxycycline). As a non-limiting example, tetracycline-controlled transactivator (tTA) is an inducing agent whose activity is inhibited by tetracycline. As a non-limiting example, reverse tetracycline-controlled transactivator (rtTA) is an inducing agent whose activity is activated by tetracycline. The inducing agent (e.g., rtTA or tTA) may be encoded by a fourth nucleic acid (e.g., engineered nucleic acid) that is administered with a nucleic acid. In certain embodiments, the inducing agent (e.g., a chemical agent, a nucleic acid (e.g., engineered nucleic acid) (e.g., a nucleic acid comprising RNA and/or DNA encoding an inducing agent), a protein, light, a particular pH, or temperature) is introduced simultaneously with the nucleic acids (e.g., engineered nucleic acids) encoding OCT4, SOX2, and KLF4. In certain embodiments, the inducing agent (e.g., a chemical agent, a nucleic acid (e.g., engineered nucleic acid) (e.g., a nucleic acid comprising RNA and/or DNA encoding an inducing agent), a protein, light, a particular pH, or temperature) is introduced simultaneously with the nucleic acids (e.g., engineered nucleic acids) encoding one or more (e.g., two or more or three or more) transcription factors selected from OCT4; SOX2; KLF4; and any combinations thereof. A promoter (e.g., constitutive promoter, including CAG and Ubc, or an inducible promoter) may be operably linked to the nucleic acid (e.g., engineered nucleic acid) encoding the inducing agent. In certain embodiments, the promoter operably linked to the nucleic acid (e.g., engineered nucleic acid) encoding the inducing agent is a tissue-specific promoter.

In certain embodiments, the nucleic acid (e.g., engineered nucleic acid) encoding the inducing agent is present on the same expression vector as at least one of the nucleic acids (e.g., engineered nucleic acids) encoding OCT4, SOX2, KLF4, or a combination thereof. In certain embodiments, the nucleic acid (e.g., engineered nucleic acid) encoding the inducing agent is present on a separate expression vector from the nucleic acid (e.g., engineered nucleic acid) encoding OCT4, the nucleic acid (e.g., engineered nucleic acid) SOX2, and the nucleic acid (e.g., engineered nucleic acid) encoding KLF4. In certain embodiments, the nucleic acids (e.g., engineered nucleic acids) encoding OCT4, SOX2, and KLF4 are present on a first expression vector, and the fourth nucleic acid (e.g., engineered nucleic acid) is present on a second expression vector.

In some embodiments, a nucleic acid encoding OCT4, SOX2, KLF4, and/or an inducing agent is not present on a viral vector. In some embodiments, a nucleic acid encoding one or more (e.g., two or more or three or more) transcription factors selected from the group consisting of OCT4; SOX2; KLF4; and any combinations thereof is not present on a viral vector. In some embodiments, the nucleic acid is delivered without a viral vector. In some embodiments, delivery of the nucleic acid that is not on a viral vector comprises administration of a naked nucleic acid, electroporation, use of a nanoparticle, and/or use of a liposome.

The expression vectors may be viral vectors (e.g., lentivirus vectors, adenovirus vectors, retrovirus vectors, herpes virus vectors, alphavirus, vaccinia virus, or AAV vectors). For example, the first expression vector encoding OCT4, SOX2, and KLF4 may comprise the nucleic acid (e.g., engineered nucleic acid) sequence set forth in SEQ ID NO: 16. In some embodiments, the expression vector encoding an inducing agent comprises the sequence provided in SEQ ID NO: 17 (e.g., FIG. 12), SEQ ID NO: 31 (e.g., FIG. 18), or SEQ ID NO: 32 (e.g., FIG. 19).

In certain embodiments, the fourth nucleic acid (e.g., engineered nucleic acid) encoding the inducing agent further comprises an SV-40-derived terminator sequence, including a sequence that is at least 70% identical to SEQ ID NO: 8.

In certain embodiments, the inducing agent is capable of inducing expression from the inducible promoter in the presence of tetracycline (e.g., doxycycline). In certain embodiments, the inducing agent is rtTA (e.g., rtTA3, including rtTA3 with a sequence that is at least 70% identical to SEQ ID NO: 11, and rtTA4, including rtTA4 with a sequence that is at least 70% identical to SEQ ID NO: 13). In certain embodiments, the method further comprises administering tetracycline (e.g., doxycycline) to the cell, tissue, or subject. In certain embodiments, the method comprises removing tetracycline (e.g., doxycycline) from the cell, tissue, or subject.

In certain embodiments, the inducing agent is capable of inducing expression from the inducible promoter in the absence of tetracycline (e.g., doxycycline). In certain embodiments, the inducing agent is a tetracycline transactivator (tTA). Without being bound by a particular theory, tetracycline (e.g., doxycycline) may bind to the tTA and prevent tTA from binding its cognate promoter (e.g., a promoter comprising a tetracycline response element (TRE)) and driving expression of an operably linked nucleic acid. Without being bound by a particular theory, a nucleic acid (e.g., engineered nucleic acid) encoding an inducing agent may not be on the same vector as any of the nucleic acids (e.g., engineered nucleic acids) encoding OCT4, KLF4, and SOX2 to reduce the size of a viral vector and improve viral titer.

In certain embodiments, one or more expression vectors (e.g., AAV comprising an expression vector) is administered to a cell, tissue, or a subject in need thereof. The subject may have an injury or condition, is suspected of having a condition or injury, or is at risk for a condition or injury. Without being bound by a particular theory, expression of the transcription factors OCT4, SOX2, and KLF4 induces cellular reprogramming. In some embodiments, when the nucleic acid (e.g., engineered nucleic acid) encoding OCT4, SOX2, KLF4, or a combination thereof is operably linked to an inducible promoter, administration of an inducing agent (e.g., chemical, a protein, a nucleic acid (e.g., engineered nucleic acid) (e.g., a nucleic acid (e.g., engineered nucleic acid) encoding an inducing agent) under the appropriate conditions (e.g., in the presence or absence of tetracycline). In certain embodiments, an inducing agent (e.g., rtTA) is capable of binding a promoter and driving expression of an operably linked nucleic acid (e.g., engineered nucleic acid) only when the inducing agent is bound to tetracycline. In certain embodiments, an inducing agent (e.g., tTA) cannot bind a promoter and drive expression of an operably linked nucleic acid (e.g., engineered nucleic acid) when the inducing agent is bound to tetracycline. The condition may be an ocular disease, (e.g., a retinal disease, a corneal disease, or any disease affecting the eye), cancer, aging, an age-related disease, injury, or a neurodegenerative disease. In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine.

In certain embodiments, the tissue is damaged (e.g., due to an injury, an accident, or an iatrogenic injury) and/or is aged tissue. In certain embodiments, the tissue may be considered healthy but suboptimal for performance or survival in current or future conditions (e.g., in agriculture or adverse conditions including toxic therapies, sun exposure, or travel outside the earth's atmosphere).

In certain embodiments, the method comprises further comprises regulation of a biological process. In some embodiments, the methods described herein comprise regulating any biological process, including, cellular reprogramming, tissue repair, tissue survival, tissue regeneration, tissue growth, tissue function, organ regeneration, organ survival, organ function, or any combination thereof. In some embodiments, the methods comprise inducing cellular reprogramming, reversing aging, improving tissue function, improving organ function, promoting tissue repair, promoting tissue survival, promoting tissue regeneration, promoting tissue growth, promoting angiogenesis, reducing scar formation, reducing the appearance of aging including alopecia, hair thining, hair greying, sagging skin, and skin wrinkles, promoting organ regeneration, promoting organ survival, altering the taste and quality of agricultural products derived from animals, treating a disease, or any combination thereof, in vivo or in vitro. For example, the method may induce cellular reprogramming, cell survival, organ regeneration, tissue regeneration, or a combination thereof. In certain embodiments, the method comprises inducing and then stopping cellular reprogramming, cell survival, tissue regeneration, organ regeneration, aging, or a combination thereof. In certain embodiments, the method reverses aging of a cell, tissue, organ, or subject. In some embodiments, the method does not induce teratoma formation. In some embodiments, the method does not induce unwanted cell proliferation. In some embodiments, the method does not induce malignant cell growth. In some embodiments, the method does not induce cancer. In some embodiments, the method does not induce tumor growth or tumor formation. In some embodiments, the method does not induce glaucoma.

In some embodiments, a method described herein reverses the epigenetic clock of a cell, a tissue, an organ, a subject, or any combination thereof. In some embodiments, the epigenetic clock is determined using a DNA methylation-based (DNAm) age estimator. In some embodiments, the method alters the expression of one or more genes associated with ageing. In some embodiments, the method reduces expression of one or more genes associated with ageing. In some embodiments, the method alters the expression of one or more genes associated with ageing. In some embodiments, the one or more genes is one or more sensory genes.

In some embodiments, the method reduces expression of one or more genes associated with ageing. In some embodiments, the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Ccl9, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galnt18, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4c1, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sell13, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. In some embodiments, the method reduces expression of Ace, Kcnk4, Lamc3, Edn1, Syt10, Ngfr, Gprc5c, Cd36, Chrna4, Ednrb, Drd2, or a combination thereof.

In some embodiments, the method increases expression of one or more genes associated with ageing. In some embodiments, the method increases expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1c1, Ankrd1, Asb15, Atp2c2, AU018091, AW822073, Btn110, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps811, EU599041, Fam90ala, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Mucl2, Mug1, Mybl2, Myh15, Nek10, Neurod6, Nr1h5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof. In some embodiments, the method increases expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otog1, Olfr943, Olfr1406, Olfr273, Olfr466, Olfr1043, Olfr427, Olfr890, Rbp4, or any combination thereof.

Further aspects of the disclosure relate to methods of reprogramming comprising rejuvenating the epigenetic clock of a cell, tissue, organ, subject, or any combination thereof.

Further aspects of the disclosure relate to methods of reprogramming comprising altering the expression of one or more genes associated with ageing.

Further aspects of the disclosure relate to methods comprising resetting the transcriptional profile of an old cell, an old organ, an old tissue, and/or any combination thereof in vitro.

Further aspects of the disclosure relate to methods comprising resetting the transcriptional profile of an old cell, an old organ, an old tissue, an old subject and/or any combination thereof in vivo.

Further aspects of the disclosure relate to methods of transdifferentiating cells.

Another aspect of the present disclosure provides engineered cells generated by any of the methods described herein. The methods described herein may be useful in the production of any engineered cell, including induced pluripotent stem cells. The engineered cells of the present disclosure may be produced ex vivo and the methods may further comprise generating an engineered tissue or engineered organ. In some embodiments, the methods of the present disclosure comprise administering an engineered cell, engineered tissue, and/or engineered organ of the present disclosure to a subject in need thereof. In some embodiments, the method further comprises treating a disease.

Aspects of the present disclosure also provide compositions comprising any of the nucleic acids (e.g., engineered nucleic acid) capable of inducing OCT4, KLF4, inducing agent, and/or SOX2 expression (e.g., expression vector), any of the engineered proteins described herein, any of the chemical agents activating (e.g., inducing expression of) OCT4, KLF4, an inducing agent, and/or SOX2, any of the antibodies activating (e.g., inducing expression of) OCT4, KLF4, an inducing agent, and/or SOX2, and/or any of the recombinant viruses (e.g., lentivirus, adenovirus, alphavirus, vaccinia virus, retrovirus, herpes virus, or AAV) described herein, alone, or in combination. In some embodiments, the pharmaceutical compositions of the present disclosure further comprise a pharmaceutically acceptable carrier. In some embodiments, the pharmaceutical composition further comprises a second engineered nucleic acid (e.g., engineered nucleic acid) (e.g., expression vector including viral vector) encoding an inducing agent (e.g., rtTA or tTA).

Aspects of the present disclosure also provide compositions comprising any of the nucleic acids (e.g., engineered nucleic acid) acids capable of inducing OCT4, KLF4, and/or SOX2 (e.g., expression vector, including an inducible expression vector), any of the engineered proteins described herein, any of the chemical agents capable of activating (e.g., inducing expression of) OCT4, KLF4, and/or SOX2, any of the antibodies capable of activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) described herein, alone or in combination. In some embodiments, the composition further comprises a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent. In some embodiments, the pharmaceutical compositions of the present disclosure further comprise a pharmaceutically acceptable carrier. In some embodiments, the pharmaceutical composition further comprises a second engineered nucleic acid (e.g., engineered nucleic acid) (e.g., expression vector including viral vector) encoding an inducing agent (e.g., rtTA or tTA).

Aspects of the present disclosure also provide compositions comprising any of the nucleic acids (e.g., engineered nucleic acid) (e.g., expression vector) capable of inducing expression of one or more transcription factors selected from OCT4; SOX2; KLF4; and any combination thereof, any of the engineered proteins described herein, any of the chemical agents activating (e.g., inducing expression of) one or more transcription factors selected from the group consisting of OCT4; SOX2; KLF4; and any combinations thereof, any of the antibodies activating (e.g., inducing expression of) one or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. In certain embodiments, a composition comprises any of the nucleic acids (e.g., engineered nucleic acid) (e.g., expression vector) capable of inducing expression of two or more transcription factors selected from OCT4; SOX2; KLF4; and any combination thereof, any of the engineered proteins described herein, any of the chemical agents activating (e.g., inducing expression of) two or more transcription selected from the group consisting of OCT4; SOX2; KLF4; and any combinations thereof, any of the antibodies activating (e.g., inducing expression of) two or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. The two or more transcription factors may comprise OCT4 and SOX2, OCT4 and KLF4, OCT4, KLF4, and SOX2, or SOX2 and KLF4. In certain embodiments, a composition comprises any of the nucleic acids (e.g., engineered nucleic acid) (e.g., expression vector) capable of inducing expression of three or more transcription factors selected from OCT4, SOX2, KLF4, and combinations thereof expression, any of the engineered proteins described herein, any of the chemical agents activating (e.g., inducing expression of) three or more transcription selected from the group consisting of OCT4; SOX2; KLF4; and any combinations thereof, any of the antibodies activating (e.g., inducing expression of) three or more transcription factors selected from the group consisting of OCT4; SOX2; KLF4; and any combinations thereof, and/or any of the recombinant viruses (e.g., lentivirus, adenovirus, alphavirus, vaccinia virus, retrovirus, herpes virus, or AAV) described herein, alone or in combination. In certain embodiments, the three or more transcription factors may comprise OCT4, SOX2, and KLF4. In some embodiments, a pharmaceutical composition further comprises a nucleic acid (e.g., engineered nucleic acid) (e.g., expression vector) encoding an inducing agent (e.g., rtTA or tTA), any of the engineered proteins encoding an inducing agent, any of the chemical agents capable of activating (e.g., inducing expression of) an inducing agent, and/or any of the recombinant viruses (e.g., lentivirus, adenovirus, alphavirus, vaccinia virus, retrovirus, herpes virus, or AAV) encoding an inducing agent. In some embodiments, the pharmaceutical compositions of the present disclosure further comprise a pharmaceutically acceptable carrier.

In yet another aspect, the present disclosure provides kits comprising any of the nucleic acids (e.g., engineered nucleic acid) capable of inducing OCT4, KLF4, inducing agent, and/or SOX2 expression (e.g., expression vector), any of the engineered proteins described herein, any of the chemical agents activating (e.g., inducing expression of) OCT4, KLF4, an inducing agent, and/or SOX2, any of the antibodies activating (e.g., inducing expression of) OCT4, KLF4, an inducing agent, and/or SOX2, and/or any of the recombinant viruses (e.g., lentivirus, adenovirus, alphavirus, vaccinia virus, retrovirus, herpes virus, or AAV) described herein.

In yet another aspect, the present disclosure provides kits comprising any of the nucleic acids (e.g., engineered nucleic acid) acids capable of inducing OCT4, KLF4, and/or SOX2 expression (e.g., expression vector), any of the engineered proteins described herein, any of the chemical agents activating (e.g., inducing expression of) OCT4, KLF4, and/or SOX2, any of the antibodies activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) described herein. In some embodiments, the kit further comprises a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent.

In yet another aspect, the present disclosure provides kits comprising any of the nucleic acids (e.g., engineered nucleic acid) (e.g., expression vector) capable of inducing expression of one or more transcription factors selected from the group consisting of OCT4; SOX2; KLF4; and any combinations thereof, any of the engineered proteins described herein, any of the chemical agents activating (e.g., inducing expression of) one or more transcription factors selected from the group consisting of OCT4; SOX2; KLF4; and any combinations thereof, any of the antibodies activating (e.g., inducing expression of) OCT4; SOX2; KLF4; and any combinations thereof, and/or any of the recombinant viruses (e.g., lentivirus, adenovirus, alphavirus, vaccinia virus, retrovirus, herpes virus, or AAV) described herein. In certain embodiments, a kit further comprises a nucleic acid (e.g., engineered nucleic acid) (e.g., expression vector) encoding an inducing agent (e.g., rtTA or tTA), any of the engineered proteins encoding an inducing agent, any of the chemical agents capable of activating (e.g., inducing expression of) an inducing agent, and/or any of the recombinant viruses (e.g., lentivirus, adenovirus, alphavirus, vaccinia virus, retrovirus, herpes virus, or AAV) encoding an inducing agent.

The details of one or more embodiments of the invention are set forth herein. Other features, objects, and advantages of the invention will be apparent from the Detailed Description, Examples, Figures, and Claims.

References cited in this application are incorporated herein by reference.

Definitions

Definitions of specific terms are described in more detail below. The disclosure is not intended to be limited in any manner by the exemplary listing of substituents described herein.

"AAV" or "adeno-associated virus" is a nonenveloped virus that is capable of carrying and delivering nucleic acids (e.g., engineered nucleic acids) (e.g., nucleic acids (e.g., engineered nucleic acids) encoding OCT4; KLF4; SOX2; or any combination thereof) and belongs to the genus Dependoparvovirus. In some instances, an AAV is capable of delivering a nucleic acid encoding an inducing agent. In general, AAV does not integrate into the genome. The tissue-specific targeting capabilities of AAV is often determined by the AAV capsid serotype (see, e.g., Table 1 below for examples of AAV serotypes and their utility in tissue-specific delivery). Non-limiting serotypes of AAV include AAV1, AAV2, AAV3, AAV4, AAV5, AAV6, AAV7, AAV8, AAV9, AAV10, AAV11, and variants thereof. In certain embodiments, the AAV serotype is a variant of AAV9 (e.g., AAV PHP.b).

A "recombinant virus" is a virus (e.g., lentivirus, adenovirus, retrovirus, herpes virus, alphavirus, vaccinia virus or adeno-associated virus (AAV))) that has been isolated from its natural environment (e.g., from a host cell, tissue, or a subject) or is artificially produced.

The term "AAV vector" as used herein is a nucleic acid (e.g., engineered nucleic acid) that comprises AAV inverted terminal repeats (ITRs) flanking an expression cassette (e.g., an expression cassette comprising a nucleic acid (e.g., engineered nucleic acid) encoding OCT4, KLF4, and SOX2, each alone or in combination, or an expression cassette encoding rtTA or tTA). An AAV vector may further comprise a promoter sequence.

The terms "administer," "administering," or "administration," as used herein refers to introduction of any of the compositions described herein, any of the nucleic acids (e.g., engineered nucleic acid) capable of inducing OCT4, KLF4, and/or SOX2 expression (e.g., expression vector), any of the nucleic acids (e.g., engineered nucleic acid) (e.g., expression vector) capable of inducing expression of one or more transcription factors selected from the group consisting of OCT4; KLF4; SOX2; and any combinations thereof, any of the engineered proteins described herein, any of the chemical agents activating (e.g., inducing expression of) OCT4, KLF4, and/or SOX2, any of the chemical agents activating (e.g., inducing expression of) one or more transcription factors selected from OCT4; KLF4; SOX2; and any combinations thereof, any of the antibodies activating (e.g., inducing expression of) OCT4, KLF4, and/or SOX2, any of the antibodies activating (e.g., inducing expression of) one or more transcription factors selected from OCT4; KLF4; SOX2; and any combinations thereof, and/or any of the recombinant viruses (e.g., lentivirus, adenovirus, alphavirus, vaccinia virus, retrovirus, herpes virus, or AAV) described herein, alone, or in combination to any cell, tissue, organ, and/or subject. In some embodiments, a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject. Any of the compositions described herein, comprising any of the nucleic acids (e.g., engineered nucleic acid) capable of inducing OCT4, KLF4, and/or SOX2 expression (e.g., expression vector), comprising any of the nucleic acids (e.g., engineered nucleic acid) (e.g., expression vector) capable of inducing expression of one or more transcription factors selected from OCT4; KLF4; SOX2; and any combinations thereof, any of the engineered proteins described herein, any of the chemical agents activating (e.g., inducing expression of) OCT4, KLF4, and/or SOX2, any of the engineered proteins encoding OCT4, SOX2, KLF4, or any combinations thereof, any of the chemical agents activating (e.g., inducing expression of) OCT4; KLF4; SOX2; or any combination thereof, any of the antibodies activating (e.g., inducing expression of) OCT4, KLF4, and/or SOX2, any of the antibodies activating (e.g., inducing expression of) OCT4; KLF4; SOX2; or any combination thereof, and/or any of the recombinant viruses (e.g., lentivirus, adenovirus, alphavirus, vaccinia virus, retrovirus, herpes virus, or AAV) described herein, alone, or in combination may be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art (see, for example, *Remington's Pharmaceutical Sciences* (1990), incorporated herein by reference). In some embodiments, a composition comprising a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject is administered using any suitable method.

The term "epigenome" or "epigenetics" refers to the modification and structural changes within a cell that control the expression of nucleic acids (e.g., engineered nucleic acids) or genomic information in a cell. Changes to the epigenome occur during, and drive the processes of embryonic development, disease progression, and aging.

The term "epigenetic clock" may refer to an age estimator or an innate biological process. In some embodiments, rejuvenating or reversing the epigenetic clock refers to reducing the estimated age of a cell, tissue, organ, or a subject. The epigenetic clock may be partially or fully reversed or rejuvenated by any of the methods described herein. In some embodiments, an age estimator is an epigenetic age estimator. For example, an epigenetic age estimator may be sets of CpG dinucleotides that when used in combination with a mathematical algorithm may be used to estimate age of a DNA source, including cells, organs, or tissues. In some embodiments, an age estimator is a DNA methylation-based (DNAm) age estimator. In some embodiments, a DNAm age estimator is calculated as an age correlation using Pearson correlation coefficient r, between DNA methylation-based (DNam) age (also known as estimated age) and chronological age. In some embodiments, the DNA methylation-based (DNAm) age estimator is a single-tissue DNA methylation-based age estimator. In some embodiments, the DNA methylation-based age estimator is a multi-tissue DNA methylation-based age estimator. In some embodiments, the DNAm age estimator is DNAm PhenoAge. See, e.g., Horvath and Raj, Nat Rev Genet. 2018 June; 19(6):371-384; Levine et al., Aging (Albany NY). 2018 Apr. 18; 10(4):573-591; and the Examples below.

"Epigenetic information" as used herein includes covalent modifications to DNA, such as 5-methylcytosine(5mC), hydroxymethylcytosine (5hmeC), 5-formylcytosine (fC), and 5-carboxylcytosine (caC), and to certain proteins, such as lysine acetylation, lysine and arginine methylation, serine and threonine phosphorylation, and lysine ubiquitination and sumoylation of histone proteins, and the 3D architecture of cells, including TADs (topologically associated domains) and compartments. Epigenetic information is sometimes referred to as the "analog" information of the cell.

"Restoring the expression" of at least one gene in Table 5 to youthful levels is meant to include increasing the expression of a downregulated gene or decreasing the expression of an upregulated gene that changes during aging.

As used herein, the term "cell" is meant not only to include an individual cell but refers also to the particular tissue or organ from which it originates.

The term "cellular senescence" refers to a cell that has exited the cell cycle, displays epigenetic markers consistent with senescence, or expressing senescence cell markers (e.g. senescence-associated beta-galactosidase, or inflammatory cytokines). Cellular senescence may be partial or complete.

The term "gene expression" refers to the degree to which certain genes or all genes in a cell or tissue are transcribed into RNA. In some instances, the RNA is translated by the cell into a protein. The epigenome dictates gene expression patterns.

The term "cellular reprogramming" refers to the process of altering the epigenome of a cell using reprogramming factors (e.g. reversing or preventing epigenetic changes in cells that are causes of dysfunction, deterioration, cell death, senescence or aging). Cellular reprogramming may be complete reprogramming, such that a differentiated cell (e.g., somatic cell) is reprogrammed to a pluripotent stem cell. Cellular reprogramming may be incomplete, such that a differentiated cell (e.g., somatic cell) retains its cellular identity (e.g., lineage-specific stem cell). Cellular reprogramming may be incomplete, e.g., a stem cell is not created, such that a cell is rejuvenated, or takes on more youthful attributes (e.g. increased survival, reduced inflammation, or ability to divide). Cellular reprogramming may provide additional cellular functions, or prevent cellular aging (e.g., transdifferentiation, or transition into cellular senescence). Cellular reprogramming may induce temporary or permanent gene expression changes. In some embodiments, incomplete cellular reprogramming is shown by the lack of Nanog expression. In some embodiments, cellular reprogramming prevents senescence from occurring.

The term "rejuvenating a cell" as used herein is meant to include preventing or reversing the cellular causes of aging without inducing a pluripotent state. A rejuvenated cell as used herein includes for example a retinal ganglion cell that expresses RBPMS and or Brn3a.

A "pluripotent state" as used herein is meant to include a state in which the cell expresses at least one stem cell marker such as but not limited to Esrrb, Nanog, Lin28, TRA-1-60/TRA-1-81/TRA-2-54, SSEA1, or SSEA4. Methods of measuring the expression of stem cell markers on the cell are known in the art and include the methods described herein.

The term "transdifferentiation" refers to a process in which one cell type is changed into another cell type without entering a pluripotent state. Transdifferentiation may also be referred to as lineage reprogramming or lineage conversion. See, e.g., Cieślar-Pobuda et al., Biochim Biophys Acta Mol Cell Res. 2017 July; 1864(7):1359-1369, which is herein incorporated by reference in its entirety.

The terms "condition," "disease," and "disorder" are used interchangeably. Non-limiting examples of conditions, diseases, and disorders include acute injuries, neurodegenerative diseases, chronic diseases, proliferative diseases, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject. For example, age-related conditions include, heart failure, stroke, heart disease, atherosclerosis, neurodegenerative diseases (e.g., Parkinson's disease and Alzheimer's disease), cognitive decline, memory loss, diabetes, osteoporosis, arthritis, muscle loss, hearing loss (partial or total), eye-related conditions (e.g., poor eye sight or retinal disease), glaucoma, a progeroid syndrome (e.g., Hutchinson-Gilford progeria syndrome), and cancer. In certain embodiments, the disease is a retinal disease (e.g., macular degeneration). In some embodiments, an age-related condition is senescence. As a non-limiting example, senescence of glial cells may be a cause of Alzheimer's disease. See e.g., Bussian, et al., Nature. 2018 Sep. 19. In some instances, the condition is nerve damage. In some instances, the condition is damage in the central nervous system (CNS). In some instances, the nerve damage is peripheral nerve damage. In some instances, the nerve damage is neurapraxia, axonotmesis, or neurotmesis.

In some instances, a condition increases the DNA methylation-based age of a cell, a tissue, an organ, and/or a subject relative to a control. In some instances, a condition increases the DNA methylation-based age of a cell, a tissue, an organ, and/or a subject by at least 1%, at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1,000% relative to a control. In some instances, the control is a cell, a tissue, an organ, and/or a subject that does not have the condition. In some instances, the control is the same cell, tissue, organ, and/or subject prior to having the condition. Without being bound by a particular theory, any of the methods described herein may be useful in decreasing the DNA methylation-based age of a diseased cell, a diseased tissue, a diseased organ, and/or a subject who has, is at risk for, or is suspected of having a disease. In some instances, the disease increases the DNA-methylation-based age of the cell, tissue, organ, and/or subject. In some instances, the disease is an injury.

In some instances, the condition is ageing. In some instances, aging is driven by epigenetic noise. See, e.g., Oberdoerffer and Sinclair. Nat Rev Mol Cell Biol 8, 692-702, doi:10.1038/nrm2238 (2007); Oberdoerffer et al. Cell 135, 907-918, doi:10.1016/j.cell.2008.10.025 (2008). Without being bound by a particular theory, mammalian cells may retain a faithful copy of epigenetic information from earlier in life, analogous to Shannon's "observer" system in Information Theory, essentially a back-up copy of the original signal to allow for its reconstitution at the receiving end if information is lost or noise is introduced during transmission. See, e.g., Shannon, The Bell System Technical Journal 27, 379-423 (1948) for a description of the observer system.

As used herein, an "ocular disease" or "eye disease" is a disease or condition of the eye. Non-limiting examples of conditions that affect the eye include Ectropion, Lagophthalmos, Blepharochalasis, Ptosis, Stye, Xanthelasma, Dermatitis, Demodex, leishmaniasis, loiasis, onchocerciasis, phthiriasis, (herpes simplex), leprosy, molluscum contagiosum, tuberculosis, yaws, zoster, impetigo, Dacryoadenitis, Epiphora, exophthalmos, Conjunctivitis, Scleritis, Keratitis, Corneal ulcer/Corneal abrasion, Snow blindness/Arc eye, Thygeson's superficial punctate keratopathy, Corneal neovascularization, Fuchs' dystrophy, Keratoconus, Keratoconjunctivitis sicca, Iritis, iris, Uveitis, Sympathetic ophthalmia, Cataract, lens, Chorioretinal inflammation, Focal chorioretinal inflammation, chorioretinitis, choroiditis, retinitis, retinochoroiditis, Disseminated chorioretinal inflammation, exudative retinopathy, Posterior cyclitis, Pars planitis, chorioretinal inflammations, Harada's disease, Chorioretinal inflammation, choroid, Chorioretinal scars, Macula scars, posterior pole (postinflammatory) (post-traumatic), Solar retinopathy, Choroidal degeneration, Atrophy, Sclerosis, angioid streaks, choroidal dystrophy, Choroideremia, choroidal, areolar, (peripapillary), Gyrate atrophy, choroid, ornithinaemia, Choroidal haemorrhage, Choroidal detachment, Chorioretinal, Chorioretinal inflammation, infectious and parasitic diseases, Chorioretinitis, syphilitic, toxoplasma, tuberculosis, chorioretinal, Retinal detachment, retina, choroid, distorted vision, Retinoschisis, Hypertensive retinopathy, Diabetic retinopathy, Retinopathy, Retinopathy of prematurity, Age-related macular degeneration, macula, Macular degeneration, Bull's Eye Maculopathy, Epiretinal membrane, Peripheral retinal degeneration, Hereditary retinal dystrophy, Retinitis pigmentosa, Retinal haemorrhage, retinal layers, Central serous retinopathy, Retinal detachment, retinal disorders, Macular edema, macula, Retinal disorder, Diabetic retinopathy, Glaucoma, optic neuropathy, ocular hypertension, open-angle glaucoma, angle-closure glaucoma, Normal Tension glaucoma, open-angle glaucoma, angle-closure glaucoma, Floaters, Leber's hereditary optic neuropathy, Optic disc drusen, Strabismus, Ophthalmoparesis, eye muscles, Progressive external ophthalmoplegia, Esotropia, Exotropia, Disorders of refraction, accommodation, Hypermetropia, Myopia, Astigmatism, Anisometropia, Presbyopia, ophthalmoplegia, Amblyopia, Leber's congenital amaurosis, Scotoma, Anopsia, Color blindness, Achromatopsia/Maskun, cone cells, Nyctalopia, Blindness, River blindness, Micropthalmia/coloboma, optic nerve, brain, spinal cord, Red eye, Argyll Robertson pupil, pupils, Keratomycosis, Xerophthalmia, and Aniridia. In some embodiments, the ocular disease is acute or chronic eye injury.

In some embodiments, the ocular disease is a scratched cornea.

In some embodiments, the ocular disease is glaucoma.

In some embodiments, an ocular disease is a corneal disease (e.g., a disease affecting the cornea or corneal cells). In some embodiments, an ocular disease is acanthamoeba keratitis, ectropion, lagoph amblyopia, anisocoria, astigmatism, Bell's Palsy, blepharitis, blurry vision, burning eyes, cataracts, macular degeneration, age-related macular degeneration, diabetic eye disease, glaucoma, dry eye, poor vision (e.g., low vision), astigmatism, blepharitis, cataract, chalazion, conjunctivitis, diabetic retinopathy, dry eye, glaucoma, keratitis, keratonconus, macular degeneration, ocular hypertension, pinquecula, pterygium, retinitis pigmentosa, or ocular cancer (e.g., retinoblastoma, melanoma of the eye, lymphoma of the eye, medulloepithelioma, squamous cell cancer of the conjunctiva). Examples of corneal diseases include, but are not limited to, corneal neovascularization (NV), corneal dystrophy, corneal inflammation, corneal abrasion, and corneal fibrosis. In some embodiments, the ocular disease is Keritaconus. In some embodiments, an ocular disease is macular degeneration. Additional non-limiting examples of eye diseases may be found in the International Statistical Classification of Diseases and Related Health Problems (e.g., VII Diseases of the eye and adnexa).

An ocular disease may affect any part of the eye and/or adnexa. In some embodiments, the ocular disease is a disorder of the eyelid, lacrimal system and/or orbit. In some embodiments, the ocular disease is a disorders of conjunctiva. In some embodiments, the ocular disease is a disorder of sclera, cornea, iris, and/or ciliary body. In some embodiments, the ocular disease is a disorder of the lens. In some embodiments, the ocular disease is a disorder of choroid and/or retina. In some embodiments, the ocular disease is glaucoma. In some embodiments, the ocular disease is a disorder of vitreous body and/or globe. In some embodiments, the ocular disease is a disorder of optic nerve and/or visual pathways. In some embodiments, the ocular disease is a disorder of ocular muscles, binocular movement, accommodation, and/or refraction. In some embodiments, the ocular disease is a visual disturbance and/or blindness. In some embodiments, the ocular disease is associated with aging, for example, vision loss associated with aging, decline in visual acuity associated with aging, and/or decline in retinal function.

Any suitable method may be used to measure ocular function. Non-limiting examples include visual acuity tests, pattern electroretinograms, and pathology.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, a progeroid syndrome (e.g., Hutchinson-Gilford progeria syndrome), and Zellweger syndrome.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation. In some embodiments, the inflammatory disease is inflammaging (e.g., inflammation that is a side effect of aging).

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HIV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases and injuries that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, vascular dementias, stroke, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illnesses include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is Proteus syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis. In some embodiments, the disease is a musculoskeletal disease.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

In some embodiments, a disease is characterized by cellular dysfunction. For example, a disease may be a mitochondrial disease. Non-limiting mitochondrial diseases include Freidrich's ataxia, alphers disease, barth syndrome, beta-oxidation defects, carnitine deficiency, CPT I deficiency, and mitochondrial DNA depletion. Cellular dysfunction may include mitochondria dysfunction, RNA replication dysfunction, DNA replication dysfunction, translation dysfunction, and/or protein folding dysfunction.

In some embodiments, the disease or condition by a wood, bleeding out, injuries (e.g., broken bones, gunshot wound, cut, scarring during surgery (e.g., cesarean).

In some embodiments, the disease is an infectious disease (e.g., a disease caused by a pathogen and/or virus). Non-limiting examples of infectious diseases include tuberculosis, HIV/AIDS, rabies, plague, cholera, dengue fever, measles, malaria, meningitis, whooping cough, Lyme disease, influenza, hepatitis C, typhoid fever, and poliomyelitis.

"Cellular causes of aging" as used herein include loss or modification of epigenetic information.

The terms "c-Myc" or "Myc" refer to a nuclear phosphoprotein that has been implicated in cell cycle progression. c-Myc is capable of forming a heterodimer with the transcription factor MAX and the heterodimer is capable of binding to an E box consequence sequence on nucleic acids (e.g., engineered nucleic acids) to regulate transcription of target genes. In certain embodiments, a nucleotide sequence encoding c-Myc comprises a sequence that is at least 70% (e.g., at least 75%, 80%, 85%, 90%, 95%, 98%, 99%, or 100%) identical to a sequence as described in the NCBI RefSeq database under accession number NM_001354870.1 or NM_002467.5. In certain embodiments, an amino acid sequence encoding c-Myc comprises a sequence that is at least 70% (e.g., at least 75%, 80%, 85%, 90%, 95%, 98%, 99%, or 100%) identical to NP_002458.2 or NP_001341799.1. In certain embodiments, the methods comprise inducing expression of OCT4; KLF4; SOX2; or any combination thereof in the absence of inducing c-Myc expression or in the absence of activating c-Myc. Absence of inducing c-Myc expression may refer to absence of substantial induction of c-Myc expression over endogenous levels of c-Myc expression in a cell, tissue, subject, or any combination thereof. Absence of substantial induction of c-Myc expression as compared to endogenous levels of c-Myc expression in a cell, tissue, subject, or any combination thereof, may refer to increasing c-Myc expression by less than 70%, less than 60%, less than 50%, less than 40%, less than 30%, less than 20%, less than 10%, or any values in between as compared to endogenous levels of c-Myc expression in the cell, tissue, subject, or any combination thereof. Absence of activating c-Myc expression may refer to absence of substantial activation of c-Myc (e.g., activity) over endogenous c-Myc activity in a cell, tissue, subject, or any combination thereof. Absence of substantial induction of c-Myc activity as compared to endogenous c-Myc activity in a cell, tissue, subject, or any combination thereof, may refer to increasing c-Myc activity by less than 70%, less than 60%, less than 50%, less than 40%, less than 30%, less than 20%, less than 10%, or any values in between as compared to endogenous c-Myc activity in the cell, tissue, subject, or any combination thereof.

The terms "effective amount" and "therapeutically effective amount," as used herein, refer to the amount or concentration of an inventive compound, that, when administered to a subject, is effective to at least partially treat a condition from which the subject is suffering.

As used herein, a protein that is "functional" or "active" is one that retains its biological activity (e.g., capable of acting as a transcription factor or as an inducing agent). Conversely, a protein that is not functional or is inactive is one that is not capable of performing one or more of its wild-type functions.

The term "gene" refers to a nucleic acid (e.g., engineered nucleic acid) fragment that expresses a protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Homolog" or "homologous" refers to sequences (e.g., nucleic acid (e.g., engineered nucleic acid) or amino acid sequences) that share a certain percent identity (e.g., at least 5%, at least 10%, at least 15%, at least 20%, at least 25%, at least 30%, at least 35%, at least 40%, at least 45%, at least 50%, at least 55%, at least 60%, at least 65%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% percent identity). Homologous sequences include but are not limited to paralogous or orthologous sequences. Paralogous sequences arise from duplication of a gene within a genome of a species, while orthologous sequences diverge after a speciation event. A functional homolog retains one or more biological activities of a wild-type protein. In certain embodiments, a functional homolog of OCT4, KLF4, or SOX2 retains at least 10%, at least 20%, at least 30%, at least 40%, at least 50%, at least 60%, at least 70%, at least 80%, at least 90%, or at least 100% of the biological activity (e.g., transcription factor activity) of a wild-type counterpart.

"KLF4" may also be referred to as Kruppel-like factor 4, EZF, or GKLF and is a zinc-finger transcription factor. KLF4 has been implicated in regulation of differentiation and proliferation and is capable of interacting with co-activators, including members of the p300-CBP coactivator family. A KLF4 transcription factor, homolog (e.g., functional homolog), or variant thereof, as used herein, may be derived from any species, including humans. In certain embodiments, the nucleic acid (e.g., engineered nucleic acid) encoding human KLF4 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq database under accession number NM_004235.5 or NM_001314052.1. Non-limiting examples of KLF4 variants include Krueppel-like factor 4 transcript variant 1 and Krueppel-like factor 4 transcript variant 2. In certain embodiments, KLF4 comprises a nucleic acid (e.g., engineered nucleic acid) sequence that is at least 70% (e.g., at least 75%, 80%, 85%, 90%, 95%, 98%, 99%, or 100%) identical to SEQ ID NO: 5 or SEQ ID NO: 44. SEQ ID NO: 5 is a non-limiting example of a nucleotide sequence encoding KLF4 from *Mus musculus*. SEQ ID NO: 44 is a non-limiting example of a nucleotide sequence encoding human KLF4. In certain embodiments, KLF4 comprises an amino acid sequence that is at least 70% (e.g., at least 75%, 80%, 85%, 90%, 95%, 98%, 99%, or 100%) identical to NP_001300981.1 or NP_004226.3. In certain embodiments, KLF4 comprises an amino acid sequence that is at least 70% (e.g., at least 75%, 80%, 85%, 90%, 95%, 98%, 99%, or 100%) identical to SEQ ID NO: 6. In certain embodiments, KLF4 comprises an amino acid sequence that is at least 70% (e.g., at least 75%, 80%, 85%, 90%, 95%, 98%, 99%, or 100%) identical to SEQ ID NO: 45. SEQ ID NO: 6 is a non-limiting example of an amino acid sequence encoding KLF4 from *Mus musculus*. SEQ ID NO: 45 is a non-limiting example of an amino acid sequence encoding human KLF4.

"Inverted terminal repeats" or "ITRs" are nucleic acid (e.g., engineered nucleic acid) sequences that are reverse complements of one another. In general, in an AAV vector, ITRs are found on either side of a cassette (e.g., an expression cassette comprising a nucleic acid (e.g., engineered nucleic acid) encoding OCT4; KLF4; SOX2; or any combination thereof). In some instances, the cassette encodes an inducing agent. AAV ITRs include ITRs from AAV1, AAV2, AAV3, AAV4, AAV5, AAV6, AAV7, AAV8, AAV9, AAV10, AAV11, and AAV variants thereof.

The terms "nucleic acid," "polynucleotide", "nucleotide sequence", "nucleic acid (e.g., engineered nucleic acid) molecule", "nucleic acid (e.g., engineered nucleic acid) sequence", and "oligonucleotide" refer to a series of nucleotide bases (also called "nucleotides") in DNA and RNA, and mean any chain of two or more nucleotides. The terms "nucleic acid" or "nucleic acid (e.g., engineered nucleic acid) sequence", "nucleic acid (e.g., engineered nucleic acid) molecule", "nucleic acid (e.g., engineered nucleic acid) fragment" or "polynucleotide" may be used interchangeably with "gene", "mRNA encoded by a gene" and "cDNA".

The nucleic acids (e.g., engineered nucleic acids) can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids (e.g., engineered nucleic acids)" (PNAs) formed by conjugating bases to an amino acid backbone. This also includes nucleic acids (e.g., engineered nucleic acids) containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The nucleic acids (e.g., engineered nucleic acids) described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The nucleic acids (e.g., engineered nucleic acids) may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids (e.g., engineered nucleic acids) may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoramidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, epitope tags, isotopes (e.g., radioactive isotopes), biotin, and the like.

A "recombinant nucleic acid (e.g., engineered nucleic acid) molecule" or "engineered nucleic acid" is a nucleic acid (e.g., engineered nucleic acid) molecule that has undergone a molecular biological manipulation, i.e., non-naturally occurring nucleic acid (e.g., engineered nucleic acid) molecule or genetically engineered nucleic acid (e.g., engineered nucleic acid) molecule. Furthermore, the terms "recombinant DNA molecule" or "engineered nucleic acid" refer to a nucleic acid (e.g., engineered nucleic acid) sequence which is not naturally occurring, or can be made by the artificial combination of two otherwise separated segments of nucleic acid (e.g., engineered nucleic acid) sequence, i.e., by ligating together pieces of DNA that are not normally continuous. By "recombinantly produced" is meant artificial combination often accomplished by either chemical synthesis means, or by the artificial manipulation of isolated segments of nucleic acids (e.g., engineered nucleic acids), e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al., *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid (e.g., engineered nucleic acid) segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design.

"OCT4" may also be referred to as Octamer-binding transcription factor 4, OCT3, OCT3/4, POU5F1, or POU class 5 homeobox 1 and is a transcription factor that has been implicated in embryonic development and determination of cell fate. Similar to other OCT transcription factors, OCT4 is characterized by a bipartite DNA binding domain called a POU domain. An OCT4 transcription factor, homolog, or variant thereof, as used herein, may be derived from any species, including humans. In certain embodiments, the nucleic acid (e.g., engineered nucleic acid) encoding human OCT4 is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_002701, NM_203289, NM_001173531, NM_001285986, or NM_001285987. In certain embodiments, the nucleic acid (e.g., engineered nucleic acid) encoding an OCT4 comprises a sequence that is at least 70% (e.g., at least 75%, 80%, 85%, 90%, 95%, 98%, 99%, or 100%) identical to a nucleic acid (e.g., engineered nucleic acid) sequence provided as SEQ ID NO: 1. SEQ ID NO: 1 is a non-limiting example of a nucleotide sequence encoding OCT4 from *Mus musculus*. In certain embodiments, the nucleic acid (e.g., engineered nucleic acid) encoding a human OCT4 comprises a sequence that is at least 70% (e.g., at least 75%, 80%, 85%, 90%, 95%, 98%, 99%, or 100%) identical to a nucleic acid (e.g., engineered nucleic acid) sequence provided as SEQ ID NO: 40. SEQ ID NO: 40 is a non-limiting example of a nucleotide sequence encoding human OCT4. Non-limiting examples of OCT4 variants encompassed herein include POU5F1, transcript variant 1, POU5F1, transcript variant 2, POU5F1, transcript variant 3, POU5F1, transcript variant 4, and POU5F1 transcript variant 5. In certain embodiments, the amino acid sequence encoding human OCT4 is at least 70% (e.g., at least 75%, 80%, 85%, 90%, 95%, 98%, 99%, or 100%) identical to a nucleic acid (e.g., engineered nucleic acid) described in the NCBI RefSeq under accession number NP_001167002.1, NP_001272915.1, NP_001272916.1, NP_002692.2, or NP_976034.4. In certain embodiments, an OCT4 comprises an amino acid sequence that is at least 70% (e.g., at least 75%, 80%, 85%, 90%, 95%, 98%, 99%, or 100%) identical to SEQ ID NO: 2. SEQ ID NO: 2 is a non-limiting example of an amino acid sequence encoding OCT4 from *Mus musculus*. In certain embodiments, an OCT4 comprises an amino acid sequence that is at least 70% (e.g., at least 75%, 80%, 85%, 90%, 95%, 98%, 99%, or 100%) identical to SEQ ID NO: 41. SEQ ID NO: 41 is a non-limiting example of an amino acid sequence encoding human OCT4. Other OCT4 transcription factors (e.g., from other species) are known and nucleic acids (e.g., engineered nucleic acids) encoding OCT4 transcription factors can be found in publically available databases, including GenBank.

The term "promoter" refers to a control region of a nucleic acid (e.g., engineered nucleic acid) sequence at which initiation and rate of transcription of the remainder of a nucleic acid (e.g., engineered nucleic acid) sequence are controlled. A promoter may also contain sub-regions at which regulatory proteins and molecules may bind, such as RNA polymerase and other transcription factors. Promoters may be constitutive, inducible, activatable, repressible, tissue-specific, or any combination thereof. A promoter drives expression or drives transcription of the nucleic acid (e.g., engineered nucleic acid) sequence that it regulates. Herein, a promoter is considered to be "operably linked" when it is in a correct functional location and orientation in relation to a nucleic acid (e.g., engineered nucleic acid) sequence it regulates to control ("drive") transcriptional initiation of that sequence, expression of that sequence, or a combination thereof.

A promoter may promote ubiquitous expression or tissue-specific expression of an operably linked nucleic acid (e.g., engineered nucleic acid) sequence from any species, including humans. In some embodiments, the promoter is a eukaryotic promoter. Non-limiting examples of eukaryotic promoters include TDH3, PGK1, PKC1, TDH2, PYK1, TPI1, AT1, CMV, EF1 alpha, SV40, PGK1 (human or mouse), Ubc, human beta actin, CAG, TRE, UAS, Ac5, Polyhedrin, CaMKIIa, GAL1, GAL10, TEF1, GDS, ADH1, CaMV35S, Ubi, H1, and U6, as would be known to one of ordinary skill in the art (see, e.g., Addgene website: blog.addgene.org/plasmids-101-the-promoter-region).

Non-limiting examples of ubiquitous promoters include tetracycline-responsive promoters (under the relevant conditions), CMV (e.g., SEQ ID NO: 48), EF1 alpha, a SV40 promoter, PGK1, Ubc, CAG, human beta actin gene promoter, a RSV promoter (e.g., SEQ ID NO: 47), an EFS promoter (e.g., SEQ ID NO: 49), and a promoter comprising an upstream activating sequence (UAS). In certain embodiments, the promoter is a mammalian promoter.

Non-limiting examples of tissue-specific promoters include brain-specific, liver-specific, muscle-specific, nerve cell-specific, lung-specific, heart-specific, bone-specific, intestine-specific, skin-specific promoters, brain-specific promoters, and eye-specific promoters. As an example, a muscle-specific promoter is a desmin promoter (e.g., a sequence that is at least 70% (e.g., at least 75%, 80%, 85%, 90%, 95%, 98%, 99%, or 100%) identical to SEQ ID NO: 29). Non-limiting examples of eye-specific promoters include human GRK1 (rhodopsin kinase) promoter (e.g., SEQ ID NO: 50), human CRX (cone rod homeobox transcription factor) promoter (e.g., SEQ ID NO: 51), and human NRL promoter (neural retina leucine zipper transcription factor enhancer upstream of the human TK terminal promoter).

In some embodiments, a promoter is specific for senescent cells. For example, a promoter may specifically induce expression of an operably linked nucleic acid in a senescent cell and not in non-senescent cells. As a non-limiting example, the p16 promoter may be used to promote expression of a operably linked nucleic acid in senescent cells.

In some embodiments, a promoter of the present disclosure is suitable for use in AAV vectors. See, e.g., U.S. Patent Application Publication No. 2018/0155789, which is hereby incorporated by reference in its entirety for this purpose.

Non-limiting examples of constitutive promoters include CP1, CMV, EF1 alpha, SV40, PGK1, Ubc, human beta actin, beta tubulin, CAG, Ac5, Rosa26 promoter, COL1A1 promoter, polyhedrin, TEF1, GDS, CaM3 5S, Ubi, H1, U6, red opsin promoter (red promoter), rhodopsin promoter (rho promoter), cone arrestin promoter (car promoter), rhodopsin kinase promoter (rk promoter). An Ubc promoter may comprise a sequence that is at least 70% (e.g., at least 75%, 80%, 85%, 90%, 95%, 98%, 99%, or 100%) identical to SEQ ID NO: 18. In some instances, the constitutive promoter is a Rosa26 promoter. In some instances, the constitutive promoter is a COL1A1 promoter. A red opsin promoter may comprise a sequence that is at least 70% (e.g., at least 75%, 80%, 85%, 90%, 95%, 98%, 99%, or 100%) identical to SEQ ID NO: 101. A rho promoter may comprise a sequence that is at least 70% (e.g., at least 75%, 80%, 85%, 90%, 95%, 98%, 99%, or 100%) identical to SEQ ID NO: 102. A cone arrestin promoter may comprise a sequence that is at least 70% (e.g., at least 75%, 80%, 85%, 90%, 95%, 98%, 99%, or 100%) identical to SEQ ID NO: 103. A rhodopsin kinase promoter may comprise a sequence that is at least 70% (e.g., at least 75%, 80%, 85%, 90%, 95%, 98%, 99%, or 100%) identical to SEQ ID NO: 104. A tissue-specific promoter may be used to drive expression of an engineered nucleic acid, including e.g., a nucleic acid encoding a rtTA, tTA, OCT4, KLF4, SOX2, or any combination thereof. In some embodiments, a tissue-specific promoter is used to drive expression of a rtTA or a rTA. Ins one embodiments, a tissue-specific promoter is used to drive expression of OCT4, KLF4, and SOX2. In some embodiments, the tissue-specific promoter is selected from the group consisting of SEQ ID NOS: 101-104. In some embodiments, the hRK promoter is used to drive expression of OCT4, KLF4, and SOX2.

An "inducible promoter" is one that is characterized by initiating or enhancing transcriptional activity when in the presence of, influenced by, or contacted by an inducing agent. An inducing agent may be endogenous or a normally exogenous condition, compound, agent, or protein that contacts an engineered nucleic acid (e.g., engineered nucleic acid) in such a way as to be active in inducing transcriptional activity from the inducible promoter. In certain embodiments, an inducing agent is a tetracycline-sensitive protein (e.g., tTA or rtTA, TetR family regulators).

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (TetR, e.g., SEQ ID NO: 26, or TetRKRAB, e.g., SEQ ID NO: 27), a tetracycline operator sequence (tetO) and a tetracycline transactivator fusion protein (tTA), and a tetracycline operator sequence (tetO) and a reverse tetracycline transactivator fusion protein (rtTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), pH-regulated promoters, and light-regulated promoters. A non-limiting example of an inducible system that uses a light-regulated promoter is provided in Wang et al., *Nat. Methods.* 2012 Feb. 12; 9(3):266-9.

In certain embodiments, an inducible promoter comprises a tetracycline (Tet)-responsive element. For example, an inducible promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7). As an example, a TRE (e.g., TRE2) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 23. As an example, a TRE (e.g., P tight) promoter may comprise a nucleic acid (e.g., engineered nucleic acid) sequence that is at least 70% (e.g., at least 75%, 80%, 85%, 90%, 95%, 98%, 99%, or 100%) identical to SEQ ID NO: 24.

Additional non-limiting examples of inducible promoters include mifepristone-responsive promoters (e.g., GAL4-E1b promoter) and coumermycin-responsive promoters. See, e.g., Zhao et al., *Hum Gene Ther.* 2003 Nov. 20; 14(17): 1619-29.

A "reverse tetracycline transactivator" ("rtTA"), as used herein, is an inducing agent that binds to a TRE promoter (e.g., a TRE3G, a TRE2 promoter, or a P tight promoter) in the presence of tetracycline (e.g., doxycycline) and is capable of driving expression of a transgene that is operably linked to the TRE promoter. rtTAs generally comprise a mutant tetracycline repressor DNA binding protein (TetR) and a transactivation domain (see, e.g., Gossen et al., *Science.* 1995 Jun. 23; 268(5218):1766-9 and any of the transactivation domains listed herein). The mutant TetR domain is capable of binding to a TRE promoter when bound to tetracycline. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

"SRY-box 2" or "SOX2" is a member of the SRY-related HMG-box (SOX) family of transcription factors. SOX2 has been implicated in promoting embryonic development. Members of the SOX (SRY-related HMG-box) family of transcription factors are characterized by a high mobility group 5 (HMG)-box DNA sequence. This HMG box is a DNA binding domain that is highly conserved throughout eukaryotic species. A SOX2 transcription factor, homolog or variant thereof, as used herein, may be derived from any species, including humans. In certain embodiments, the nucleic acid (e.g., engineered nucleic acid) encoding SOX2 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_011443.4. In certain embodiments, the nucleic acid (e.g., engineered nucleic acid) encoding a human SOX2 comprises a sequence that is at least 70% (e.g., at least 75%, 80%, 85%, 90%, 95%, 98%, 99%, or 100%) identical to a nucleic acid (e.g., engineered nucleic acid) described in the NCBI RefSeq under accession number NM_003106.4. In certain embodiments, SOX2 comprises a nucleic acid (e.g., engineered nucleic acid) sequence that is at least 70% (e.g., at least 75%, 80%, 85%, 90%, 95%, 98%, 99%, or 100%) identical to SEQ ID NO: 3 or SEQ ID NO: 42. SEQ ID NO: 3 is a non-limiting example of a nucleotide sequence encoding SOX2 from *Mus musculus*. SEQ ID NO: 42 is a non-limiting example of a nucleotide sequence encoding human SOX2. In certain embodiments, the nucleic acid (e.g., engineered nucleic acid) encoding human SOX2 comprises a sequence that is at least 70% (e.g., at least 75%, 80%, 85%, 90%, 95%, 98%, 99%, or 100%) identical to the amino acid sequence described in the NCBI RefSeq under accession number NP_003097.1. In some instances, SOX2 comprises an amino acid sequence that is at least 70% (e.g., at least 75%, 80%, 85%, 90%, 95%, 98%, 99%, or 100%) identical to SEQ ID NO: 4. In some instances, SOX2 comprises an amino acid sequence that is at least 70% (e.g., at least 75%, 80%, 85%, 90%, 95%, 98%, 99%, or 100%) identical to SEQ ID NO: 43. SEQ ID NO: 4 is a non-limiting example of an amino acid sequence encoding SOX2 from *Mus musculus*. SEQ ID NO: 43 is a non-limiting example of an amino acid sequence encoding human SOX2.

A "multicistronic vector" is a vector that encodes more than one amino acid sequence (e.g., a vector encoding OCT4 and KLF4, OCT4 and SOX2, KLF4 and SOX2, or OCT4, SOX2, and KL4 (OSK)). A multicistronic vector allows for expression of multiple amino acid sequences from a nucleic acid (e.g., engineered nucleic acid) sequence. Nucleic acid (e.g., engineered nucleic acid) sequences encoding each transcription factor (e.g., OCT4, KLF4, or SOX2) may be connected or separated such that they produce unconnected proteins. For example, internal ribosome entry sites (IRES) or polypeptide cleavage signals may be placed between nucleic acid (e.g., engineered nucleic acid) sequences encoding each transcription factor in a vector. Exemplary polypeptide cleavage signals include 2A peptides (e.g., T2A, P2A, E2A, and F2A). A 2A peptide may comprise a sequence that is at least 70% (e.g., at least 75%, 80%, 85%, 90%, 95%, 98%, 99%, or 100%) identical to SEQ ID NO: 9. In some embodiments, an expression vector of the present disclosure is a multicistronic expression vector.

"Reversing aging" or "reversing ageing" as used herein refers to modifying the physical characteristics associated with aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the animal is a mammal. The animal may be a male or female and at any stage of development. A non-human animal may be a transgenic animal.

One of ordinary skill in the art would recognize that the biological age of a pediatric subject or adult subject may vary depending on the type of animal. As a non-limiting example, an adult mouse may be 1 year of age, while an adult human may be more than 21 years of age. In some embodiments, a pediatric subject is less than 21 years of age, less than 20 years of age, less than 15 years of age, less than 10 years of age, less than 9 years of age, less than 8 years of age, less than 7 years of age, less than 6 years of age, less than 5 years of age, less than 4 years of age, less than 3 years of age, less than 2 years of age, less than 1 year of age, less than 10 months of age, less than 9 months of age, less than 8 months of age, less than 7 months of age, less than 6 months of age, less than 5 months of age, less than 4 months of age, less than 2 months of age, or less than 1 month of age. In some embodiments, an adult subject is at least 3 weeks of age, 1 month of age, at least 2 months of age, at least 3 months of age, at least 4 months of age, at least 5 months of age, at least 6 months of age, at least 7 months of age, at least 8 months of age, at least 9 months of age, at least 10 months of age, at least 11 months of age, at least 1 year of age, at least 2 years of age, at least 3 years of age, at least 5 years of age, at least 10 years of age, at least 15 years of age, at least 20 years of age, at least 25 years of age, at least 30 years of age, at least 40 years of age, at least 50 years of age, at least 55 years of age, at least 60 years of age, at least 65 years of age, at least 70 years of age, at least 75 years of age, at least 80 years of age, at least 90 years of age, or at least 100 years of age. In some embodiments, a middle-aged adult subject is between 1 and 6 months of age, between 6 and 12 months of age, between 1 year and 5 years of age, between 5 years and 10 years of age, between 10 and 20 years of age, between 20 and 30 years of age, between 30 and 50 years of age, between 50 and 60 years of age, between 40 and 60 years of age, between 40 and 50 years of age, or between 45 and 65 years of age. In some embodiments, a senior adult subject is at least 1 month of age, at least 2 months of age, at least 3 months of age, at least 4 months of age, at least 5 months of age, at least 6 months of age, at least 7 months of age, at least 8 months of age, at least 9 months of age, at least 10 months of age, at least 11 months of age, at least 1 year of age, at least 2 years of age, at least 3 years of age, at least 5 years of age, at least 10 years of age, at least 15 years of age, at least 20 years of age, at least 25 years of age, at least 30 years of age, at least 40 years of age, at least 50 years of age, at least 55 years of age, at least 60 years of age, at least 65 years of age, at least 70 years of age, at least 75 years of age, at least 80 years of age, at least 90 years of age, or at least 100 years of age.

A "terminator" or "terminator sequence," as used herein, is a nucleic acid (e.g., engineered nucleic acid) sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid (e.g., engineered nucleic acid) sequences by upstream promoters. Thus, in certain embodiments, a terminator that ends the production of an RNA transcript is contemplated.

The most commonly used type of terminator is a forward terminator. When placed downstream of a nucleic acid (e.g., engineered nucleic acid) sequence that is usually transcribed, a forward transcriptional terminator will cause transcription to abort. In some embodiments, bidirectional transcriptional terminators may be used, which usually cause transcription to terminate on both the forward and reverse strand. In some embodiments, reverse transcriptional terminators may be used, which usually terminate transcription on the reverse strand only.

Non-limiting examples of mammalian terminator sequences include bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA, and arcA terminator. In certain embodiments, the terminator sequence is SV40 and comprises a sequence that is at least 70% (e.g., at least 75%, 80%, 85%, 90%, 95%, 98%, 99%, or 100%) identical to SEQ ID NO: 8.

A "Tet-Off" system, as used herein, is a type of inducible system that is capable of repressing expression of a particular transgene in the presence of tetracycline (e.g., doxycycline (DOX)). Conversely, a Tet-Off system is capable of inducing expression of a particular transgene in the absence of tetracycline (e.g., doxycycline, DOX). In certain embodiments, a Tet-Off system comprises a tetracycline-responsive promoter operably linked to a transgene (e.g., encoding OCT4; KLF4; SOX2; or any combination thereof) and a tetracycline-controlled transactivator (tTA). The transgene with the tetracycline-responsive promoter (e.g., TRE3G, P tight, or TRE2) and the tetracycline-controlled transactivator may be encoded on the same vector or be encoded on separate vectors. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

A "Tet-On" system, as used herein, is a type of inducible system that is capable of inducing expression of a particular transgene in the presence of tetracycline (e.g., doxycycline (DOX)). In certain embodiments, a Tet-On system comprises a tetracycline-responsive promoter operably linked to a transgene (e.g., encoding OCT4; KLF4; SOX2; or any combination thereof) and a reverse tetracycline-controlled transactivator (rtTA). For example, the rtTA may be rtTA3, rtTA4, or variants thereof. In certain embodiments, a nucleic acid (e.g., engineered nucleic acid) encoding rtTA3 comprises a sequence that is at least 70% (e.g., at least 75%, at least 80%, at least 85%, at least 90%, at least 95%, or at least 100%) identical to SEQ ID NO: 10. In certain embodiments, an amino acid sequence encoding rtTA3 comprises a sequence that is at least 70% (e.g., at least 75%, at least 80%, at least 85%, at least 90%, at least 95%, at least 98%, at least 99%, or at least 100%) identical to (SEQ ID NO: 11). In certain embodiments, a nucleic acid (e.g., engineered nucleic acid) encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 12. In certain embodiments, an amino acid sequence encoding rtTA4 comprises a sequence that is at least 70% (e.g., at least 75%, at least 80%, at least 85%, at least 90%, at least 95%, at least 98%, at least 99%, or at least 100%) identical to (SEQ ID NO: 13). The expression cassette encoding a tetracycline-responsive promoter (e.g., a promoter comprising a TRE, including TRE3G, P tight, and TRE2) and a reverse tetracycline-controlled transactivator may be encoded on the same vector or be encoded on separate vectors. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal, damaged, or unhealthy tissue, which may need to be treated. A tissue may also be a normal or healthy tissue that is under a higher than normal risk of becoming abnormal or unhealthy, which may need to be prevented. In certain embodiments, the tissue is considered healthy but suboptimal for performance or survival in current or future conditions. For example, in agricultural practice, environmental conditions including weather and growing conditions (e.g., nutrition) may benefit from any of the methods described herein. In certain embodiments, the tissue is the central nervous system. In certain embodiments, the tissue refers to tissue from the In certain embodiments, the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine. In certain embodiments, the tissue is damaged (e.g., due to a congenital defect, an injury, an accident, or an iatrogenic injury) and/or is aged tissue. In certain embodiments, the tissue is a deep tissue that is reachable with a fiber optic probe.

The term "tetracycline repressor" or "TetR" refers to a protein that is capable of binding to a Tet-O sequence (e.g., a Tet-O sequence in a TRE, e.g., a Tet-O sequence may comprise SEQ ID NO: 19) in the absence of tetracycline (e.g., doxycycline) and prevents binding of rtTA (e.g., rtTA3, rtTA4, or variants thereof) in the absence of tetracycline (e.g., doxycycline). TetRs prevent gene expression from promoters comprising a TRE in the absence of tetracycline (e.g., doxycycline). In the presence of tetracycline, TetRs cannot bind promoters comprising a TRE, and TetR cannot prevent transcription. Non-limiting examples of TetRs include tetR (e.g., SEQ ID NO: 26), tetRKRAB (e.g., SEQ ID NO: 28). In some embodiments, a TetR is a TetR fusion (e.g., TRSID, which may be created by fusing TetR to a mSIN30interacting domain (SID) of Madl). See, e.g., Zhang et al., J Biol Chem. 2001 Nov. 30; 276(48):45168-74.

As used herein, a "TRE promoter" is a promoter comprising a tetracycline-responsive element (TRE). As used herein, a TRE comprises at least one (e.g., at least 2, 3, 4, 5, 6, 7, 8, 9, 10, 11, 12, 13, 14, 15, 16, 17, 18, 19, or 20) Tet-O sequences. A non-limiting example of a Tet-O sequence is sequence that is at least 70% (e.g., 75%, 80%, 85%, 90%, 95%, 98%, 99%, or 100%) identical to SEQ ID NO: 19. In some embodiments, a TRE promoter further comprises a minimal promoter located downstream of a tet-O sequence. A minimal promoter is a promoter that comprises the minimal elements of a promoter (e.g., TATA box and transcription initiation site), but is inactive in the absence of an upstream enhancer (e.g., sequences comprising Tet-O). As an example, a minimal promoter may be a minimal CMV promoter that comprises a sequence that is at least 70% (e.g., at least 75%, 80%, 85%, 90%, 95%, 98%, 99%, or 100%) identical to SEQ ID NO: 20. For example, a TRE promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7. In some embodiments, a TRE promoter is a TRE2 promoter comprising a sequence that is at least 70% (e.g., at least 75%, 80%, 85%, 90%, 95%, 98%, 99%, or 100%) identical to SEQ ID NO: 23. In some embodiments, a TRE promoter is a P tight promoter comprising a sequence that is at least 70% (e.g., at least 75%, 80%, 85%, 90%, 95%, 98%, 99%, or 100%) identical to SEQ ID NO: 24.

The term "tissue repair" in the context of damaged tissue refers to restoration of tissue architecture, function following tissue damage, or a combination thereof. Tissue repair includes tissue regeneration, cell growth, tissue replacement, and/or rewiring of existing tissue (reprogramming).

The term "tissue regeneration" refers to production of new tissue or cells within a tissue that are the same type as the tissue of interest (e.g., same type as the damaged tissue or cell). In some embodiments, the methods provided herein promote organ regeneration.

The term "tissue replacement" refers to production of a different type of tissue compared to the tissue of interest (e.g., connective tissue to replace damaged tissue).

As used herein, the terms "treatment," "treat," and "treating" refer to reversing, alleviating, delaying the onset of, or inhibiting the progress of a disease or disorder, or one or more symptoms thereof, as described herein. In certain embodiments, treatment may be administered after one or more symptoms have developed. In other embodiments, treatment may be administered in the absence of symptoms. For example, treatment may be administered to a susceptible individual prior to the onset of symptoms or may be treated with another damaging agent (e.g., in light of a history of symptoms, in light of genetic or other susceptibility factors, a disease therapy, or any combination thereof). Treatment may also be continued after symptoms have resolved, for example, to prevent or delay their recurrence.

The term "variant" refers to a sequence that comprises a modification relative to a wild-type sequence. Non-limiting modifications in an amino acid sequence include insertions, deletions, and point mutations. Non-limiting modifications to nucleic acid (e.g., engineered nucleic acid) sequences include frameshift mutations, nucleotide insertions, and nucleotide deletions.

The term "WPRE" refers to a Woodchuck Hepatitis Virus (WHP) Posttranscriptional Regulatory Element (WPRE). WPREs create tertiary structures in nucleic acids (e.g., expression vectors) and are capable of enhancing transgene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 21.

These and other exemplary substituents are described in more detail in the Detailed Description, Examples, and claims. The invention is not intended to be limited in any manner by the above exemplary listing of substituents.

BRIEF DESCRIPTION OF THE DRAWINGS

FIGS. 4A-4AL show SEQ ID NO: 16 from 5' to 3'. FIGS. 4G-4AC show the protein sequence, SEQ ID NO: 123.

FIGS. 5A-5D show the nucleotide positions and lengths of the nucleic acid (e.g., engineered nucleic acid) sequences of the features shown in FIGS. 4A-4AL.

FIG. 6A shows the effect of doxycycline on protein expression in cells infected with AAV9 virus harboring the TRE3G–OSK–SV40 pA vector and with AAV9 virus harboring a vector that encodes rtTA3 (tetracycline (Tet)-on system). FIG. 6B shows the effect of DOX on protein expression in cells infected with AAV2 virus harboring the TRE3G–OSK–SV40 pA vector and with AAV2 virus harboring a vector that encodes tTA (Tet-Off system). FIG. 6C shows the effect of DOX treatment and DOX removal on protein expression in cells infected with AAV.PHP.b virus harboring the TRE3G–OSK–SV40 pA vector and with AAV.PHP.b virus harboring a vector that encodes rtTA3 (Tet-On system). The length of DOX treatment (+DOX) or DOX removal (−DOX) in days is indicated in parenthesis.

FIG. 7A includes a series of photos showing that injection of TRE–OSK–SV40 AAV virus and CAG-tTA AAV virus into mouse retina resulted in expression of KLF4 in mouse retina ganglion cells (RGCs). RBPMS (RGC marker) and KLF4 staining of an optical coherence tomography (OCT) section from mouse retina is shown. FIG. 7B includes a series of photos showing that injection of TRE–OSK–SV40 AAV virus and CAG-tTA AAV virus resulted in inducible expression of KLF4 and OCT4 in mouse retina. OCT4 and KLF4 staining of a whole retina mount in the absence of doxycycline treatment (top two photos) and after four days of DOX treatment (bottom two photos) is shown. FIG. 7C shows an experimental timeline to determine the effect of TRE–OSK–SV40 AAV virus alone or in combination with CAG-tTA AAV virus on optical nerve regeneration following optic nerve crush damage. CTB stands for cholera toxin β-subunit and allows for fluorescence imaging of axons. FIG. 7D shows the co-localization staining of OCT4 and KLF4 from a whole mount retina with TRE–OSK–SV40 AAV virus injected in combination with CAG-tTA, RBPMS stains retina ganglion cells specifically. FIG. 7E shows fluorescence imaging of CTB-labeled axons in an optical nerve after crush damage in mouse retina injected with TRE–OSK–SV40 AAV virus alone (left) or TRE–OSK–SV40 AAV in combination with CAG-tTA AAV (right). Stars represent the site of the lesion. FIG. 7F shows additional fluorescence images of optical nerves treated as in FIG. 7E with viruses as indicated.

FIG. 8A shows the effect of virus encoding tTA in combination with virus encoding TRE–OSK–SV40 in the absence of DOX (circles, n=9), with virus encoding TRE–OSK–SV40 in the presence of dox (triangles, n=5), or with virus encoding d2EGFP (squares, control, n=5) on RGC axon regeneration. The number of estimated axons per nerve is shown as a function of the distance from the site of injury (μm).

FIG. 8B is an experimental timeline to determine the effect of d2EGFP expression on RGC axon regeneration. FIG. 8C is a series of images showing CTB-labeled axons from the experiment outlined in FIG. 8B. FIG. 8D is an experimental timeline to determine the effect of uninduced OSK expression on axon regeneration. FIG. 8E is a series of images showing CTB-labeled axons from the experiment outlined in FIG. 4D. FIG. 8F is an experimental timeline to determine the effect of induced OSK expression on axon regeneration. FIG. 8G is a series of images showing CTB-labeled axons from the experiment outlined in FIG. 8F. Stars indicate the site of the lesion.

FIG. 9A shows staining for RBPMS and GFP in GFP AAV-infected uncrushed RGCs (upper left) and in crushed RGCs (upper right). staining for RBPMS and KLF4 in OSK AAV-infected uncrushed RGCs (lower left) and in crushed RGCs (lower right). FIG. 9B shows the ratio of RBPMS (RNA binding protein with multiple splicing)-positive (+) cells for uncrushed and crushed RGCs infected with a destabilized form of GFP (d2EGFP) virus or OSK virus. GFP infected RGCs has the same survival rate as uninfected RGCs, therefore GFP+ RBPMs+% remains the same after crush injury. OSK infected RGCs had triple the survival rate compared to uninfected RGC, therefore, KLF4+ RBPMS+% increased after crush injury. FIG. 9C shows survived RGCs under uncrushed (left) and crushed (right) condition, with OSK virus infection. FIG. 9D shows the survival of RGCs (RBPMS+) under uncrushed and crushed condition, when they were infected with d2EGFP virus or OSK virus.

FIG. 10A is a series of images showing RBPMS and pS6 staining of control and OSK-infected RGCs that were uncrushed or crushed. FIG. 10B is a graph quantifying the percentage of pS6 positive cells from series of pictures like FIG. 10A.

FIGS. 11A-11D show that an AAV Tet-On system comprising a CMV-rtTA vector (SEQ ID NO: 31) induces faster gene expression compared to an AAV Tet-Off system in retinal cells after nerve crush. FIG. 11A shows an experimental timeline to test the effect of doxycycline removal on GFP expression in an AAV Tet-Off system. Lines indicate the length of DOX treatment. Treatments A-D as indicated correspond to photographs 1-4 of FIG. 7B, respectively. FIG. 11B is a series of photos showing results of the experiment outlined in FIG. 11A. GFP-positive cells from mouse retina that was infected with virus encoding tTA and virus encoding TRE-d2EGFP at indicated days of DOX removal are shown. FIG. 11C shows an experimental timeline to test the effect of doxycycline treatment on GFP expression in an AAV Tet-On system comprising a CMV-rtTA vector (SEQ ID NO: 31). Lines indicate the length of DOX treatment. Treatments A-C as indicated correspond to photographs 1-3 of FIG. 11D, respectively. FIG. 11D is a series of photos showing results of the experiment outlined in FIG. 11C. GFP-positive cells from mouse retina that was infected with virus encoding rtTA and virus encoding TRE-d2EGFP at the indicated days of DOX treatment are shown.

FIGS. 13A-13C include data showing that a Tet-On system comprising rtTA4 (SEQ ID NO: 13) has low leakiness in the liver of mice. FIG. 13A is a series of immunofluorescence images showing expression of KLF4 in the livers of mice that have been administered AAVs harboring nucleic acids (e.g., engineered nucleic acids) shown in FIG. 13B in the absence of doxycycline (no DOX) and in the presence of doxycycline (with DOX). DAPI is a nuclear stain that was used to visualize cells. FIG. 13B is a schematic depicting the two nucleic acids (e.g., engineered nucleic acids) that were administered to mice in AAV9 viruses. FIG. 13C is a western blot of liver samples from mice that received the constructs depicted in FIG. 13B and were treated with no doxycycline or with doxycycline. OCT4, KLF4, and SOX2 levels were detected as indicated using antibodies. Actin is shown as a loading control.

FIG. 21 is a series of images showing successful chemical reprogramming of mouse embryonic fibroblasts.

FIG. 22 includes a schematic showing a non-limiting example of a Tet-Off system to express OCT4, SOX2, and KLF4 in the absence of tetracycline (top panel) and a schematic showing a non-limiting example of a Tet-ON system to express OCT4, SOX2, and KLF4 (OSK) in the presence of tetracycline (bottom panel).

FIG. 23A is a series of images showing CTB-labeled axons from mice at indicated ages (in months) and comparing the effect of AAV2 virus encoding TRE–OSK–SV40 with the effect of AAV2 virus encoding GFP. Experiments were conducted in the absence of DOX using the Tet-Off system depicted in FIG. 22, top panel. FIG. 23B quantifies the number of estimated axons per nerve for mice with the indicated ages and treatments as a function of the distance from the site of injury (μm). FIG. 23C is a chart showing that OSK increased the survival of RGCs after optic nerve injury in adult (3 month old) and aged (12 month old) mice compared to control GFP. The survival of RGCs (RBPMS+) is shown for mice of the indicated ages receiving virus encoding d2EGFP or OSK.

FIG. 24A is a series of photos showing CTB-labeled axons from 12 month old mice five weeks after optic nerve crush injury. Mice were administered virus encoding GFP or encoding TRE-SV40-OSK and virus encoding tTA prior to nerve crush injury. FIG. 24B is a graph quantifying the number of estimated axons per nerve as a function of the distance from the site of injury (μm) from FIG. 24A.

FIG. 25A includes schematics showing treatment timelines to determine the effect of OSK expression before or after optic nerve crush. In the Tet-On system, induction of OSK expression prior to optic nerve crush injury (pre-injury induction) and induction of OSK expression after optic nerve crush injury (post-injury induction) are shown (top panel). Doxycycline treatment was used to induce OSK expression. In the Tet-Off system, suppression of OSK induction with doxycycline treatment prior to optic nerve crush (pre-injury suppression) and suppression of OSK induction with doxycycline treatment after optic nerve crush (post-injury suppression) are shown (bottom panel). The shaded lines on the timeline indicate the length of doxycycline (DOX) treatment. Cholera toxin β-subunit (CTB) injection for imaging of axons is also shown. FIG. 25B is a chart quantifying the number of estimated axons per nerve as a function of the distance from the site of injury (μm) for four-week old (young) mice with no OSK induction (n=4), OSK induction pre-injury only (n=5), OSK expression suppressed from injury (n=5), and OSK induction post injury (n=5). The protocols for pre-injury and post-injury induction used were as shown in FIG. 25A. FIG. 25C is a chart quantifying the number of RBPMS+ cells from four-week old (young) mice with no OSK induction, OSK induction pre-injury only, OSK suppressed from injury, and OSK induction post injury.

FIG. 26A is a schematic showing the AAV combinations injected in each group two weeks before the crush injury and non-limiting exemplary expression cassettes in Tet-Off systems encoding OCT4, SOX2, and/or KLF4. FIG. 26B is a chart showing that expression of OSK from a single transcript improved axon regeneration relative to expression of OCT4, SOX2, and KLF4 from separate transcripts. The number of estimated axons per nerve after optic nerve crush injury as a function of the distance from the site of injury (μm) was quantified for mice receiving tTA virus and one of the following (1) OCT4 virus, (2) SOX2 virus, (3) KLF4 virus, (4) virus with a vector encoding OCT4 and SOX2 under one promoter (OCT4-SOX2), (5) separate OCT4, SOX2, and KLF4 viruses (Oct4, Sox2, KLF4 or O,S,K), or (6) virus with a vector encoding OCT4, KLF4, and SOX2 under one promoter (Oct4-Sox2-KLF4 or OSK). The various vectors used are depicted in FIG. 26A. FIG. 26C is a chart showing that expression of OSK from a single transcript improved RGC survival relative to expression of OCT4, SOX2, and KLF4 from separate transcripts. FIG. 26D includes whole mount staining of mouse retina showing that a heterogeneous population of cells with few RBPMS+ cells were detected when separate viral vectors encoding OCT4, SOX2, and KLF4 in separate viruses were delivered to the eye of mice. Arrows point to seven different types of cells expressing OCT4, SOX2, KLF4, and/or RBPMS in the upper left image under the schematic of the vectors. FIG. 26E includes data showing that a more homogenous population of cells was detected when virus comprising a viral vector encoding OSK under one promoter was delivered to the eye of mice as compared to FIG. 26D. More OSK-expressing cells that were also RBPMS+ were detected as compared to FIG. 26D. In the upper left image under the schematic of the vector used, the long white arrow points to RBPMS+ cells expressing OCT4, SOX2, and KLF4 and the shorter arrow indicates even some cells that did not express RBPMS expressed OSK.

FIG. 28 is a chart showing that intravitreal injection of mice with virus encoding tTA and virus encoding TRE-OSK in the absence of doxycycline (OSK induction condition) reversed the age-related decrease in the spatial frequency threshold (cycles/degree, visual acuity test) observed in aged mice (12 month old (12 m) and 18 month old (18 m) mice). A visual acuity test based on optomotor response (OMR) was used. As controls, age-matched mice received virus encoding virus encoding rtTA and virus TRE-OSK in the absence of doxycycline (uninduced control). Adult mice (3 month old (3 m)) were also used as a control.

FIG. 29 is a chart showing the measurement of electrical waves generated from RGCs from adult (3 month old (3 m)) and aged (12 month old (12 m) and 18 month old (18 m)) mice. A pattern electroretinogram (pattern ERG) was used. Mice were injected with rtTA virus and TRE-OSK virus without doxycycline (uninduced control (ctl)) or with tTA virus and TRE-OSK virus (induced, OSK) without doxycycline. Results were obtained one month after virus injection.

FIG. 30A is a chart showing that polystyrene microbeads induced glaucoma as measured by an increase in intraocular pressure (IOP) compared to saline treatment in adult C57BL/6J mice. The IOP measurements are shown in the first four weeks after microbead injection. FIGS. 30B-30C show that 4 weeks after microbeads injection into the anterior chamber of the eye, there was significant loss of axon density and RGC density. AAVs were intravitreally injected at 3 weeks post microbeads and it took another week before OSK expression was observed. FIG. 30B includes a chart quantifying axon density (left panel) using p-phenylenediamine (PPD) staining (shown, for example, on the right). FIG. 30C includes a chart quantifying RGC cell density (left panel) using Brn3a staining (shown, for example, on the right). FIG. 30D is a chart showing visual acuity improvement by OSK AAV treatment in glaucoma-induced mice. Mice were intravitreally injected with microbeads to induce glaucoma or saline without microbeads (no glaucoma control; saline). Three weeks after microbeads injection, mice are then treated with (1) virus encoding rtTA and virus TRE-OSK in the absence of doxycycline (beads (OSK AAV OFF)); (2) virus encoding tTA and virus encoding TRE-OSK in the absence of doxycycline (beads (OSK AAV ON)). Results at 3 weeks after saline or microbead injection (pre-AAV injection) and 4 weeks after AAV injection (7 week post microbeads) are shown. FIG. 30E is a chart showing RGC function results by pattern electroretinogram in mice treated as in FIG. 30B.

FIG. 31A includes a series of images showing the effect of inducing OSK expression (OSK On) compared to no induction of OSK expression (OSK Off) on the structure of neurons. Images were taken at day 3 and at day 9 after 24 hours of VCS treatment. The outlines of the neuronal cell area are shown at Day 9. FIG. 31B is a chart quantifying neuron cell area ($\mu m^2$) at indicated days after 24 hours of VCS treatment for cells in which OSK expression was induced (OSK On) and for cells in which OSK expression was not induced (OSK Off). FIG. 31C is a chart quantifying neuron cell area ($\mu m^2$) at indicated days after 48 hours of VCS treatment for cells in which OSK expression was induced (OSK On) and for cells in which OSK expression was not induced (OSK Off).

FIG. 32A is a schematic of the Tet-On and Tet-Off AAV vectors used in the study to control OSK expression. FIG. 32B shows body weight of WT mice, OSK transgenic mice, and AAV-mediated OSK-expressing mice ($1.0 \times 10^{12}$ gene copies) with or without doxycycline induction in the first 4 weeks (n=5, 3, 6, 4, 6, 3, respectively). FIG. 32C is a schematic showing intravitreal AAV injection to target retina ganglion cells. Immunofluorescence of the whole-mounted display and cross section of retina, showing the infection rate and targeted retina layer. The scale bars represent 1 mm and 100 μm, respectively. FIG. 32D shows an experimental outline of the optic nerve crush study using the Tet-Off system. FIG. 32E shows quantification of the regenerating fibers by to d2EGFP, Oct4, Sox2, Klf4, OS, O+S+K, or OSK AAV at different distances distal to the lesion site. Error bars indicate s.e.m. (n=4-7). **, P<0.0001, ANOVA with Bonferroni posttests. FIG. 32F shows the survival of RBPMS-positive cells in the RGC layer transduced with different AAV vectors at day 14 post crush injury (n=4-8). *, P<0.001, ****, P<0.0001, one-way ANOVA with Bonferroni post-tests, relative to d2EGFP.

FIG. 32G shows representative images of optic nerve sections showing CTB-labeled axons in wild-type mice with intravitreal injection of AAV2–tTA and TRE–OSK in the presence and absence of DOX at 2 weeks after optic nerve injury. The crush site is indicated by asterisks. The scale bars represent 200 μm.

FIGS. 33A-33K show that OSK expression promotes axon regeneration and neuronal survival through a Tet-dependent mechanism. FIG. 33A shows experimental strategies for pre- and post-injury induction of OSK expression. FIG. 33B shows RGC survival in retinas with pre- and post-injury OSK expression. FIG. 33C shows the quantification of regenerating fibers from pre- and post-injury OSK expression models. FIG. 33D shows representative images of optic nerves showing regenerating axons at 4 weeks after injury, with or without post injury OSK expression. The crush site is indicated with asterisks. The scale bars represent 200 μm. FIGS. 33E-33F show the quantification of regenerating fibers and RGC survival in retinas co-transduced with AAV2 vectors encoding polycistronic OSK, tTA, and shRNA vectors with a scrambled sequence (Scr), Tet1, or Tet2 sequences to knockdown Tet DNA dioxygenases/demethylases. FIG. 33G shows experimental outlines for examining axon regeneration in human neurons post vincristine (VCS) damage. FIG. 33H shows that OSK rejuvenates human neurons according to the skin & blood clock. In the top panel of FIG. 33H, P value is calculated by linear regression model to see if DNAmAge decrease with time. In the bottom panel of FIG. 33H, DNA methylation age of human neurons with OSK expression pre (Day –) or after VCS damage (Day 1 and 9), estimated by skin and blood cell clocks is shown. FIG. 33I shows the neurite area in each AAV treatment group. *p<0.05, p<0.01, **p<0.0001, one-way ANOVA with Tukey's multiple comparison test. FIG. 33J shows representative images of human neurons and the neurite area after 9 days of recovery from VCS damage. FIG. 33K shows rDNA methylation age of 1-month-old RGCs isolated from axon-intact retina infected with or without GFP, or from axon-injured retinas infected with GFP-AAV or OSK-AAV 4 days after nerve crush.

FIG. 34A is a schematic showing the experimental outline. FIG. 34B shows Intraocular pressure measured weekly by rebound tonometry for the first 4 weeks post-microbead injection. FIG. 34C shows Representative micrographs of PPD-stained optic nerve cross-sections at 4 wks post AAV2 or PBS injection. Scale bars, 50 μm. OSK Off (rtTA+TRE–OSK); OSK On (tTA+TRE–OSK). FIG. 34D shows a quantification of healthy axons of the optic nerve at 4 weeks post PBS or AAV injection. FIG. 34E is a Schematic of High-contrast visual stimulation assay to measure optomotor response. A reflexive head movement in response to the rotation of a moving stripe pattern that increases in spatial frequency was used to assess vision. FIG. 34F shows Spatial frequency threshold response of each mouse measured before treatment and 4 weeks after intravitreal injection of AAV vectors. FIG. 34G shows Representative pERG waveforms recorded from the same eye at baseline before treatment and four weeks later after treatment with OSK-OFF AAV (top graph) or OSK-ON AAV (bottom graph). FIG. 34H shows the Mean pERG amplitudes of recordings measured from each mouse at baseline before treatment and 4 weeks after intravitreal injection of AAVs. *P<0.05; P<0.01; *P<0.001, ****P<0.0001 Two-way ANOVA with Turkey posttests between groups was used for the overall effect of time and treatment. A paired t-test was used to compare before and after treatments.

FIG. 35A shows an Experimental outline for testing the effects of OSK AAV treatment in aged mice on axon regeneration following optic nerve crush and restoration of vision loss associated with physiological aging. FIG. 35B shows Axon regeneration in 12-month-old mice with OSK AAV or control AAV (d2EGFP) treatment following 2 or 5 weeks post optic nerve crush. FIG. 35C Representative confocal images of longitudinal sections through the optic nerve showing CTB-labeled axons after 5 weeks of OSK treatment. Scale bar represents 200 μm. FIG. 35D The spatial frequency threshold in young mice (4 months) and old mice (12 months) treated with OSK-Off or OSK-On AAVs. FIGS. 35E-35F show Spatial frequency threshold and pERG amplitudes in old mice (12 months) treated with: (i) OSK-Off, (ii) OSK-On, or (iii) OSK-On plus either: sh-Scr, sh-Tet1- or sh-Tet2-mediated knockdown of DNA demethylases. OSK-Off, (rtTA+TRE–OSK); OSK-On, (tTA+OSK). FIG. 35G is hierarchical clustered heatmap showing RNA-Seq expression of 464 differentially expressed genes in cell sorted purified RGCs from intact young mice (5 months) or intact old mice (12 months), or old mice treated with either control AAV (TRE–OSK) or OSK-On AAV. FIG. 35H is a scatter plot of OSK-induced changes in RNA levels versus age-associated changes in mRNA levels. Dots represent differentially expressed genes in RGCs. FIG. 35I shows rDNA methylation age of 12-month-old RGCs FACS isolated from retinas infected for 4 weeks with –OSK or +OSK AAV together with short-hairpin DNAs with a scrambled sequence (sh-Scr) or targeted to Tet1 or Tet2 (sh-Tet1/sh-Tet2). Gene exclusion criteria for FIG. 35G and FIG. 35H: genes with low overall expression (log 2(CPM)<2), genes that did not significantly change with age (absolute log 2 fold-change <1) or genes altered by the virus (differentially expressed between intact old and old treatd with TRE–OSK AAV). *P<0.05; P<0.01; *P<0.001, ****P<0.0001. Two-way ANOVA in FIG. 35D; One-way ANOVA in FIGS. 35B, 35E and 35F.

FIGS. 36A-36H show an exploration of OSK (no Myc) effects on ageing and the safety of OSK AAV. FIG. 36A is a schematic of an experimental outline of testing reprogramming effect in young and old transgenic mouse fibroblasts. FIG. 36B shows OSKM expression rescues age-associated transcriptional changes without inducing pluripotency. For example, Nanog expression is not induced. FIG. 36C shows OSK expression rescues age-associated transcriptional changes without inducing pluripotency. For example, Nanog expression is not induced. FIG. 36D shows OSK AAV9 expression in the liver compared to transgenic mice. FIG. 36E shows the body weight of WT mice and AAV-mediated OSK-expressing mice ($1.0 \times 10^{12}$ gene copies total) with or without doxycycline in the following 9 months after first 4 weeks (n=5, 3, 6, 4, respectively). FIG. 36F shows AAV-UBC–rtTA and AAV–TRE–Luc vectors used for measuring tissue distribution. FIG. 36G shows luciferase imaging of WT mice at 2 months after retro-orbital injections of AAV9-UBC-rtTA and AAV9-TRE-Luc (1.0×10^12 gene copies total). Doxycycline was delivered in drinking water (1 mg/mL) for 7 days to the mouse shown on the right. FIG. 36H shows luciferase imaging of eye (Ey), brain (Br), pituitary gland (Pi), heart (He), thymus (Th), lung (Lu), liver (Li), kidney (Ki), spleen (Sp), pancreas (Pa), testis (Te), adipose (Ad), muscle (Mu), spinal cord (SC), stomach (St), small intestine (In), and cecum (Ce) 2 months after retro-orbital injection of AAV9-UBC-rtTA and AAV9-TRE-Luc followed by treatment with doxycycline for 7 days. The luciferase signal is primarily in liver. Imaging the same tissues with a longer exposure time (FIG. 36H, lower panel) revealed lower levels of luciferase signal in pancreas (liver was removed).

FIG. 37A shows an Immunofluorescence analysis of the whole-mounted retina transduced with a polycistronic AAV vector expressing OCT4, SOX2, and KLF4 in the same cell. Arrows point at triple positive cells. FIG. 37B shows an immunofluorescence analysis of the whole-mounted retina transduced with AAVs separately encoding OCT4, SOX2, and KLF4. Dotted arrows point to double-positive cells. Solid arrows point at single-positive cells, except for arrow in lower right corner of each image, which points at a triple positive cell. FIGS. 37C-37D are images showing whole-mounted retina display of RBPMS and Klf4 immunofluorescence. FIG. 37C shows that expression from AAV2 Tet-Off system can be turned off by Dox drinking water (2 mg/mL 3 days). FIG. 37D shows that expression from AAV2 Tet-On system can be turned on by Dox drinking water (2 mg/mL 2 days). Scale bars represent 1 mm.

FIG. 38A shows retina whole-mount staining showing OSK infected RGCs have no proliferation marker Ki67 (left), while proliferating 293T cells have Ki67 signal (right). The scale bars represent 100 μm. FIG. 38B shows whole nerve imaging of optic nerves showing regenerating axons from control (no AAV) or OSK AAV treatment at 3 months after injury. The scale bars represent 200 μm. FIG. 38C shows whole nerve imaging showing CTB-labeled regenerative axons at 16 weeks post-injury (wpc) in wild-type mice with intravitreal injection of AAV2-tTA and TRE-OSK. Scale bars represent 200 m.

FIG. 39A shows Representative images showing the d2EGFP expression in retina from Tet-Off AAV system with different Dox treatment. When pre-treated with DOX to suppress expression (on DOX), the GFP expression only showed up sparsely after DOX been withdrawal for 8 days, much weaker compared to peak expression (Never DOX). FIG. 39B are representative images showing the d2EGFP in retina from Tet-On AAV system. No GFP expression was observed in the absence of DOX, and GFP expression reached peak in 2 days after Dox induction and didn't get stronger with 5 days of DOX induction. FIG. 39C shows representative Immunofluorescence image of GFP-positive or KLF4-positive RGCs in intact and crushed samples. FIG. 39D shows quantification of GFP- or KLF4-positive cells indicating higher survival rate of OSK expressing RGCs after crush. Scale bars represent 200 μm in FIG. 39A, FIG. 39B, and FIG. 39C.

FIG. 40A Representative images of retinal whole mounts transduced with d2EGFP- or OSK-encoding AAV2 in the presence or absence of crush injury. The retinal whole mounts were immunostained for RGC marker RBPMS and mTOR activation marker pS6. FIG. 40B shows the quantification of pS6 positive RGC % in intact and crushed samples. FIG. 40C quantification of transduction rate of shRNA-YFP AAV in the OSK expressed RGCs. FIG. 40D shows representative images of retinal whole mounts transduced with OSK-encoding AAV2 in the combination with sh-Scr, sh-Tet1 or sh-Tet2 YFP AAV. The retinal whole mounts were immunostained for Klf4. Scale bars represent 100 μm in FIG. 40A and FIG. 40D. FIG. 40E shows Tet1 versus GAPDH mRNA level with sh-Scr or sh-Tet1 treatment in mouse RGCs in the presence of OSK expression. FIG. 40F shows Tet2 versus GAPDH mRNA level with sh-Scr or sh-Tet2 AAV in mouse RGCs in the presence of OSK expression.

FIG. 41A shows immunofluorescence of differentiated human neurons with transduction of AAV-DJ vectors encoding TRE-OSK and tTA (OSK On) or TRE-OSK alone (OSK Off). FIG. 41B shows mRNA level of Oct4, Sox2 and Klf4 of human neurons transduced with AAV-DJ vectors as in FIG. 41A. FIG. 41C shows the FACS profile of G1, S, and G2 phases in undifferentiated cells and differentiated cells with OSK On or Off. FIG. 41D shows the quantification of cell population that are in proliferating S phase. FIG. 41E shows representative images and the neurite area of human neurons post vincristine damage with or without OSK expression. FIG. 41F shows the quantification of neurite area at different time points post vincristine damage. FIG. 41G shows Tet2 mRNA level with sh-Scr and sh-Tet2 AAV treatment in human neurons. FIG. 41H shows the phosphorylation level of S6 in human neurons with Rapamycin treatment (10 nM) for 5 days. FIG. 41I shows the effect of mTOR inhibition on axon regeneration of differentiated neurons with OSK Off or OSK On. FIG. 41J shows DNA methylation age of human neurons before vincristine (VCS) damage (Day -) or 1 and 9 days post-damage in the absence of OSK expression, estimated using a skin or a blood cell clock. FIG. 41K shows mouse Oct4 mRNA level with sh-Scr or sh-Tet2 AAV in human neurons in the absence or presence of OSK expression.

FIG. 42A shows the quantification of RGCs and representative confocal microscopic images from retinal flat-mounts stained with anti-Brn3a, an RGC-specific marker, and DAPI, a nuclear stain, at 4 weeks post-microbead or post-saline injection. The scale bar represents 75 mm. FIG. 42B shows the quantification of healthy axons of optic nerve and representative photomicrographs of PPD-stained optic nerve cross-sections, at 4 weeks post-microbead or post-saline injection. The scale bars represent 10 μm. FIG. 42C shows the quantification of RGCs and representative confocal microscopic images at 4 weeks post AAV injection and 8 weeks post-microbead or post-saline injection.

FIG. 43A shows the effect of OSK expression on RGC survival in young, adult, and aged mice after optic nerve crush. FIG. 43B shows the axon regeneration promoted by OSK expression compared to the d2EGFP controls in young (1 month old), adult (3 months old), and aged (12 months old) mice at 2 weeks post injury. FIG. 43C shows a comparison of pERG measurements in different ages at one month post OSK off or OSK On treatment. OSK Off, rtTA+TRE=OSK AAV; OSK On, tTA+OSK AAV. FIG. 43D shows comparison of RGC cell density in 4 m- and 12 m-old mice at one month post OSK off or OSK On treatment. FIG. 43E shows a comparison of axon density in 4 m- and 12 m-old-mice at one month post OSK off or OSK On treatment. FIG. 43F shows comparison of pERG measurement in different ages at one-month after −OSK or +OSK treatment. −OSK: AAV-rtTA+AAV-TRE-OSK; +OSK: AAVtTA+AAV-TRE-OSK. FIG. 43G shows spatial frequency threshold in 18-month-old mice treated with −OSK or +OSK AAV for 4 weeks.

FIG. 44A is a scatter plot of OSK-induced changes in RNA levels versus age-associated changes in mRNA levels. Dots represent differentially expressed genes in RGCs are shown. Gene exclusion criteria: genes with low overall expression (log 2(CPM)<2), genes that did not significantly change with age (absolute log 2 fold-change <1) or genes altered by the virus (differentially expressed between intact old and old treatd with TRE-OSK AAV). FIG. 44B is a hierarchical clustered heatmap showing RNA-Seq expression of sensory genes in cell sorted purified RGCs from intact young mice (5 months) or intact old mice (12 months), or old mice treated with either control AAV (TRE-OSK) or OSK-On AAV. FIG. 44C shows the top 10 biological process that are lower in old compared to young and restored by OSK. FIG. 44D shows the top 10 biological process that are higher in old compared to young and reduced by OSK.

FIG. 45A shows correlation between rDNA methylation age and chronological age of sorted mouse RGCs. FIG. 45B shows average DNA methylation levels of RGCs from different ages and treatments. FIG. 45C shows average DNA methylation levels of human neurons treated with OSK before treatment with vincristine (VCS) (−) or days post-VCS damage (1 and 9).

FIG. 46A are representative optic nerve images. FIG. 46B is a graph quantifying axon numbers.

DETAILED DESCRIPTION OF CERTAIN EMBODIMENTS OF THE INVENTION

Figure 1:
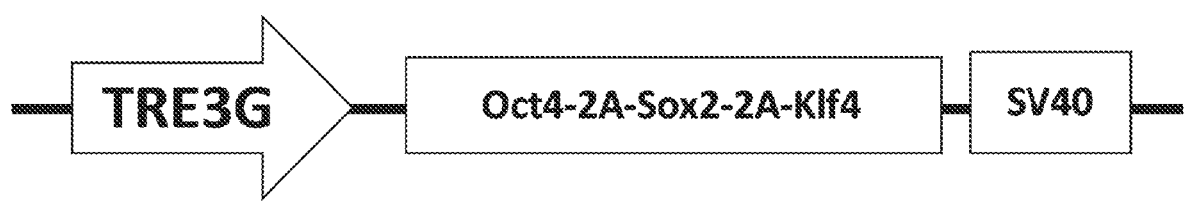
FIG. 1 is a schematic with a linear representation of an expression vector encoding OCT4, SOX2, and KLF4. TRE3G is shown as an exemplary inducible promoter, and SV40 is shown as an exemplary terminator sequence.

The present disclosure is based, at least in part, on the unexpected results demonstrating that expression of OCT4, SOX2, and KLF4 in the absence of exogenous c-Myc expression can be used to promote partial reprogramming and tissue regeneration in vivo. Surprisingly, using the eye as a model tissue, as described herein, in some embodiments, it was determined that the combination of OCT4, SOX2, and KLF4 (OSK) could be used to reset the youthful gene expression patterns and epigenetic age of retinal ganglion cells to promote optic nerve regrowth and the restoration of vision in a rodent model of glaucoma and in old animals. In some embodiments, the DNA demethylases Tet1 and Tet2 are required for these restorative activities, which without being bound by a particular theory, suggests that the DNA methylation clock is not just a correlate of age but a regulator of it.

Provided herein, in certain embodiments, are engineered nucleic acids (e.g., expression vectors, including viral vectors) encoding OCT4, SOX2, and KLF4, each alone or in combination, recombinant viruses (e.g., lentivirus, alphavirus, vaccinia virus, retrovirus, adenovirus, herpes virus, or AAV) comprising the same, pharmaceutical compositions comprising the engineered nucleic acids and/or recombinant viruses, kits comprising the engineered nucleic acids and/or recombinant viruses, and methods of regulating (e.g., inducing, inducing and then stopping, etc.) cellular reprogramming, reversing aging, tissue repair, organ regeneration, and tissue regeneration.

In certain embodiments, the expression of one of more of the genes is transient (e.g., using an inducible promoter to regulate gene expression). Expression of one or more of the genes (e.g., OCT4, SOX2, KLF4, or a combination thereof) may be modulated by altering the activity of an inducing agent. As a non-limiting example, tetracycline transactivator (tTA) is capable of inducing expression from a tetracycline-responsive promoter in the absence of tetracycline. When tetracycline is added, tTA can no longer bind to the promoter and induce cannot expression. As another non-limiting example, reverse tetracycline transactivator (rtTA) is capable of inducing expression from a tetracycline-responsive promoter in the presence of tetracycline. When tetracycline is removed, rtTA can no longer bind to the promoter and cannot induce expression. As described herein, an inducible AAV vector encoding OCT4, SOX2, and KLF4 (OSK) promoted optic regeneration in vivo following damage. Therefore, the expression of these three genes may be useful in tissue and organ regeneration, tissue and organ repair, reversing aging, treating neurodegenerative diseases and conditions, cellular reprogramming, As described below, the vectors described herein may be packaged, in some instances, into viruses with a titer of more than $2\times10^{12}$ particles per preparation and allow for precise control of OSK expression in mammalian cells in vitro and in vivo.

Cellular reprograming allows for the production of numerous cell types from existing somatic cells. Although the Yamanaka factors (OCT4, SOX2, KLF4 and c-Myc, also known collectively as OSKM) have been shown to induce pluripotency in differentiated cells, administration of these factors may induce teratomas or other cancers in vivo (Takahashi et al., Cell. 2006 Aug. 25; 126(4):663-76); (Abad et al., Nature. 2013 Oct. 17; 502(7471):340-5). As a result of these safety concerns, use of the Yamanaka factors has largely been limited to in vitro applications. Furthermore, existing methods of gene therapy are plagued by inefficient and inconsistent gene transduction of target cells. The engineered nucleic acids, recombinant viruses comprising the same, pharmaceutical compositions thereof and kits provided herein overcome many of these limitations.

Engineered Nucleic Acids

The engineered nucleic acids of the present disclosure may encode OCT4, SOX2, KLF4, and homologs or variants (e.g., functional variants) thereof, each alone or in combination. In certain embodiments, an engineered nucleic acid (e.g., engineered nucleic acid) does not encode c-Myc. In certain embodiments, an engineered nucleic acid (e.g., engineered nucleic acid) does not encode a functional c-Myc because it lacks a c-Myc sequence. Assays to determine transcription factor (e.g., OCT4, SOX2, KLF4, or any combination thereof) activity are known in the art and include cell-based transcription assays and in vitro transcription assays. Transcription factor expression may also be determined using other methods including enzyme-linked immunosorbent assays (ELISAs), western blots, and quantification of RNA (e.g., using reverse transcription polymerase chain reaction).

A transcription factor (e.g., OCT4, SOX2, KLF4, or homologs or variants thereof, including mammalian OCT4, mammalian SOX2, and mammalian KLF4) may be encoded by a single nucleic acid, or a single nucleic acid (e.g., engineered nucleic acid) may encode two or more transcription factors (e.g., each operably linked to a different promoter, or both operably linked to the same promoter). For example, in certain embodiments, a nucleic acid (e.g., engineered nucleic acid) may encode OCT4; SOX2; KLF4; OCT4 and SOX2; OCT4 and KLF4; SOX2 and KLF4; or OCT4, SOX2, and KLF4, in any order.

In certain embodiments, an engineered nucleic acid (e.g., engineered nucleic acid) encodes an inducing agent (e.g., tTA or rtTA). In certain embodiments, a nucleic acid (e.g., engineered nucleic acid) may encode one or more transcription factors (e.g., one, two or three transcription factors) and an inducing agent. In certain embodiments, an inducing agent is encoded by a separate nucleic acid (e.g., engineered nucleic acid) that does not also encode a transcription factor (e.g., OCT4, SOX2, or KLF4). In certain embodiments, an inducing agent is encoded by a the nucleic acid (e.g., engineered nucleic acid) that also encodes a transcription factor (e.g., OCT4, SOX2, and/or KLF4). In certain embodiments, an inducing agent is encoded by a nucleic acid (e.g., engineered nucleic acid) that also encodes one or more transcription factors selected from the group consisting of OCT4; SOX2; KLF4; and any combinations thereof (e.g., OCT4; SOX2; KLF4; OCT4 and SOX2; OCT4 and KLF4; SOX2 and KLF4; or OCT4, SOX2, and KLF4).

The transcription factors described herein (e.g., OCT4, SOX2, KLF4, or any combination thereof) or inducing agents may comprise one or more amino acid substitutions. Variants can be prepared according to methods for altering polypeptide sequences known to one of ordinary skill in the art such as those found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In certain embodiments, the engineered nucleic acids of the present disclosure comprise RNA (e.g., mRNA) and/or DNA. In some embodiments, the RNA and/or DNA is further modified. As a non-limiting example, an nucleic acid (e.g., engineered nucleic acid) of the present disclosure, may be modified RNA (e.g., mRNA) encoding OCT4, KLF4, SOX2, an inducing, or any combination thereof. See, e.g., Warren et al., Cell Stem Cell. 2010 Nov. 5; 7(5):618-30. As a non-limiting example, the engineered nucleic acids (e.g., RNA, including mRNA, or DNA) of the present disclosure may be formulated in a nanoparticle for delivery. See, e.g., Dong et al., Nano Lett. 2016 Feb. 10; 16(2):842-8. In some embodiments, the nanoparticle comprises acetylated galactose. See, e.g., Lozano-Torres et al., J Am Chem Soc. 2017 Jul. 5; 139(26):8808-8811. In some embodiments, the engineered nucleic acids (e.g., RNA, including mRNA, or DNA) is electroporated or transfected into a cell. In certain embodiments, the engineered nucleic acids are delivered as a naked nucleic acid (e.g., naked DNA or naked RNA).

In some embodiments, an engineered nucleic acid that is formulated in a nanoparticle for delivery is not an AAV vector. Suitable vector backbones for formulation in a nanoparticle include, but are not limited to, NANOPLASMID™ vectors and NTC '8' Series Mammalian Expression Vectors. Non-limiting examples of vector backbones for formulation in a nanoparticle include NTC9385R and NTC8685. Without being bound by a particular theory, NTC '8' Series Mammalian Expression Vectors may be useful as they are generally cleared by cells within weeks. The NTC '8' Series Mammalian Expression Vector comprises a CMV promoter, which can be operably linked to a sequence encoding OCT4, KLF4, SOX2, or a combination thereof. Without being bound by a particular theory, the NANOPLASMID™ vector may be less immunogenic than other vectors and express at a higher level and may express for a long time, which could be useful in long-term expression of an operably linked nucleic acid. In some embodiments, the NANOPLASMID™ vector may be useful in long term expression of OCT4, KLF4, SOX2, or a combination thereof.

In some embodiments, engineered nucleic acids encoding OSK may be useful in making induced pluripotent stem cells). Without being bound by a particular theory, modified RNA (e.g., mRNA) may have an advantage of minimal activation of innate immune responses and limited cytotoxicity, thereby allowing robust and sustained protein expression. In some embodiments, the RNA (e.g., mRNA) comprises modifications including complete substitution of either 5-methylcytidine (5mC) for cytidine or pseudouridine (psi) for uridine.

In some embodiments, OCT4, KLF4, and/or SOX2 expression may be activated using a CRISPR-activating system. In some embodiments, expression of one or more transcription factors selected from the group consisting of OCT4, KLF4, SOX2, and combinations thereof may be activated using a CRISPR-activating system. See, e.g., Liao et al., Cell. 2017 Dec. 14; 171(7):1495-1507.e15; Liu et al., 2018, Cell Stem Cell 22, 1-10 Feb. 1, 2018. In general, a CRISPR-activating system comprises an enzymatically dead Cas9 nuclease (or nuclease-deficient Cas9 (dCas9)) fused to a transcription activation complex (e.g., comprising VP64, P65, Rta, and/or MPH). Non-limiting examples of sequences encoding VP64, P65, Rta, and/or MPH are provided below. A VP64, P65, Rta, or MPH may be encoded by a sequence that comprises a sequence that is at least 70% (e.g., 75%, 80%, 85%, 90%, 95%, 98%, 99%, or 100%) identical to any of the VP64, P65, Rta, and/or MPH sequences described herein. This Cas9 fusion protein may be referred to as a CRISPR activator. A guide RNA targeting the promoter and/or enhancer region of a gene of interest is used in a CRISPR-activating system to target the dCas9-transcription activation complex and drive expression of the endogenous gene.

In some embodiments, expression of OCT4; KLF4; SOX2; or any combination thereof may be activated using a transcription activator-like effector nucleases (TALEN) or a Zinc-finger nuclease (ZFN) system.

The engineered nucleic acids of the present disclosure may encode sgRNA to target and the promoter and/or enhancer region of the endogenous locus of OCT4, SOX2, and/or KLF4 in a cell. The engineered nucleic acids of the present disclosure may encode sgRNA to target and the promoter and/or enhancer region of the endogenous locus of one or more transcription factors selected from OCT4; SOX2; KLF4; and any combinations thereof in a cell. In some embodiments, the engineered nucleic acid (e.g., expression vector) further encodes a dCas9 (dead Cas9) and a transcriptional activation complex (e.g., VP64, P65, Rta, MPH). In some embodiments, the dCas9 (dead Cas9) and a transcriptional activation complex (e.g., VP64, P65, Rta, MPH) is administered to a cell on a engineered nucleic acid (e.g. expression vector). In some embodiments, the vector encoding the sgRNA and/or a dCas9 (dead Cas9) and a transcriptional activation complex (e.g., VP64, P65, Rta, MPH) is a viral vector (e.g., AAV vector). In some embodiments, dCas9 (dead Cas9) and a transcriptional activation complex (e.g., VP64, P65, Rta, MPH) is introduced into a cell as protein.

In some embodiments, guide RNA targeting the enhancer and/or promoter region of OCT4, SOX2, and/or KLF4 is formulated in a nanoparticle and injected with dCas9-VP64 protein. In some embodiments, guide RNA targeting the enhancer and/or promoter region of OCT4, SOX2, KLF4, or any combination thereof is formulated in a nanoparticle and injected with dCas9-VP64 protein. In some embodiments, the guide RNA and/or nucleic acid encoding dCas9 (dead Cas9) and a transcriptional activation complex (e.g., VP64, P65, Rta, MPH) is administered as naked nucleic acid (e.g., naked DNA formulated in a nanoparticle). In some embodiments, the guide RNA and/or nucleic acid encoding dCas9 (dead Cas9) and a transcriptional activation complex (e.g., VP64, P65, Rta, MPH) is delivered via a recombinant virus (e.g., lentivirus, adenovirus, retrovirus, herpes virus, alphavirus, vaccinia virus or adeno-associated virus (AAV)).

Non-limiting example, sequences of guide RNAs targeting the endogenous OCT4 locus or SOX2 locus are provided in Liu et al., Cell Stem Cell. 2018 Feb. 1; 22(2):252-261.e4. Non-limiting examples of guide RNAs targeting OCT4, SOX2, and/or KLF4 are also provided in Weltner et al., Nat Commun. 2018 Jul. 6; 9(1):2643.

Without being bound by a particular theory, use of a CRISPR-CAS9 system to activation endogenous expression of OCT4, KLF4, and/or SOX2 in the absence of c-Myc expression may obviate potential toxicity associated with exogenous gene expression and/or superphysiological gene expression.

Nucleic acids (e.g., engineered nucleic acids) encoding a transcription factor (OCT4, SOX2, KLF4, or any combination thereof) or encoding an inducing agent) may be introduced into an expression vector using conventional cloning techniques. Suitable expression vectors include vectors with a promoter (e.g., a constitutive or inducible promoter, including a TRE promoter) operably-linked to a nucleic acid (e.g., engineered nucleic acid) encoding OCT4, SOX2, KLF4, or any combination thereof, and a terminator sequence (e.g., a SV40 sequence as described herein). In some embodiments, a nucleic acid (e.g., engineered nucleic acid) encodes a promoter operably linked to a nucleic acid encoding an inducing agent. In some embodiments, a vector comprises a WPRE sequence. Expression vectors containing the necessary elements for expression are commercially available and known to one of ordinary skill in the art (see, e.g., Sambrook et al., Molecular Cloning: A Laboratory Manual, Fourth Edition, Cold Spring Harbor Laboratory Press, 2012).

Vectors of the invention may further comprise a marker sequence for use in the identification of cells that have or have not been transformed or transfected with the vector, or have been reprogrammed. Markers include, for example, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., β-galactosidase, senescence-associated beta-galactosidase, luciferase or alkaline phosphatase), and genes that visibly affect the phenotype of transformed or transfected cells, hosts, colonies or plaques (e.g., green fluorescent protein). In some embodiments, the vectors used herein are capable of autonomous replication and expression of the structural gene products present in the DNA segments to which they are operably linked.

In certain embodiments, the expression vector comprises an inducible promoter (e.g., a tetracycline-responsive promoter) operably linked to a sequence encoding a transcription factor (e.g., OCT4, SOX2, KLF4, or any combination thereof). In certain embodiments, the promoter operably linked to a sequence encoding a transcription factor (e.g., OCT4, SOX2, KLF4, or any combination thereof) is a tissue-specific or cell type-specific promoter (e.g., brain-specific, liver-specific, muscle-specific, nerve cell-specific, glial cell-specific, endothelial cell-specific, lung-specific, heart-specific, bone-specific, intestine-specific, skin-specific promoters, or eye-specific promoter). As an example, the muscle-specific promoter may be a desmin promoter (e.g., a sequence that is at least 70% (e.g., at least 75%, 80%, 85%, 90%, 95%, 98%, 99%, or 100%) identical to SEQ ID NO: 29). In some embodiments, an eye-specific promoter may be a promoter that is at least 70% (e.g., at least 75%, 80%, 85%, 90%, 95%, 98%, 99%, or 100%) identical to a sequence selected from SEQ ID NOs: 101-104.

In certain embodiments, the promoter operably linked to a sequence encoding a transcription factor (e.g., OCT4, SOX2, KLF4, or any combination thereof) is age- or senescence-specific (e.g. the age- or senescence-specific promoter may be a p16 promoter or a Cas9-directed transcription factor that binds to methylated DNA, which is known to accumulate with age).

In certain embodiments, an expression vector comprises a constitutive promoter operably linked to a nucleic acid (e.g., engineered nucleic acid) encoding OCT4, SOX2, KLF4, or any combination thereof. In some embodiments, such a vector may be inactivated using a Clustered Regularly Interspaced Short Palindromic Repeats (CRISPR)/guide RNA system. For example, a guide RNA may be complementary to the vector and is capable of targeting a Cas9 nuclease to the vector. In some embodiments, the guide RNA is complementary to a transgene (e.g. transgene encoding OCT4, KLF4, SOX2, or a combination thereof) in any of the expression vectors described herein. Cas9 may then generate double-stranded breaks in the vector and/or mutate the vector, rendering the vector inactive.

In certain embodiments, the promoter operably linked to a sequence encoding an inducing agent is a constitutive promoter (e.g., CMV, EF1 alpha, a SV40 promoter, PGK1, UBC, CAG, human beta actin gene promoter, or UAS). In certain embodiments, the promoter operably linked to a sequence encoding an inducing agent is a tissue-specific promoter (e.g., brain-specific, liver-specific, muscle-specific, nerve cell-specific, lung-specific, heart-specific, bone-specific, intestine-specific, skin-specific promoters, or eye-specific promoter). As an example, the muscle-specific promoter may be a desmin promoter (e.g., a sequence that is at least 70% (e.g., at least 75%, 80%, 85%, 90%, 95%, 98%, 99%, or 100%) identical to SEQ ID NO: 29).

A nucleic acid (e.g., engineered nucleic acid) (e.g., an expression vector) may further comprise a separator sequence (e.g., an IRES or a polypeptide cleavage signal).

Exemplary polypeptide cleavage signals include 2A peptides (e.g., T2A, P2A, E2A, and F2A). A 2A peptide may comprise a sequence that is at least 70% (e.g., at least 75%, 80%, 85%, 90%, 95%, 98%, 99%, or 100%) identical to SEQ ID NO: 9. For nucleic acids (e.g., engineered nucleic acids) (e.g., expression vectors) encoding more than one transcription factor (e.g., OCT4, SOX2, KLF4, or any combination thereof), each transcription factor may be operably linked to a different promoter or to the same promoter. The transcription factors may be separated (e.g., by peptide separator sequence) on the nucleic acid. Expression of the nucleic acid (e.g., engineered nucleic acid) results in separate amino acid sequences encoding each transcription factor.

In certain embodiments, an expression vector (e.g., an expression vector encoding OCT4, KLF, SOX2, or a combination thereof) of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In certain embodiments, an expression vector encoding an inducing agent of the present disclosure may further comprise a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In certain embodiments, an expression vector (e.g., encoding OCT4, SOX2, KLF4, or any combination thereof) is present on a viral vector (e.g., AAV vector). In certain embodiments, an expression vector encoding an inducing agent is present on a viral vector (e.g., AAV vector). An AAV vector, as used herein, generally comprises ITRs flanking an expression cassette (e.g., a nucleic acid (e.g., engineered nucleic acid) comprising a promoter sequence operably linked to a sequence encoding OCT4, SOX2, KLF4, or any combination thereof and a terminator sequence, a nucleic acid (e.g., engineered nucleic acid) comprising a promoter sequence operably linked to a sequence encoding an inducing agent, or a combination thereof).

In certain embodiments, the number of base pairs between two ITRs in an AAV vector of the present disclosure is less than 5 kilobases (kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb). In certain embodiments, an AAV vector with a distance of less than 4.7 kb between two ITRs is capable of being packaged into virus at a titer of at least $0.5\times10^{10}$ particle forming units per ml (pfu/ml), at least $1\times10^{10}$ pfu/ml, at least $5\times10^{10}$ pfu/ml, at least $1\times10^{11}$ pfu/ml, at least $5\times10^{11}$ pfu/ml, at least $1\times10^{12}$ pfu/ml, at least $2\times10^{12}$ pfu/ml, at least $3\times10^{12}$ pfu/ml, at least $4\times10^{12}$ pfu/ml, at least $5\times10^{12}$ pfu/ml, at least $6\times10^{12}$ pfu/ml, at least $7\times10^{12}$ pfu/ml, at least $8\times10^{12}$ pfu/ml, at least $9\times10^{12}$ pfu/ml, or at least $1\times10^{13}$ pfu/ml.

In certain embodiments, an expression vector of the present disclosure is at least 1 kilobase (kb) (e.g., at least 1 kb, 2 kb, 3 kb, 4 kb, 5 kb, 6 kb, 7 kb, 8 kb, 9 kb, 10 kb, 50 kb, or 100 kb). In certain embodiments, an expression vector of the present disclosure is less than 10 kb (e.g., less than 9 kb, less 8 kb, less than 7 kb, less than 6 kb, less than 5 kb, less than 4 kb, less than 3 kb, less than 2 kb, or less than 1 kb).

Without being bound by a particular theory, an expression vector (e.g., an AAV vector) that encodes OCT4, SOX2, and KLF4 under one promoter results in more efficient transduction of all three transcription factors in vivo compared to separate nucleic acids (e.g., engineered nucleic acids) encoding one or two of the transcription factors. In certain embodiments, the infection efficiency of a recombinant virus (e.g., lentivirus, alphavirus, vaccinia virus, retrovirus, adenovirus, herpes virus, or AAV) harboring a vector of the present disclosure in cells (e.g., animal cells, including mammalian cells) is at least 20% (e.g., at least 30%, at least 40%, at least 50%, at least 60%, at least 70%, at least 80%, or at least 90%, or 100%).

Recombinant Viruses

Aspects of the present disclosure provide recombinant viruses (e.g., lentiviruses, alphaviruses, vaccinia viruses, adenoviruses, herpes viruses, retroviruses, or AAVs). The recombinant viruses (e.g., lentiviruses, alphaviruses, vaccinia viruses, adenoviruses, herpes viruses, retroviruses, or AAVs) may harbor a nucleic acid (e.g., engineered nucleic acid) (e.g., expression vector) encoding a transcription factor (e.g., OCT4, SOX2, KLF4, or any combination thereof), or a combination thereof. In some embodiments, a recombinant virus harbors a nucleic acid encoding at least two transcription factors selected from OCT4, SOX2, and KLF4 (e.g., OCT4 and SOX2; KLF4 and SOX2; OCT4, KLF4, and SOX2; or OCT4 and KLF4). In some embodiments, a recombinant virus harbors a nucleic acid encoding at least three transcription factors selected from OCT4, SOX2, and KLF4 (e.g., OCT4, SOX2, and KLF4). In some instances, a recombinant virus of the present disclosure comprises a nucleic acid encoding an inducing agent.

In certain embodiments, recombinant virus is a recombinant AAV. In some embodiments, a recombinant AAV has tissue-specific targeting capabilities, such that a transgene of the AAV will be delivered specifically to one or more predetermined tissue(s). Generally, the AAV capsid is a relevant factor in determining the tissue-specific targeting capabilities of an AAV. An AAV capsid may comprise an amino acid sequence derived from AAV1, AAV2, AAV3, AAV4, AAV5, AAV6, AAV7, AAV8, AAV9, AAV10, AAV11, and variants thereof. Non-limiting examples of the tissue-specificity of AAV serotypes are provided in Table 1. An "x" indicates that the indicated AAV serotype is capable of delivering a transgene to a specific tissue.

TABLE 1

Non-limiting examples of AAV serotypes and their utility in specific tissues.

| AAV serotype | Relevant Tissue | | | | | | | | |
|---|---|---|---|---|---|---|---|---|---|
| | Liver | Heart | Muscle (e.g., Skeletal Muscle) | Eye | Central Nervous System (CNS) | Central Nervous System (Blood-brain barrier) | Pancreas | Lung | Immune System (T-cells, B-cells and Dendritic Cells) |
| AAV1 | | x | x | | x | | | | |
| AAV2 | x | | x | x | x | | | | |
| AAV3 | x | | x | x | | | | x | |
| AAV4 | | | x | x | x | | | | |
| AAV5 | | | | x | x | | x | x | |
| AAV6 (e.g., AAV6.2) | | x | x | | | | | x | x |
| AAV7 | x | | x | | | | | | |
| AAV8 | x | | x | | x | | x | | |
| AAV9 | x | x | x | x | x | x | x | x | |
| AAV10 (e.g., AAVrh10) | x | x | x | x | x | x | x | x | |
| AAVDJ | x | | x | | x | | | | |
| AAVPHP.B | | | | | x | x | | | |

Recombinant AAVs comprising a particular capsid protein may be produced using any suitable method. See, e.g., U.S. Patent Application Publication, US 2003/0138772, which is incorporated herein by reference. AAV capsid protein sequences also known in the art. See, e.g., Published PCT Application, WO 2010/138263, which is incorporated herein by reference. Generally, recombinant AAV is produced in a host cell with the following components: (1) a nucleic acid (e.g., engineered nucleic acid) sequence encoding an AAV capsid protein or a fragment thereof, (2) a nucleic acid (e.g., engineered nucleic acid) encoding a functional rep gene, (3) a recombinant AAV vector comprising AAV inverted terminal repeats flanking a transgene (e.g., nucleic acids (e.g., engineered nucleic acids) encoding OCT4, KLF4, SOX2, or a combination thereof), and (4) helper functions that allow for packaging of the recombinant AAV vector into AAV capsid proteins. In some instances, a recombinant AAV vector comprises a nucleic acid encoding an inducing agent. In certain embodiments, the helper functions are introduced via a helper vector that is known in the art.

In some instances, a suitable host cell line (e.g., HEK293T cells) may be used for producing a recombinant AAV disclosed herein following routine practice. One or more expression vectors encoding one or more of the components described above may be introduced into a host cell by exogenous nucleic acids (e.g., engineered nucleic acids), which can be cultured under suitable conditions allowing for production of AAV particles. When needed, a helper vector can be used to facilitate replication, to facilitate assembly of the AAV particles, or any combination thereof. In certain embodiments, the recombinant AAV vector is present on a separate nucleic acid (e.g., engineered nucleic acid) from the other components (e.g., a nucleic acid (e.g., engineered nucleic acid) sequence encoding an AAV capsid protein or a fragment thereof, a nucleic acid (e.g., engineered nucleic acid) encoding a functional rep gene, and helper functions that allow for packaging of the recombinant AAV vector into AAV capsid proteins. In certain embodiments, a host cell may stably express one or more components needed to produce AAV virus. In that case, the remaining components may be introduced into the host cell. The supernatant of the cell culture may be collected, and the viral particles contained therein can be collected via routine methodology.

Methods of Activating OCT4, SOX2, and KLF4, Each Alone or in Combination, and Replacements Thereof Aspects of the present disclosure, in some embodiments, relate to activating OCT4, SOX2, and KLF4, each alone or in combination, in a cell, tissue and/or organ. In some embodiments, OCT4, SOX2, and KLF4, each alone or in combination, is activated in the absence of c-Myc activation. The cell, tissue, and/or organ may be in vivo (e.g., in a subject) or be ex vivo. As used herein, activation includes any nucleic acid (e.g., nucleic acid comprising RNA, comprising DNA, or any combination thereof), protein, antibody, chemical agent, or any combination thereof that is capable of increasing the biological activity of a protein of interest (e.g., OCT4, SOX2, and/or KLF4). Biological activity (e.g., gene expression, reprogramming ability, transcription factor activity, etc.) may be measured using any routine method known in the art. In some embodiments, any nucleic acid (e.g., nucleic acid comprising RNA, comprising DNA, or any combination thereof), protein, antibody, chemical agent, or any combination thereof described herein replaces OCT4, SOX2 and/or KLF4. In some embodiments, any nucleic acid (e.g., nucleic acid comprising RNA, comprising DNA, or any combination thereof), protein, antibody, chemical agent, or any combination thereof described herein replaces OCT4, SOX2, KLF4, or any combination thereof. In some embodiments, any of the nucleic acids (e.g., engineered nucleic acid) encoding an inducing agent, engineered proteins encoding an inducing agent, chemical agents capable of modulating (e.g., activating or inhibiting) the activity of an inducing agent, and/or recombinant viruses encoding an inducing agent described herein is used to activate an inducing agent.

Activation of OCT4, SOX2, and KLF4, each alone or in combination includes increasing expression (e.g., RNA and/or protein expression) of OCT4, SOX2, and KLF4, each alone or in combination. In some embodiments, the expression of OCT4, SOX2, and KLF4, each alone or in combination is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding OCT4, SOX2, and/or KLF4, protein encoding OCT4, SOX2, and/or KLF4, antibody capable of activating encoding OCT4, SOX2, and/or KLF4, chemical agent capable of activating encoding OCT4, SOX2, and/or KLF4, or any combination thereof to a cell, tissue, organ, and/or subject compared to before administration. In some embodiments, the expression of OCT4, SOX2, and KLF4, each alone or in combination is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding OCT4, SOX2, KLF4, or any combination thereof, protein encoding OCT4, SOX2, KLF4, or any combination thereof, antibody capable of activating encoding OCT4, SOX2, KLF4, or any combination thereof, chemical agent capable of activating encoding OCT4, SOX2, KLF4, or any combination thereof, or any combination thereof to a cell, tissue, organ, and/or subject compared to before administration.

Activation of a inducing agent includes increasing expression (e.g., RNA and/or protein expression) of an inducing agent. In some embodiments, the expression of an inducing agent, is increased by at least 1%, 5%, 10%, 20%, 30%, 40%, 50%, 60%, 70%, 80%, 90%, 100%, 200%, 300%, 400%, 500%, 600%, 700%, 800%, 900%, or 1000% after administration of a nucleic acid (e.g., nucleic acid comprising RNA, comprising DNA, or any combination thereof) encoding the inducing agent, protein encoding the inducing agent, chemical agent capable of modulating the activity of the inducing agent, or any combination thereof to a cell, tissue, organ, and/or subject compared to before administration.

Expression may be measured by any routine method known in the art, including quantification of the level of a protein of interest (e.g., using an ELISA, and/or western blot analysis with antibodies that recognize a protein of interest) or quantification of RNA (e.g., mRNA) levels for a gene of interest (e.g., using reverse transcription polymerase chain reaction).

In addition to the engineered nucleic acids discussed herein, OCT4, SOX2, KLF4, alone or in combination may be activated in a cell, tissue, organ, and/or subject through the use of engineered proteins. For example, protein encoding OCT4, SOX2, and/or KLF4 may be generated (e.g., recombinantly or synthetically) and administered to a cell, tissue, organ, and/or subject through any suitable route. For example, protein encoding one or more transcription factors selected from the group consisting of OCT4; SOX2; KLF4; and any combinations thereof may be generated (e.g., recombinantly or synthetically) and administered to a cell, tissue, organ, and/or subject through any suitable route.

In some embodiments, activating expression of OCT4; SOX2; KLF4; a replacement thereof; or any combination thereof from a tetracycline-inducible expression vector comprises administering a tetracycline (e.g., doxycycline) to a cell, organ, tissue, or a subject. As one of ordinary skill in the art would appreciate, the route of tetracycline administration may be dependent on the type of cell, organ, tissue, and/or characteristics of a subject. In some embodiments, tetracycline is administered directly to a cell, organ, and/or tissue. As a non-limiting example, tetracycline may be administered to the eye of a subject through any suitable method, including eye drops comprising tetracycline, sustained release devices (e.g., micropumps, particles, and/or drug depots), and medicated contact lenses comprising a tetracycline). In some embodiments, tetracycline is administered systemically (e.g., through drinking water or intravenous injection) to a subject. Tetracycline may be administered topically (e.g., in a cream) or through a subcutaneous pump (e.g., to deliver tetracycline to a particular tissue). Tetracycline may be administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in particles (e.g., nanoparticles, microparticles), in lipid compositions (e.g., liposomes), or by other method or any combination of the forgoing as would be known to one of ordinary skill in the art (see, for example, *Remington's Pharmaceutical Sciences* (1990), incorporated herein by reference).

As a non-limiting example, an engineered protein may be further modified or formulated for delivery to a cell, tissue, organ, and/or subject. For example, protein transduction domains (i.e., PTD or cell-penetrating peptides) may be attached to an engineered protein (e.g., OCT4, SOX2, and/or KLF4). As a non-limiting example, a protein transduction domain (i.e., PTD or cell-penetrating peptide) may be attached to an engineered protein encoding an inducing agent. Without being bound by a particular theory, a protein transduction domain facilitate delivery of a cargo (e.g., a protein, nucleic acids, nanoparticles, viral particles, etc.) across cellular membranes. Protein transduction domains include cationic peptides, hydrophobic peptides, and/or a cell specific peptides. See, e.g., Zhou et al., Cell Stem Cell. 2009 May 8; 4(5):381-4; Zahid et al., Curr Gene Ther. 2012 October; 12(5):374-80.

In some embodiments, a protein encoding OCT4, SOX2, and/or KLF4, and/or an inducing agent is formulated in a nanoparticle (e.g., for nuclear delivery). In some embodiments, a protein encoding OCT4, SOX2, KLF4, or any combination thereof (e.g., OCT4 and SOX2; KLF4 and SOX2; OCT4 and KLF4; or KLF4, SOX2, and OCT4) is formulated in a nanoparticle (e.g., for nuclear delivery). In certain embodiments, a nanoparticle further comprises a protein encoding an inducing agent. For example, chitosan [poly(N-acetyl glucosamine)] is a biodegradable polysaccharide and may be used to formulate nanoparticles by several methods. In some embodiments, a chitosan polymeric nanoparticle is loaded with protein encoding OCT4, SOX2, and/or KLF4, and/or an inducing agent and is delivered to the nucleus of a cell. See, e.g., Tammam et al., Oncotarget. 2016 Jun. 21; 7(25):37728-37739.

In some embodiments, a chemical agent, antibody and/or protein replaces OCT4, SOX2, and/or KLF4. In some embodiments, a chemical agent, antibody, a protein, or any combination thereof replaces OCT4, SOX2, KLF4, or any combination thereof (e.g., OCT4 and SOX2; OCT4 and KLF4; KLF4 and SOX2; or KLF4, SOX2, and OCT4). For example, a chemical agent, antibody and/or protein may promote expression of OCT4, SOX2, and/or KLF4. In certain instances, a chemical agent, antibody and/or protein may promote expression of one or more transcription factors selected from OCT4; SOX2; KLF4; and any combinations thereof. In some embodiments, a chemical agent, antibody and/or protein may activate target genes downstream of OCT4, SOX2, and/or KLF4. In some embodiments, a chemical agent, antibody, a protein, or any combination thereof may activate target genes downstream of one or more transcription factors selected from the group consisting of OCT4; SOX2; KLF4; and any combinations thereof. In some embodiments, a chemical agent, antibody and/or protein is said to replace OCT4, SOX2, and/or KLF4 if the chemical agent, antibody and/or protein may be used together with the other two transcription factors and promote cellular reprogramming. In some embodiments, a chemical agent, antibody, protein, or any combination thereof is said to replace OCT4, SOX2, KLF4, or any combination thereof if the chemical agent, antibody, protein or any combination thereof may be used together with the other two transcription factors and promote cellular reprogramming. For example, cellular reprogramming may be determined by measuring gene expression (e.g., expression of embryonic markers and/or pluripotency markers). In some embodiments, pluripotency markers include AP, SSEA1, and/or Nanog.

In some embodiments, an antibody is used to activate OCT4, SOX2, and/or KLF4. In some embodiments, an antibody is used to activate one or more transcription factors selected from OCT4, SOX2, KLF4, or any combination thereof. In some embodiments, the antibody does not target OCT4, SOX2, and/or KLF4. In some embodiments, the antibody does not target OCT4, SOX2, KLF4, or any combination thereof. In some embodiments, the antibody increases expression of OCT4, SOX2, and/or KLF4. In some embodiments, the antibody increases expression of OCT4, SOX2, KLF4, or any combination thereof. In some embodiments, the antibody does not increase expression of OCT4, SOX2, and/or KLF4. In some embodiments, an antibody replaces OCT4, SOX2, and/or KLF4. In some embodiments, the antibody does not increase expression of OCT4, SOX2, KLF4, or any combination thereof. In some embodiments, an antibody replaces OCT4, SOX2, KLF4, or any combination thereof. Any suitable method of identifying antibodies that can replace a transcription factor (e.g., OCT4, SOX2, and/or KLF4) may be used. Any suitable method of identifying antibodies that can replace a transcription factor (e.g., OCT4, SOX2, KLF4, or any combination thereof) may be used. See, e.g., Blanchard et al., Nat Biotechnol. 2017 October; 35(10):960-968.

In some embodiments, another protein (e.g., a nucleic acid encoding the protein or a polypeptide encoding the protein) may be used to replace OCT4, SOX2, and/or KLF4. In some embodiments, another protein (e.g., a nucleic acid encoding the protein or a polypeptide encoding the protein) may be used to replace OCT4, SOX2, KLF4, or a combination thereof. For example, OCT4 may be replaced by Tet1, NR5A-2, Sall4, E-cadherin, NKX3-1, or any combination thereof. In some embodiments, OCT4, SOX2, and/or KLF4 may be replaced by NANOG and/or TET2. In some embodiments, OCT4, SOX2, KLF4, or any combination thereof may be replaced by NANOG and/or TET2. See, e.g., Nat Cell Biol. 2018 August; 20(8):900-908; Gao et al., Cell Stem Cell. 2013 Apr. 4; 12(4):453-69. Nanog and Lin28 can replace Klf4. See, e.g., Yu et al, Science. 318, 1917-1920, 2007). In some embodiments, OCT4, SOX2, and/or KLF4 is replaced by Tet3 (tet methylcytosine dioxygenase 3). In some embodiments, OCT4, SOX2, KLF4, or any combination thereof is replaced by Tet3 (tet methylcytosine dioxygenase 3). In some embodiments, a nucleic acid encoding a Tet1 DNA demethylase comprises a sequence that is at least 70% (e.g., at least 75%, 80%, 85%, 90%, 95%, 98%, 99%, or 100%) identical to NM_030625.3 or NM_001253857.2.

In some embodiments, an amino acid encoding a Tet1 DNA demethylase comprises a sequence that is at least 70% (e.g., at least 75%, 80%, 85%, 90%, 95%, 98%, 99%, or 100%) identical to NP_085128.2 or NP_001240786.1. In some embodiments, a nucleic acid encoding a Tet2 DNA demethylase comprises a sequence that is at least 70% (e.g., at least 75%, 80%, 85%, 90%, 95%, 98%, 99%, or 100%) identical to NM_001127208.2, NM_001040400.2, NM_001346736.1, or NM_017628.4. In some embodiments, an amino acid encoding a Tet2 DNA demethylase comprises a sequence that is at least 70% (e.g., at least 75%, 80%, 85%, 90%, 95%, 98%, 99%, or 100%) identical to NP_060098.3, NP_001035490.2, NP_001333665.1, or NP_001120680.1. In some embodiments, a nucleic acid encoding a Tet3 DNA demethylase comprises a sequence that is at least 70% (e.g., at least 75%, 80%, 85%, 90%, 95%, 98%, 99%, or 100%) identical to NM_001287491.2, NM_001347313.1, NM_183138.2, or NM_001366022.1. In some embodiments, an amino acid encoding a Tet3 DNA demethylase comprises a sequence that is at least 70% (e.g., at least 75%, 80%, 85%, 90%, 95%, 98%, 99%, or 100%) identical to NP_001274420.1, NP_001334242.1, NP_898961.2, or NP_001352951.1. Tet1, Tet2, and/or Tet3 may be derived from any species. In some embodiments, Tet1, Tet2, and/or Tet3 is a truncated form of a wild-type counterpart. As a non-limiting example, Tet1, Tet2, and/or Tet3 is N-terminally truncated compared to a wild-type Tet1, Tet2, and/or Tet3 counterpart and is catalytically active. In some embodiments, Tet1, Tet2, and/or Tet3 only comprises the catalytic domain of Tet1, Tet2, and/or Tet3. In some embodiments, Tet1, Tet2, and/or Tet3 comprises the catalytic domain of Tet1, Tet2, Tet3, or any combination thereof. Non-limiting examples of functional truncated Tet1 may be found in Hrit et al., Elife. 2018 Oct. 16; 7. pii: e34870.

Additional methods of replacing OCT4, SOX2, and/or KLF4 to promote cellular reprogramming are known in the art. See, e.g., Heng et al., Cell Stem Cell 6, 167-174 (2010); Eguchi et al., Proc. Natl Acad. Sci. USA 113, E8257-E8266 (2016); Gao et al., Cell Stem Cell 12, 453-469 (2013); Long et al., Cell Res. 25, 1171-1174 (2015); Hou et al., Science 341, 651-654 (2013); Redmer et al., EMBO Rep. 12, 720-726 (2011); Tan et al., J. Biol. Chem. 290, 4500-4511 (2014); Anokye-Danso et al., Cell Stem Cell 8, 376-388 (2011); Miyoshi et al., Cell Stem Cell 8, 633-638 (2011); Shu et al., Cell 153, 963-975 (2013); Yu, J. et al., Science 318, 1917-1920 (2007).

In some embodiments, a chemical agent replaces OCT4, SOX2, and/or KLF4 (e.g., can be used in place of OCT4, SOX2, and/or KLF4 along with the other two transcription factors to promote cellular reprogramming). In some embodiments, a chemical agent replaces OCT4, SOX2, KLF4, or any combination thereof (e.g., can be used in place of OCT4, SOX2, KLF4, or any combination thereof, along with the other two transcription factors to promote cellular reprogramming). For example, SOX2 may be replaced by CHIR, FSK, or 616452. OCT4 may be replaced by DZNep. Since Sall4 may be used to replace OCT4 as mentioned above, any compound that replaces Sall4 may also be used to replace OCT4. For example, CHIR, FSK, and 616452 may be used to replace Sall4. Nanog may be replaced with 2i medium. See, e.g., Hou et al., Science. 2013 Aug. 9; 341(6146):651-4. See, also, e.g., Zhao et al., Cell. 2015 Dec. 17; 163(7):1678-91.

In some embodiments, chemical reprogramming comprises using chemicals that reduce the toxicity of chemical agents that induce reprogramming. Non-limiting examples of chemicals that reduce the toxicity of chemical reprogramming include ROCK inhibitors (e.g., Y27632 and Fasudil) and P38 MAPK inhibitors (e.g., SB203580 and BIRB796). See, e.g., Li et al., Cell Stem Cell. 2015 Aug. 6; 17(2):195-203.

OCT4, KLF4, SOX2, replacements, or any combination thereof may be activated (e.g., expression may be induced) in combination with activating an enhancer of reprogramming and/or inhibiting a barrier of reprogramming. An enhancer of reprogramming may be activated using any suitable method known in the art, including overexpression of the enhancer, increasing expression of an endogenous gene encoding the enhancer (e.g., using CRISPR technology), use of a chemical agent and/or antibody to increase the biological activity of the enhancer, and use a chemical agent and/or antibody to promote expression of the enhancer. A barrier of reprogramming may be inhibited using any suitable method known in the art, including knocking down expression of the inhibitor (e.g., with siRNAs, miRNAs, shRNAs), knocking out an endogenous copy of the inhibitor (e.g., using CRISPR technology, TALENs, zinc finger nucleases, etc.), using a chemical agent and/or antibody to decrease the biological activity of the inhibitor, and using a chemical agent and/or antibody to decrease expression of the inhibitor.

Non-limiting examples of enhancers and barriers of reprogramming are provided in Table 2. See also, e.g., Ebrahimi, Cell Regen (Lond). 2015 Nov. 11; 4:10, which is incorporated by reference in its entirety for this purpose.

TABLE 2

Non-limiting examples of strategies to enhance reprogramming.

| Reprogramming Enhancing Strategy | Enhancers |
|---|---|
| Activation of Enhancers | C/EBPα; UTF1; Mef2c; Tdgf1; FOXH1; GLIS1; mutated reprogramming factors, MDM2; Bcl-2; CCL2; Kdm3a, Kdm3b, Kdm4c, and Kdm4b/2b; Jhdm1a/1b; MOF; Mbd1-4 (or their small molecule activators); Wnt/β-catenin signaling; small molecule Pitstops 1 and 2; vitamin C, palbiociclib; cytokines, e.g. IL-6; CDK4, CDK8, CDK19; lincU |
| Inhibition of Barriers | Barriers p53, p57, p38, p16$^{Ink4a}$/p19$^{Arf}$, p21$^{Cip1}$, Rb TGF-β, MAP kinase, Aurora A kinase, MEK/ERK, Gsk3, Wnt/β-catenin signaling pathways, LATS2, PKC, IP3K, CDK8, CDK19. Native/somatic gene or transcriptional regulatory network (GRN/TRN). Specific members of ADAM family (e.g., ADAM7, ADAM21, ADAM29), endocytosis: (e.g., DRAM1, SLC17A5, ARSD), phosphatase: (e.g., PTPRJ, PTPRK, PTPN11). Chromatin regulators: (e.g., ATF7IP, MacroH2A, Mbd1-4, Setdb1a. Transcription factors: (e.g., TTF1, TTF2, TMF1, T), Bright. Fbxw7 (a member of ubiquitin-proteasome system (UPS)) Lzts1, Ssbp3, Arx, Tfdp1, Nfe2, Ankrd22, Msx3, Dbx1, Lasp1, and Hspa8. Cytokines e.g., TNFα Cells (e.g., senescent cells and NK cells) (e.g., navitoclax, BAY117082) NuRD, Mbd1-4, Gatad2a, Chd4 (see, e.g., Mor et al., Cell Stem Cell. |

TABLE 2-continued

Non-limiting examples of strategies to enhance reprogramming.

| Reprogramming Enhancing Strategy | Enhancers |
|---|---|
| | 2018 Sep. 6; 23(3):412-425.e10) KDM1a Kaiso (see, e.g., Kaplun et al., Biochemistry (Mosc). 2019 March; 84(3):283-290) |

Additional reprogramming enhancers that may be activated in combination with activation of OCT4, KLF4, SOX2, replacements thereof, or any combination thereof, include histone lysine demethylases (e.g., KDM2, KDM3, and KDM4). Histone lysine demethylases may be activated by being overexpressed in a cell, tissue, organ, and/or a subject. Chemical activators of histone lysine demethylases are also encompassed by the present disclosure. For example, vitamin C may be used to activate KDM3 and/or KDM4.

In some embodiments, OCT4, SOX2, KLF4, replacements thereof, or any combination thereof, is activated along with activation of C/EBPα and Tfcp2l1. Without being bound by a particular theory, C/EBPα, and Tfcp2l1 together with Klf4 may drive Tet2-mediated enhancer demethylation and activation during reprogramming.

In some embodiments, OCT4, SOX2, KLF4, replacements thereof, or any combination thereof are activated in a cell, tissue, organ and/or a subject in combination with a cytokine that facilitates reprogramming. IL6 is a non-limiting example of a cytokine. See, e.g., Mosteiro et al, Science. 2016 Nov. 25; 354(6315), which is hereby incorporated by reference in its entirety for this purpose.

In some embodiments, OCT4, SOX2, KLF4, replacements thereof, or any combination thereof are activated in a cell, tissue, organ and/or a subject in combination with activation of a miRNA (e.g., administration of a miRNA and/or expression of a miRNA). For example, a miRNA that promotes cell cycle progression may be introduced to a cell, tissue, organ, and/or subject. Non-limiting examples of miRNAs that promote cell cycle progression include miR 302-367, miR 371-373, miR-200b, miR-200c, miR-205, miR 290-295, miR-93, miR-106, and miR 135b.

As a non-limiting example, nerve regeneration may be enhanced by combining activation of OCT4, SOX2, KLF4, replacements thereof, or any combination thereof with activation of an enhancer. Non-limiting activation of enhancers include overexpression of a member of the KLF family (e.g., KLF7), overexpression of c-Myc, STAT3 activation, SOX11 overexpression, overexpression of Lin28, overexpression of or delivery of soluble protein encoding insulin-like growth factor 1 (IGF1) and osteopontin (OPN), and activation of B-RAF (e.g., introduction of a gain of function mutation). See also, e.g., Blackmore et al., Proc Natl Acad Sci USA. 2012 May 8; 109(19):7517-22; Belin et al., Neuron. 2015 May 20; 86(4):1000-1014; Bareyre et al., Proc Natl Acad Sci USA. 2011 Apr. 12; 108(15):6282-7; Norsworthy et al., Neuron. 2017 Jun. 21; 94(6):1112-1120.e4; Wang et al., Cell Rep. 2018 Sep. 4; 24(10):2540-2552.e6; Liu et al., Neuron. 2017 Aug. 16; 95(4):817-833; O'Donovan et al., J Exp Med, 2014, 211(5): p. 801-14, which is each hereby incorporated by reference in its entirety for this purpose.

In some embodiments, OCT4, SOX2, KLF4, replacements thereof, or any combination thereof, are activated in a cell, tissue, organ, and/or a subject in combination with suppression or knockdown of reprogramming barriers. Non-limiting examples of reprogramming barriers include Chaf1a, Chaf1b, Ube2i, sumo2, and/or Nudt21. See, e.g., Brumbaugh et al., Cell. 2018 Jan. 11; 172(1-2):106-120.e21; Cheloufi et al., Nature. 2015 Dec. 10; 528(7581):218-24; and Borkent et al., Stem Cell Reports, 2016. 6(5): p. 704-716, which is each hereby incorporated by reference in its entirety for this purpose.

As a non-limiting example, a reprogramming barrier may be a DNA methyltransferase (DNMT) may be and a DNMT may be inhibited to promote reprogramming of a tissue, cell, and/or organ. Most DNA methyltransferases use S-adenosyl-L-methionine as a methyl donor. DNMT may be from any species. There are at least three different types of methyltransferases. m6A methyltransferases are capable of methylating the amino group at the c-6 position of adenines in DNA (e.g., Enzyme Commission (EC) No. 2.1.1.72). m4C methyltransferases are capable of generating N4-methylcytosine (e.g., Enzyme Commission (EC) No. 2.1.1.113). M5C methyltransferases are capable of generating C5-methylcytosine (e.g., Enzyme Commission (EC) No. 2.1.1.37).

Non-limiting examples of mammalian DNA methyltransferases (DNMTs) include DNMT1 and its isoforms DNMT1b and DNMT1o (oocytes-specific), DNMT3a, DNMT3b, DNMT3L. GenBank Accession Nos. NM_001130823.3 (isoform a), NM_001318730.1 (isoform c), NM_001318731.1 (isoform d), and NM_001379.3 (isoform b) are non-limiting examples of nucleotide sequences encoding human DNMT1. A nucleic acid encoding a DNMT1 may comprise a sequence that is at least 70% (e.g., at least 75%, 80%, 85%, 90%, 95%, 98%, 99%, or 100%) identical to a sequence set forth in GenBank Accession Nos. NM_001130823.3 (isoform a), NM_001318730.1 (isoform c), NM_001318731.1 (isoform d), and/or NM_001379.3 (isoform b). GenBank Accession Nos. NP_001124295.1 (isoform a), NP_001305659.1 (isoform c), NP_001305660.1 (isoform d), and NP_001370.1 (isoform b) are non-limiting examples of amino acid sequences encoding human DNMT1. An amino acid sequence encoding a DNMT1 may comprise a sequence that is at least 70% (e.g., at least 75%, 80%, 85%, 90%, 95%, 98%, 99%, or 100%) identical to a sequence set forth in GenBank Accession Nos. NP_001124295.1 (isoform a), NP_001305659.1 (isoform c), NP_001305660.1 (isoform d), and/or NP_001370.1 (isoform b). A nucleic acid encoding human DNMT3A includes GenBank Accession No. NM_001320892.1, NM_001320893.1, NM_022552.4, NM_153759.3, NM_175629.2, and NM_175630.1. A nucleic acid encoding a DNMT3A may be at least 70% (e.g., at least 75%, 80%, 85%, 90%, 95%, 98%, 99%, or 100%) identical to a sequence set forth in GenBank Accession Nos. NM_001320892.1, NM_001320893.1, NM_022552.4, NM_153759.3, NM_175629.2, and/or NM_175630.1. An amino acid sequence encoding human DNMT3A includes GenBank Accession Nos. NP_001307821.1, NP_001307822.1, NP_072046.2, NP_715640.2, NP_783328.1, and NP_783329.1. An amino acid sequence encoding a DNMT3A may be at least 70% (e.g., at least 75%, 80%, 85%, 90%, 95%, 98%, 99%, or 100%) identical to a sequence set forth in GenBank Accession Nos. NP_001307821.1, NP_001307822.1, NP_072046.2, NP_715640.2, NP_783328.1, and/or NP_783329.1. A nucleic acid encoding human DNMT3B includes GenBank Accession No. NM_001207055.1, NM_001207056.1, NM_006892.3, NM_175848.1, NM_175849.1, and NM_175850.2. A nucleic acid encoding a DNMT3B may be at least 70% (e.g., at least 75%, 80%, 85%, 90%, 95%, 98%, 99%, or 100%) identical to a sequence set forth in GenBank Accession Nos. NM_001207055.1, NM_001207056.1, NM_006892.3, NM_175848.1, NM_175849.1, and/or NM_175850.2. An amino acid sequence encoding human DNMT3B includes GenBank Accession Nos. NP_001193984.1, NP_001193985.1, NP_008823.1, NP_787044.1, NP_787045.1, and NP_787046.1. An amino acid sequence encoding a DNMT3B may be at least 70% (e.g., at least 75%, 80%, 85%, 90%, 95%, 98%, 99%, or 100%) identical to a sequence set forth in GenBank Accession Nos. NP_001193984.1, NP_001193985.1, NP_008823.1, NP_787044.1, NP_787045.1, and/or NP_787046.1. A nucleic acid encoding human DNMT3L includes GenBank Accession No. NM_013369.3 and NM_175867.2. A nucleic acid encoding a DNMT3L may be at least 70% (e.g., at least 75%, 80%, 85%, 90%, 95%, 98%, 99%, or 100%) identical to a sequence set forth in GenBank Accession Nos. NM_013369.3 and/or NM_175867.2. An amino acid sequence encoding human DNMT3L includes GenBank Accession Nos. NP_037501.2 and NP_787063.1. An amino acid sequence encoding a DNMT3L may be at least 70% (e.g., at least 75%, 80%, 85%, 90%, 95%, 98%, 99%, or 100%) identical to a sequence set forth in GenBank Accession Nos. NP 037501.2 and/or NP 787063.1.

A DNMT may be inhibited using any suitable method known in the art. Suitable methods include knockdown of a DNMT mRNA, genetically knocking out a DNMT, and use of a DNMT inhibitor (e.g., chemical inhibitors). DNMT inhibitors are being investigated in clinical trials (e.g., phase III clinical trials) in the United States of America and beyond. Non-limiting examples of DNMT inhibitors include VIDAZA™ (azacitidine) (e.g., for the treatment of Myelodysplastic Syndromes and treatment of acute myeloid leukemia (AML)), DACOGEN™ (decitabine) (e.g., for treatment of AML and treatment of Chronic myeloid leukemia (CML)), and Guadecitabine (SGI-110) (e.g., for treatment of AML). In 2012, the European Union approved DACOGEN™ (decitabine) for use in patients with AML.

A DNMT may be inhibited by inhibiting a DNMT stabilizer. Suitable methods of inhibiting a DNMT stabilizer include knockdown of the mRNA encoding the stabilizer, genetically knocking out the gene that encodes the stabilizer and use of an inhibitor (e.g., chemical inhibitors). As a non-limiting example, KDM1a, which is also referred to as Lsd1 or Aof2, is a stabilizer of DNMT1. See, e.g., Wang et al., Nat Genet. 2009 January; 41(1):125-9. In some embodiments, KDM1a expression is knocked down using a shRNA disclosed herein or known in the art. In some embodiments, KDM1a is inhibited to prevent injury induced by hypermethylation from DNMTs, which could be useful in promoting reprogramming.

In some embodiments, a histone methyltransferase is a reprogramming barrier and is inhibited to facilitate reprogramming of a cell, tissue and/or organ. Histone methyltransferases may be inhibited by any suitable method, including use of chemical inhibitors. For example, 3-deazaneplanocin A (Dznep), epz004777, and BIX-01294 are examples of histone methyltransferase inhibitors.

In some embodiments, a reprogramming barrier is a histone deacetylase (HDAC) and a HDAC is inhibited to facilitate reprogramming of a cell, tissue, and/or organ. Non-limiting examples of HDAC inhibitors include valproic acid (VPA), trichostatin A (TSA), suberoylanilide hydroxamic Acid (SAHA), sodium butyrate (SB), Belinostat (PXD101), Panobinostat (LBH589), Quisinostat (JNJ-26481585), Abexinostat (PCI-24781), Givinostat (ITF2357), Resminostat (4SC-201), Phenylbutyrate (PBA), Depsipeptide (romidepsin), Entinostat (MS-275), Mocetinostat (MGCD0103), and Tubastatin A (TBA).

In some embodiments, a reprogramming barrier is a NF-κB, and it is inhibited to facilitate reprogramming of a cell, tissue, and/or organ. Non-limiting examples of NF-κB inhibitor includes BAY 11-7082, TPCA 1, and p65 siRNA. See, e.g., the NF-κB small molecule guide compiled by Abcam, which is available on the Abcam website (www.abcam.com/reagents/nf-kb-small-molecule-guide).

In some embodiments, a repogramming barrier is a cytokine secreted from senescent cells in which a cytokine is inhibited to facilitate reprogramming of a cell, tissue, and/or organ. None limiting examples of cytokines inhibitors include Anti-TNFα (Mahmoudi et al, Biorxiv, 2018) and drugs, including Navitoclax, that kill senescence cells.

In some embodiments, a reprogramming barrier is a microRNA (miRNA) and a microRNA is inhibited to facilitate reprogramming of a cell, tissue, and/or organ. Non-limiting examples of microRNAs that are reprogramming barriers include miR Let-7 and miR-34. Without being bound by a particular theory, inhibition of miR Let-7 may increase the efficiency of reprogramming because miR Let-7 inhibits the cell cycle and inhibition of miR-34 may facilitate reprogramming because miR-34 inhibits the translation of p53.

In some embodiments, OCT4, SOX2, KLF4, replacements thereof, or any combination thereof is activated in a cell, tissue, organ and/or a subject in combination with inhibition of PTEN, SOCS3, RhoA, and/or ROCK to enhance nerve regeneration. In some embodiments, PTEN is deleted, SOCS3 is deleted, RhoA is knocked down, and/or ROCK is knocked down in a cell, tissue, organ and/or subject. See, e.g., Park et al., Science. 2008 Nov. 7; 322 (5903):963-6; Smith et al., Neuron. 2009 Dec. 10; 64(5): 617-23; Koch et al., Front Cell Neurosci. 2014 Sep. 5; 8:273; Koch et al., Cell Death Dis. 2014 May 15; 5:e1225 for descriptions of inhibition of PTEN, SOCS3, RhoA, and/or ROCK. Each reference is hereby incorporated by reference in its entirety for this purpose.

In some embodiments, OCT4, SOX2, KLF4, replacements thereof, or any combination thereof is activated in a cell, tissue, organ and/or a subject in combination with neuronal electrical stimulation (e.g., high-contrast visual stimulation) to promote nerve regeneration. See, e.g., Lim et al., Nat Neurosci. 2016 August; 19(8):1073-84 for a description of high-contrast visual stimulation. This reference is hereby incorporated by reference in its entirety for this purpose.

In some embodiments, OCT4, SOX2, KLF4, replacements thereof, or any combination thereof is activated in a cell, tissue, organ and/or a subject in combination with gamma band light stimulation to promote nerve regeneration. See, e.g., McDermott et al., J Alzheimers Dis. 2018; 65(2): 363-392 for a description of gamma band light stimulation. This reference is hereby incorporated by reference in its entirety for this purpose.

Engineered Cells

Engineered cells and method of producing engineered cells are also encompassed by the present disclosure. The engineered cells, for example, may be useful in cell-based therapies (e.g., stem cell therapies). Although stem cell therapy is currently in clinical trials (see, e.g., David Cyranoski, Nature 557, 619-620 (2018), toxicity (e.g., off-target toxicity) is a concern, Without being bound by a particular theory, the engineered cells of the present disclosure (e.g., cells engineered using AAV vectors encoding OCT4, KLF4, and/or SOX2, and/or an inducing agent) may have a lower toxicity because AAV is does not integrate into the genome of host cells and use of the inducible systems described herein to control expression of OCT4, KLF4, and/or SOX2 may allow for precise control (e.g., amount and timing) of gene expression.

Any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced into a host cell, host tissue, or organ to produce an engineered cell, an engineered tissue, or an engineered organ. Any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced into a host cell, host tissue, or organ to produce an engineered cell, an engineered tissue, or an engineered organ. In some embodiments, a nucleic acid (e.g., engineered nucleic acid) encoding an inducing agent, an engineered protein encoding an inducing agent, a chemical agent capable of modulating (e.g., activating or inhibiting) the activity of an inducing agent, and/or a recombinant virus encoding an inducing agent is also introduced into a host cell, host tissue, or organ to produce an engineered cell, an engineered tissue, or an engineered organ.

In some embodiments, the engineered cell is an induced pluripotent stem cell (iPSC).

In some embodiments, a viral vector (e.g., an AAV vector, including a vector with a TRE promoter operably linked to a nucleic acid encoding OCT4, KLF4, and SOX2) is packaged into a virus with an AAV-DJ capsid. In some embodiments, the AAV-DJ capsid increases the transduction efficiency into cultured cells compared to cells without the AAV-DJ capsid. In some embodiments, the AAV virus encoding OSK is administered to a cell. In some embodiments, an AAV virus (e.g., AAV-DJ virus) encoding the inducing agent or a protein encoding the inducing agent is administered to the same cells. In some embodiments, this system produces an engineered cell (e.g., an induced pluripotent stem cell). In some embodiments, the engineered cell is further differentiated into (e.g., differentiated into an eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell). In some embodiments, the differentiated cell is used for transplantation purposes. In some embodiments, the engineered cell is cultured to create an engineered tissue. In some embodiments, the engineered cell is cultured to create an engineered organ. In some embodiments, the engineered cells are retina pigment epithelium cells, neuron cells, pancreatic beta-cells, or cardiac cells.

Compositions

The compositions of the disclosure may comprise at least one of any of the nucleic acids (e.g., engineered nucleic acid) capable of inducing OCT4, KLF4, and/or SOX2 expression (e.g., expression vector), engineered proteins, engineered cells, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein alone, or in combination. In certain embodiments, the compositions of the disclosure comprise at least one of any of the nucleic acids (e.g., engineered nucleic acid) (e.g., expression vector) capable of inducing expression of OCT4; KLF4; SOX2; or any combination thereof, engineered proteins, engineered cells, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein alone, or in combination. In some embodiments, a composition comprises 1, 2, 3, 4, 5, 6, 7, 8, 9, 10, or more different nucleic acids (e.g., engineered nucleic acids) capable of inducing OCT4, KLF4, and/or SOX2 expression (e.g., expression vectors encoding OCT4, KLF4, and/or SOX2). In some embodiments, a composition comprises 1, 2, 3, 4, 5, 6, 7, 8, 9, 10, or more different nucleic acids (e.g., engineered nucleic acids) capable of inducing expression of OCT4; KLF4; SOX2; or any combination thereof (e.g., expression vectors encoding OCT4; KLF4; SOX2; or any combination thereof). In some embodiments, a composition comprises 1, 2, 3, 4, 5, 6, 7, 8, 9, 10, or more different viruses (e.g., lentivirus, alphavirus, vaccinia virus, adenovirus, retrovirus, herpes virus, or AAV) each having one or more different transgenes. In some embodiments, a composition comprises 1, 2, 3, 4, 5, 6, 7, 8, 9, 10, or more different chemical agents activating (e.g., inducing expression of) OCT4, KLF4, and/ or SOX2. In some embodiments, a composition comprises 1, 2, 3, 4, 5, 6, 7, 8, 9, 10, or more different chemical agents activating (e.g., inducing expression of) OCT4; KLF4; SOX2; or any combination thereof. In some embodiments, a composition further comprises one or more nucleic acids (e.g., engineered nucleic acids) encoding an inducing agent, one or more engineered proteins encoding an inducing agent, one or more chemical agents capable of modulating (e.g., activating or inhibiting) the activity of an inducing agent, and/or one or more recombinant viruses encoding an inducing agent. In some embodiments, a composition comprises engineered cells (e.g., induced pluripotent stem cells and/or differentiated cells). In some embodiments, a composition comprises an engineered protein encoding OCT4, SOX2, and/or KLF4. In some embodiments, a composition comprises an engineered protein encoding OCT4, SOX2, KLF4, or any combination thereof. In some embodiments, a composition further comprises an engineered protein encoding an inducing agent.

In some embodiments, a composition further comprises a pharmaceutically acceptable carrier. Suitable carriers may be readily selected by one of skill in the art in view of the indication for which the nucleic acids (e.g., engineered nucleic acid) capable of inducing OCT4, KLF4, and/or SOX2 expression (e.g., expression vector), chemical agents activating (e.g., inducing expression of) OCT4, KLF4, and/ or SOX2, antibodies activating (e.g., inducing expression of) OCT4, KLF4, and/or SOX2, engineered proteins, engineered cells, and/or recombinant viruses (e.g., lentivirus, adenovirus, alphavirus, vaccinia virus, retrovirus, herpes virus, or AAV) e.g. is directed. Suitable carriers may be readily selected by one of skill in the art in view of the indication for which the nucleic acids (e.g., engineered nucleic acid) (e.g., expression vectors) capable of inducing expression of OCT4; KLF4; SOX2; or any combination thereof, chemical agents activating (e.g., inducing expression of) OCT4; KLF4; SOX2; or any combination thereof, antibodies activating (e.g., inducing expression of) OCT4; KLF4; SOX2; or any combination thereof, engineered proteins, engineered cells, and/or recombinant viruses (e.g., lentivirus, adenovirus, alphavirus, vaccinia virus, retrovirus, herpes virus, or AAV) e.g. is directed. Suitable carriers may also be readily selected by one of skill in the art in view of the indication for which the nucleic acids (e.g., engineered nucleic acids) encoding an inducing agent, engineered proteins encoding an inducing agent, chemical agents capable of modulating (e.g., activating or inhibiting) the activity of an inducing agent, and/or recombinant viruses (e.g., lentivirus, adenovirus, alphavirus, vaccinia virus, retrovirus, herpes virus, or AAV) comprising an inducing agent e.g. is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may comprise, in addition to the nucleic acids (e.g., engineered nucleic acid) capable of inducing OCT4, KLF4, and/or SOX2 expression (e.g., expression vector), engineered cells comprising OCT4, KLF4, and/or SOX2, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) e.g. and carrier(s), other pharmaceutical ingredients, such as preservatives, or chemical stabilizers. Optionally, the compositions of the disclosure may comprise, in addition to the nucleic acids (e.g., engineered nucleic acid) (e.g., expression vector) capable of inducing expression of OCT4; KLF4; SOX2; or any combination thereof, engineered cells comprising OCT4; KLF4; SOX2; or any combination thereof, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) e.g. and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. The compositions of the present disclosure may further comprise a nucleic acid (e.g., engineered nucleic acids) encoding an inducing agent, an engineered protein encoding an inducing agent, chemical agents capable of modulating (e.g., activating or inhibiting) the activity of an inducing agent, and/or recombinant viruses encoding an inducing agent.

The nucleic acid (e.g., engineered nucleic acid) (e.g., expression vector) capable of inducing expression of OCT4; KLF4; SOX2; or any combination thereof, engineered cells, chemical agents activating (e.g., inducing expression of) OCT4; KLF4; SOX2; or any combination thereof, engineered proteins encoding OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) encoding the same described herein are administered in sufficient amounts to transfect the cells of a desired tissue (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine tissue) and to provide sufficient levels of gene transfer and expression without undue adverse effects. Any of the nucleic acids (e.g., engineered nucleic acids) encoding an inducing agent, an engineered protein encoding an inducing agent, chemical agents capable of modulating (e.g., activating or inhibiting) the activity of an inducing agent, and/or recombinant viruses encoding an inducing agent are administered in sufficient amounts to transfect the cells of a desired tissue (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine tissue) and to provide sufficient levels of gene transfer and expression without undue adverse effects. Examples of pharmaceutically acceptable routes of administration include, but are not limited to, direct delivery to the selected organ (e.g., direct delivery to eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). Any of the nucleic acids (e.g., engineered nucleic acids) capable of inducing OCT4, KLF4, and/or SOX2 expression (e.g., expression vector), engineered cells, chemical agents activating (e.g., inducing expression of) OCT4, KLF4, and/or SOX2, engineered proteins, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Any of the nucleic acids (e.g., engineered nucleic acids) (e.g., expression vectors) capable of inducing expression of OCT4; KLF4; SOX2; or any combination thereof, engineered cells, chemical agents activating (e.g., inducing expression of) OCT4; KLF4; SOX2; or any combination thereof, engineered proteins, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Any of the nucleic acids encoding an inducing agent, chemical agents capable of modulating the activity of an inducing agent, engineered proteins encoding an inducing agent, and/or recombinant viruses encoding an inducing agent may be may be delivered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art. Routes of administration may be combined, if desired.

In some embodiments, a nucleic acid is delivered non-virally (e.g., not on a viral vector and/or not in a virus). In some embodiments, a nucleic acid (e.g., RNA or DNA) encoding OCT4, SOX2, and/or KLF4 and/or an inducing agent is administered in a liposome. In some embodiments, a nucleic acid (e.g., RNA or DNA) encoding OCT4, SOX2, KLF4, or any combination thereof, and/or an inducing agent is administered in a liposome. In some embodiments, a nucleic acid (e.g., RNA or DNA) encoding OCT4, SOX2, and/or KLF4 and/or an inducing agent is administered in a particle. In some embodiments, a nucleic acid (e.g., RNA or DNA) encoding OCT4, SOX2, KLF4, or any combination thereof, and/or an inducing agent is administered in a particle. In some embodiments, the nucleic acid is RNA (e.g., mRNA).

In some embodiments, a pharmaceutical composition comprising an expression vector encoding OCT4, KLF4, and/or SOX2 or a pharmaceutical composition comprising a virus harboring the expression vector is administered to a cell, tissue, organ or a subject. In some embodiments, a pharmaceutical composition comprising an expression vector encoding an inducing agent or a pharmaceutical composition comprising a virus harboring the expression vector is administered to a cell, tissue, organ or a subject. In some embodiments, the virus and/or expression vector encoding OCT4, KLF4, and/or SOX2 is administered systemically. In some embodiments, the virus and/or expression vector encoding an inducing agent is administered systemically. In some embodiments, the virus and/or expression vector encoding OCT4, KLF4, and/or SOX2 is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, a virus and/or expression vector encoding an inducing agent is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered using the same route of administration as the OCT4, KLF4, and/or SOX2 (e.g., nucleic acid encoding OCT4, KLF4, and/or SOX2). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered via a different route of administration as the OCT4, KLF4, and/or SOX2 (e.g., nucleic acid encoding OCT4, KLF4, and/or SOX2).

In some embodiments, a pharmaceutical composition comprising an expression vector encoding OCT4; KLF4; SOX2; or any combination thereof, or a pharmaceutical composition comprising a virus harboring the expression vector is administered to a cell, tissue, organ, or subject. In some embodiments, a pharmaceutical composition comprising an expression vector encoding an inducing agent or a pharmaceutical composition comprising a virus harboring the expression vector is administered to a cell, tissue, organ, or subject. In some embodiments, the virus and/or expression vector encoding OCT4; KLF4; SOX2; or any combination thereof is administered systemically. In some embodiments, the virus and/or expression vector encoding an inducing agent is administered systemically. In some embodiments, the virus and/or expression vector encoding OCT4; KLF4; SOX2; or any combination thereof is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, a virus and/or expression vector encoding an inducing agent is administered locally (e.g., directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered using the same route of administration as the OCT4; KLF4; SOX2; or any combination thereof (e.g., nucleic acid encoding OCT4; KLF4; SOX2; OCT4 and SOX2; OCT4 and KLF4; KLF4 and SOX2; or KLF4, OCT4, and SOX2). In some embodiments, the inducing agent (e.g., a nucleic acid encoding the inducing agent, a protein encoding the inducing agent, or a virus encoding the inducing agent) and/or chemical agent capable of modulating (e.g., activating or inhibiting) the activity of the inducing agent is administered via a different route of administration as the OCT4; KLF4; SOX2; or any combination thereof (e.g., nucleic acid encoding nucleic acid encoding OCT4; KLF4; SOX2; OCT4 and SOX2; OCT4 and KLF4; KLF4 and SOX2; or KLF4, OCT4, and SOX2).

In some embodiments, the expression vector is an inducible vector in which a nucleic acid encoding OCT4, KLF4, and/or SOX2 and/or inducing agent, is operably linked to an inducible TRE promoter (e.g., TRE3G, TRE2, or P tight). In some embodiments, the expression vector is an inducible vector in which a nucleic acid encoding OCT4; KLF4; SOX2; or any combination thereof, and/or inducing agent, is operably linked to an inducible TRE promoter (e.g., TRE3G, TRE2, or P tight). In some embodiments, the virus and/or inducible vector is administered with tetracycline (e.g., doxycycline). In some embodiments, the virus and/or expression vector comprising a TRE promoter is administered separately from tetracycline (e.g., doxycycline). For example, any of the viruses and/or expression vectors comprising a TRE promoter described herein may be administered systemically and the tetracycline may be administered locally (e.g., to an organ or tissue of interest). In some embodiments, any of the viruses and/or expression vectors comprising a TRE promoter described herein may be administered locally (e.g., to directly to a tissue or organ of interest, including eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) and the tetracycline may be administered systemically. As a non-limiting example, a virus and/or expression vector comprising a TRE promoter is administered directly (e.g., injected) into the eye of a subject and the tetracycline (e.g., doxycycline) is administered systemically (e.g., orally as a pill).

In some embodiments, tetracycline is administered intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, or in lipid compositions. In some embodiments, tetracycline is administered directly to a cell, organ, and/or tissue. As a non-limiting example, tetracycline may be administered to the eye of a subject through any suitable method, including eye drops comprising tetracycline, sustained release devices (e.g., micropumps, particles, and/or drug depots), and medicated contact lenses comprising tetracycline. In some embodiments, tetracycline is administered systemically (e.g., through drinking water or intravenous injection) to a subject. Tetracycline may be administered topically (e.g., in a cream) or through a subcutaneous pump (e.g., to deliver tetracycline to a particular tissue).

As an example, the dose of recombinant virus (e.g., lentivirus, alphaviruses, vaccinia viruses, adenovirus, retrovirus, herpes virus, or AAV) virions required to achieve a particular therapeutic effect, e.g., the units of dose in genome copies/per kilogram of body weight (GC/kg), will vary based on several factors including, but not limited to: the route of recombinant virus (e.g., lentivirus, alphaviruses, vaccinia viruses, adenovirus, retrovirus, herpes virus, or AAV) virion administration, the level of gene or RNA expression required to achieve a therapeutic effect, the specific disease or disorder being treated, and the stability of the gene or RNA product. One of skill in the art can readily determine a recombinant virus (e.g., lentivirus, alphaviruses, vaccinia viruses, adenovirus, retrovirus, herpes virus, or AAV virion) dose range to treat a patient having a particular disease or disorder based on the aforementioned factors, as well as other factors.

An effective amount of a recombinant virus (e.g., lentivirus, alphaviruses, vaccinia viruses, adenovirus, retrovirus, herpes virus, or AAV) is an amount sufficient to target infect an animal, target a desired tissue. In some embodiments, an effective amount of an recombinant virus (e.g., lentivirus, alphavirus, vaccinia virus, adenovirus, retrovirus, herpes virus, or AAV) is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the recombinant virus (e.g., lentivirus, alphavirus, vaccinia virus, adenovirus, retrovirus, herpes virus, or AAV) is generally in the range of from about 1 ml to about 100 ml of solution containing from about $10^9$ to $10^{16}$ genome copies. In some cases, a dosage between about $10^{11}$ to $10^{13}$ recombinant virus (e.g., lentivirus, adenovirus, retrovirus, alphavirus, vaccinia virus, herpes virus, or AAV) genome copies is appropriate. In certain embodiments, $10^{10}$ or $10^{11}$ recombinant virus (e.g., lentivirus, adenovirus, retrovirus, alphavirus, vaccinia virus, herpes virus, or AAV) genome copies is effective to target ocular tissue (e.g., retinal tissue). In some cases, stable transgenic animals are produced by multiple doses of a recombinant virus (e.g., lentivirus, adenovirus, retrovirus, herpes virus, alphavirus, vaccinia virus, or AAV).

In some embodiments, a dose of recombinant virus (e.g., lentivirus, adenovirus, retrovirus, herpes virus, alphavirus, vaccinia virus, or AAV) is administered to a subject no more than once per calendar day (e.g., a 24-hour period). In some embodiments, a dose of recombinant virus (e.g., lentivirus, alphavirus, vaccinia virus, adenovirus, retrovirus, herpes virus, or AAV) is administered to a subject no more than once per 2, 3, 4, 5, 6, or 7 calendar days. In some embodiments, a dose of recombinant virus (e.g., lentivirus, alphavirus, vaccinia virus, adenovirus, retrovirus, herpes virus, or AAV) is administered to a subject no more than once per calendar week (e.g., 7 calendar days). In some embodiments, a dose of recombinant virus (e.g., lentivirus, alphavirus, vaccinia virus, adenovirus, retrovirus, herpes virus, or AAV) is administered to a subject no more than bi-weekly (e.g., once in a two calendar week period). In some embodiments, a dose of recombinant virus (e.g., lentivirus, alphavirus, vaccinia virus, adenovirus, retrovirus, herpes virus, or AAV) is administered to a subject no more than once per calendar month (e.g., once in 30 calendar days). In some embodiments, a dose of recombinant virus (e.g., lentivirus, alphavirus, vaccinia virus, adenovirus, retrovirus, herpes virus, or AAV) is administered to a subject no more than once per six calendar months. In some embodiments, a dose of recombinant virus (e.g., lentivirus, alphavirus, vaccinia virus, adenovirus, retrovirus, herpes virus, or AAV) is administered to a subject no more than once per calendar year (e.g., 365 days or 366 days in a leap year).

In some embodiments, recombinant virus (e.g., lentivirus, alphavirus, vaccinia virus, adenovirus, retrovirus, herpes virus, or AAV) compositions are formulated to reduce aggregation of AAV particles in the composition, particularly where high recombinant virus (e.g., lentivirus, alphavirus, vaccinia virus, adenovirus, retrovirus, herpes virus, or AAV) concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

As a non-limiting example, delivery of transgenes via AAV have been shown to be feasible and non-toxic in humans. For example, AAV may be delivered to the eye. See, e.g., Smalley Nat Biotechnol. 2017 Nov. 9; 35(11):998-999.

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, the nucleic acids (e.g., engineered nucleic acid) capable of inducing OCT4, KLF4, and/or SOX2 expression (e.g., expression vector), engineered cells comprising OCT4, KLF4, and/or SOX2, engineered proteins encoding Oct4, KLF4, and/or SOX2, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In some embodiments, the nucleic acids (e.g., engineered nucleic acid) (e.g., expression vector) capable of inducing expression of OCT4; KLF4; SOX2; or any combination thereof, engineered cells comprising OCT4; KLF4; SOX2; or any combination thereof, engineered proteins encoding Oct4, KLF4, SOX2, or a combination thereof, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

In some embodiments, the nucleic acids (e.g., engineered nucleic acid) encoding an inducing agent (e.g., an expression vector), engineered cells comprising an inducing agent, engineered proteins encoding a inducing agent, chemical agents capable of modulating the activity of an inducing agent, and/or recombinant viruses (e.g., lentiviruses, adenoviruses, alphaviruses, vaccinia viruses, retroviruses, herpes viruses, or AAVs) encoding an inducing agent e.g. in suitably formulated pharmaceutical compositions disclosed herein are delivered directly to target tissue, e.g., direct to a tissue of interest (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

However, in certain circumstances it may be desirable to separately or in addition deliver any of the nucleic acids (e.g., engineered nucleic acid) capable of inducing OCT4, KLF4, and/or SOX2 expression (e.g., expression vector) and/or nucleic acid encoding an inducing agent, nucleic acids (e.g., engineered nucleic acid) capable of inducing expression of a combination of transcription factors selected from OCT4, KLF4, and/or nucleic acid encoding an inducing agent, engineered cells, engineered proteins, chemical agents activating (e.g., inducing expression of) OCT4, KLF4, and/or SOX2, chemical agents activating (e.g., inducing expression of) a combination of transcription factors selected from OCT4, KLF4, and SOX2, chemical agents capable of modulating (e.g., inhibiting or activating) the activity of an inducing agent, antibodies activating (e.g., inducing expression of) OCT4, KLF4, and/or SOX2, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver recombinant virus (e.g., lentivirus, alphavirus, vaccinia virus, adenovirus, retrovirus, herpes virus, or AAVs). In some embodiments, a preferred mode of administration is by intrastromal injection.

In some embodiments, a nucleic acid (e.g., mRNA) encoding OCT4, SOX2, KLF4, or any combination thereof is nanoformulated into a polyplex, which may be useful, for example, for noninvasive aerosol inhalation and delivery of the nucleic acid to the lung (e.g., lung epithelium). See, e.g., Patel et al., Adv Mater. 2019 Jan. 4:e1805116. doi: 10.1002/adma.201805116 for description of nanoformulated mRNA polyplexes, which is hereby incorporated by reference in its entirety for this purpose.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid (e.g., engineered nucleic acid) capable of inducing OCT4, KLF4, and/or SOX2 expression (e.g., expression vector), engineered cells, engineered proteins, chemical agents activating (e.g., inducing expression of) OCT4, KLF4, an and/or SOX2, antibodies activating (e.g., inducing expression of) OCT4, KLF4, and/or SOX2, and/or active recombinant viruses (e.g., lentivirus, adenovirus, alphavirus, vaccinia virus, retrovirus, herpes virus, or AAV) e.g. in the required amount in the appropriate solvent with various of the other ingredients enumerated herein, as required, followed by filtered sterilization. Sterile injectable solutions are prepared by incorporating the nucleic acid (e.g., engineered nucleic acid) (e.g., expression vector) capable of inducing expression of OCT4, KLF4, SOX2, or any combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or active recombinant viruses (e.g., lentivirus, adenovirus, alphavirus, vaccinia virus, retrovirus, herpes virus, or AAV) e.g. in the required amount in the appropriate solvent with various of the other ingredients enumerated herein, as required, followed by filtered sterilization. In certain embodiments, the sterile injectable solutions are prepared by incorporating a nucleic acid (e.g., engineered nucleic acid) encoding an inducing agent, engineered protein encoding an inducing agent, chemical agents capable of modulating the activity of an inducing agent and/or active recombinant viruses (e.g., lentivirus, adenovirus, alphavirus, vaccinia virus, retrovirus, herpes virus, or AAV) encoding an inducing agent e.g. in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions comprising nucleic acids (e.g., engineered nucleic acids) encoding OCT4, KLF4, and/or SOX2 (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) disclosed herein may also be formulated in a neutral or salt form. The compositions comprising nucleic acids (e.g., engineered nucleic acids) (e.g., expression vector) encoding OCT4; KLF4; SOX2; or any combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) disclosed herein may also be formulated in a neutral or salt form. The compositions may comprise an inducing agent (e.g., a nucleic acid encoding an inducing agent or a protein encoding an inducing agent and/or a recombinant virus encoding an inducing agent) and/or a chemical agent capable of modulating the activity of an inducing agent. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

A carrier includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of the compositions of the present disclosure into suitable host cells. In particular, any of the nucleic acids (e.g., engineered nucleic acids) capable of inducing OCT4, KLF4, and/or SOX2 expression (e.g., expression vector), any of the engineered proteins, any of the chemical agents activating (e.g., inducing expression of) OCT4, KLF4, and/or SOX2, any of the antibodies activating (e.g., inducing expression of) OCT4, KLF4, and/or SOX2, engineered cells, and/or any of the recombinant viruses (e.g., lentivirus, adenovirus, alphavirus, vaccinia virus, retrovirus, herpes virus, or AAV) may be encapsulated in a lipid particle, a liposome, a vesicle, a nanosphere, or a nanoparticle or the like. In some embodiments, any of the nucleic acids (e.g., engineered nucleic acids) (e.g., expression vector) capable of inducing expression of OCT4; KLF4; SOX2; or any combination thereof, any of the engineered proteins, any of the chemical agents activating (e.g., inducing expression of) OCT4; KLF4; SOX2; or any combination thereof, any of the antibodies activating (e.g., inducing expression of) OCT4; KLF4; SOX2; or any combination thereof, engineered cells, and/or any of the recombinant viruses (e.g., lentivirus, adenovirus, alphavirus, vaccinia virus, retrovirus, herpes virus, or AAV) may be encapsulated in a lipid particle, a liposome, a vesicle, a nanosphere, or a nanoparticle or the like. An inducing agent (e.g., a nucleic acid encoding an inducing agent or a protein encoding an inducing agent and/or a recombinant virus encoding an inducing agent) and/or a chemical agent capable of modulating the activity of an inducing agent may be encapsulated in a lipid particle, a liposome, a vesicle, a nanosphere, or a nanoparticle or the like.

In some embodiments, the delivery vehicle targets the cargo. For example, any of the nucleic acids, engineered proteins, chemical agents, antibodies, and/or recombinant viruses (e.g., lentivirus, adenovirus, alphavirus, vaccinia virus, retrovirus, herpes virus, or AAV) described herein may be delivered via a nanoparticle that delivers the cargo to a certain tissue or cell type. Nanoparticles coated in galactose polymers, for example, are known to release their cargo within senescent cells as a result of their endogenous beta-galactosidase activity. See e.g., Lozano-Torres et al., J Am Chem Soc. 2017 Jul. 5; 139(26):8808-8811.

In some embodiments, any of the nucleic acids, engineered proteins, chemical agents, antibodies, and/or recombinant viruses (e.g., lentivirus, adenovirus, alphavirus, vaccinia virus, retrovirus, herpes virus, or AAV) is formulated in a poly(glycoamidoamine) brush nanoparticles. See, e.g., Dong et al., Nano Lett. 2016 Feb. 10; 16(2):842-8.

In some embodiments, any of the nucleic acids, engineered proteins, chemical agents, antibodies, and/or recombinant viruses (e.g., lentivirus, adenovirus, alphavirus, vaccinia virus, retrovirus, herpes virus, or AAV) is formulated in a lipid nanoparticle. See, e.g., Cullis and Hope Mol Ther. 2017 Jul. 5; 25(7):1467-1475. In some embodiments, the lipid nanoparticle comprises one or more membrane fusion proteins, which deliver plasmids directly into the cytoplasm or the factors OCT4; KLF4; SOX2; or any combination thereof may be fused directly to the targeting protein with or without nanoparticle encapsulation. In some embodiments, the lipid nanoparticle is a Fusogenix lipid nanoparticle. In some embodiments, the lipid nanoparticle is a "Wrapped Liposomes" (WL). See, e.g., Yamauchi et al., Biochim Biophys Acta. 2006 January; 1758(1):90-7. In some embodiments, the lipid nanoparticle is a PEGylated liposome (e.g., DOXIL™) (e.g., Allen & Hansen, Biochim Biophys Acta. 1991 Jul. 1; 1066(1):29-36.), 1, 2-dioleoyl-sn-glycerol-3 phosphatidylethanolamine (DOPE), a neutral helper lipid phosphatidylethanolamine (PE), or combinations thereof (e.g., Farhood et al., Biochim Biophys Acta. 1995 May 4; 1235(2):289-95; Zhou & Huang, Biochim Biophys Acta. 1994 Jan. 19; 1189(2):195-203.). In some embodiments, the lipid nanoparticle or fusion protein comprises employs a molecule or protein to mimic methods employed by viruses for intracellular delivery of macromolecules (e.g., Kobayashi et al., Bioconjug Chem. 2009 May 20; 20(5):953-9), e.g., using a variety of pH sensitive peptides such as vesicular stomatitis virus proteins (VSV G), phage coat proteins and/or shGALA, and/or Fusion associated small transmembrane (FAST) proteins, e.g., avian reovirus (ARV), nelson bay reovirus (NBV), and baboon reovirus (BBV), aquareovirus reovirus (AQV) and reptilian reovirus (RRV), and/or Bombesin targeting peptide. See, e.g., Peisajovich et al., Eur J Biochem. 2002 September; 269(17):4342-50.; Sakurai et al., 2011. See also Nesbitt, Targeted Intracellular Therapeutic Delivery Using Liposomes Formulated with Multifunctional FAST proteins, Western University Thesis, 2012. https://www.google.com/url?sa=t&rct=j&q=&esrc=s&source=web&cd=14&ved=2ahUKEwi X-YW5puzfAhXGTd8KHUmCATOQFjANegQIAhAB&url=http %3A %2F %2Fir.lib.uwo.ca %2Fcgi %2Fviewcontent.cgi %3Farticle %3D1571%26context %3Detd&usg=AOvVaw3A20aOef HfJIJSZRR_-kPD In some embodiments, a nucleic acid (e.g., RNA or DNA, including a plasmid) encoding OCT4, KLF4, SOX2, or a combination thereof is encapsulated in a Fusogenix lipid nanoparticle. In some embodiments, a nucleic acid encoding an inducing agent (e.g., rtTA or tTA) is encapsulated in a Fusogenix lipid nanoparticle. In some embodiments, a lipid nanoparticle comprises a viral membrane protein. Without being bound by a particular theory, a lipid nanoparticle may be non-toxic because it comprises a membrane fusion protein that is not a viral membrane fusion protein. Non-limiting examples of membrane fusion proteins include membrane fusion proteins disclosed in U.S. Pat. Nos. 7,851,595, 8,252,901, International Application Publication No. WO 2012/040825, and International Application Publication No. WO 2002/044206.

In some embodiments, a composition of the present disclosure (e.g., comprising a nucleic acid encoding OCT4, KLF4, SOX2, or a combination thereof) is delivered non-virally. Methods of non-viral delivery of nucleic acids include lipofection, nucleofection, microinjection, biolistics, virosomes, liposomes, immunoliposomes, polycation or lipid:nucleic acid conjugates, naked nucleic acid (e.g., RNA or DNA), artificial virions, and agent-enhanced uptake of a nucleic acid (e.g., RNA or DNA).

In some embodiments, a cationic lipid is used to deliver a nucleic acid. A cationic lipid is a lipid which has a cationic, or positive, charge at physiologic pH. Cationic lipids can take a variety of forms including, but not limited to, liposomes or micelles. Cationic lipids useful for certain aspects of the present disclosure are known in the art, and, generally comprise both polar and non-polar domains, bind to polyanions, such as nucleic acid molecules or negatively supercharged proteins, and are typically known to facilitate the delivery of nucleic acids into cells. Examples of useful cationic lipids include polyethylenimine, polyamidoamine (PAMAM) starburst dendrimers, Lipofectin (a combination of DOTMA and DOPE, see, e.g., U.S. Pat. Nos. 5,049,386, 4,946,787; and 4,897,355), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 30-[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Cationic lipids have been used in the art to deliver nucleic acid molecules to cells (see, e.g., U.S. Pat. Nos. 5,855,910; 5,851,548; 5,830,430; 5,780,053; 5,767,099; 8,569,256; 8,691,750; 8,748,667; 8,758,810; 8,759,104; 8,771,728; Lewis et al. 1996. Proc. Natl. Acad. Sci. USA 93:3176; Hope et al. 1998. Molecular Membrane Biology 15:1).

In addition, other lipid compositions are also known in the art and include, e.g., those taught in U.S. Pat. Nos. 4,235,871; 4,501,728; 4,837,028; 4,737,323. Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Polymer-based delivery systems may also be used to deliver a nucleic acid. Polymers including polyethylenimine (PEI), chitosan, Poly (DL-Lactide) (PLA) and Poly (DL-Lactide-co-glycoside) (PLGA), dedrimers, and Polymethacrylate may be used. See, e.g., Yang et al., Macromol Biosci. 2012 December; 12(12):1600-14; Ramamoorth et al., J Clin Diagn Res. 2015 January; 9(1): GE01-GE06. As a non-limiting example, a cationic polymer may be used. A cationic polymer is a polymer having a net positive charge. Cationic polymers are well known in the art, and include those described in Samal et al., Cationic polymers and their therapeutic potential. Chem Soc Rev. 2012 Nov. 7; 41(21): 7147-94; in published U.S. patent applications U.S. 2014/0141487 A1, U.S. 2014/0141094 A1, U.S. 2014/0044793 A1, U.S. 2014/0018404 A1, U.S. 2014/0005269 A1, and U.S. 2013/0344117 A1; and in U.S. Pat. Nos. 8,709,466; 8,728,526; 8,759,103; and 8,790,664; the entire contents of each are incorporated herein by reference. Exemplary cationic polymers include, but are not limited to, polyallylamine (PAH); polyethyleneimine (PEI); poly(L-lysine) (PLL); poly(L-arginine) (PLA); polyvinylamine homo- or copolymer; a poly(vinylbenzyl-tri-C1-C4-alkylammonium salt); a polymer of an aliphatic or araliphatic dihalide and an aliphatic N,N,N',N'-tetra-C1-C4-alkyl-alkylenediamine; a poly(vinylpyridin) or poly(vinylpyridinium salt); a poly(N,N-diallyl-N,N-di-C1-C4-alkyl-ammoniumhalide); a homo- or copolymer of a quaternized di-C1-C4-alkyl-aminoethyl acrylate or methacrylate; POLYQUAD™; a polyaminoamide; and the like.

Such formulations may be preferred for the introduction of pharmaceutically acceptable formulations of any of the nucleic acids, engineered proteins, chemical agents, antibodies, and/or recombinant viruses (e.g., lentivirus, adenovirus, alphavirus, vaccinia virus, retrovirus, herpes virus, or AAV) disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868; and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500. ANG., containing an aqueous solution in the core.

Alternatively, nanocapsule formulations of the recombinant virus (e.g., lentivirus, alphavirus, vaccinia virus, adenovirus, retrovirus, herpes virus, or AAV) may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

Kits and Related Compositions

Any of the nucleic acids, engineered proteins, chemical agents, antibodies, and/or recombinant viruses described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a recombinant virus (e.g., lentivirus, alphavirus, vaccinia virus, adenovirus, retrovirus, herpes virus, or AAV) and/or engineered cells, the kit comprising a container housing an engineered nucleic acid (e.g., engineered nucleic acid) encoding OCT4, KLF4, SOX2, or a combination thereof and/or host cells. In some embodiments, the kit further comprises instructions for producing the recombinant virus (e.g., lentivirus, alphavirus, vaccinia virus, adenovirus, retrovirus, herpes virus, or AAV) and/or instructions for producing engineered cells. In some embodiments, the kit further comprises at least one container housing a recombinant AAV vector, wherein the recombinant AAV vector comprises a transgene (e.g., a gene associated with ocular disease, such as corneal disease).

In some embodiments, the instant disclosure relates to a kit comprising a container housing any of the engineered nucleic acids (e.g., expression vectors), chemical agents, antibodies, engineered cells, or recombinant viruses described herein. For example, an expression vector or recombinant virus encoding KLF4, SOX2, OCT4, or a combination thereof may comprise a sequence that is at least 70% (e.g., at least 75%, 80%, 85%, 90%, 95%, 98%, 99%, or 100%) identical to SEQ ID NO: 16, SEQ ID NO: 105, or SEQ ID NO: 121. In some embodiments, an expression vector or recombinant virus encoding KLF4, SOX2, OCT4, or a combination thereof comprises SEQ ID NO: 16, SEQ ID NO: 105, or SEQ ID NO: 121. In some embodiments, the expression vector encoding these three transcription factors consists of SEQ ID NO: 16, SEQ ID NO: 105, or SEQ ID NO: 121. The kit may further comprise an expression vector or recombinant virus encoding an inducing agent. In some embodiments, an expression vector encoding an inducing agent comprises SEQ ID NO: 17, SEQ ID NO: 31, or SEQ ID NO: 32. In some embodiments, the expression vector encoding an inducing agent consists of SEQ ID NO: 17, SEQ ID NO: 31, or SEQ ID NO: 32. See, e.g., U.S. Provisional Application No. 62/738,894, entitled MUTANT REVERSE TETRACYCLINE TRANSACTIVATORS FOR EXPRESSION OF GENES, which was filed on Sep. 28, 2018, and is herein incorporated by reference in its entirety.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink-wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

Therapeutic Applications

Any of the nucleic acids (e.g., engineered nucleic acids) capable of inducing OCT4, KLF4, and/or SOX2 expression (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be used for regulating (e.g., inducing or inducing and stopping) cellular reprogramming, tissue repair, tissue regeneration, organ regeneration, reversing aging, treating a disease, or any combination thereof. Any of the nucleic acids (e.g., engineered nucleic acids) capable of inducing expression of a combination of transcription factors selected from OCT4, KLF4, and SOX2 (e.g., OCT4 and KLF4, OCT4 and SOX2, SOX2 and KLF4, or KLF4, OCT4, and SOX2), engineered cells, engineered proteins, chemical agents activating (e.g., inducing expression of) a combination of transcription factors selected from OCT4, KLF4, and SOX2 (e.g., OCT4 and KLF4, OCT4 and SOX2, SOX2 and KLF4, or KLF4, OCT4, and SOX2), antibodies activating (e.g., inducing expression of) combination of transcription factors selected from OCT4, KLF4, and SOX2 (e.g., OCT4 and KLF4, OCT4 and SOX2, SOX2 and KLF4, or KLF4, OCT4, and SOX2), and/or recombinant viruses (e.g., lentivirus, adenovirus, alphavirus, vaccinia virus, retrovirus, herpes virus, or AAV) described herein may be used for regulating (e.g., inducing or inducing and stopping) cellular reprogramming, tissue repair, tissue regeneration, organ regeneration, reversing aging, treating a disease, or any combination thereof. In some embodiments, any of the nucleic acid (e.g., engineered nucleic acid) capable of inducing OCT4, KLF4, and/or SOX2 expression (e.g., expression vector), any of the engineered cells, any of the engineered proteins, any of the chemical agents activating (e.g., inducing expression of) OCT4, KLF4, and/or SOX2, any of the antibodies activating (e.g., inducing expression of) OCT4, KLF4, and/or SOX2, and/or any of the recombinant viruses (e.g., lentivirus, adenovirus, alphavirus, vaccinia virus, retrovirus, herpes virus, or AAV) may be useful in regulating cellular reprogramming, tissue repair, tissue survival, tissue regeneration, tissue growth, tissue function, organ regeneration, organ survival, organ function, or any combination thereof, optionally wherein regulating comprises inducing cellular reprogramming, reversing aging, improving tissue function, improving organ function, tissue repair, tissue survival, tissue regeneration, tissue growth, angiogenesis, scar formation, the appearance of aging, organ regeneration, organ survival, altering the taste and quality of agricultural products derived from animals, treating a disease, or any combination thereof, in vivo or in vitro may be administered to a cell, tissue, or organ that is in vivo (e.g., part of a subject), or may be administered to a cell, tissue, or organ ex vivo. In some embodiments, any of the nucleic acid (e.g., engineered nucleic acid) (e.g., expression vector) capable of inducing expression of OCT4; KLF4; SOX2; or any combination thereof, any of the engineered cells, any of the engineered proteins, any of the chemical agents activating (e.g., inducing expression of) OCT4; KLF4; SOX2; or any combination thereof, any of the antibodies activating (e.g., inducing expression of) OCT4, KLF4, SOX2, or a combination thereof, and/or any of the recombinant viruses (e.g., lentivirus, adenovirus, alphavirus, vaccinia virus, retrovirus, herpes virus, or AAV) may be useful in regulating cellular reprogramming, tissue repair, tissue survival, tissue regeneration, tissue growth, tissue function, organ regeneration, organ survival, organ function, or any combination thereof, optionally wherein regulating comprises inducing cellular reprogramming, reversing aging, improving tissue function, improving organ function, tissue repair, tissue survival, tissue regeneration, tissue growth, angiogenesis, scar formation, the appearance of aging, organ regeneration, organ survival, altering the taste and quality of agricultural products derived from animals, treating a disease, or any combination thereof, in vivo or in vitro may be administered to a cell, tissue, or organ that is in vivo (e.g., part of a subject), or may be administered to a cell, tissue, or organ ex vivo. As used herein, regulating may refer to any type of modulation, including inducing or promoting, inhibiting, and/or stopping. Angiogenesis refers to growth of new blood vessels, including capillaries.

In some instances, a viral vector (e.g., lentivirus vector, alphavirus vector, vaccinia virus vector, adenovirus vector, herpes virus vector, retrovirus vector, or AAV vector) is administered in a recombinant virus (e.g., lentivirus, alphavirus, vaccinia virus, adenovirus, herpes virus, retrovirus, or AAV). Without being bound by a particular theory, transient expression of OCT4, SOX2, and KLF4 may result in partial reprogramming of a cell. For example, partial reprogramming may induce a fully differentiated cell to rejuvenate and gain pluripotency. In some embodiments, transient expression of OCT4, SOX2, and/or KLF4 does not induce expression of stem cell markers (e.g., Nanog).

In some embodiments, transient expression of OCT4, SOX2, KLF4, or a combination thereof does not induce expression of stem cell markers (e.g., Nanog). Without being bound by any particular theory, Nanog activation may induce teratomas and cause death of the host. In some embodiments, the method does not induce teratoma formation. In some embodiments, the method does not induce unwanted cell proliferation. In some embodiments, the method does not induce malignant cell growth. In some embodiments, the method does not induce cancer. In some embodiments, the method does not induce glaucoma. In some embodiments, transient expression is at most 1 hour, 5 hours, 24 hours, 2 days, 3 days, 4 days, 5, days, or 1 week. In some instances, prolonged expression (e.g., continued expression for at least 5 days, at least 1 week, or at least 1 month) of OCT4, SOX2, and KLF4, results in full reprogramming of a cell. For example, a cell may be fully reprogrammed into a pluripotent cell (e.g., induced pluripotent cell). In some instances, prolonged expression (e.g., continued expression for at least 5 days, at least 1 week, or at least 1 month) of OCT4, SOX2, KLF4, or a combination thereof, results in full reprogramming of a cell. For example, a cell may be fully reprogrammed into a pluripotent cell (e.g., induced pluripotent cell).

Without being bound by a particular theory, expression of OCT4, SOX2, and KLF4 may promote cellular reprogramming, promote tissue regeneration, promote organ regeneration, reverse aging, treat a disease, or any combination thereof because OCT4, SOX2, and KLF4 induce partial reprogramming. As used herein, partial or incomplete reprogramming of a cell refers to a cell that are not stem cells, but have youthful characteristics. In some embodiments, a youthful characteristic is an epigenome that is similar to a young cell. In some embodiments, a stem cell shows higher levels of Nanog expression compared to a cell that is not a stem cell. In some embodiments, youthful characteristics refers to rejuvenation of a cell without changing cell identity. See, e.g., shown in FIG. 16, in which the expression of histone and Chaf (Chromatin assembly factor) genes decline during aging in ear fibroblasts from aged mice (12 months or 15 months) compared to those from young mice, short term of OSKM (3 days) or OSK expression (5 days) induction can reset their gene expression level to young state, without making the cells into a stem cell (e.g., Nanog expression is not induced in these cells).

To practice this embodiment, an effective amount of any of the nucleic acids (e.g., engineered nucleic acids) capable of inducing OCT4, KLF4, and/or SOX2 expression (e.g., expression vector), engineered proteins, chemical agents activating (e.g., inducing expression of) OCT4, KLF4, and/ or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) are administered to a cell, a tissue, organ, and/or subject. In some embodiments, an effective amount of any of the nucleic acids (e.g., engineered nucleic acids) (e.g., expression vector) capable of inducing expression of OCT4, KLF4, SOX2, or a combination thereof, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) are administered to a cell, a tissue, organ, and/or subject. Engineered cells may be administered to any tissue, organ, and/or subject. When the expression vector comprises an inducible promoter (e.g., a TRE promoter, including a TRE3G, TRE2, or P tight), the inducing agent may also be introduced into the cell (e.g., simultaneously or sequentially with one or more nucleic acids (e.g., engineered nucleic acids) encoding OCT4, SOX2, KLF4, or any combination thereof). In one embodiment, OCT4, SOX2, and KLF4 are encoded by one expression vector that is separate from an expression vector encoding the inducing agent. In some instances, the inducing agent is encoded by the same expression vector that encodes OCT4, SOX2, KLF4, or any combination thereof.

In some instances, an inducing agent (e.g., a nucleic acid encoding an inducing agent, an engineered protein encoding an inducing agent, or a virus encoding an inducing agent) and/or a chemical agent (e.g., tetracycline) that is capable of modulating (e.g., activating or inhibiting) activity of the inducing agent is also introduced into a cell, tissue, organ, and/or subject. In certain embodiments, a cell, tissue, subject, and/or organ is further cultured in the presence or absence of a chemical agent that is capable of modulating the activity of an inducing agent (e.g., tetracycline, which includes doxycycline). For a Tet-On system, the inducing agent may be rtTA (e.g., rtTA3 or rtTA4), and the inducing agent promotes expression of OCT4, SOX2, KLF4, or any combination thereof in the presence of tetracycline. For a Tet-Off system, the inducing agent may be tTA, and the inducing agent promotes expression of OCT4, SOX2, KLF4, or any combination thereof in the absence of tetracycline.

Administration of an expression vector encoding a transcription factor described herein and in some cases the inducing agent (e.g., a nucleic acid (e.g., engineered nucleic acid) encoding an inducing agent or the inducing agent as protein) and/or chemical agent that is capable of modulating the activity of the inducing agent under suitable conditions for expression may increase expression of the transgene by at least 10%, at least 20%, at least 30%, at least 40%, at least 50%, at least 60%, at least 70%, at least 80%, at least 90%, at least 100%, at least 200%, at least 300%, at least 400%, at least 500%, at least 500%, at least 600%, at least 700%, at least 800%, at least 900%, or at least 1,000% in a cell. Gene expression may be determined by routine methods including enzyme-linked immunosorbent assays (ELISAs), western blots, and quantification of RNA (e.g., reverse transcription polymerase chain reaction).

In some embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a tissue, cell, or organ ex vivo (e.g., not in a subject) and the tissue, cell, and/or organ may be further cultured ex vivo. In some embodiments, any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced to a tissue, cell, or organ ex vivo (e.g., not in a subject) and the tissue, cell, and/or organ may be further cultured ex vivo. In some instances, an inducing agent and/or a chemical agent capable of modulating the activity of the inducing agent is introduced to a tissue, cell, and/or organ ex vivo and the tissue, cell, and/or organ may be further cultured ex vivo. In some embodiments, engineered cells are cultured to produce an engineered tissue. In some embodiments, engineered cells are cultured to produce an engineered organ. In some embodiments, an engineered tissue is cultured to produce an engineered organ. These methods may be useful in producing an engineered (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) cell, engineered (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) tissue or organ (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine) for transplantation into a subject. In some embodiments, the engineered cell, tissue, and/or organ is transplanted into a subject.

In some embodiments, cells, tissues, organs, or any combination thereof to be engineered are autologous to the subject, e.g., obtained from a subject in need thereof. Administration of autologous cells, autologous tissues, autologous organs, or any combination thereof may result in reduced rejection of the cells, tissues, organs, or any combination thereof compared to administration of non-autologous cells, non-autologous tissue and/or non-autologous organs. Alternatively, the cells, tissues, or organs to be engineered may be allogenic cells, allogenic tissues, or allogenic organs. For example, allogenic cells, allogenic tissue, allogenic organs, or any combination thereof may be derived from a donor (e.g., from a particular species) and administered to a recipient (e.g., from the same species) who is different from the donor. In some embodiments, allogenic cells, allogenic tissue, allogenic organs, or any combination thereof may be derived from a donor subject from a particular species and administered to a recipient subject from a different species from the donor.

In some embodiments, the engineered cell is a stem cell (iPSC) including naïve iPSC that can different into three germ layers. In some embodiments, the iPSC is further differentiated into another cell type (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). The iPSC may be further differentiated using methods known in the art (e.g., ex vivo)

In some embodiments, engineered cells comprise more than one cell type (e.g., eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine).

As a non-limiting example, any of the engineered nucleic acids (e.g., naked nucleic acids or nucleic acids formulated in a delivery vehicle, including a viral vector and/or nanoparticle) encoding OCT4, KLF4, and SOX2, may be delivered to a cell (e.g., a differentiated cell) to produce an induced pluripotent stem cell. In some embodiments, the induced pluripotent stem cell is further differentiated (e.g., differentiated into an eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell). In some embodiments, cells are engineered ex vivo and administered to a subject in need thereof. In some embodiments, an organ or a tissue may be regenerated in vitro using iPSCs and the organ or tissue is transplanted into an individual.

As a non-limiting example, the methods described herein may be used to produce engineered skin, an engineered liver, an engineered eye, an engineered liver, any engineered cell, any engineered organ, or any engineered tissue ex vivo. The engineered organ, engineered tissue, engineered organ, or any combination thereof may be administered to a subject. In some embodiments, administration of an engineered cell, engineered tissue, engineered organ, or a combination thereof improves survival of a subject (e.g., increases the lifespan of a subject relative to not receiving the engineered cell, tissue, or organ).

A pharmaceutical composition described herein may be administered to a subject in need thereof. Non-limiting examples of subjects include any animal (e.g., mammals, including humans). A subject may be suspected of having, be at risk for or have a condition. For example, the condition may be an injury or a disease and the condition may affect any tissue (e.g., ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine). Non-limiting examples of conditions, diseases, and disorders include acute injuries, neurodegenerative disease, chronic diseases, proliferative diseases, cardiovascular diseases, genetic diseases, inflammatory diseases, autoimmunue diseases, neurological diseases, hematological diseases, painful conditions, psychiatric disorders, metabolic disorders, cancers, aging, age-related diseases, and diseases affecting any tissue in a subject. In some embodiments, the disease is an ocular disease.

In certain embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a subject prior to the onset of a disease (e.g., to prevent a disease or to prevent damage to a cell, tissue, or organ). In certain embodiments, any of the nucleic acids (e.g., engineered nucleic acid) (e.g., expression vector) capable of inducing expression of OCT4; KLF4; SOX2; or any combination thereof, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone, or in combination may be introduced to a subject prior to the onset of a disease (e.g., to prevent a disease or to prevent damage to a cell, tissue, or organ). In certain embodiments, an inducing agent and/or a chemical agent capable of modulating activity of the inducing agent may be introduced to a subject prior to the onset of a disease. In some embodiments, the subject may be a healthy subject.

In certain embodiments, any of the nucleic acids (e.g., engineered nucleic acid) capable of inducing OCT4, KLF4, and/or SOX2 expression (e.g., expression vector), engineered proteins described herein, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein, alone, or in combination may be introduced to a subject following the onset of disease (e.g., to alleviate the damage or symptoms associated with a disease). In certain embodiments, any of the nucleic acids (e.g., engineered nucleic acid) capable of inducing expression of OCT4; KLF4; SOX2; or any combination thereof expression, engineered proteins described herein, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein, alone or in combination, may be introduced to a subject following the onset of disease (e.g., to alleviate the damage or symptoms associated with a disease). In some embodiments, OCT4, KLF4, and/or SOX2 expression is induced prior to the onset of a disease. In some embodiments, expression of OCT4; KLF4; SOX2; or any combination thereof is induced prior to the onset of a disease. In some embodiments, OCT4, KLF4, and/or SOX2 expression is induced after the onset of a disease. In some embodiments, expression of OCT4; KLF4; SOX2; or any combination thereof is induced after the onset of a disease. In some embodiments, OCT4, KLF4, and/or SOX2 expression is induced in a young subject, young cell, young tissue, and/or young organ. In some embodiments, OCT4, KLF4, and/or SOX2 expression is induced in an aged subject, aged cell, aged tissue, and/or aged organ. In some embodiments, expression of OCT4; KLF4; SOX2; or any combination thereof is induced in a young subject, young cell, young tissue, and/or young organ. In some embodiments expression of, OCT4; KLF4; SOX2; or any combination thereof is induced in an aged subject, aged cell, aged tissue, and/or aged organ. In certain embodiments, an inducing agent and/or a chemical agent capable of modulating activity of the inducing agent may be introduced to a subject following the onset of a disease.

In certain embodiments, the tissue may be considered healthy but suboptimal for performance or survival in current or future conditions (e.g., in agriculture, or adverse conditions including disease treatments, toxic therapies, sun exposure, or space travel outside the earth's atmosphere).

In certain embodiments, the condition is aging. All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypermelanosis, osteoporosis, cerebral cortical atrophy, lymphoid depletion, thymic atrophy, increased incidence of diabetes type II, atherosclerosis, cancer, and heart disease. Nehlin et al. (2000), *Annals NY Acad Sci* 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), *Nature* 415:45-53.

Those skilled in the art will recognize that the aging process is also manifested at the cellular level, as well as in mitochondria. Cellular aging is manifested in loss of doubling capacity, increased levels of apoptosis, changes in differentiated phenotype, and changes in metabolism, e.g., decreased levels of protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid (e.g., engineered nucleic acid) metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etoposide, UV irradiation, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern); resistance to oxidative stress; metabolic parameters (e.g., protein synthesis or degradation, ubiquinone biosynthesis, cholesterol biosynthesis, ATP levels, glucose metabolism, nucleic acid (e.g., engineered nucleic acid) metabolism, ribosomal translation rates, etc.); and cellular proliferation (e.g., of retinal cells, bone cells, white blood cells, etc.).

Aging can also be determined by the rate of change of biomarkers (e.g., epigenetic marks including DNA methylation level of CpG island in the genome (known as the "Horvath Clock") beta-galactosidase-positive cells in cells, gene expression changes, or certain changes to the abundance of molecules in the bloodstream). An example is an algorithm from Segterra Inc. that determines "InnerAge" based on blood biomarkers (see InsideTracker.com).

As shown in the Examples herein, recombinant viruses (e.g., AAVs) encoding OCT4, KLF4, and SOX2 promoted regeneration of axons, which may be used to prevent or alleviate neurodegeneration that is often associated with aging. The methods may be used to prevent or alleviate neurodegeneration and peripheral neuropathies associated. Neurodegenerative diseases include Parkinson's disease, Alzheimer's disease, multiple sclerosis, amniotropic lateral sclerosis (ALS), Huntington's disease, and muscular dystrophy. Neurodegeneration may be quantified using any method known in the art. For example, the executive function of an individual may be determined (Moreira et al., Front Aging Neurosci. 2017 Nov. 9; 9:369).

In some embodiments, expression, induction, or activation of OCT4, SOX2, KLF4, or a combination thereof as described herein increases the number of axons per nerve in a tissue, organ, or a subject relative to a control. In some embodiments, a method described herein increases the number of axons per nerve by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the number of axons per nerve in the tissue, organ, or subject prior to expression, induction, or activation of OCT4, SOX2, KLF4, or a combination thereof.

Additional age-related conditions which may be treated include heart failure, stroke, diabetes, liver diseases, fibrotic diseases, osteoporosis, arthritis, hearing loss (partial or total), eye-related conditions (e.g., poor eye sight, retinal disease, any ocular disease (e.g., any condition affecting the eye)), glaucoma, muscle diseases (e.g., sarcopenia and muscular dystrophies), frailty, a progeroid syndrome (e.g., Hutchinson-Gilford progeria syndrome), and cancer. In certain embodiments, the disease is a retinal disease (e.g., macular degeneration).

In some embodiments, expression, induction, or activation of OCT4, SOX2, KLF4, or a combination thereof in a neuron increases neurite area of the neuron by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to the neuron without expression, induction, or activation of OCT4, SOX2, KLF4, or a combination thereof.

In some embodiments, expression, induction, or activation of OCT4, SOX2, KLF4, or a combination thereof as described herein increases the axon density in a tissue, organ, or a subject relative to a control. In some embodiments, a method described herein increases axon density at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the axon density in the tissue, organ, or subject prior to expression, induction, or activation of OCT4, SOX2, KLF4, or a combination thereof.

In some embodiments, expression, induction, or activation of OCT4, SOX2, KLF4, or a combination thereof in a subject increases the visual acuity of the subject relative to a control. In some embodiments, a method described herein increases the visual acuity of a subject by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the visual acuity of the subject prior to expression, induction, or activation of OCT4, SOX2, KLF4, or a combination thereof. In some embodiments, visual acuity is measured by optomotor acuity. In some embodiments, visual acuity is measured using a pattern electroretinogram response. In some embodiments, visual acuity is measured using a distance visual acuity test, which may include the use of a Snellen chart or E chart. See, e.g., Marsden et al., Community Eye Health. 2014; 27(85): 16 and the Examples below.

In some embodiments, expression, induction, or activation of OCT4, SOX2, KLF4, or a combination thereof in a subject decreases the intraocular pressure of the subject relative to a control. In some embodiments, a method described herein decreases the intraocular pressure of a subject by at least 1.5 fold, by at least 2 fold, by at least 3 fold, by at least 5 fold, by at least 6 fold, by at least 7 fold, by at least 8 fold, by at least 9 fold, by at least 10 fold, by at least 20 fold, by at least 30 fold, by at least 40 fold, by at least 50 fold, by at least 60 fold, by at least 70 fold, by at least 80 fold, by at least 90 fold, or by at least 100 fold relative to a control. In some embodiments, the control is the intraocular pressure of the subject prior to expression, induction, or activation of OCT4, SOX2, KLF4, or a combination thereof. See, e.g., the Examples below.

In some embodiments, any of the nucleic acids (e.g., engineered nucleic acids) capable of inducing OCT4, KLF4, and/or SOX2 expression (e.g., expression vector), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein may be used to treat and/or prevent any of the diseases described herein. In some embodiments, an inducing agent and/or a chemical agent capable of modulating activity of the inducing agent is also used.

As a non-limiting example, an engineered cell of the present disclosure may be used to replace a dysfunctional cell in a subject in need thereof. As another non-limiting example, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) may be used to (e.g., incompletely or fully) reprogram a cell in vivo or in vitro. In some embodiments, an inducing agent and/or a chemical agent capable of modulating activity of the inducing agent is also used. For example, any of the any of the nucleic acids (e.g., engineered nucleic acids) capable of inducing OCT4, KLF4, and/or SOX2 expression (e.g., expression vector), engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) may be used to produce an engineered cell (e.g., an induced pluripotent stem cell). For example, any of the nucleic acids (e.g., engineered nucleic acids) (e.g., expression vector) capable of inducing expression of OCT4, KLF4, SOX2, or a combination thereof, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) may be used to produce an engineered cell (e.g., an induced pluripotent stem cell). The engineered cell (e.g., induced pluripotent stem cell) may then be administered to a subject in need thereof. In some embodiments, the engineered cell is cultured in the presence of an inducing agent and/or a chemical agent capable of modulating activity of the inducing agent. In some embodiments, an inducing agent and/or a chemical agent capable of modulating activity of the inducing agent is also administered to the subject.

Non-limiting uses of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, engineered cells, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) include wound healing, bleed out, injuries, broken bones, gunshot wounds, cuts, scarring during surgery (e.g., cesarean). In some embodiments, an inducing agent and/or a chemical agent capable of modulating activity of the inducing agent is also used.

In some embodiments, any of the of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, an KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) are used to treat disease that affects a non-human subject (e.g., a disease affecting livestock, domesticated pets, and/or other non-human animals). In some embodiments, an inducing agent and/or a chemical agent capable of modulating activity of the inducing agent is also used. For example, the disease may be a cattle disease, a primate (e.g., cynomolgus monkeys, rhesus monkeys) disease, a disease affecting a commercially relevant animal, such as cattle, pigs, horses, sheep, goats, cats, and/or dogs) and/or a disease affecting birds (e.g., commercially relevant birds, such as chickens, ducks, geese, and/or turkeys).

In some embodiments, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) described herein are used to promote wound healing (e.g., for a cut), treat an injury (e.g., broken bones, bleeding out, gun shot injury, and/or reduce scarring during surgery). In some embodiments, surgery includes cesarean. In some embodiments, an inducing agent and/or a chemical agent capable of modulating activity of the inducing agent is also used.

In some embodiments, any of the nucleic acids (e.g., engineered nucleic acids) capable of inducing OCT4, KLF4, and/or SOX2 expression (e.g., expression vector), nucleic acids (e.g., engineered nucleic acids) (e.g., expression vector) capable of inducing expression of a combination of at least two (e.g., at least three) transcription factors selected from OCT4, KLF4, and SOX2, engineered cells, engineered proteins, chemical agents activating (e.g., inducing expression of) OCT4, KLF4, and/or SOX2, chemical agents activating (e.g., inducing expression of) a combination of at least two (e.g., at least three) transcription factors selected from OCT4, KLF4, and SOX2, antibodies activating (e.g., inducing expression of) OCT4, KLF4, and/or SOX2, antibodies activating (e.g., inducing expression of) a combination of at least two (e.g., at least three) transcription factors selected from OCT4, KLF4, and SOX2, and/or recombinant viruses (e.g., lentivirus, adenovirus, alphavirus, vaccinia virus, retrovirus, herpes virus, or AAV) described herein are useful in healing an injury and/or inflammation. In some embodiments, an inducing agent and/or a chemical agent capable of modulating activity of the inducing agent is also used. In some embodiments, the inflammation is hyperinflammation, which may be a side effect of aging. In some embodiments, the hyperinflammation is inflammaging.

In some embodiments, any of the nucleic acids (e.g., engineered nucleic acids) capable of inducing OCT4, KLF4, and/or SOX2 expression (e.g., expression vectors), engineered cells, engineered proteins, chemical agents activating (e.g., inducing expression of) OCT4, KLF4, and/or SOX2, antibodies activating (e.g., inducing expression of) OCT4, KLF4, and/or SOX2, and/or recombinant viruses (e.g., lentivirus, adenovirus, alphavirus, vaccinia virus, retrovirus, herpes virus, or AAV) described herein provide a healing capacity.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein provide a healing capacity.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein are useful in enhancing or rejuvenating optimal or sub-optimal organs. As a non-limiting example, any of the compositions described herein (e.g., recombinant viruses including recombinant AAV viruses) encoding OCT4, KLF4, SOX2, or a combination thereof may be useful in enhancing or rejuvenating suboptimal organs (e.g., from older individuals) that are used for transplantation or to promote organ survival during transport or to promote organ survival after reimplantation of the organ into a subject.

Any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein may be used to rejuvenate or increase the survival and longevity of cells (e.g., hematopoietic stem cells, T-cells, etc.) that are used for transplantation. In some embodiments, recombinant viruses (e.g., AAV viruses) encoding OCT4, KLF4, SOX2, or a combination thereof are useful in rejuvenating or increasing the survival and longevity of cells (e.g., hematopoietic stem cells, T-cells, etc.) that are used for transplantation.

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein is used to prevent or relieve the side effects of a toxin and/or a drug (e.g., a chemotherapy) in a subject. Non-limiting examples of side effects include hair loss and peripheral neuropathy. Chemotherapies include vincristine (VCS). See, e.g., example 15. In certain embodiments, a composition comprising a recombinant virus (e.g., AAV virus) encoding SOX2, KLF4, OCT4, or a combination thereof, is administered to treat (e.g., recover from) or prevent the side effects induced by a toxin and/or damaging drug therapy (e.g., a chemotherapy drug including VCS).

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4, KLF4, SOX2, or a combination thereof, antibodies activating (e.g., inducing expression of) OCT4, KLF4, SOX2, or a combination thereof, and/or recombinant viruses (e.g., lentivirus, adenovirus, alphavirus, vaccinia virus, retrovirus, herpes virus, or AAV) described herein is administered to a subject to prevent or relieve the side effects of a toxin and/or a drug (e.g., a chemotherapy).

In some embodiments, any of the nucleic acids (e.g., engineered nucleic acids) (e.g., expression vectors) capable of inducing expression of OCT4, KLF4, SOX2, or a combination thereof, engineered cells, engineered proteins, chemical agents activating (e.g., inducing expression of) OCT4; KLF4; SOX2; or any combination thereof, antibodies activating (e.g., inducing expression of) OCT4; KLF4; SOX2; or any combination thereof, and/or recombinant viruses (e.g., lentivirus, adenovirus, alphavirus, vaccinia virus, retrovirus, herpes virus, or AAV) described herein is administered to a subject to protect a tissue, organ, and/or entire body of the subject from radiation (e.g., prevent the damaging effects of radiation). In certain embodiments, AAV encoding OCT4, SOX2, KLF4, or any combination thereof, is administered to a subject to protect a tissue, organ, and/or entire body of the subject from radiation protect (e.g., prevent the damaging effects of radiation).

Methods for identifying subjects suspected of having a condition may include physical examination, subject's family medical history, subject's medical history, biopsy, genetic testing, DNA sequencing of pathogens or the microbiome, proteomics, or a number of imaging technologies such as ultrasonography, computed tomography, magnetic resonance imaging, magnetic resonance spectroscopy, or positron emission tomography.

Effective amounts of the engineered nucleic acids (e.g., expression vectors, including viral vectors), viruses (e.g., lentiviruses, retroviruses, adenoviruses, retroviruses, alphaviruses, vaccinia viruses, or AAVs) or compositions thereof vary, as recognized by those skilled in the art, depending on route of administration, excipient usage, and co-usage with other active agents. The quantity to be administered depends on the subject to be treated, including, for example, the age of the subject, the gravity of the condition, the weight of the subject, the genetics of the subject, the cells, tissue, or organ to be targeted, or any combination thereof.

Expression of one or more transcription factors of the present disclosure (e.g., OCT4; KLF4; SOX2; or any combination thereof) may result in reprogramming of a cell, tissue repair, tissue regeneration, increase blood flow, organ regeneration, improved immunity, reversal of aging, counter senescence, or any combination thereof. Cellular reprogramming may be determined by determining the extent of differentiation of a cell (e.g., by determining the expression of one or more lineage markers or pluripotency markers, including OCT4, KLF4, SOX2, NANOG, ESRRB, NR4A2, and C/EBPα). The differentiation potential of a cell may also be determined using routine differentiation assays or gene expression patterns. Tissue repair may be determined by tissue replacement and tissue regeneration assays. For example, tissue replacement assays include wound healing assays in cell culture or in mice. Tissue regeneration may be determined by quantifying a particular cell type following expression of one or more transcription factors compared to before expression of OCT4, KLF4, and SOX2 (see, e.g., the Examples provided below). Tissue regeneration may be determined by quantifying a particular cell type following expression of one or more transcription factors compared to before expression of OCT4; KLF4; SOX2; or any combination thereof. In some instances, the methods described herein promote organ regeneration (e.g. liver regeneration or reversal of liver fibrosis and regrowth). In some instances, the methods described herein promote tissue and cell survival. Cell survival in the face of adversity and damage may be determined using assays for cell viability that are standard in the art (e.g., testing neuronal survival with the nano-glo live cell assay from Promega corp.). In some instances, the methods described herein may prevent axonal or Wallerian degeneration, which may be determined by quantifying the rate of axonal degeneration after nerve crush in vitro using nerve cell cultures or in rat and mouse nerve crush models known to those skilled in the art.

In some embodiments, the methods described herein do not induce teratoma formation. In some embodiments, expression of OCT4, SOX2, KLF4, or a combination thereof or activation of OCT4, SOX2, KLF4, or a combination thereof in a subject, tissue, or organ, results in at least 10%, at least 20%, at least 30%, at least 40%, at least 50%, at least 60%, at least 70%, at least 80%, at least 90%, or at least 100% reduction in teratoma formation as compared to expression of OCT4, SOX2, KLF4, or a combination thereof and c-MYC or activation of OCT4, SOX2, KLF4, or a combination thereof and c-MYC in the subject, tissue, or organ. In some embodiments, expression of OCT4, SOX2, and KLF4 or activation of OCT4, SOX2, and KLF4 in a subject, tissue, or organ, results in at least 10%, at least 20%, at least 30%, at least 40%, at least 50%, at least 60%, at least 70%, at least 80%, at least 90%, or at least 100% reduction in teratoma formation as compared to expression of OCT4, SOX2, and KLF4, and c-MYC or activation of OCT4, SOX2, KLF4, and c-MYC in the subject, tissue, or organ. In some embodiments, the number of teratomas or the size of a teratoma in a subject, tissue, or organ is the same or is reduced following expression of OCT4, SOX2, KLF4, or a combination thereof or activation of OCT4, SOX2, KLF4, or a combination thereof in a subject, tissue, or organ as compared to the number of teratomas or the size of a teratoma in the subject, tissue, or organ prior to activation or expression of OCT4, SOX2, KLF4, or a combination thereof.

In some embodiments, the methods described herein do not induce unwanted cell proliferation. In some embodiments, the unwanted cell proliferation is aberrant cell proliferation, which may be benign or cancerous. In some embodiments, expression of OCT4, SOX2, KLF4, or a combination thereof or activation of OCT4, SOX2, KLF4, or a combination thereof in a subject, tissue, or organ reduces unwanted cell proliferation in a subject, tissue, or organ, by at least 10%, at least 20%, at least 30%, at least 40%, at least 50%, at least 60%, at least 70%, at least 80%, at least 90%, or at least 100% as compared to the same method with c-Myc expression or activation. In some embodiments, unwanted cell proliferation in a subject, tissue, or organ is the same or is reduced following expression of OCT4, SOX2, KLF4, or a combination thereof or activation of OCT4, SOX2, KLF4, or a combination thereof in a subject, tissue, or organ as compared to the amount of unwanted cell proliferation in the subject, tissue, or organ prior to activation or expression of OCT4, SOX2, KLF4, or a combination thereof.

In some embodiments, the methods described herein do not induce tumor formation or tumor growth. In some embodiments, expression of OCT4, SOX2, KLF4, or a combination thereof or activation of OCT4, SOX2, KLF4, or a combination thereof in a subject, tissue, or organ reduces the number of tumors or the size of a tumor in a subject, tissue, or organ, by at least 10%, at least 20%, at least 30%, at least 40%, at least 50%, at least 60%, at least 70%, at least 80%, at least 90%, or at least 100% as compared to the same method with c-Myc expression or activation. In some embodiments, the number of tumors or the size of a tumor in a subject, tissue, or organ is the same or is reduced following expression of OCT4, SOX2, KLF4, or a combination thereof or activation of OCT4, SOX2, KLF4, or a combination thereof in a subject, tissue, or organ as compared to the number of tumors or the size of a tumor in the subject, tissue, or organ prior to activation or expression of OCT4, SOX2, KLF4, or a combination thereof. In some embodiments, a method described herein does not induce cancer. In some embodiments, a method described herein does not induce glaucoma.

Methods of reprogramming are also provided herein. In some embodiments, a method of reprogramming described herein comprises reversing or rejuvenating the epigenetic clock of a cell, tissue, organ, or a subject. In some embodiments, the epigenetic clock may be partially or fully reversed. In some embodiments, the epigenetic clock of a cell, tissue, organ, or a subject is measured using DNA methylation-based age (DNAmAGE or DNAm age). In some embodiments, a method described herein reduces the DNAmAge age of a cell by 1%, 5%, 10%, 20%, 30%, 40%, 50%, 60%, 70%, 80%, 90%, or 100%.

In some embodiments, a method of reprogramming described herein comprises altering the expression of one or more genes associated with ageing. In some embodiments, expression of a gene is increased by at least 1%, at least 5%, at least 10%, at least 20%, at least 30%, at least 40%, at least 50%, at least 60%, at least 70%, at least 80%, at least 90%, or at least 100%. In some embodiments, expression of a gene is reduced by at least 1%, at least 5%, at least 10%, at least 20%, at least 30%, at least 40%, at least 50%, at least 60%, at least 70%, at least 80%, at least 90%, or at least 100%. In some embodiments, expression of one or more genes following performance of a method is determined relative to expression of the one or more genes prior to performance of the method. In some embodiments, expression of one or more genes is determined relative to expression of the one or more genes in a young cell, a young subject, a young tissue, a young organ, or any combination thereof. In some embodiments, expression of one or more genes is determined relative to expression of the one or more genes in an old cell, an old subject, an old tissue, an old organ, or any combination thereof.

A gene associated with ageing may be a gene whose expression is altered in an old, an old tissue, an old organ, an old subject, or any combination thereof as compared to a young counterpart. In some embodiments, the gene associated with ageing is 1700031P21Rik, 1810053B23Rik, 2900045O20Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1cl, Ankrd1, Asb15, Atp2c2, AU018091, AW822073, Btnl10, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps8l1, EU599041, Fam90a1a, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Muc12, Mug1, Mybl2, Myh15, Nek10, Neurod6, Nrlh5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, A1504432, Best3, Boc, Cadm3, Cand2, Cc19, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galntl8, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman1l, Lrfn2, Lrrc38, Lrrn4c1, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sell13, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. In some embodiments, the gene is a sensory gene.

In some embodiments, a method described herein reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, A1504432, Best3, Boc, Cadm3, Cand2, Cc19, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galnt15, Galntl8, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman1l, Lrfn2, Lrrc38, Lrrn4c1, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sell13, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof. See, e.g., Table 5 for genes associated with ageing.

In some embodiments, a method described herein increases expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549C19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1c1, Ankrd1, Asb15, Atp2c2, AU018091, AW822073, Btn110, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps811, EU599041, Fam90ala, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Muc12, Mug1, Mybl2, Myh15, Nek10, Neurod6, Nrlh5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Aspects of the present disclosure relate to methods comprising resetting the transcriptional profile of an old cell, an old organ, an old tissue, and/or any combination thereof in vitro. Aspects of the present disclosure relate to methods comprising resetting the transcriptional profile of an old cell, an old organ, an old tissue, an old subject and/or any combination thereof in vivo. In some embodiments, resetting the transcriptional profile an old cell, an old organ, an old tissue, an old subject and/or any combination thereof comprises altering the gene expression of one or more genes associated with ageing. In some embodiments, resetting the transcriptional profile an old cell, an old organ, an old tissue, an old subject and/or any combination thereof comprises reversing the epigenetic clock. In some embodiments, the transcription profile of an old cell is reset. In some embodiments, the transcriptional profile of an old cell, an old organ, an old tissue, an old subject, or any combination thereof is reset to that of a young cell, a young tissue, a young organ, a young subject, or any combination thereof. In some embodiments, a method described herein reverses one or more changes in gene expression that are detected between an old cell, an old organ, an old tissue, an old subject, or any combination thereof and a control. In some embodiments, the control is a young cell, a young organ, a young tissue, a young subject, or any combination thereof. In some embodiments, the transcriptional profile of an old cell, an old organ, an old tissue, an old subject, or any combination thereof is changed from a young counterpart. In some embodiments, a method described herein resets at least 10%, at least 20%, at least 30%, at least 40%, at least 50%, at least 60%, at least 70%, at least 80%, at least 90%, or 100% of the gene expression change in an old cell, an old organ, an old tissue, an old subject, or any combination thereof to a young level. In some embodiments, a sensory gene is a sensory receptor gene. Without being bound by a particular theory, resetting of a sensor receptor gene expression level in an aged cell to a young level may be indicative of an improvement of retina ganglion cell function.

In some aspects, the cellular reprogramming methods described herein may be used to promote the transdifferentiation of cells, which may be useful in treatment of disease. In some embodiments, the methods described herein may improve the efficiency of existing methods of transdifferentiation. For example, OCT4, SOX2, KLF4, or a combination thereof may be activated (e.g., expressed) in one cell type along with one or more perturbations of genes that affect cell fate to promote lineage reprogramming or conversion to another cell type. In some embodiments, the perturbation is reducing expression of a lineage determining factor. In some embodiments, the perturbation is expression of a lineage determining factor. In some embodiments, the lineage determining factor is a lineage transcription factor.

As a non-limiting example, night blindness is caused by rod death and daytime blindness is caused by cone death. Cell types including cones, rods, and muller cells could be reprogrammed into another cell type needed to restore vision. For example, loss of Nrl promotes transdifferentiation of adult rods into cone cells. See, e.g., Montana et al., Proc Natl Acad Sci USA. 2013 Jan. 29; 110(5):1732-7. In some embodiments, transcription factors that promote rod cell fate include Otx2, Crx and Nrl. As a non-limiting example, Müller glia (MG) can be reprogrammed into rod cells by expressing β-catenin, Otx2, Crx, and Nrl. See, e.g., Yao et al., Nature. 2018 August; 560(7719):484-488.

As another non-limiting example, pancreatic alpha may be reprogrammed into beta cells for treating autoimmune diseases and diabetes. Transcription factors including Pdx1 and MafA can be used to reprogram mouse alpha cells into beta cells. See, e.g., Xiao et al., Cell Stem Cell. 2018 Jan. 4; 22(1):78-90.e4.

Additional non-limiting examples of transdifferentiation inducing factors for production of various cell types may be found in Cieślar-Pobuda et al., Biochim Biophys Acta Mol Cell Res. 2017 July; 1864(7):1359-1369, which is herein incorporated by reference in its entirety. See e.g., Table 4 of Cieślar-Pobuda et al., Biochim Biophys Acta Mol Cell Res. 2017 July; 1864(7):1359-1369.

Induction of OCT4, SOX2, KLF4, or a combination thereof may increase the efficiency of trandifferentiation of cells by at least 1%, at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000%, including all values in between, as compared to a control. The efficiency of transdifferentiation may be measured by any suitable method including comparing the percentage of cells that were transdifferentiated when OCT4, SOX2, KLF4, or a combination thereof was activated as compared to control cells in which OCT4, SOX2, KLF4, or a combination thereof was not activated.

These and other aspects of the present invention will be further appreciated upon consideration of the following Examples, which are intended to illustrate certain particular embodiments of the invention but are not intended to limit its scope, as defined by the claims.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Figure 2:
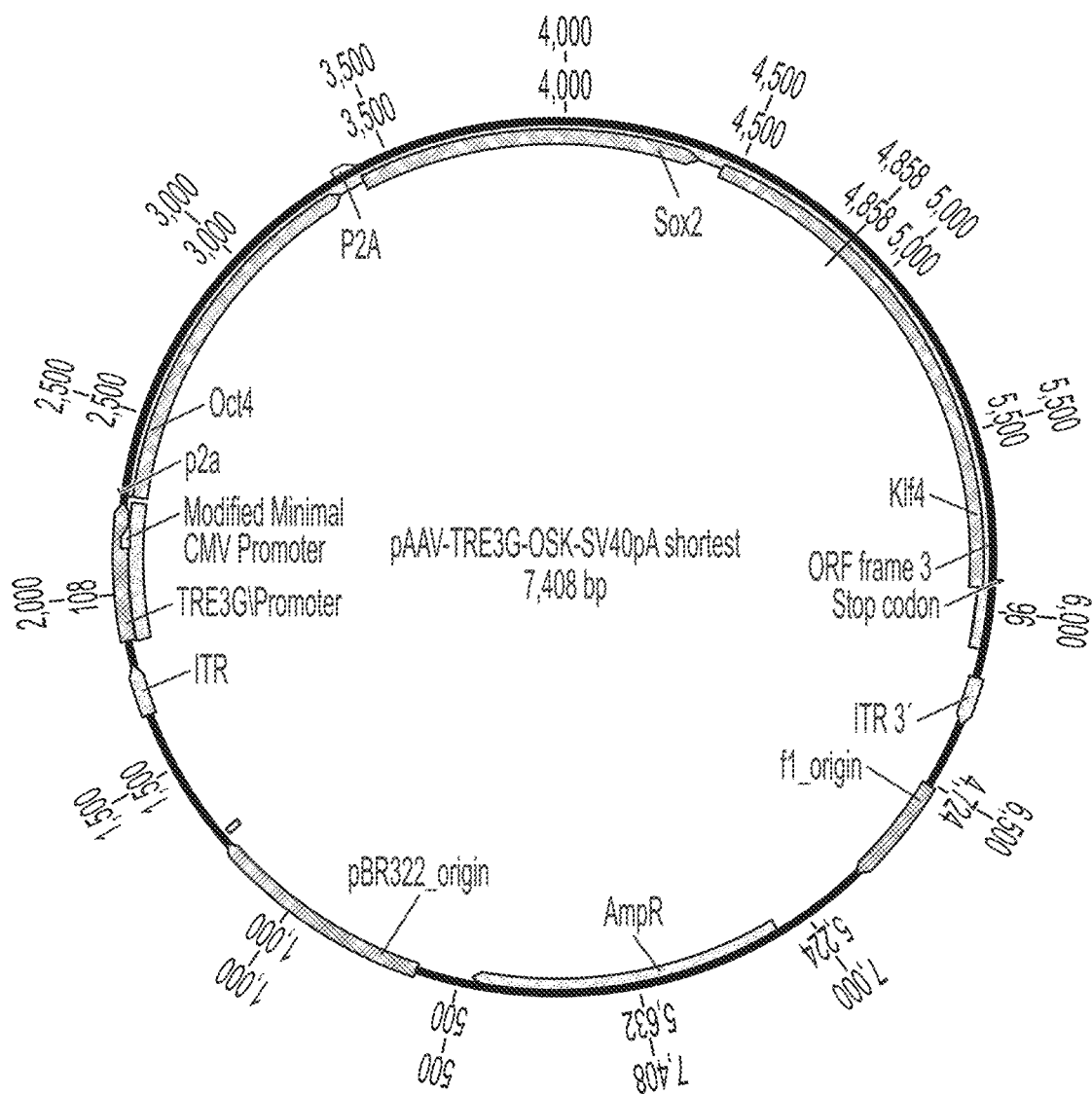
FIG. 2 is a vector map of TRE3G–OSK–SV40 pA, an AAV vector encoding OSK. Features including the location of sequences encoding OCT4, SOX2, and KLF4 and inverted terminal repeat sequences (ITRs) are indicated.
Figure 3:
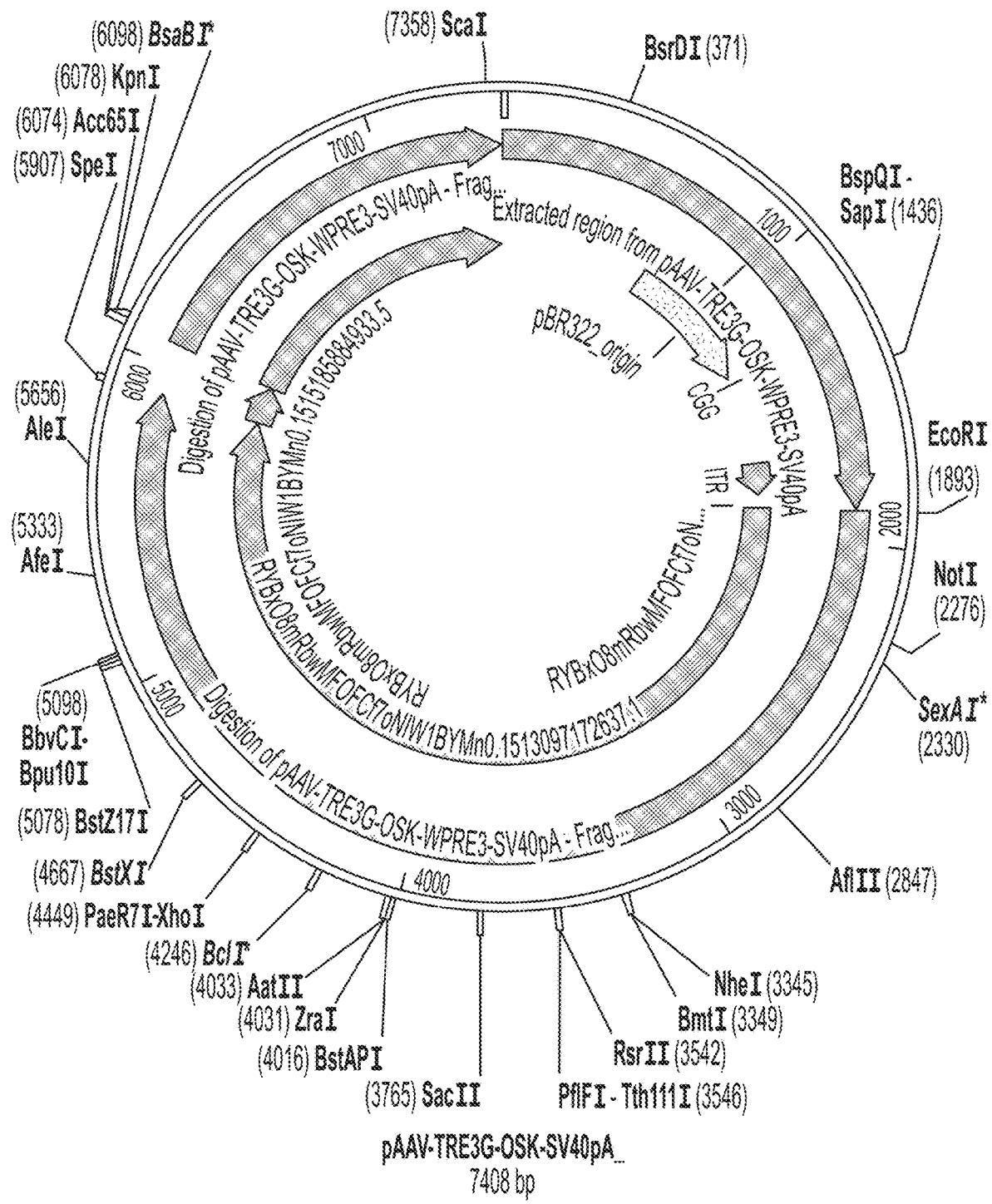
FIG. 3 is a vector map showing the location of restriction enzyme digestion sites in TRE3G–OSK–SV40 pA.

Example 1: Development of an
Adenovirus-Associated Virus (AAV) Vector for
Inducible Expression of OCT4, SOX2, and KLF4
(OSK) in Mammalian Cells An AAV vector that is capable of expressing OCT4, SOX2, and KLF4 in mammalian cells was developed as described herein. As shown in FIG. 1, such a vector comprises a TRE3G promoter (SEQ ID NO: 7), nucleic acids (e.g., engineered nucleic acids) encoding OCT4, SOX2, KLF4, and an SV40 polyA (SV40 pA) terminator sequence (SEQ ID NO: 8). This vector will be referred to as TRE3G–OSK–SV40 pA. Nucleic acid (e.g., engineered nucleic acid) sequences encoding self-cleaving peptides (T2A, a 2A peptide, SEQ ID NO: 9) were used to separate the nucleic acids (e.g., engineered nucleic acids) encoding OCT4, SOX2, and KLF4. As shown in FIG. 2, the entire vector is 7,408 base pairs in length and two inverted terminal repeats (ITRs) flank the OSK sequences. The restriction enzyme digestion sites in the vector are depicted in FIG. 3. A schematic mapping the features shown in the vector maps of FIGS. 4A-4AL onto the nucleic acid (e.g., engineered nucleic acid)

sequence of the vector is shown in FIGS. 2-3. The restriction enzyme cut sites are shown in Table 3 below. As shown in FIGS. 5A-5D, the open reading frame (ORF frame 3) encoding OSK and intervening 2A peptides (T2A peptides) is 3,610 base pairs.

TABLE 3

Restriction Enzyme Cut Sites in the TRE3G-OSK-SV40pA vector.

| Enzymes | Sites | Location |
| --- | --- | --- |
| AatII | 1 | 4033 |
| Acc65I | 1 | 6074 |
| AfeI | 1 | 5333 |
| AflII | 1 | 2847 |
| AleI | 1 | 5656 |
| BbvCI | 1 | 5098 |
| BclI | 1* | 4246* |
| BmtI | 1 | 3349 |
| Bpu10I | 1 | 5098 |
| BsaBI | 1* | 6098* |
| BspQI | 1 | 1436 |
| BsrDI | 1 | 371 |
| BstAPI | 1 | 4016 |
| BstXI | 1 | 4667 |
| BstZ17I | 1 | 5078 |
| EcoRI | 1 | 1893 |
| KpnI | 1 | 6078 |
| NheI | 1 | 3345 |
| NotI | 1 | 2276 |
| PaeR7I | 1 | 4449 |
| PflFI | 1 | 3546 |
| RsrII | 1 | 3542 |
| SacII | 1 | 3765 |
| SapI | 1 | 1436 |
| ScaI | 1 | 7358 |
| SexAI | 1* | 2330* |
| SpeI | 1 | 5907 |
| Tth111I | 1 | 3546 |
| XhoI | 1 | 4449 |
| ZraI | 1 | 4031 |

Figure 4D:
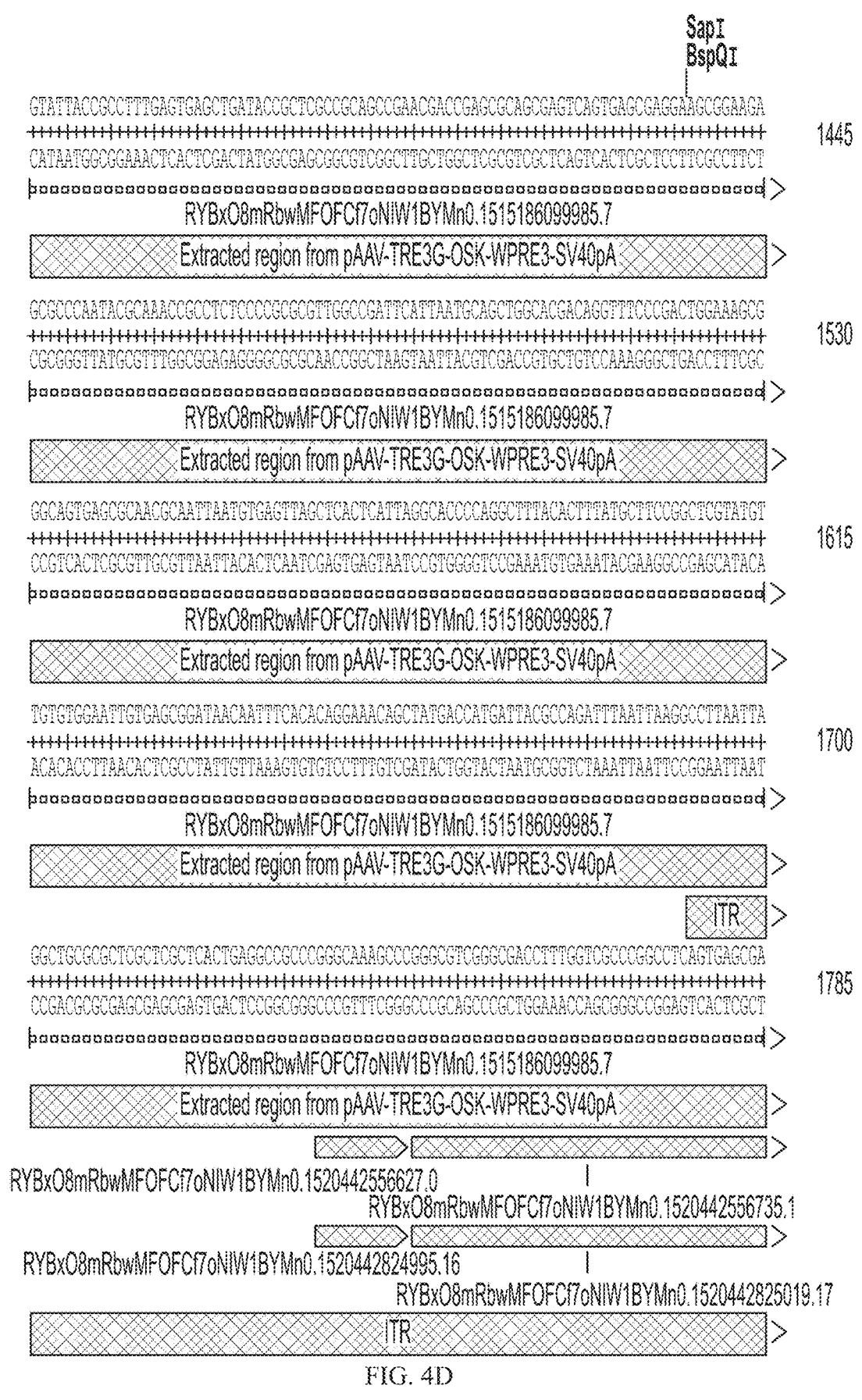
Figure 4E:
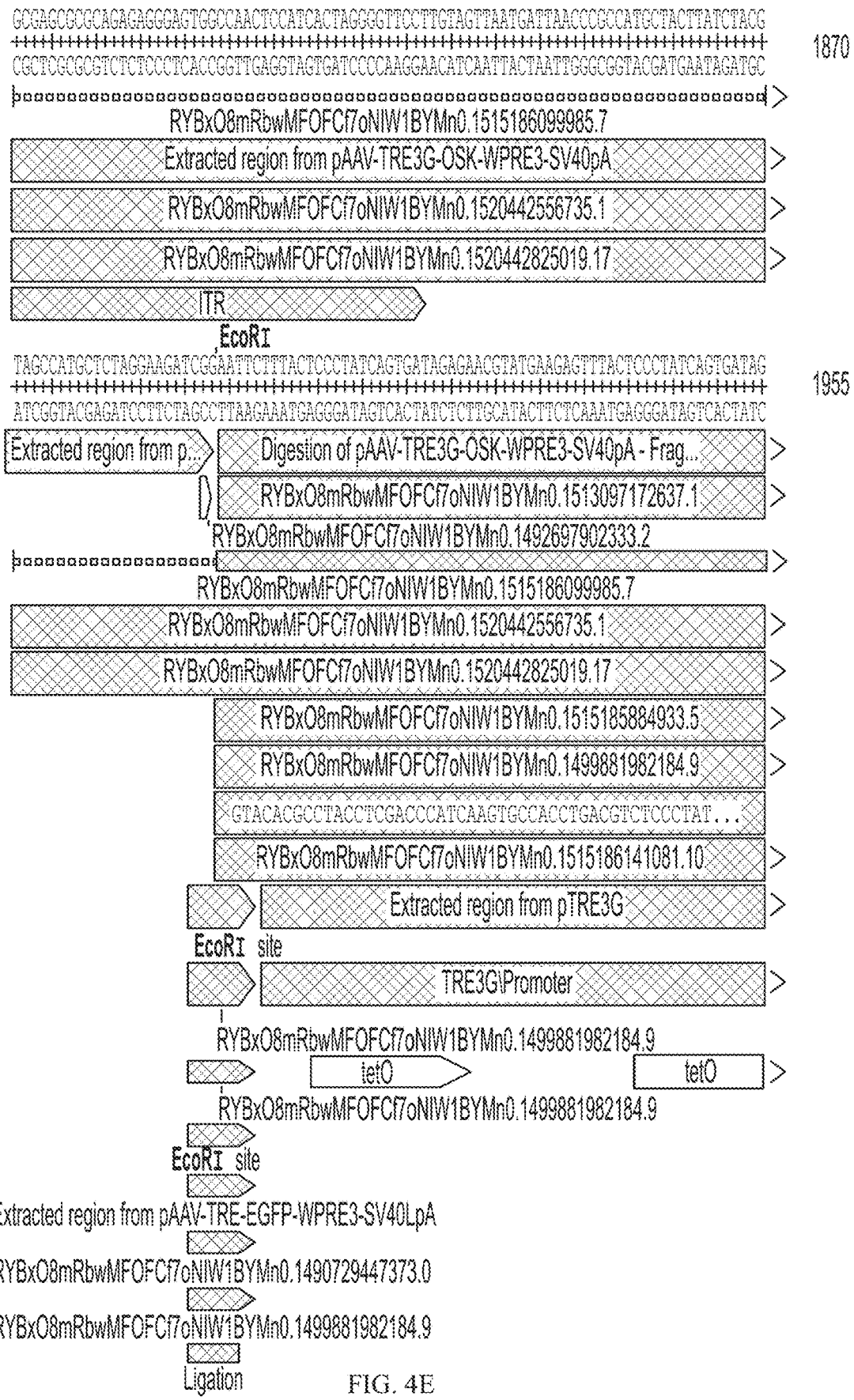
Figure 4F:
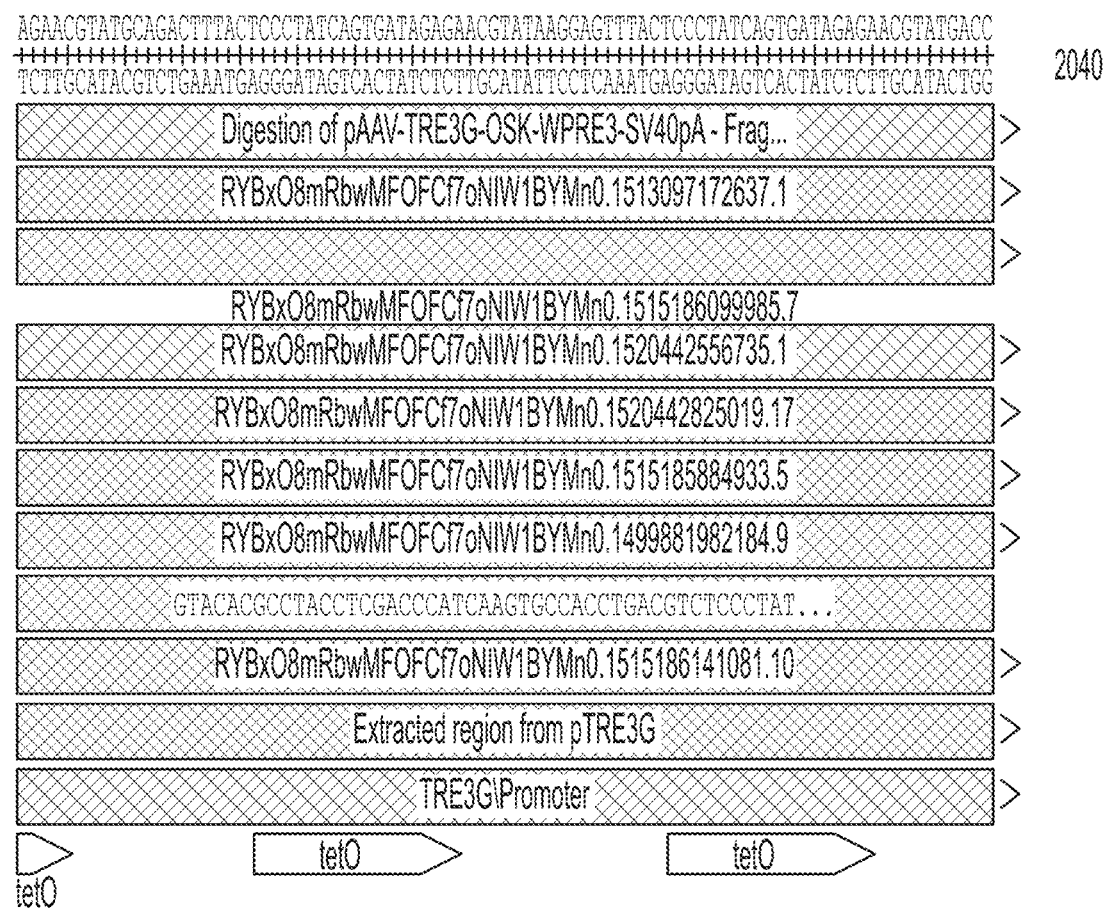
Figure 4G:
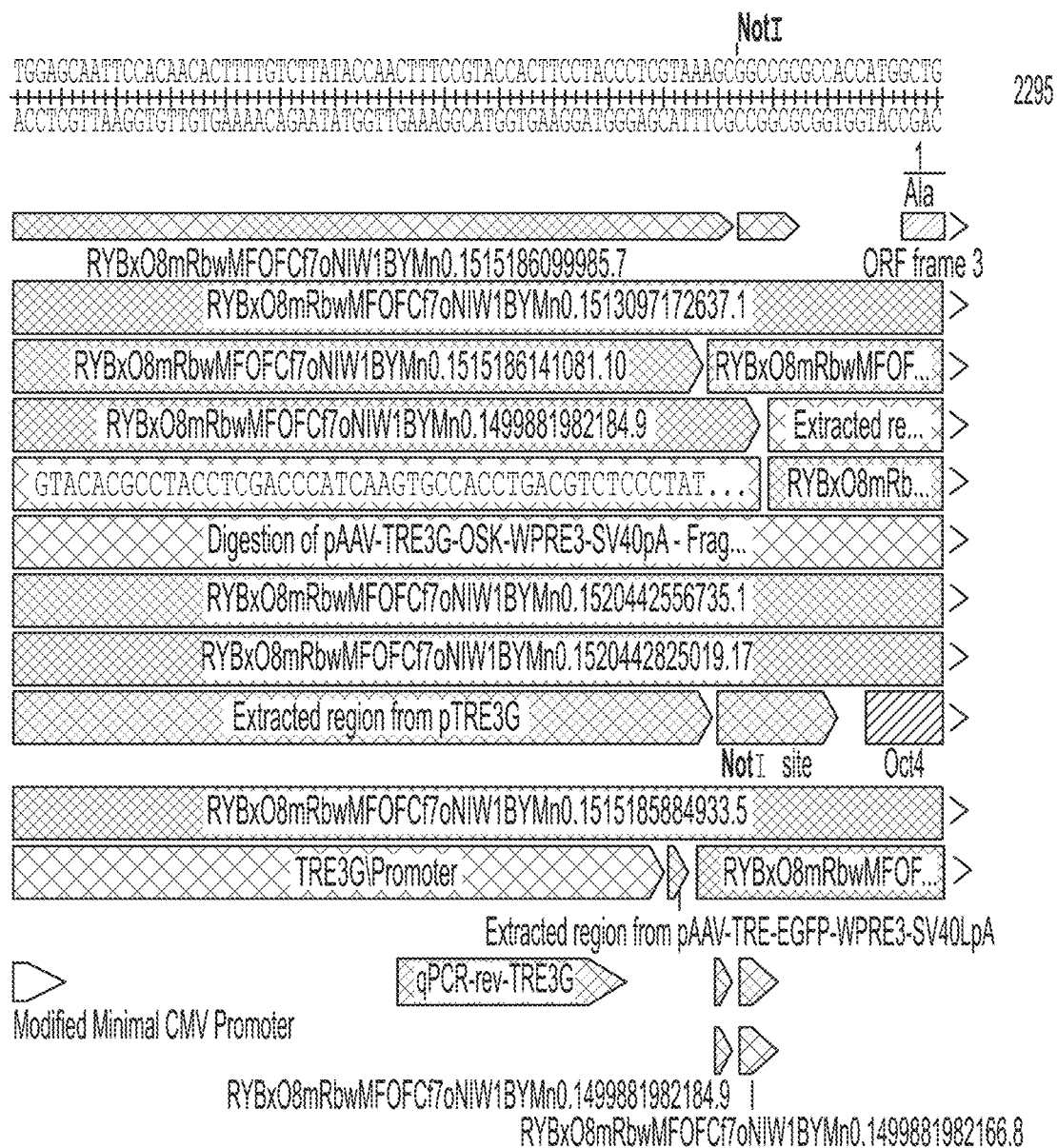
Figure 4H:
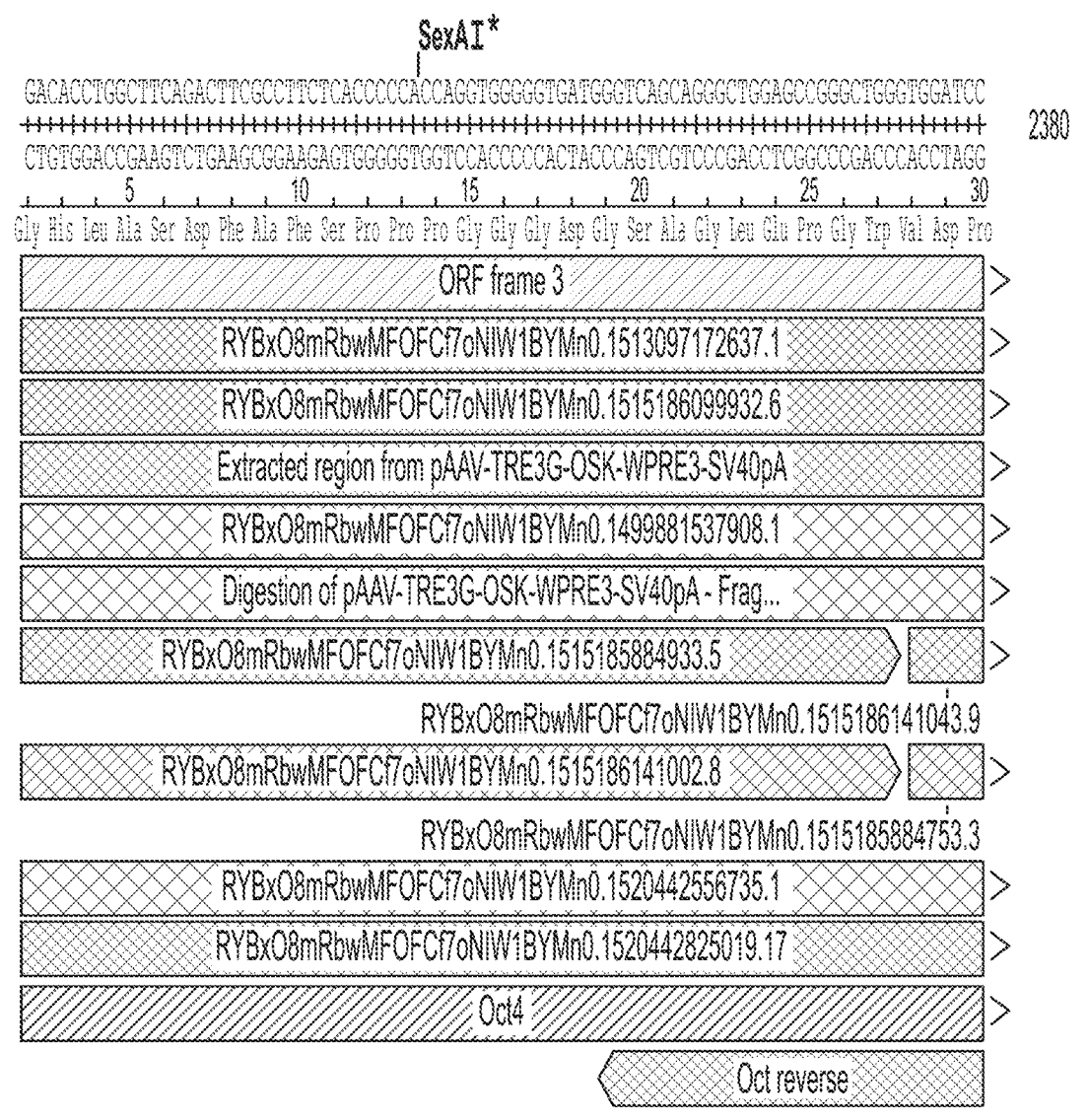
Figure 4H:
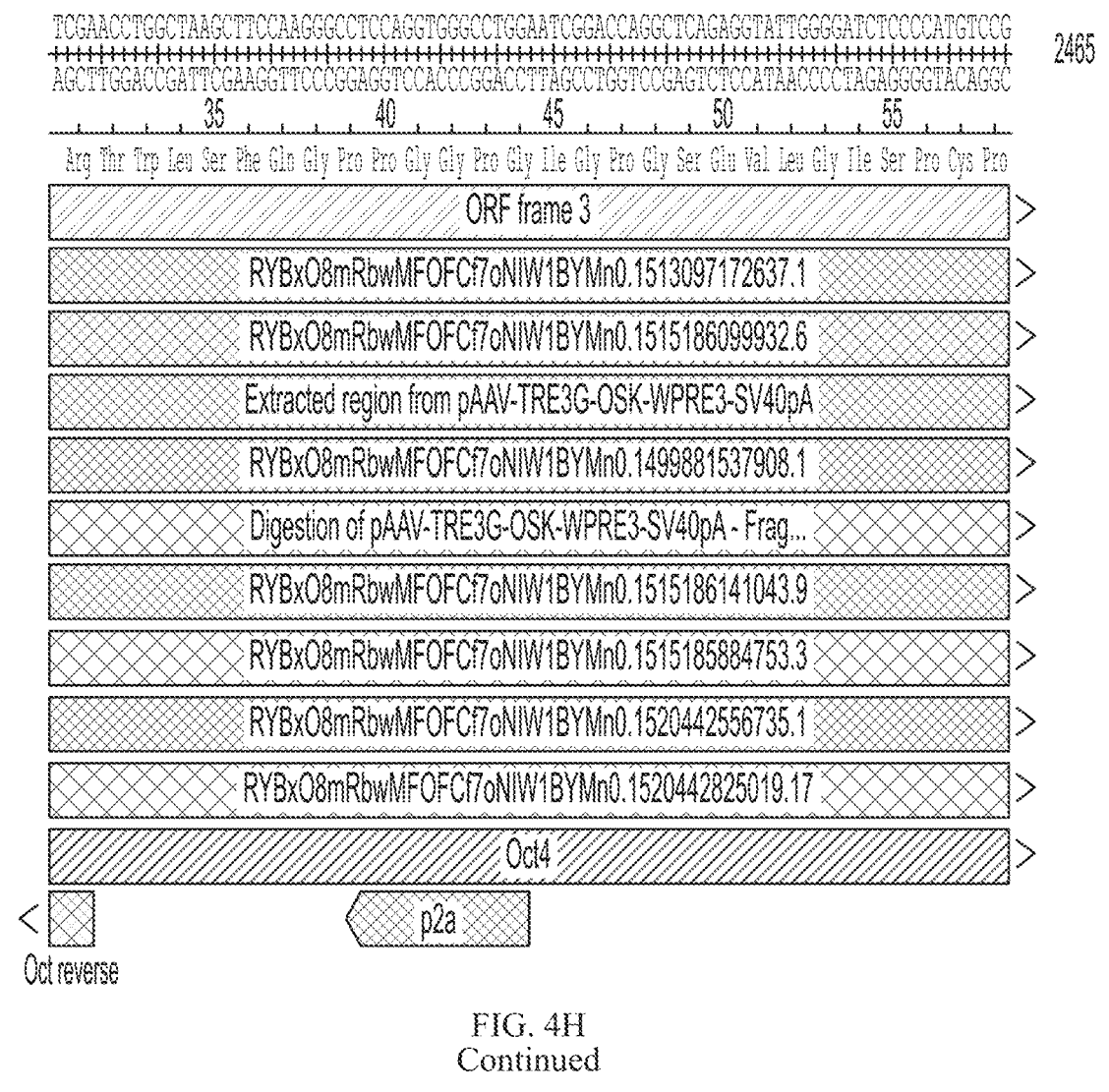
Figure 4L:
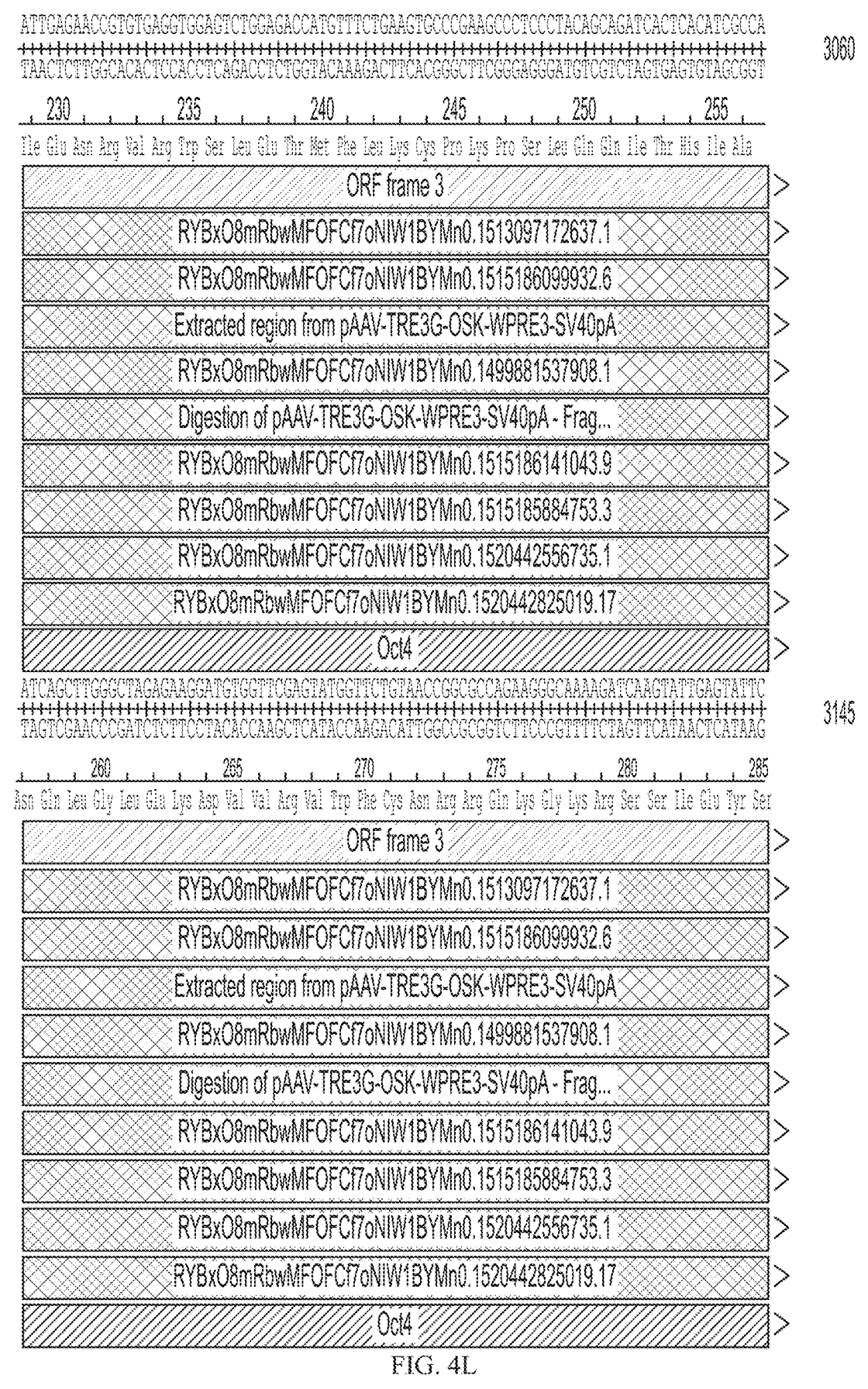
Figure 4M:
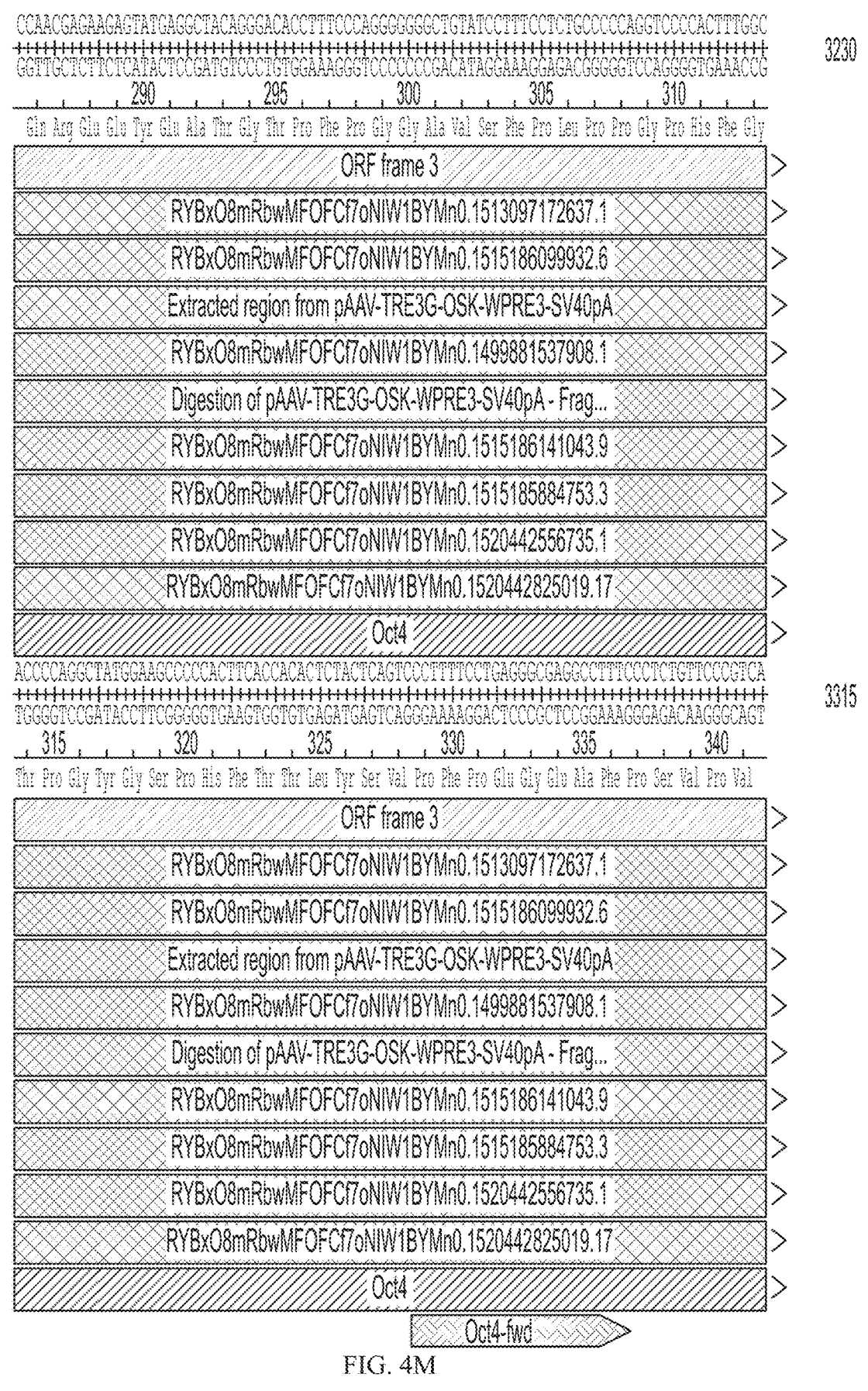
Figure 4O:
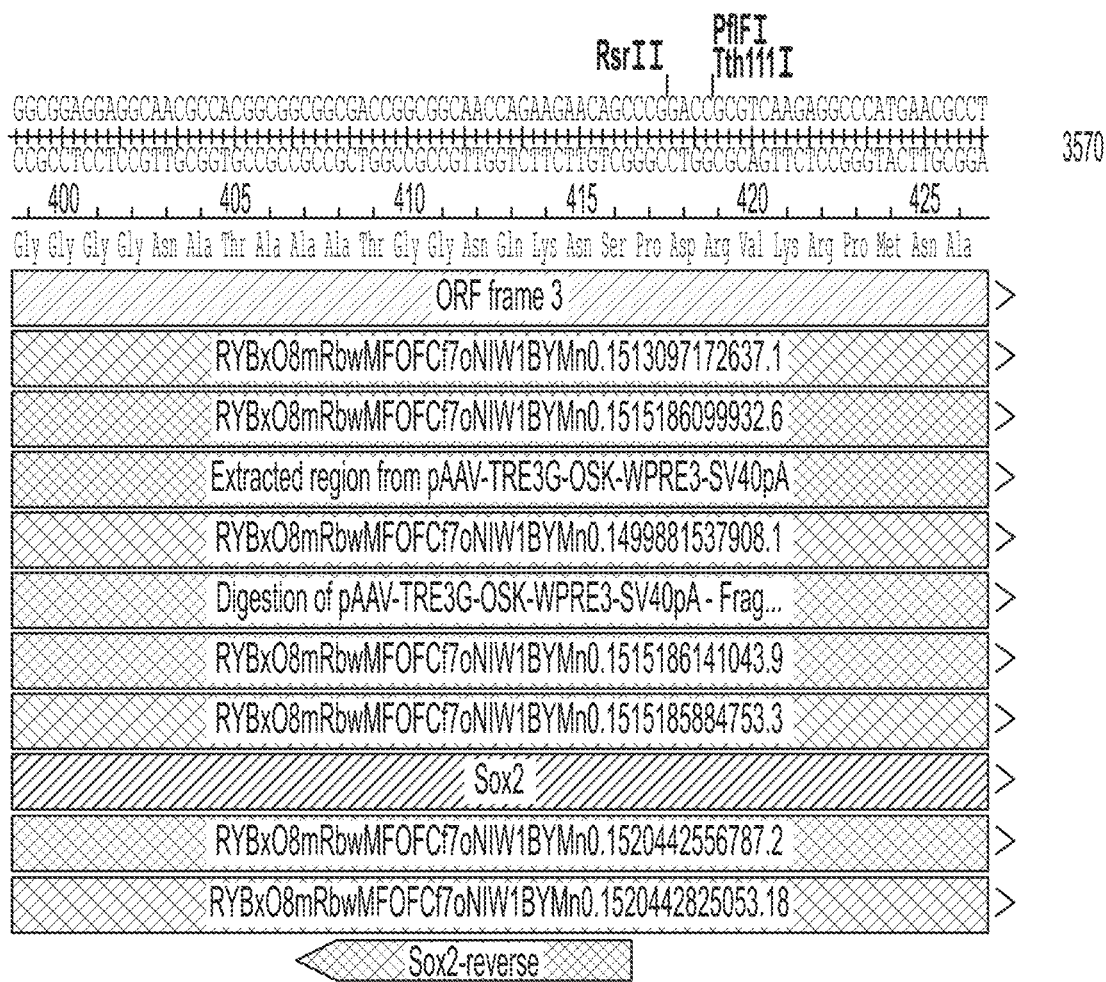
Figure 4Q:
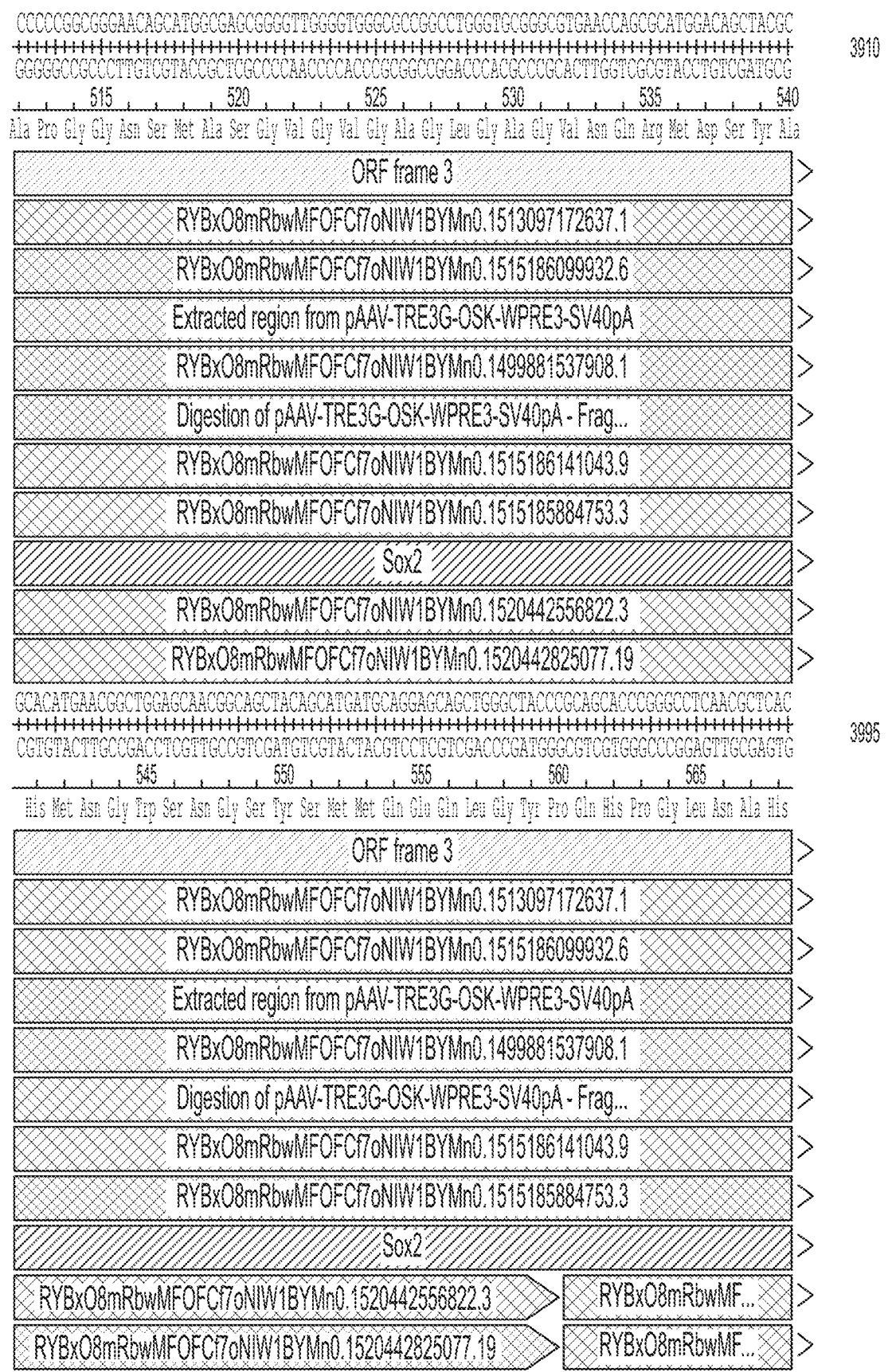
Figure 4R:
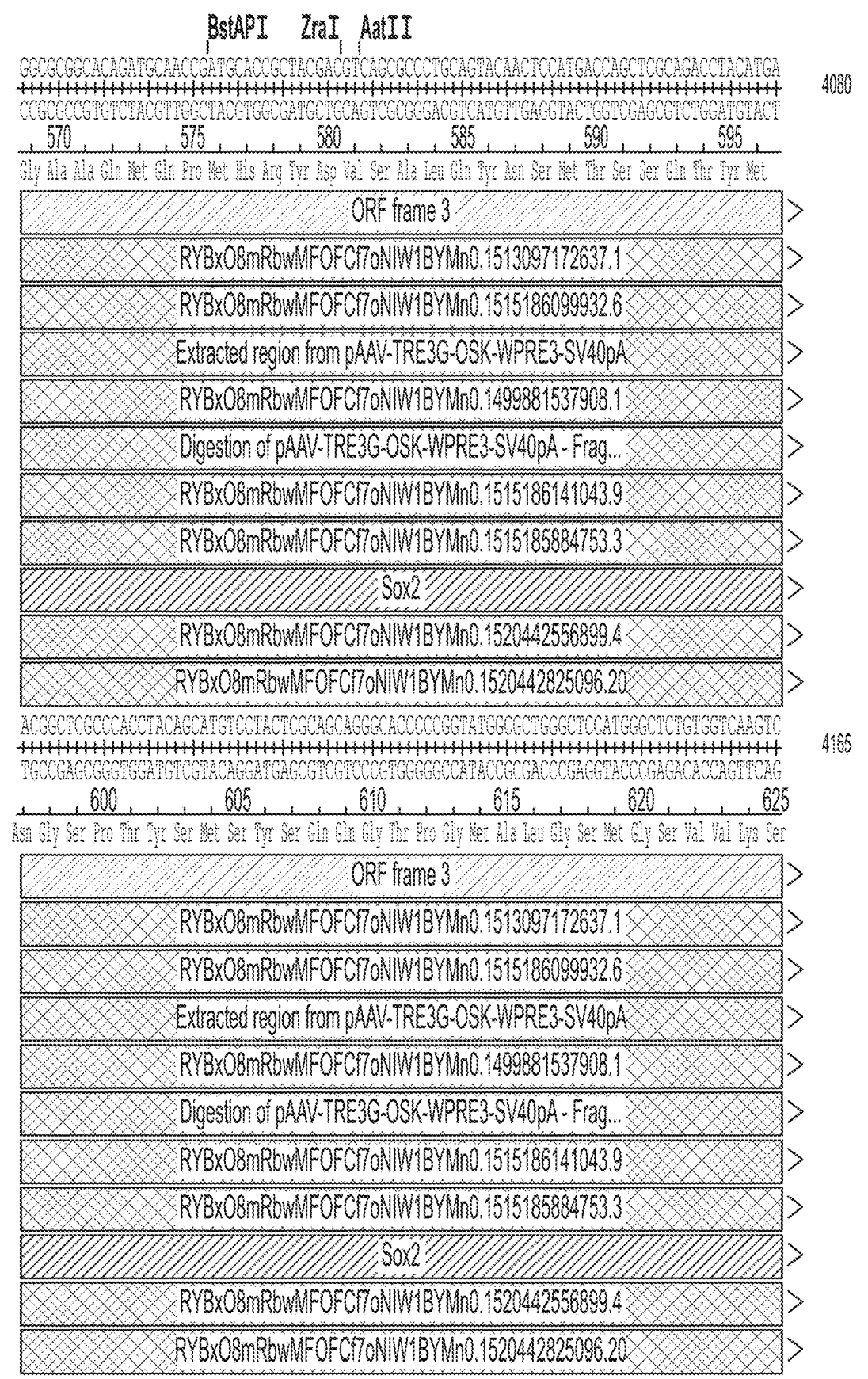
Figure 4S:
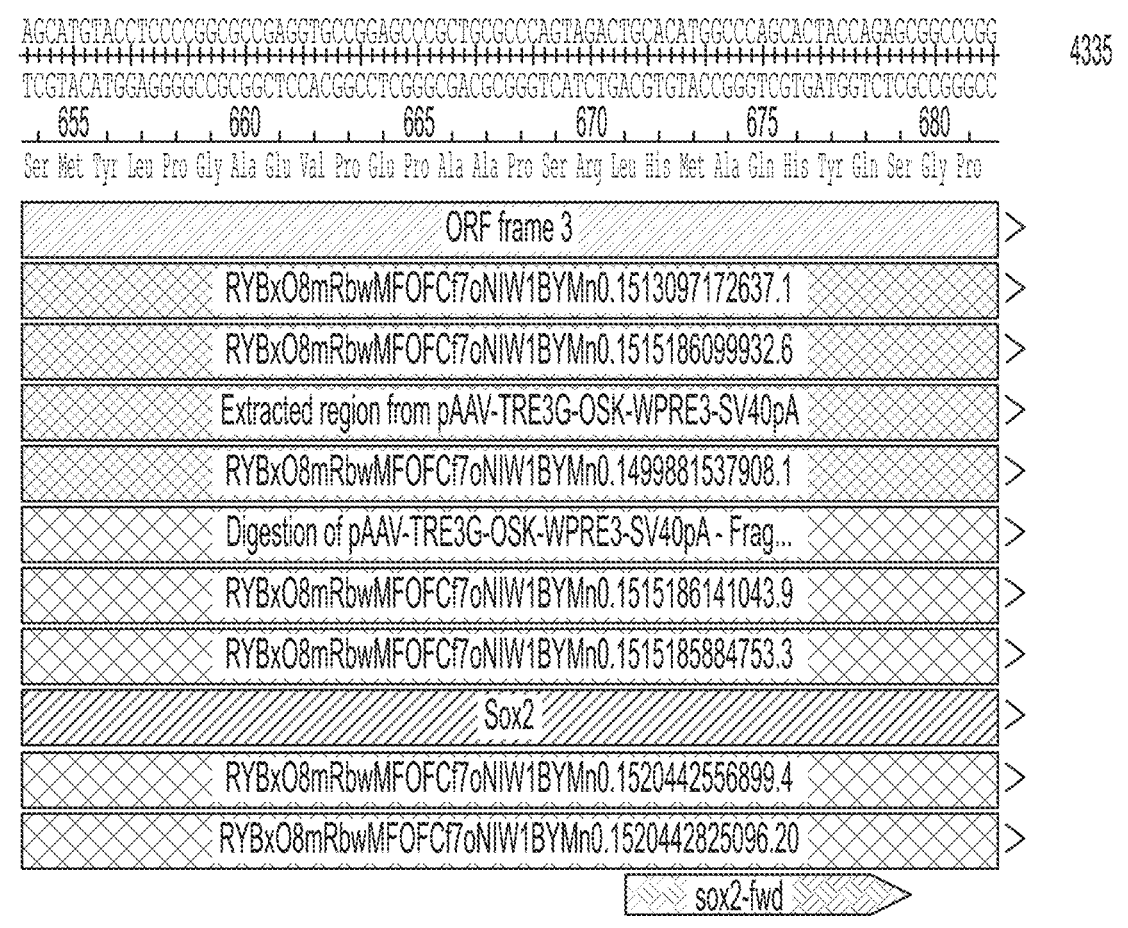
Figure 4T:
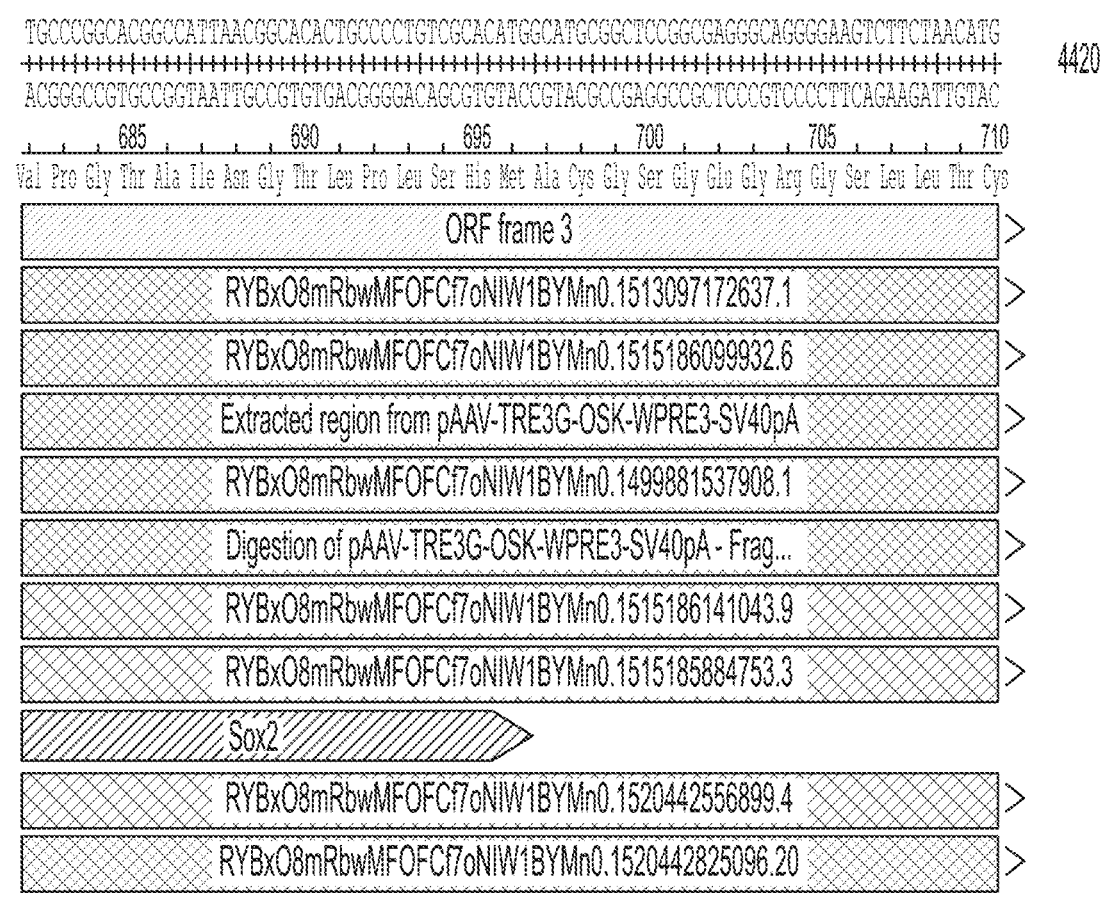
Figure 4T:
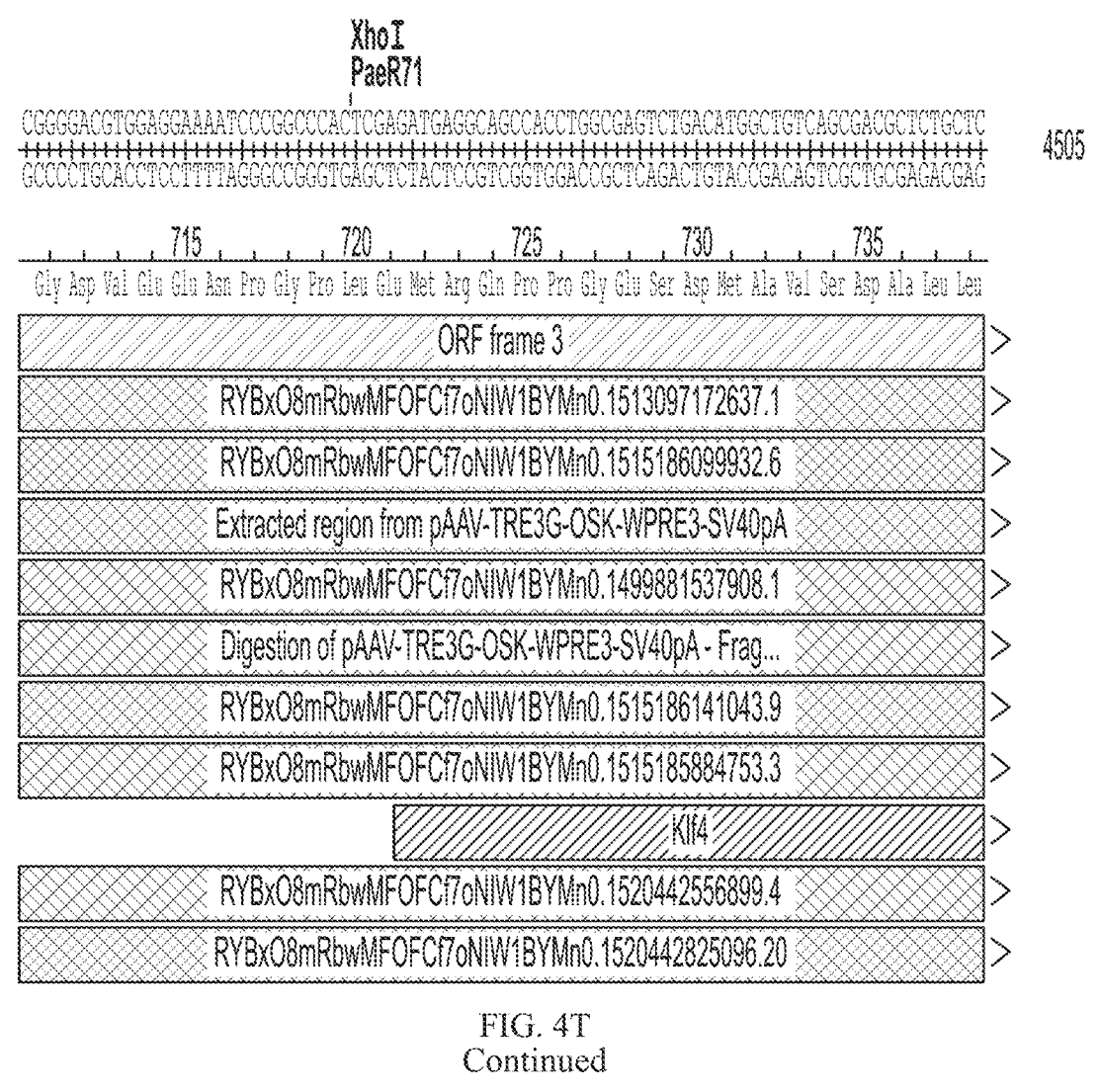
Figure 4U:
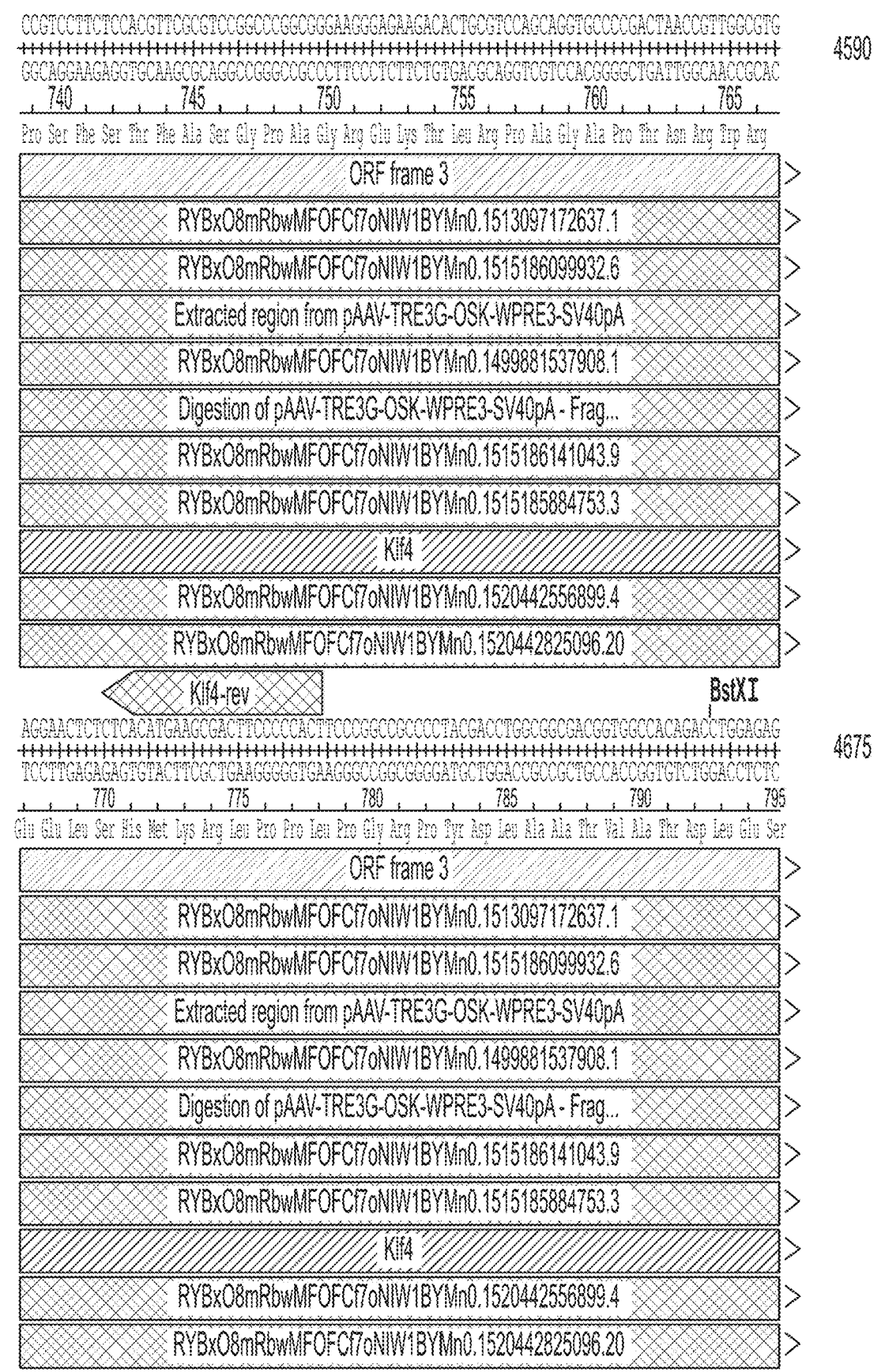
Figure 4X:
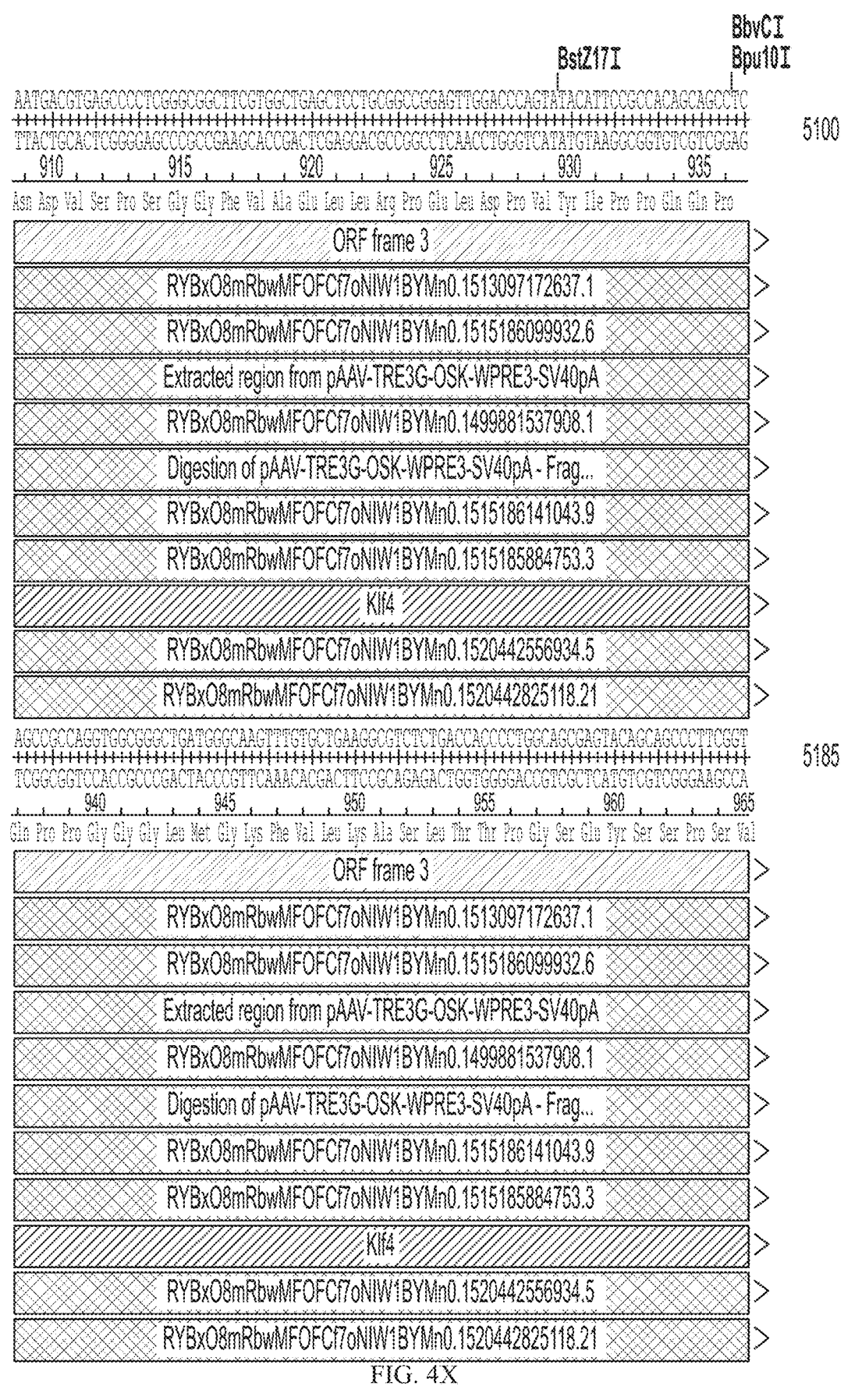
Figure 4A:
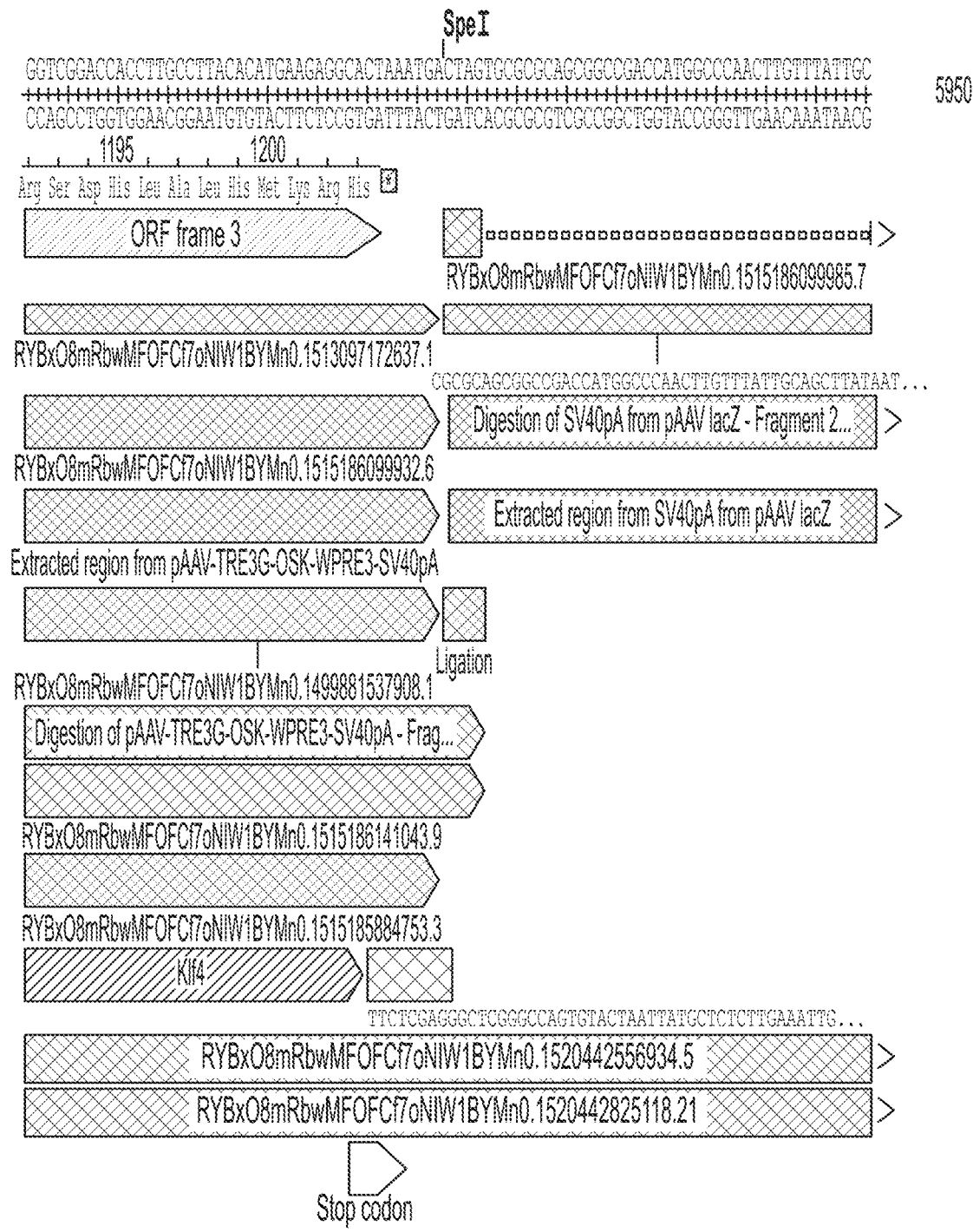
FIGS. 4A-4AL include a series of schematics mapping the features shown in FIGS. 2 and 3 onto the nucleic acid (e.g., engineered nucleic acid) sequence of TRE3G–OSK–SV40 pA.
Figure 4A:
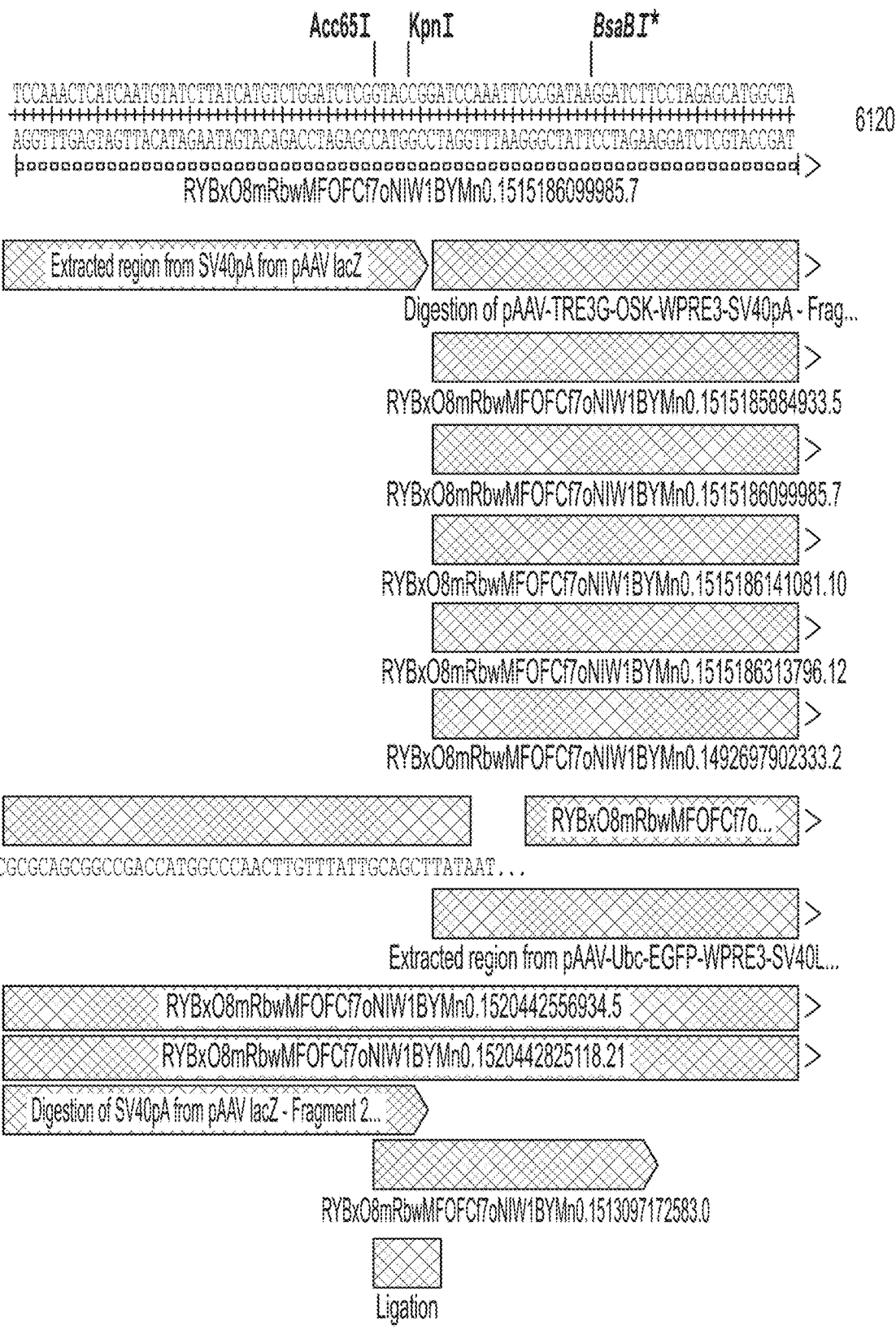
Figure 17:
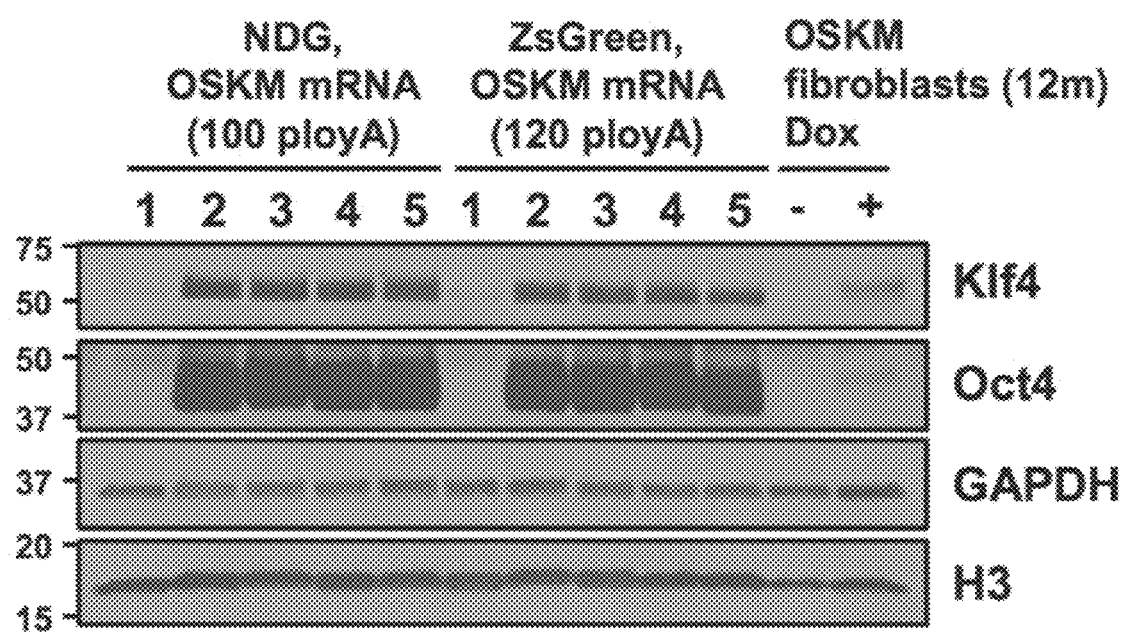
FIG. 17 is a western blot showing that administration of modified mRNA encoding OCT4, SOX2, and KLF4 induced expression of KLF4 and OCT4 in mouse cells. Antibodies against KLF4, OCT4, GAPDH, and H3 were used to detect indicated proteins.
Figure 18:
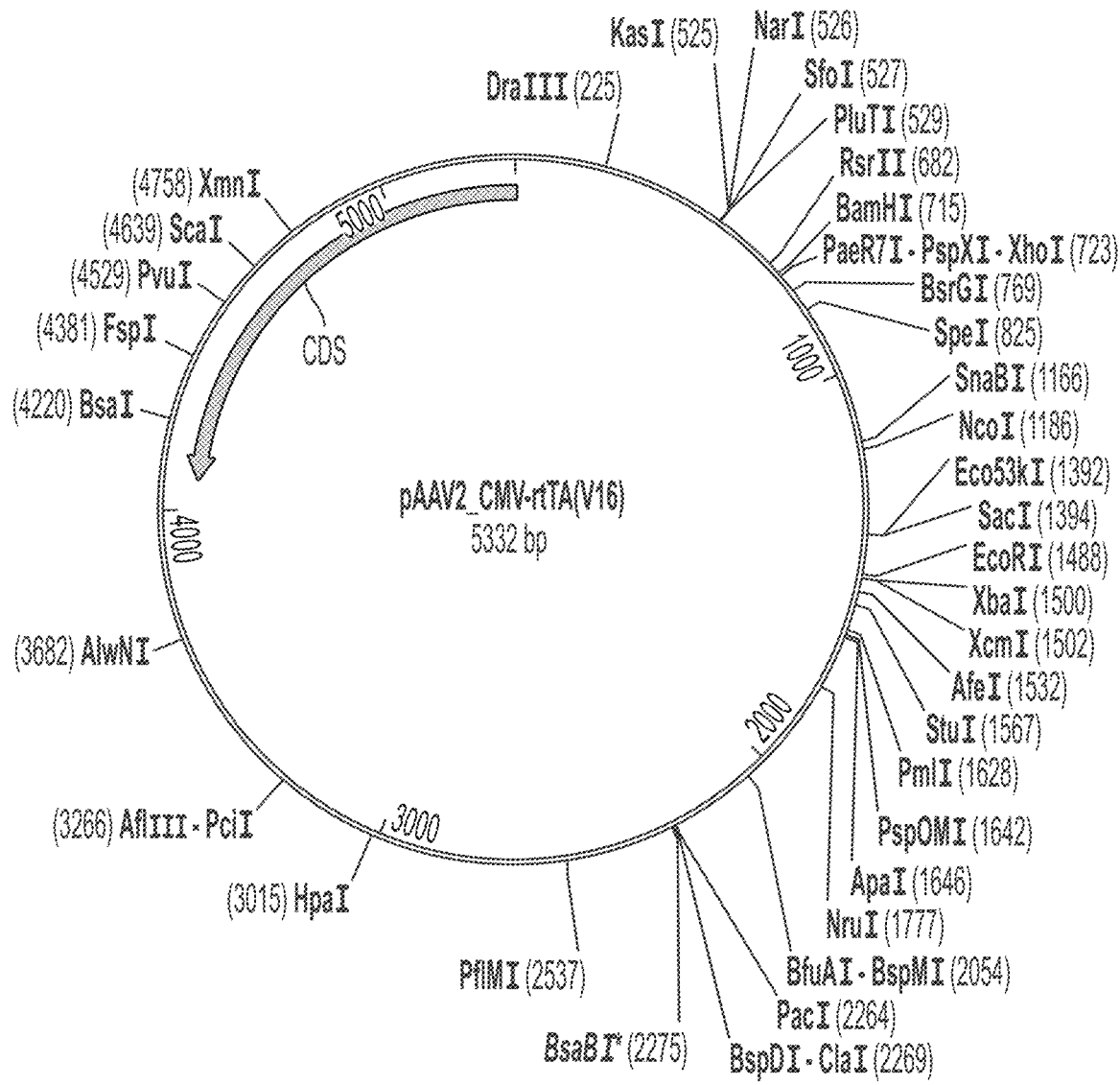
FIG. 18 is a vector map of pAAV2_CMV_rtTA(VP16) (SEQ ID NO: 31). This vector is a non-limiting example of a vector encoding rtTA.
Figure 19:
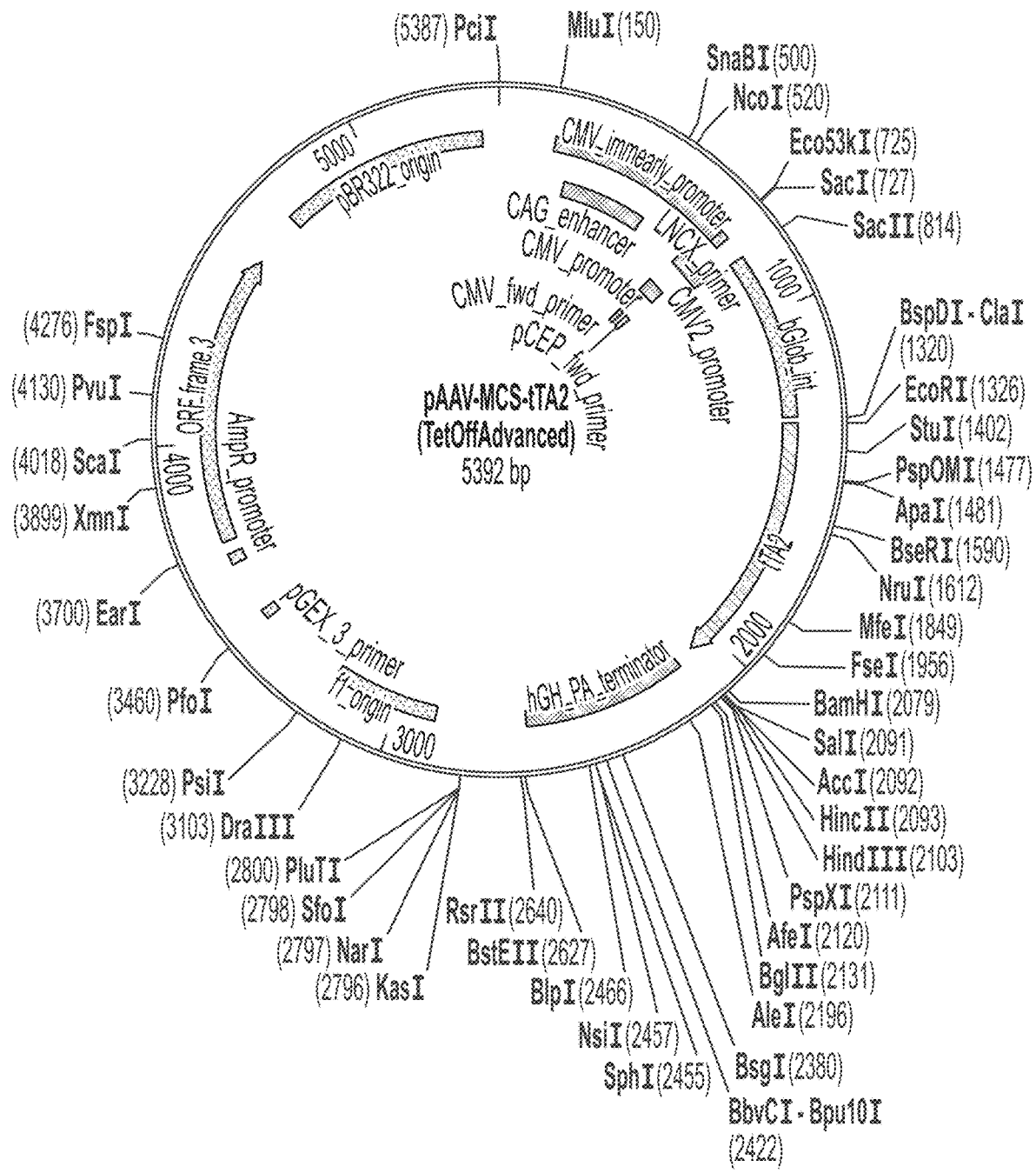
FIG. 19 is a vector map of pAAV–MCS–tTA2 (or CAG-tTA) (SEQ ID NO: 32). This vector is a non-limiting example of a vector encoding tTA under a CAG promoter.
Figure 20:
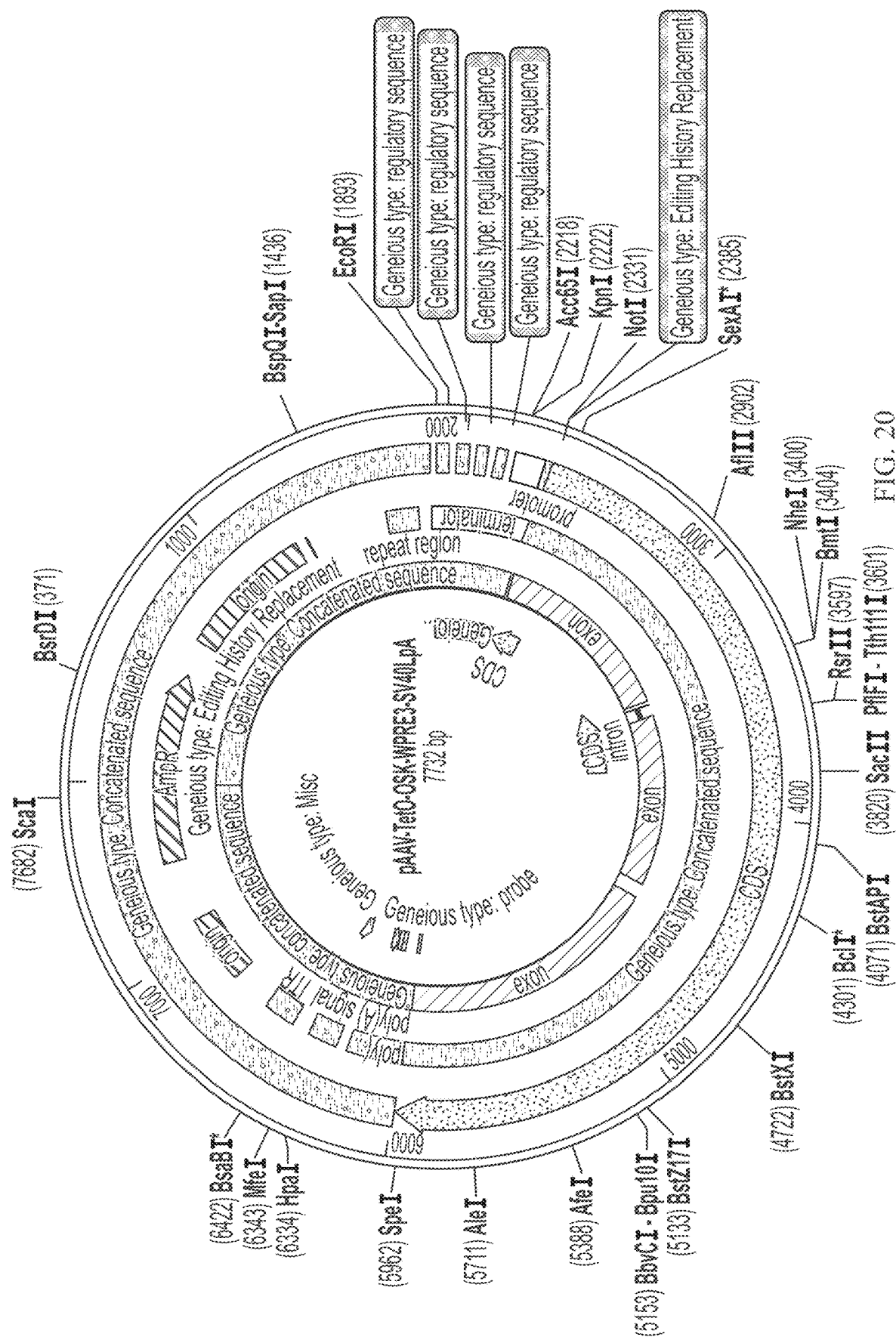
FIG. 20 is a vector map of p-AAV–TetO–OSK–WPRE3-SV50LpA (TRE2–OSK, pAAV–TRE2–OSK–SV40LpA, or TRE2–OSK) (SEQ ID NO: 33). This vector is a non-limiting example of an AAV vector comprising a nucleic acid (e.g., engineered nucleic acid) sequence that is greater than 4.7 kb between the two ITRs in the vector.

The vector shown in FIGS. 3 and 4A-4AL was cloned using routine methods. Briefly, a TRE3G promoter sequence (SEQ ID NO: 7) from Clonetech was synthesized using flanking restriction sites, primers were designed to clone OSK out of a TetO-FUW-OSKM plasmid, and a stop codon was added. To make the vector shorter, a short SV40 sequence was synthesized with flanking restriction cut sites. Whereas conventional AAV vectors encoding OSK is over the packaging limit of AAV, could only be packaged into AAV9 capsid with low titer (less than $2\times10^{12}$ particles per viral prep), and the low titer virus is not functional due to possible truncation as shown in FIG. 17. The vector depicted in FIGS. 3 and 4A-4AL produced virus with more than $2\times10^{12}$ viral partial per prep or $1\times10^{13}$ per mL (data not shown).

To determine whether the OSK vector could be used for inducible OSK expression in mammalian cells, the OSK vector and was packaged into different serotypes of AAV virus (AAV9 (FIG. 6A), AAV2 (FIG. 6B), and AAV.PhP.b (FIG. 6C)) using routine methods. Additional batches of AAV9 and AAV.PHP.b virus with a vector encoding rtTA3 (Tet-On system) and AAV2 virus with a vector encoding tTA (Tet-Off system) were produced. Then, mammalian 293T cells were co-infected with the OSK virus along with the same serotype of rtTA3 or tTA virus. Cells were subsequently treated with or without doxycycline (DOX) and expression of OCT4, KLF4 and the loading control H3 was determined by western blot with antibodies against OCT4, KLF4, and H3.

Figure 6A:
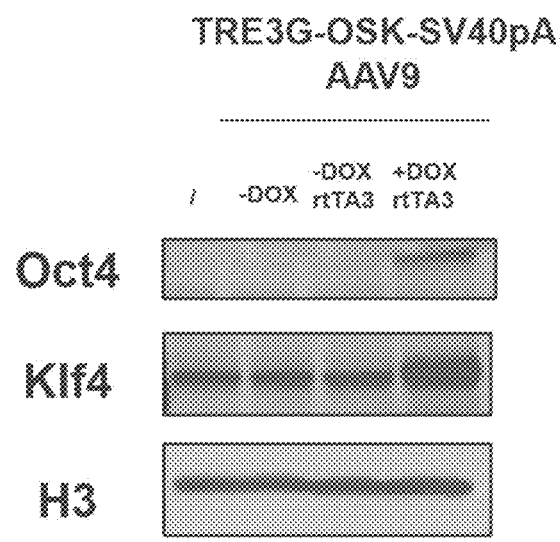
FIGS. 6A-6C include western blot data showing that different serotypes of AAVs encoding OSK (TRE3G–OSK–SV40 pA, SEQ ID NO: 16) were successfully used in a doxycycline (DOX)-inducible system to control OSK expression in 293T cells. OCT4, KLF4, and H3 expression were detected with antibodies. H3 refers to histone 3 and is a loading control.
Figure 6B:
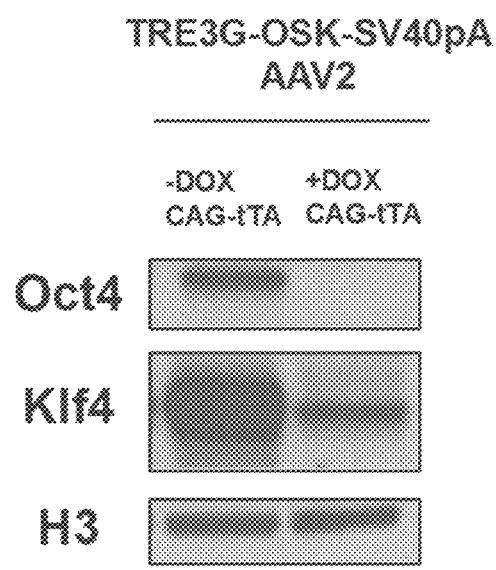
Figure 6C:
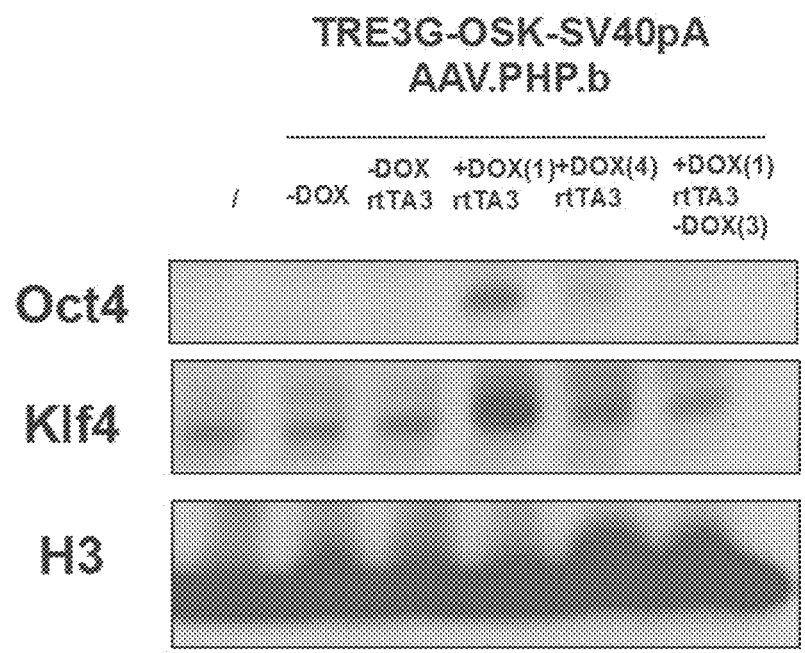

As shown with the Tet-On system in FIG. 6A, doxycycline treatment increased OCT4 and KLF4 expression in 293T cells infected with AAV9 viruses encoding OSK and rtTA3. The OSK expression could also be controlled with a Tet-Off system. DOX treatment decreased OCT4 and KLF4 expression in 293T cells infected with OSK AAV2 and AAV2 with a vector driving tTA expression under a constitutive CAG promoter (FIG. 6B). Furthermore, OSK expression could be tightly controlled even after stimulation of transgene expression. As shown in the fourth lane of FIG. 6C, one day of DOX treatment is sufficient to increase OCT4 and KLF4 expression in 293T cells infected with TRE3G-OSK-SV40 pA AAV.PHP.b virus and with Ubc-rTtA3-p2a-mkate AAV.PHP.b virus. Removal of DOX for three days after one day of DOX treatment, however, returns OCT4 and KLF4 expression back to uninduced levels (last lane of FIG. 6C). The Ubc-rtTA3-p2a-mkate vector comprises a constitutive Ubc promoter that drives expression of rtTA3, a self-cleaving 2A peptide, and a far-red fluorescent protein (mKate).

Therefore, an AAV vector that allows for controlled expression of OSK in mammalian cells (e.g., in vivo) was developed. Furthermore, the AAV vector was packaged into different AAV serotypes that successfully delivered a functional vector into 293T cells.

Figure 7A:
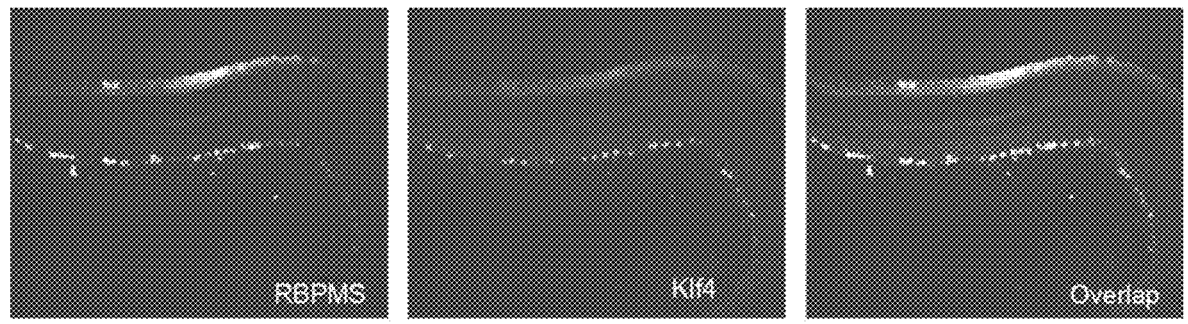
FIGS. 7A-7F include data showing that AAV encoding OSK induced partial reprogramming and promoted regeneration of optic nerves after nerve crush in an inducible manner.

Example 2: AAV Encoding OSK Promoted Optic Nerve Regeneration and Survival of Retina Ganglion Cells (RGCs) Nerves after Nerve Crush in an Inducible Manner To determine whether OSK could be delivered by AAV and inducibly expressed in vivo, AAV virus with the TRE-OSK-SV40 vector and AAV virus encoding tTA under the CAG constitutive promoter were produced through routine methods and injected into the retina of mice. Next, an optical coherence tomography (OCT) section was stained with antibody against RBPMS to identify retina ganglion cells (RGCs) and with an antibody against KLF4 to detect KLF4 expression. As shown in FIG. 7A, KLF4 was expressed in RGCs (RBPMS-positive cells), which suggested that the vectors were functional.

Figure 7B:
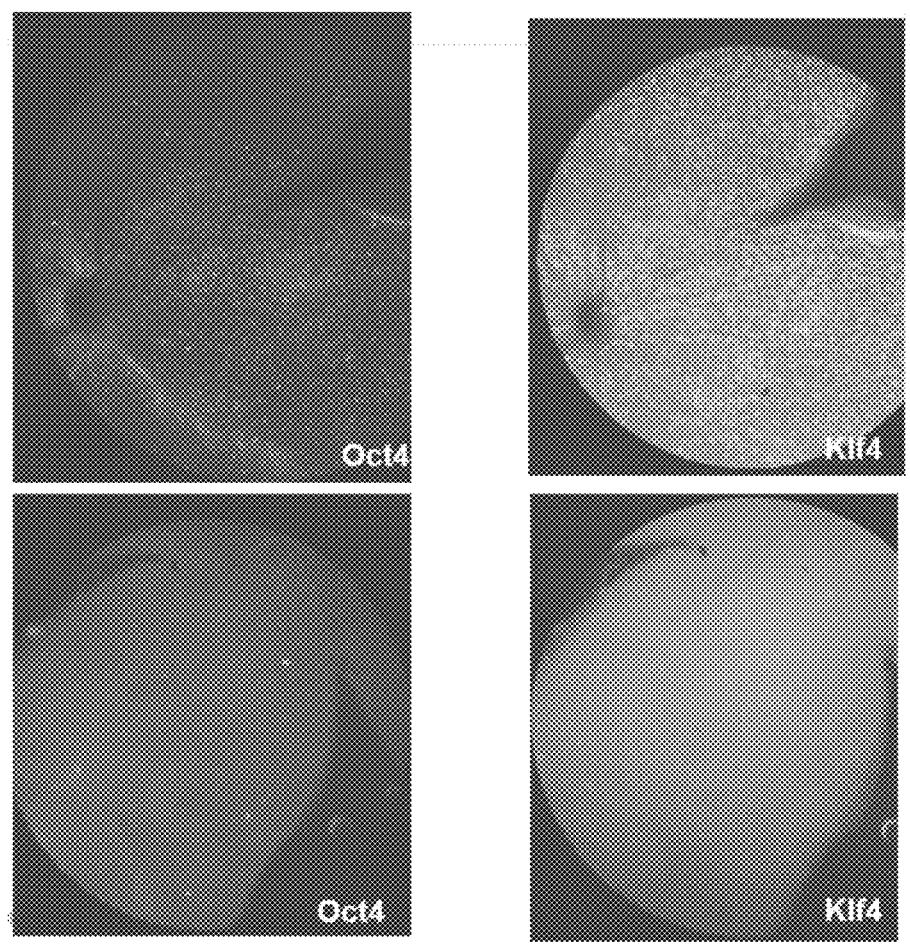

The inducibility of the system was also tested in vivo. In the absence of DOX treatment, OCT4 and KLF4 were expressed in the mouse retina as determined by whole retina mount staining (FIG. 7B, top). After four days of DOX treatment, however, OCT4 and KLF4 staining was significantly reduced, indicating that expression from the TRE-OSK-SV40 vector was turned off (FIG. 7B, bottom). Therefore, OSK vector expression could be tightly controlled.

Figure 7C:
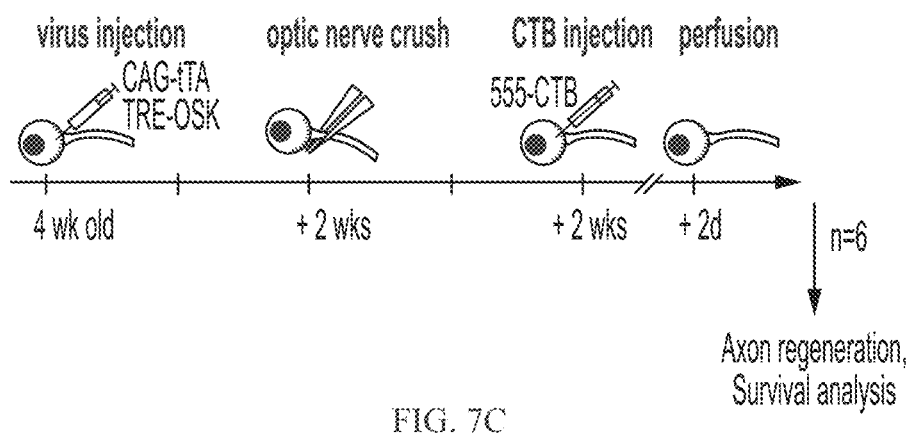

To determine whether inducible OSK expression could induce partial reprogramming and promote regeneration following nerve damage, AAV virus with the TRE-OSK-SV40 vector and AAV virus encoding tTA under the CAG constitutive promoter were injected into the retina of 4-week old mice (n=6) as shown in the experimental timeline provided in FIG. 7C. As a control, a separate cohort of mice (n=2) were only injected with the OSK virus. Mechanical damage was induced through optic nerve crush in both cohorts two weeks after virus injection. To trace axon regeneration by fluorescent microscopy of the optic nerve, fluorescently labeled cholera toxin β-subunit (CTB) was intraocularly injected into mice and perfusion was performed two days after CTB injection. Axon regeneration and axon survival analysis was subsequently conducted.

Figure 7D:
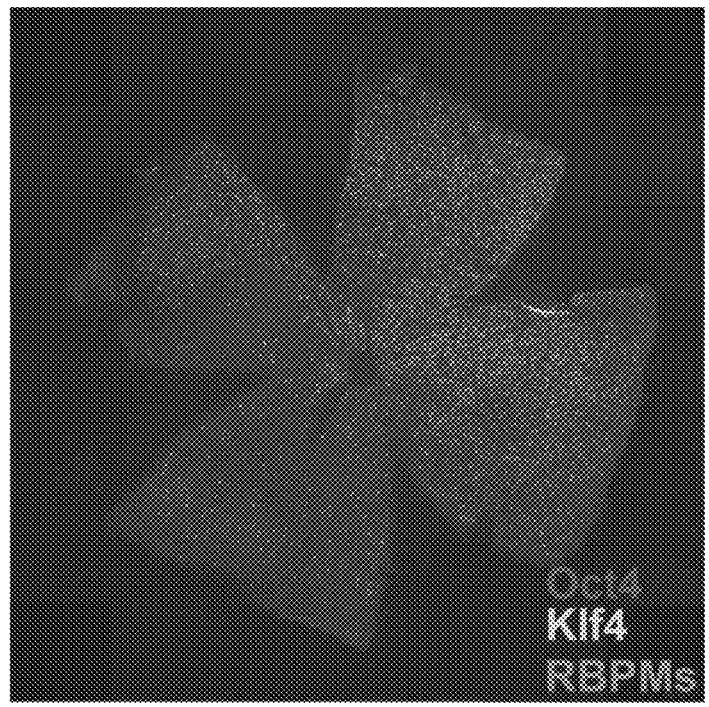
Figure 7E:
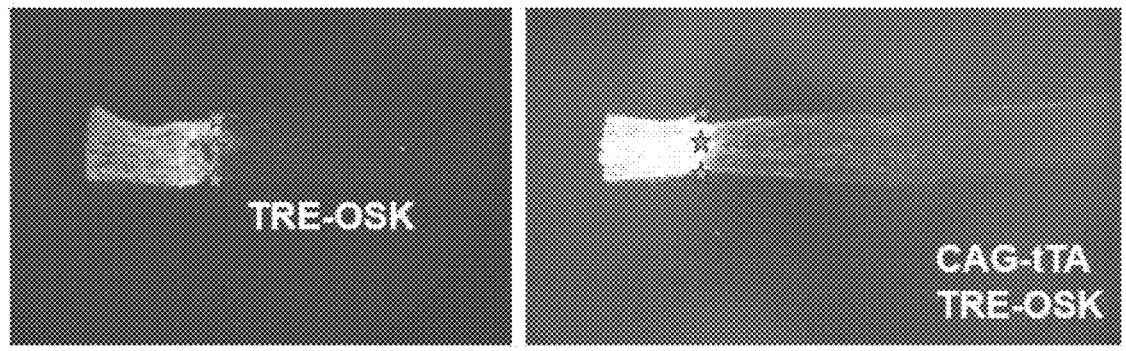
Figure 7F:
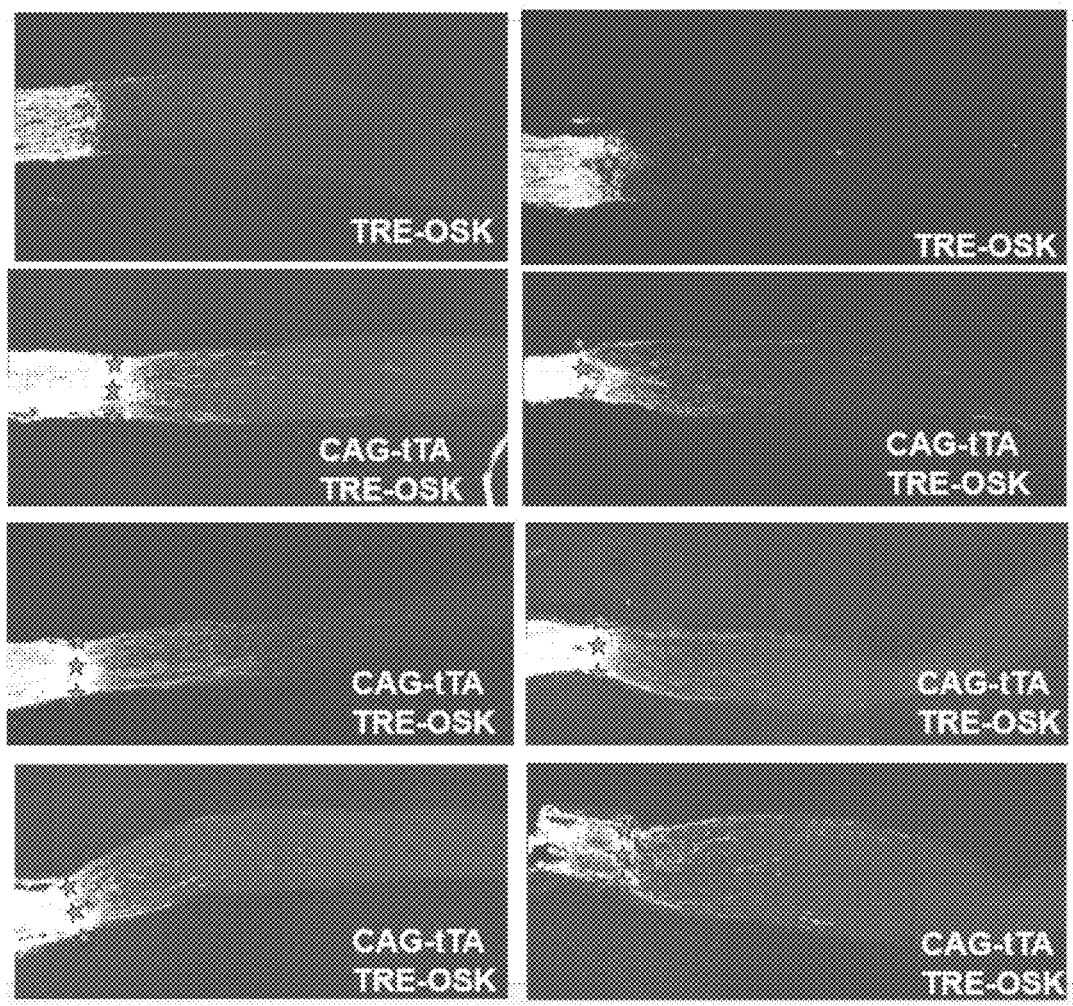

Axon regeneration was determined by estimating the number of axons per nerve. As shown in FIG. 7D, coadministration of OSK and tTA virus significantly promoted optic nerve regeneration away from the site of the optic nerve crush compared to administration of OSK virus alone. This effect was also visually apparent when comparing the fluorescence intensity of optic nerves from mice receiving both OSK and tTA virus compared to mice receiving OSK virus alone. The fluorescence intensity of optic nerves from mice receiving both viruses was higher than that of mice receiving OSK virus alone, indicating that nerve regeneration was higher with combination treatment (FIGS. 7E-7F).

Figure 8A:
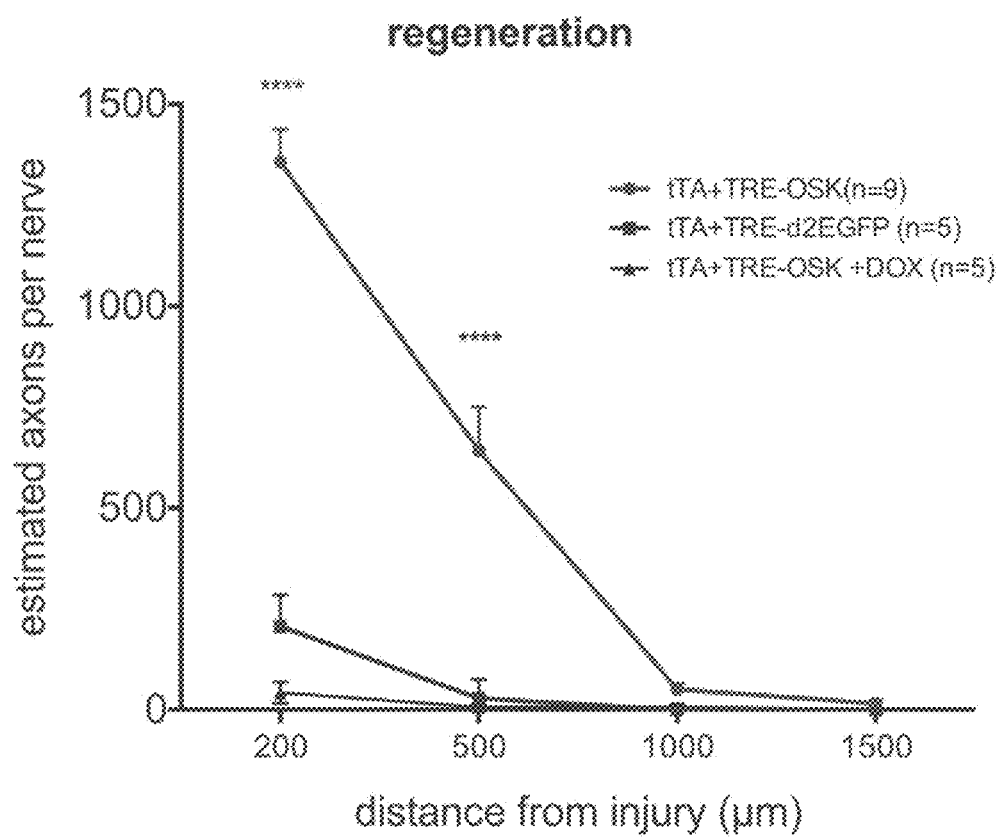
FIGS. 8A-8G shows administration of virus encoding OSK improved RGC axon regeneration after nerve crush injury.
Figure 8B:
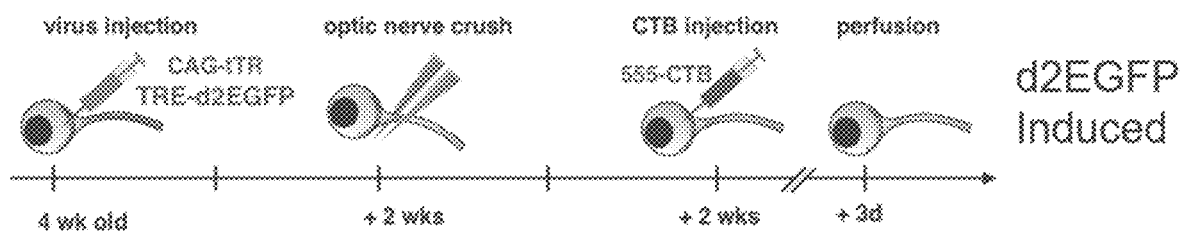
Figure 8C:
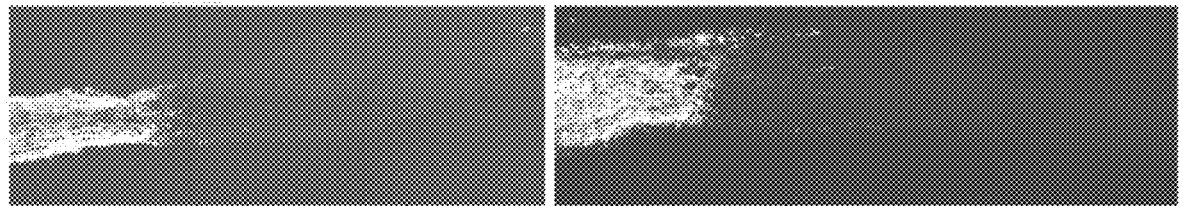
Figure 8D:
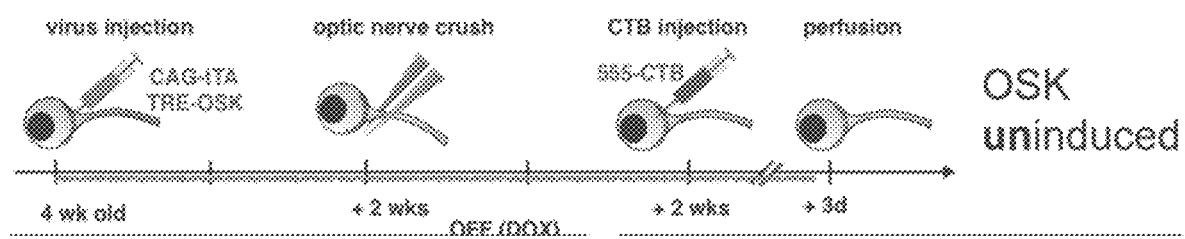
Figure 8E:
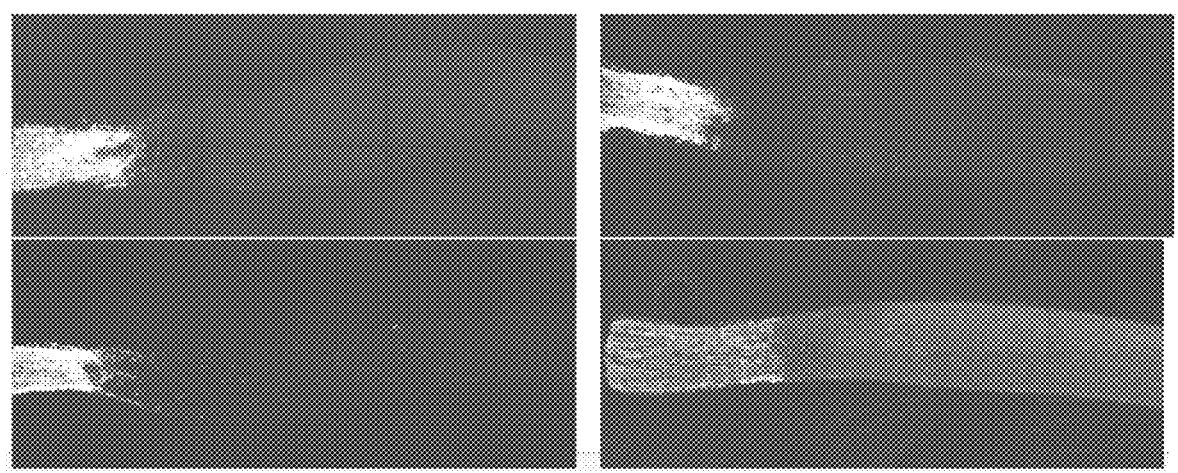
Figure 8F:
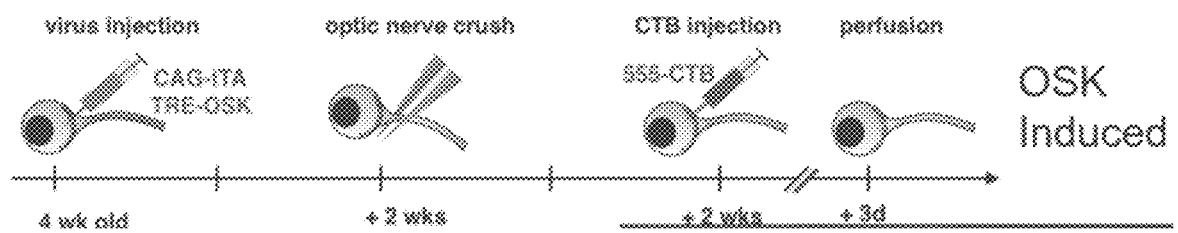
Figure 8G:
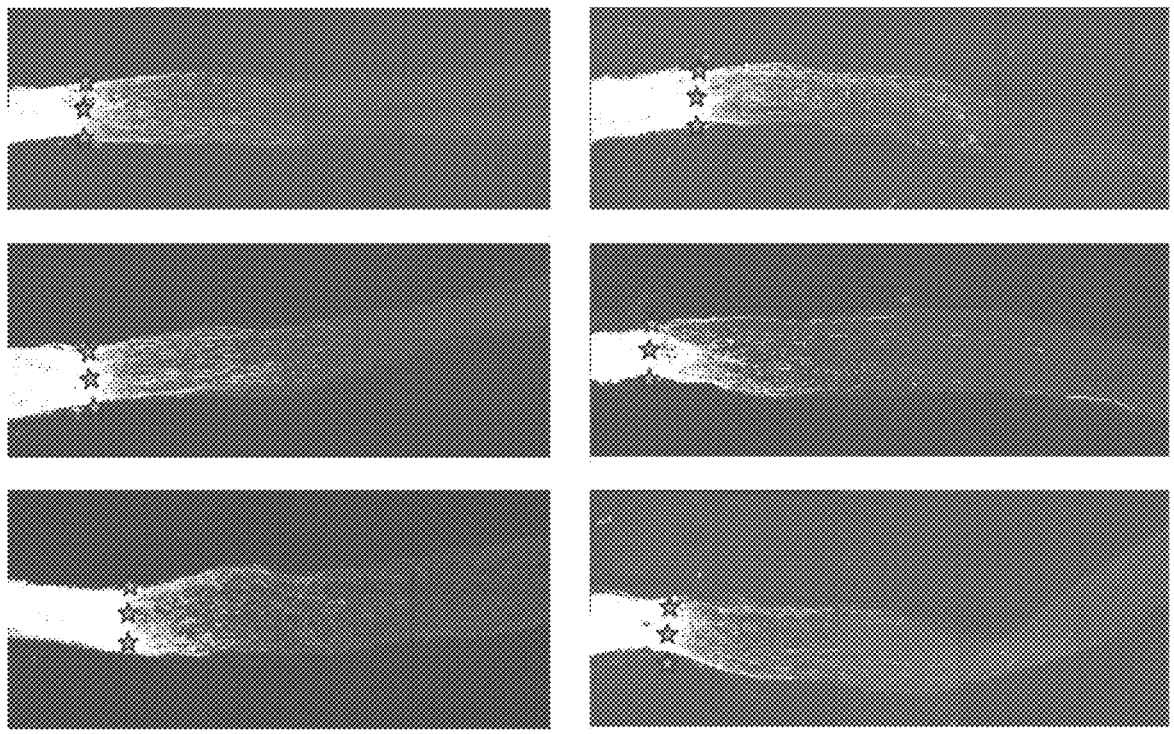

To show that the observed axon regeneration after crush injury was specifically mediated by OSK, an axon regeneration experiment was used to compare the effects of tTA virus in combination with (1) TRE–OSK virus with no DOX treatment, (2) TRE-d2EGFP virus with no DOX treatment, and (3) TRE–OSK virus with DOX treatment. The experimental timeline of treatments (1)-(3) are indicated in FIGS. 8B, 8D, and 8F, respectively. Fluorescently-labeled CTB was used to visualize axons. As shown in FIGS. 8A and 8G, the extent of optic nerve regeneration in mice in which OSK expression was induced (mice receiving OSK and tTA viruses in the absence of DOX) was very significant at 200 μm and 500 μm from crush site. In contrast, even when d2EGFP expression was induced (mice receiving d2EGFP and tTA viruses in the absence of DOX), minimal regeneration was observed (FIG. 8A and FIG. 8C). Notably, axon regeneration was dependent on induction of OSK expression. When mice were treated with DOX to inhibit OSK expression as outlined in FIG. 8D, administration of tTA and OSK viruses did not induce axon regeneration (FIG. 8A). The intensity of CTB-labeled axons in these DOX-treated mice were similar to mice receiving control d2EGFP virus (compare FIG. 8E with FIG. 8C). Therefore, administration of an AAV-based inducible OSK expression system could be used to promote regeneration following optic nerve damage.

Figure 9A:
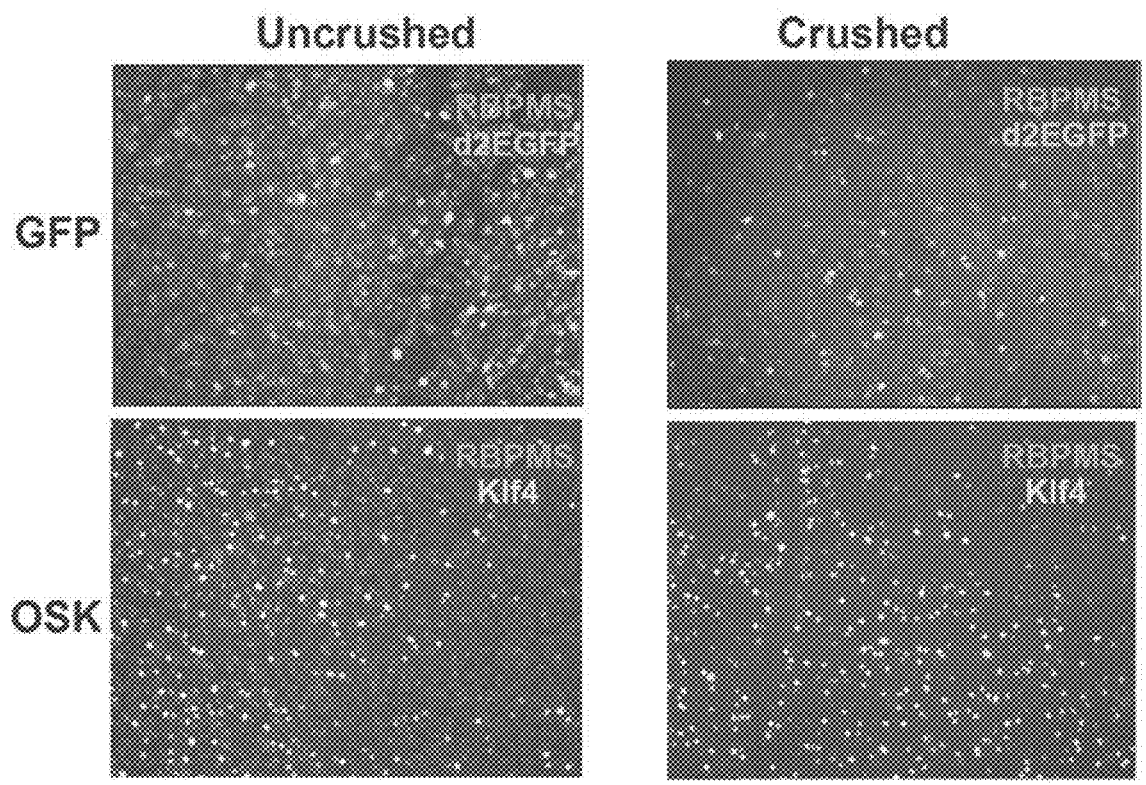
FIGS. 9A-9D show OSK-infected RGCs have a higher survival rate compared to cells not infected with OSK virus following nerve crush.
Figure 9B:
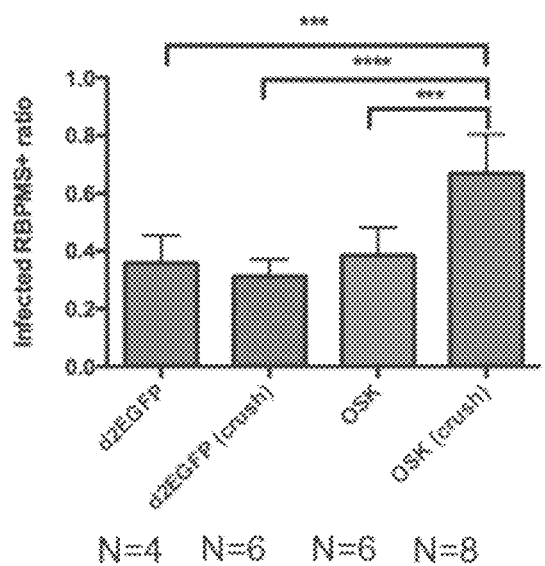
Figure 9C:
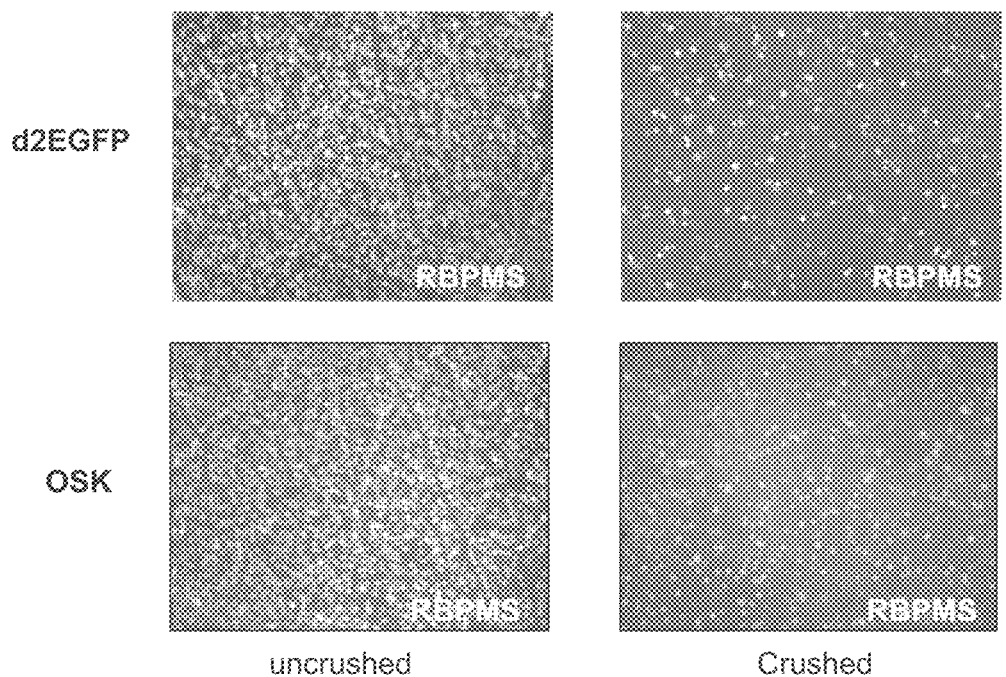
Figure 9D:
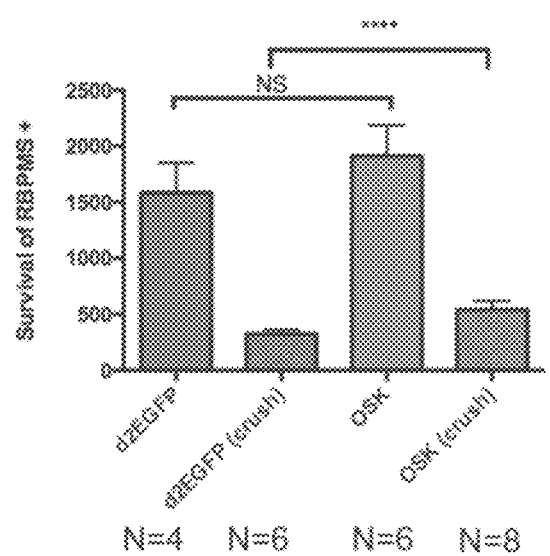
Figure 10A:
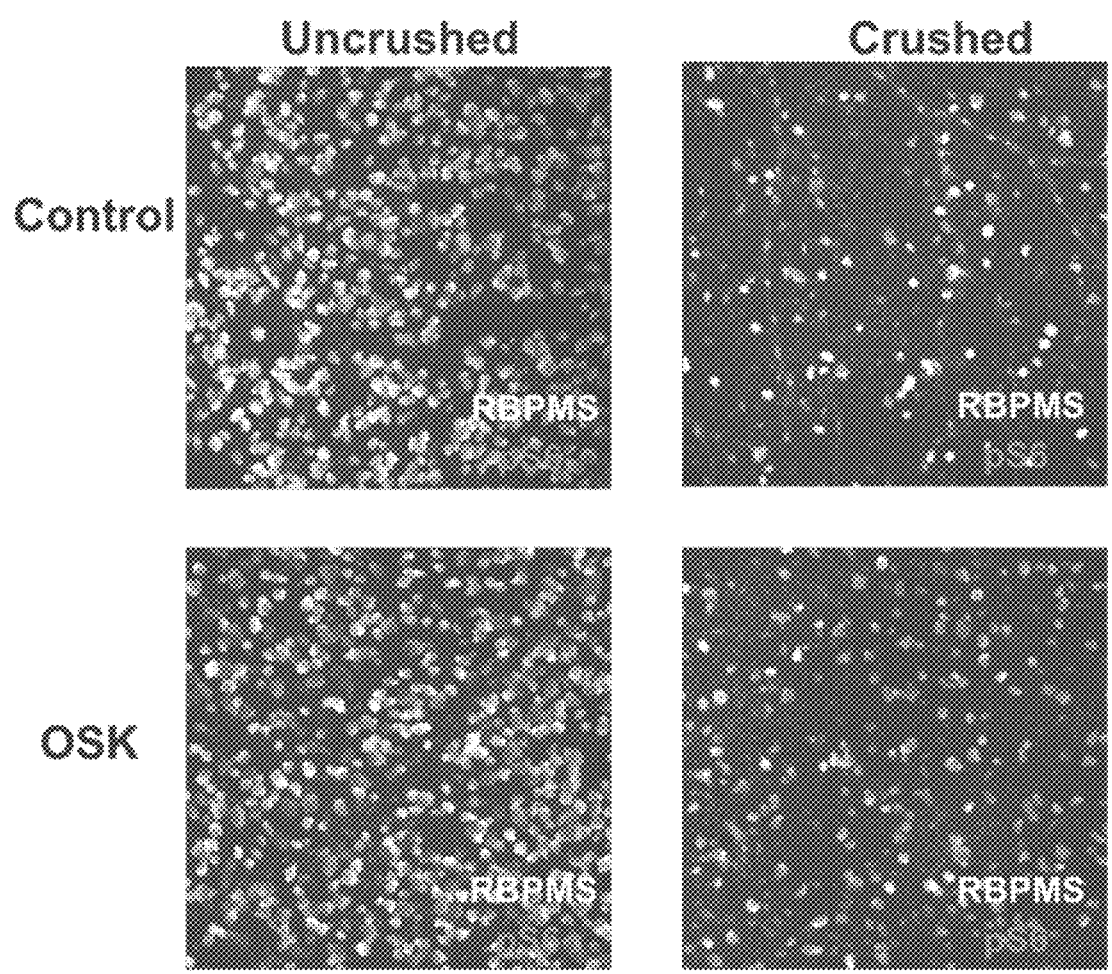
FIGS. 10A-10B show that OSK-mediated regeneration and protection is independent of mTOR activation.
Figure 10B:
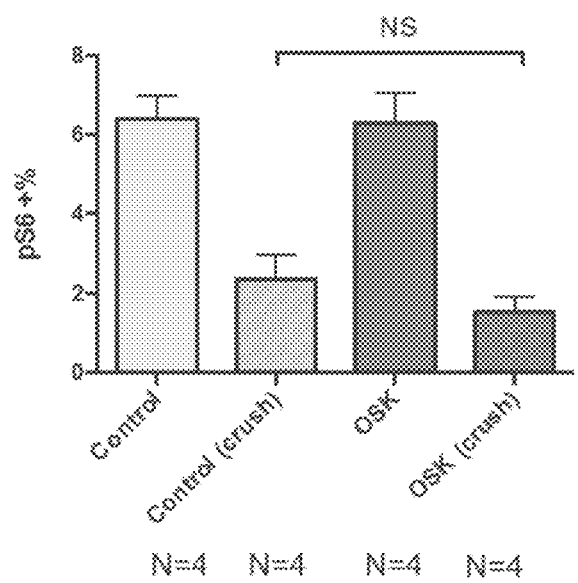

The effect of OSK on the survival rate of retina ganglion cells (RGCs) was also assessed. As shown in FIGS. 9A-9D, OSK significantly increases RGC survival rate. RGCs (RBPMS positive cells) that were infected with OSK and tTA virus (green) or uninfected with both (red) shown following optic nerve crush, OSK-infected RGC had 3 times higher survival rate (54% vs 18%) after crush compared to cells without OSK infection, quantification from a series of pictures like shown (FIG. 9A). Therefore, the percentage of RBPMS-positive cells expressing KLF4 (OSK-infected cells) was lower than 40% before crush, but significantly increased to around 70% following optic nerve crush due to its higher survival rate. While the percentage of d2EGFP-infected cells maintained at 35-40% after crush. This indicates a strong cell protection effect from OSK expression (FIG. 9B). As shown in FIG. 9C, in d2EGFP or OSK plus CAG-tTA (SEQ ID NO: 32) AAV infected retina, there is no significant difference in RGC number (RBPMs positive) without uncrushed, but after crush there is clearly more RGCs survived when they infected with OSK and CAG-tTA compared to those infected with d2EGFP and CAG-tTA. FIG. 9D shows the quantification of survived RGC numbers from each group. Though lower than 40% cells infected with both OSK and CAG-tTA AAV, it increases the total survival RGC number compared to d2EGFP(542 compared to 323).

mTOR activation has reported as a pathway for optic nerve regeneration (Parker et al., Science, 322(5903), 963-966 November 2008). To determine whether OSK expression activated the mTOR pathway, control and OSK virus-infected cells were imaged using antibodies against RBPMS and phosphorylated S6 (pS6) in the absence of damage (uncrushed) and after damage (crushed). Representative images of the staining is shown in FIG. 10A, and as quantified in FIG. 10B, the percentage of pS6-positive cells was not significantly different between control cells and OSK-infected cells following optic nerve crush.

Figure 11A:
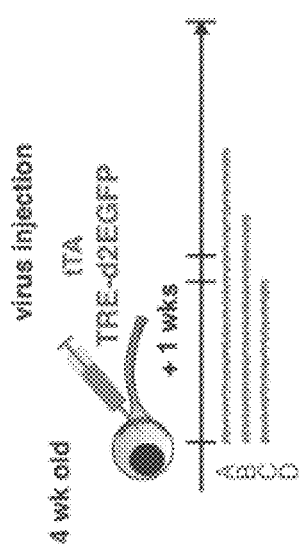
Figure 11B:
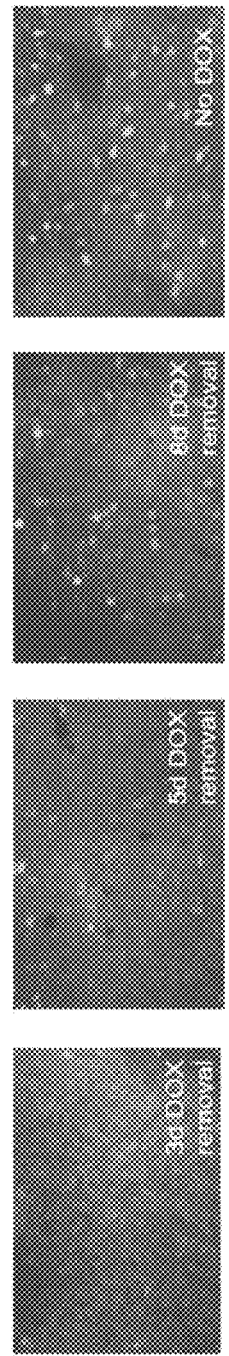

Example 3. An AAV Tet-on System Induces Faster Gene Expression Compared to an AAV Tet-Off System in Retinal Cells after Nerve Crush To compare the rate of gene expression between AAV-based Tet-On and Tet-Off systems, TRE-d2EGFP virus and (1) virus encoding tTA (Tet-Off) or (2) virus encoding rtTA (Tet-On) were administered into the retina of 4-week old mice. In the Tet-Off system, mice were given DOX starting from virus injection and DOX was removed for 3 days, 5 days or 8 days (FIG. 11A). As a control, a cohort of mice in the Tet-Off system were given no DOX. Approximately 8 days of DOX removal was needed to induce the same level of GFP expression as no DOX treatment in the Tet-Off system (FIG. 11B). In the Tet-On system, mice were treated as indicated in FIG. 11C. GFP expression was observed after only 2 days of DOX treatment in the Tet-On system (FIG. 11D). Therefore, a shorter period of time was needed to induce transgene expression in mice retina infected with an AAV-based Tet-On system compared to infection with an AAV-based Tet-Off system.

Figure 13B:
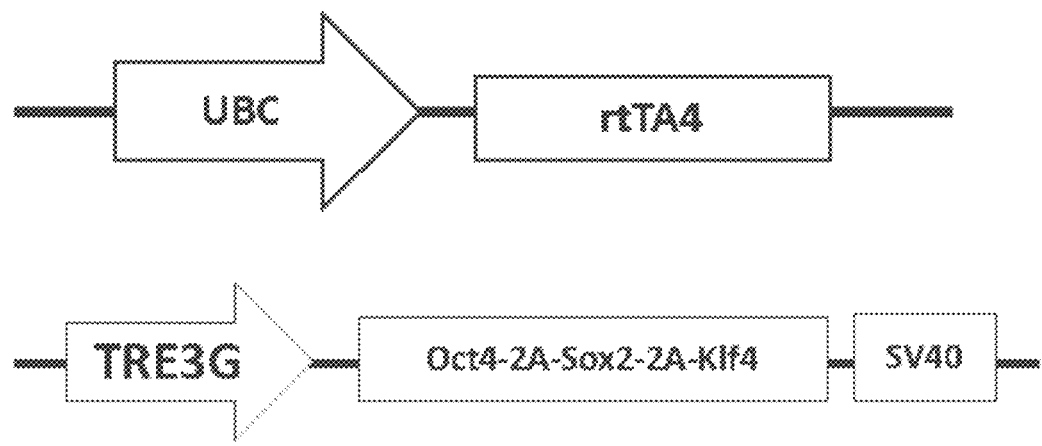
Figure 13C:
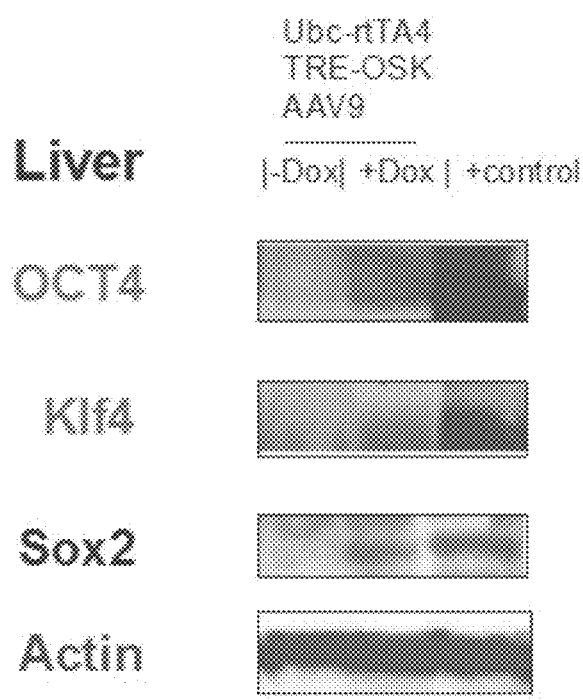
Figure 14:
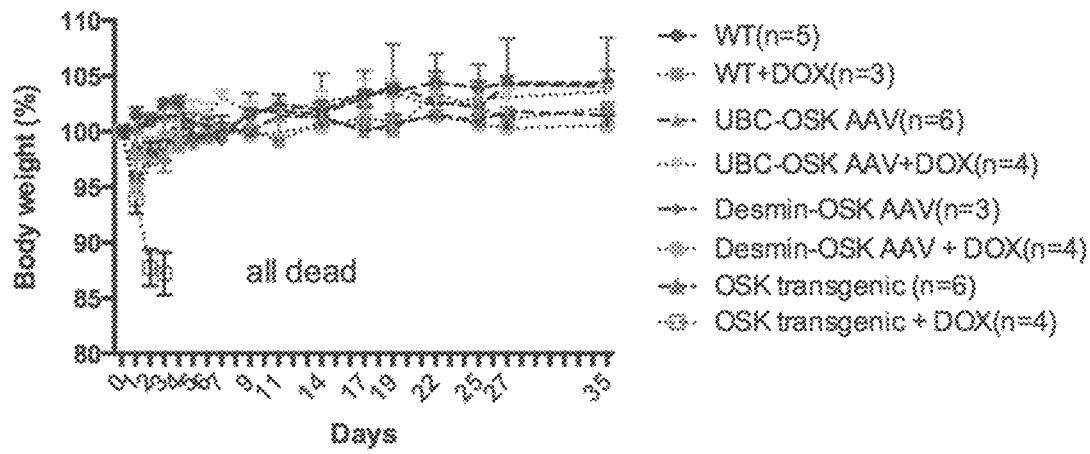
FIG. 14 is a graph comparing the body weights of mice under various treatments as indicated. WT indicates wild-type mice without exogenous OSK expression. All dead indicates that OSK transgenic mice treated with doxycycline were all dead.

Example 4: An AAV Vector Encoding Mutant Reverse Tetracycline Transactivator (rtTA) Showed Low Leakiness in the Liver of Mice and Low Toxicity As shown in FIGS. 13A-13C, OCT4, SOX2, and KLF4 through AAV9 delivery (TRE–OSK with UBC–rtTA4) can be successfully induced in liver of the mice with DOX treatment, shown with both western blot and immune staining. While mice with transgene of OCT4, SOX2, KLF4 died after 2 days-induction from doxycycline water (FIG. 14) due to generalized cytological and architectural dysplasia in the intestinal epithelium, expression from the OCT4, SOX2, and KLF4 AAV described herein did not cause toxicity or teratoma in vivo even with continuous expression through doxycycline administration in their drinking water. No teratoma or body weight loss were detected for three months when AAV9 encoding these three transcription factors were delivered to the entire body of mice (FIG. 14).

Figure 15A:
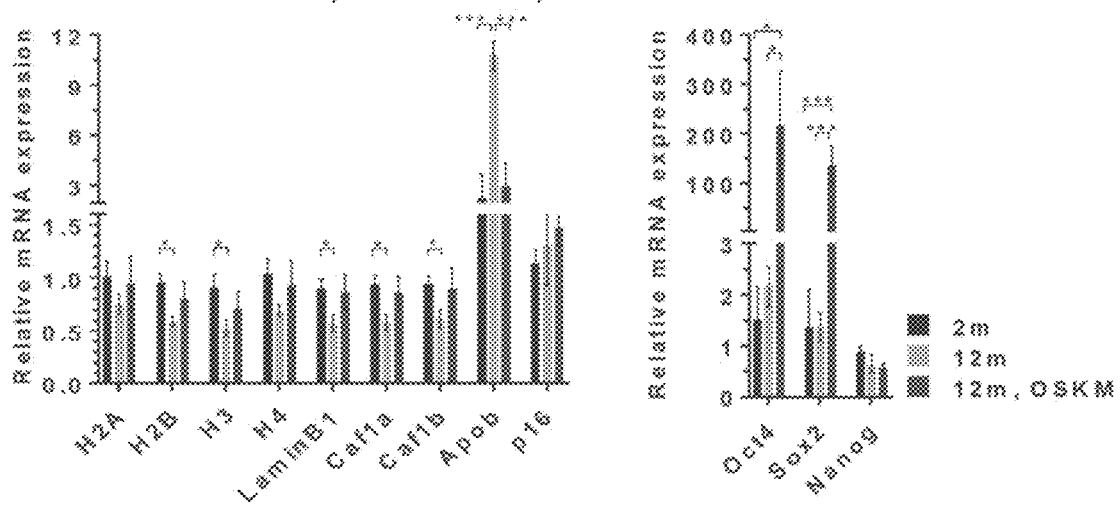
FIGS. 15A-15B include data showing that induction of OCT4, KLF4, and SOX2 expression reversed aging of mice ear fibroblasts as indicated by expression of histone and Chaf (Chromatin assembly factor) genes but did not induce Nanog expression. The asterisk (*) indicates endogenous KLF4 expression from the 293T cell line.
Figure 15B:
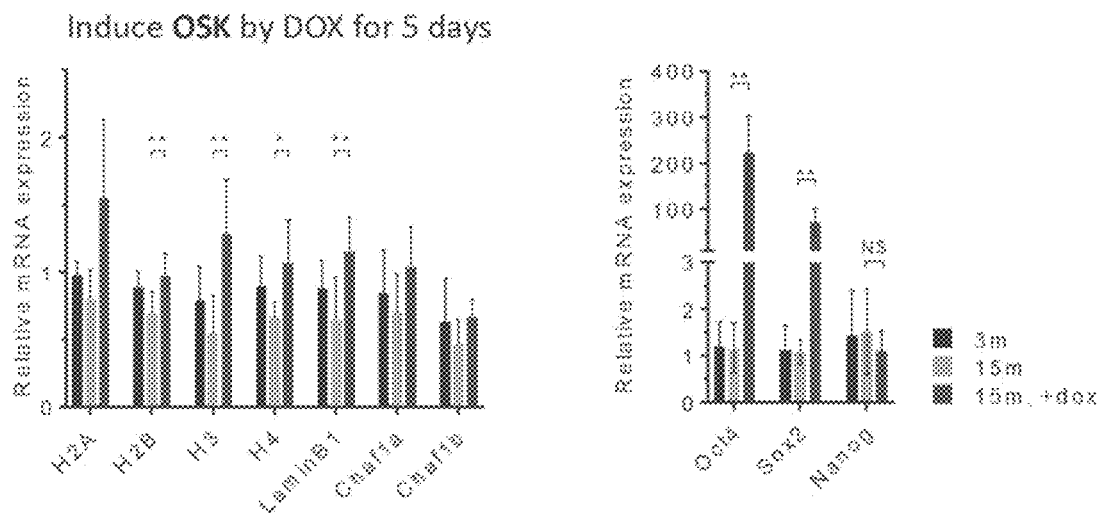

Example 5: Expression of OCT4, SOX2, and KLF4 Induced Partial Reprogramming in Mice FIGS. 15A-15B show that the expression of histone and Chaf (Chromatin assembly factor) genes declined during aging in ear fibroblasts from aged mice (12 months or 15 months) compared to those from young mice, short term of OSKM (3 days) or OSK expression (5 days) induction reset their gene expression level to young state, without making them into stem cell (e.g., Nanog was not been turned on).

Figure 16:
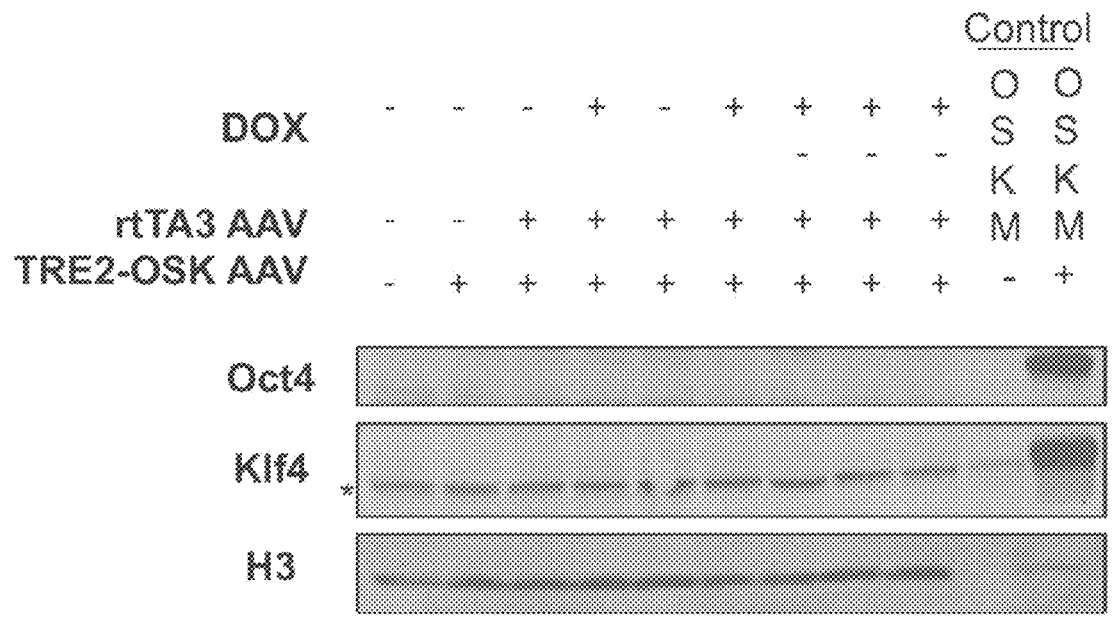
FIG. 16 is a western blot showing that an AAV vector comprising a nucleic acid (e.g., engineered nucleic acid) sequence that is greater than 4.7 kb between the two ITRs in the vector has low viral titer when incorporated into an AAV and produces non-functional AAV. The TRE2-OSK vector is provided as SEQ ID NO: 33. Expression of OCT4, KLF4 and H3 was detected using antibodies. H3 is shown as a loading control. Asterisk (*) indicates endogenous Klf4 from 293T cell line.

Conventional AAV vectors encoding OSK is over the packaging limit of AAV (e.g., 4.7 Kb), could only be packaged into AAV9 capsid with low titer (less than 2×10^12 particles per viral prep), and the low titer virus is not functional (e.g., no overexpression of OCT4 or KLF4 was detected) due to possible truncation as shown in FIG. 16.

Figure 12:
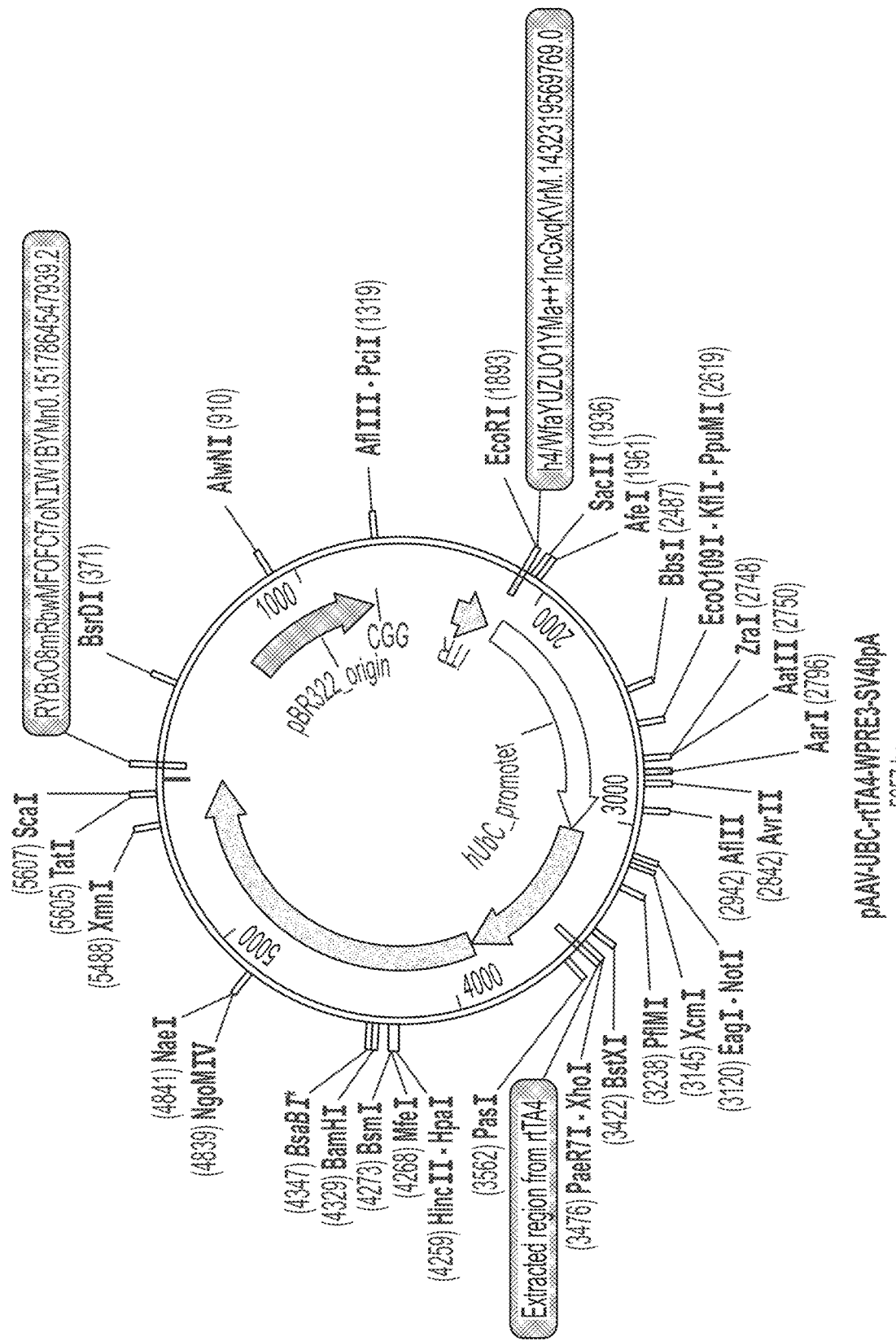
FIG. 12 is a vector map showing features in an adeno-associated virus (AAV) vector encoding reverse tetracycline-transactivator 4 (rtTA4). Ubc is a constitutive promoter that is operably linked to the nucleic acid (e.g., engineered nucleic acid) encoding rtTA4. SV40 pA is an SV40-derived terminator sequence. The sequence of this vector is provided in SEQ ID NO: 17.

Example 6: An AAV Vector Encoding Mutant Reverse Tetracycline Transactivator (rtTA) Showed Low Leakiness in the Liver of Mice A Tet-On system comprising rtTA4 (SEQ ID NO: 13) was also tested in vivo using recombinant AAV9 viruses. Two AAV vectors comprising components shown in FIG. 13B were used. AAV virus encoding rtTA4 operably linked to a UBC promoter (pAAV-UBC–rtTA4-WPRE3-SV40 pA vector is provided as SEQ ID NO: 17 and an exemplary vector map of SEQ ID NO: 17 is provided in FIG. 12) and AAV virus encoding an AAV TRE3G–OSK–SV40 pA vector (SEQ ID NO: 16) with a vector map depicted in FIG. 3 were administered to mice. Mice were treated without doxycycline or with doxycycline and liver samples were collected. As shown in the immunofluorescence images of FIG. 13A, in the absence of doxycycline, KLF4 expression was not detectable in the liver. When mice were treated with doxycycline through their drinking water, KLF4 expression was detected in the liver (FIG. 13A). These results were also evident by western blot using antibodies against OCT4, KLF4, and SOX2 to determine expression of these protein (FIG. 13C). Actin was used as a loading control (FIG. 13C). OCT4, KLF4, and SOX2 were only detected in the liver when mice were treated with doxycycline (FIG. 13C).

Example 7. Modified mRNAs Encoding OCT4, SOX2, and KLF4(OSK) Induced Expression of OSK in Mouse Fibroblasts Mouse fibroblasts were successfully transfected with modified mRNA encoding OCT4, SOX2, KLF4, and c-MYC (OSKM). Lipofectamine™ MessengerMAX™ Transfection Reagent from Invitrogen was used to transfect the modified mRNAs. The modifications were complete substitution of either 5-methylcytidine (5mC) for cytidine or pseudouridine (psi) for uridine. See, e.g., Warren et al., Cell Stem Cell. 2010 Nov. 5; 7(5):618-30; Mandal et al., Nat Protoc. 2013 March; 8(3):568-82. The dose of each RNA that was used is provided in Table 4 below. The numbers 1-5 in the first column of Table 4 correspond to the numbers 1-5 in FIG. 17.

TABLE 4

Doses of mRNA administered.

mRNA (μg)

| | NDG | O | S | K | M | Total |
|---|---|---|---|---|---|---|
| 1 | 0 | 0 | 0 | 0 | 0 | 0 |
| 2 | 1X | 0.2 | 0.6 | 0.2 | 0.2 | 0.2 | 1.4 |
| 3 | 2X | 0.4 | 1.2 | 0.4 | 0.4 | 0.4 | 2.8 |
| 4 | 4X | 0.8 | 2.4 | 0.8 | 0.8 | 0.8 | 5.6 |
| 5 | 6X | 1.2 | 3.6 | 1.2 | 1.2 | 1.2 | 8.4 |

A western blot was used to confirm that administration of the modified mRNA induced expression of protein in the mouse fibroblasts. As shown in FIG. 17, transfection of OSK modified mRNA into mouse fibroblasts cells to induce expression of OCT4, KLF4, and SOX2 protein (NDG and zsGreen are modified mRNA that express green fluorescent protein to indicate the efficiency of transfection).

This example shows that delivery of RNA (e.g., mRNA, modified RNA, modified mRNA, etc.) encoding OCT4, KLF4, and SOX2 to mouse cells is feasible. These findings may be extended to in vivo delivery of mRNA encoding OCT4, KLF4, and SOX2. As an example, for in vivo muscle delivery, electroporation, is used. As an example, for liver and other internal organ delivery, nanoparticles comprising RNA encoding OCT4, KLF4, and SOX2, nanoparticles are used. See, e.g., Dong et al., Nano Lett. 2016 Feb. 10; 16(2):842-8.

Example 8. Chemical Reprogramming of Cells

A non-limiting of a protocol to chemically reprogram a mouse embryonic fibroblast to an induced pluripotent stem cell is provided below. A similar protocol may be found at Zhao et al., Cell. 2015 Dec. 17; 163(7):1678-91. FIG. 21 shows the results after using the protocol provided below.
Stage 1
  100 ng/ml bFGF
  0.5 mM VPA,
  20 μM CHIR99021,
  10 μM 616452,
  5 μM tranylcypromine,
  50 μM forskolin,
  0.05 μM AM580
  5 μM EPZ004777
  On day 12, the cells were trypsinized, harvested and then re-plated at 50,000-200,000 cells per well of a 6-well plate (1:10-15)
  During days 12-16, concentrations of bFGF, CHIR, and forskolin were reduced to 25 ng/ml, 10 μM, and 10 μM, respectively.
  On day 16, XEN-like epithelial colonies were formed and the culture was changed into stage 2 medium
Stage 2
  25 ng/ml bFGF,
  0.5 mM VPA,
  10 μM CHIR99021,
  10 μM 616452,
  5 μM tranylcypromine,
  10 μM forskolin,
  0.05 μM AM580,
  0.05 μM DZNep,
  0.5 μM 5-aza-dC,
  5 μM SGC0946
  On day 28, the culture was transferred into stage 3 medium.
Stage 3
  N2B27-2iL medium
  3 μM CHIR99021,
  1 μM PD0325901,
  1,000 U/ml LIF
  After another 8-12 days, 2i-competent, ESC-like, and GFP-positive (if using pOct4-GFP reporter) CiPSC colonies emerged and were then picked up for expansion and characterization.

Example 9. Expression of OCT4, SOX2, and KLF4 Improved Axon Regeneration in Adult and Aged Mice after Optic Nerve Crush Injury The Tet-Off system depicted in FIG. 22, top panel was used to determine whether a vector encoding TRE–OSK–SV40 (SEQ ID NO: 16) could be used to promote optic nerve axon regeneration in adult (3 month old) and aged (12 month old) mice.

AAV2 virus with the TRE–OSK–SV40 vector and AAV2 virus encoding tTA under the CAG constitutive promoter were injected into the retina of 1 month old, 3 month old, or 12 month old mice (n=5-9), similar to the experimental timeline provided in FIG. 7C. As a control, a separate cohort of 1 month old mice (n=5-6) were injected with AAV2 virus with a AAV2 vector TRE-d2EGFP-SV40 and the AAV2 virus encoding tTA. Mechanical damage was induced through optic nerve crush in both cohorts two weeks after virus injection. To trace axon regeneration by fluorescent microscopy of the optic nerve, fluorescently labeled cholera toxin β-subunit (CTB) was intraocularly injected into mice two weeks after optic nerve crush injury and perfusion was performed two days after CTB injection. Axon regeneration analysis was subsequently conducted.

Figure 23A:
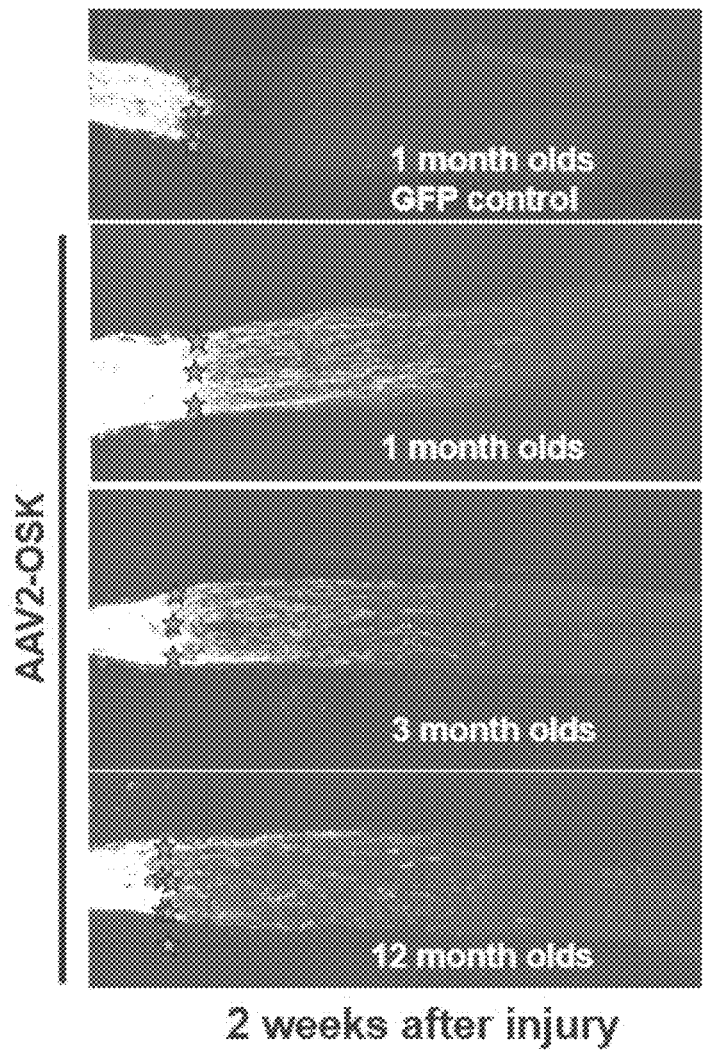
FIGS. 23A-23C include data showing that administration of AAV2 virus encoding OCT4, SOX2, and KLF4 improved axon regeneration and RGC survival in adult and aged mice two weeks after optic nerve crush.
Figure 23B:
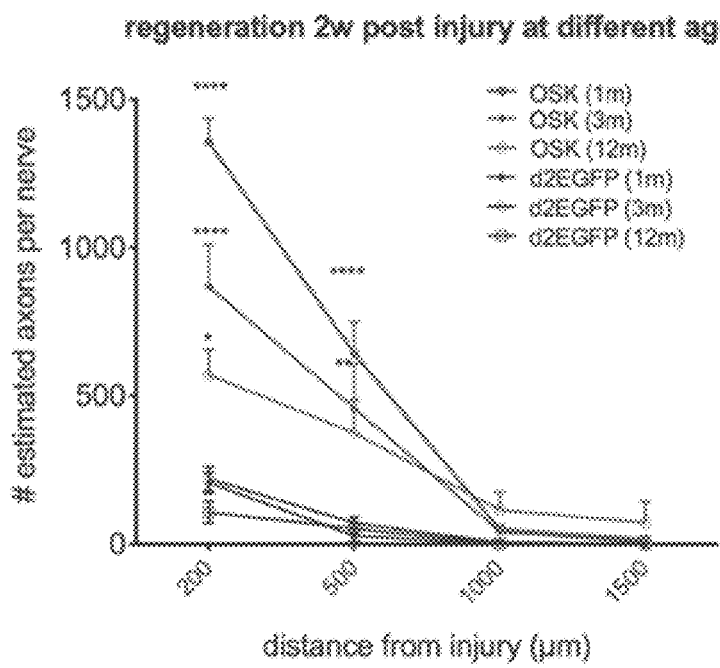
Figure 23C:
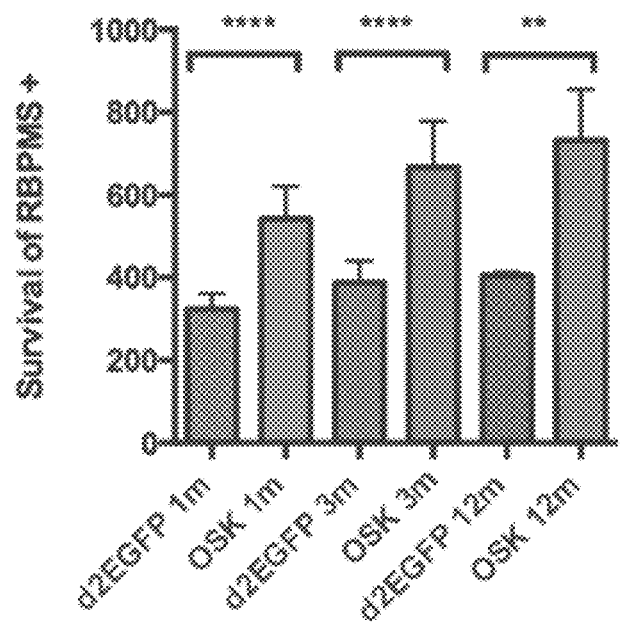

As shown in FIGS. 23A-23B, administration of AAV2 virus encoding OSK increased the number of estimated axons per nerve in 1 month old (young), 3 month old (adult), and 12 month old (aged) mice relative to administration of control virus encoding d2EGFP. Furthermore, TRE-OSK virus also increased the survival of RGCs after optic nerve injury in adult (3 month old) and aged (12 month old) mice compared to control GFP (FIG. 23C). Therefore, OSK expression surprisingly promoted axon regeneration and RGC survival after nerve crush injury in young, adult, and aged mice.

Figure 24A:
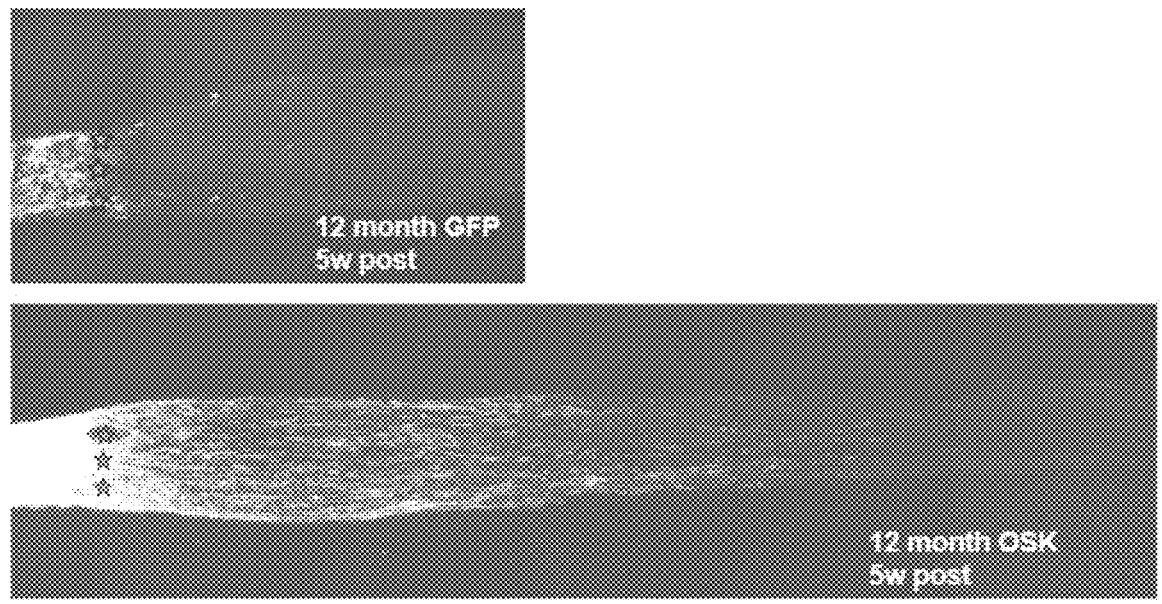
FIGS. 24A-24B include data showing that increasing the time of reprogramming from two weeks to five weeks improved regeneration in aged mice.
Figure 24B:
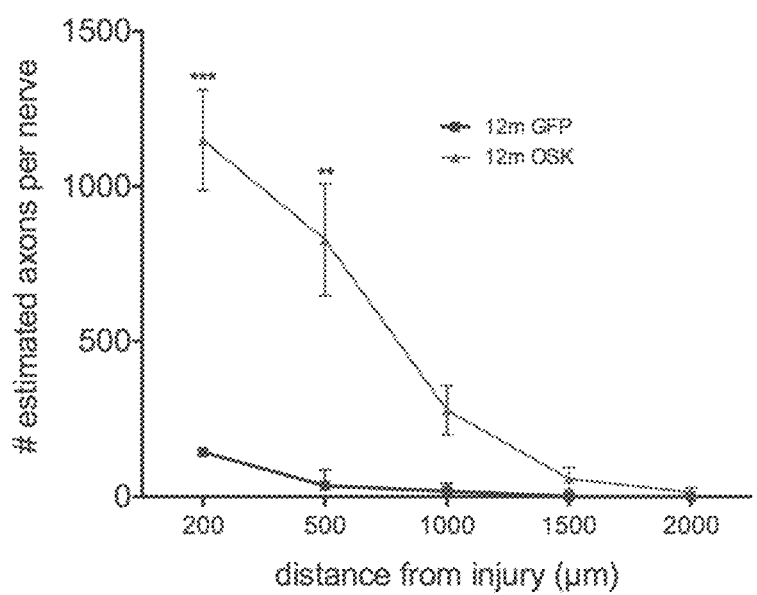

Next, the impact of the length of time of OSK expression on axon regeneration in aged mice was determined. Mice were administered tTA virus and either TRE-OSK virus or TRE-GFP virus 2 weeks prior to optic nerve crush. Then, fluorescently labeled cholera toxin β-subunit (CTB) was intraocularly injected into mice that were five weeks instead of two weeks after optic nerve crush injury. As shown in FIGS. 24A-24B, increasing the length of time of post-injury OSK expression to five weeks increased the number of estimated axons per nerve in the 12 month old mice compared to two weeks post-injury of OSK expression in FIG. 23B. In contrast, increasing the length of time of post injury GFP expression had no effect on axon regeneration (compare results with GFP in FIGS. 24A-24B with those shown in FIGS. 23A-23B). Therefore, the data suggests that a longer time of OSK expression may be beneficial in promoting axon regeneration and RGC survival after nerve crush injury in aged mice.

Figure 25A:
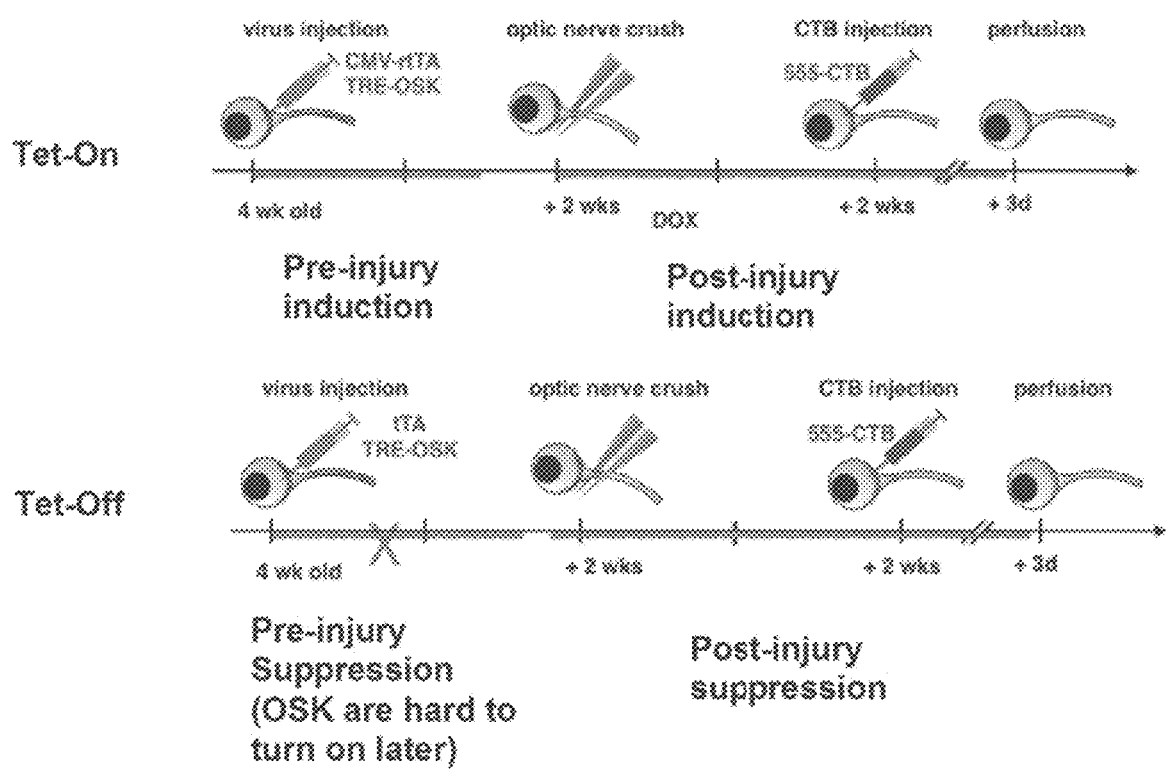
FIGS. 25A-25C include data showing that induction of OSK expression using Tet-On and Tet-Off systems even after optic nerve crush injury improved regeneration and RGC cell survival in mice.

Example 10. Induction of OSK Expression Following Optic Nerve Crush Injury Increased Axon Regeneration and RGC Survival in Mice It was also determined whether induction of OSK expression after optic nerve crush injury would promote axon regeneration and RGC survival. Both the Tet-On and Tet-Off systems depicted in the panel of FIG. 22 were used. In the Tet-On system, AAV virus with the TRE-OSK-SV40 vector and AAV virus encoding rtTA under the CMV constitutive promoter were produced through routine methods and injected into the retina of mice. As depicted in FIG. 25A, in the Tet-On system (top panel), OSK expression was induced by giving mice doxycycline either prior to optic nerve crush injury or after optic nerve crush injury. A cohort of mice were not treated with doxycycline as a control (no induction). In the Tet-Off system, AAV virus with the TRE-OSK-SV40 vector and AAV virus encoding tTA under the CAG constitutive promoter were produced through routine methods and injected into the retina of mice. As depicted in FIG. 25A, in the Tet-Off system (bottom panel), OSK expression was suppressed after optic nerve crush injury. Fluorescently labeled cholera toxin β-subunit (CTB) injection was used to visualize axons.

Figure 25B:
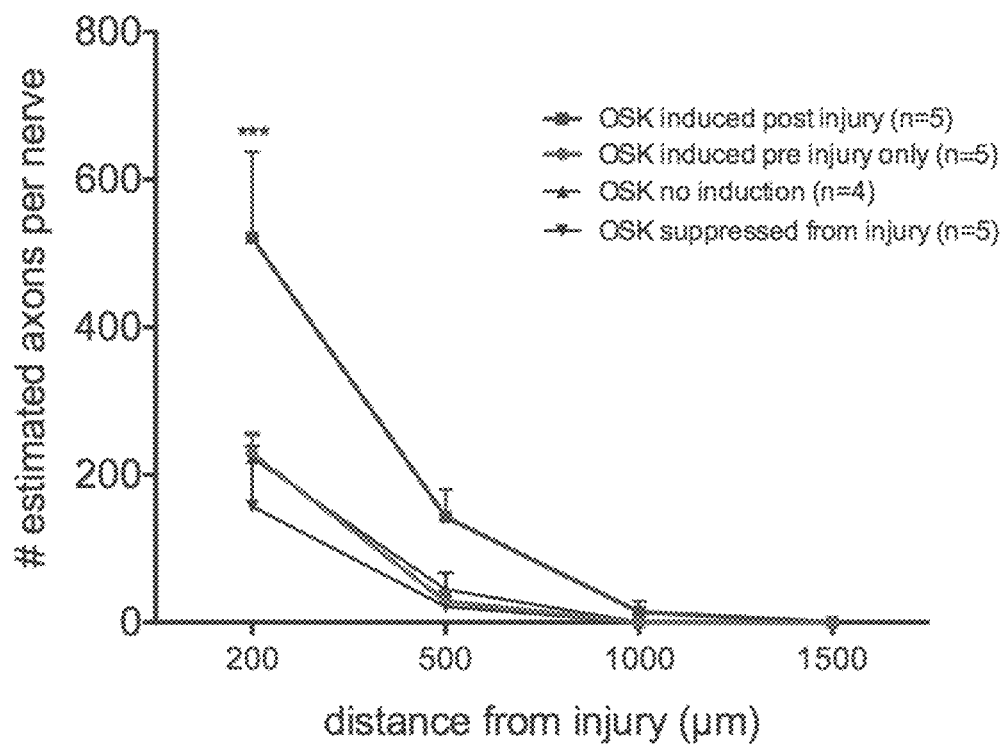
Figure 25C:
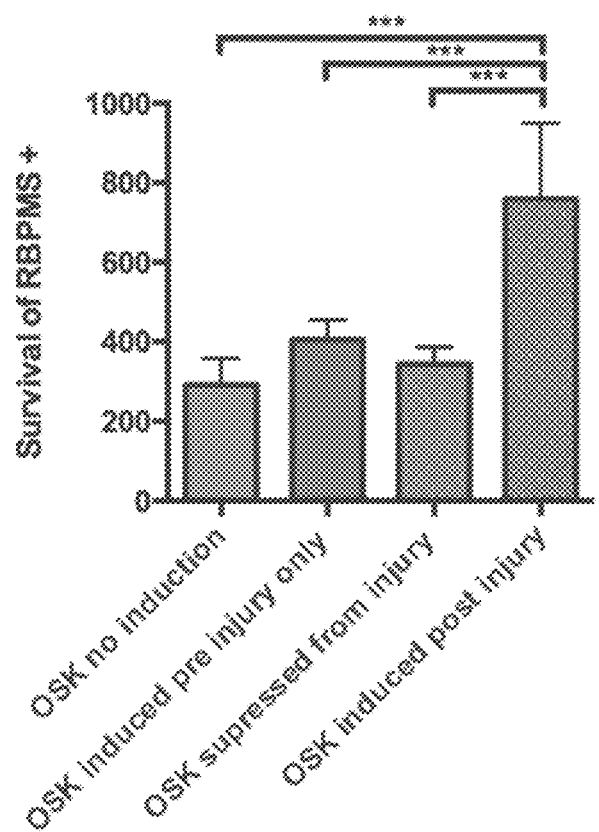

As shown in FIG. 25B, induction of OSK expression post injury through Tet-On system significantly increased the number of estimated axons per nerve compared to no induction of OSK or induction of OSK prior to injury (pre-injury) only through either Tet-On or Tet-Off system. Furthermore, induction of OSK expression post injury significantly increased the survival of RBPMS+ cells compared to no induction of OSK expression or compared to OSK induction pre-injury only through either Tet-On or Tet-Off system (FIG. 25C). Therefore, the Tet-On system depicted in FIG. 25A, top panel, allowed for temporal control of OSK expression and induction of OSK after optic nerve crush injury promoted axon regeneration and RGC survival. Without being bound by a particular theory, induction of OCT4, KLF4, and SOX2 expression using a Tet-Off system following an injury may promote regeneration when recovery from an injury does not require immediate expression of OCT4, KLF4, and/or SOX2.

Figure 26A:
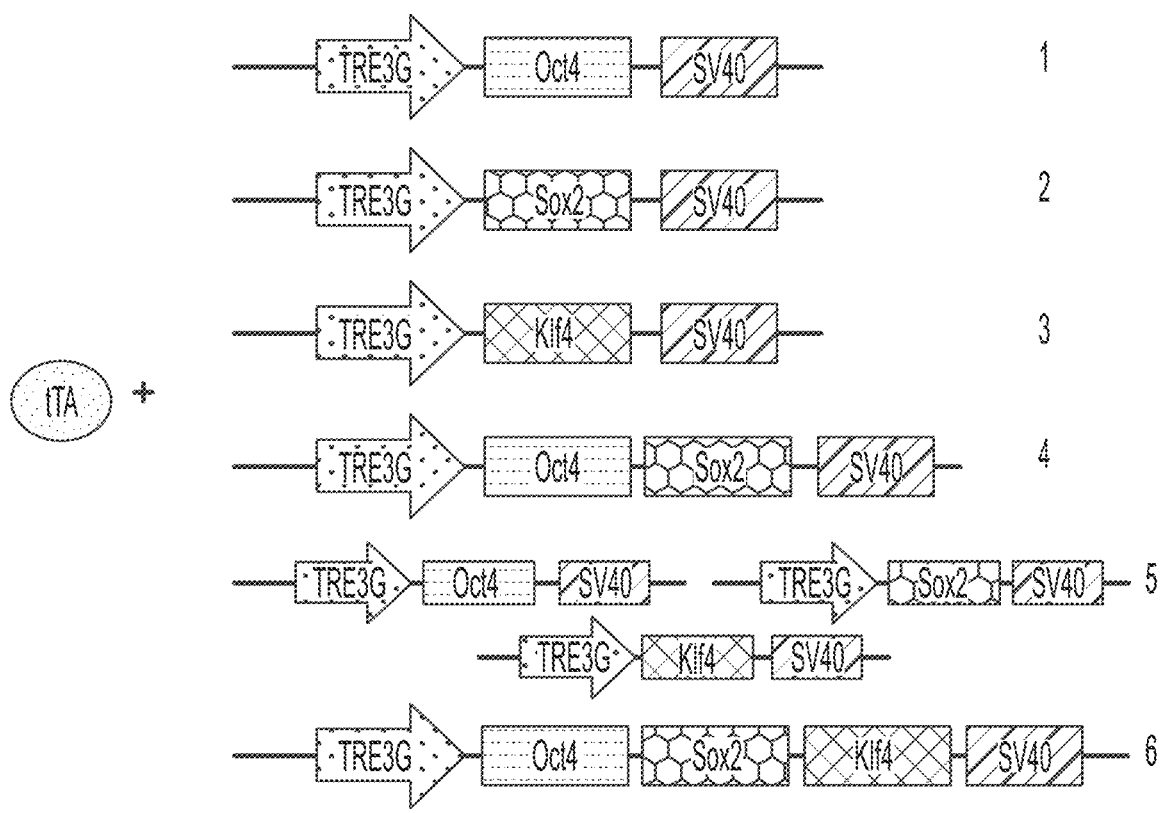
FIGS. 26A-26E include data showing that expression of OSK from a single transcript improved axon regeneration and retina ganglion cell (RGC) survival two weeks after optic nerve crush injury compared to expression of OCT4, SOX2, and KLF4 from separate transcripts.

Example 11. Superior Effect of OCT4, SOX2, and KLF4 (OSK) Expression from a Single Transcript Compared to Individual Transcripts in Promoting Axon Regeneration This example explored the effect of expressing OCT4, SOX2, and KLF4 under one promoter as compared to expression of OCT4, SOX2, KLF4 alone or in combination under separate promoters. AAV virus encoding tTA under the CAG constitutive promoter and AAV virus or viruses encoding (1) OCT4 under the TRE promoter, (2) SOX2 under a TRE promoter, (3) KLF4 under a TRE promoter, (4) OCT4 and SOX2 under one TRE promoter, (5) OCT4, SOX2, and KLF4 each under separate promoters, or (6) OCT4, SOX2, and KLF4 under the same promoter were injected into the retina of mice. A schematic showing the various vectors used in this study is shown in FIG. 26A. Optic nerve crush injury was induced 2 weeks after virus administration. Fluorescently labeled cholera toxin (3-subunit (CTB) injection 2 weeks after optic nerve crush was used to image axons.

Figure 26B:
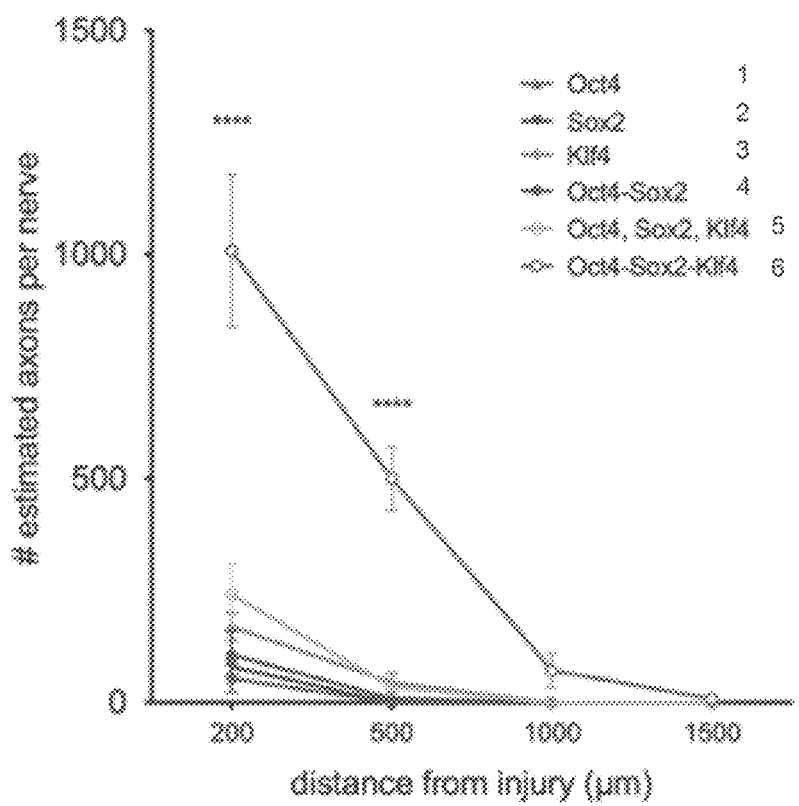

As shown in FIG. 26B, when all three transcription factors (OSK) were expressed under one promoter, the number of estimated axons per nerve was at least four times higher than when OCT4, SOX2, and KLF4 were each expressed under a separate promoter (e.g., compare OCT4, SOX2, KLF4 (5), and OCT4-SOX2-KLF4 (6) results). Similarly, the number of estimated axons per nerve was also at least four times higher when OSK was expressed on a single transcript than when OCT4, SOX2, and KLF4 expression alone (FIG. 26B) (e.g., compare OCT4 (1), SOX2 (2), and KLF4 (3) with OCT4-SOX2-KLF4 (6) results). The increase in axon regeneration was likely attributed to expression of all three transcription factors (OSK) under one promoter, as expression of OCT4 and SOX2 under one promoter did not significantly increase the number of estimated axons per nerve relative to expression of each transcription factor alone (FIG. 26B) (e.g., compare OCT4-SOX2 (4) with OCT4-SOX2-KLF4 (6) results).

Figure 26C:
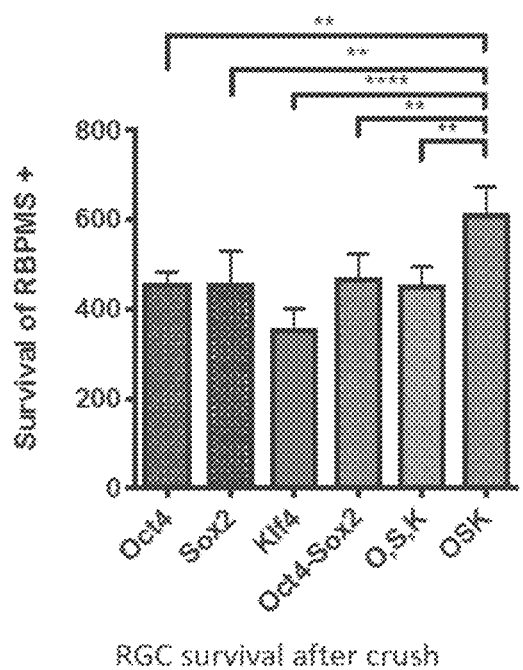

Analysis of retina ganglion cell (RGC) survival was also conducted by quantifying RBPMS+ cells. As shown in FIG. 26C, expression of OSK from one promoter increased the survival of RBPMS+ cells relative to expression of OCT4, SOX2, or KLF4 alone and relative to expression of OCT4 and SOX2 under one promoter. Expression of OSK from one promoter also increased the survival of RBPMS+ cells relative to expression of OCT4, SOX2, or KLF4 from separate vectors in separate viruses.

Figure 26D:
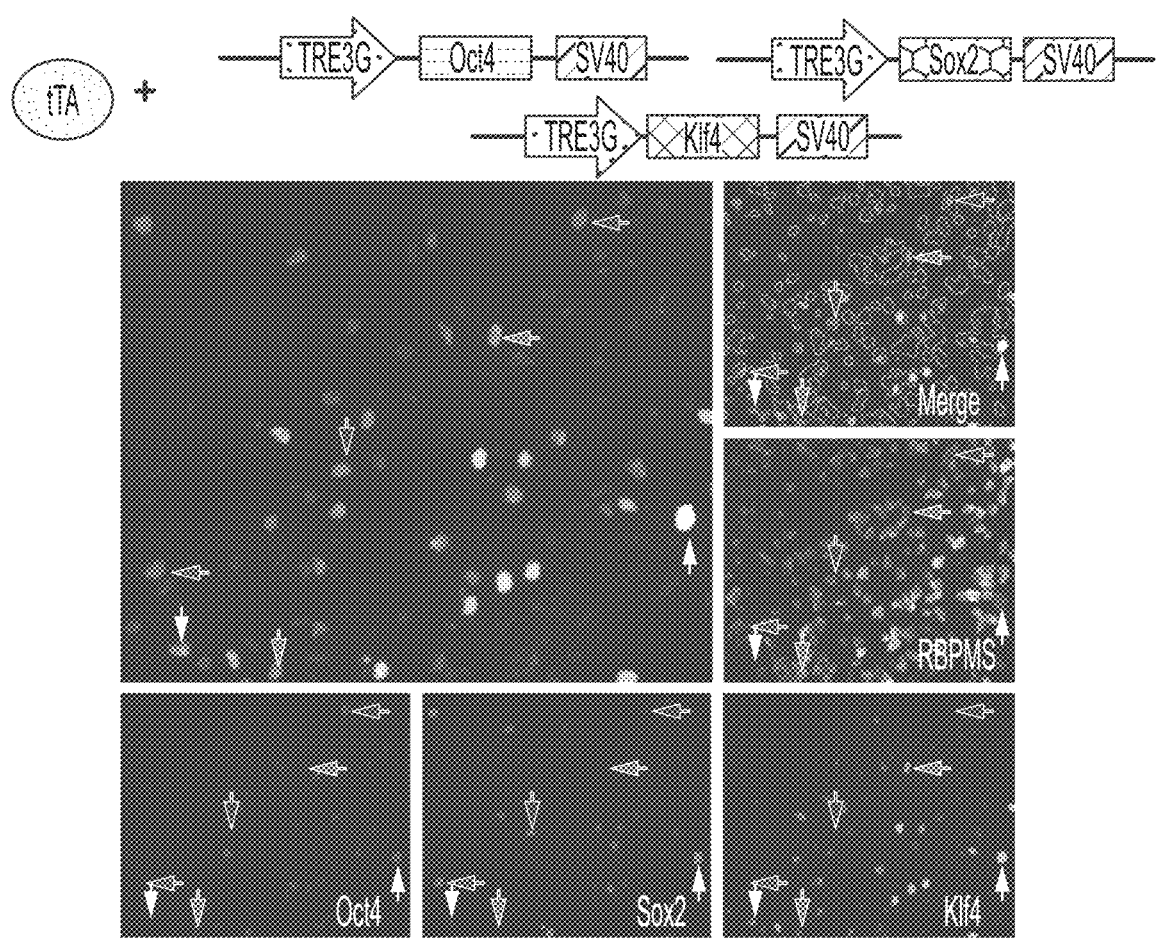
Figure 26E:
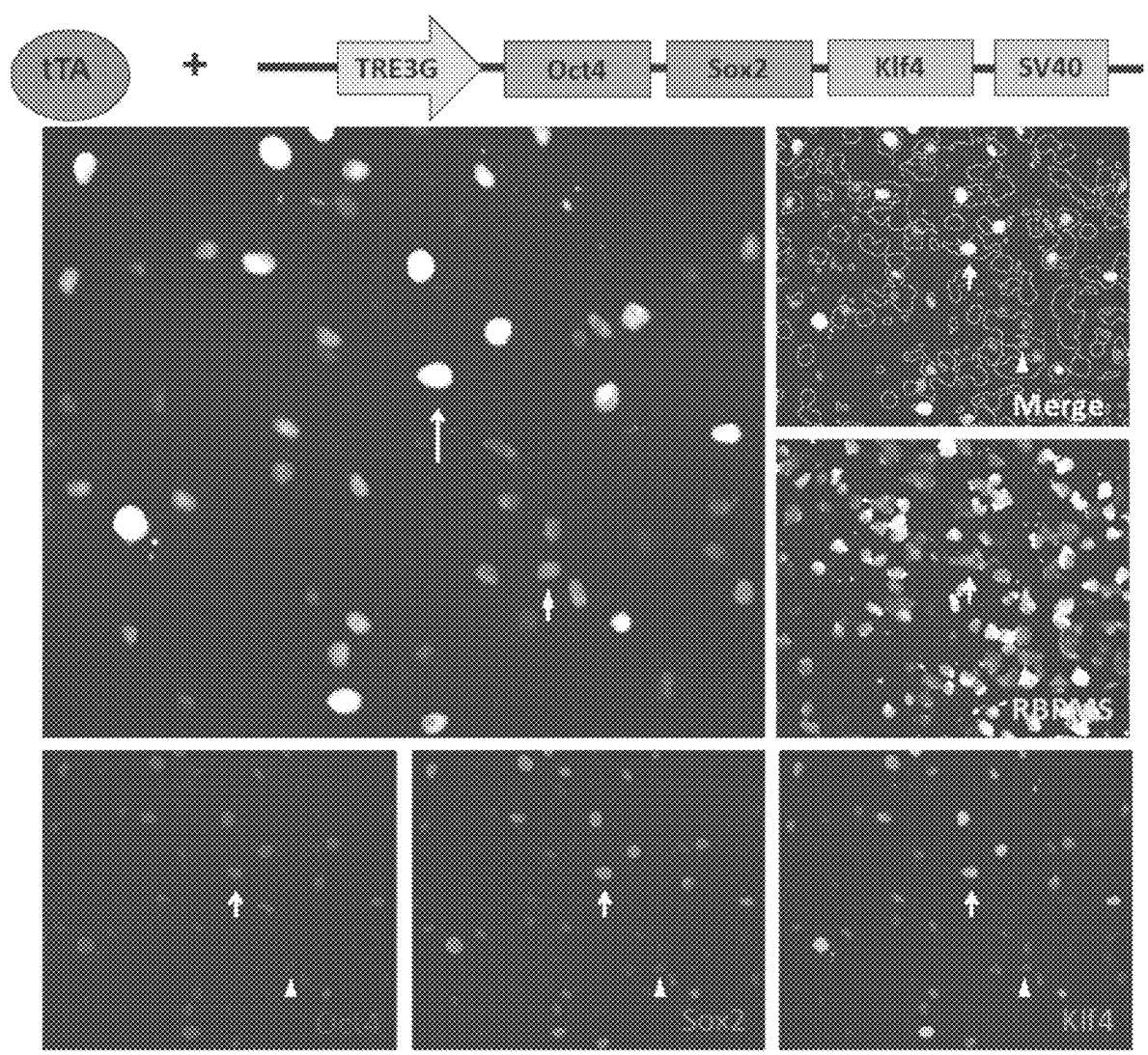

As shown by the fluorescence staining depicted in FIG. 26D, expression of OCT4, SOX2, and KLF4 in separate vectors in separate viruses resulted in a heterogeneous population of RGCs. Some cells only expressed OCT4, SOX2, or KLF4. Some cells expressed a combination of only two out of the three transcription factors and only a few three-factor positive RGCs were detected (white color cell in the bottom right corner of the top left panel in FIG. 26D). In contrast, as shown in FIG. 26E, expression of OCT4, SOX2, and KLF4 from a single vector resulted in a more homogenous population. All of the cells expressed all three of the OSK transcription factors (white color cells in the top left panel). Even in cells that were not pure white, expression of all three transcription factors were detected as shown in FIG. 26E, suggesting that the results were due to differences in staining intensity for the three transcription factors.

Therefore, this example shows that expression of OCT4, SOX2, and KLF4 using one promoter had greater therapeutic effect (e.g., increased axon regeneration and a greater survival of retina ganglion cells) compared to expression of each transcription factor alone, expression of all three transcription factors under separate promoters, or expression of only two of the transcription factors (e.g., OCT4 and SOX2) under one promoter.

Example 12. Knockdown of Tet1 or Tet2 Abrogated OSK-Induced Axon Regeneration Following Optic Nerve Crush Injury This example determined the effect of knocking down DNA demethylases Tet1 and Tet2 on OSK-induced axon regeneration. A Tet-Off system was used. AAV2 of CAG-tTA+TRE–OSK–SV40 were injected into mice through intravitreal injection two weeks before crush together with AAV2 of U6-shRNA. Mice were one month old with four mice in each group.

Addgene AAV plasmids encoding shRNA sequences were used. Control shRNA comprised the sequence 5'-GTTCA-GATGTGCGGCGAGT-3' (plasmid #85741 from Addgene). mTET1 (Tet1 shRNA) comprised the sequence 5'-GCT-CATGGAGACTAGGTTTGG-3' (plasmid #85742 from Addgene). mTet2 (Tet2 shRNA) comprised the sequence 5'-GGATGTAAGTTTGCCAGAAGC-3' (Plasmid #85743 from Addgene).

Figure 27:
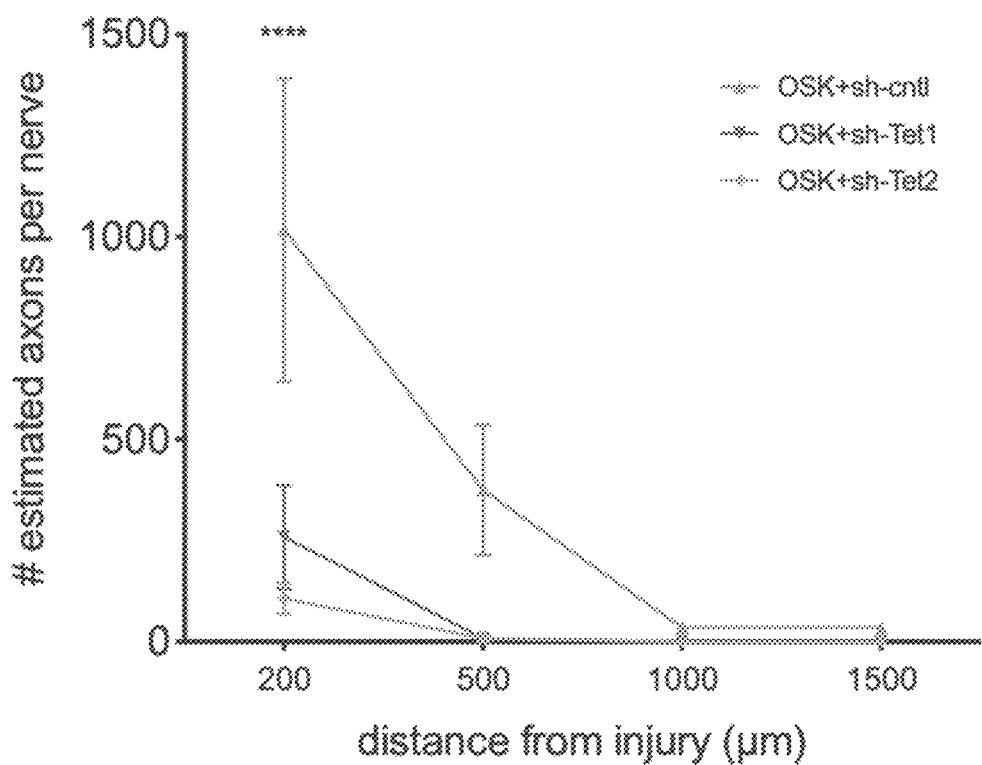
FIG. 27 is a chart showing that Tet1 and Tet2 DNA demethylases play a role in OSK-induced regeneration. The number of estimated axons per nerve after optic nerve crush was quantified in mice receiving (1) OSK virus and a short hairpin control, (2) OSK virus and a short hairpin against Tet1, or (3) OSK virus and a short hairpin against Tet2.

As shown in FIG. 27, knockdown of either Tet1 or Tet2 significantly reduced the number of estimated axons per nerve in animals also treated with OSK virus and subjected to optic nerve crush injury compared to the control hairpin (sh-cntl).

These results suggest that Tet DNA methylases may be involved in OSK-induced axon regeneration and overexpression of Tet (e.g., Tet1 or Tet2) alone or in combination with OSK expression may promote regeneration.

As a non-limiting example, mTet3 comprising the sequence 5'-GCTCCAACGAGAAGCTATTTG-3' (Plasmid #85740 from Addgene) may be used to knockdown Tet3.

Example 13. Expression of OSK Reversed Age-Related Decline in Visual Acuity and Reversed Age-Related Decline in Retina Ganglion Cell (RGC) Function To determine whether age-related visual acuity loss may be reversed with OSK expression, an optomotor response (OMR) assay was conducted on adult mice (3 month old mice) and aged mice (12 month old and 18 month old mice). OMR is a reflexive head movement used to assess visual acuity. To induce OMR, individual mice are placed on a platform in the middle of an arena surrounded by computer monitors displaying stripes. The rotation of the striped pattern elicits mouse head tracking in the same direction by reflexive neck movements. Tracking is monitored by two independent masked observers. Visual acuity is quantified by increasing the spatial frequency of the stripes until an OMR cannot be elicited.

Mice were retinally injected with AAV virus encoding tTA and AAV virus encoding TRE–OSK in the absence of doxycycline (OSK induction condition). In this Tet-Off system, OSK is expressed from a single promoter in the absence of doxycycline. As controls, age-matched mice were administered virus encoding virus encoding rtTA and virus TRE–OSK in the absence of doxycycline (uninduced control, ctl). In the control Tet-On system, OSK expression requires doxycycline treatment. Adult mice (3 month old (3 m)) were also used as a control. An OMR study was conducted to measure the spatial frequency threshold one month after virus injection.

Figure 28:
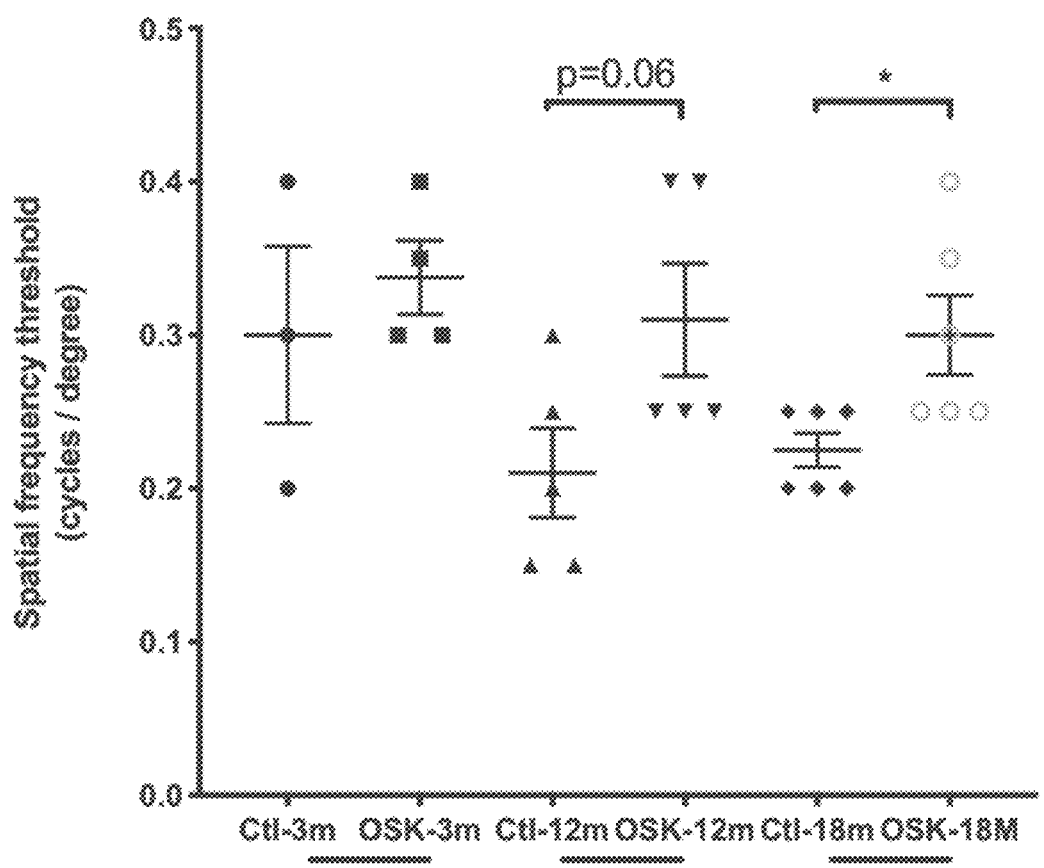
FIG. 28 includes data showing that expression of OSK using a Tet-Off system reversed age-related visual acuity loss in aged mice one month post injection of AAV virus encoding TRE-OSK and AAV virus encoding tTA.

As shown in FIG. 28, in the absence of OSK expression (control (ctl) condition) the aged mice (12 month old and 18 month old mice) had vision loss compared to the adult mice (3 month old mice). The decrease in the spatial frequency threshold for the aged mice relative to the 3 month old mice indicated vision loss in the absence of OSK expression. When OSK was expressed, however, the spatial frequency threshold on average increased for the 12 month old and 18 month old mice relative to no OSK expression. Furthermore, the spatial frequency thresholds for the 12 month old and 18 month old mice with OSK expression were similar to that of the 3 month old control mice in the presence and absence of OSK expression. These results demonstrate that induction of OSK expression reversed age-related vision loss in mice.

To determine whether age-related decline in retina ganglion cell (RGC) function could also be reversed by OSK treatment, electrical waves from RGCs were measured using pattern electroretinograms (pattern ERGs or pERGs). In pERG assays, a checkerboard light and dark pattern stimulus is projected via electrodes placed on the cornea of mice of various ages (3 month old, 12 month old, or 18 month old mice). A contrast reversing pattern is displayed with no overall change in luminance. Electrical waves generated from the RGCs are then measured.

Mice were retinally injected with AAV virus encoding tTA and AAV virus encoding TRE–OSK in the absence of doxycycline (OSK induction condition). In this Tet-Off system, OSK is expressed from a single promoter in the absence of doxycycline. As controls, age-matched mice were administered virus encoding virus encoding rtTA and virus TRE–OSK in the absence of doxycycline (uninduced control, ctl). In the control Tet-On system, OSK expression requires doxycycline treatment. Adult mice (3 month old (3 m)) were also used as a control. A pERG study was conducted to measure the amplitude of the electrical waves in the RGCs following the pattern stimulus one month after virus injection.

Figure 29:
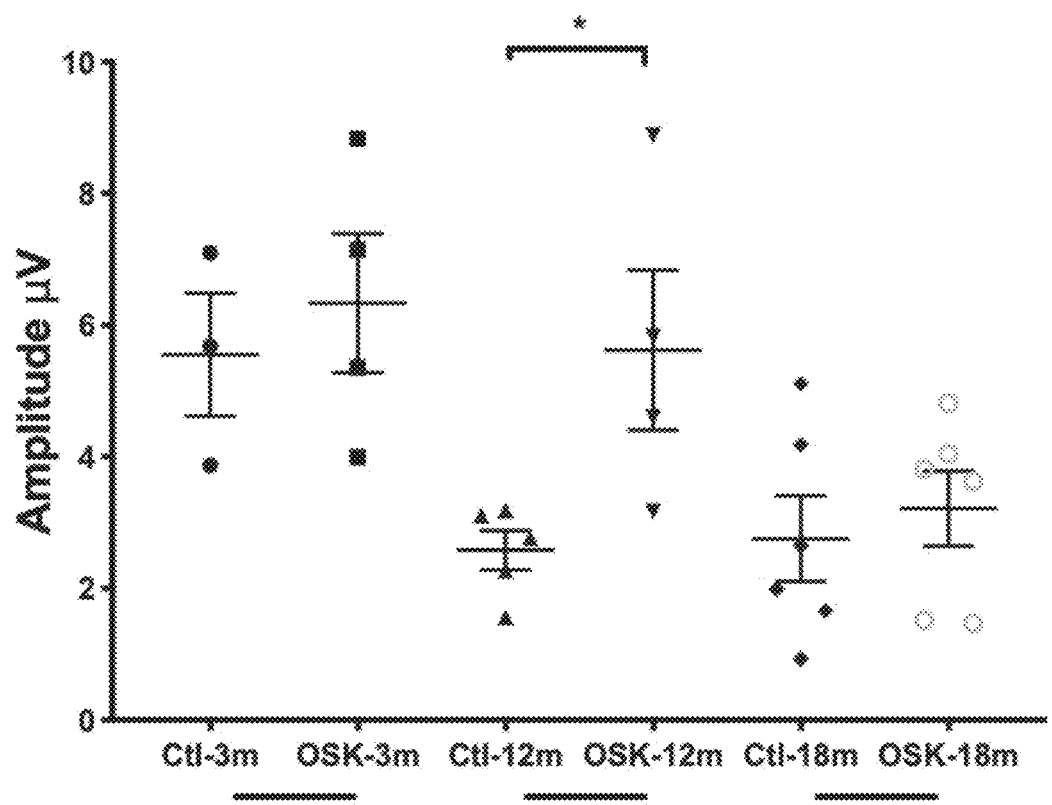
FIG. 29 includes data showing that expression of OSK reversed age-related decline in retina ganglion cell (RGC) function in aged mice.

As shown in FIG. 29, electrical waves generated from RGCs declined in aged mice (3 month old mice compared to 12 month old and 18 month old mice) in the absence of OSK expression (ctl condition). In contrast, administration of AAV virus encoding tTA and AAV virus encoding TRE–OSK in the absence of doxycycline (OSK induction condition) restored RGC electrical waves in 12 month old mice. For 18 month old mice, however, RGC function was likely not restored because corneal opacity blocked the pattern stimulus. These results suggest that expression of OSK improved RGC function in aged (12 month old) mice.

Therefore, this example demonstrates that induction of OSK expression can improve vision acuity and RGC function that is caused by aging.

Figure 30A:
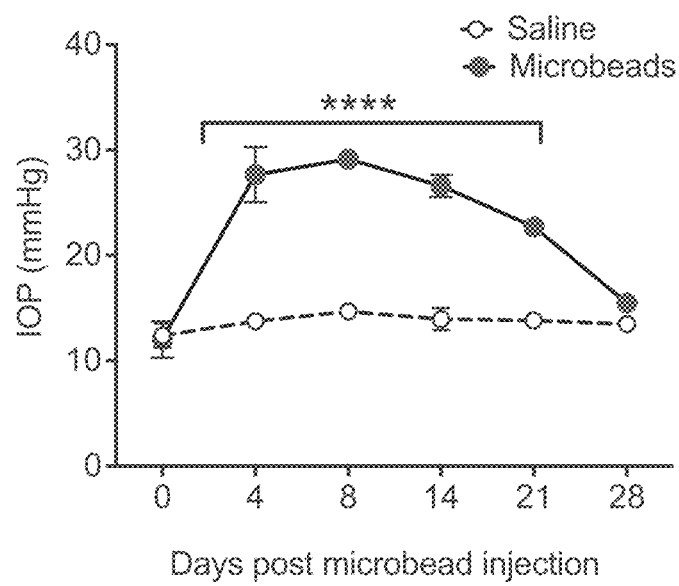
FIGS. 30A-30E include data showing that expression of OSK improved glaucoma-induced declines in visual acuity and RGC function in one month-old mice.
Figure 30B:
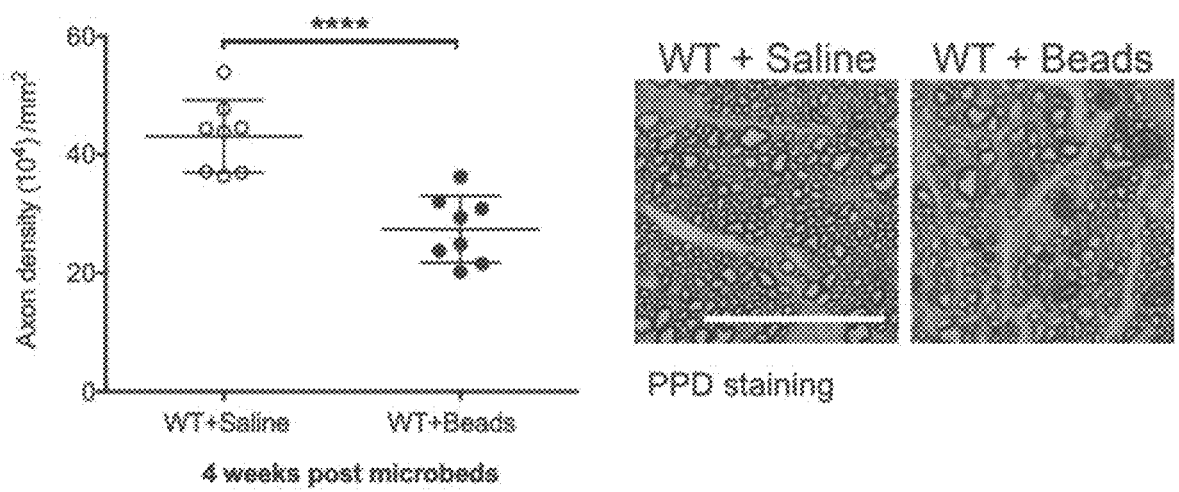
Figure 30C:
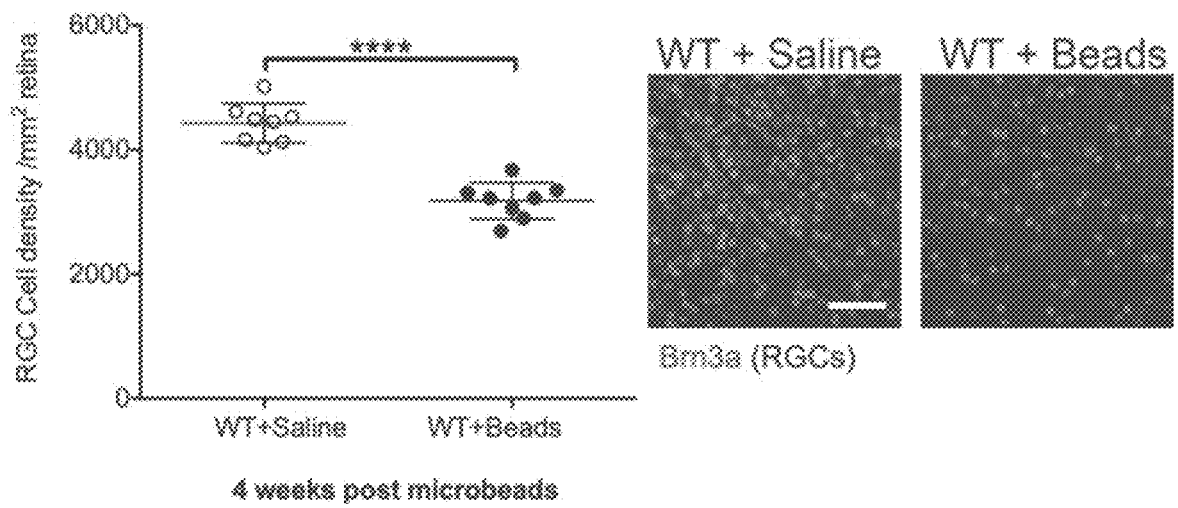

Example 14. Expression of OSK Reversed Glaucoma-Induced Decline in Visual Acuity and Reversed Glaucoma-Induced Decline in Retina Ganglion Cell (RGC) Function To determine whether OSK expression could be used to reverse glaucoma-induced declines in visual acuity and RGC function, a mouse model of glaucoma was used. Chronic elevation of intraocular pressure (IOP) was induced unilaterally in adult C57BL/6J mice by injecting polystyrene microbeads to the anterior chamber. IOP was measured in the first four weeks. As shown in FIG. 30A, microbead injection increased IOP 4-21 days after microbead injection. Axon density was quantified using p-phenylenediamine (PPD) staining (FIG. 30B). FIG. 30C includes a chart quantifying RGC cell density (left panel) using Brn3a staining (shown, for example, on the right). FIGS. 30B-30C show that 4 weeks after microbeads injection into the anterior chamber of the eye, there was significant loss of axon density and RGC density in wild-type (WT) mice that were not treated with AAV virus encoding TRE–OSK.

In these experiments, glaucoma was induced with microbead injection and then three weeks later, OMR and pERG assays were conducted (pre AAV injection measurements in FIGS. 30D-30E). Then, mice were divided into two treatment groups. One group of mice were retinally injected with AAV virus encoding rtTA and AAV virus encoding TRE–OSK in the absence of tetracycline (OSK AAV OFF) or with AAV virus encoding tTA and AAV virus encoding TRE–OSK (OSK AAV ON). Four weeks post AAV virus injection, OMR and pERG assays were conducted again (4w post AAV) measurements in FIGS. 30D-30E). As a control, experiments were also conducted with injection of saline instead of microbeads (no glaucoma control).

Figure 30D:
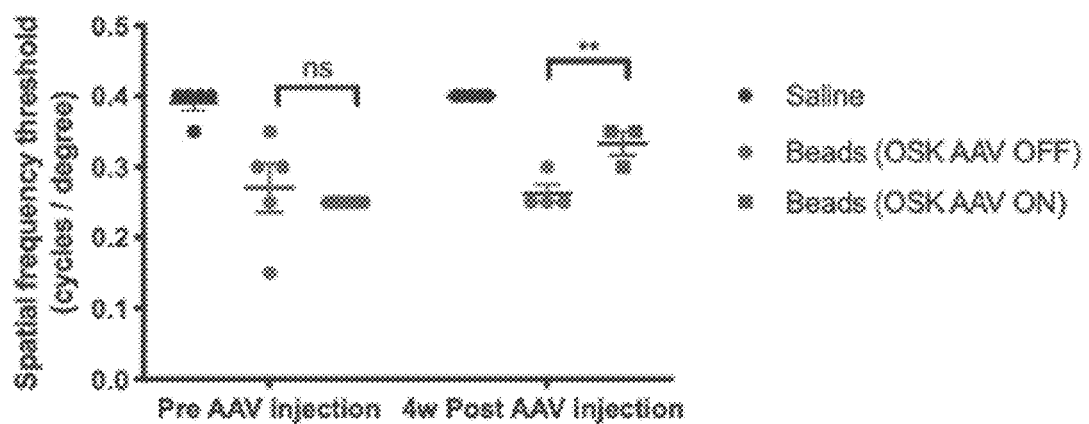

As shown in FIG. 30D, induction of OSK expression (OSK AAV ON) increased the spatial frequency threshold compared to no induction of OSK expression (OSK AAV OFF) for mice with glaucoma (mice injected with microbeads). These results suggest that induction of OSK expression can improve glaucoma-related vision loss.

Figure 30E:
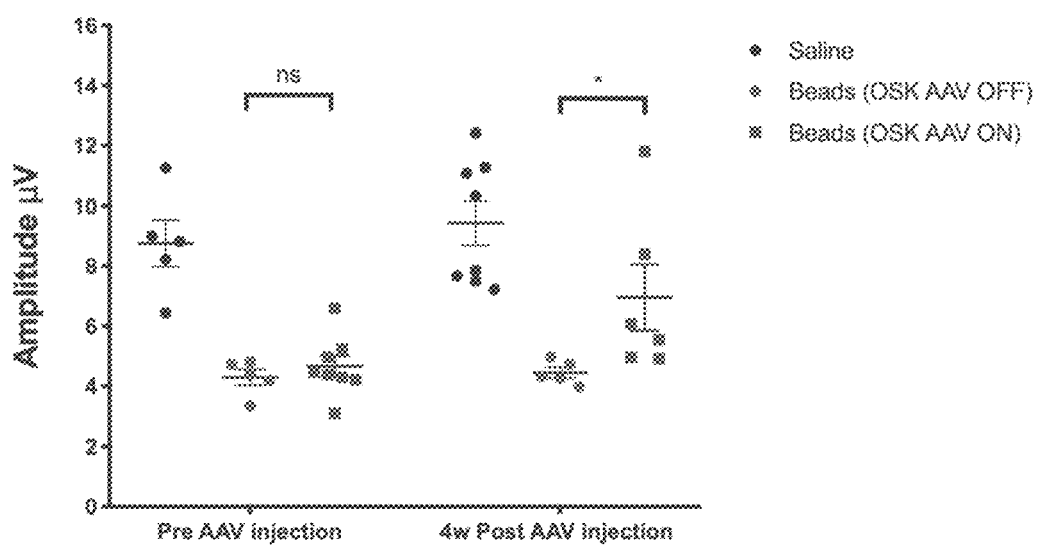

As shown in FIG. 30E, induction of OSK expression restored the electrical wave amplitude in mice with microbead-induced glaucoma. These results suggest that induction of OSK expression can also reverse glaucoma-related decline in RGC function.

Therefore, induction of OSK expression can improve the symptoms induced by glaucoma.

Example 15. Expression of Human OSK Promoted Survival of Human Neurons and Axon Regrowth Following Vincristine-Induced Neuronal Damage To determine whether expression of human OCT4, human KLF4, and human SOX2 (human OSK) could protect human neuronal cells and regenerate axons in vitro, a neurite regeneration assay was used as described below. SH-SY5Y cells, which are human neuroblastoma cells, were differentiated into neurons and were transduced with a AAV.DJ vector encoding human OCT4, human KLF4, and human SOX2 under a Tet-inducible promoter (using a Tet-Off system). In the OSK Off condition, OSK expression was not induced in cells. In the OSK On condition, OSK expression was induced in cells. Five days after transduction, vincristine (VCS) was used to induce neurite degeneration. Cells were treated with VCS for 24 hours or 48 hours. A schematic of a treatment timeline (with 24 hour VCS treatment) is provided in the left portion of FIG. 31A. VCS is a chemotherapy drug that disrupts microtubules. It is often used in vitro to determine whether treatments maintain and/or promote cellular function (e.g., neuronal function) after damage. As described herein, VCS was used determine the effect of OSK treatment on neuronal survival and axon regrowth. After VCS treatment, cells were grown in differentiation medium and neurite outgrowth was assayed.

Figure 31A:
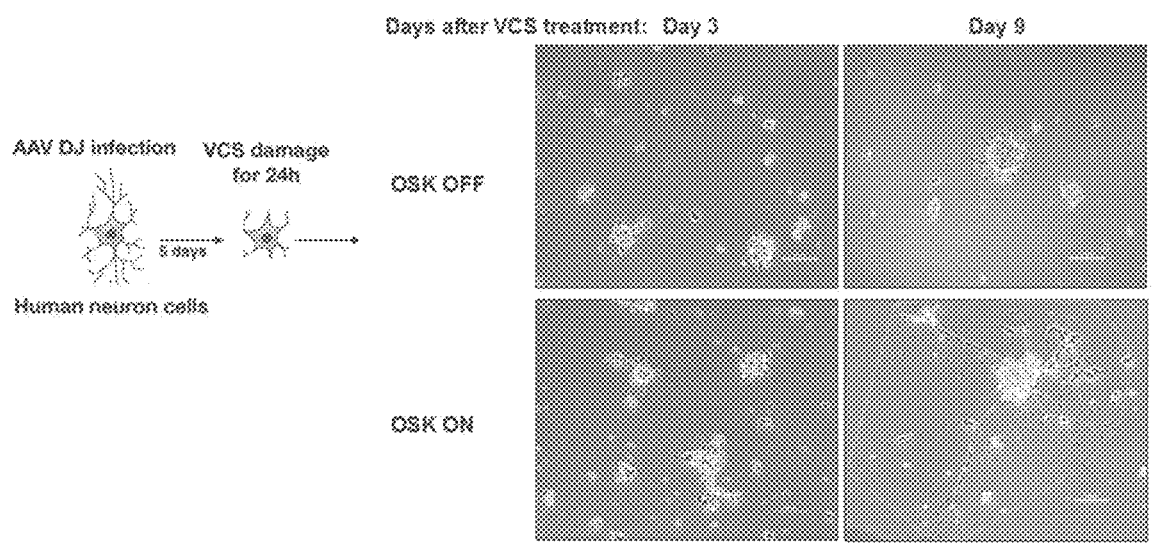
FIGS. 31A-31C include data showing that expression of OSK promoted neuronal survival and axon regeneration of human SH-SY5Y neuronal cells following vincristine (VCS)-induced damage.
Figure 31B:
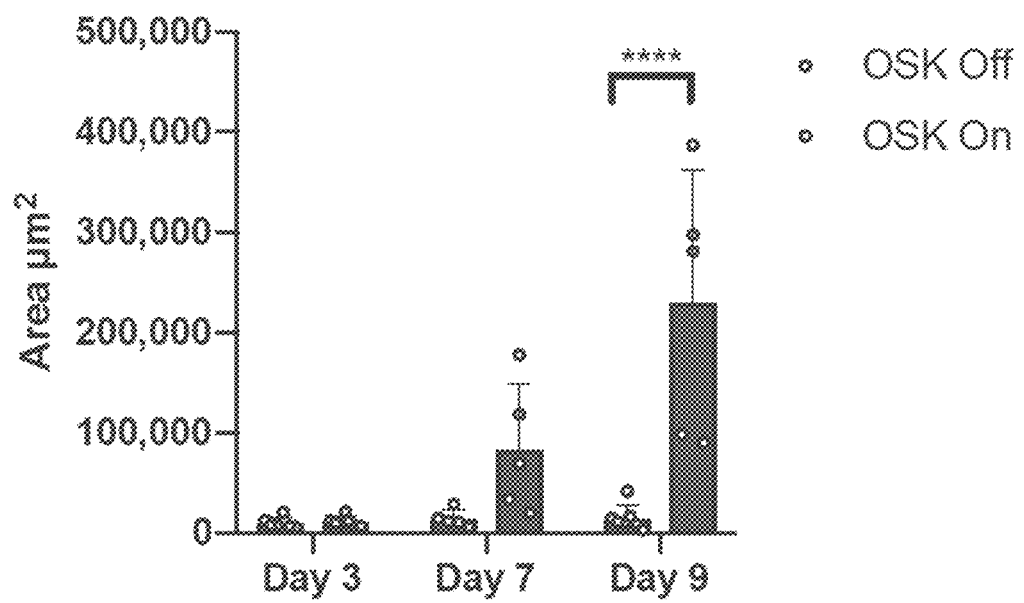
Figure 31C:
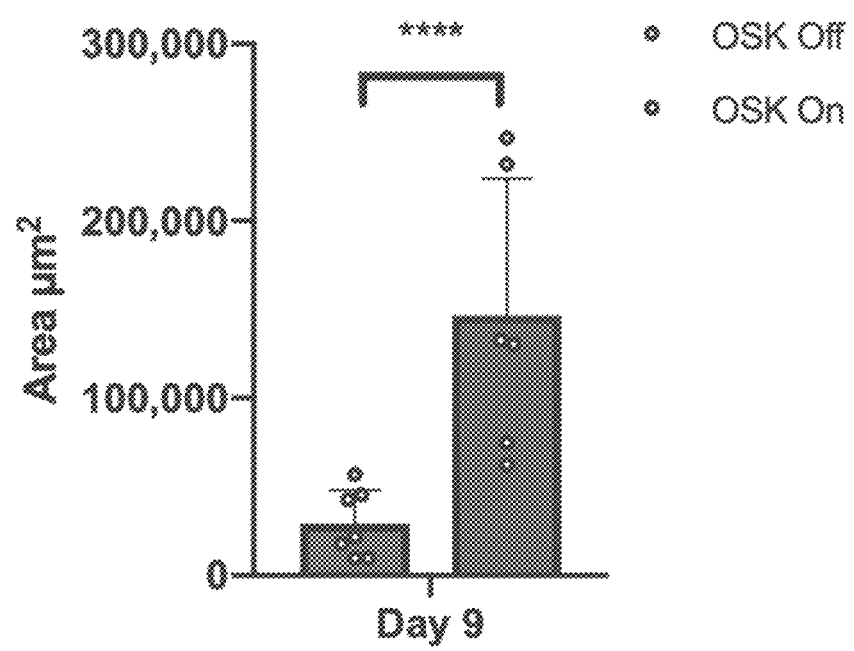

In FIG. 31A, cells were assayed for neuronal outgrowth nine days after cells were treated with VCS for 24 hours. Cells in which OSK expression was induced (OSK On condition) showed increased neuronal survival and axon outgrowth relative to cells in which OSK expression was not induced (OSK Off condition) (FIG. 31A). Quantification of neuronal cell area similarly showed that OSK expression increased the cell area of neurons by at least 8 times compared to no OSK expression (FIG. 31B). Similar results were also observed with 48 hours of VCS treatment (FIG. 31C).

These results show that expression of human OSK protected human neuron cells against VCS-induced neuron degeneration.

Methods

Cell Culture and Differentiation Protocol

SH-SY5Y neuroblastoma cells were obtained from the American Tissue Culture Collection (ATCC, CRL-2266) and maintained according to ATCC recommendations. The cells were cultured in a 1:1 mixture of Eagle's Minimum Essential Medium (EMEM, ATCC, 30-2003) and F12 medium (ThermoFisher Scientific, 11765054), supplemented with 10% fetal bovine serum (FBS, Sigma, F0926) and 1×penicillin/streptomycin (ThermoFisher Scientific, 15140122). Cells were cultured at 37° C. with 5% $CO_2$ and 3% $O_2$. Cells were passaged at ~80% confluency.

SH-SY5Y cells were differentiated into neurons as previously described (Encinas et al., J Neurochem. 2000 September; 75(3):991-1003; Shipley et al., J Vis Exp. 2016 Feb. 17; (108):53193), with some modifications. Briefly, 1 day after plating, cells started to be differentiated in EMEM/F12 medium (1:1) containing 2.5% FBS, 1× penicillin/streptomycin, and 10 µM all-trans retinoic acid (ATRA, Stemcell Technologies, 72264) (Differentiation Medium 1) for 3 days, followed by treating the cells in EMEM/F12 (1:1) containing 1% FBS, 1×penicillin/streptomycin, and 10 µM ATRA (Differentiation Medium 2) for 3 days. Cells were then split into 35 mm cell culture plates coated with poly-D-lysine (ThermoFisher Scientific, A3890401). One day after splitting, neurons were matured in serum-free neurobasal/B27 plus culture medium (ThermoFisher Scientific, A3653401) containing 1×Glutamax (ThermoFisher Scientific, 35050061), 1×penicillin/streptomycin, and 50 ng/ml BDNF (Alomone labs) (Differentiation Medium 3) for at least 5 days.

Neurite Regeneration Assay

The differentiated neurons from SH-SY5Y cells were transduced with AAV.DJ vectors at $10^6$ genome copy per cell. Five days after transduction, 100 nM vincristine (Sigma, V8879) was added to the cells for 24 hours or 48 hours to induce neurite degeneration. After vincristine treatment, neurons were washed in PBS twice and fresh differentiation medium was added back to the plates. Neurons were followed for neurite outgrowth for up to 2 weeks.

Figure 36A:
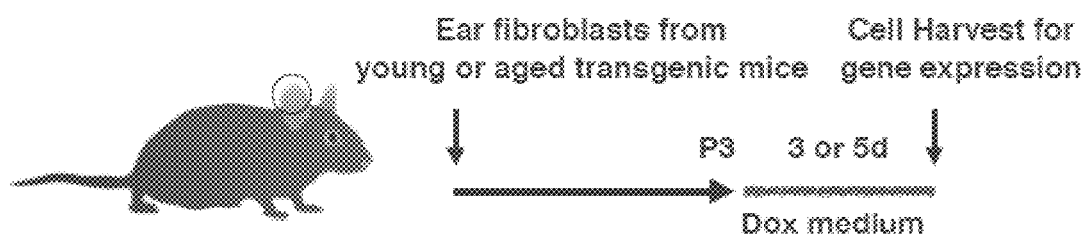

Example 16. Recovery from Injury and Restoration of Vision by Tet-Dependent Resetting of the Epigenetic Clock To determine whether mammalian cells might retain a faithful copy of epigenetic information from earlier in life, it was tested whether the three gene combination of OSK was sufficient to reset age. The three-gene OSK combination into fibroblasts from old mice and measured its effect on RNA levels of genes known to be altered with age, such as H2A, H2B, LaminB1, and Chaf1b. OSK treatment of fibroblasts from old mice restored youthful gene expression patterns, similar to what OSKM does, with no apparent loss of cellular identity or the induction of Nanog, an early embryonic transcription factor that can induce teratomas (FIG. 36A-36C).

Figure 32A:
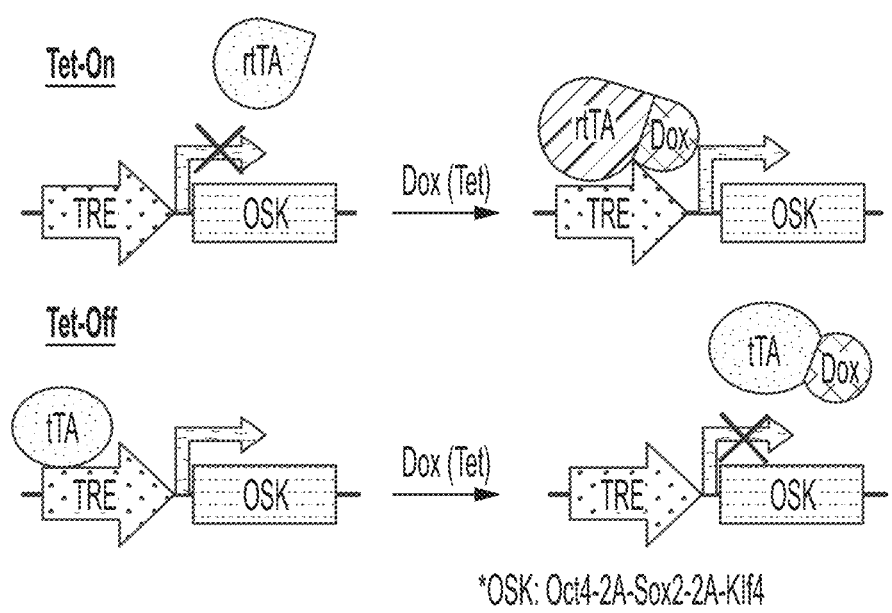
FIGS. 32A-32G show that partial reprogramming with AAV-delivered polycistronic OSK is non-toxic and induces CNS axon regeneration.
Figure 32B:
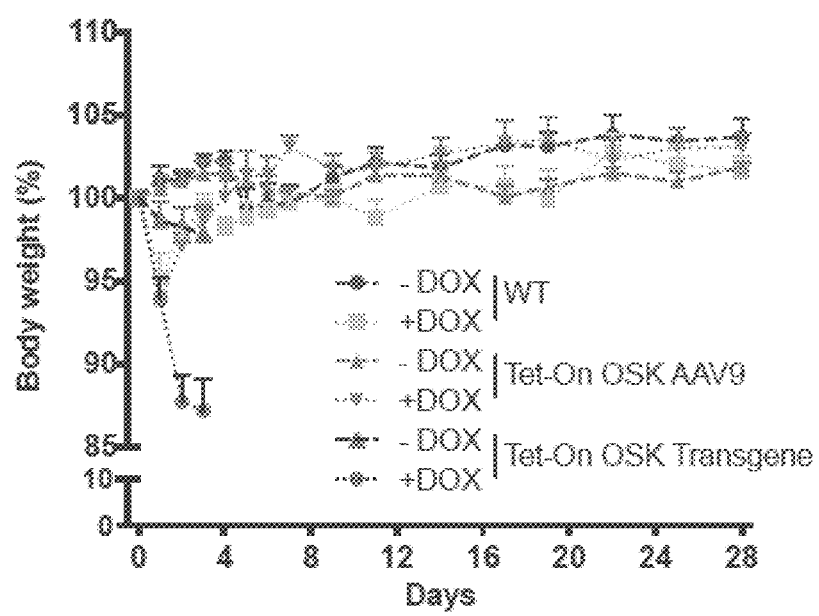
Figure 36E:
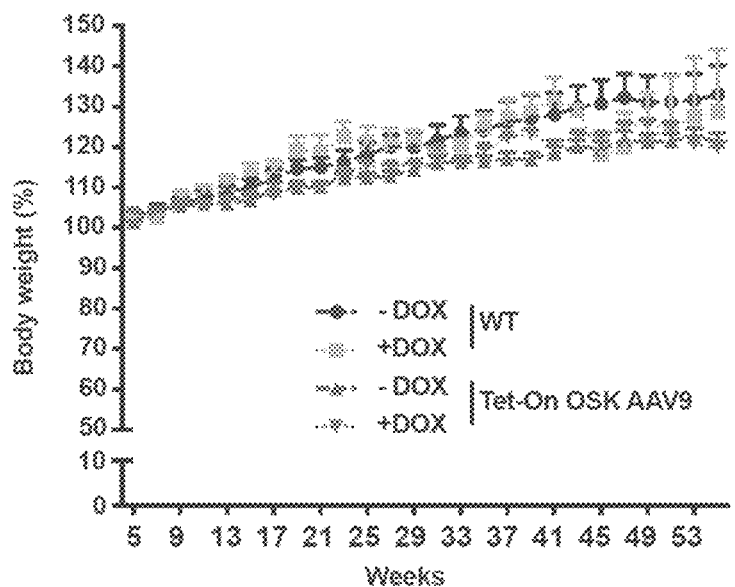
Figure 36F:
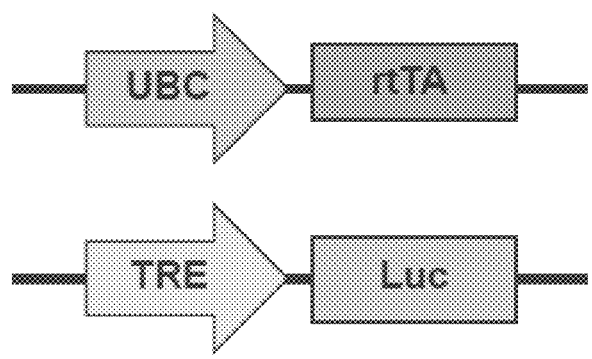
Figure 36G:
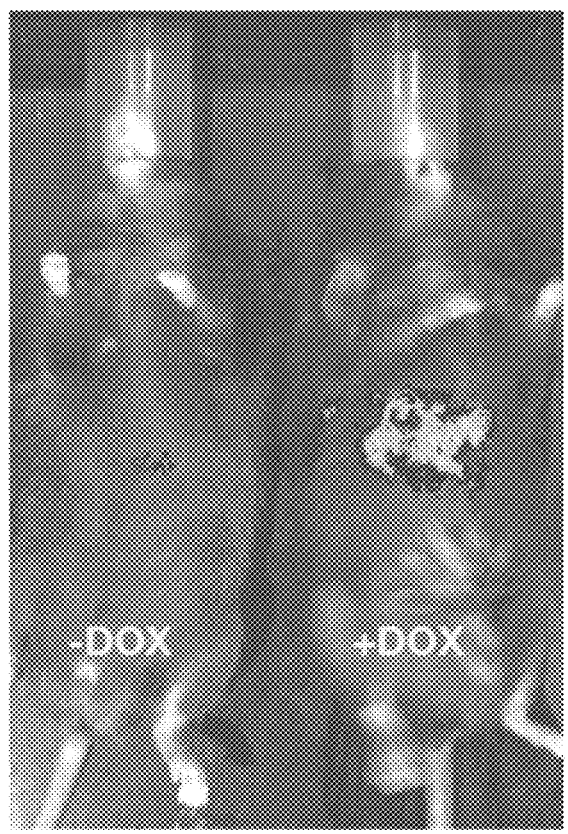

To deliver and control OSK expression in vivo, a tightly regulated Tet-ON and Tet-OFF adeno-associated viral (AAV) vector system was developed to accommodate all three reprogramming genes in one viral particle (Smalley et al., First AAV gene therapy poised for landmark approval. Nat Biotechnol, 2017. 35(11): p. 998-999; Senis et al., AAV vector-mediated in vivo reprogramming into pluripotency. Nat Commun, 2018. 9(1): p. 2651) (FIG. 32A). First, to test if induction of OSK AAVs caused toxicity in vivo, 5-month-old C57BL/6J mice were infected with rtTA and TRE–OSK AAV9s and induced expression to levels comparable to those of transgenic mice (FIG. 36D). Surprisingly, continuous induction of OSK for over a year had no discernable negative effect on the mice for over a year (FIG. 32B and FIG. 36E). Without being bound by a particular theory, there was ostensibly no discernable negative effect on the mice because high-level expression in the intestine was avoided (FIGS. 36F-36H), thus avoiding the dysplasia and weight loss seen in other studies, including Abad et al., Nature 502, 340-345, doi:10.1038/nature12586 (2013).

Figure 32C:
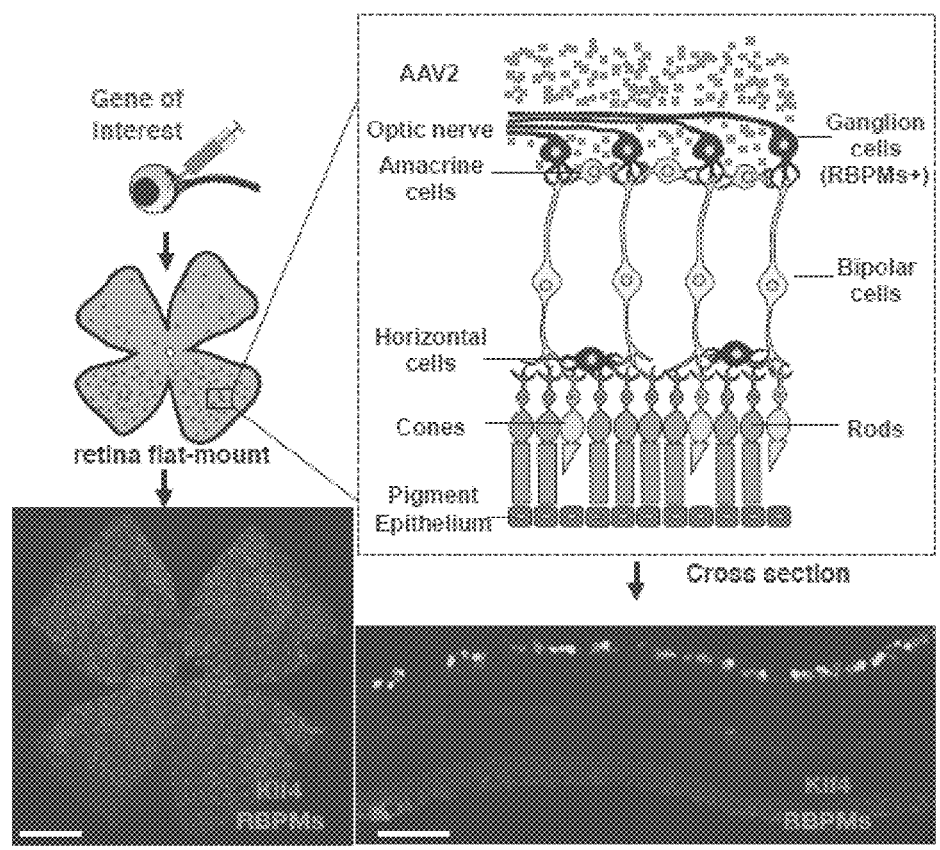
Figure 32D:
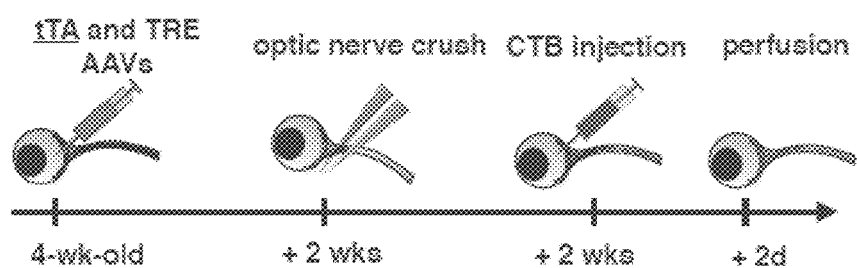
Figure 37A:
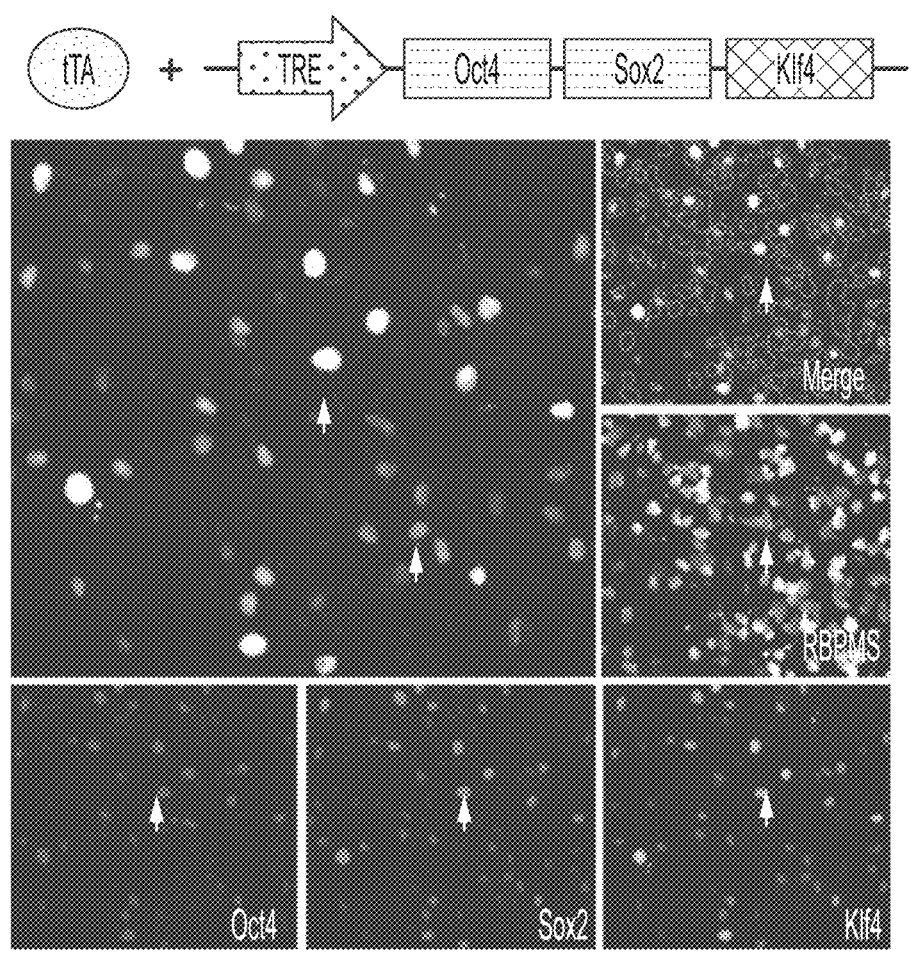
FIGS. 37A-37D show the characterization of an inducible polycistronic AAV system.
Figure 37B:
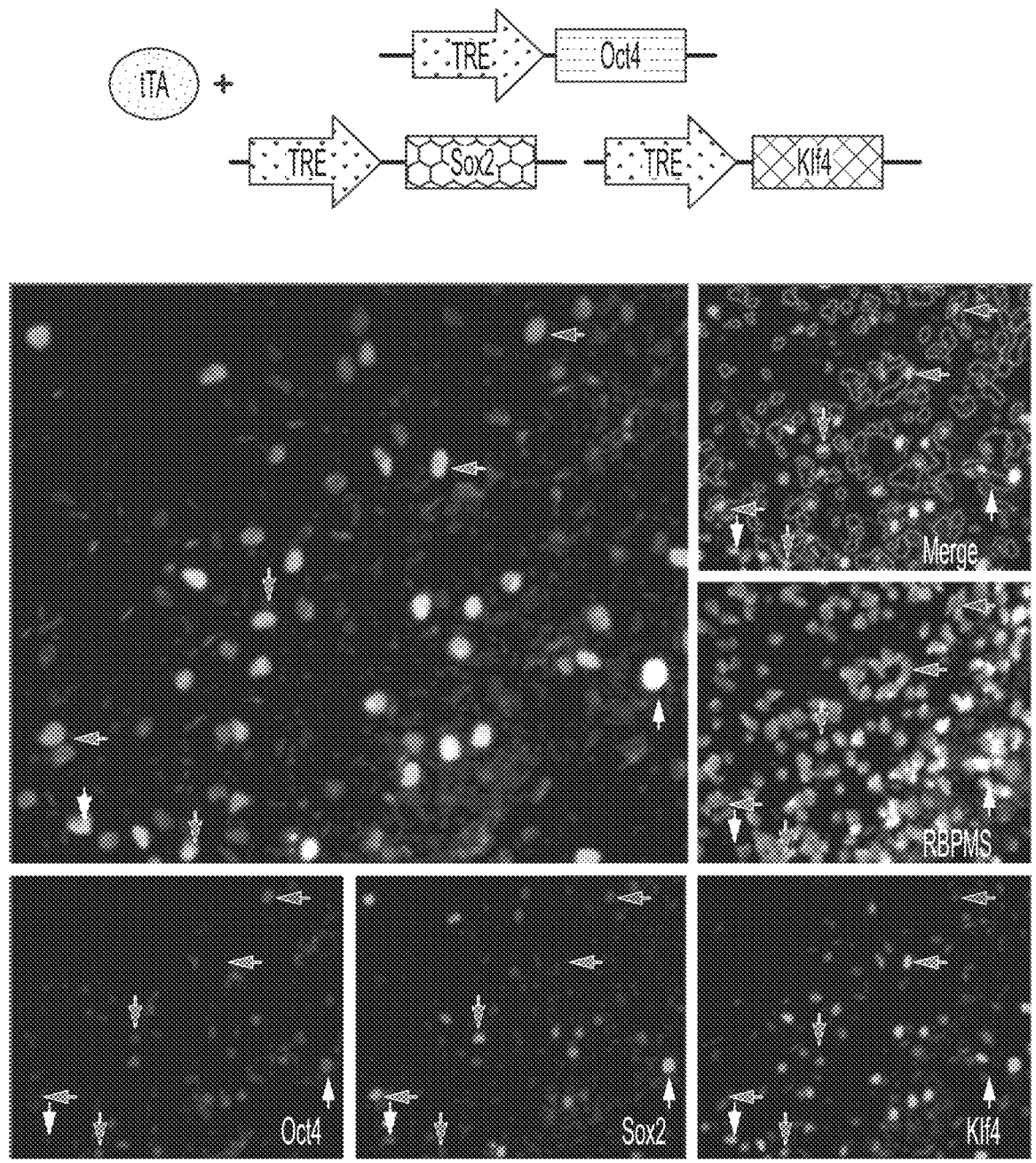
Figure 37C:
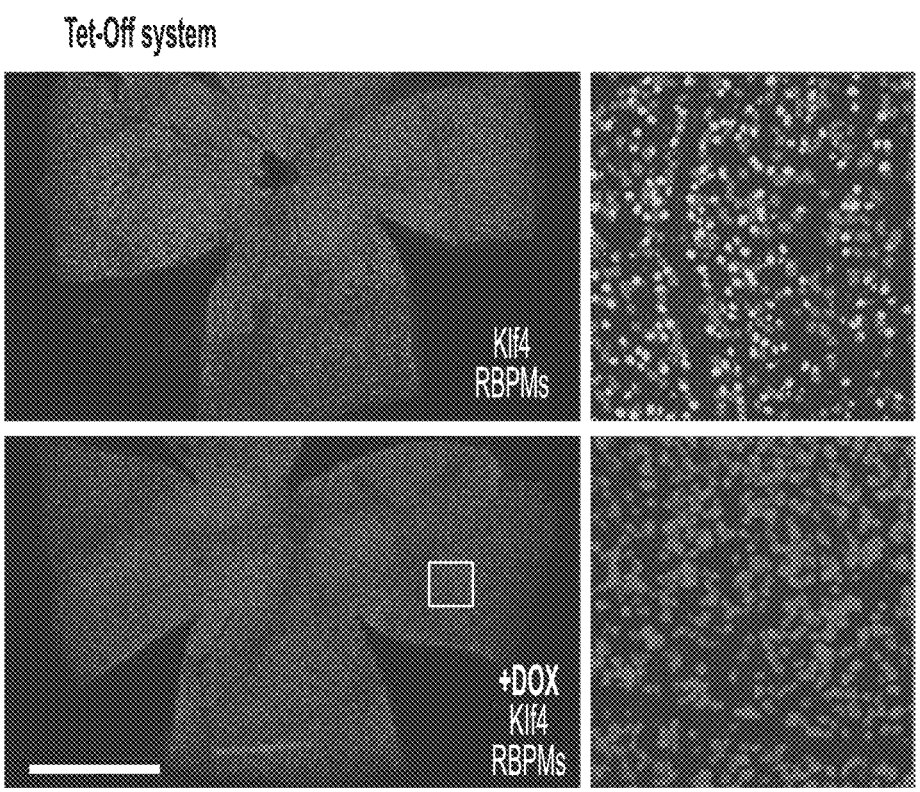

Almost all species experience a decline in regenerative potential during ageing. In mammals, one of the first systems to lose this potential is the central nervous system (CNS). A canonical CNS cell type, the retinal ganglion cell, projects an axon away from the retina towards the brain, forming the optic nerve. During embryogenesis and in neonates, RGCs can regenerate if damaged, but this capacity is soon lost (Goldberg et al., Science, 2002. 296(5574): p. 1860-4). Over time, as organisms age, the overall function and resilience of the CNS continues to decline (Geoffroy et al., Cell Rep, 2016. 15(2): p. 238-46). To explore whether it is possible to restore an early epigenetic profile in adult RGCs, OSK expression was induced in a nerve crush injury model in adult mice of various ages. The Tet-Off system (Tet-Off tTA–AAV2) carrying OSK, either in separate AAVs or in the same AAV, was injected into the vitreous body, resulting in efficient, selective, and doxycycline-responsive gene expression in RGCs. As a negative control, a group of mice were also treated with doxycycline to repress the AAVs (FIG. 32C and FIG. 37C). Two weeks post-injection, optic nerve crush was performed, and, two weeks after that, axon length and optic nerve density were calculated (FIG. 32D).

Figure 32E:
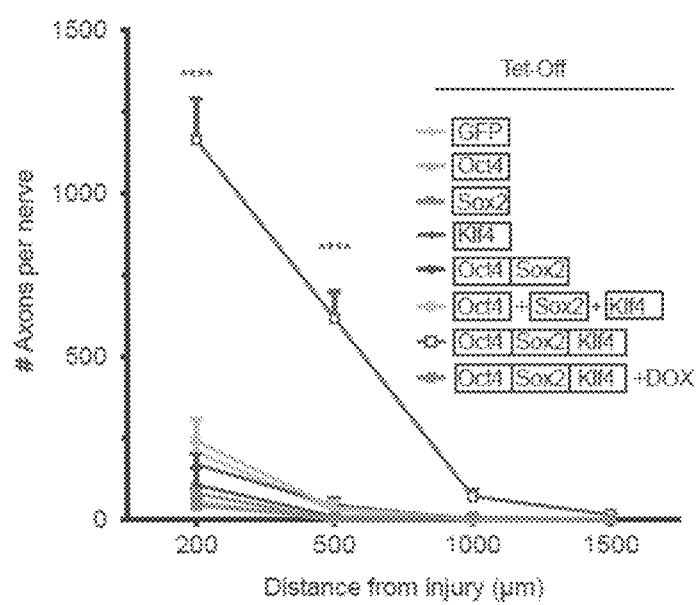
Figure 32F:
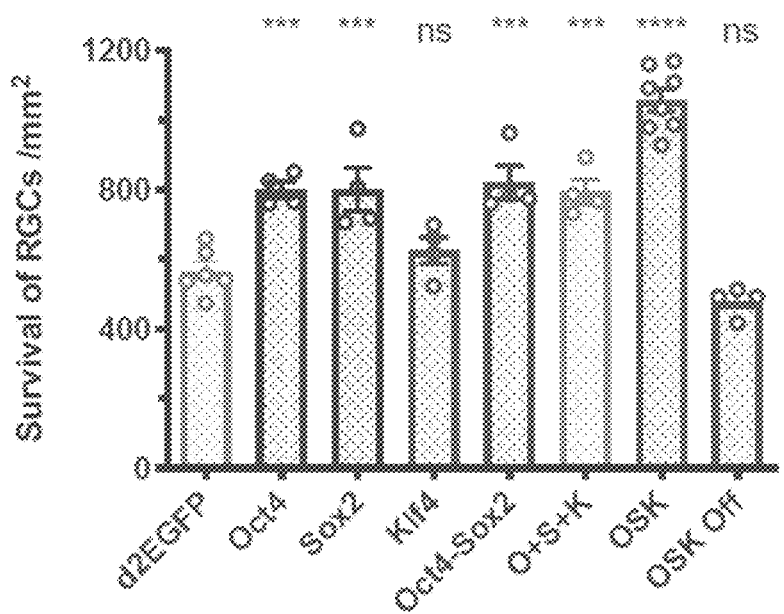
Figure 32G:
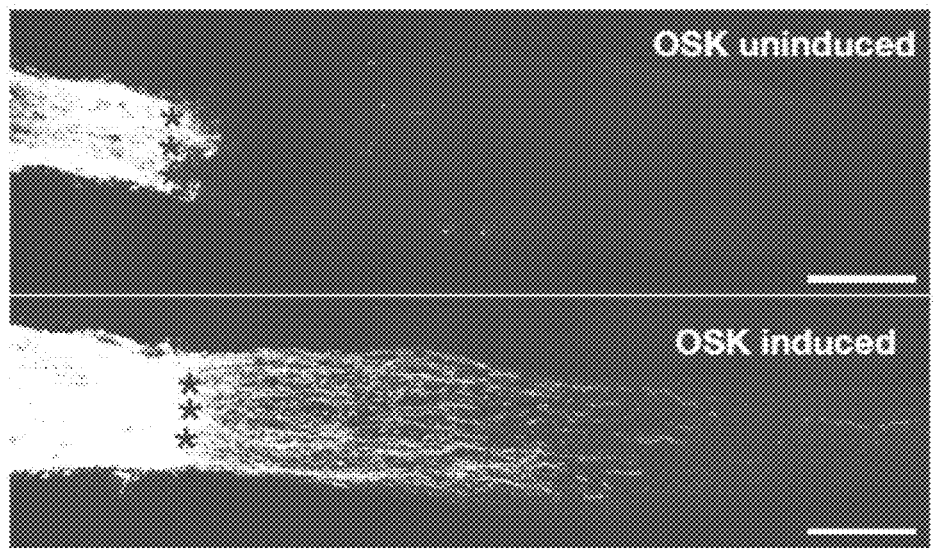
Figure 37D:
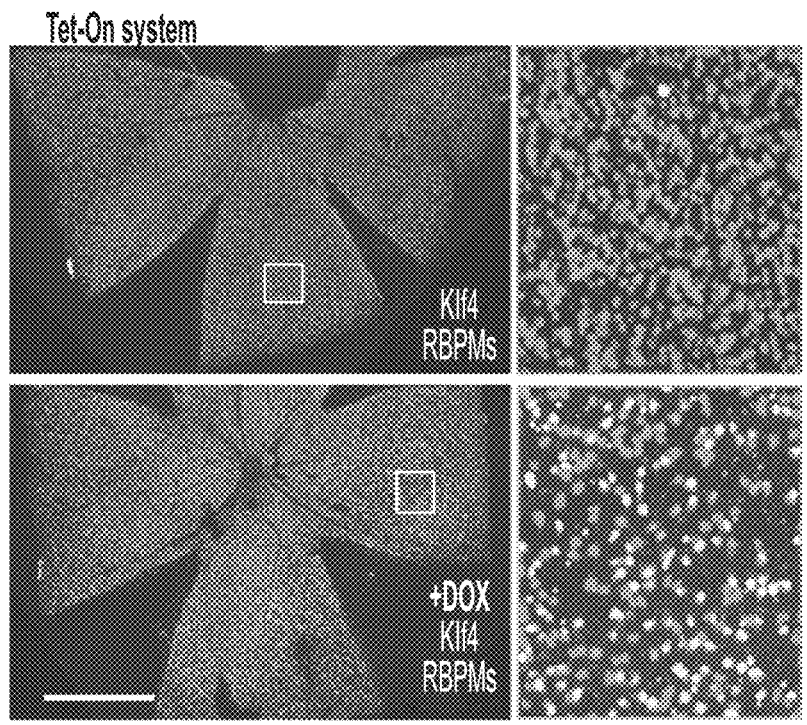
Figure 38A:
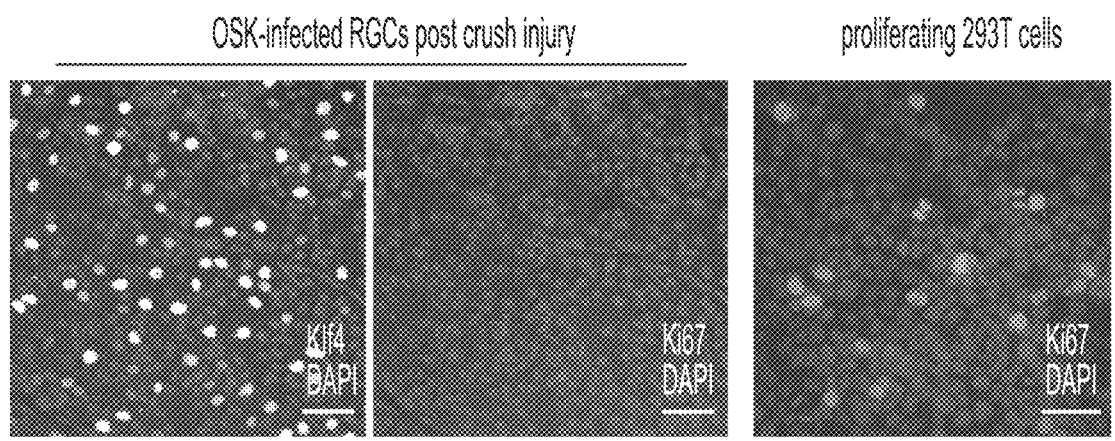
FIGS. 38A-38C show that OSK induces long-term axon regeneration post injury without RGC proliferation.
Figure 38B:
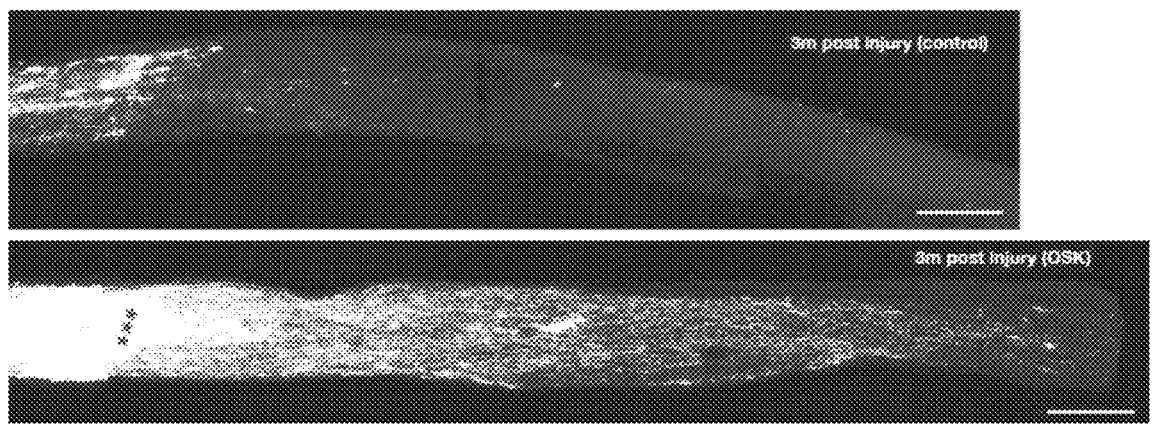
Figure 38C:
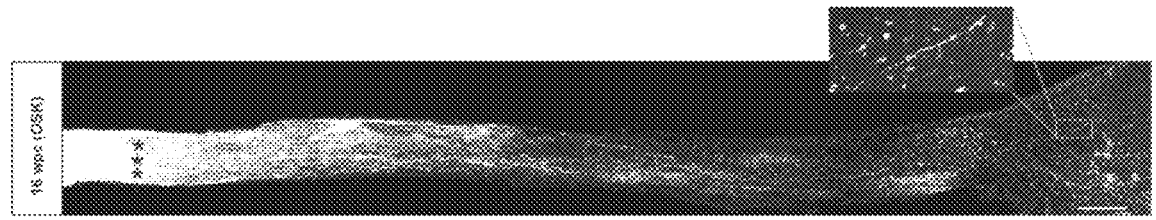

Induction of the polycistronic OSK-AAV2 caused a significant increase in RGC survival and long-distance axonal regeneration (FIG. 32E and FIG. 37D) without any sign of RGC proliferation (FIG. 38A). In contrast, when introduced on separate AAVs, OCT4, SOX2, KLF4 had no effect on regenerative capacity (FIG. 32E), ostensibly due to the lower frequency of co-infection (FIG. 37A and FIG. 37B). Because Klf4 can repress axonal growth (Moore et al., Science, 2009. 326(5950): p. 298-301; Qin et al., Nat Commun, 2013. 4: p. 2633), OCT4, SOX2, and KLF4 were also individually and a dual-cistron of Oct4 and Sox2 was tested. No regenerative effect, however, was observed in the absence of Klf4. Remarkably, if poly-cistronic OSK was induced for 3-months, RGC axon fibers extended all the way to the chiasm, a distance of over 3 mm (FIG. 38B). Indeed, when polycistronic OSK was induced for 12-16 weeks, regenerating RGC axon fibers further extended into the chiasm (5 mm away from crush site), where optic nerve connects to brain (FIGS. 38B-38C).

Figure 39A:
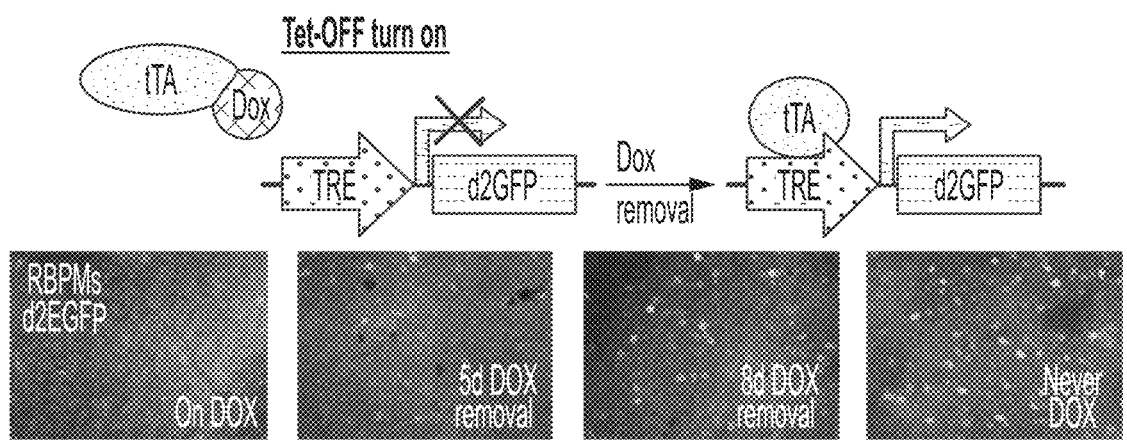
FIGS. 39A-39D show Tet-On system has better turn on rate and OSK transduced RGCs have higher survival rate.
Figure 39B:
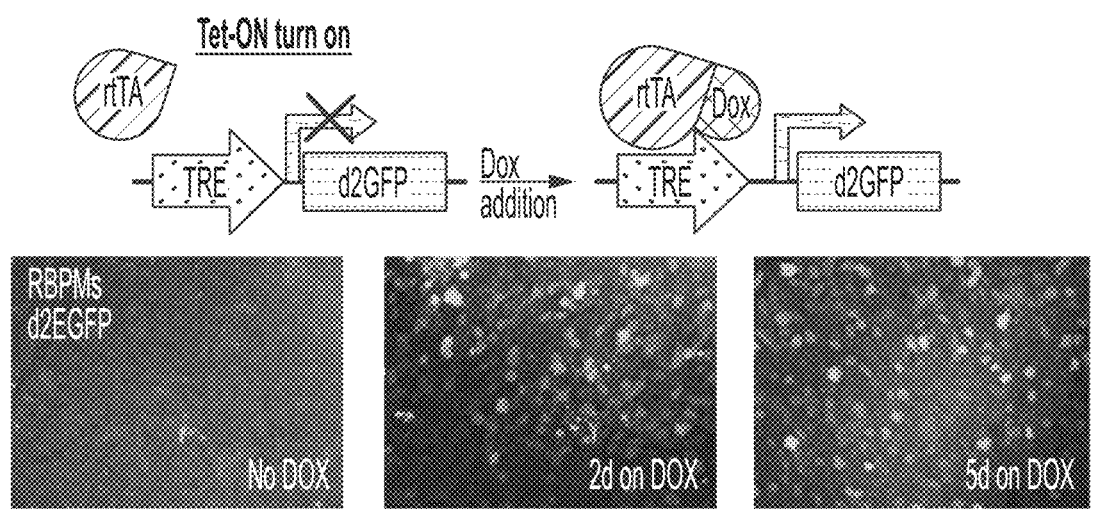
Figure 39C:
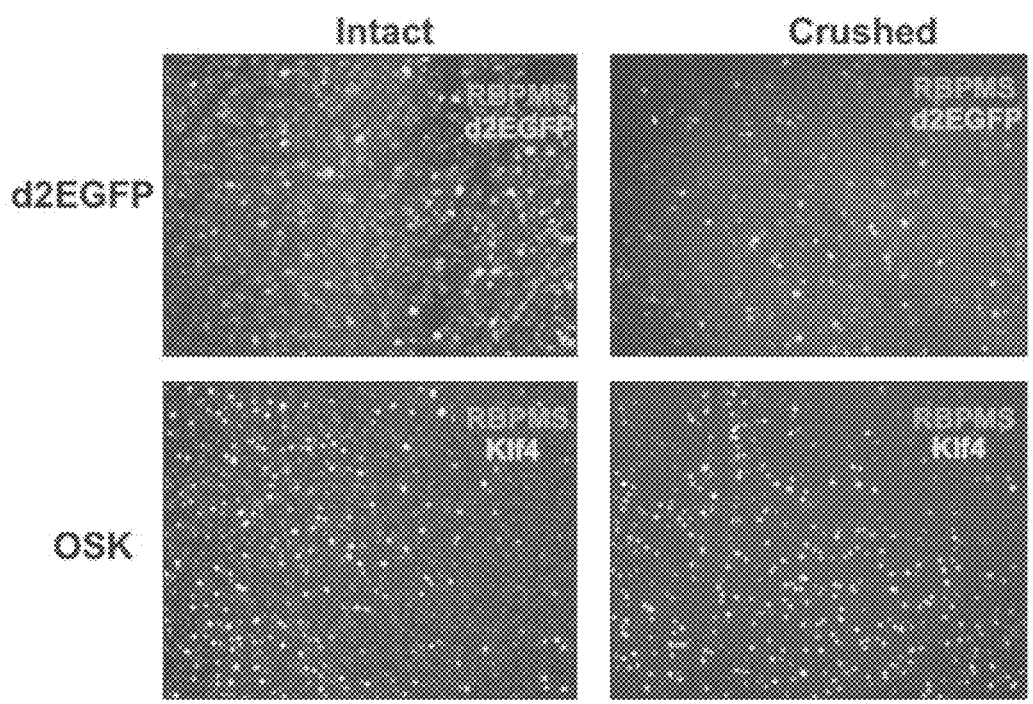
Figure 39D:
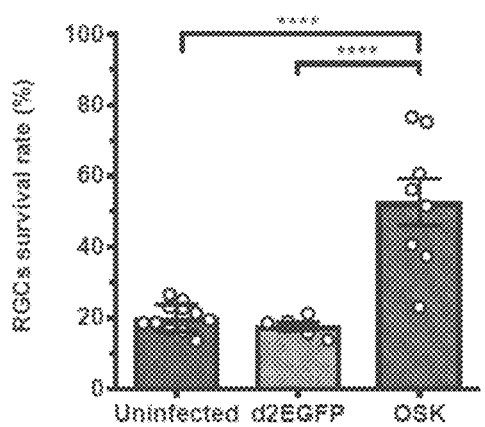
Figure 40A:
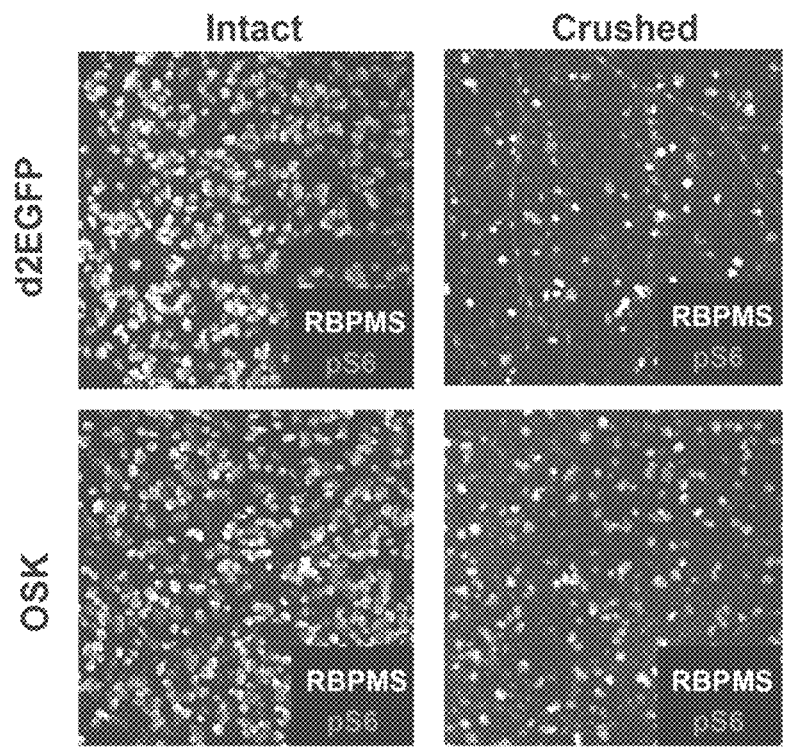
FIGS. 40A-40F show identification of epigenetic mechanism underlying OSK effect.
Figure 40B:
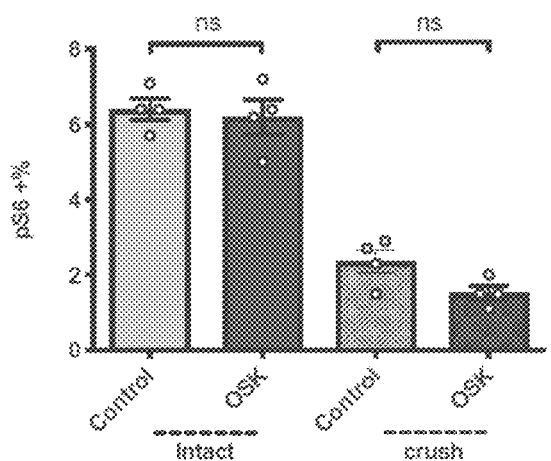
Figure 40C:
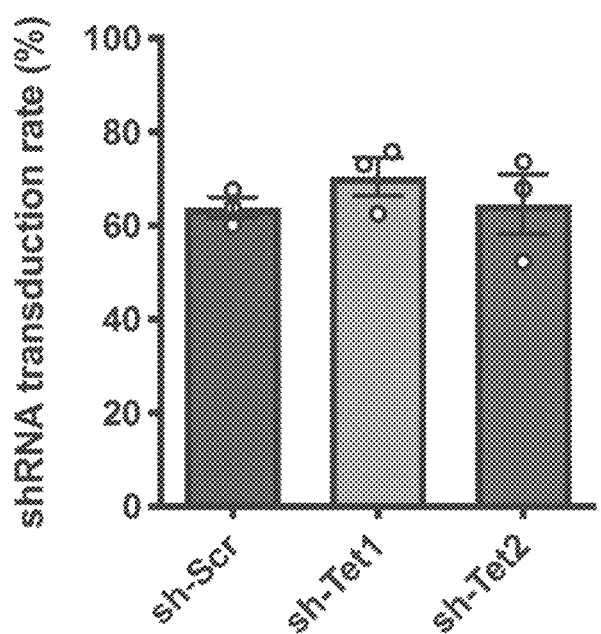
Figure 40D:
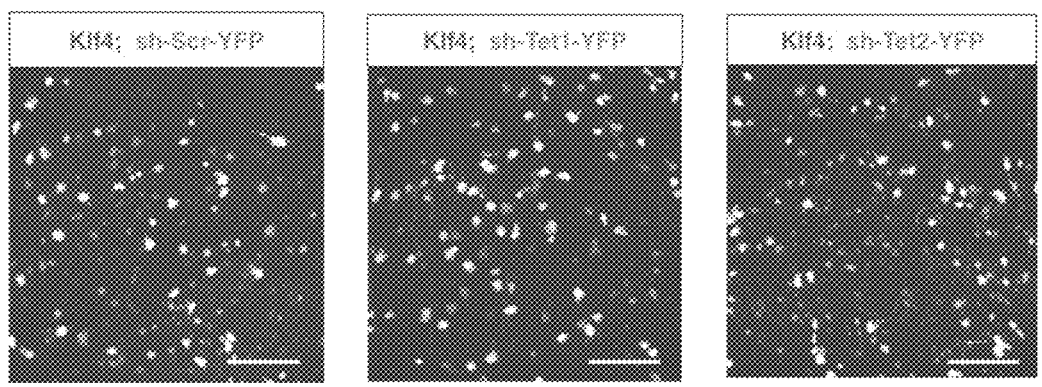
Figure 40E:
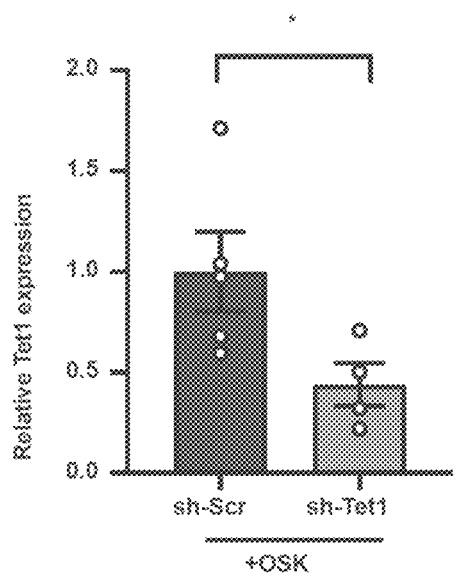
Figure 40F:
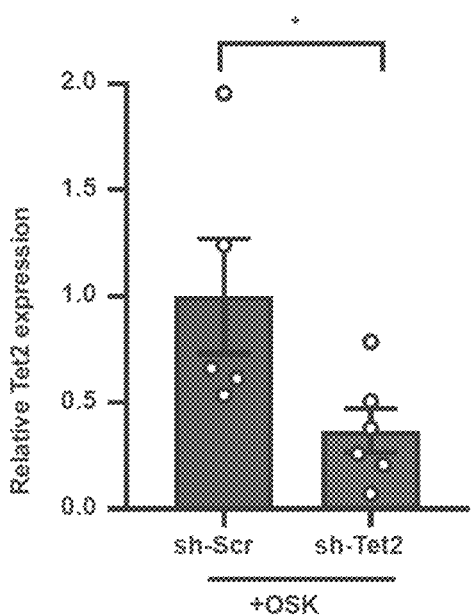

Next, the requisite timing of OSK expression was tested to promote neuronal survival and regeneration. For these experiments, the Tet-On AAV system was utilized due to its rapid on-rate (FIG. 37D and FIGS. 39A-39B). Significant improvement in axon regeneration only occurred when OSK expression was induced after injury and the longer OSK was induced, the greater distance the neurons extended, with no increase in the total number of RGCs (FIGS. 33B, 33C, and 33D). By co-staining for OSK and performing neuronal counts, survival rate was estimated to be 2.5-3 times of uninfected or GFP-infected RGCs (52 vs. 17%-20%) (FIGS. 39C and 39D), suggesting OSK effect is cell-intrinsic. The Pten-mTOR-S6K pathway, previously shown to improve neuronal survival in vivo, was not activated in OSK-infected cells post-injury (FIG. 40A and FIG. 40B), indicating a new pathway might be involved.

Figure 45A:
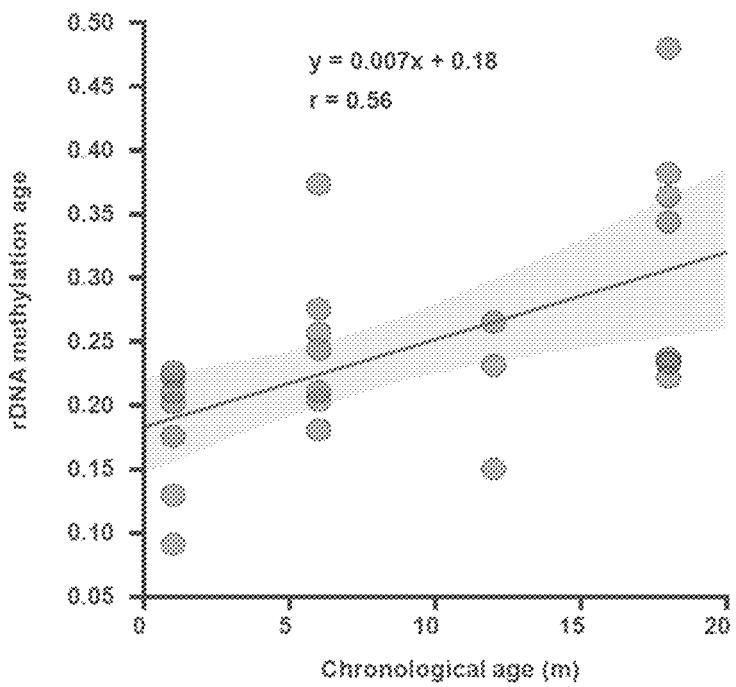
FIGS. 45A-45C show methylation clock analysis of mouse RGCs and human neurons.
Figure 45B:
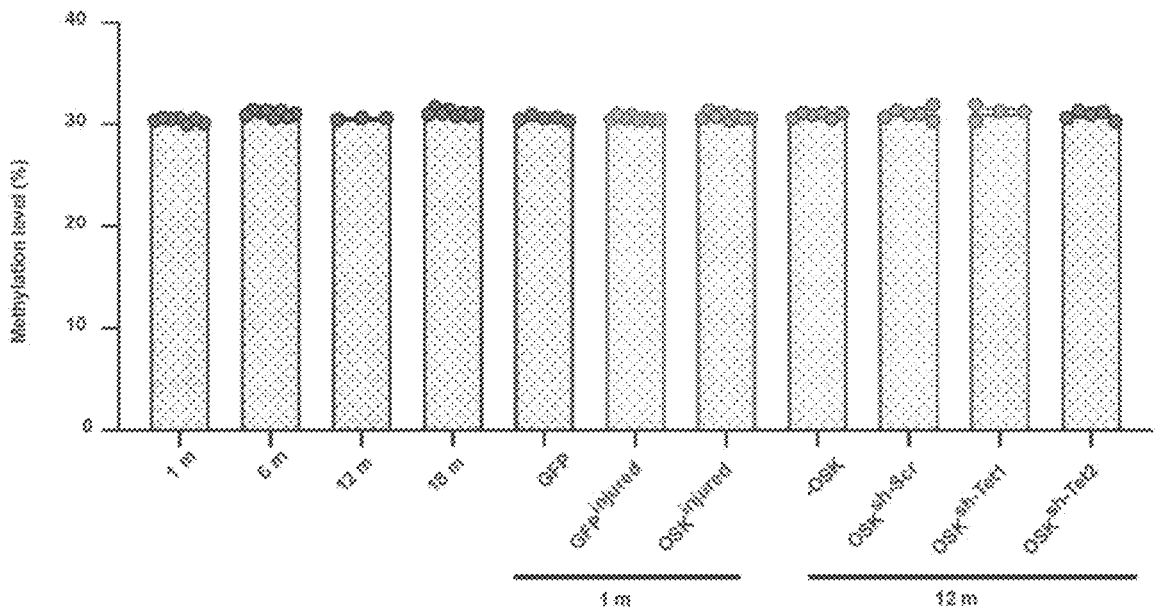

It was determined whether neuronal injury advanced epigenomic age and whether OSK's benefits were due to the preservation of a younger epigenome. Genomic DNA from RGCs was FACS-isolated before injury or 4-days after injury in the presence or absence of OSK induction, and subjected reduced-representation bisulfite sequencing (RRBS-Seq). Without being bound by a particular theory, rDNAme clock (Wang et al., Genome Res 29, 325-333, doi:10.1101/gr.241745.118 (2019)) provided the best site coverage (70/72 CpG sites) relative to other available mouse clocks (Meer et al., Elife 7, doi:10.7554/eLife.40675 (2018); Thompson et al., Aging (Albany NY) 10, 2832-2854, doi:10.18632/aging.101590 (2018)) and its age estimate remained highly correlated with chronological age of RGCs (FIG. 45A and Methods). In the absence of global methylation changes, injured RGCs experienced an acceleration of the epigenetic clockand OSK expression counteracted this effect (FIG. 33K and FIG. 45B).

It was determined whether that the effect of OSK on neuronal survival and regeneration occurred by restoring a younger epigenome. If so, these effects should be dependent on the reversal of the epigenetic clock, which would require the removal of methyl groups from DNA via the activity of Ten-Eleven-Translocation (TET) dioxygenases. Previously characterized AAVs expressing short-hairpin RNAs against Tet1 and Tet2 (sh-Tet1 and sh-Tet2) (Guo et al., Cell 145, 423-434, doi:10.1016/j.cell.2011.03.022 (2011); Yu et al., Nat Neurosci 18, 836-843, doi:10.1038/nn.4008 (2015); Weng et al., Neuron 94, 337-346.e336, doi:10.1016/j.neuron.2017.03.034 (2017)) were utilized, and the transduction rate and knockdown efficiency in vivo was validated (FIGS. 40C-40F). Knockdown of either Tet1 or Tet2 (sh-Tet1 and sh-Tet2 AAV2, at 1/5 titer of OSK AAV), which transduced around 70% of OSK positive cells (FIGS. 40C and 40D), efficiently blocked OSK from regenerating axons and improved RGC survival (FIGS. 33E and 33F).

Figure 33A:
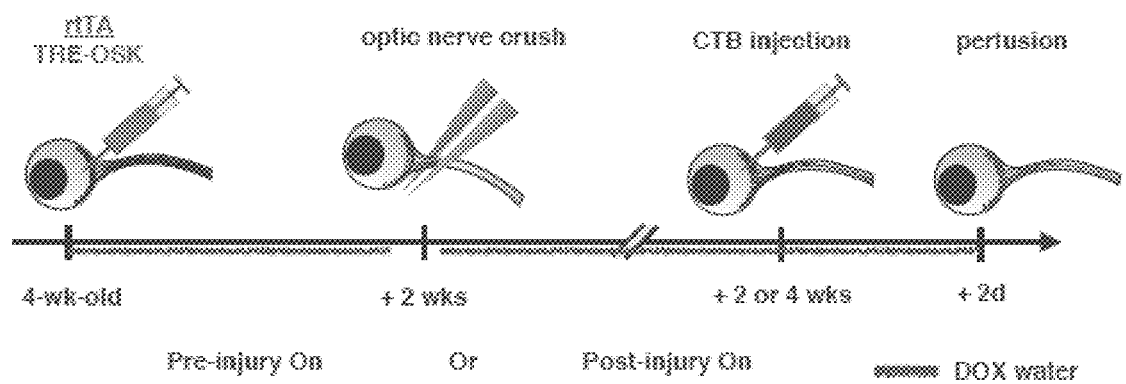
Figure 33B:
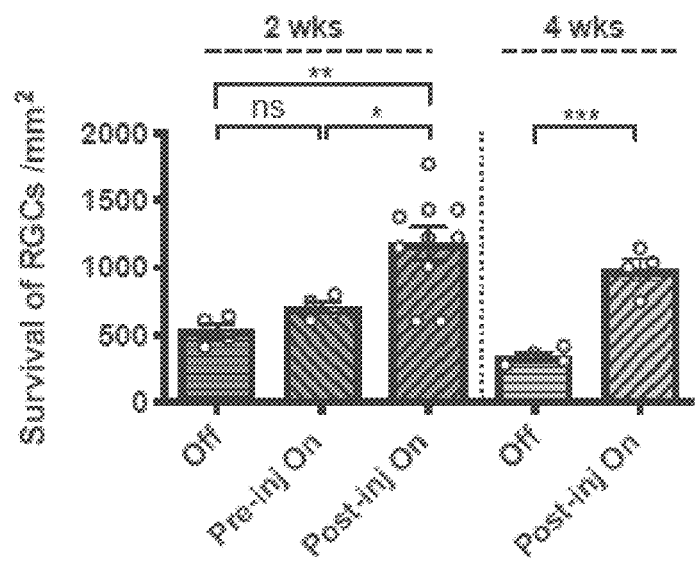
Figure 33C:
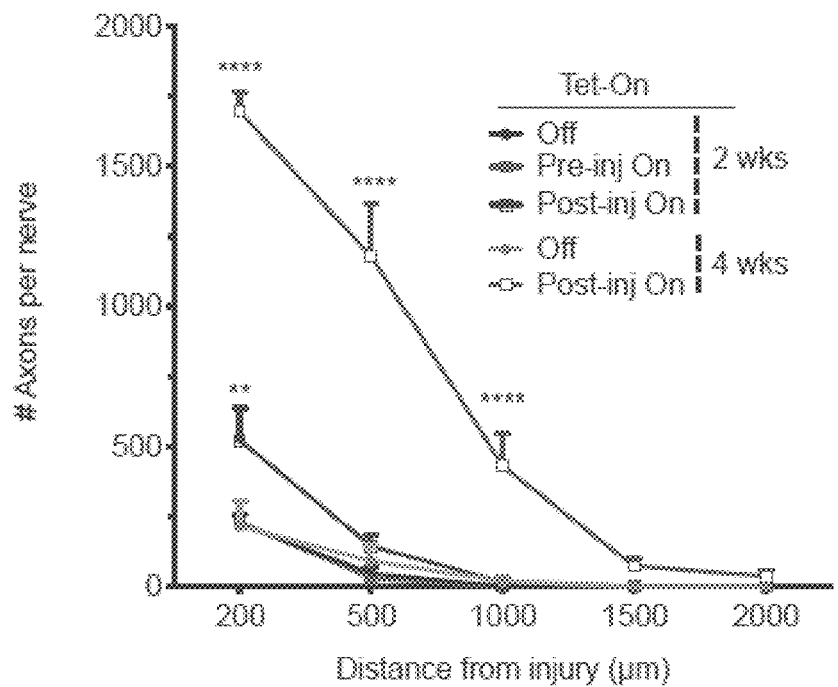
Figure 33D:
Figure 33E:
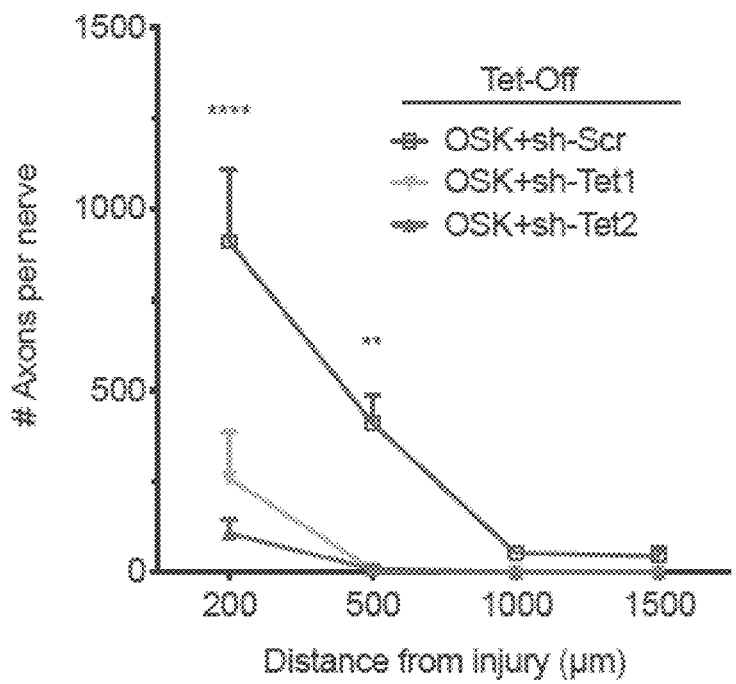
Figure 33F:
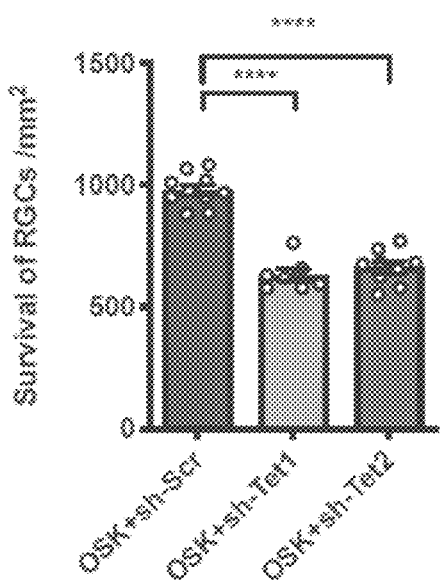
Figure 33I:
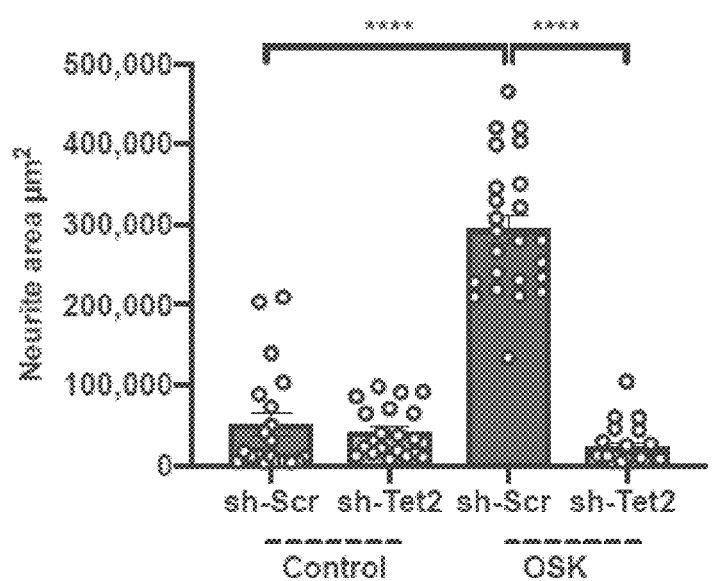
Figure 33J:
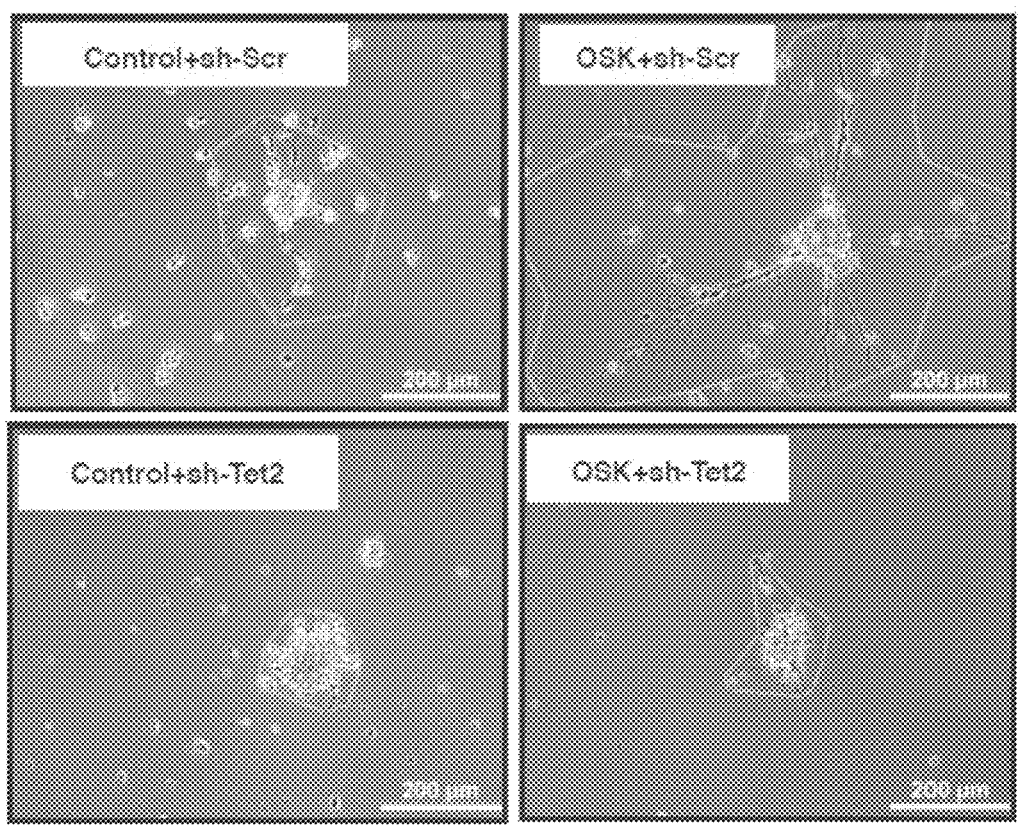
Figure 33K:
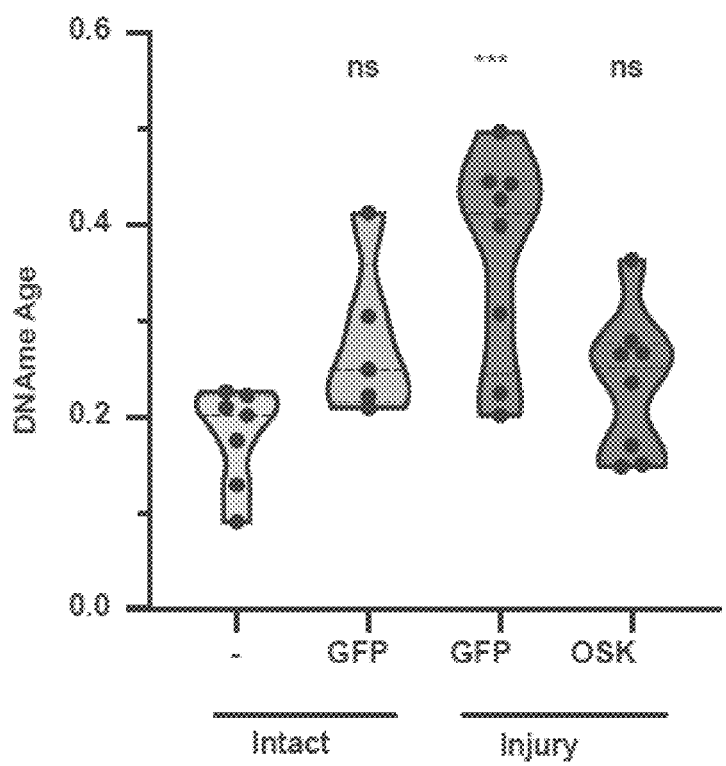
Figure 41A:
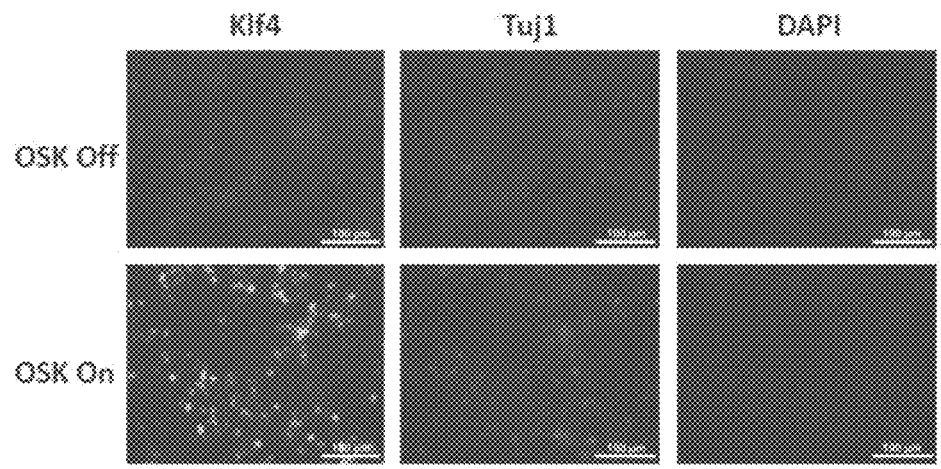
FIGS. 41A-41K show that OSK robustly induces human neuron axon regeneration independent of mTOR pathway.
Figure 41B:
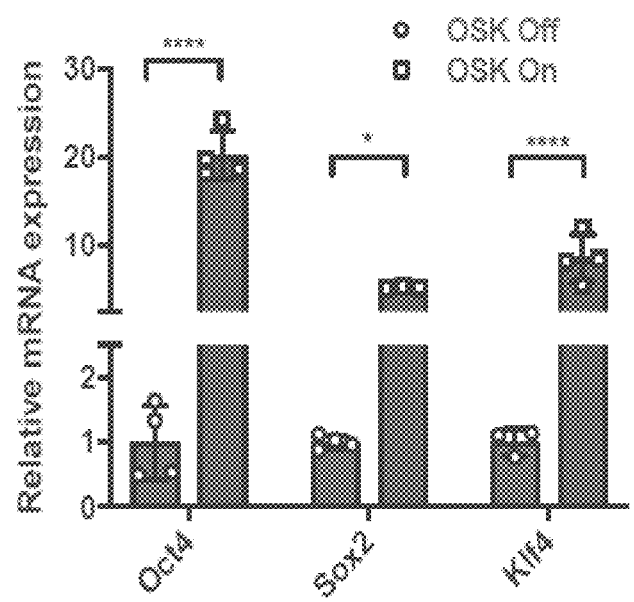
Figure 41C:
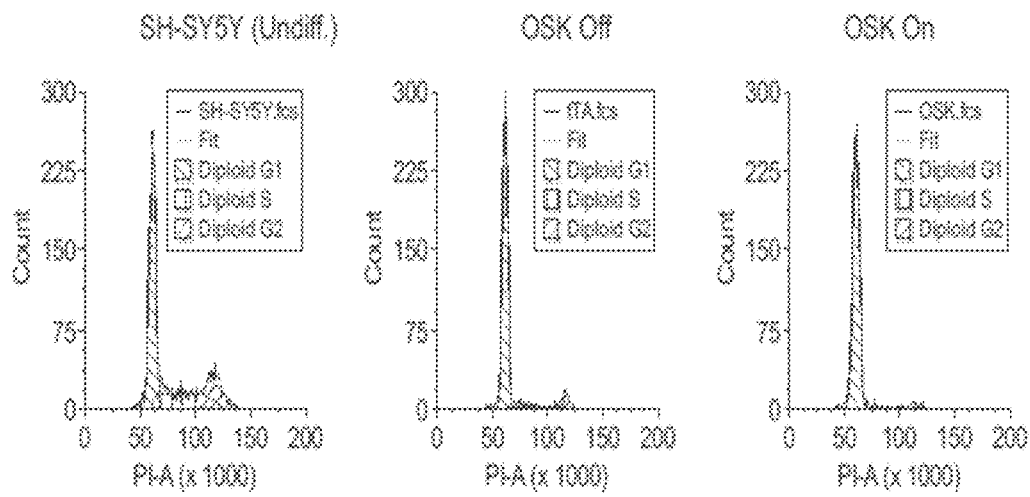
Figure 41D:
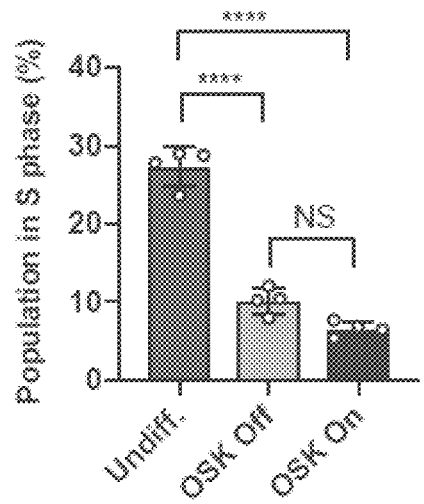
Figure 41E:
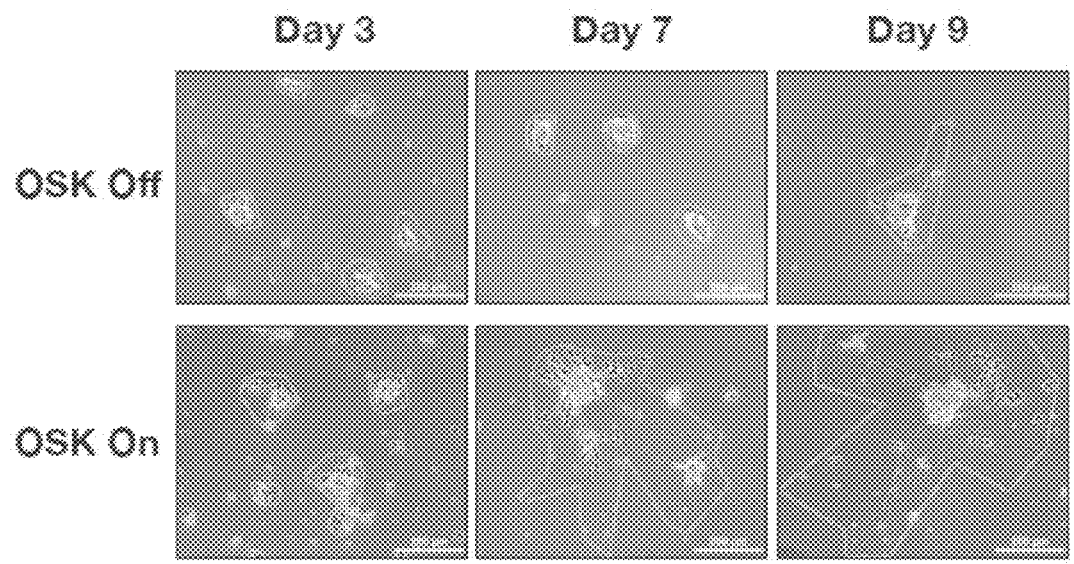
Figure 41F:
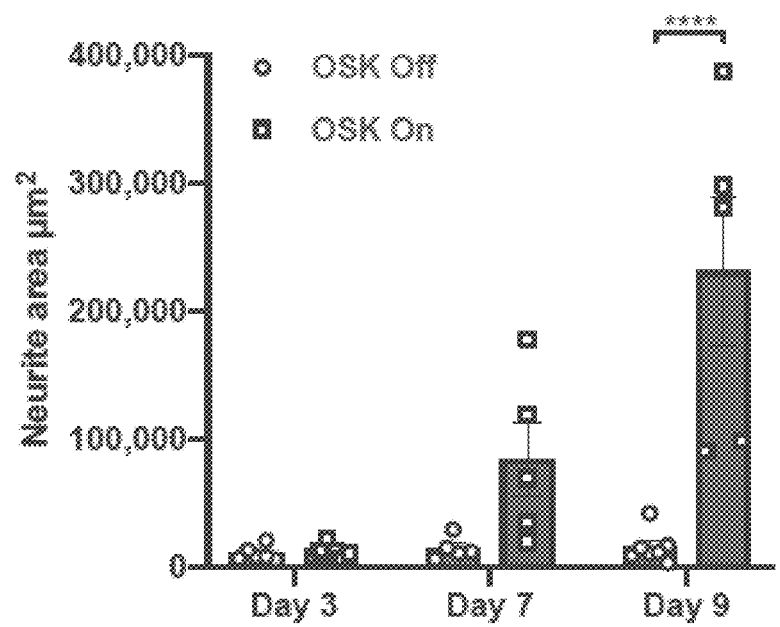
Figure 41G:
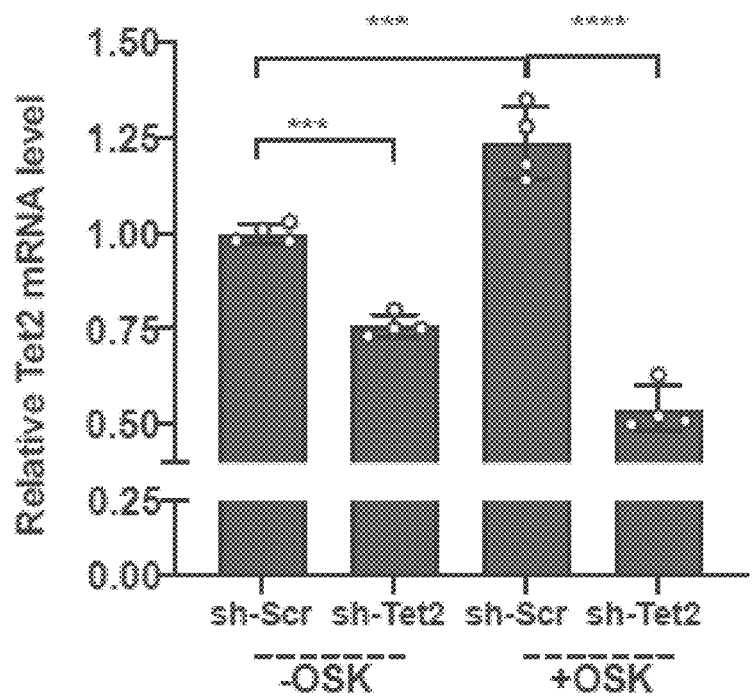
Figure 41H:
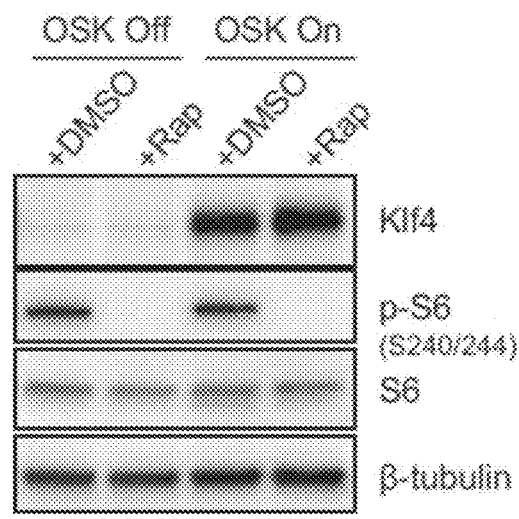
Figure 41I:
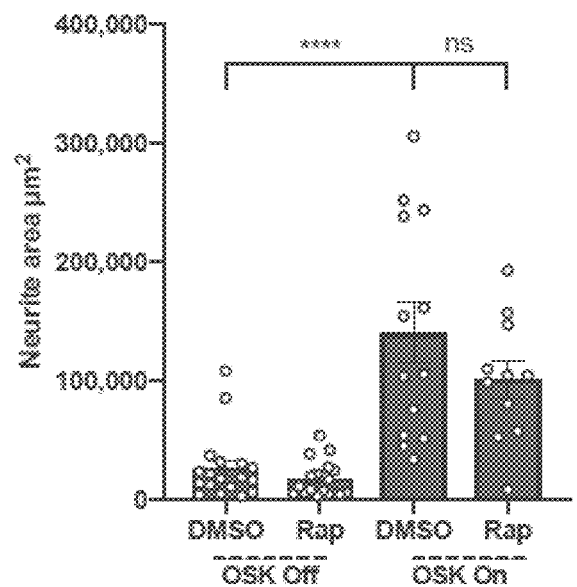
Figure 41J:
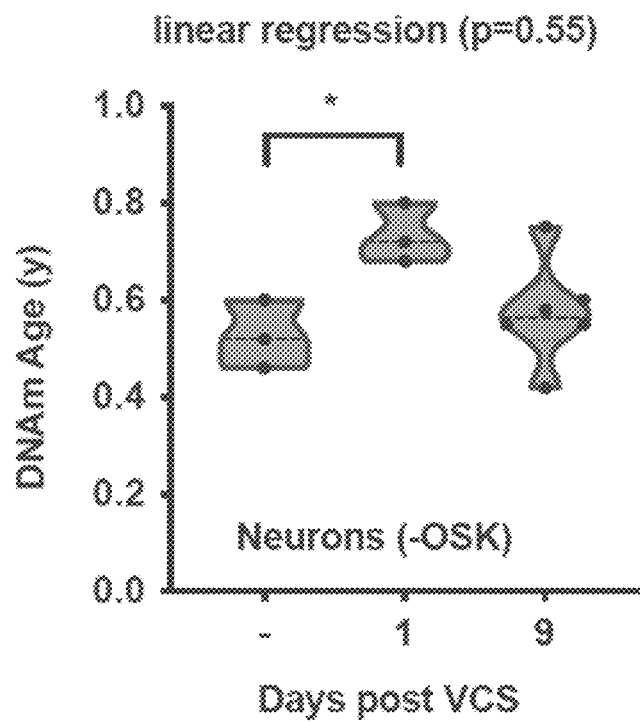
Figure 41K:
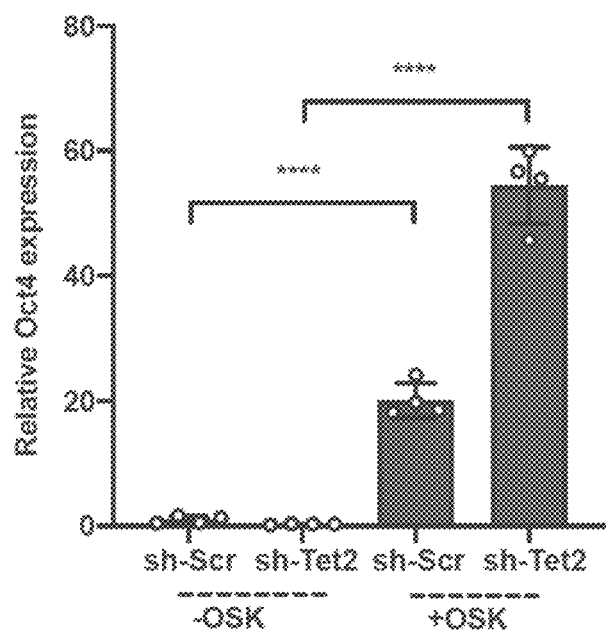
Figure 45C:
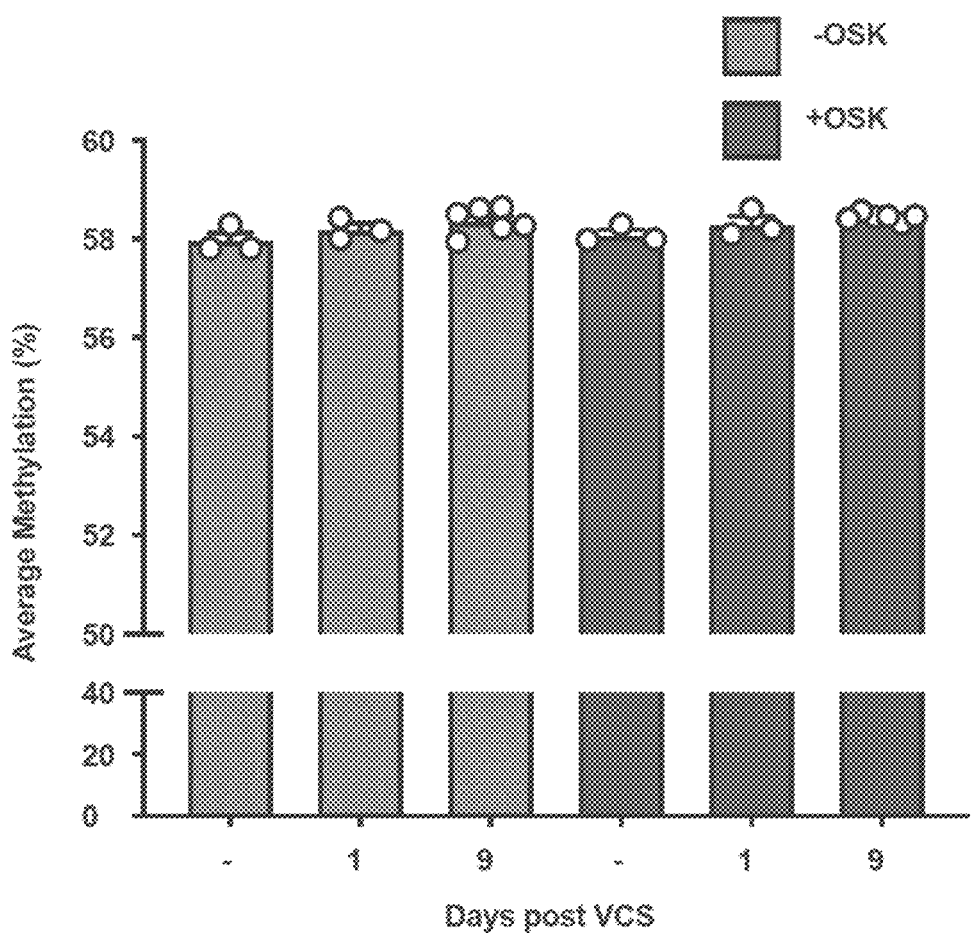

To test whether neuronal rejuvenation by OSK is specific for mouse RGCs, axon regeneration assays were performed in human neurons in vitro (FIG. 33G). Human neuroblastoma SH-SY5Y cells were differentiated into neurons and transduced them with AAV-DJ vectors to express OSK (FIG. 33G, FIG. 41A, and FIG. 41B). Similar to mouse RGCs in vivo (FIG. 38A), OSK did not induce cell proliferation (FIGS. 41C-41D). Axon degeneration was then induced by a 24 hour treatment with vincristine (VCS), a chemotherapeutic agent, and cells were then allowed to recover for 9 days. The epigenetic clock of these neurons were measured using the skin and blood cell clock (Horvath and Raj, Nat Rev Genet. 2018 June; 19(6):371-384). Similarly, DNA methylation age is significantly increased after VCS damage in human neurons (FIG. 41J), and OSK expression not only prevented this increase of DNA methylation age, but also restored a younger DNA methylation age without a global reduction of DNA methylation (FIG. 33H, bottom panel and FIG. 45C). DNAmAge is significantly decreased with experiment day 9 post VCS damage in OSK treated cells, but not in cells not treated by OSK (FIG. 33H). At Day 9 post damage, the neurite area was 15-fold greater in the rejuvenated OSK-transduced cells than controls (FIG. 41E and FIG. 41F) and the recovery from damage was dependent on the Tet2 demethylase (FIG. 33I, FIG. 33J, and FIG. 41G), even in presence of high OSK expression (FIG. 41K) but not the mTOR-S6K pathway, paralleling mouse retinal ganglia cells (FIG. 41H and FIG. 41I). Thus, the ability of OSK to reprogram neurons and promote axon growth is cell intrinsic, conserved in mammals, and requires epigenetic rejuvenation through DNA demethylation. This process is referred to herein as the recovery of information via epigenetic reprogramming, or "REVIVER" for short.

Figure 34A:
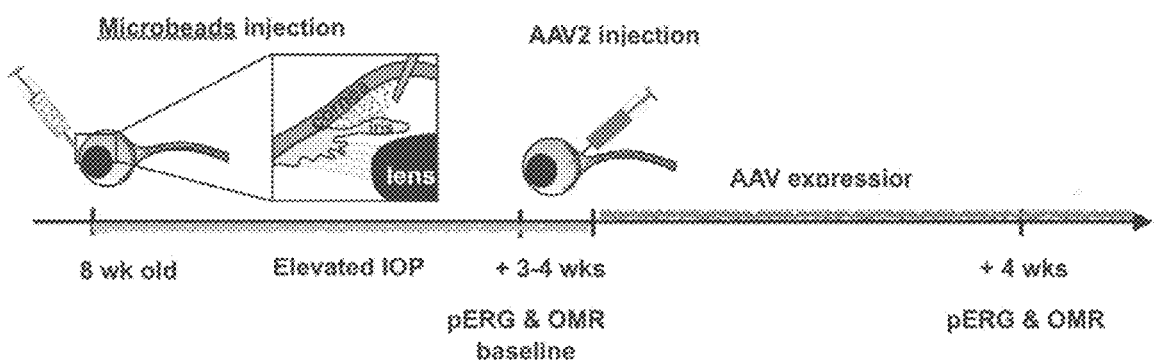
FIGS. 34A-34H show the reversal of glaucoma by OSK AAV treatment.
Figure 34B:
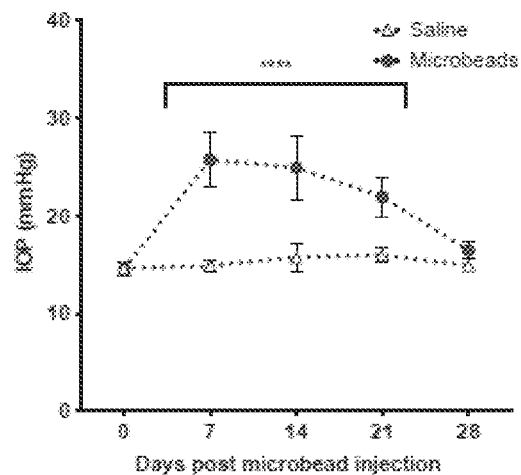
Figure 34C:
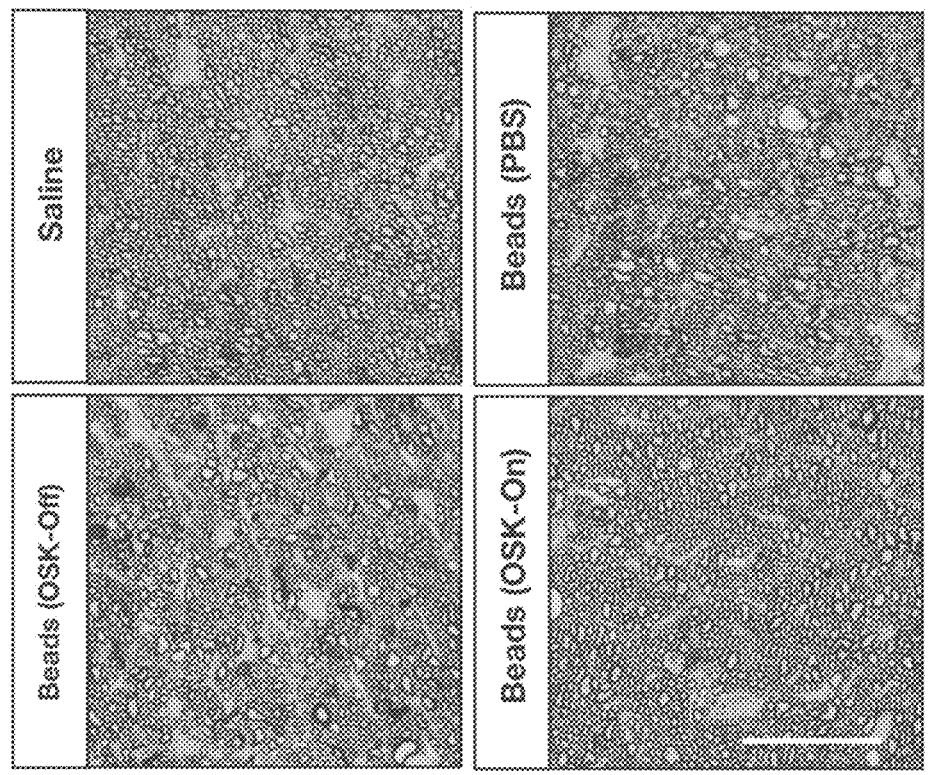
Figure 34D:
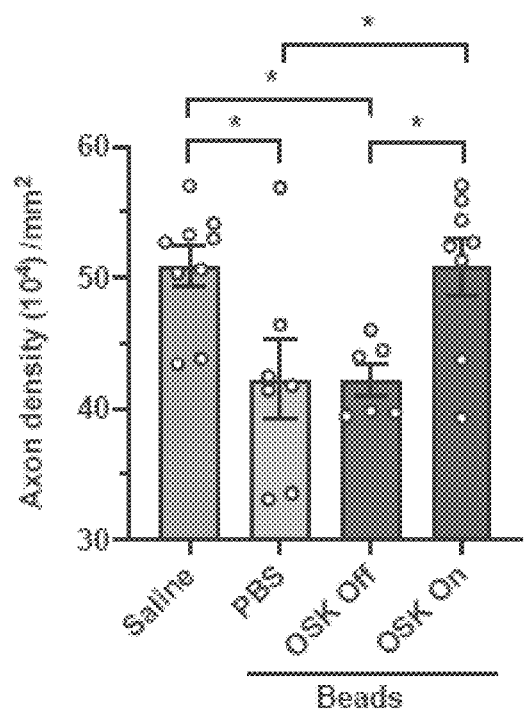
Figure 42A:
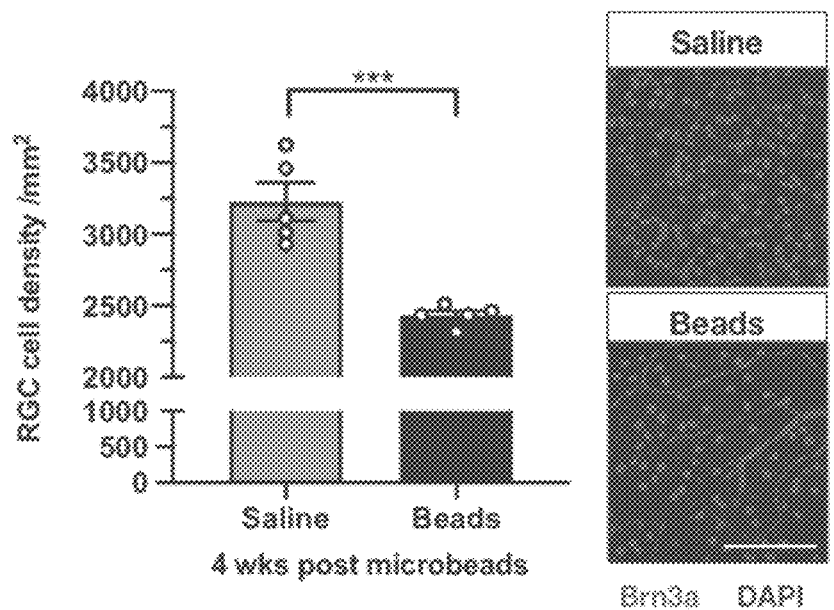
FIGS. 42A-42C show the effect of OSK in a Microbead-induced mouse model.
Figure 42B:
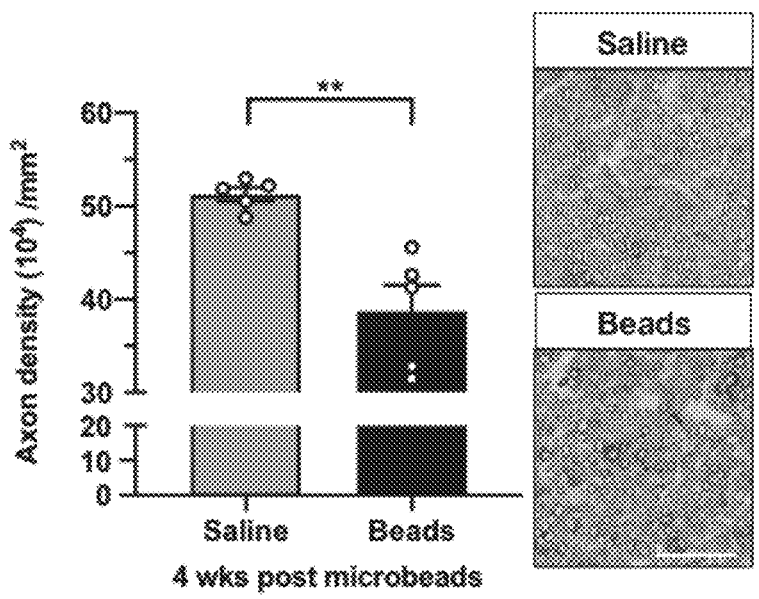
Figure 42C:
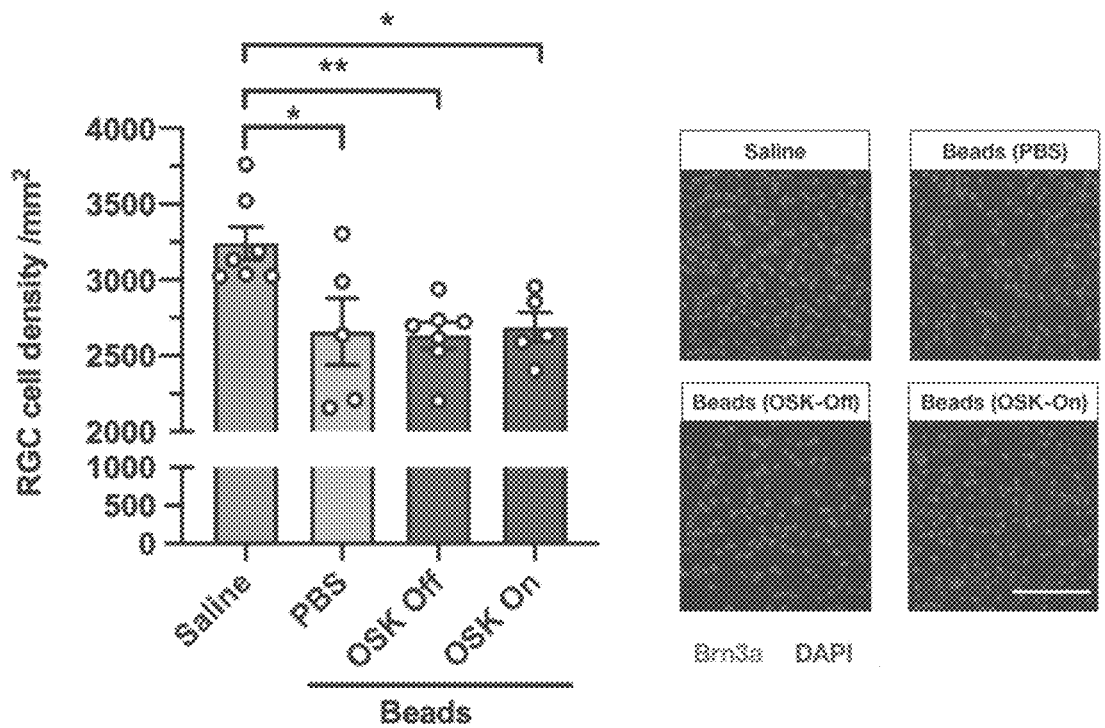

Glaucoma, a progressive loss of RGCs and their axons, most often due to increased intraocular pressure, is a leading cause of age-related blindness worldwide. Although some treatments can slow down disease progression, it is currently not possible to restore vision once it has been lost. Given the ability of OSK to regenerate axons after acute nerve damage, we decided to test whether REVIVER treatment could restore the function of RGCs in achronic setting like glaucoma (FIG. 34A). Elevated intraocular pressure (IOP) was induced unilaterally for 4-21 days by injection of microbeads into the anterior chamber. OSK AAVs or PBS were then injected intravitreally, and express at a time point when glaucomatous damage was established, with a significant decrease in RGCs and axonal density (FIG. 34B, FIG. 42A, and FIG. 42B) (Krishnan et al., J Immunol, 2016. 197(12): p. 4626-4638). At four weeks post-AAV injection, OSK-On treated mice presented with a significant increase in axon density when compared to PBS and OSK-Off treated mice. The increased axon density observed was equivalent to the axon density in the saline-only, non-glaucomatous mice (FIGS. 34C and 34D), and was not associated with proliferation of RGCs (FIG. 42C).

Figure 34E:
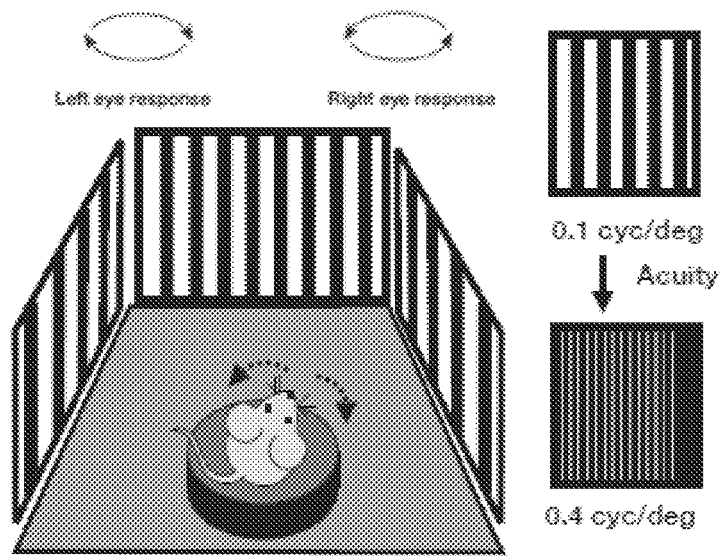
Figure 34F:
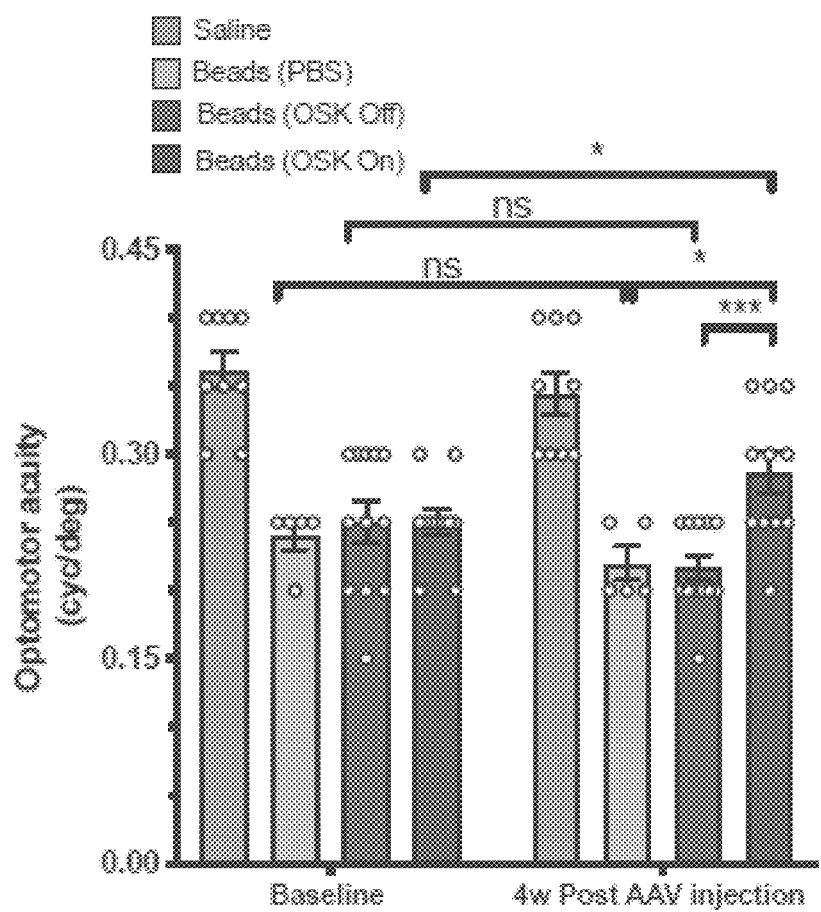
Figure 34G:
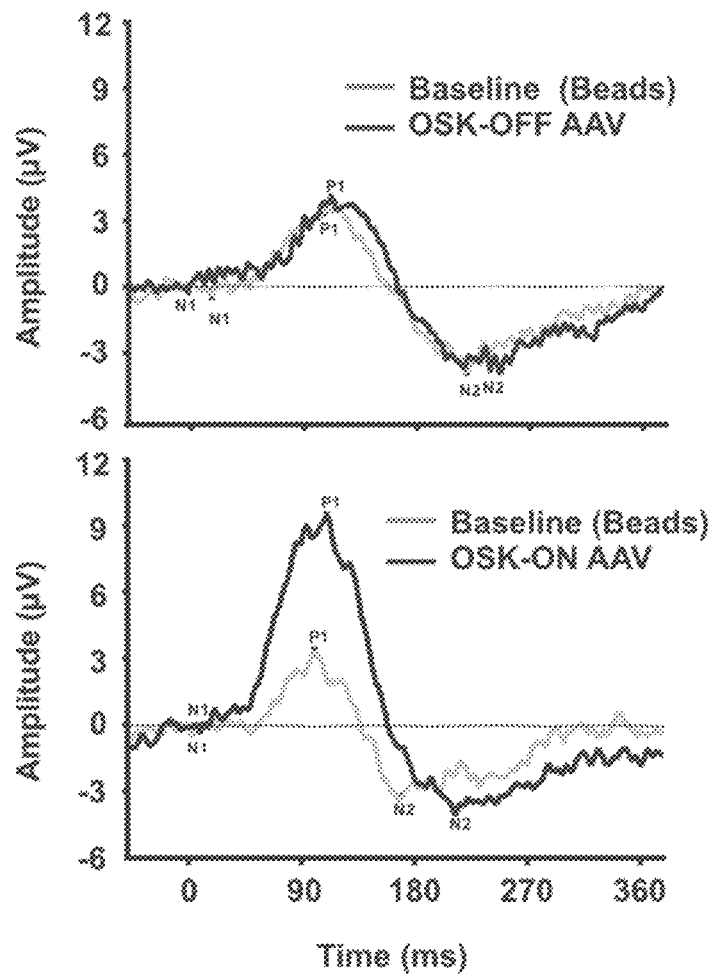
Figure 34H:
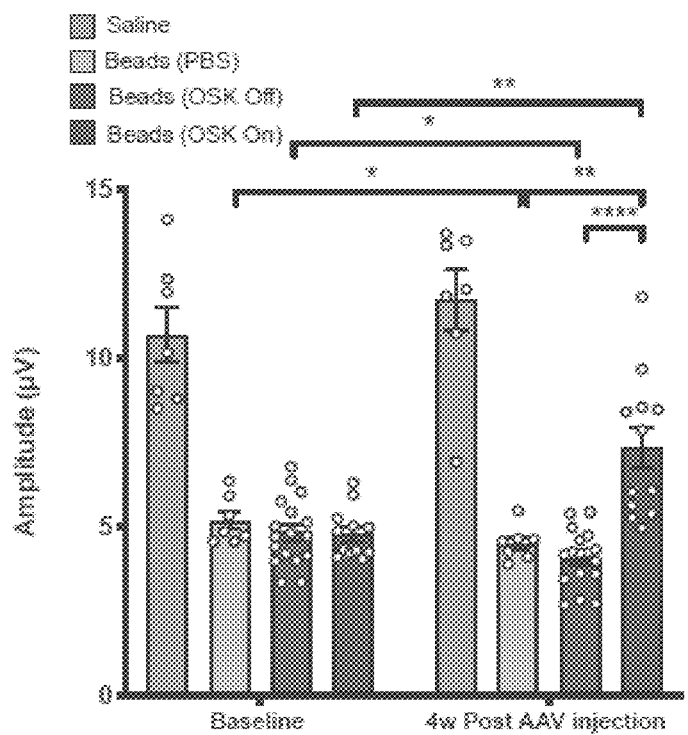

To determine whether the increased axon density observed in OSK treated mice coincided with increased vision, a behavior assay, optomotor response (OMR), was used (FIG. 34E) to track the visual acuity of each mouse. Compared to mice that received either PBS or the OSK-Off AAV, OSK treatment significantly increased visual acuity relative to the pre-treatment baseline measurement, restoring more than half of the vision loss (FIG. 34F). A readout of electrical waves generated by RGCs in response to a reversing contrast checkerboard pattern, known as Pattern electroretinogram response (pERG) analysis, showed that OSK treatment significantly improved RGC function relative to the pre-treatment baseline measurements, as well as, compared with either PBS or OSK-Off AAV treated mice (FIGS. 34G and H). Without being bound by a particular theory, treatment with OSK AAV, as shown herein, may be the first treatment to reverse vision loss in any glaucoma model. Notably, OSK reversed vision loss in a glaucoma model.

Given the ability of OSK to induce axon regeneration following optic nerve crush and to restore vision after glaucomatous damage in young mice, it was determined whether OSK could also restore vision loss associated with physiological aging and regenerate axons following optic nerve injury in aged mice. This is particularly important since a recently reported retinal rod photoreceptor regenerative approach that was successful when treating young mice was significantly diminished when treating older mice (Yao, K., et al., Restoration of vision after de novo genesis of rod photoreceptors in mammalian retinas. Nature, 2018. 560 (7719): p. 484-488.).

Figure 35A:
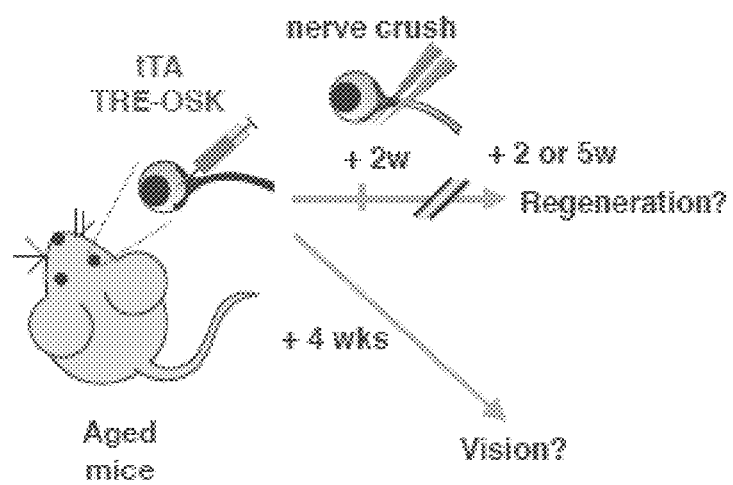
FIGS. 35A-35I show that OSK AAV induces axon regeneration and restores visual function in aged mice.
Figure 35B:
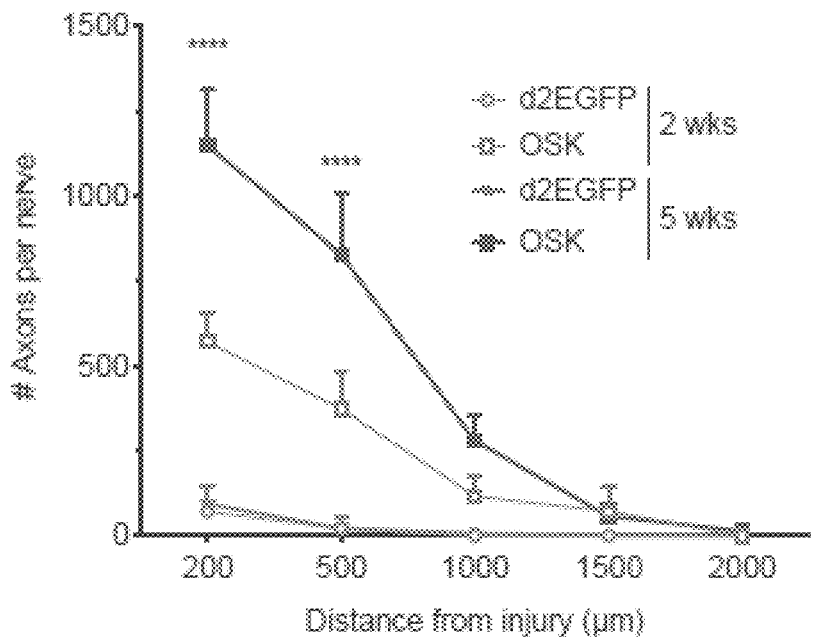
Figure 35C:
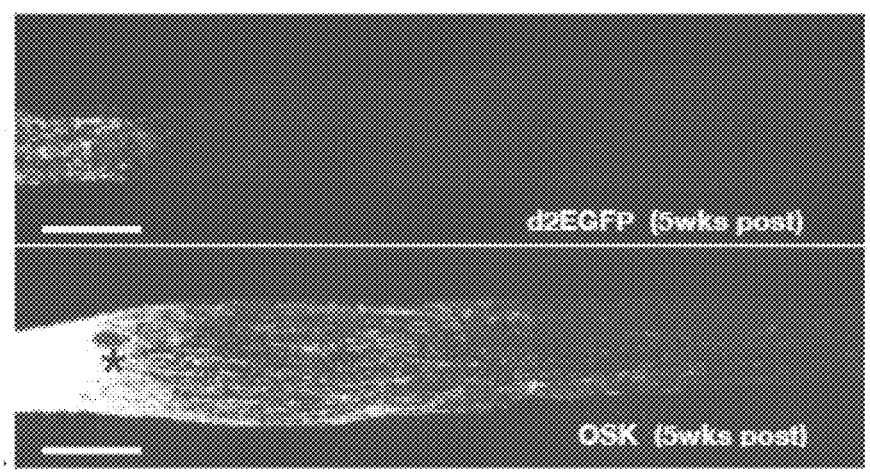
Figure 43A:
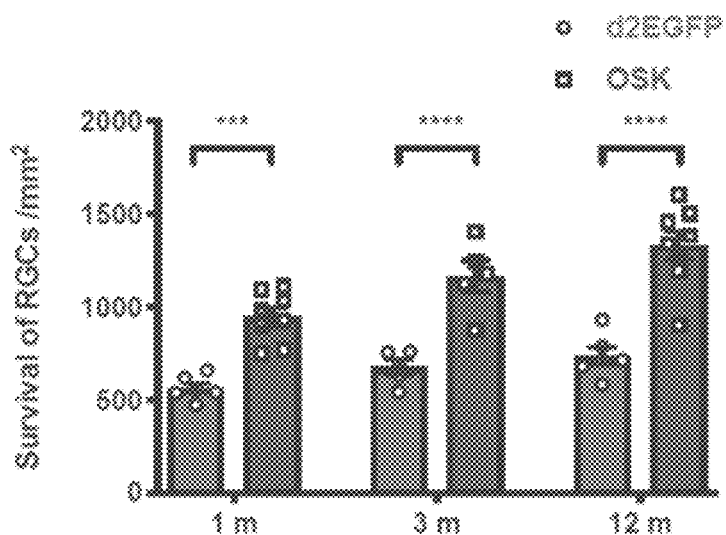
FIG. 43A-43G show the effect of OSK in aged mice.
Figure 43B:
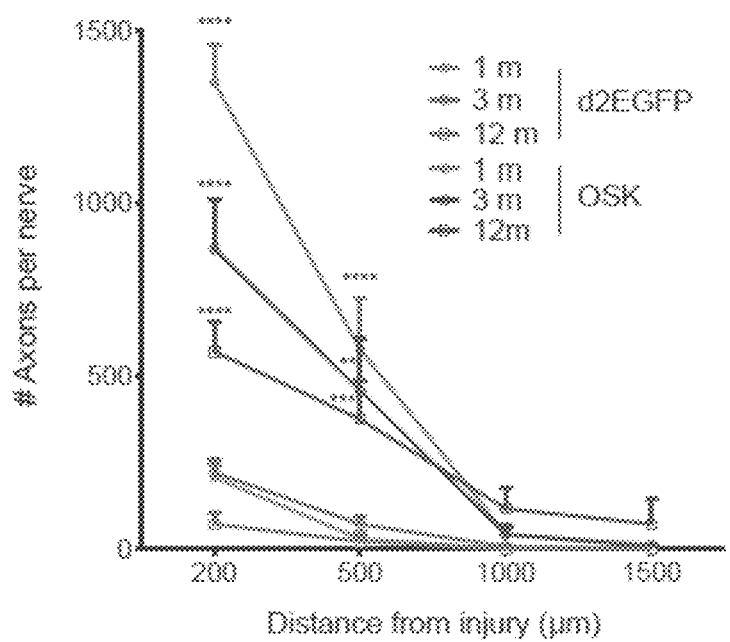

To determine whether OSK AAV treatment could induce axon regeneration in aging mice, the optic nerve crush injury model was performed on 12-month-old mice using the same protocol as in FIG. 32D with the experimental design shown (FIG. 35A). In aged mice, OSK AAV treatment for two weeks post-injury showed doubled RGC survival, similar to that observed in young mice (FIG. 43A). Though the axon regeneration is slightly less than young mice at two weeks post injury (FIG. 43B), OSK AAV treatment in aged mice for five weeks post-injury showed a significant increase in axon regeneration (FIGS. 35B and 35C), similar to that observed in young mice. These data indicate that aging does not diminish the effectiveness of OSK AAV treatment in inducing axon regeneration following an optic nerve crush injury.

Figure 35D:
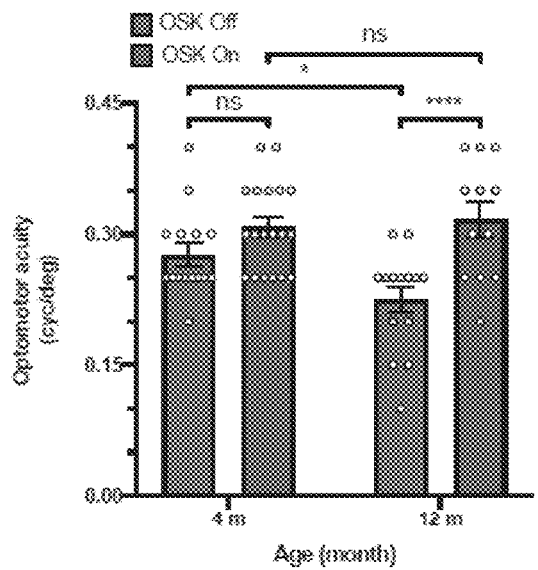
Figure 43C:
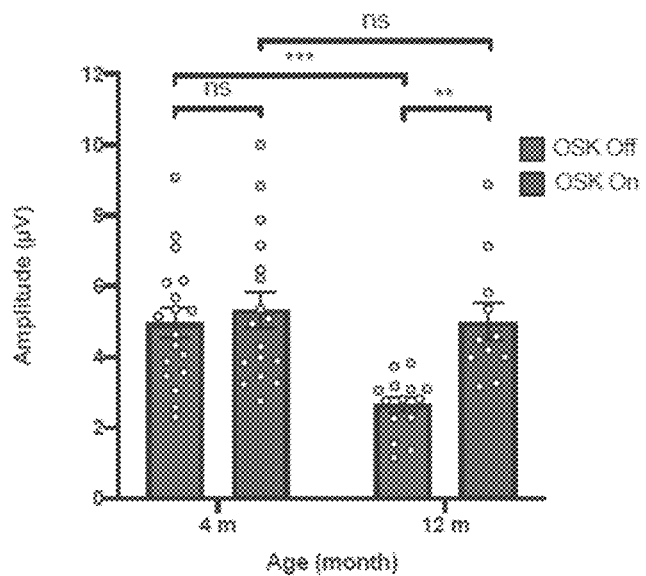
Figure 43D:
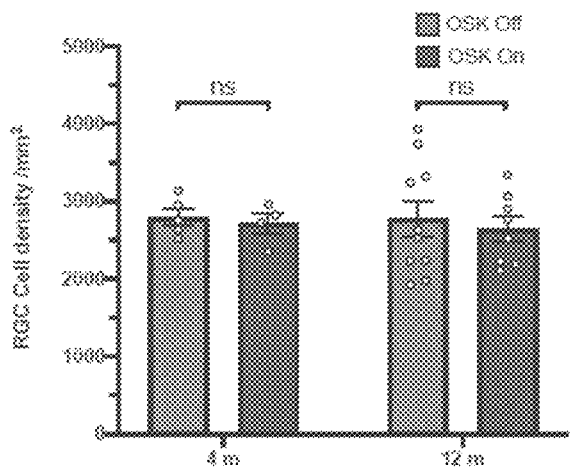
Figure 43E:
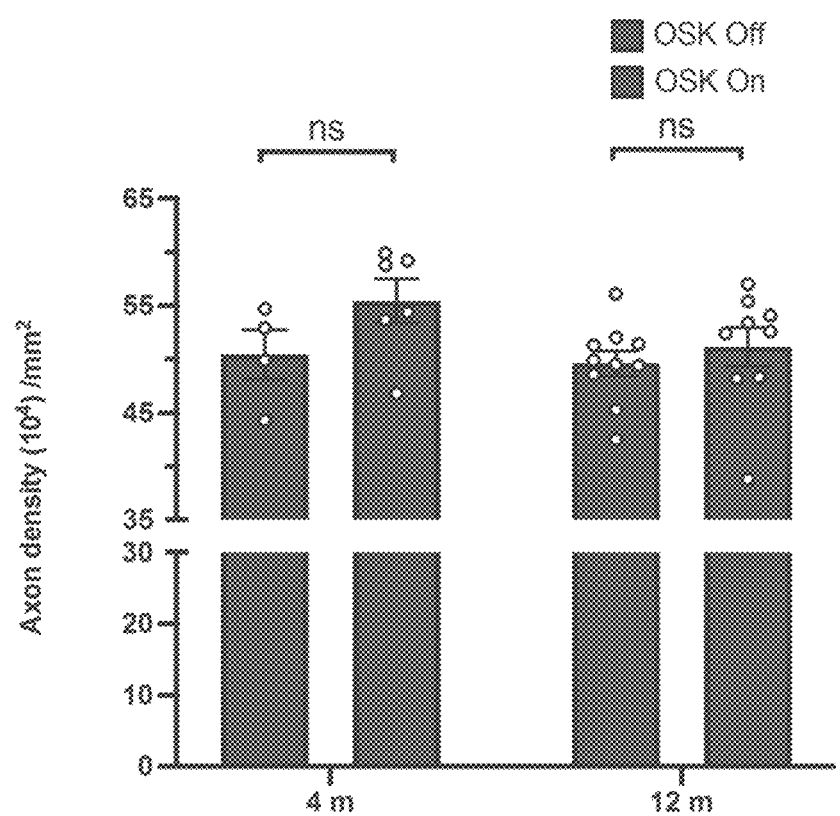
Figure 43F:
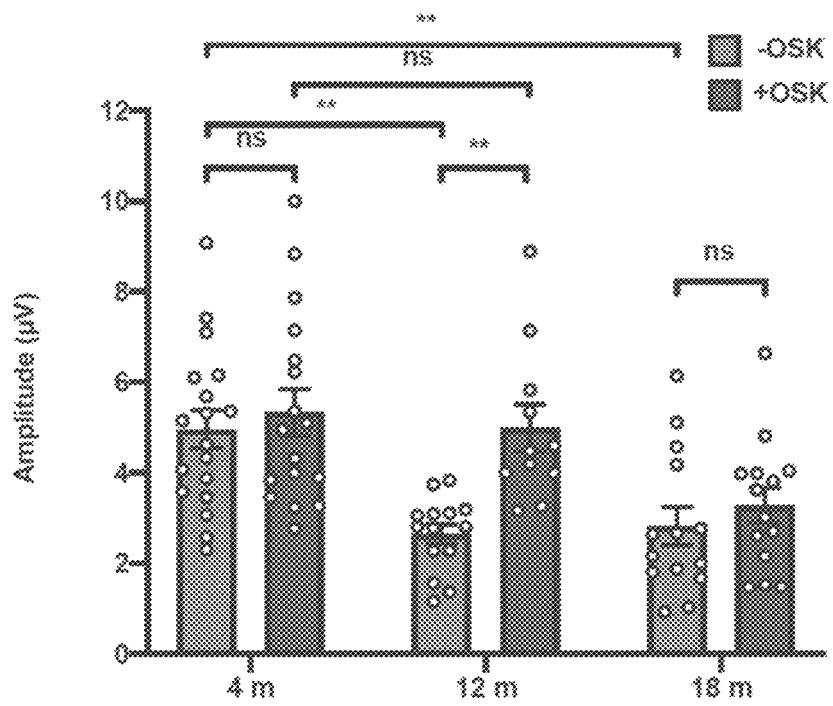
Figure 43G:
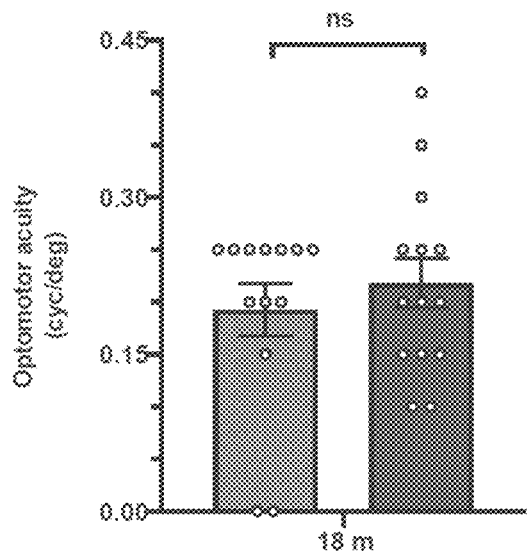

To test whether OSK treatment could reverse vision loss associated with physiological aging, 4- and 12-month-old mice received intravitreal injections of OSK-Off or OSK-On AAV. As expected, at one year of age, mice showed a significant reduction in visual acuity and RGC function as measured by OMR and pERG, which was restored by OSK AAV treatment (FIG. 35D and FIG. 43C). Such restoration was not observed in 18 month-old mice (FIG. 43F-43G) likely due to spontaneous corneal opacity developed at this age (McClellan et al., Am J Pathol 184, 631-643, doi: 10.1016/j.ajpath.2013.11.019 (2014)), suggesting the restoration effect is specifically contributed by AAV-infected RGC layer.

Figure 35E:
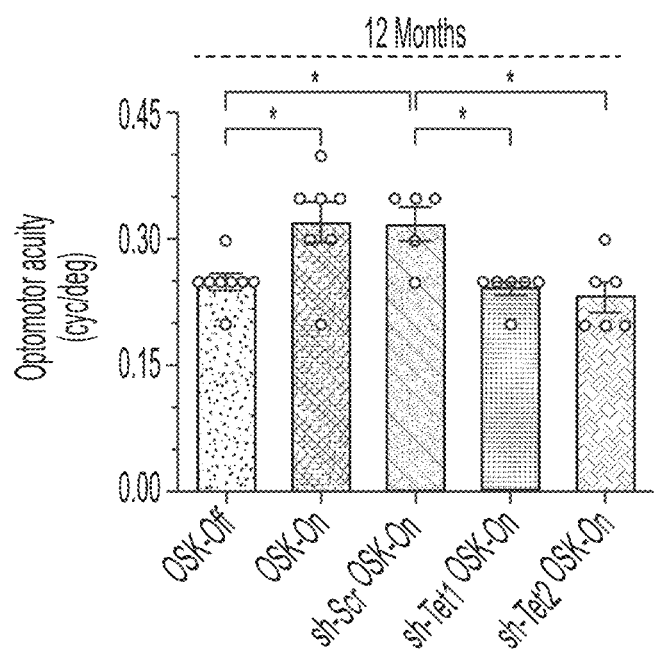
Figure 35F:
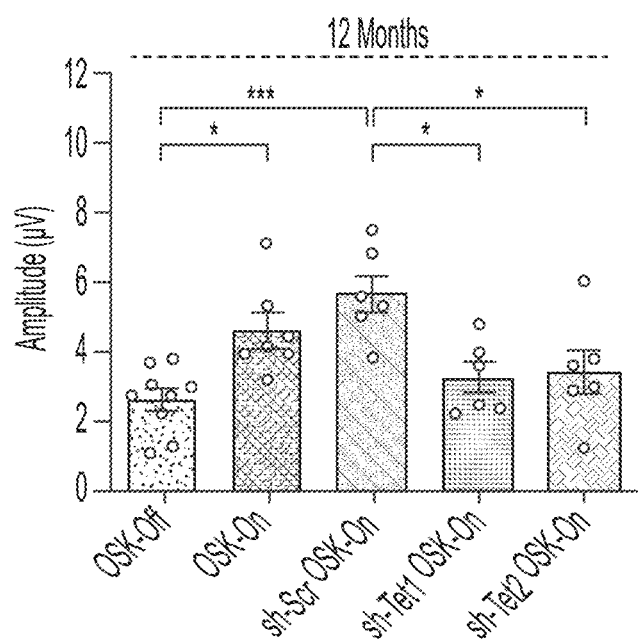

Next, it was determined whether restoration of youthful transcriptome by OSK indicates a youthful epigenome and thus would requires Tet enzymes. Remarkably, Tet1 or Tet2 knockdown completely blocked the rejuvenation effect of OSK-On AAV treatment as measured by both OMR and pERG analyses (FIG. 35E and FIG. 35F), consistent with DNA methylation as the key process for vision restoration. Notably, there is no obvious RGC and axon density increase by OSK in aged mice (FIG. 43D and FIG. 43E), suggesting functional improvement of existing RGCs. The rDNA methylation age of FACS-sorted RGCs from 12 month-old mice was measured. OSK AAV expression for 4 weeks significantly decreased the DNA methylation age and Tet1 and Tet2 knockdown blocked such rejuvenation (FIG. 35I). Together, these results demonstrate that Tet-dependent in vivo reprogramming can restore youthful gene expression patterns, reverse the DNA methylation clock, and restore the function and regenerative capacity of a complex tissue.

Figure 46A:
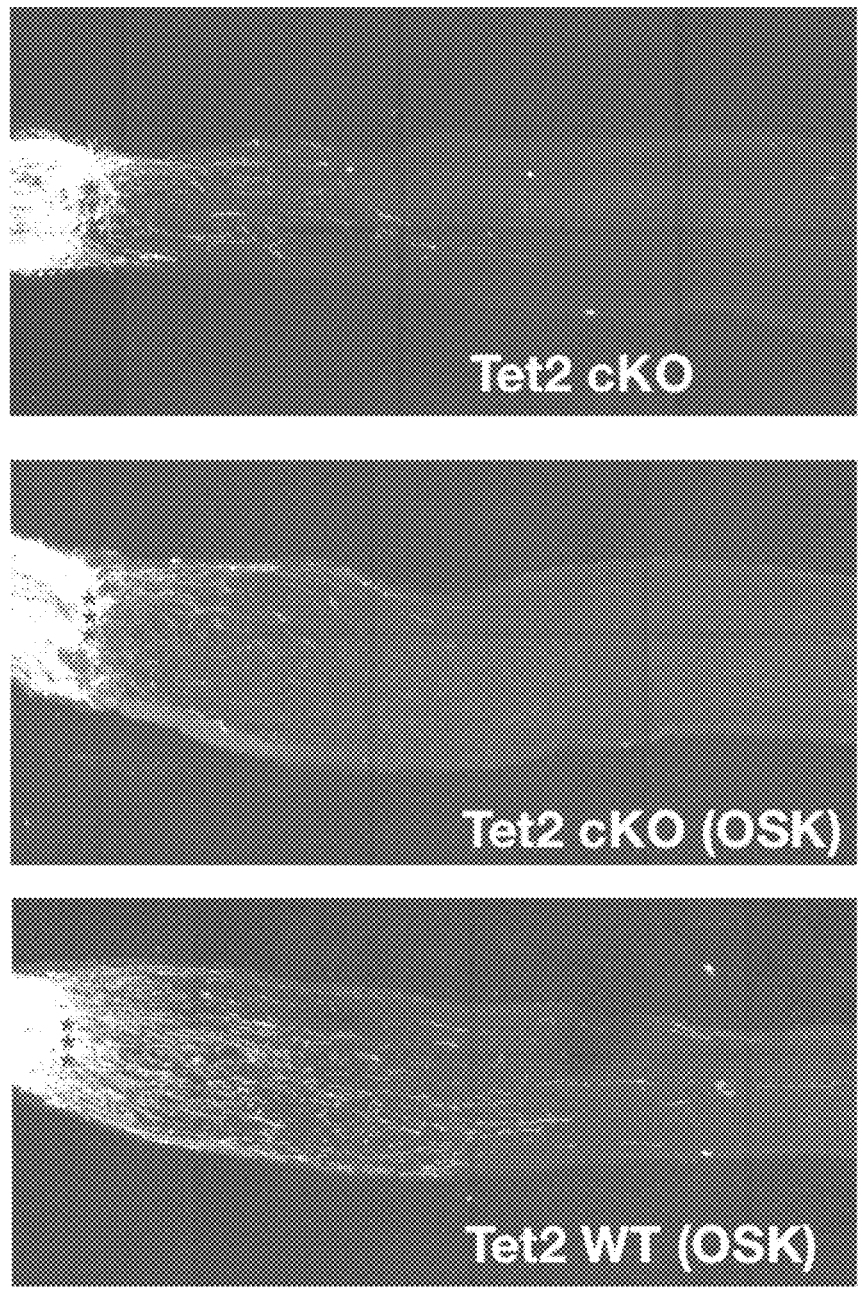
FIGS. 46A-46B show that OSK mediates axon regeneration in a Tet2-dependent manner. A Tet2 conditional knock-out mouse was used. Mouse eyes were injected with (1) AAV-CRE (Tet2 cKO); (2) AAV-tTA+AAV-TRE-OSK: OSK (Tet2 WT); or (3) AAV-tTA+AAV-TRE-OSK+AAV-CRE: OSK (Tet2 cKO). Axon regeneration was assayed after optic nerve crush.
Figure 46B:
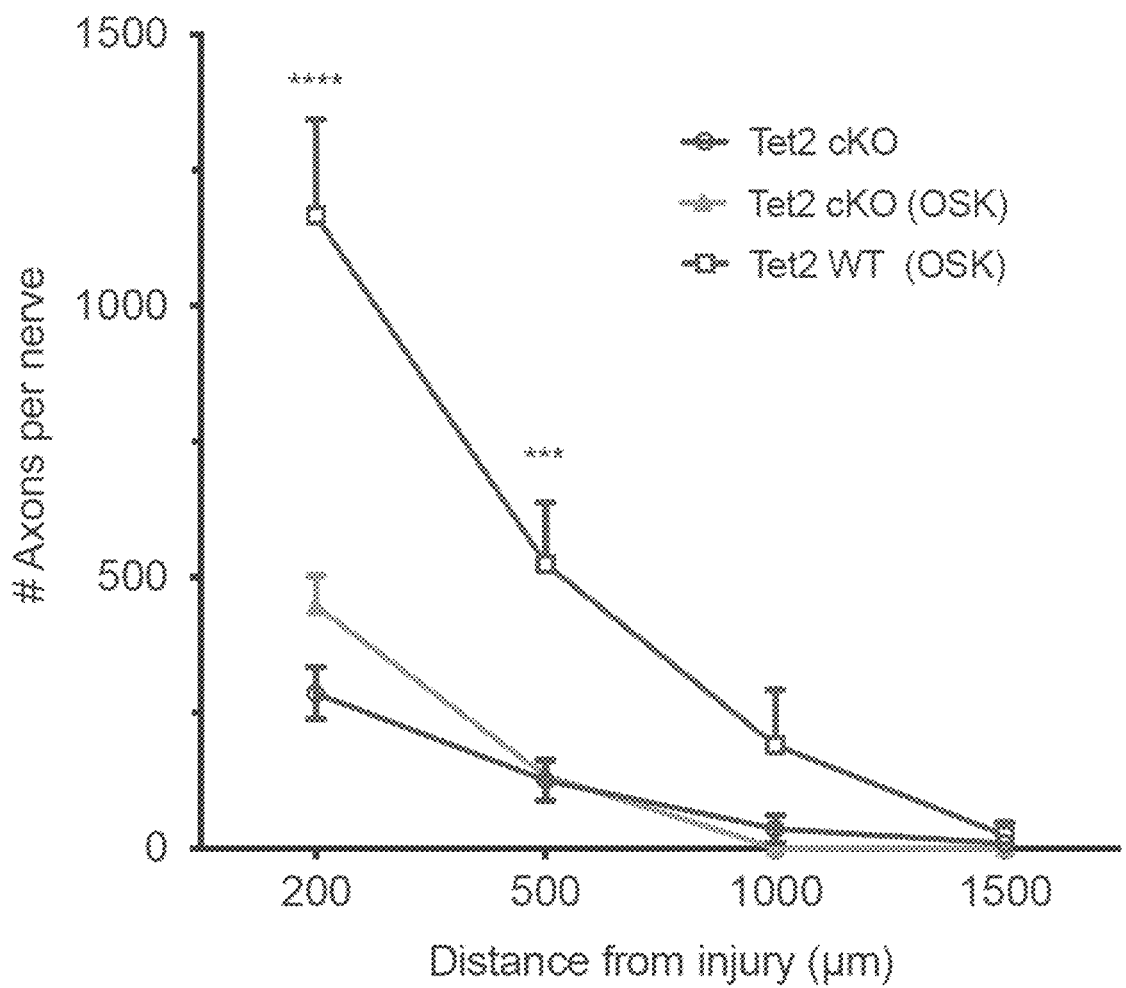

To further determine whether Tet2 knockout can block the effect of OSK on axon regeneration, mouse OSK and Tet2 conditional knockout mice (B6; 129S-Tet2tm1.1Iaai/J) were used. Mouse eyes were injected with (1) AAV–CRE (Tet2 cKO); (2) AAV-tTA+AAV–TRE–OSK: OSK (Tet2 WT); or (3) AAV-tTA+AAV–TRE–OSK+AAV–CRE: OSK (Tet2 cKO). After two weeks, optic nerve crush was conducted. CTB was administered two weeks after optic nerve crush and mice were sacrificed two days after CTB administration to determine the extent of axon regeneration following injury. As shown in FIGS. 46A-46B, the number of axons per nerve up to at least 500 μm from the injury site was significantly higher in Tet2 wild-type mice that were administered OSK as compared to Tet2 knockout mice that were administered OSK. These results suggest that OSK-mediated axon regeneration is Tet2-dependent.

Figure 44A:
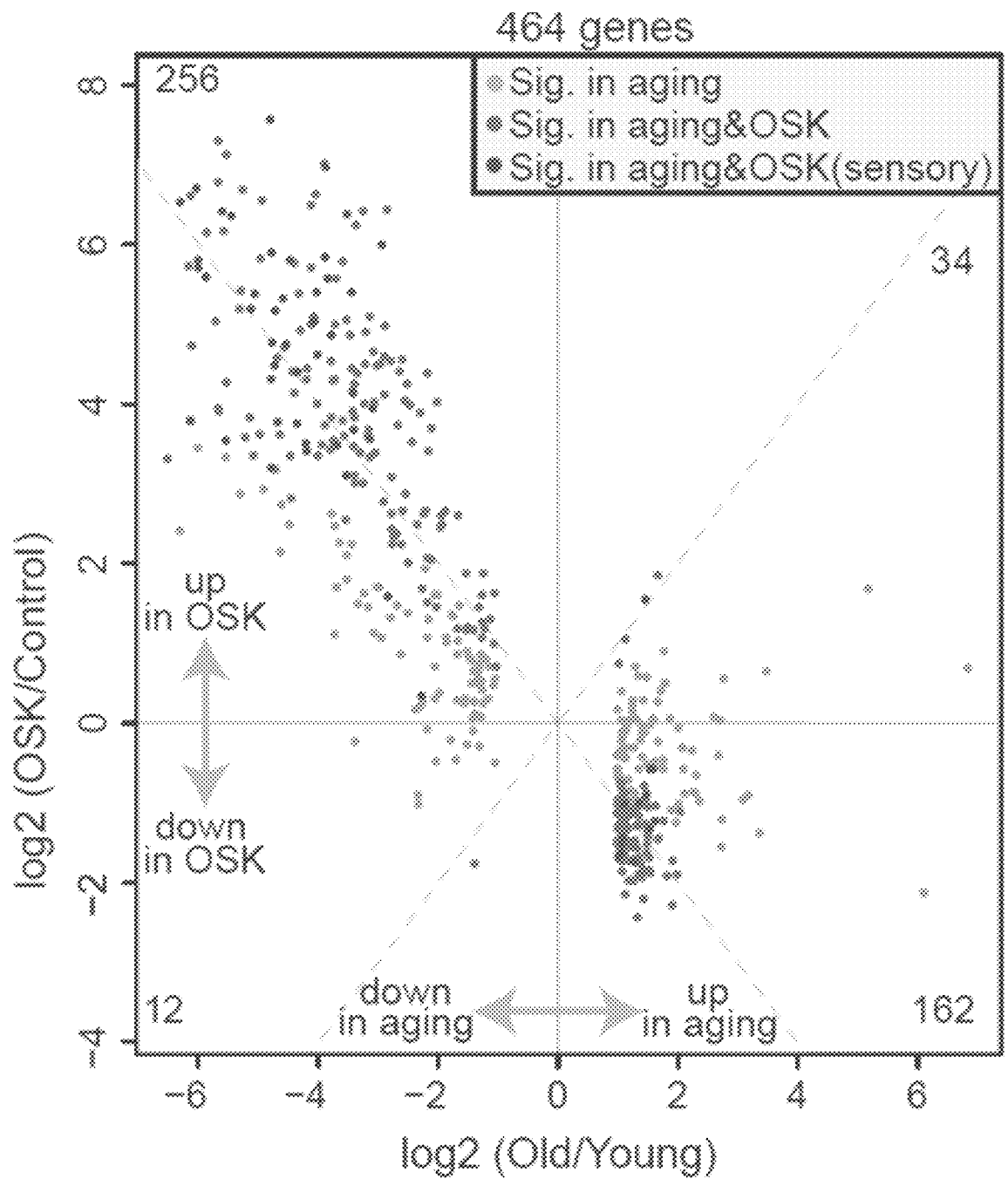
FIGS. 44A-44D show RNA-seq analysis of genes that reset their expression by Reviver treatment.
Figure 44B:
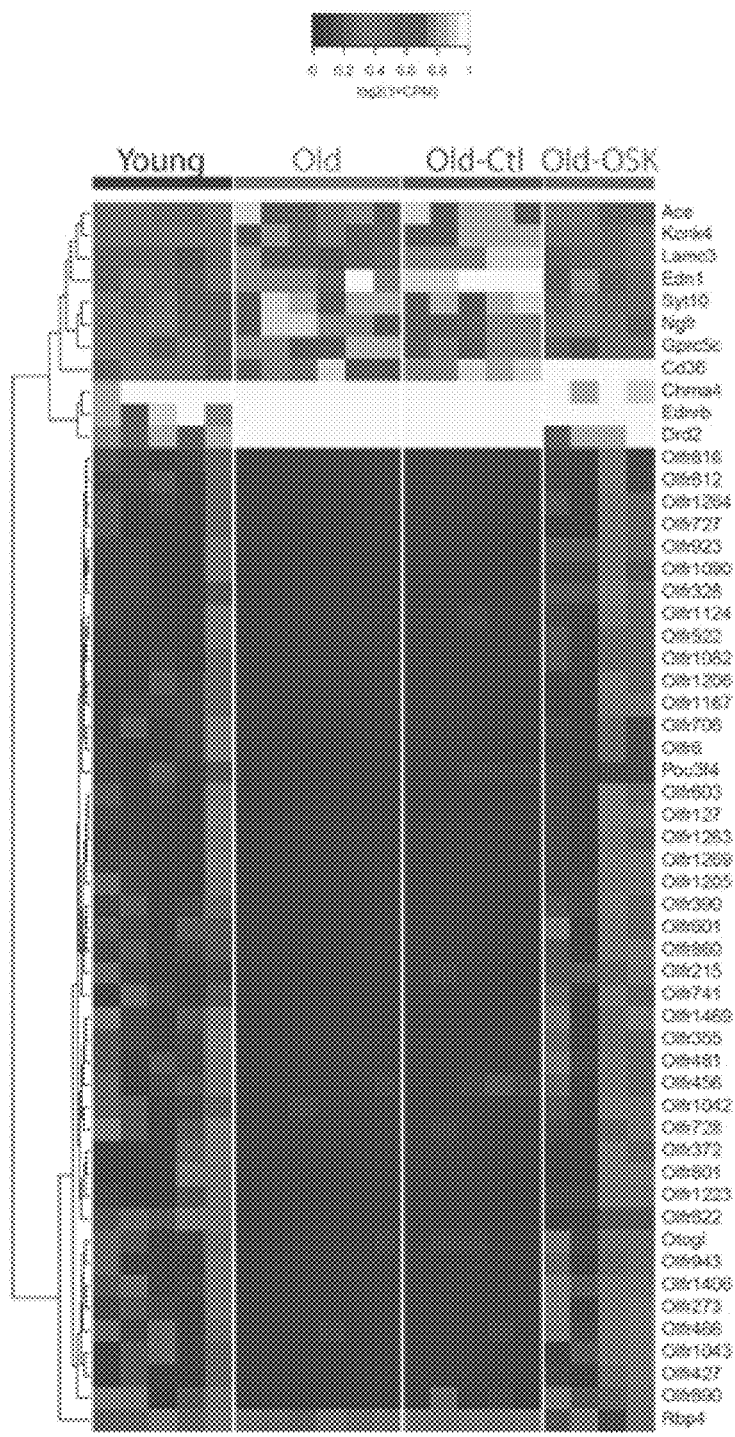
Figure 44C:
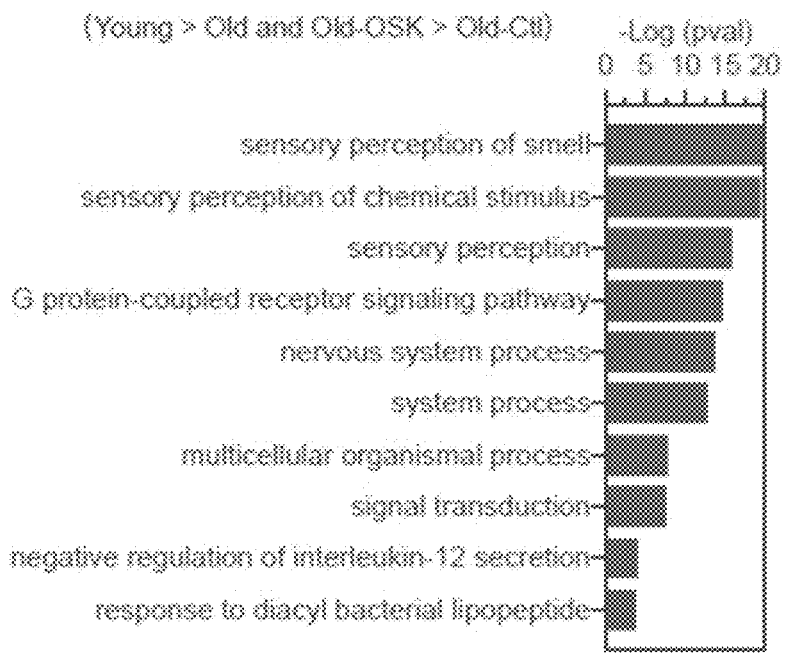
Figure 44D:
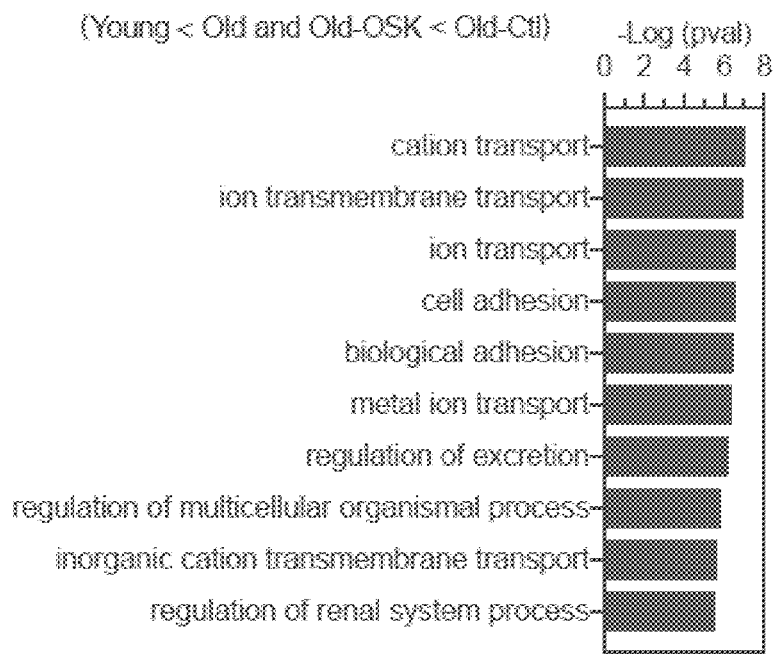

In order to determine the effect of reprogramming on the transcriptome in the retina, FACS-purified RGCs from intact old mice (12 month) and those that were either treated with empty control AAV (TRE-OSK) or OSK-On (tTA+TRE-OSK) were analyzed by genome-wide RNA-seq. Compared to RGCs from intact young mice (5 month), 464 genes were identified that were differentially-expressed during ageing (FIG. 35G, FIG. 35I, FIG. 44A, and Table 5) and not induced by empty AAV alone. Of these, 268 genes were down-regulated during aging which were enriched in sensory perception genes (FIG. 35I), suggesting a decline of signaling receptors/sensory function during aging (FIGS. 44B and 44C). Interestingly, 116 of these genes appear uncharacterized, lacking an official gene name. The other 196 genes that are slightly up-regulated during aging are enriched of ion transporter genes (FIG. 44D).

Figure 35G:
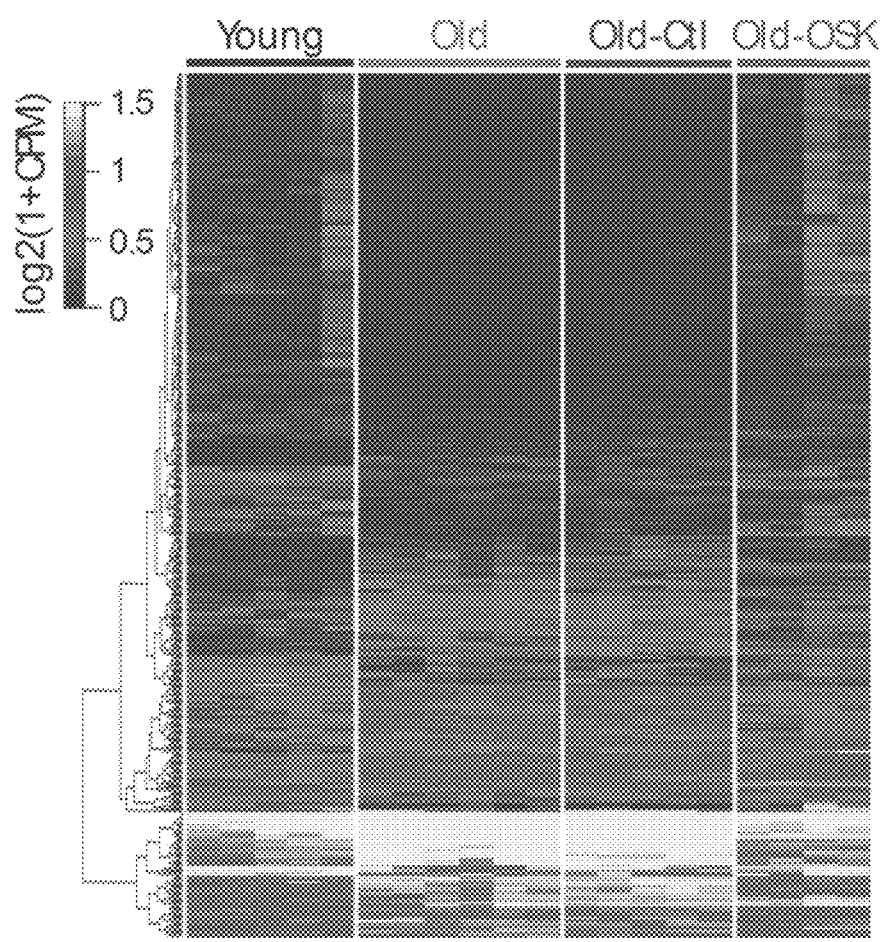
Figure 35H:
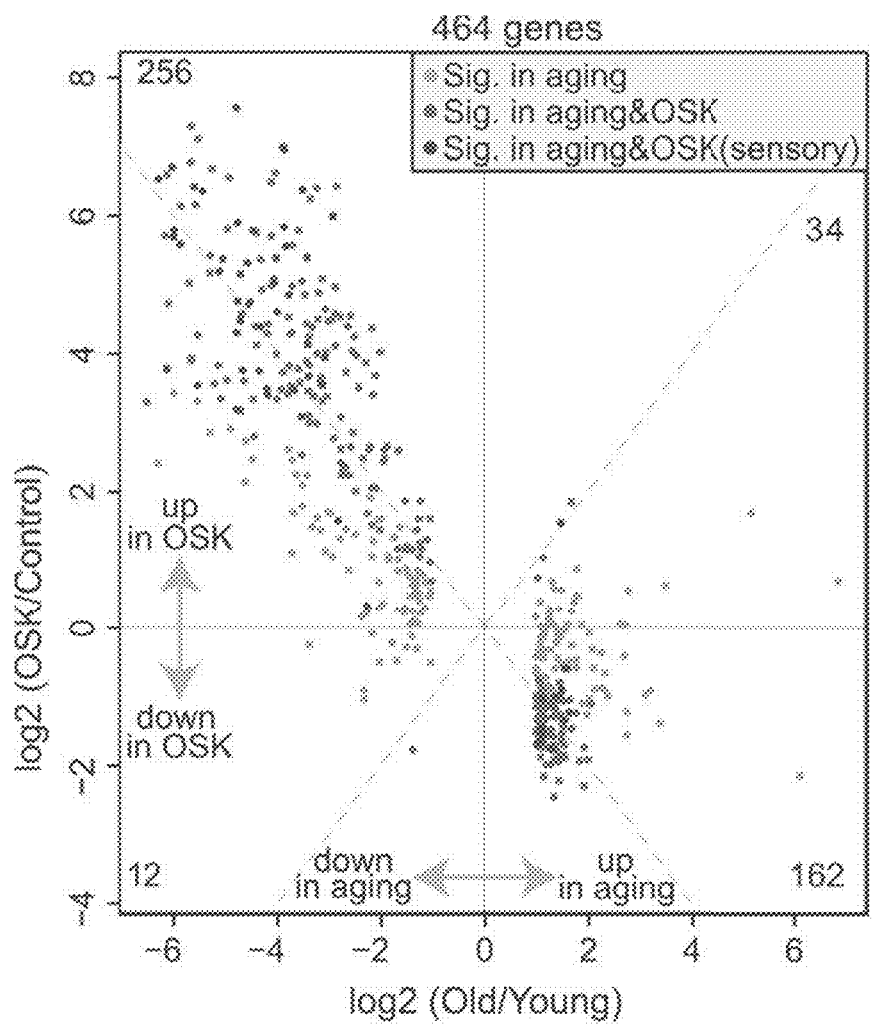
Figure 35I:
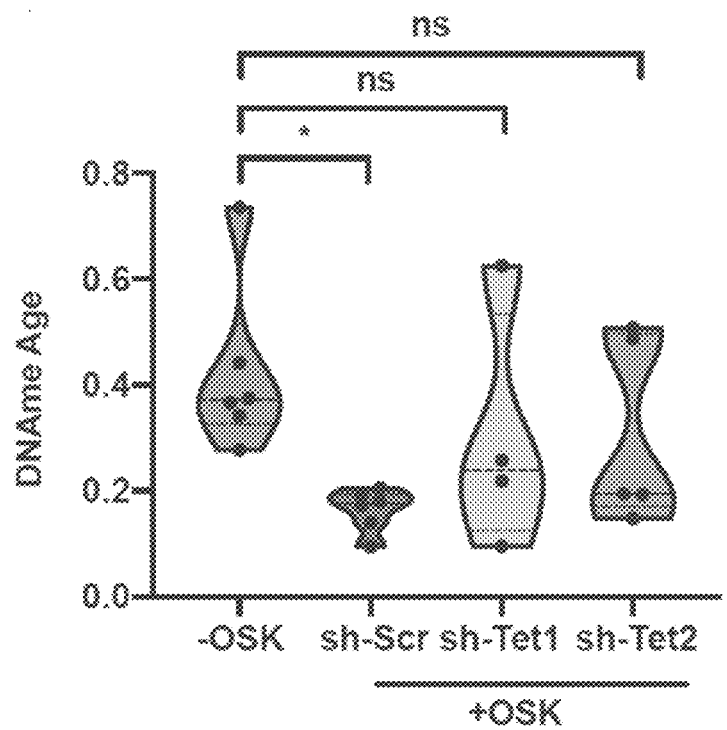

Remarkably, consistent with OSK resetting the epigenomic landscape, the vast majority (90%, 418) of the 464 genes that change in expression during aging were restored towards youthful levels after treatment (FIGS. 35G and 35H). Together, these results demonstrate that Tet-dependent in vivo reprogramming can restore youthful gene expression patterns, reverse the epigenetic clock, and restore the function of a tissue as complex as the retina.

Post-mitotic neurons in the central nervous system are some of the first cells in the body to lose their ability or regenerate. In this study, it was shown that in vivo reprogramming of aged neurons can reverse epigenetic age and allow them to regenerate and function as though they were young again. The requirement of the DNA demethylases Tet1 and Tet2 for this process indicates that DNA methylation at clock sites are not merely an indicator of ageing, but an active participant in it. It was concluded that mammalian cells retain a set of original epigenetic information, in the same way Shannon's observer stores information to ensure the recovery of lost information at a later time (SHANNON, C. E., *A Mathematical Theory of Communication*. The Bell System Technical Journal, 1948. 27: p. 379-423). How cells are able to find and remove the appropriate DNA methylation moieties and restore youthful gene expression patterns is still an open question, but even in the absence of this knowledge, our data indicate that the reversal of epigenetic age could be an effective translational strategy, not just to restore vision, but to give other tissues the ability to recover from injury and resist age-related decline.

TABLE 5

Genes that were differentially expressed during ageing in mice RGCs.

| Downregulated genes | Upregulated Genes |
| --- | --- |
| 1700031P21Rik | 0610040J01Rik |
| 1810053B23Rik | 1700080N15Rik |
| 2900045O20Rik | 2900064F13Rik |
| 2900060B14Rik | 4833417C18Rik |
| 4921504E06Rik | 4921522P10Rik |
| 4930402F11Rik | 4930447C04Rik |
| 4930453C13Rik | 4930488N15Rik |
| 4930455B14Rik | Ace |
| 4930500H12Rik | Ackr1 |
| 4930549P19Rik | Acot10 |
| 4930555B11Rik | Acvr1 |
| 4930556J02Rik | Adamts17 |
| 4932442E05Rik | Adra1b |
| 4933431K23Rik | AI504432 |
| 4933438K21Rik | Best3 |
| 6720475M21Rik | Boc |
| 9830132P13Rik | Cadm3 |
| A430010J10Rik | Cand2 |
| A530064D06Rik | Ccl9 |
| A530065N20Rik | Cd14 |
| Abcb5 | Cd36 |
| Abhd17c | Cfh |
| AC116759.2 | Chrm3 |
| AC131705.1 | Chrna4 |
| AC166779.3 | Cntn4 |
| Acot12 | Cracr2b |
| Adig | Cryaa |
| Akr1c1 | CT573017.2 |
| Ankrd1 | Cyp26a1 |
| Asb15 | Cyp27a1 |
| Atp2c2 | D330050G23Rik |
| AU018091 | D930007P13Rik |
| AW822073 | Ddo |
| Btn110 | Dgkg |
| C130093G08Rik | Dlk2 |
| C730027H18Rik | Dnaja1-ps |
| Ccdc162 | Drd2 |
| Chi16 | Dsel |
| Col26a1 | Dytn |
| Corin | Ecscr |
| Crls1 | Edn1 |
| Cybrd1 | Ednrb |
| Cyp2d12 | Efemp1 |
| Cyp7a1 | Elfn2 |
| D830005E20Rik | Epha10 |
| Dlx3 | Ephx1 |
| Dnah14 | Erbb4 |
| Dsc3 | Fam20a |
| Dthd1 | Fbxw21 |
| Eid2 | Ffar4 |
| Eps811 | Flt4 |
| EU599041 | Fmod |
| Fam90a1a | Foxp4 |
| Fancf | Fzd7 |
| Fau-ps2 | Gabrd |
| Fezf1 | Galnt15 |
| Gja5 | Galnt18 |
| Gm10248 | Gfra2 |
| Gm10513 | Ggt1 |
| Gm10635 | Gm10416 |
| Gm10638 | Gm14964 |
| Gm10718 | Gm17634 |
| Gm10722 | Gm2065 |
| Gm10800 | Gm32352 |
| Gm10801 | Gm33172 |
| Gm11228 | Gm34280 |
| Gm11251 | Gm35853 |
| Gm11264 | Gm36298 |
| Gm11337 | Gm36356 |
| Gm11368 | Gm36937 |
| Gm11485 | Gm3898 |
| Gm11693 | Gm42303 |
| Gm12793 | Gm42484 |
| Gm13050 | Gm42537 |
| Gm13066 | Gm42743 |
| Gm13323 | Gm43151 |
| Gm13339 | Gm43843 |
| Gm13346 | Gm44545 |
| Gm13857 | Gm44722 |
| Gm14387 | Gm45516 |
| Gm14770 | Gm45532 |
| Gm15638 | Gm47494 |
| Gm16072 | Gm47982 |
| Gm16161 | Gm47989 |
| Gm16181 | Gm48398 |
| Gm17200 | Gm48495 |
| Gm17791 | Gm48593 |
| Gm18025 | Gm48958 |
| Gm18757 | Gm49089 |
| Gm18795 | Gm49326 |
| Gm18848 | Gm49331 |
| Gm19719 | Gm49760 |
| Gm20121 | Gm5796 |
| Gm20356 | Gm6374 |
| Gm2093 | Gm7276 |
| Gm21738 | Gm8237 |
| Gm21940 | Gm9796 |

TABLE 5-continued

Genes that were differentially expressed during ageing in mice RGCs.

| Downregulated genes | Upregulated Genes |
|---|---|
| Gm22933 | Gm9954 |
| Gm24000 | Gpr75 |
| Gm24119 | Gprc5c |
| Gm25394 | Grid2ip |
| Gm26555 | Gsg1l2 |
| Gm27047 | Hapln4 |
| Gm28262 | Hcn3 |
| Gm28530 | Hoxl4 |
| Gm29295 | Hhat1 |
| Gm29825 | Hs6st2 |
| Gm29844 | Htr3a |
| Gm3081 | Il1rap |
| Gm32051 | Il1rapl2 |
| Gm32122 | Inka1 |
| Gm33056 | Kbtbd12 |
| Gm33680 | Kcnj11 |
| Gm34354 | Kcnk4 |
| Gm34643 | Kdelc2 |
| Gm3551 | Klhl33 |
| Gm36660 | Lamc3 |
| Gm36948 | Lilra5 |
| Gm37052 | Lman1l |
| Gm37142 | Lrfn2 |
| Gm37262 | Lrrc38 |
| Gm37535 | Lrrn4cl |
| Gm37569 | Ltc4s |
| Gm37589 | Manscl |
| Gm37647 | Mir344c |
| Gm37648 | Msr1 |
| Gm37762 | Mycbpap |
| Gm38058 | Myoc |
| Gm38069 | Ngfr |
| Gm38137 | Nipal2 |
| Gm38218 | Olfr1372-ps1 |
| Gm39139 | Otop3 |
| Gm42535 | P2rx5 |
| Gm42680 | P2ry12 |
| Gm42895 | P4ha2 |
| Gm42994 | Pcdha12 |
| Gm43027 | Pcdha2 |
| Gm43158 | Pcdhac2 |
| Gm43288 | Pcdhb18 |
| Gm43366 | Pcdhb5 |
| Gm44044 | Pcsk2os1 |
| Gm44081 | Pcsk6 |
| Gm44187 | Perp |
| Gm44280 | Pkp1 |
| Gm44535 | Plxna4 |
| Gm45338 | Prickle2 |
| Gm45644 | Qsox1 |
| Gm45740 | Rapgef4os2 |
| Gm46555 | Rbp4 |
| Gm46565 | Rcn3 |
| Gm4742 | Sec14l5 |
| Gm47485 | Sell3 |
| Gm47853 | Serpinh1 |
| Gm47992 | Sgpp2 |
| Gm48225 | Shisa6 |
| Gm48314 | Siah3 |
| Gm48383 | Siglech |
| Gm48673 | Slc12a4 |
| Gm48804 | Slc24a2 |
| Gm48832 | Slc2a5 |
| Gm4994 | Slc4a4 |
| Gm5487 | Slitrk3 |
| Gm5724 | Smagp |
| Gm595 | Smoc2 |
| Gm6012 | Speer4b |
| Gm6024 | Spon2 |
| Gm7669 | Sstr2 |
| Gm7730 | Sstr3 |
| Gm8043 | St3gal3 |
| Gm8953 | Stc1 |
| Gm9348 | Stc2 |
| Gm9369 | Syndig1 |
| Gm9495 | Syt10 |
| H2al2a | Thsd7a |
| Ido2 | Tlr8 |
| Igfbp1 | Tmem132a |
| Kif7 | Tmem132d |
| Klhl31 | Tmem200a |
| Lrrc31 | Tmem44 |
| Mc5r | Trpc4 |
| Mgam | Trpv4 |
| Msh4 | Unc5b |
| Muc12 | Vgf |
| Mug1 | Vmn1r90 |
| Myb12 | Vwc21 |
| Myh15 | Wfikkn2 |
| Nek10 | Wnt11 |
| Neurod6 | Wnt6 |
| Nr1h5 | Zeb2os |
| Olfr1042 | Zfp608 |
| Olfr1043 | Zfp976 |
| Olfr1082 | |
| Olfr1090 | |
| Olfr1124 | |
| Olfr1167 | |
| Olfr1205 | |
| Olfr1206 | |
| Olfr1223 | |
| Olfr1263 | |
| Olfr1264 | |
| Olfr1269 | |
| Olfr127 | |
| Olfr1291-ps1 | |
| Olfr1406 | |
| Olfr1469 | |
| Olfr215 | |
| Olfr273 | |
| Olfr328 | |
| Olfr355 | |
| Olfr372 | |
| Olfr390 | |
| Olfr427 | |
| Olfr456 | |
| Olfr466 | |
| Olfr481 | |
| Olfr522 | |
| Olfr6 | |
| Olfr601 | |
| Olfr603 | |
| Olfr706 | |
| Olfr727 | |
| Olfr728 | |
| Olfr741 | |
| Olfr801 | |
| Olfr812 | |
| Olfr816 | |
| Olfr822 | |
| Olfr860 | |
| Olfr890 | |
| Olfr923 | |
| Olfr943 | |
| Otogl | |
| Pi15 | |
| Pkhd1 | |
| Pkhd1l1 | |
| Platr6 | |
| Pou3f4 | |
| Prr9 | |
| Pvalb | |
| Rhag | |
| Sav1 | |
| Serpinb9b | |
| Skint1 | |
| Skint3 | |
| Skint5 | |
| Slc10a5 | |
| Slc6a4 | |
| Smok2a | |
| Tcaf3 | |

TABLE 5-continued

Genes that were differentially expressed during ageing in mice RGCs.

| Downregulated genes | Upregulated Genes |
|---|---|
| Tomm20l | |
| Trcg1 | |
| Trdn | |
| Ugt1a6a | |
| Usp17la | |
| Vmn1r178 | |
| Vmn1r179 | |
| Vmn1r33 | |
| Vmn1r74 | |
| Vmn1r87 | |
| Vmn2r102 | |
| Vmn2r113 | |
| Vmn2r17 | |
| Vmn2r52 | |
| Vmn2r66 | |
| Vmn2r68 | |
| Vmn2r76 | |
| Vmn2r78 | |
| Wnt16 | |

Methods

Mouse Lines

C57BL6/J wild type mice are purchased from Jackson Laboratory(000664) for optic nerve crush and glaucoma model experiment. For ageing experiment, females from NIA Aged Rodent Colonies (https://www.nia.nih.gov/research/dab/aged-rodent-colonies-handbook) are used. Col1a1-tetOP-OKS-mCherry/Rosa26-M2rtTA alleles are described in Bar-Nur et al., Nat Methods. 2014. 11(11): p. 1170-6. All animal work was approved by Harvard Medical School, Boston Children's Hospital, Mass Eye and Ear Institutional animal care and use committees.

Production of AAVs

Vectors of AAV–TRE–OSK were made by cloning mouse Oct4, Sox2 and Klf4 cDNA into an AAV plasmid consisting of the a Tet Response Element (TRE3G promoter) and SV40 element. The other vectors were directly chemically synthesized. All pAAVs, as listed in Table 6, were then packaged into AAVs of serotype 2/2 or 2/9 (titers: $>5 \times 10^{12}$ genome copies per milliliter). Adeno associated viruses were produced by Boston Children's Hospital Viral Core.

Systemical Delivery of AAV9 to Internal Organs

Expression in internal organs was achieved through retro-orbital injection of AAV9 ($3 \times 10^{11}$ TRE–OSK plus $7 \times 10^{11}$ UBC–rtTA4). 1 mg/mL doxycycline was treated 3 weeks post injection continuously to induce OSK expression.

Cell Culture and Differentiation

Ear fibroblasts (EFs) were isolated from Reprogramming 4F (Jackson Laboratory 011011) or 3F (Hochedlinger lab) mice and cultured at 37° C. in DMEM (Invitrogen) containing Gluta-MAX, non-essential amino acids, and 10% fetal bovine serum (FBS). EFs of WT 4F and WT 3F mice were passaged to P3 and treated with doxycycline (2 mg/ml) for the indicated time periods in the culture medium.

SH-SY5Y neuroblastoma cells were obtained from the American Tissue Culture Collection (ATCC, CRL-2266) and maintained according to ATCC recommendations. Basically, the cells were cultured in a 1:1 mixture of Eagle's Minimum Essential Medium (EMEM, ATCC, 30-2003) and F12 medium (ThermoFisher Scientific, 11765054), supplemented with 10% fetal bovine serum (FBS, Sigma, F0926) and 1× penicillin/streptomycin (ThermoFisher Scientific, 15140122). Cells were cultured at 37° C. with 5% $CO_2$ and 3% $O_2$. Cells were passaged when reaching ~80% confluency.

SH-SY5Y cells were differentiated into neurons as previously describedl,2, with some modifications. Briefly, 1 day after plating, cells started to be differentiated in EMEM/F12 medium (1:1) containing 2.5% FBS, 1x penicillin/streptomycin, and 10 μM all-trans retinoic acid (ATRA, Stemcell Technologies, 72264) (Differentiation Medium 1) for 3 days, followed by treating the cells in EMEM/F12 (1:1) containing 1% FBS, 1×penicillin/streptomycin, and 10 μM ATRA (Differentiation Medium 2) for 3 days. Cells were then splitted into 35 mm cell culture plates coated with poly-D-lysine (ThermoFisher Scientific, A3890401). 1 day after splitting, neurons were matured in serum-free neurobasal/B27 plus culture medium (ThermoFisher Scientific, A3653401) containing 1×Glutamax (ThermoFisher Scientific, 35050061), 1×penicillin/streptomycin, and 50 ng/ml BDNF (Alomone labs) (Differentiation Medium 3) for at least 5 days.

Neurite Regeneration Assay

The differentiated neurons from SH-SY5Y cells were transduced with AAV.DJ vectors at $10^6$ genome copy per cell. 5 days after transduction, 100 nM vincristine (Sigma, V8879) was added to the cells for 24 hours to induce neurite degeneration. After vincristine treatment, neurons were washed in PBS twice and fresh Differentiation medium 3 was added back to the plates. Neurons were followed for neurite outgrowth for 2-3 weeks. Phase-contrast images were taken at 100× magnification every three to four days. Neurite area was quantified using Image J.

Cell Cycle Analysis

Cells were harvested and fixed with 70% cold ethanol for 16 hours at 4° C. After fixation, cells were washed twice with PBS, followed by incubation with PBS containing 50 g/mL propidium iodide (Biotium, 40017) and 100 μg/mL RNase A (Omega) for 1 hour at room temperature. PI stained samples were analyzed on BD LSR II analyzer, and only single cells were gated for analysis. Cell cycle profiles were analyzed using FCS Express 6 (De Novo Software).

Human Neuron Methylation Studies and Epigenetic Clock

DNA was extracted from cells using the Zymo Quick DNA mini-prep plus kit (D4069) according to the manufacturer's instructions and DNA methylation levels were measured on Illumina 850 EPIC arrays according to the manufacturer's instructions. The Illumina BeadChip (EPIC) measures bisulfite-conversion-based, single-CpG resolution DNAm levels at different CpG sites in the human genome. These data were generated by following the standard protocol of Illumina methylation assays, which quantifies methylation levels by the $\beta$ value using the ratio of intensities between methylated and un-methylated alleles. Specifically, the $\beta$ value is calculated from the intensity of the methylated (M corresponding to signal A) and un-methylated (U corresponding to signal B) alleles, as the ratio of fluorescent signals $\beta=Max(M,0)/[Max(M,0)+Max(U,0)+100]$. Thus, $\beta$ values range from 0 (completely un-methylated) to 1 (completely methylated). We used the "noob" normalization method, which is implemented in the "minfi" R package (Triche et al., NAR 2013, Fortin et al., Bioinformatics 2017). The mathematical algorithm and available software underlying the skin & blood clock (based on 391 CpGs) is presented in Horvath et al., Aging 2018.

AAV2 Virus Intravitreal Injection

For intravitreal injection, adult animals were anesthetized with ketamine/xylazine (100/10 mg/kg) and then AAV (1-3 μl) was injected intravitreally, just posterior to the limbus-parallel conjunctival vessels, with a fine glass pipette attached to the Hamilton syringe using plastic tubing. In elevated IOP model, mice received a 1 µl intravitreal injection between 3-4 weeks post microbead injection.

Optic Nerve Crush

For optic nerve crush in anesthetized animals, the optic nerve was accessed intraorbitally and crushed using a pair of Dumont #5 forceps (FST), two weeks after AAV injection. Alexa-conjugated cholera toxin beta subunit (CTB-555, 1 mg/ml; 1-2 µl) injection was performed 2-3 days before euthanasia to trace regenerating RGC axons. More detailed surgical methods were described by Park et al., Science, 2008. 322(5903): p. 963-6.

In Vivo Doxycycline Induction or Suppression

Induction of Tet-On system or suppression of Tet-Off system in the retina were performed by administration of doxycycline hyclate(2 mg/ml) (Sigma) in the drinking water. Induction of Tet-On system in the whole body were performed by administration of doxycycline (1 mg/ml) (USP grade, MP Biomedicals 0219895505) in the drinking water.

Axon Regeneration Quantification

Number of regenerating axons in the optic nerve was estimated by counting the number of CTB-labeled axons at different distances from the crush site as described previously (Park, K. K., et al., *Promoting axon regeneration in the adult CNS by modulation of the PTEN/mTOR pathway*. Science, 2008. 322(5903): p. 963-6).

Whole-Mount Optic Nerve Preparation

Optic nerves and connecting chiasm were dehydrated in methanol for 5 min, then incubated overnight with Visikol® HISTO-1™. Next day nerves were transferred to Visikol® HISTO-2™ and then incubated for 3 hr. Finally, optic nerves and connecting chiasm were mounted with Visikol® HISTO-2™.

Immunofluorescence

Whole-mount retinas were blocked with horse serum 4° C. overnight then incubated at 4° C. for 3 days with primary antibodies: Mouse anti-Oct4 (1:100, BD bioscience, 611203), Rabbit anti-Sox2 (1:100, Cell signaling, 14962), Goat anti-Klf4 (1:100, R&D system, AF3158), Rabbit anti-Brn3a (1:200, EMD Millipore, MAB1585), and Guinea pig anti-RBPMS (1:400, Raygene custom order A008712 to peptide GGKAEKENTPSEANLQEEEVRC) diluted in PBS, BSA (3%) Triton X-100 (0.5%). Then, tissues were incubated at 4° C. overnight with appropriate Alexa Fluor conjugate secondary antibodies (Alexa 405, 488, 567, 674; Invitrogen) diluted with the same blocking solution as the primary antibodies, generally used at 1:400 final dilution. For section staining, primary overnight at 4° C. and then secondary at room temperature for 2 h. Sections or whole-mount retinas were mounted with VECTASHIELD Antifade Mounting Medium.

Western Blot

SDS-PAGE and western blot analysis was performed according to standard procedures and detected with the ECL detection kit. Antibody used: Rabbit anti-Sox2 (1:100, EMD Millipore, AB5603), Mouse anti-Klf4 (1:1000, ReproCell, 09-0021), Rabbit anti-p-S6 (S240/244) (1:1000, CST, 2215), Mouse anti-S6 (1:1000, CST, 2317), Mouse anti-β-Tubulin (1:1000, Sigma-Aldrich, 05-661), Mouse anti-β-Actin-Peroxidase antibody (1:20,000, Sigma-Aldrich, A3854).

RGCs Survival and Phospho-S6 Signal

RBPMS-positive cells in the ganglion layer were counted using a fluorescent microscope after immunostaining whole-mount retinas with anti-RBPMs antibodies. A total of four random fields per retina were enumerated. The average number per field was determined, and the percentages of viable RGCs were obtained by comparing the values determined from the uninjured contralateral retinas. In the same condition, after phospho-S6 staining, the densities of phospho-S6-positive RGCs were obtained by comparing the value from the uninjured contralateral retinas.

RGC Enrichment

Retinas were fresh dissected and dissociated in AMES media using papain, then triturated carefully and stained with Thy1.2-PE-Cy7 anti-body (Invitrogen 25-0902-81) and Calcine Blue live-dead cell stain, then flow sorted on a BD FACS Aria using an 130 µm nozzle to collect over 10,000 Thy1.2+ and Clacine blue+ cells (1-2% of total events). Freezed cells were sent to Genewiz for RNA extraction and ultra low input RNA-seq sequencing, or to Zymo research for DNA extraction and ultra low input RRBS sequencing.

Classic RRBS Library Preparation

DNA was extracted using Quick-DNA Plus Kit Microprep Kit. 2-10 ng of starting input genomic DNA was digested with 30 units of MspI (NEB). Fragments were ligated to pre-annealed adapters containing 5'-methyl-cytosine instead of cytosine according to Illumina's specified guidelines. Adaptor-ligated fragments ≥50 bp in size were recovered using the DNA Clean & Concentrator™-5 (Cat #: D4003). The fragments were then bisulfite-treated using the EZ DNA Methylation-Lightning™ Kit (Cat #: D5030). Preparative-scale PCR was performed and the resulting products were purified with DNA Clean & Concentrator™-5 (Cat #: D4003) for sequencing on an Illumina HiSeq using 2×125 bp PE.

DNA Methylation Age Analysis of Mouse RGC

Reads were filtered using trim galore v0.4.1 and mapped to the mouse genome GRCm38 using Bismark v0.15.0. Methylation counts on both positions of each CpG site were combined. Only CpG sites covered in all samples were considered for analysis. This resulted in total of 708156 sites. For the rDNA methylation clock reads were mapped to BK000964 and the coordinates were adjusted accordingly (Wang et al., Genome Res 29, 325-333, doi:10.1101/gr.241745.118 (2019)). 70/72 sites were covered for rDNA clock, compared to 102/435 sites of whole lifespan multi-tissue clock (Meer et al., Elife 7, doi:10.7554/eLife.40675 (2018)), or 248/582 and 77,342/193,651 sites (ridge) of two entire lifespan multi-tissue clocks (Thompson et al., Aging (Albany NY) 10, 2832-2854, doi:10.18632/aging.101590 (2018)).

Microbead-Induced Mouse Model of Elevated IOP

Mice were anesthetized by intraperitoneal injection of a mixture of ketamine (100 mg/kg; Ketaset; Fort Dodge Animal Health, Fort Dodge, IA) and xylazine (9 mg/kg; TranquiVed; Vedco, Inc., St. Joseph, MO) supplemented by topical application of proparacaine (0.5%; Bausch & Lomb, Tampa, FL). Elevation of IOP was induced unilaterally by injection of polystyrene microbeads (FluoSpheres; Invitrogen, Carlsbad, CA; 15-µm diameter) to the anterior chamber of the right eye of each animal under a surgical microscope, as previously reported (Krishnan et al., J Immunol, 2016. 197(12): p. 4626-4638). Briefly, microbeads were prepared at a concentration of $5.0 \times 10^6$ beads/mL in sterile physiologic saline. The right cornea was gently punctured near the center using a sharp glass micropipette (World Precision Instruments Inc., Sarasota, FL). A 2 µL volume of microbeads was injected through the preformed hole into the anterior chamber followed by injection of an air bubble via the micropipette connected with a Hamilton syringe. Any mice that developed signs of inflammation (clouding of the cornea, edematous cornea etc) were excluded from the study.

IOP (Intraocular Pressure) Measurements

IOPs were measured with a rebound TonoLab tonometer (Colonial Medical Supply, Espoo, Finland), as previously described (Krishnan et al., J Immunol, 2016. 197(12): p. 4626-4638; Mukai et al., PLoS One, 2019. 14(1): p. e0208713). Mice were anesthetized by 3% isoflurane in 100% oxygen (induction) followed by 1.5% isoflurane in 100% oxygen (maintenance) delivered with a precision vaporizer. IOP measurement was initiated within 2 to 3 min after the loss of a toe pinch reflex or tail pinch response. Anesthetized mice were placed on a platform and the tip of the pressure sensor was placed approximately ⅛ inch from the central cornea. Average IOP was displayed automatically after 6 measurements after elimination of the highest and lowest values. The machine-generated mean was considered as one reading, and six readings were obtained for each eye. All IOPs were taken at the same time of day (between 10:00 and 12:00 hours) due to the variation of IOP throughout the day.

Optomotor Response

Visual acuity of mice was measured using an optomotor re-flex-based spatial frequency threshold test (Gao et al., Am J Pathol, 2016. 186(4): p. 985-1005; Sun et al., Glia, 2013. 61(8): p. 1218-1235). Mice would be able to freely move and were placed on a pedestal located in the center of an area formed by four computer monitors arranged in a quadrangle. The monitors displayed a moving vertical black and white sinusoidal grating pattern. A blinded observer, unable to see the direction of the moving bars, monitored the tracking behavior of the mouse. Tracking was considered positive when there was a movement of the head (motor response) to the direction of the bars or rotation of the body in the direction concordant with the stimulus. Each eye would be tested separately depending on the direction of rotation of the grating. The staircase method was used to determine the spatial frequency start from 0.15 to 0.40 cycles/deg, the interval is 0.05 cycles/deg. Rotation speed (12°/s) and contrast (100%) were kept constant. Responses were measured before and after treatment by individuals blinded to the group of the animal and the treatment.

Pattern Electroretinogram (pERG)

Mice were anesthetized with ketamine/xylazine (100 mg/kg and 20 mg/kg) and the pupils dilated with one drop of 1% tropicamide ophthalmic solution. The mice were placed on a built-in warming plate (Celeris, Full-Field and Pattern Stimulation for the rodent model), that maintained the body temperature at 37 C and kept under dim red light throughout the procedure. The visual stimuli of a black and white reversing checkerboard pattern with a check size of 1° was displayed on light guide electrode-stimulators placed directly on the ocular surface of both eyes and centered with the pupil. The visual stimuli were presented at 98% contrast and constant mean luminance of 50 cd/m$^2$, spatial frequency:0.05 cyc/deg; temporal frequency:1 Hz. A total of 300 complete contrast reversals of pERG were repeated twice in each eye and the 600 cycles were segmented and averaged and recorded. The averaged PERGs were analyzed to evaluate the peak to trough N1 to P1 (positive wave) amplitude.

Quantification of Optic Nerve Axons

For quantification of axons, optic nerves were dissected and fixed overnight in Karnovsky's reagent (50% in phosphate buffer). Semi-thin cross-sections of the nerve were taken at 1.0 mm posterior to the globe and stained with 1% p-phenylenediamine (PPD) for evaluation by light microscopy. Optic nerve cross sections were imaged at 60× magnification using a Nikon microscope (Eclipse E800, Nikon, Japan) with the DPController software (Olympus, Japan) and 6-8 non-overlapping photomicrographs were taken to cover the entire area of each optic nerve cross-section. Using ImageJ (Version 2.0.0-rc-65/1.51u), a 100 μM×100 μM square was placed on each 60× image and all axons within the square (0.01 mm$^2$) were counted using the threshold and analyze particles function in image J as previously described (Krishnan et al., J Immunol, 2016. 197(12): p. 4626-4638; Mukai et al., PLoS One, 2019. 14(1): p. e0208713; Gao et al., Am J Pathol, 2016. 186(4): p. 985-1005). Damaged axons stain darkly with PPD and are not counted. The average axon counts in the 6-8 images were used to calculate the axon density per square millimeter of optic nerve. Individuals blinded to the experimental groups performed all axon counts.

Quantification of Retinal Ganglion Cells

For ganglion cell counting, images of whole mount retinas were acquired using a 63× oil immersion objective of the Leica TCS SP5 confocal microscope (Leica Microsystems). The retinal whole mount was divided into four quadrants and three to four images (248.53 m by 248.53 m in size) were taken from the midperipheral and peripheral regions of each quadrant, for a total of twelve to sixteen images per retina. were taken from the midperipheral and peripheral regions (4 images per quadrant). The images were obtained as z-stacks (0.5 m) and all Brn3a positive cells in the ganglion cell layer of each image were counted manually as previously described (Gao et al., Am J Pathol, 2016. 186(4): p. 985-1005). Briefly, RGCs were counted using the "Cell Counter" plugin (fiji.sc/Cell_Counter) in Fiji is Just ImageJ software (ImageJ Fiji,version 2.0.0-rc-69/1.52n). Each image was loaded into Fiji and a color counter type was chosen to mark all Brn3a stained RGCs within each image (0.025 mm$^2$). The average number of RGCs in the 12 to sixteen images were used to calculate the RGC density per square millimeter of retina. Two individuals blinded to the experimental groups performed all RGC counts.

Total RNA Extraction and Sample QC

Total RNA was extracted following the Trizol Reagent User Guide (Thermo Fisher Scientific). 1 ul 10 mg/ml Glycogen was added to the supernatant to increase RNA recovery. RNA was quantified using Qubit 2.0 Fluorometer (Life Technologies, Carlsbad, CA, USA) and RNA integrity was checked with TapeStation (Agilent Technologies, Palo Alto, CA, USA) to see if the concentration met the requirements.

Ultra-Low Input RNA Library Preparation and Multiplexing

RNA samples were quantified using Qubit 2.0 Fluorometer (Life Technologies, Carlsbad, CA, USA) and RNA integrity was checked with 2100 TapeStation (Agilent Technologies, Palo Alto, CA, USA). RNA library preparations, sequencing reactions, and initial bioinformatics analysis were conducted at GENEWIZ, LLC. (South Plainfield, NJ, USA). SMART-Seq v4 Ultra Low Input Kit for Sequencing was used for full-length cDNA synthesis and amplification (Clontech, Mountain View, CA), and Illumina Nextera XT library was used for sequencing library preparation. Briefly, cDNA was fragmented and adaptor was added using Transposase, followed by limited-cycle PCR to enrich and add index to the cDNA fragments. The final library was assessed with Qubit 2.0 Fluorometer and Agilent TapeStation.

Sequencing 2×150 bp PE

The sequencing libraries were multiplexed and clustered on two lanes of a flowcell. After clustering, the flowcell were loaded on the Illumina HiSeq instrument according to manufacturer's instructions. The samples were sequenced using a 2×150 Paired End (PE) configuration. Image analysis and base calling were conducted by the HiSeq Control Software (HCS) on the HiSeq instrument. Raw sequence data (.bcl files) generated from Illumina HiSeq were be converted into fastq files and de-multiplexed using Illumina bcl2fastq v. 2.17 program. One mis-match was allowed for index sequence identification.

RNA-seq Analysis

Paired-end reads were aligned with hisat2 v2.1.0 to the Ensembl GRCm38 primary assembly using splice junctions from the Ensembl release 84 annotation. Paired read counts were quantified using featureCounts v1.6.4 using reads with a MAPQ>=20. Diffentially-expressed genes for each pair-wise comparison were identified with edgeR v3.26, testing only genes with at least 0.1 counts-per-million (CPM) in at least three samples. Gene ontology analysis of differentially-expressed genes was performed with AmiGO v2.5.12. Age-associated sensory perception genes were extracted from the mouse Sensory Perception (GO:0007600) category the Gene Ontology database, including genes that were differentially expressed (q<=0.05) in 12 versus 5 month old mice, excluding genes that were induced by the Control virus alone (q<=0.1).

TABLE 6

AAV vectors used in Example 16

| Vector | qPCR Primer for measuring titer | Source |
|---|---|---|
| pAAV-TRE-Oct4 | TRE3G | Disclosed herein |
| pAAV-TRE-Sox2 | TRE3G | Disclosed herein |
| pAAV-TRE-Klf4 | TRE3G | Disclosed herein |
| pAAV-TRE-Oct4-Sox2 | TRE3G | Disclosed herein |
| pAAV-TRE-OSK | TRE3G | Disclosed herein |

TABLE 6-continued

AAV vectors used in Example 16

| Vector | qPCR Primer for measuring titer | Source |
|---|---|---|
| pAAV-TRE-d2EGFP | TRE3G | Disclosed herein |
| pAAV-CMV-rtTAV16 | WPRE | Disclosed herein |
| pAAV-CAG-tTA | hGH | Disclosed herein |
| pAAV-sh-Scr-YFP | WPRE | Plasmid #85741 |
| pAAV-Sh-Tet1-YFP | WPRE | Plasmid #85742 |
| pAAV-sh-Tet2-YFP | WPRE | Plasmid #85743 |

TABLE 7

Primers

| Primer name | Sequence | SEQ ID NO: |
|---|---|---|
| TRE3G F | AACGTATCTACAGTTTACTCCCTATC | 53 |
| TRE3G R | GGTAGGAAGTGGTACGGAAAG | 54 |
| WPRE F | CACTGACAATTCCGTGGTGT | 55 |
| WPRE R | GAGATCCGACTCGTCTGAGG | 56 |
| hGH F | TGGGAAGACAACCTGTAGGG | 57 |
| hGH R | TGAAACCCCGTCTCTACCAA | 58 |

TABLE 8

Primers used for RT-PCR

| Gene | Primer sequence | SEQ ID NO: |
|---|---|---|
| mOct4 F | ACA TCG CCA ATC AGC TTG G | 59 |
| mOct4 R | AGA ACC ATA CTC GAA CCA CAT CC | 60 |
| mSox2 F | ACA GAT GCA ACC GAT GCA CC | 61 |
| mSox2 R | TGG AGT TGT ACT GCA GGG CG | 62 |
| mKlf4 F | GTGCCCCGACTAACCGTTG | 63 |
| mKlf4 R | GTCGTTGAACTCCTCGGTCT | 64 |
| mMyc F | ATGCCCCTCAACGTGAACTTC | 65 |
| mMyc R | CGCAACATAGGATGGAGAGCA | 66 |
| mHist1 h2a F | GCG ACA ACA AGA AGA CGC GCA T | 67 |
| mHist1 h2a R | CTG GAT GTT GGG CAG GAC GCC | 68 |
| mHist1 h2b F | AAG AAG GAC GGC AAG AAG CGC A | 69 |
| mHist1 h2b R | CGC TCG AAG ATG TCG TTC ACG A | 70 |
| mHIST1 H3.1/H3.2 F | GAA GAA GCC TCA CCG CTA CCG | 71 |
| mHIST1 H3.1/H3.2 R | GGT TGG TGT CCT CAA ACA GAC CC | 72 |
| mHist1 h4 F | AAC ATC CAG GGC ATC ACC AAG C | 73 |
| mHist1 h4 R | GTT CTC CAG GAA CAC CTT CAG C | 74 |
| mLmnb1 F | CCG GCC TCA AGG CTC TCT A | 75 |
| mLmnb1 R | TGC CGC CTC ATA CTC TCG AA | 76 |
| mActb F | AGT GTG ACG TTG ACA TCC GT | 77 |

TABLE 8-continued

Primers used for RT-PCR

| Gene | Primer sequence | SEQ ID NO: |
|---|---|---|
| mActb R | TGC TAG GAG CCA GAG CAG TA | 78 |
| mNanog F | TCTTCCTGGTCCCCACAGTTT | 79 |
| mNanog R | GCAAGAATAGTTCTCGGGATGAA | 80 |
| mChaf1a R | GTG TCT TCC TCA ACT TTC TCC TTG G | 81 |
| mChaf1a F | CGC GGA CAG CCG CGG CCG TGG ATT GC | 82 |
| mChaf1b R | GGC TCC TTG CTG TCA TTC ATC TTC CAC | 83 |
| mChaf1b F | CAC CGC CGT CAG GAT CTG GAA GTT GG | 84 |
| mLmnb1 F | CCG GCC TCA AGG CTC TCT A | 85 |
| mLmnb1 R | TGC CGC CTC ATA CTC TCG AA | 86 |
| mTet1 F | TCAAGCAATGGACCACTGGG | 87 |
| mTet1 R | TCTCCATGAGCTCCCTGACA | 88 |
| mTet2 F | ACT CCT GGT GAA CAA AGT CAG A | 89 |
| mTet2 R | CAT CCC TGA GAG CTC TTG CC | 90 |
| mGAPDHF | CCA ATG TGT CCG TCG TGG ATC T | 91 |
| mGAPDHR | GTT GAA GTC GCA GGA GAC AAC C | 92 |
| mp16 (Cdkn2a) F | ACA TCA AGA CAT CGT GCG ATA TT | 93 |
| mp16 (Cdkn2a) R | CCA GCG GTA CAC AAA GAC CA | 94 |
| mApob F | AAG CAC CTC CGA AAG TAC GTG | 95 |
| mApob R | CTC CAG CTC TAC CTT ACA GTT GA | 96 |
| hTet2 F | GATAGAACCAACCATGTTGAGGG | 97 |
| hTet2 R | TGGAGCTTTGTAGCCAGAGGT | 98 |
| hActb F | CACCATTGGCAATGAGCGGTTC | 99 |
| hActb R | AGGTCTTTGCGGATGTCCACGT | 100 |

Example 17. Non-Limiting Examples of Sequences

```
Nucleotide sequence encoding Mus Musculus OCT4 (no stop codon) (SEQ ID
NO: 1):
ATGGCTGGACACCTGGCTTCAGACTTCGCCTTCTCACCCCCACCAGGTGGGGGTG

ATGGGTCAGCAGGGCTGGAGCCGGGCTGGGTGGATCCTCGAACCTGGCTAAGCT

TCCAAGGGCCTCCAGGTGGGCCTGGAATCGGACCAGGCTCAGAGGTATTGGGGA

TCTCCCCATGTCCGCCCGCATACGAGTTCTGCGGAGGGATGGCATACTGTGGACC

TCAGGTTGGACTGGGCCTAGTCCCCCAAGTTGGCGTGGAGACTTTGCAGCCTGAG

GGCCAGGCAGGAGCACGAGTGGAAAGCAACTCAGAGGGAACCTCCTCTGAGCCC

TGTGCCGACCGCCCCAATGCCGTGAAGTTGGAGAAGGTGGAACCAACTCCCGAG

GAGTCCCAGGACATGAAAGCCCTGCAGAAGGAGCTAGAACAGTTTGCCAAGCTG

CTGAAGCAGAAGAGGATCACCTTGGGGTACACCCAGGCCGACGTGGGGCTCACC

CTGGGCGTTCTCTTTGGAAAGGTGTTCAGCCAGACCACCATCTGTCGCTTCGAGG

CCTTGCAGCTCAGCCTTAAGAACATGTGTAAGCTGCGGCCCCTGCTGGAGAAGTG
```

-continued

```
GGTGGAGGAAGCCGACAACAATGAGAACCTTCAGGAGATATGCAAATCGGAGA

CCCTGGTGCAGGCCCGGAAGAGAAAGCGAACTAGCATTGAGAACCGTGTGAGGT

GGAGTCTGGAGACCATGTTTCTGAAGTGCCCGAAGCCCTCCCTACAGCAGATCAC

TCACATCGCCAATCAGCTTGGGCTAGAGAAGGATGTGGTTCGAGTATGGTTCTGT

AACCGGCGCCAGAAGGGCAAAAGATCAAGTATTGAGTATTCCCAACGAGAAGAG

TATGAGGCTACAGGGACACCTTTCCCAGGGGGGCTGTATCCTTTCCTCTGCCCC

CAGGTCCCCACTTTGGCACCCCAGGCTATGGAAGCCCCCACTTCACCACACTCTA

CTCAGTCCCTTTTCCTGAGGGCGAGGCCTTTCCCTCTGTTCCCGTCACTGCTCTGG

GCTCTCCCATGCATTCAAAC
```

Amino acid sequence encoding *Mus Musculus* OCT 4 (SEQ ID NO: 2):
```
MAGHLASDFAFSPPPGGGDGSAGLEPGWVDPRTWLSFQGPPGGPGIGPGSEVLGISP

CPPAYEFCGGMAYCGPQVGLGLVPQVGVETLQPEGQAGARVESNSEGTSSEPCADR

PNAVKLEKVEPTPEESQDMKALQKELEQFAKLLKQKRITLGYTQADVGLTLGVLFG

KVFSQTTICRFEALQLSLKNMCKLRPLLEKWVEEADNNENLQEICKSETLVQARKRK

RTSIENRVRWSLETMELKCPKPSLQQITHIANQLGLEKDVVRVWFCNRRQKGKRSSI

EYSQREEYEATGTPFPGGAVSFPLPPGPHFGTPGYGSPHFTTLYSVPFPEGEAFPSVPV

TALGSPMHSN
```

Nucleotide sequence encoding *Mus Musculus* SOX2 (no stop codon) (SEQ ID NO: 3):
```
ATGTATAACATGATGGAGACGGAGCTGAAGCCGCCGGGCCCGCAGCAAGCTTCG

GGGGGCGGCGGCGGAGGAGGCAACGCCACGGCGGCGGCGACCGGCGGCAACCA

GAAGAACAGCCCGGACCGCGTCAAGAGGCCCATGAACGCCTTCATGGTATGGTC

CCGGGGGCAGCGGCGTAAGATGGCCCAGGAGAACCCCAAGATGCACAACTCGG

AGATCAGCAAGCGCCTGGGCGCGGAGTGGAAACTTTTGTCCGAGACCGAGAAGC

GGCCGTTCATCGACGAGGCCAAGCGGCTGCGCGCTCTGCACATGAAGGAGCACC

CGGATTATAAATACCGGCCGCGGCGGAAAACCAAGACGCTCATGAAGAAGGATA

AGTACACGCTTCCCGGAGGCTTGCTGGCCCCCGGCGGGAACAGCATGGCGAGCG

GGGTTGGGGTGGGCGCCGGCCTGGGTGCGGGCGTGAACCAGCGCATGGACAGCT

ACGCGCACATGAACGGCTGGAGCAACGGCAGCTACAGCATGATGCAGGAGCAG

CTGGGCTACCCGCAGCACCCGGGCCTCAACGCTCACGGCGCGGCACAGATGCAA

CCGATGCACCGCTACGACGTCAGCGCCCTGCAGTACAACTCCATGACCAGCTCGC

AGACCTACATGAACGGCTCGCCCACCTACAGCATGTCCTACTCGCAGCAGGGCA

CCCCCGGTATGGCGCTGGGCTCCATGGGCTCTGTGGTCAAGTCCGAGGCCAGCTC

CAGCCCCCCCGTGGTTACCTCTTCCTCCCACTCCAGGGCGCCCTGCCAGGCCGGG

GACCTCCGGGACATGATCAGCATGTACCTCCCCGGCGCCGAGGTGCCGGAGCCC

GCTGCGCCCAGTAGACTGCACATGGCCCAGCACTACCAGAGCGGCCCGGTGCCC

GGCACGGCCATTAACGGCACACTGCCCCTGTCGCACATG
```

Amino acid sequence encoding *Mus Musculus* SOX2 (translated) (SEQ ID NO: 4)
```
MYNMMETELKPPGPQQASGGGGGGNATAAATGGNQKNSPDRVKRPMNAFMVW

SRGQRRKMAQENPKMHNSEISKRIGAEWKLLSETEKRPFIDEAKRLRALHMKEHPD

YKYRPRRKTKTLMKKDKYTLPGGLLAPGGNSMASGVGVGAGLGAGVNQRMDSYA

HMNGWSNGSYSMMQEQLGYPQHPGLNAHGAAQMQPMHRYDVSALQYNSMTSSQ
```

-continued

TYMNGSPTYSMSYSQQGTPGMALGSMGSVVKSEASSSPPVVTSSSHSRAPCQAGDL

RDMISMYLPGAEVPEPAAPSRLHMAQHYQSGPVPGTAINGTLPLSHM

Nucleotide sequence encoding *Mus Musculus* KLF4 (no stop codon) (SEQ ID NO: 5):
ATGAGGCAGCCACCTGGCGAGTCTGACATGGCTGTCAGCGACGCTCTGCTCCCGT

CCTTCTCCACGTTCGCGTCCGGCCCGGCGGGAAGGGAGAAGACACTGCGTCCAG

CAGGTGCCCCGACTAACCGTTGGCGTGAGGAACTCTCTCACATGAAGCGACTTCC

CCCACTTCCCGGCCGCCCCTACGACCTGGCGGCGACGGTGGCCACAGACCTGGA

GAGTGGCGGAGCTGGTGCAGCTTGCAGCAGTAACAACCCGGCCCTCCTAGCCCG

GAGGGAGACCGAGGAGTTCAACGACCTCCTGGACCTAGACTTTATCCTTTCCAAC

TCGCTAACCCACCAGGAATCGGTGGCCGCCACCGTGACCACCTCGGCGTCAGCTT

CATCCTCGTCTTCCCCAGCGAGCAGCGGCCCTGCCAGCGCGCCCTCCACCTGCAG

CTTCAGCTATCCGATCCGGGCCGGGGGTGACCCGGGCGTGGCTGCCAGCAACAC

AGGTGGAGGGCTCCTCTACAGCCGAGAATCTGCGCCACCTCCCACGGCCCCCTTC

AACCTGGCGGACATCAATGACGTGAGCCCCTCGGGCGGCTTCGTGGCTGAGCTC

CTGCGGCCGGAGTTGGACCCAGTATACATTCCGCCACAGCAGCCTCAGCCGCCA

GGTGGCGGGCTGATGGGCAAGTTTGTGCTGAAGGCGTCTCTGACCACCCCTGGCA

GCGAGTACAGCAGCCCTTCGGTCATCAGTGTTAGCAAAGGAAGCCCAGACGGCA

GCCACCCCGTGGTAGTGGCGCCCTACAGCGGTGGCCCGCCGCGCATGTGCCCCA

AGATTAAGCAAGAGGCGGTCCCGTCCTGCACGGTCAGCCGGTCCCTAGAGGCCC

ATTTGAGCGCTGGACCCCAGCTCAGCAACGGCCACCGGCCCAACACACACGACT

TCCCCCTGGGGCGGCAGCTCCCCACCAGGACTACCCCTACACTGAGTCCCGAGG

AACTGCTGAACAGCAGGGACTGTCACCCTGGCCTGCCTCTTCCCCCAGGATTCCA

TCCCCATCCGGGGCCCAACTACCCTCCTTTCCTGCCAGACCAGATGCAGTCACAA

GTCCCCTCTCTCCATTATCAAGAGCTCATGCCACCGGGTTCCTGCCTGCCAGAGG

AGCCCAAGCCAAAGAGGGGAAGAAGGTCGTGGCCCCGGAAAAGAACAGCCACC

CACACTTGIGACTATGCAGGCTGTGGCAAAACCTATACCAAGAGTTCTCATCTCA

AGGCACACCTGCGAACTCACACAGGCGAGAAACCTTACCACTGTGACTGGGACG

GCTGTGGGTGGAAATTCGCCCGCTCCGATGAACTGACCAGGCACTACCGCAAAC

ACACAGGGCACCGGCCCTTTCAGTGCCAGAAGTGCGACAGGGCCTTTTCCAGGT

CGGACCACCTTGCCTTACACATGAAGAGGCAC

Amino acid sequence encoding *Mus Musculus* KLF4 (translated) (SEQ ID NO: 6):
MRQPPGESDMAVSDALLPSFSTFASGPAGREKTLRPAGAPTNRWREELSHMKRLPPL

PGRPYDLAATVATDLESGGAGAACSSNNPALLARRETEEFNDLLDLDFILSNSLTHQE

SVAATVTTSASASSSSSPASSGPASAPSTCSFSYPIRAGGDPGVAASNTGGGLLYSRES

APPPTAPFNLADINDVSPSGGFVAELLRPELDPVYIPPQQPQPPGGGLMGKFVLKASL

TTPGSEYSSPSVISVSKGSPDGSHPVVVAPYSGGPPRMCPKIKQEAVPSCTVSRSLEAH

LSAGPQLSNGHRPNTHDFPLGRQLPTRTTPTLSPEELLNSRDCHPGLPLPPGFHPHPGP

NYPPFLPDQMQSQVPSLHYQELMPPGSCLPEEPKPKRGRRSWPRKRTATHTCDYAG

CGKTYTKSSHLKAHLRTHTGEKPYHCDWDCGWKFARSDELTRHYRKHTGHRPFQ

CQKCDRAFSRSDHLALHMKRH

TRE3G promoter sequence (non-limiting example of a TRE promoter) (SEQ ID NO: 7):
TTTACTCCCTATCAGTGATAGAGAACGTATGAAGAGTTTACTCCCTATCAGTGAT

AGAGAACGTATGCAGACTTTACTCCCTATCAGTGATAGAGAACGTATAAGGAGT

TTACTCCCTATCAGTGATAGAGAACGTATGACCAGTTTACTCCCTATCAGTGATA

GAGAACGTATCTACAGTTTACTCCCTATCAGTGATAGAGAACGTATATCCAGTTT

ACTCCCTATCAGTGATAGAGAACGTATAAGCTTTAGGCGTGTACGGTGGGCGCCT

ATAAAAGCAGAGCTCGTTTAGTGAACCGTCAGATCGCCTGGAGCAATTCCACAA

CACTTTTGTCTTATACCAACTTTCCGTACCACTTCCTACCCTCGTAAA

SV40-derived terminator sequence (SEQ ID NO: 8):
TGCGCGCAGCGGCCGACCATGGCCCAACTTGTTTATTGCAGCTTATAATGGTTAC

AAATAAAGCAATAGCATCACAAATTTCACAAATAAAGCATTTTTTTCACTGCATT

CTAGTTGTGGTTTGTCCAAACTCATCAATGTATCTTATCATGTCTGGATCTCGGTA

CCG

T2A sequence (SEQ ID NO: 9):
GSGEGRGSLLTCGDVEENPGP

Nucleotide sequence encoding rtTA3 (with 2 VP16 domain at 3' end) (SEQ ID NO: 10):
ATGTCTAGGCTGGACAAGAGCAAAGTCATAAACGGAGCTCTGGAATTACTCAAT

GGTGTCGGTATCGAAGGCCTGACGACAAGGAAACTCGCTCAAAAGCTGGGAGTT

GAGCAGCCTACCCTGTACTGGCACGTGAAGAACAAGCGGGCCCTGCTCGATGCC

CTGCCAATCGAGATGCTGGACAGGCATCATACCCACTTCTGCCCCCTGGAAGGCG

AGTCATGGCAAGACTTTCTGCGGAACAACGCCAAGTCATACCGCTGTGCTCTCCT

CTCACATCGCGACGGGGCTAAAGTGCATCTCGGCACCCGCCCAACAGAGAAACA

GTACGAAACCCTGGAAAATCAGCTCGCGTTCCTGTGTCAGCAAGGCTTCTCCCTG

GAGAACGCACTGTACGCTCTGTCCGCCGTGGGCCACTTTACACTGGGCTGCGTAT

TGGAGGAACAGGAGCATCAAGTAGCAAAGAGGAAAGAGAGACACCTACCACC

GATTCTATGCCCCCACTTCTGAGACAAGCAATTGAGCTGTTCGACCGGCAGGGAG

CCGAACCTGCCTTCCTTTTCGGCCTGGAACTAATCATATGTGGCCTGGAGAAACA

GCTAAAGTGCGAAAGCGGCGGGCCGACCGACGCCCTTGACGATTTTGACTTAGA

CATGCTCCCAGCCGATGCCCTTGACGATTTTGACCTTGACATGCTCCCCGGGTAA

Amino acid sequence encoding rtTA3 (SEQ ID NO: 11):
MSRLDKSKVINGALELLNGVGIEGLTTRKLAQKLGVEQPTLYWHVKNKRALLDALP

IEMLDRHHTHFCPLEGESWQDFLRNNAKSYRCALLSHRDGAKVHLGTRPTEKQYET

LENQLAFLCQQGFSLENALYALSAVGHFTLGCVLEEQEHQVAKEERETPTTDSMPPL

LRQAIELFDRQGAEPAFLFGLELIICGLEKQLKCESGGPTDALDDFDLDMLPADALDD

FDLDMLPG

Nucleotide sequence encoding rtTA4 (with 3 VP16 domain at 3' end) (SEQ ID NO: 12):
ATGTCCCGCTTGGATAAGAGCAAGGTAATAAATAGCGCACTCGAACTCCTCAAC

GGCGTGGGCATCGAAGGTCTGACTACTCGAAAGCTCGCCCAGAAATTGGGTGTG

GAGCAACCTACATTGTATTGGCATGTCAAGAACAAAAGAGCCCTGCTGGACGCT

CTTCCTATTGAAATGCTTGACAGGCATCACACTCATTCCTGCCCCCTTGAGGTCG

AGAGTTGGCAAGATTTTCTCCGAAACAATGCAAAGTCCTACCGCTGCGCACTTTT

GTCCCATAGGGATGGAGCAAAAGTGCACCTGGGAACCAGGCCAACAGAGAAAC

-continued

```
AATACGAGACTCTCGAGAACCAGTTGGCTTTCTTGTGCCAACAGGGGTTCTCACT

TGAAAATGCCCTTTACGCACTGTCAGCCGTTGGACATTTTACCCTGGGGTGCGTT

CTTGAGGAGCAAGAACATCAGGTTGCTAAGGAGGAGCGCGAGACTCCAACCACT

GATTCTATGCCACCTTTGCTGAAACAGGCCATTGAACTTTTCGATAGACAGGGTG

CTGAACCTGCCTTTCTCTTCGGGTTGGAGCTGATTATTTGTGGTCTCGAAAAACA

GCTGAAATGTGAAAGTGGTGGCCCTACTGACGCCCTCGATGATTTCGACCTGGAT

ATGCTGCCAGCCGATGCACTTGATGATTTCGATTTGGATATGCTTCCAGCCGACG

CACTGGACGACTTCGATTTGGACATGCTTCCCGGTTAA
```

Amino acid sequence encoding rtTA4 (SEQ ID NO: 13):
```
MSRLDKSKVINSALELLNGVGIEGLTTRKLAQKLGVEQPTLYWHVKNKRALLDALPI

EMLDRHHTHSCPLEVESWQDFLRNNAKSYRCALLSHRDGAKVHLGTRPTEKQYETL

ENQLAFLCQQGFSLENALYALSAVGHFTLGCVLEEQEHQVAKEERETPTTDSMPPLL

KQAIELFDRQGAEPAFLFGLELIICGLEKQLKCESGGPTDALDDFDLDMLPADALDDF

DLDMLPADALDDFDLDMLPG
```

Nucleotide sequence encoding M2-rtTA (SEQ ID NO: 14):
```
ATGCCTTTGTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGCAACGTG

GCGTGGTGTGCACTGTGTTTGCTGACGCAACCCCCACTGGTTGGGGCATTGCCAC

CACCTGTCAGCTCCTTTCCGGGACTTTCGCTTTCCCCCTCCCTATTGCCACGGCGG

AACTCATCGCCGCCTGCCTTGCCCGCTGCTGGACAGGGGCTCGGCTGTTGGGCAC

TGACAATTCCGTGGTGTTGTCGGGGAAATCATCGTCCTTTCCTTGGCTGCTCGCCT

GTGTTGCCACCTGGATTCTGCGCGGGACGTCCTTCTGCTACGTCCCTTCGGCCCTC

AATCCAGCGGACCTTCCTTCCCGCGGCCTGCTGCCGGCTCTGCGGCCTCTTCCGC

GTCTTCGCCTTCGCCCTCAGACGAGTCGGATCTCCCTTTGGGCCGCCTCCCCGCAT

CGATACCGTCGACCTCGAGACCTAGAAAAACATGGAGCAATCACAAGTAGCAAT

ACAGCAGCTACCAATGCTGATTGTGCCTGGCTAGAAGCACAAGAGGAGGAGGAG

GTGGGTTTTCCAGTCACACCTCAGGTACCTTTAAGACCAATGACTTACAAGGCAG

CTGTAGATCTTAGCCACTTTTTAAAAGAAAAGGGGGGACTGGAAGGGCTAATTC

ACTCCCAACGAAGACAAGATATCCTTGATCTGTGGATCTACCACACACAAGGCTA

CTTCCCTGATTGGCAGAACTACACACCAGGGCCAGGGATCAGATATCCACTGAC

CTTTGGATGGTGCTACAAGCTAGTACCAGTTGAGCAAGAGAAGGTAGAAGAAGC

CAATGAAGGAGAGAACACCCGCTTGTTACACCCTGTGAGCCTGCATGGGATGGA

TGACCCGGAGAGAGAAGTATTAGAGTGGAGGTTTGACAGCCGCCTAGCATTTCA

TCACATGGCCCGAGAGCTGCATCCGGACTGTACTGGGTCTCTCTGGTTAGACCAG

ATCTGA
```

Amino acid sequence encoding M2-rtTA (SEQ ID NO: 15):
```
MPLYHAIASRMAFIFSSLYKSWLLSLYEELWPVVRQRGVVCTVFADATPTGWGIATT

CQLLSGTFAFPLPIATAELIAACLARCWTGARLLGTDNSVVLSGKSSSFPWLLACVAT

WILRGTSFCYVPSALNPADLPSRGLLPALRPLPRLRLRPQTSRISLWAASPHRYRRPR

DLEKHGAITSSNTAATNADCAWLEAQEEEEVGFPVTPQVPLRPMTYKAAVDLSHFL
```

-continued

KEKGGLEGLIHSQRRQDILDLWIYHTQGYFPDWQNYTPGPGIRYPLTFGWCYKLVPV

EQEKVEEANEGENTRLLHPVSLHGMDDPEREVLEWRFDSRLAFHHMARELHPDCTG

SLWLDQI

Nucleic acid sequence of pAAV-TRE3G-OSK-SV40pA, TRE-OSK-SV40, or
TRE3G-OSK-SV40pA vector (SEQ ID NO: 16):
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG

GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCTTTACTCCCTATCAGT

GATAGAGAACGTATGAAGAGTTTACTCCCTATCAGTGATAGAGAACGTATGCAG

ACTTTACTCCCTATCAGTGATAGAGAACGTATAAGGAGTTTACTCCCTATCAGTG

-continued

```
ATAGAGAACGTATGACCAGTTTACTCCCTATCAGTGATAGAGAACGTATCTACAG

TTTACTCCCTATCAGTGATAGAGAACGTATATCCAGTTTACTCCCTATCAGTGATA

GAGAACGTATAAGCTTTAGGCGTGTACGGTGGGCGCCTATAAAAGCAGAGCTCG

TTTAGTGAACCGTCAGATCGCCTGGAGCAATTCCACAACACTTTTGTCTTATACC

AACTTTCCGTACCACTTCCTACCCTCGTAAAGCGGCCGCGCCACCATGGCTGGAC

ACCTGGCTTCAGACTTCGCCTTCTCACCCCCACCAGGTGGGGGTGATGGGTCAGC

AGGGCTGGAGCCGGGCTGGGTGGATCCTCGAACCTGGCTAAGCTTCCAAGGGCC

TCCAGGTGGGCCTGGAATCGGACCAGGCTCAGAGGTATTGGGGATCTCCCCATGT

CCGCCCGCATACGAGTTCTGCGGAGGGATGGCATACTGTGGACCTCAGGTTGGA

CTGGGCCTAGTCCCCCAAGTTGGCGTGGAGACTTTGCAGCCTGAGGGCCAGGCA

GGAGCACGAGTGGAAAGCAACTCAGAGGGAACCTCCTCTGAGCCCTGTGCCGAC

CGCCCCAATGCCGTGAAGTTGGAGAAGGTGGAACCAACTCCCGAGGAGTCCCAG

GACATGAAAGCCCTGCAGAAGGAGCTAGAACAGTTTGCCAAGCTGCTGAAGCAG

AAGAGGATCACCTTGGGGTACACCCAGGCCGACGTGGGGCTCACCCTGGGCGTT

CTCTTTGGAAAGGTGTTCAGCCAGACCACCATCTGTCGCTTCGAGGCCTTGCAGC

TCAGCCTTAAGAACATGTGTAAGCTGCGGCCCCTGCTGGAGAAGTGGGTGGAGG

AAGCCGACAACAATGAGAACCTTCAGGAGATATGCAAATCGGAGACCCTGGTGC

AGGCCCGGAAGAGAAAGCGAACTAGCATTGAGAACCGTGTGAGGTGGAGTCTGG

AGACCATGTTTCTGAAGTGCCCGAAGCCCTCCCTACAGCAGATCACTCACATCGC

CAATCAGCTTGGGCTAGAGAAGGATGTGGTTCGAGTATGGTTCTGTAACCGGCGC

CAGAAGGGCAAAAGATCAAGTATTGAGTATTCCCAACGAGAAGAGTATGAGGCT

ACAGGGACACCTTTCCCAGGGGGGGCTGTATCCTTTCCTCTGCCCCCAGGTCCCC

ACTTTGGCACCCCAGGCTATGGAAGCCCCCACTTCACCACACTCTACTCAGTCCC

TTTTCCTGAGGGCGAGGCCTTTCCCTCTGTTCCCGTCACTGCTCTGGGCTCTCCCA

TGCATTCAAACGCTAGCGGCAGCGGCGCCACGAACTTCTCTCTGTTAAAGCAAGC

AGGAGATCTTGAAGAAAACCCCGGGCCTGCATCCATGTATAACATGATGGAGAC

GGAGCTGAAGCCGCCGGGCCCGCAGCAAGCTTCGGGGGGCGGCGGCGGAGGAG

GCAACGCCACGGCGGCGGCGACCGGCGGCAACCAGAAGAACAGCCCGGACCGC

GTCAAGAGGCCCATGAACGCCTTCATGGTATGGTCCCGGGGGCAGCGGCGTAAG

ATGGCCCAGGAGAACCCCAAGATGCACAACTCGGAGATCAGCAAGCGCCTGGGC

GCGGAGTGGAAACTTTTGTCCGAGACCGAGAAGCGGCCGTTCATCGACGAGGCC

AAGCGGCTGCGCGCTCTGCACATGAAGGAGCACCCGGATTATAAATACCGGCCG

CGGCGGAAAACCAAGACGCTCATGAAGAAGGATAAGTACACGCTTCCCGGAGGC

TTGCTGGCCCCCGGCGGGAACAGCATGGCGAGCGGGGTTGGGGTGGGCGCCGGC

CTGGGTGCGGGCGTGAACCAGCGCATGGACAGCTACGCGCACATGAACGGCTGG

AGCAACGGCAGCTACAGCATGATGCAGGAGCAGCTGGGCTACCCGCAGCACCCG

GGCCTCAACGCTCACGGCGCGGCACAGATGCAACCGATGCACCGCTACGACGTC

AGCGCCCTGCAGTACAACTCCATGACCAGCTCGCAGACCTACATGAACGGCTCG

CCCACCTACAGCATGTCCTACTCGCAGCAGGGCACCCCCGGTATGGCGCTGGGCT

CCATGGGCTCTGTGGTCAAGTCCGAGGCCAGCTCCAGCCCCCCCGTGGTTACCTC
```

-continued

```
TTCCTCCCACTCCAGGGCGCCCTGCCAGGCCGGGGACCTCCGGGACATGATCAGC

ATGTACCTCCCCGGCGCCGAGGTGCCGGAGCCCGCTGCGCCCAGTAGACTGCAC

ATGGCCCAGCACTACCAGAGCGGCCCGGTGCCCGGCACGGCCATTAACGGCACA

CTGCCCCTGTCGCACATGGCATGCGGCTCCGGCGAGGGCAGGGGAAGTCTTCTA

ACATGCGGGACGTGGAGGAAAATCCCGGCCCACTCGAGATGAGGCAGCCACCT

GGCGAGTCTGACATGGCTGTCAGCGACGCTCTGCTCCCGTCCTTCTCCACGTTCG

CGTCCGGCCCGGCGGGAAGGGAGAAGACACTGCGTCCAGCAGGTGCCCCGACTA

ACCGTTGGCGTGAGGAACTCTCTCACATGAAGCGACTTCCCCCACTTCCCGGCCG

CCCCTACGACCTGGCGGCGACGGTGGCCACAGACCTGGAGAGTGGCGGAGCTGG

TGCAGCTTGCAGCAGTAACAACCCGGCCCTCCTAGCCCGGAGGGAGACCGAGGA

GTTCAACGACCTCCTGGACCTAGACTTTATCCTTTCCAACTCGCTAACCCACCAG

GAATCGGTGGCCGCCACCGTGACCACCTCGGCGTCAGCTTCATCCTCGTCTTCCC

CAGCGAGCAGCGGCCCTGCCAGCGCGCCCTCCACCTGCAGCTTCAGCTATCCGAT

CCGGGCCGGGGTGACCCGGGCGTGGCTGCCAGCAACACAGGTGGAGGGCTCCT

CTACAGCCGAGAATCTGCGCCACCTCCCACGGCCCCCTTCAACCTGGCGGACATC

AATGACGTGAGCCCCTCGGGCGGCTTCGTGGCTGAGCTCCTGCGGCCGGAGTTGG

ACCCAGTATACATTCCGCCACAGCAGCCTCAGCCGCCAGGTGGCGGGCTGATGG

GCAAGTTTGTGCTGAAGGCGTCTCTGACCACCCCTGGCAGCGAGTACAGCAGCC

CTTCGGTCATCAGTGTTAGCAAAGGAAGCCCAGACGGCAGCCACCCCGTGGTAG

TGGCGCCCTACAGCGGTGGCCCGCCGCGCATGTGCCCCAAGATTAAGCAAGAGG

CGGTCCCGTCCTGCACGGTCAGCCGGTCCCTAGAGGCCCATTTGAGCGCTGGACC

CCAGCTCAGCAACGGCCACCGGCCCAACACACACGACTTCCCCCTGGGGCGGCA

GCTCCCCACCAGGACTACCCCTACACTGAGTCCCGAGGAACTGCTGAACAGCAG

GGACTGTCACCCTGGCCTGCCTCTTCCCCCAGGATTCCATCCCCATCCGGGGCCC

AACTACCCTCCTTTCCTGCCAGACCAGATGCAGTCACAAGTCCCCTCTCTCCATT

ATCAAGAGCTCATGCCACCGGGTTCCTGCCTGCCAGAGGAGCCCAAGCCAAAGA

GGGGAAGAAGGTCGTGGCCCCGGAAAAGAACAGCCACCCACACTTGTGACTATG

CAGGCTGTGGCAAAACCTATACCAAGAGTTCTCATCTCAAGGCACACCTGCGAA

CTCACACAGGCGAGAAACCTTACCACTGTGACTGGGACGGCTGTGGGTGGAAAT

TCGCCCGCTCCGATGAACTGACCAGGCACTACCGCAAACACACAGGGCACCGGC

CCTTTCAGTGCCAGAAGTGCGACAGGGCCTTTTCCAGGTCGGACCACCTTGCCTT

ACACATGAAGAGGCACTAAATGACTAGTGCGCGCAGCGGCCGACCATGGCCCAA

CTTGTTTATTGCAGCTTATAATGCTTACAAATAAAGCAATAGCATCACAAATTTC

ACAAATAAAGCATTTTTTTCACTTGCATTCTAGTTGTGGTTTGTCCAAACTCATCAA

TGTATCTTATCATGTCTGGATCTCGGTACCGGATCCAAATTCCCGATAAGGATCTT

CCTAGAGCATGGCTACGTAGATAAGTAGCATGGCGGGTTAATCATTAACTACAA

GGAACCCCTAGTGATGGAGTTGGCCACTCCCTCTCTGCGCGCTCGCTCGCTCACT

GAGGCCGGGCGACCAAAGGTCGCCCGACGCCCGGGCTTTGCCCGGGCGGCCTCA

GTGAGCGAGCGAGCGCGCAGCCTTAATTAACCTAATTCACTGGCCGTCGTTTTAC

AACGTCGTGACTGGGAAAACCCTGGCGTTACCCAACTTAATCGCCTTGCAGCACA

TCCCCCTTTCGCCAGCTGGCGTAATAGCGAAGAGGCCCGCACCGATCGCCCTTCC
```

-continued

```
CAACAGTTGCGCAGCCTGAATGGCGAATGGGACGCGCCCTGTAGCGGCGCATTA

AGCGCGGCGGGTGTGGTGGTTACGCGCAGCGTGACCGCTACACTTGCCAGCGCC

CTAGCGCCCGCTCCTTTCGCTTTCTTCCCTTCCTTTCTCGCCACGTTCGCCGGCTTT

CCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTG

GACTCTTGTTCCAAACTGGAACAACACTCAACCCTATCTCGGTCTATTCTTTTGAT

TTATAAGGGATTTTGCCGATTTCGGCCTATTGGTTAAAAAATGAGCTGATTTAAC

AAAAATTTAACGCGAATTTTAACAAAATATTAACGTTTATAATTTCAGGTGGCAT

CTTTCGGGGAAATGTGCGCGGAACCCCTATTTGTTTATTTTTCTAAATACATTCAA

ATATGTATCCGCTCATGAGACAATAACCCTGATAAATGCTTCAATAATATTGAAA

AAGGAAGAGTATGAGTATTCAACATTTCCGTGTCGCCCTTATTCCCTTTTTTGCGG

CATTTTGCCTTCCTGTTTTGCTCACCCAGAAACGCTGGTGAAAGTAAAAGATGC

TGAAGATCAGTTGGGTGCACGAGTGGGTTACATCGAACTGGATCTCAATAGTGGT

AAGATCCTTGAGAGTTTTCGCCCCGAAGAACGTTTTCCAATGATGAGCACTTTTA

AAGTTCTGCTATGTGGCGCGGTATTATCCCGTATTGACGCCGGGCAAGAGCAACT

CGGTCGCCGCATACACTATTCTCAGAATGACTTGGTTGAGTACTCACCAGTCACA

GAAAAGCATCTTACGGATGGCATGACAGTAAGAGAA
```

Nucleic acid sequence of pAAV-UBC-rtTA4-WPRE3-SV40pA vector (SEQ ID NO: 17):

```
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA
```

-continued

```
CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG

GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCCTGATCTGGCCTCCG

CGCCGGGTTTTGGCGCCTCCCGCGGGCGCCCCCCTCCTCACGGCGAGCGCTGCCA

CGTCAGACGAAGGGCGCAGCGAGCGTCCTGATCCTTCCGCCCGGACGCTCAGGA

CAGCGGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCAGAGAG

CGGAACAGGCGAGGAAAAGTAGTCCCTTCTCGGCGATTCTGCGGAGGGATCTCC

GTGGGGCGGTGAACGCCGATGATTATATAAGGACGCGCCGGGTGTGGCACAGCT

AGTTCCGTCGCAGCCGGGATTTGGGTCGCGGTTCTTGTTTGTGGATCGCTGTGAT

CGTCACTTGGTGAGTAGCGGGCTGCTGGGCTGGCCGGGGCTTTCGTGGCCGCCGG

GCCGCTCGGTGGGACGGAAGCGTGTGGAGAGACCGCCAAGGGCTGTAGTCTGGG

TCCGCGAGCAAGGTTGCCCTGAACTGGGGGTTGGGGGGAGCGCAGCAAAATGGC

GGCTGTTCCCGAGTCTTGAATGGAAGACGCTTGTGAGGCGGGCTGTGAGGTCGTT

GAAACAAGGTGGGGGGCATGGTGGGCGGCAAGAACCCAAGGTCTTGAGGCCTTC

GCTAATGCGGGAAAGCTCTTATTCGGGTGAGATGGGCTGGGGCACCATCTGGGG

ACCCTGACGTGAAGTTTGTCACTGACTGGAGAACTCGGTTTGTCGTCTGTTGCGG

GGGCGGCAGTTATGCGGTGCCGTTGGGCAGTGCACCCGTACCTTTGGGAGCGCG

CGCCTCGTCGTGTCGTGACGTCACCCGTTCTGTTGGCTTATAATGCAGGGTGGGG

CCACCTGCCGGTAGGTGTGCGGTAGGCTTTTCTCCGTCGCAGGACGCAGGGTTCG

GGCCTAGGGTAGGCTCTCCTGAATCGACAGGCGCCGGACCTCTGGTGAGGGAG

GGATAAGTGAGGCGTCAGTTTCTTTGGTCGGTTTTATGTACCTATCTTCTTAAGTA

GCTGAAGCTCCGGTTTTGAACTATGCGCTCGGGGTTGGCGAGTGTGTTTTGTGAA

GTTTTTTAGGCACCTTTTGAAATGTAATCATTTGGGTCAATATGTAATTTTCAGTG

TTAGACTAGTAAATTGTCCGCTAAATTCTGGCCGTTTTTGGCTTTTTTGTTAGACG

AAGCGGCCGCATTAAACGCCACCATGTCCCGCTTGGATAAGAGCAAGGTAATAA

ATAGCGCACTCGAACTCCTCAACGGCGTGGGCATCGAAGGTCTGACTACTCGAA

AGCTCGCCCAGAAATTGGGTGTGGAGCAACCTACATTGTATTGGCATGTCAAGA

ACAAAAGAGCCCTGCTGGACGCTCTTCCTATTGAAATGCTTGACAGGCATCACAC

TCATTCCTGCCCCCTTGAGGTCGAGAGTTGGCAAGATTTTCTCCGAAACAATGCA
```

-continued

```
AAGTCCTACCGCTGCGCACTTTTGTCCCATAGGGATGGAGCAAAAGTGCACCTGG
GAACCAGGCCAACAGAGAAACAATACGAGACTCTCGAGAACCAGTTGGCTTTCT
TGTGCCAACAGGGGTTCTCACTTGAAAATGCCCTTTACGCACTGTCAGCCGTTGG
ACATTTTACCCTGGGGTGCGTTCTTGAGGAGCAAGAACATCAGGTTGCTAAGGAG
GAGCGCGAGACTCCAACCACTGATTCTATGCCACCTTTGCTGAAACAGGCCATTG
AACTTTTCGATAGACAGGGTGCTGAACCTGCCTTTCTCTTCGGGTTGGAGCTGAT
TATTTGTGGTCTCGAAAAACAGCTGAAATGTGAAAGTGGTGGCCCTACTGACGCC
CTCGATGATTTCGACCTGGATATGCTGCCAGCCGATGCACTTGATGATTTCGATTT
GGATATGCTTCCAGCCGACGCACTGGACGACTTCGATTTGGACATGCTTCCCGGT
TAAACTAGTCTAGCAATCAACCTCTGGATTACAAAATTTGTGAAAGATTGACTGG
TATTCTTAACTATGTTGCTCCTTTTACGCTATGTGGATACGCTGCTTTAATGCCTTT
GTATCATGCTATTGCTTCCCGTATGGCTTTCATTTTCTCCTCCTTGTATAAATCCTG
GTTAGTTCTTGCCACGGCGGAACTCATCGCCGCCTGCCTTGCCCGCTGCTGGACA
GGGGCTCGGCTGTTGGGCACTGACAATTCCGTGGTGTTTATTTGTGAAATTTGTG
ATGCTATTGCTTTATTTGTAACCATTCTAGCTTTATTTGTGAAATTTGTGATGCTA
TTGCTTTATTTGTAACCATTATAAGCTGCAATAAACAAGTTAACAACAACAATTG
CATTCATTTTATGTTTCAGGTTCAGGGGAGATGTGGGAGGTTTTTTAAAGCGGG
GGATCCAAATTCCCGATAAGGATCTTCCTAGAGCATGGCTACGTAGATAAGTAGC
ATGGCGGGTTAATCATTAACTACAAGGAACCCCTAGTGATGGAGTTGGCCACTCC
CTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCCTTAATTAA
CCTAATTCACTGGCCGTCGTTTTACAACGTCGTGACTGGGAAAACCCTGGCGTTA
CCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATG
GGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCCT
TTAGGGTTCCGATTTAGTGCTTTACGGCACCTCGACCCCAAAAAACTTGATTAGG
GTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTC
AACCCTATCTCGGTCTATTCTTTTGATTTATAAGGGATTTTGCCGATTTCGGCCTA
TTGGTTAAAAAATGAGCTGATTTAACAAAAATTTAACGCGAATTTTAACAAAATA
TTAACGTTTATAATTTCAGGTGGCATCTTTCGGGGAAATGTGCGCGGAACCCCTA
TTTGTTTATTTTTCTAAATACATTCAAATATGTATCCGCTCATGAGACAATAACCC
TGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTT
ACATCGAACTGGATCTCAATAGTGGTAAGATCCTTGAGAGTTTTCGCCCCGAAGA
ACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
```

```
ACTTGGTTGAGTACTCACCAGTCACAGAAAAGCATCTTACGGATGGCATGACAGT

AAGAGAA
```

UBC promoter sequence (SEQ ID NO: 18):
```
GATCTGGCCTCCGCGCCGGGTTTTGGCGCCTCCCGCGGGCGCCCCCTCCTCACG

GCGAGCGCTGCCACGTCAGACGAAGGGCGCAGCGAGCGTCCTGATCCTTCCGCC

CGGACGCTCAGGACAGCGGCCCGCTGCTCATAAGACTCGGCCTTAGAACCCCAG

TATCAGCAGAAGGACATTTTAGGACGGGACTTGGGTGACTCTAGGGCACTGGTTT

TCTTTCCAGAGAGCGGAACAGGCGAGGAAAAGTAGTCCCTTCTCGGCGATTCTGC

GGAGGGATCTCCGTGGGGCGGTGAACGCCGATGATTATATAAGGACGCGCCGGG

TGTGGCACAGCTAGTTCCGTCGCAGCCGGGATTTGGGTCGCGGTTCTTGTTTGTG

GATCGCTGTGATCGTCACTTGGTGAGTAGCGGGCTGCTGGGCTGGCCGGGGCTTT

CGTGGCCGCCGGGCCGCTCGGTGGGACGGAAGCGTGTGGAGAGACCGCCAAGG

GCTGTAGTCTGGGTCCGCGAGCAAGGTTGCCCTGAACTGGGGGTTGGGGGGAGC

GCAGCAAAATGGCGGCTGTTCCCGAGTCTTGAATGGAAGACGCTTGTGAGGCGG

GCTGTGAGGTCGTTGAAACAAGGTGGGGGGCATGGTGGGCGGCAAGAACCCAAG

GTCTTGAGGCCTTCGCTAATGCGGGAAAGCTCTTATTCGGGTGAGATGGGCTGGG

GCACCATCTGGGGACCCTGACGTGAAGTTTGTCACTGACTGGAGAACTCGGTTTG

TCGTCTGTTGCGGGGGCGGCAGTTATGCGGTGCCGTTGGGCAGTGCACCCGTACC

TTTGGGAGCGCGCGCCTCGTCGTGTCGTGACGTCACCCGTTCTGTTGGCTTATAAT

GCAGGGTGGGGCCACCTGCCGGTAGGTGTGCGGTAGGCTTTTCTCCGTCGCAGGA

CGCAGGGTTCGGGCCTAGGGTAGGCTCTCCTGAATCGACAGGCGCCGGACCTCT

GGTGAGGGGAGGGATAAGTGAGGCGTCAGTTTCTTTGGTCGGTTTTATGTACCTA

TCTTCTTAAGTAGCTGAAGCTCCGGTTTTGAACTATGCGCTCGGGGTTGGCGAGT

GTGTTTTGTGAAGTTTTTTAGGCACCTTTTGAAATGTAATCATTTGGGTCAATATG

TAATTTTCAGTGTTAGACTAGTAAATTGTCCGCTAAATTCTGGCCGTTTTTGGCTT

TTTTGTTAGAC
```

Tet-O sequence (SEQ ID NO: 19):
```
TCCCTATCAGTGATAGAGA
```

Nucleic acid sequence encoding minimal CMV promoter (SEQ ID NO: 20):
```
GCTTTAGGCGTGTACGGTGGGCGCCTATAAAAGCAGAGCTCGTTTAGTGAACCGT

CAGATCGCCTGGA
```

Nucleic acid sequence encoding WPRE (SEQ ID NO: 21):
```
AATCAACCTCTGGATTACAAAATTTGTGAAAGATTGACTGGTATTCTT

AACTATGTTGCTCCTTTTACGCTATGTGGATACGCTGCTTTAATGCCTTTGTATCA

TGCTATTGCTTCCCGTATGGCTTTCATTTTCTCCTCCTTGTATAAATCCTGGTTAGT

TCTTGCCACGGCGGAACTCATCGCCGCCTGCCTTGCCCGCTGCTGGACAGGGCT

CGGCTGTTGGGCACTGACAATTCCGTGGTGTT
```

Nucleic acid sequence encoding inverted terminal repeat sequence (SEQ ID NO: 22):
```
CCTTAATTAGGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCAGAGA

GGGAGTGGCCAACTCCATCACTAGGGGTTCCT
```

-continued

Nucleic acid sequence of a TRE2 promoter (a non-limiting example of a TRE promoter) (SEQ ID NO: 23):
AATTCGTACACGCCTACCTCGACCCATCAAGTGCCACCTGACGTCTCCCTATCAG

TGATAGAGAAGTCGACACGTCTCGAGCTCCCTATCAGTGATAGAGAAGGTACGT

CTAGAACGTCTCCCTATCAGTGATAGAGAAGTCGACACGTCTCGAGCTCCCTATC

AGTGATAGAGAAGGTACGTCTAGAACGTCTCCCTATCAGTGATAGAGAAGTCGA

CACGTCTCGAGCTCCCTATCAGTGATAGAGAAGGTACGTCTAGAACGTCTCCCTA

TCAGTGATAGAGAAGTCGACACGTCTCGAGCTCCCTATCAGTGATAGAGAAGGT

ACCCCCTATATAAGCAGAGCTCGTTTAGTGAACCGTCAGATCGCCTGGAGACGCC

ATCCACGCTGTTTTGACCTCCATAGAAGACACCGGGACCGATCCAGCCTGGATCG

C

Nucleic acid sequence of P tight promoter (a non-limiting example of a TRE promoter) (SEQ ID NO: 24):
GAGTTTACTCCCTATCAGTGATAGAGAACGTATGTCGAGTTTACTCCCTATCAGT

GATAGAGAACGATGTCGAGTTTACTCCCTATCAGTGATAGAGAACGTATGTCGA

GTTTACTCCCTATCAGTGATAGAGAACGTATGTCGAGTTTACTCCCTATCAGTGA

TAGAGAACGTATGTCGAGTTTATCCCTATCAGTGATAGAGAACGTATGTCGAGTT

TACTCCCTATCAGTGATAGAGAACGTATGTCGAGGTAGGCGTGTACGGTGGGAG

GCCTATATAAGCAGAGCTCGTTTAGTGAACCGTCAGATCGCC

Nucleic acid sequence encoding TetR (SEQ ID NO: 25):
ATGGCTAGATTAGATAAAAGTAAAGTGATTAACAGCGCATTAGAGCTGCTTAAT

GAGGTCGGAATCGAAGGTTTAACAACCCGTAAACTCGCCCAGAAGCTAGGTGTA

GAGCAGCCTACATTGTATTGGCATGTAAAAAATAAGCGGGCTTTGCTCGACGCCT

TAGCCATTGAGATGTTAGATAGGCACCATACTCACTTTTGCCCTTTAGAAGGGGA

AAGCTGGCAAGATTTTTTACGTAATAACGCTAAAAGTTTTAGATGTGCTTTACTA

AGTCATCGCGATGGAGCAAAAGTACATTTAGGTACACGGCCTACAGAAAAACAG

TATGAAACTCTCGAAAATCAATTAGCCTTTTTATGCCAACAAGGTTTTTCACTAG

AGAATGCATTATATGCACTCAGCGCTGTGGGGCATTTTACTTTAGGTTGCGTATT

GGAAGATCAAGAGCATCAAGTCGCTAAAGAAGAAAGGGAAACACCTACTACTG

ATAGTATGCCGCCATTATTACGACAAGCTATCGAATTATTTGATCACCAAGGTGC

AGAGCCAGCCTTCTTATTCGGCCTTGAATTGATCATATGCGGATTAGAAAAACAA

CTTAAATGTGAAAGTGGG

Amino acid sequence encoding TetR (SEQ ID NO: 26):
MARLDKSKVINSALELLNEVGIEGLTTRKLAQKLGVEQPTLYWHVKNKRALLDALA

IEMLDRHHTHFCPLEGESWQDFLRNNAKSFRCALLSHRDGAKVHLGTRPTEKQYET

LENQLAFLCQQGFSLENALYALSAVGHFTLGCVLEDQEHQVAKEERETPTTDSMPPL

LRQAIELFDHQGAEPAFLFGLELIICGLEKQLKCESG

Nucleic acid sequence encoding TetR-Krab (SEQ ID NO: 27)
ATGGCTAGATTAGATAAAAGTAAAGTGATTAACAGCGCATTAGAGCTGCTTAAT

GAGGTCGGAATCGAAGGTTTAACAACCCGTAAACTCGCCCAGAAGCTAGGTGTA

GAGCAGCCTACATTGTATTGGCATGTAAAAAATAAGCGGGCTTTGCTCGACGCCT

TAGCCATTGAGATGTTAGATAGGCACCATACTCACTTTTGCCCTTTAGAAGGGGA

AAGCTGGCAAGATTTTTTACGTAATAACGCTAAAAGTTTTAGATGTGCTTTACTA

AGTCATCGCGATGGAGCAAAAGTACATTTAGGTACACGGCCTACAGAAAAACAG

```
TATGAAACTCTCGAAAATCAATTAGCCTTTTTATGCCAACAAGGTTTTTCACTAG

AGAATGCATTATATGCACTCAGCGCTGTGGGCATTTTACTTTAGGTTGCGTATT

GGAAGATCAAGAGCATCAAGTCGCTAAAGAAGAAAGGGAAACACCTACTACTG

ATAGTATGCCGCCATTATTACGACAAGCTATCGAATTATTGATCACCAAGGTGC

AGAGCCAGCCTTCTTATTCGGCCTTGAATTGATCATATGCGGATTAGAAAAACAA

CTTAAATGTGAAAGTGGGTCGCCAAAAAAGAAGAGAAAGGTCGACGGCGGTGGT

GCTTTGTCTCCTCAGCACTCTGCTGTCACTCAAGGAAGTATCATCAAGAACAAGG

AGGGCATGGATGCTAAGTCACTAACTGCCTGGTCCCGGACACTGGTGACCTTCAA

GGATGTATTTGTGGACTTCACCAGGGAGGAGTGGAAGCTGCTGGACACTGCTCA

GCAGATCGTGTACAGAAATGTGATGCTGGAGAACTATAAGAACCTGGTTTCCTTG

GGTTATCAGCTTACTAAGCCAGATGTGATCCTCCGGTTGGAGAAGGGAGAAGAG

CCCTGGCTGGTGGAGAGAGAAATTCACCAAGAGACCCATCCTGATTCAGAGACT

GCATTTGAAATCAAATCATCAGTTTAA

Amino acid sequence encoding TetR-KRAB (SEQ ID NO: 28):
MARLDKSKVINSALELLNEVGIEGLTTRKLAQKLGVEQPTLYWHVKNKRALLDALA

IEMLDRHHTHFCPLEGESWQDFLRNNAKSFRCALLSHRDGAKVHLGTRPTEKQYET

LENQLAFLCQQGFSLENALYALSAVGHFTLGCVLEDQEHQVAKEERETPTTDSMPPL

LRQAIELFDHQGAEPAFLFGLELIICGLEKQLKCESGSPKKKRKVDGGGALSPQHSAV

TQGSIIKNKEGMDAKSLTAWSRTLVTFKDVFVDFTREEWKLLDTAQQIVYRNVMLE

NYKNLVSLGYQLTKPDVILRLEKGEEPWLVEREIHQETHPDSETAFEIKSSV

Desmin promoter (SEQ ID NO: 29):
ACCTTGCTTCCTAGCTGGGCCTTTCCTTCTCCTCTATAAATACCAGCTCTGGTATT

TCGCCTTGGCAGCTGTTGCTGCTAGGGAGACGGCTGGCTTGACATGCATCTCCTG

ACAAAACACAAACCCGTGGTGTGAGTGGGTGTGGGCGGTGTGAGTAGGGGGATG

AATCAGAGAGGGGGCGAGGGAGACAGGGGCGCAGGAGTCAGGCAAAGGCGATG

CGGGGGTGCGACTACACGCAGTTGGAAACAGTCGTCAGAAGATTCTGGAAACTA

TCTTGCTGGCTATAAACTTGAGGGAAGCAGAAGGCCAACATTCCTCCCAAGGGA

AACTGAGGCTCAGAGTTAAAACCCAGGTATCAGTGATATGCATGTGCCCCGGCC

AGGGTCACTCTCTGACTAACCGGTACCTACCCTACAGGCCTACCTAGAGACTCTT

TTGAAAGGATGGTAGAGACCTGTCCGGGCTTTGCCCACAGTCGTTGGAAACCTCA

GCATTTTCTAGGCAACTTGTGCGAATAAAACACTTCGGGGGTCCTTCTTGTTCATT

CCAATAACCTAAAACCTCTCCTCGGAGAAAATAGGGGGCCTCAAACAAACGAAA

TTCTCTAGCCCGCTTTCCCCAGGATAAGGCAGGCATCCAAATGGAAAAAAAGGG

GCCGGCCGGGGGTCTCCTGTCAGCTCCTTGCCCTGTGAAACCCAGCAGGCCTGCC

TGTCTTCTGTCCTCTTGGGGCTGTCCAGGGGCGCAGGCCTCTTGCGGGGGAGCTG

GCCTCCCCGCCCCCTCGCCTGTGGCCGCCCTTTTCCTGGCAGGACAGAGGGATCC

TGCAGCTGTCAGGGGAGGGGCGCCGGGGGGTGATGTCAGGAGGGCTACAAATAG

TGCAGACAGCTAAGGGGCTCCGTCACCCATCTTCACATCCACTCCAGCCGGCTGC

CCGCCCGCTGCCTCCTCTGTGCGTCCGCCCAGCCAGCCTCGTCCACGCC

Desmin-rtTA4 vector (SEQ ID NO: 30):
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC
```

-continued

```
ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG

GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCCTAGATCTACCTTGC

TTCCTAGCTGGGCCTTTCCTTCTCCTCTATAAATACCAGCTCTGGTATTTCGCCTT

GGCAGCTGTTGCTGCTAGGGAGACGGCTGGCTTGACATGCATCTCCTGACAAAAC

ACAAACCCGTGGTGTGAGTGGGTGTGGGCGGTTGTGAGTAGGGGATGAATCAGA

GAGGGGGCGAGGGAGACAGGGGCGCAGGAGTCAGGCAAAGGCGATGCGGGGGT

GCGACTACACGCAGTTGGAAACAGTCGTCAGAAGATTCTGGAAACTATCTTGCTG

GCTATAAACTTGAGGGAAGCAGAAGGCCAACATTCCTCCCAAGGGAAACTGAGG

CTCAGAGTTAAAACCCAGGTATCAGTGATATGCATGTGCCCCGGCCAGGGTCACT

CTCTGACTAACCGGTACCTACCCTACAGGCCTACCTAGAGACTCTTTTGAAAGGA
```

-continued

```
TGGTAGAGACCTGTCCGGGCTTTGCCCACAGTCGTTGGAAACCTCAGCATTTTCT
AGGCAACTTGTGCGAATAAAACACTTCGGGGGTCCTTCTTGTTCATTCCAATAAC
CTAAAACCTCTCCTCGGAGAAAATAGGGGGCCTCAAACAAACGAAATTCTCTAG
CCCGCTTTCCCCAGGATAAGGCAGGCATCCAAATGGAAAAAAAGGGGCCGGCCG
GGGGTCTCCTGTCAGCTCCTTGCCCTGTGAAACCCAGCAGGCCTGCCTGTCTTCT
GTCCTCTTGGGGCTGTCCAGGGGCGCAGGCCTCTTGCGGGGGAGCTGGCCTCCCC
GCCCCCTCGCCTGTGGCCGCCCTTTTCCTGGCAGGACAGAGGGATCCTGCAGCTG
TCAGGGGAGGGGCGCCGGGGGGTGATGTCAGGAGGGCTACAAATAGTGCAGAC
AGCTAAGGGGCTCCGTCACCCATCTTCACATCCACTCCAGCCGGCTGCCCGCCCG
CTGCCTCCTCTGTGCGTCCGCCCAGCCAGCCTCGTCCACGCCAAGCTTGCGGCCG
CATTAAACGCCACCATGTCCCGCTTGGATAAGAGCAAGGTAATAAATAGCGCAC
TCGAACTCCTCAACGGCGTGGGCATCGAAGGTCTGACTACTCGAAAGCTCGCCC
AGAAATTGGGTGTGGAGCAACCTACATTGTATTGGCATGTCAAGAACAAAAGAG
CCCTGCTGGACGCTCTTCCTATTGAAATGCTTGACAGGCATCACACTCATTCCTGC
CCCCTTGAGGTCGAGAGTTGGCAAGATTTTCTCCGAAACAATGCAAAGTCCTACC
GCTGCGCACTTTTGTCCCATAGGGATGGAGCAAAAGTGCACCTGGGAACCAGGC
CAACAGAGAAACAATACGAGACTCTCGAGAACCAGTTGGCTTTCTTGTGCCAAC
AGGGGTTCTCACTTGAAAATGCCCTTTACGCACTGTCAGCCGTTGGACATTTTAC
CCTGGGGTGCGTTCTTGAGGAGCAAGAACATCAGGTTGCTAAGGAGGAGCGCGA
GACTCCAACCACTGATTCTATGCCACCTTTGCTGAAACAGGCCATTGAACTTTTC
GATAGACAGGGTGCTGAACCTGCCTTTCTCTTCGGGTTGGAGCTGATTATTTGTG
GTCTCGAAAAACAGCTGAAATGTGAAAGTGGTGGCCCTACTGACGCCCTCGATG
ATTTCGACCTGGATATGCTGCCAGCCGATGCACTTGATGATTTCGATTTGGATAT
GCTTCCAGCCGACGCACTGGACGACTTCGATTTGGACATGCTTCCCGGTTAAACT
AGTCTAGCAATCAACCTCTGGATTACAAAATTTGTGAAAGATTGACTGGTATTCT
TAACTATGTTGCTCCTTTTACGCTATGTGGATACGCTGCTTTAATGCCTTTGTATC
ATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGC
TCGGCTGTTGGGCACTGACAATTCCGTGGTGTTTATTTGTGAAATTTGTGATGCTA
TTGCTTTATTTGTAACCATTCTAGCTTTATTTGTGAAATTTGTGATGCTATTGCTTT
ATTTGTAACCATTATAAGCTGCAATAAACAAGTTAACAACAACAATTGCATTCAT
TTTATGTTTCAGGTTCAGGGGAGATGTGGGAGGTTTTTTAAAGCGGGGATCCA
AATTCCCGATAAGGATCTTCCTAGAGCATGGCTACGTAGATAAGTAGCATGGCG
GGTTAATCATTAACTACAAGGAACCCCTAGTGATGGAGTTGGCCACTCCCTCTCT
GCGCGCTCGCTCGCTCACTGAGGCCGGGCGACCAAAGGTCGCCCGACGCCCGGG
CTTTGCCCGGGCGGCCTCAGTGAGCGAGCGAGCGCGCAGCCTTAATTAACCTAAT
TCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGC
CCGCACCGATCGCCCTTCCCAACAGTTGCGCAGCCTGAATGGCGAATGGGACGC
GCCCTGTAGCGGCGCATTAAGCGCGGCGGGTGTGGTGGTTACGCGCAGCGTGAC
```

```
CGCTACACTTGCCAGCGCCCTAGCGCCCGCTCCTTTCGCTTTCTTCCCTTCCTTTC

TCGCCACGTTCGCCGGCTTTCCCCGTCAAGCTCTAAATCGGGGCTCCCTTTAGG

GTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGG

AGTCCACGTTCTTTAATAGTGGACTCTTGTTCCAAACTGGAACAACACTCAACCC

TATCTCGGTCTATTCTTTTGATTTATAAGGGATTTTGCCGATTTCGGCCTATTGGT

TAAAAAATGAGCTGATTTAACAAAAATTTAACGCGAATTTTAACAAAATATTAAC

GTTTATAATTTCAGGTGGCATCTTTCGGGGAAATGTGCGCGGAACCCCTATTTGT

TTATTTTTCTAAATACATTCAAATATGTATCCGCTCATGAGACAATAACCCTGATA

AATGCTTCAATAATATTGAAAAAGGAAGAGTATGAGTATTCAACATTTCCGTGTC

GCCCTTATTCCCTTTTTTGCGGCATTTTGCCTTCCTGTTTTTGCTCACCCAGAAACG

CTGGTGAAAGTAAAAGATGCTGAAGATCAGTTGGGTGCACGAGTGGGTTACATC

GAACTGGATCTCAATAGTGGTAAGATCCTTGAGAGTTTTCGCCCCGAAGAACGTT

TTCCAATGATGAGCACTTTTAAAGTTCTGCTATGTGGCGCGGTATTATCCCGTATT

GACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGA

GAA pAAV2_CMV_rtTA(V16) (SEQ ID NO: 31):
AAATTGTAAACGTTAATATTTTGTTAAAATTCGCGTTAAATTTTTGTTAAATCAGC

TCATTTTTTAACCAATAGGCCGAAATCGGCAAAATCCCTTATAAATCAAAAGAAT

AGCCCGAGATAGGGTTGAGTGTTGTTCCAGTTTGGAACAAGAGTCCACTATTAAA

GAACGTGGACTCCAACGTCAAAGGGCGAAAAACCGTCTATCAGGGCGATGGCCC

ACTACGTGAACCATCACCCAAATCAAGTTTTTTGGGGTCGAGGTGCCGTAAAGCA

CTAAATCGGAACCCTAAAGGGAGCCCCCGATTTAGAGCTTGACGGGGAAAGCCG

GCGAACGTGGCGAGAAAGGAAGGGAAGAAAGCGAAAGGAGCGGGCGCTAGGGC

GCTGGCAAGTGTAGCGGTCACGCTGCGCGTAACCACCACACCCGCCGCGCTTAA

TGCGCCGCTACAGGGCGCGTACTATGGTTGCTTTGACGTATGCGGTGTGAAATAC

CGCACAGATGCGTAAGGAGAAAATACCGCATCAGGCGCCCCTGCAGGCAGCTGC

GCGCTCGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGCCAACT

CCATCACTAGGGGTTCCTGCGGCCGCTCGGTCCGCACGATCTCAATTCGGCCATT

ACGGCCGGATCCGGCTCGAGGAGCTTGGCCCATTGCATACGTTGTATCCATATCA

TAATATGTACATTTATATTGGCTCATGTCCAACATTACCGCCATGTTGACATTGAT

TATTGACTAGTTATTAATAGTAATCAATTACGGGGTCATTAGTTCATAGCCCATA

TATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAA

TAGGGACTTTCCATTGACGTCAATGGGTGGAGTATTTACGCTAAACTGCCCACTT

GGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTA

CTTGGCAGTACATCTACGTATTAGTCATCGCTATTACCATGGTGATGCGGTTTTGG

CAGTACATCAATGGGCGTGGATAGCGGTTTGACTCACGGGGATTTCCAAGTCTCC
```

-continued

```
ACCCCATTGACGTCAATGGGAGTTTGTTTTGGCACCAAAATCAACGGGACTTTCC

AAAATGTCGTAACAACTCCGCCCCATTGACGCAAATGGGCGGTAGGCGTGTACG

GTGGGAGGTCTATATAAGCAGAGCTCGTTTAGTGAACCGTCAGATCGCCTGGAG

ACGCCATCCACGCTGTTTTGACCTCCATAGAAGACACCGGGACCGATCCAGCCTC

CGCGGCCCCGAATTCACCATGTCTAGACTGGACAAGAGCAAAATCATAAACAGC

GCTCTGGAATTACTCAATGGAGTCGGTATCGAAGGCCTGACGACAAGGAAACTC

GCTCAAAAGCTGGGAGTTGAGCAGCCTACCCTGTACTGGCACGTGAAGAACAAG

CGGGCCCTGCTCGATGCCCTGCCAATCGAGATGCTGGACAGGCATCATACCCAC

AGCTGCCCCTGGAAGGCGAGTCATGGCAAGACTTTCTGCGGAACAACGCCAAG

TCATACCGCTGTGCTCTCCTCTCACATCGCGACGGGGCTAAAGTGCATCTCGGCA

CCCGCCCAACAGAGAAACAGTACGAAACCCTGGAAAATCAGCTCGCGTTCCTGT

GTCAGCAAGGCTTCTCCCTGGAGAACGCACTGTACGCTCTGTCCGCCGTGGGCCA

CTTTACACTGGGCTGCGTATTGGAGGAACAGGAGCATCAAGTAGCAAAAGAGGA

AAGAGAGACACCTACCACCGATTCTATGCCCCCACTTCTGAAGCAAGCAATTGA

GCTGTTCGACCGGCAGGGAGCCGAACCTGCCTTCCTTTTCGGCCTGGAACTAATC

ATATGTGGCCTGGAGAAACAGCTAAAGTGCGAAAGCGGCGGGCCGACCGACGCC

CTTGACGATTTTGACTTAGACATGCTCCCAGCCGATGCCCTTGACGACTTTGACCT

TGATATGCTGCCTGCTGACGCTCTTGACGATTTTGACCTTGACATGCTCCCCGGGT

AACTAAGTAAGGATCATCTTAATTAAATCGATAAGGATCTGGCCGCCTCGGCCTA

ATCAACCTCTGGATTACAAAATTTGTGAAAGATTGACTGGTATTCTTAACTATGT

TGCTCCTTTTACGCTATGTGGATACGCTGCTTTAATGCCTTTGTATCATGCTATTG

CTTCCCGTATGGCTTTCATTTTCTCCTCCTTGTATAAATCCTGGTTGCTGTCTCTTT

ATGAGGAGTTGTGGCCCGTTGTCAGGCAACGTGGCGTGGTGTGCACTGTGTTTGC

TGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGC

CCGCTGCTGGACAGGGGCTCGGCTGTTGGGCACTGACAATTCCGTGGTGTTGTCG

GGGAAATCATCGTCCTTTCCTTGGCTGCTCGCCTGTGTTGCCACCTGGATTCTGCG

CGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGAC

GAGTCGGATCTCCCTTTGGGCCGCCTCCCCGCCAGACATGATAAGATACATTGAT

GAGTTTGGACAAACCACAACTAGAATGCAGTGAAAAAAATGCTTTATTTGTGAA

ATTTGTGATGCTATTGCTTTATTTGTAACCATTATAAGCTGCAATAAACAAGTTAA

CAACAACAATTGCATTCATTTTATGTTTCAGGTTCAGGGGGAGATGTGGGAGGTT

TTTTAAAGCAAGTAAAACCTCTACAAATGTGGTAACTAGCGCGTGCGGCCGCAG

GAACCCCTAGTGATGGAGTTGGCCACTCCCTCTCTGCGCGCTCGCTCGCTCACTG

AGGCCGGGCGACCAAAGGTCGCCCGACGCCCGGGCTTTGCCCGGGCGGCCTCAG

TGAGCGAGCGAGCGCGCAGCTGCCTGCAGGACATGTGAGCAAAAGGCCAGCAA

AAGGCCAGGAACCGTAAAAAGGCCGCGTTGCTGGCGTTTTTCCATAGGCTCCGCC

CCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCG
```

-continued

TGGCGCTTTCTCATAGCTCACGCTGTAGGTATCTCAGTTCGGTGTAGGTCGTTCGC

TCCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATC

TGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTAC

GCGCAGAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACC

TATCTCAGCGATCTGTCTATTTCGTTCATCCATAGTTGCCTGACTCCCCGTCGTGT

AGATAACTACGATACGGGAGGGCTTACCATCTGGCCCCAGTGCTGCAATGATAC

CGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTAT

TAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTTGGCCG

CAGTGTTATCACTCATGGTTATGGCAGCACTGCATAATTCTCTTACTGTCATGCCA

TCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGA

AAACTCTCAAGGATCTTACCGCTGTTGAGATCCAGTTCGATGTAACCCACTCGTG

CACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTT

GAATACTCATACTCTTCCTTTTTCAATATTATTGAAGCATTTATCAGGGTTATTGT

CTCATGAGCGGATACATATTTGAATGTATTTAGAAAAATAAACAAATAGGGGTTC

CGCGCACATTTCCCCGAAAAGTGCCACCTGACGTCTAAGAAACCATTATTATCAT

GACATTAACCTATAAAAATAGGCGTATCACGAGGCCCTTTCGTCTCGCGCGTTTC

GGTGATGACGGTGAAAACCTCTGACACATGCAGCTCCCGGAGACGGTCACAGCT

TGTCTGTAAGCGGATGCCGGGAGCAGACAAGCCCGTCAGGGCGCGTCAGCGGGT

GTTGGCGGGTGTCGGGGCTGGCTTAACTATGCGGCATCAGAGCAGATTGTACTGA

GAGTGCACCATA

CAG-tTA (SEQ ID NO: 32):
CCTGCAGGCAGCTGCGCGCTCGCTCGCTCACTGAGGCCGCCCGGGCAAAGCCCG

GGCGTCGGGCGACCTTTGGTCGCCCGGCCTCAGTGAGCGAGCGAGCGCGCAGAG

AGGGAGTGGCCAACTCCATCACTAGGGGTTCCTGCGGCCGCACGCGTGGAGCTA

GTTATTAATAGTAATCAATTACGGGGTCATTAGTTCATAGCCCATATATGGAGTT

CCGCGTTACATAACTTACGGTAAATGGCCCGCCTGGCTGACCGCCCAACGACCCC

CGCCCATTGACGTCAATAATGACGTATGTTCCCATAGTAACGTCAATAGGGACTT

-continued

```
TCCATTGACGTCAATGGGTGGAGTATTTACGGTAAACTGCCCACTTGGCAGTACA
TCAAGTGTATCATATGCCAAGTACGCCCCCTATTGACGTCAATGACGGTAAATGG
CCCGCCTGGCATTATGCCCAGTACATGACCTTATGGGACTTTCCTACTTGGCAGT
ACATCTACGTATTAGTCATCGCTATTACCATGGTGATGCGGTTTTGGCAGTACAT
CAATGGGCGTGGATAGCGGTTTGACTCACGGGGATTTCCAAGTCTCCACCCCATT
GACGTCAATGGGAGTTTGTTTTGCACCAAAATCAACGGGACTTTCCAAAATGTCG
TAACAACTCCGCCCCATTGACGCAAATGGGCGGTAGGCGTGTACGGTGGGAGGT
CTATATAAGCAGAGCTCGTTTAGTGAACCGTCAGATCGCCTGGAGACGCCATCCA
CGCTGTTTTGACCTCCATAGAAGACACCGGGACCGATCCAGCCTCCGCGGATTCG
AATCCCGGCCGGGAACGGTGCATTGGAACGCGGATTCCCCGTGCCAAGAGTGAC
GTAAGTACCGCCTATAGAGTCTATAGGCCCACAAAAAATGCTTTCTTCTTTTAAT
ATACTTTTTTGTTTATCTTATTTCTAATACTTTCCCTAATCTCTTTCTTTCAGGGCA
ATAATGATACAATGTATCATGCCTCTTTGCACCATTCTAAAGAATAACAGTGATA
ATTTCTGGGTTAAGGCAATAGCAATATTTCTGCATATAAATATTTCTGCATATAA
ATTGTAACTGATGTAAGAGGTTTCATATTGCTAATAGCAGCTACAATCCAGCTAC
CATTCTGCTTTTATTTTATGGTTGGGATAAGGCTGGATTATTCTGAGTCCAAGCTA
GGCCCTTTTGCTAATCATGTTCATACCTCTTATCTTCCTCCCACAGCTCCTGGGCA
ACGTGCTGGTCTGTGTGCTGGCCCATCACTTTGGCAAAGAATTGGGATTCGAACA
TCGATTGAATTCATGTCTAGACTGGACAAGAGCAAAGTCATAAACTCTGCTCTGG
AATTACTCAATGAAGTCGGTATCGAAGGCCTGACGACAAGGAAACTCGCTCAAA
AGCTGGGAGTTGAGCAGCCTACCCTGTACTGGCACGTGAAGAACAAGCGGGCCC
TGCTCGATGCCCTGGCAATCGAGATGCTGGACAGGCATCATACCCACTTCTGCCC
CCTGGAAGGCGAGTCATGGCAAGACTTTCTGCGGAACAACGCCAAGTCATTCCG
CTGTGCTCTCCTCTCACATCGCGACGGGGCTAAAGTGCATCTCGGCACCCGCCCA
ACAGAGAAACAGTACGAAACCCTGGAAAATCAGCTCGCGTTCCTGTGTCAGCAA
GGCTTCTCCCTGGAGAACGCACTGTACGCTCTGTCCGCCGTGGGCCACTTTACAC
TGGGCTGCGTATTGGAGGATCAGGAGCATCAAGTAGCAAAAGAGGAAAGAGAG
ACACCTACCACCGATTCTATGCCCCCACTTCTGAGACAAGCAATTGAGCTGTTCG
ACCATCAGGGAGCCGAACCTGCCTTCCTTTTCGGCCTGGAACTAATCATATGTGG
CCTGGAGAAACAGCTAAAGTGCGAAAGCGGCGGGCCGGCCGACGCCCTTGACGA
TTTTGACTTAGACATGCTCCCAGCCGATGCCCTTGACGACTTTGACCTTGATATGC
TGCCTGCTGACGCTCTTGACGATTTTGACCTTGACATGCTCCCCGGATGAGGATC
CTCTAGAGTCGACCTGCAGAAGCTTGCCTCGAGCAGCGCTGCTCGAGAGATCTAC
GGGTGGCATCCCTGTGACCCCTCCCCAGTGCCTCTCCTGGCCCTGGAAGTTGCCA
CTCCAGTGCCCACCAGCCTTGTCCTAATAAAATTAAGTTGCATCATTTTGTCTGAC
TAGGTGTCCTTCTATAATATTATGGGTGGAGGGGGGTGGTATGGAGCAAGGGG
CAAGTTGGGAAGACAACCTGTAGGGCCTGCGGGGTCTATTGGGAACCAAGCTGG
AGTGCAGTGGCACAATCTTGGCTCACTGCAATCTCCGCCTCCTGGGTTCAAGCGA
TTCTCCTGCCTCAGCCTCCCGAGTTGTTGGGATTCCAGGCATGCATGACCAGGCT
CAGCTAATTTTTGTTTTTTTGGTAGAGACGGGGTTTCACCATATTGGCCAGGCTGG
```

-continued

```
TCTCCAACTCCTAATCTCAGGTGATCTACCCACCTTGGCCTCCCAAATTGCTGGG

ATTACAGGCGTGAACCACTGCTCCCTTCCCTGTCCTTCTGATTTTGTAGGTAACCA

CGTGCGGACCGAGCGGCCGCAGGAACCCCTAGTGATGGAGTTGGCCACTCCCTC

TCTGCGCGCTCGCTCGCTCACTGAGGCCGGGCGACCAAAGGTCGCCCGACGCCC

GGGCTTTGCCCGGGCGGCCTCAGTGAGCGAGCGAGCGCGCAGCTGCCTGCAGGG

GCGCCTGATGCGGTATTTTCTCCTTACGCATCTGTGCGGTATTTCACACCGCATAC

GTCAAAGCAACCATAGTACGCGCCCTGTAGCGGCGCATTAAGCGCGGCGGGTGT

GGTGGTTACGCGCAGCGTGACCGCTACACTTGCCAGCGCCCTAGCGCCCGCTCCT

TTCGCTTTCTTCCCTTCCTTTCTCGCCACGTTCGCCGGCTTTCCCCGTCAAGCTCTA

AATCGGGGGCTCCCTTTAGGGTTCCGATTTAGTGCTTTACGGCACCTCGACCCCA

AAAAACTTGATTTGGGTGATGGTTCACGTAGTGGGCCATCGCCCTGATAGACGGT

TTTTCGCCCTTTGACGTTGGAGTCCACGTTCTTTAATAGTGGACTCTTGTTCCAAA

CTGGAACAACACTCAACCCTATCTCGGGCTATTCTTTTGATTTATAAGGGATTTTG

CCGATTTCGGCCTATTGGTTAAAAAATGAGCTGATTTAACAAAAATTTAACGCGA

ATTTTAACAAAATATTAACGTTTACAATTTTATGGTGCACTCTCAGTACAATCTGC

TCTGATGCCGCATAGTTAAGCCAGCCCCGACACCCGCCAACACCCGCTGACGCG

CCCTGACGGGCTTGTCTGCTCCCGGCATCCGCTTACAGACAAGCTGTGACCGTCT

CCGGGAGCTGCATGTGTCAGAGGTTTTCACCGTCATCACCGAAACGCGCGAGAC

GAAAGGGCCTCGTGATACGCCTATTTTTATAGGTTAATGTCATGATAATAATGGT

TTCTTAGACGTCAGGTGGCACTTTTCGGGGAAATGTGCGCGGAACCCCTATTTGT

TTATTTTTCTAAATACATTCAAATATGTATCCGCTCATGAGACAATAACCCTGATA

AATGCTTCAATAATATTGAAAAAGGAAGAGTATGAGTATTCAACATTTCCGTGTC

GCCCTTATTCCCTTTTTTGCGGCATTTTGCCTTCCTGTTTTTGCTCACCCAGAAACG

CTGGTGAAAGTAAAAGATGCTGAAGATCAGTTGGGTGCACGAGTGGGTTACATC

GAACTGGATCTCAACAGCGGTAAGATCCTTGAGAGTTTTCGCCCCGAAGAACGTT

TTCCAATGATGAGCACTTTTAAAGTTCTGCTATGTGGCGCGGTATTATCCCGTATT

GACGCCGGGCAAGAGCAACTCGGTCGCCGCATACACTATTCTCAGAATGACTTG

GTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTC

TGACAACGATCGGAGGACCGAAGGAGCTAACCGCTTTTTTGCACAACATGGGGG

ATCATGTAACTCGCCTTGATCGTTGGGAACCGGAGCTGAATGAAGCCATACCAA

ACGACGAGCGTGACACCACGATGCCTGTAGCAATGGCAACAACGTTGCGCAAAC

TATTAACTGGCGAACTACTTACTCTAGCTTCCCGGCAACAATTAATAGACTGGAT

GGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAG

CACTGGGGCCAGATGGTAAGCCCTCCCGTATCGTAGTTATCTACACGACGGGGA

GTCAGGCAACTATGGATGAACGAAATAGACAGATCGCTGAGATAGGTGCCTCAC

TGATTAAGCATTGGTAACTGTCAGACCAAGTTTACTCATATATACTTTAGATTGA

TTTAAAACTTCATTTTTAATTTAAAAGGATCTAGGTGAAGATCCTTTTTGATAATC

TCATGACCAAAATCCCTTAACGTGAGTTTTCGTTCCACTGAGCGTCAGACCCCGT

AGAAAAGATCAAAGGATCTTCTTGAGATCCTTTTTTTCTGCGCGTAATCTGCTGCT
```

-continued

```
TGCAAACAAAAAAACCACCGCTACCAGCGGTGGTTTGTTTGCCGGATCAAGAGC

TACCAACTCTTTTTCCGAAGGTAACTGGCTTCAGCAGAGCGCAGATACCAAATAC

TGTCCTTCTAGTGTAGCCGTAGTTAGGCCACCACTTCAAGAACTCTGTAGCACCG

CCTACATACCTCGCTCTGCTAATCCTGTTACCAGTGGCTGCTGCCAGTGGCGATA

AGTCGTGTCTTACCGGGTTGGACTCAAGACGATAGTTACCGGATAAGGCGCAGC

GGTCGGGCTGAACGGGGGGTTCGTGCACACAGCCCAGCTTGGAGCGAACGACCT

ACACCGAACTGAGATACCTACAGCGTGAGCTATGAGAAAGCGCCACGCTTCCCG

AAGGGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGCGGAG

CCTATGGAAAAACGCCAGCAACGCGGCCTTTTTACGGTTCCTGGCCTTTTGCTGG

CCTTTTGCTCACATGT
``` pAAV-Tet-O-OSK-SV40LpA (or pAAV-TRE2-OSK-SV40LpA) (SEQ ID NO: 33):
```
TTATGCAGTGCTGCCATAACCATGAGTGATAACACTGCGGCCAACTTACTTCTGA

CAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTAT

TAACTGGCGAACTACTTACTCTAGCTTCCCGGCAACAATTAATAGACTGGATGGA

GGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGAT

TAAGCATTGGTAACTGTCAGACCAAGTTTACTCATATATACTTTAGATTGATTTA

AAACTTCATTTTTAATTTAAAAGGATCTAGGTGAAGATCCTTTTTGATAATCTCAT

GACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCA

AACAAAAAAACCACCGCTACCAGCGGTGGTTTGTTTGCCGGATCAAGAGCTACC

AACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTC

GTGTCTTACCGGGTTGGACTCAAGACGATAGTTACCGGATAAGGCGCAGCGGTC

GGGCTGAACGGGGGGTTCGTGCACACAGCCCAGCTTGGAGCGAACGACCTACAC

CGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCA

CGAGGGAGCTTCCAGGGGGAAACGCCTGGTATCTTTATAGTCCTGTCGGGTTTCG

CCACCTCTGACTTGAGCGTCGATTTTTGTGATGCTCGTCAGGGGGCGGAGCCTA

TGGAAAAACGCCAGCAACGCGGCCTTTTTACGGTTCCTGGCCTTTTGCTGGCCTT

TTGCTCACATGTTCTTTCCTGCGTTATCCCCTGATTCTGTGGATAACCGTATTACC

GCCTTTGAGTGAGCTGATACCGCTCGCCGCAGCCGAACGACCGAGCGCAGCGAG

TCAGTGAGCGAGGAAGCGGAAGAGCGCCCAATACGCAAACCGCCTCTCCCCGCG

CGTTGGCCGATTCATTAATGCAGCTGGCACGACAGGTTTCCCGACTGGAAAGCGG
```

```
GCAGTGAGCGCAACGCAATTAATGTGAGTTAGCTCACTCATTAGGCACCCCAGG

CTTTACACTTTATGCTTCCGGCTCGTATGTTGTGTGGAATTGTGAGCGGATAACA

ATTTCACACAGGAAACAGCTATGACCATGATTACGCCAGATTTAATTAAGGCCTT

AATTAGGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGG

AGTGGCCAACTCCATCACTAGGGGTTCCTTGTAGTTAATGATTAACCCGCCATGC

TACTTATCTACGTAGCCATGCTCTAGGAAGATCGGAATTCGTACACGCCTACCTC

GACCCATCAAGTGCCACCTGACGTCTCCCTATCAGTGATAGAGAAGTCGACACGT

CTCGAGCTCCCTATCAGTGATAGAGAAGGTACGTCTAGAACGTCTCCCTATCAGT

GATAGAGAAGTCGACACGTCTCGAGCTCCCTATCAGTGATAGAGAAGGTACGTC

TAGAACGTCTCCCTATCAGTGATAGAGAAGTCGACACGTCTCGAGCTCCCTATCA

GTGATAGAGAAGGTACGTCTAGAACGTCTCCCTATCAGTGATAGAGAAGTCGAC

ACGTCTCGAGCTCCCTATCAGTGATAGAGAAGGTACCCCTATATAAGCAGAGCT

CGTTTAGTGAACCGTCAGATCGCCTGGAGACGCCATCCACGCTGTTTTGACCTCC

ATAGAAGACACCGGGACCGATCCAGCCTGGATCGCGGCCGCGCCACCATGGCTG

GACACCTGGCTTCAGACTTCGCCTTCTCACCCCCACCAGGTGGGGGTGATGGGTC

AGCAGGGCTGGAGCCGGGCTGGGTGGATCCTCGAACCTGGCTAAGCTTCCAAGG

GCCTCCAGGTGGGCCTGGAATCGGACCAGGCTCAGAGGTATTGGGGATCTCCCC

ATGTCCGCCCGCATACGAGTTCTGCGGAGGGATGGCATACTGTGGACCTCAGGTT

GGACTGGGCCTAGTCCCCCAAGTTGGCGTGGAGACTTTGCAGCCTGAGGGCCAG

GCAGGAGCACGAGTGGAAAGCAACTCAGAGGGAACCTCCTCTGAGCCCTGTGCC

GACCGCCCCAATGCCGTGAAGTTGGAGAAGGTGGAACCAACTCCCGAGGAGTCC

CAGGACATGAAAGCCCTGCAGAAGGAGCTAGAACAGTTTGCCAAGCTGCTGAAG

CAGAAGAGGATCACCTTGGGGTACACCCAGGCCGACGTGGGGCTCACCCTGGGC

GTTCTCTTTGGAAAGGTGTTCAGCCAGACCACCATCTGTCGCTTCGAGGCCTTGC

AGCTCAGCCTTAAGAACATGTGTAAGCTGCGGCCCCTGCTGGAGAAGTGGGTGG

AGGAAGCCGACAACAATGAGAACCTTCAGGAGATATGCAAATCGGAGACCCTGG

TGCAGGCCCGGAAGAGAAAGCGAACTAGCATTGAGAACCGTGTGAGGTGGAGTC

TGGAGACCATGTTTCTGAAGTGCCCGAAGCCCTCCCTACAGCAGATCACTCACAT

CGCCAATCAGCTTGGGCTAGAGAAGGATGTGGTTCGAGTATGGTTCTGTAACCGG

CGCCAGAAGGGCAAAAGATCAAGTATTGAGTATTCCCAACGAGAAGAGTATGAG

GCTACAGGGACACCTTTCCCAGGGGGGCTGTATCCTTTCCTCTGCCCCCAGGTC

CCCACTTTGGCACCCCAGGCTATGGAAGCCCCCACTTCACCACACTCTACTCAGT

CCCTTTTCCTGAGGGCGAGGCCTTTCCCTCTGTTCCCGTCACTGCTCTGGGCTCTC

CCATGCATTCAAACGCTAGCGGCAGCGGCGCCACGAACTTCTCTCTGTTAAAGCA

AGCAGGAGATGTTGAAGAAAACCCCGGGCCTGCATGCATGTATAACATGATGGA

GACGGAGCTGAAGCCGCCGGGCCCGCAGCAAGCTTCGGGGGGCGGCGGCGGAG

GAGGCAACGCCACGGCGGCGGCGACCGGCGGCAACCAGAAGAACAGCCCGGAC

CGCGTCAAGAGGCCCATGAACGCCTTCATGGTATGGTCCCGGGGCAGCGGCGT

AAGATGGCCCAGGAGAACCCCAAGATGCACAACTCGGAGATCAGCAAGCGCCTG
```

-continued

```
GGCGCGGAGTGGAAACTTTTGTCCGAGACCGAGAAGCGGCCGTTCATCGACGAG

GCCAAGCGGCTGCGCGCTCTGCACATGAAGGAGCACCCGGATTATAAATACCGG

CCGCGGCGGAAAACCAAGACGCTCATGAAGAAGGATAAGTACACGCTTCCCGGA

GGCTTGCTGGCCCCCGGCGGGAACAGCATGGCGAGCGGGGTTGGGGTGGGCGCC

GGCCTGGGTGCGGGCGTGAACCAGCGCATGGACAGCTACGCGCACATGAACGGC

TGGAGCAACGGCAGCTACAGCATGATGCAGGAGCAGCTGGGCTACCCGCAGCAC

CCGGGCCTCAACGCTCACGGCGCGGCACAGATGCAACCGATGCACCGCTACGAC

GTCAGCGCCCTGCAGTACAACTCCATGACCAGCTCGCAGACCTACATGAACGGC

TCGCCCACCTACAGCATGTCCTACTCGCAGCAGGGCACCCCGGTATGGCGCTGG

GCTCCATGGGCTCTGTGGTCAAGTCCGAGGCCAGCTCCAGCCCCCCGTGGTTAC

CTCTTCCTCCCACTCCAGGGCGCCCTGCCAGGCCGGGGACCTCCGGGACATGATC

AGCATGTACCTCCCCGGCGCCGAGGTGCCGGAGCCCGCTGCGCCCAGTAGACTG

CACATGGCCCAGCACTACCAGAGCGGCCCGGTGCCCGGCACGGCCATTAACGGC

ACACTGCCCCTGTCGCACATGGCATGCGGCTCCGGCGAGGGCAGGGGAAGTCTT

CTAACATGCGGGACGTGGAGGAAAATCCCGGCCCACTCGAGATGAGGCAGCCA

CCTGGCGAGTCTGACATGGCTGTCAGCGACGCTCTGCTCCCGTCCTTCTCCACGT

TCGCGTCCGGCCCGGCGGGAAGGGAGAAGACACTGCGTCCAGCAGGTGCCCCGA

CTAACCGTTGGCGTGAGGAACTCTCTCACATGAAGCGACTTCCCCCACTTCCCGG

CCGCCCCTACGACCTGGCGGCGACGGTGGCCACAGACCTGGAGAGTGGCGGAGC

TGGTGCAGCTTGCAGCAGTAACAACCCGGCCCTCCTAGCCCGGAGGGAGACCGA

GGAGTTCAACGACCTCCTGGACCTAGACTTTATCCTTTCCAACTCGCTAACCCAC

CAGGAATCGGTGGCCGCCACCGTGACCACCTCGGCGTCAGCTTCATCCTCGTCTT

CCCCAGCGAGCAGCGGCCCTGCCAGCGCGCCCTCCACCTGCAGCTTCAGCTATCC

GATCCGGGCCGGGGGTGACCCGGGCGTGGCTGCCAGCAACACAGGTGGAGGGCT

CCTCTACAGCCGAGAATCTGCGCCACCTCCCACGGCCCCCTTCAACCTGGCGGAC

ATCAATGACGTGAGCCCCTCGGGCGGCTTCGTGGCTGAGCTCCTGCGGCCGGAGT

TGGACCCAGTATACATTCCGCCACAGCAGCCTCAGCCGCCAGGTGGCGGGCTGA

TGGGCAAGTTTGTGCTGAAGGCGTCTCTGACCACCCCTGGCAGCGAGTACAGCA

GCCCTTCGGTCATCAGTGTTAGCAAAGGAAGCCCAGACGGCAGCCACCCCGTGG

TAGTGGCGCCCTACAGCGGTGGCCCGCCGCGCATGTGCCCCAAGATTAAGCAAG

AGGCGGTCCCGTCCTGCACGGTCAGCCGGTCCCTAGAGGCCCATTTGAGCGCTGG

ACCCCAGCTCAGCAACGGCCACCGGCCCAACACACACGACTTCCCCCTGGGGCG

GCAGCTCCCCACCAGGACTACCCCTACACTGAGTCCCGAGGAACTGCTGAACAG

CAGGGACTGTCACCCTGGCCTGCCTCTTCCCCCAGGATTCCATCCCCATCCGGGG

CCCAACTACCCTCCTTTCCTGCCAGACCAGATGCAGTCACAAGTCCCCTCTCTCC

ATTATCAAGAGCTCATGCCACCGGGTTCCTGCCTGCCAGAGGAGCCCAAGCCAA

AGAGGGAAGAAGGTCGTGGCCCCGGAAAAGAACAGCCACCCACACTTGTGACT

ATGCAGGCTGTGGCAAAACCTATACCAAGAGTTCTCATCTCAAGGCACACCTGCG

AACTCACACAGGCGAGAAACCTTACCACTGTGACTGGGACGGCTGTGGGTGGAA

ATTCGCCCGCTCCGATGAACTGACCAGGCACTACCGCAAACACACAGGGCACCG

GCCCTTTCAGTGCCAGAAGTGCGACAGGGCCTTTTCCAGGTCGGACCACCTTGCC
```

-continued

```
TTACACATGAAGAGGCACTAAATGACTAGTCTAGCAATCAACCTCTGGATTACAA

AATTTGTGAAAGATTGACTGGTATTCTTAACTATGTTGCTCCTTTTACGCTATGTG

GATACGCTGCTTTAATGCCTTTGTATCATGCTATTGCTTCCCGTATGGCTTTCATT

TTCTCCTCCTTGTATAAATCCTGGTTAGTTCTTGCCACGGCGGAACTCATCGCCGC

CTGCCTTGCCCGCTGCTGGACAGGGGCTCGGCTGTTGGGCACTGACAATTCCGTG

GTGTTTATTTGTGAAATTTGTGATGCTATTGCTTTATTTGTAACCATTCTAGCTTTA

TTTGTGAAATTTGTGATGCTATTGCTTTATTTGTAACCATTATAAGCTGCAATAAA

CAAGTTAACAACAACAATTGCATTCATTTTATGTTTCAGGTTCAGGGGGAGATGT

GGGAGGTTTTTTAAAGCGGGGGATCCAAATTCCCGATAAGGATCTTCCTAGAGCA

TGGCTACGTAGATAAGTAGCATGGCGGGTTAATCATTAACTACAAGGAACCCCT

AGTGATGGAGTTGGCCACTCCCTCTCTGCGCGCTCGCTCGCTCACTGAGGCCGGG

CGACCAAAGGTCGCCCGACGCCCGGGCTTTGCCCGGGCGGCCTCAGTGAGCGAG

CGAGCGCGCAGCCTTAATTAACCTAATTCACTGGCCGTCGTTTTACAACGTCGTG

ACTGGGAAAACCCTGGCGTTACCCAACTTAATCGCCTTGCAGCACATCCCCCTTT

CGCCAGCTGGCGTAATAGCGAAGAGGCCCGCACCGATCGCCCTTCCCAACAGTT

GCGCAGCCTGAATGGCGAATGGGACGCGCCCTGTAGCGGCGCATTAAGCGCGGC

GGGTGTGGTGGTTACGCGCAGCGTGACCGCTACACTTGCCAGCGCCCTAGCGCCC

GCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCG

ACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGT

TCCAAACTGGAACAACACTCAACCCTATCTCGGTCTATTCTTTTGATTTATAAGG

GATTTTGCCGATTTCGGCCTATTGGTTAAAAAATGAGCTGATTTAACAAAAATTT

AACGCGAATTTTAACAAAATATTAACGTTTATAATTTCAGGTGGCATCTTTCGGG

GAAATGTGCGCGGAACCCCTATTTGTTTATTTTTCTAAATACATTCAAATATGTAT

CCGCTCATGAGACAATAACCCTGATAAATGCTTCAATAATATTGAAAAAGGAAG

AGTATGAGTATTCAACATTTCCGTGTCGCCCTTATTCCCTTTTTTGCGGCATTTTG

CCTTCCTGTTTTTGCTCACCCAGAAACGCTGGTGAAAGTAAAAGATGCTGAAGAT

CAGTTGGGTGCACGAGTGGGTTACATCGAACTGGATCTCAATAGTGGTAAGATCC

TTGAGAGTTTTCGCCCCGAAGAACGTTTTCCAATGATGAGCACTTTTAAAGTTCT

GCTATGTGGCGCGGTATTATCCCGTATTGACGCCGGGCAAGAGCAACTCGGTCGC

CGCATACACTATTCTCAGAATGACTTGGTTGAGTACTCACCAGTCACAGAAAAGC

ATCTTACGGATGGCATGACAGTAAGAGAA

VP64, 4 repeats of VP16 (SEQ ID NO: 34) (Non-limiting example of a
transactivation domain):
GAGGCCAGCGGTTCCGGACGGGCTGACGCATTGGACGATTTTGATCTGGATATGC

TGGGAAGTGACGCCCTCGATGATTTTGACCTTGACATGCTTGGTTCGGATGCCCT

TGATGACTTTGACCTCGACATGCTCGGCAGTGACGCCCTTGATGATTTCGACCTG

GACATGCTGATTAACTCTAGA

P65 (SEQ ID NO: 35) (Non-limiting example of a transactivation domain):
AGCCAGTACCTGCCCGACACCGACGACCGGCACCGGATCGAGGAAAAGCGGAA

GCGGACCTACGAGACATTCAAGAGCATCATGAAGAAGTCCCCCTTCAGCGGCCC
```

CACCGACCCTAGACCTCCACCTAGAAGAATCGCCGTGCCCAGCAGATCCAGCGC

CAGCGTGCCAAAACCTGCCCCCCAGCCTTACCCCTTCACCAGCAGCCTGAGCACC

ATCAACTACGACGAGTTCCCTACCATGGTGTTCCCCAGCGGCCAGATCTCTCAGG

CCTCTGCTCTGGCTCCAGCCCCTCCTCAGGTGCTGCCTCAGGCTCCTGCTCCTGCA

CCAGCTCCAGCCATGGTGTCTGCACTGGCTCAGGCACCAGCACCCGTGCCTGTGC

TGGCTCCTGGACCTCCACAGGCTGTGGCTCCACCAGCCCCTAAACCTACACAGGC

CGGCGAGGGCACACTGTCTGAAGCTCTGCTGCAGCTGCAGTTCGACGACGAGGA

TCTGGGAGCCCTGCTGGGAAACAGCACCGATCCTGCCGTGTTCACCGACCTGGCC

AGCGTGGACAACAGCGAGTTCCAGCAGCTGCTGAACCAGGGCATCCCTGTGGCC

CCTCACACCACCGAGCCCATGCTGATGGAATACCCCGAGGCCATCACCCGGCTC

GTGACAGGCGCTCAGAGGCCTCCTGATCCAGCTCCTGCCCCTCTGGGAGCACCAG

GCCTGCCTAATGGACTGCTGTCTGGCGACGAGGACTTCAGCTCTATCGC

CGATATGGATTTCTCAGCCTTGCTG

RTA (SEQ ID NO: 36) (Non-limiting example of a transactivation domain):
CGGGATTCCAGGGAAGGGATGTTTTTGCCGAAGCCTGAGGCCGGCTCCGCTATTA

GTGACGTGTTTGAGGGCCGCGAGGTGTGCCAGC CAAAACGAA TCCGGCCA

TTTCATCCTCCAGGAAGTCCATGGGCAACCGCCCACTCCCCGCCAGCCTCGCAC

CAACACCAACCGGTCCAGTACATGAGCCAGTCGGGTCACTGACCCCGGCACCAG

TCCC

TCAGCCACTGGATCCAGCGCCCGCAGTGACTCCCGAGGCCAGTCACCTGTTGGA

GGATCCCGATGAAGAGACGAGCCAGGCTGTCAAAGCCCTTCGGGAGATGGCCGA

TACTGTGATTCCCCAGAAGGAA GAGGCTGCAA TCTGTGGCCAAA

TGGACCTTTCCCA TCCGCCCCCAAGGGGCCA TCTGGA TGAGCT

GACAACCACACTTGAGTCCA

TGACCGAGGATCTGAACCTGGACTCACCCCTGACCCCGGAATTGAACGAGATTCT

GGATACCTTCCTGAACGACGAGTGCCTCTTGCATGCCATGCATATCAGCACAGGA

C TGTCCA TCTTCGACACA TCTCTGTTT

MPH MS2-P65-HSF1 (SEQ ID NO: 37) (Non-limiting example of a
transactivation domain):
GCTTCAAACTTTACTCAGTTCGTGCTCGTGGACAATGGTGGGACAGGGGATGTGA

CAGTGGCTCCTTCTAATTTCGCTAATGGGGTGGCAGAGTGGATCAGCTCCAACTC

ACGGAGCCAGGCCTACAAGGTGACATGCAGCGTCAGGCAGTCTAGTGCCCAGAA

GAGAAAGTATACCATCAAGGTGGAGGTCCCCAAAGTGGCTACCCAGACAGTGGG

CGGAGTCGAACTGCCTGTCGCCGCTTGGAGGTCCTACCTGAACATGGAGCTCACT

ATCCCAATTTTCGCTACCAATTCTGACTGTGAACTCATCGTGAAGGCAATGCAGG

GGCTCCTCAAAGACGGTAATCCTATCCCTTCCGCCATCGCCGCTAACTCAGGTAT

CTACAGCGCTGGAGGAGGTGGAAGCGGAGGAGGAGGAAGCGGAGGAGGAGGTA

GCGGACCTAAGAAAAAGAGGAAGGTGGCGGCCGCTGGATCCCCTTCAGGGCAGA

TCAGCAACCAGGCCCTGGCTCTGGCCCCTAGCTCCGCTCCAGTGCTGGCCCAGAC

TATGGTGCCCTCTAGTGCTATGGTGCCTCTGGCCCAGCCACCTGCTCCAGCCCCT

GTGCTGACCCCAGGACCACCCCAGTCACTGAGCGCTCCAGTGCCCAAGTCTACAC

AGGCCGGCGAGGGGACTCTGAGTGAAGCTCTGCTGCACCTGCAGTTCGACGCTG

-continued

ATGAGGACCTGGGAGCTCTGCTGGGGAACAGCACCGATCCCGGAGTGTTCACAG

ATCTGGCCTCCGTGGACAACTCTGAGTTTCAGCAGCTGCTGAATCAGGGCGTGTC

CATGTCTCATAGTACAGCCGAACCAATGCTGATGGAGTACCCCGAAGCCATTACC

CGGCTGGTGACCGGCAGCCAGCGGCCCCCCGACCCCGCTCCAACTCCCCTGGGA

ACCAGCGGCCTGCCTAATGGGCTGTCCGGAGATGAAGACTTCTCAAGCATCGCTG

ATATGGACTTTAGTGCCCTGCTGTCACAGATTTCCTCTAGTGGGCAGGGAGGAGG

TGGAAGCGGCTTCAGCGTGGACACCAGTGCCCTGCTGGACCTGTTCAGCCCCTCG

GTGACCGTGCCCGACATGAGCCTGCCTGACCTTGACAGCAGCCTGGCCAGTATCC

AAGAGCTCCTGTCTCCCCAGGAGCCCCCCAGGCCTCCCGAGGCAGAGAACAGCA

GCCCGGATTCAGGGAAGCAGCTGGTGCACTACACAGCGCAGCCGCTGTTCCTGC

TGGACCCCGGCTCCGTGGACACCGGGAGCAACGACCTGCCGGTGCTGTTTGAGC

TGGGAGAGGGCTCCTACTTCTCCGAAGGGGACGGCTTCGCCGAGGACCCCACCA

TCTCCCTGCTGACAGGCTCGGAGCCTCCCAAAGCCAAGGACCCCACTGTCTCC

OCT4-2A-SOX2-2A-KLF4 (non-limiting example of nucleic acid sequence
encoding human OCT4, human SOX2, and human KLF4, each separated by a 2A peptide)
(SEQ ID NO: 38):
ATGGCGGGACACCTGGCTTCGGATTTCGCCTTCTCGCCCCCTCCAGGTGGTGGAG

GTGATGGGCCAGGGGGGCCGGAGCCGGGCTGGGTTGATCCTCGGACCTGGCTAA

GCTTCCAAGGCCCTCCTGGAGGGCCAGGAATCGGGCCGGGGGTTGGGCCAGGCT

CTGAGGTGTGGGGGATTCCCCCATGCCCCCCGCCGTATGAGTTCTGTGGGGGGAT

GGCGTACTGTGGGCCCCAGGTTGGAGTGGGGCTAGTGCCCCAAGGCGGCTTGGA

GACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGA

GAAGCTGGAGCAAAACCCGGAGGAGTCCCAGGACATCAAAGCTCTGCAGAAAG

AACTCGAGCAATTTGCCAAGCTCCTGAAGCAGAAGAGGATCACCCTGGGATATA

CACAGGCCGATGTGGGGCTCACCCTGGGGGTTCTATTTGGGAAGGTATTCAGCCA

AACGACCATCTGCCGCTTTGAGGCTCTGCAGCTTAGCTTCAAGAACATGTGTAAG

CTGCGGCCCTTGCTGCAGAAGTGGGTGGAGGAAGCTGACAACAATGAAAATCTT

CAGGAGATATGCAAAGCAGAAACCCTCGTGCAGGCCCGAAAGAGAAAGCGAAC

CAGTATCGAGAACCGAGTGAGAGGCAACCTGGAGAATTTGTTCCTGCAGTGCCC

GAAACCCACACTGCAGCAGATCAGCCACATCGCCCAGCAGCTTGGGCTCGAGAA

GGATGTGGTCCGAGTGTGGTTCTGTAACCGGCGCCAGAAGGGCAAGCGATCAAG

CAGCGACTATGCACAACGAGAGGATTTTGAGGCTGCTGGGTCTCCTTTCTCAGGG

GGACCAGTGTCCTTTCCTCTGGCCCCAGGGCCCCATTTTGGTACCCCAGGCTATG

GGAGCCCTCACTTCACTGCACTGTACTCCTCGGTCCCTTTCCCTGAGGGGGAAGC

CTTTCCCCCTGTCTCTGTCACCACTCTGGGCTCTCCCATGCATTCAAACGCTAGCG

GCAGCGGCGCCACGAACTTCTCTCTCTTAAAGCAAGCAGGAGATGTTGAAGAAA

ACCCCGGGCCTGCATGCATGTACAACATGATGGAGACGGAGCTGAAGCCGCCGG

GCCCGCAGCAAACTTCGGGGGCGGCGGCGGCAACTCCACCGCGGCGGCGGCCG

GCGGCAACCAGAAAAACAGCCCGGACCGCGTCAAGCGGCCCATGAATGCCTTCA

TGGTGTGGTCCCGCGGGCAGCGGCGCAAGATGGCCCAGGAGAACCCCAAGATGC

ACAACTCGGAGATCAGCAAGCGCCTGGGCGCCGAGTGGAAACTTTTGTCGGAGA

-continued

```
CGGAGAAGCGGCCGTTCATCGACGAGGCTAAGCGGCTGCGAGCGCTGCACATGA

AGGAGCACCCGGATTATAAATACCGGCCCCGGCGGAAAACCAAGACGCTCATGA

AGAAGGATAAGTACACGCTGCCCGGCGGGCTGCTGGCCCCCGGCGGCAATAGCA

TGGCGAGCGGGTCGGGTGGGCGCCGGCCTGGGCGCGGGCGTGAACCAGCGC

ATGGACAGTTACGCGCACATGAACGGCTGGAGCAACGGCAGCTACAGCATGATG

CAGGACCAGCTGGGCTACCCGCAGCACCCGGGCCTCAATGCGCACGGCGCAGCG

CAGATGCAGCCCATGCACCGCTACGACGTGAGCGCCCTGCAGTACAACTCCATG

ACCAGCTCGCAGACCTACATGAACGGCTCGCCCACCTACAGCATGTCCTACTCGC

AGCAGGGCACCCCTGGCATGGCTCTTGGCTCCATGGGTTCGGTGGTCAAGTCCGA

GGCCAGCTCCAGCCCCCCTGTGGTTACCTCTTCCTCCCACTCCAGGGCGCCCTGC

CAGGCCGGGGACCTCCGGGACATGATCAGCATGTATCTCCCCGGCGCCGAGGTG

CCGGAACCCGCCGCCCCAGCAGACTTCACATGTCCCAGCACTACCAGAGCGGC

CCGGTGCCCGGCACGGCCATTAACGGCACACTGCCCCTCTCACACATGGCATGCG

GCTCCGGCGAGGGCAGGGGAAGTCTTCTAACATGCGGGGACGTGGAGGAAAATC

CCGGCCCACTCGAGATGGCTGTCAGCGACGCGCTGCTCCCATCTTTCTCCACGTT

CGCGTCTGGCCCGGCGGGAAGGGAGAAGACACTGCGTCAAGCAGGTGCCCCGAA

TAACCGCTGGCGGGAGGAGCTCTCCCACATGAAGCGACTTCCCCCAGTGCTTCCC

GGCCGCCCCTATGACCTGGCGGCGGCGACCGTGGCCACAGACCTGGAGAGCGGC

GGAGCCGGTGCGGCTTGCGGCGGTAGCAACCTGGCGCCCCTACCTCGGAGAGAG

ACCGAGGAGTTCAACGATCTCCTGGACCTGGACTTTATTCTCTCCAATTCGCTGA

CCCATCCTCCGGAGTCAGTGGCCGCCACCGTGTCCTCGTCAGCGTCAGCCTCCTC

TTCGTCGTCGCCGTCGAGCAGCGGCCCTGCCAGCGCGCCCTCCACCTGCAGCTTC

ACCTATCCGATCCGGGCCGGGAACGACCCGGGCGTGGCGCCGGGCGGCACGGGC

GGAGGCCTCCTCTATGGCAGGGAGTCCGCTCCCCCTCCGACGGCTCCCTTCAACC

TGGCGGACATCAACGACGTGAGCCCCTCGGGCGGCTTCGTGGCCGAGCTCCTGC

GGCCAGAATTGGACCCGGTGTACATTCCGCCGCAGCAGCCGCAGCCGCCAGGTG

GCGGGCTGATGGGCAAGTTCGTGCTGAAGGCGTCGCTGAGCGCCCCTGGCAGCG

AGTACGGCAGCCCGTCGGTCATCAGCGTCAGCAAAGGCAGCCCTGACGGCAGCC

ACCCGGTGGTGGTGGCGCCCTACAACGGCGGGCCGCCGCGCACGTGCCCCAAGA

TCAAGCAGGAGGCGGTCTCTTCGTGCACCCACTTGGGCGCTGGACCCCCTCTCAG

CAATGGCCACCGGCCGGCTGCACACGACTTCCCCCTGGGGCGGCAGCTCCCCAG

CAGGACTACCCCGACCCTGGGTCTTGAGGAAGTGCTGAGCAGCAGGGACTGTCA

CCCTGCCCTGCCGCTTCCTCCCGGCTTCCATCCCCACCCGGGGCCCAATTACCCAT

CCTTCCTGCCCGATCAGATGCAGCCGCAAGTCCCGCCGCTCCATTACCAAGAGCT

CATGCCACCCGGTTCCTGCATGCCAGAGGAGCCCAAGCCAAAGAGGGGAAGACG

ATCGTGGCCCCGGAAAAGGACCGCCACCCACACTTGTGATTACGCGGGCTGCGG

CAAAACCTACACAAAGAGTTCCCATCTCAAGGCACACCTGCGAACCCACACAGG

TGAGAAACCTTACCACTGTGACTGGGACGGCTGTGGATGGAAATTCGCCCGCTCA

GATGAACTGACCAGGCACTACCGTAAACACACGGGGCACCGCCCGTTCCAGTGC
```

-continued

CAAAAATGCGACCGAGCATTTTCCAGGTCGGACCACCTCGCCTTACACATGAAG

AGGCATTTT

OCT4-2A-SOX2-2A-KLF4 (non-limiting example of an amino acid sequence
encoding human OCT4, human SOX2, and human KLF4, each separated by a 2A peptide)
(SEQ ID NO: 39):
MAGHLASDFAFSPPPGGGGDGPGGPEPGWVDPRTWLSFQGPPGGPGIGPGVGPGSE

VWGIPPCPPPYEFCGGMAYCGPQVGVGLVPQGGLETSQPEGEAGVGVESNSDGASP

EPCTVTPGAVKLEKEKLEQNPEESQDIKALQKELEQFAKLLKQKRITLGYTQADVGL

TLGVLFGKVFSQTTICRFEALQLSFKNMCKLRPLLQKWVEEADNNENLQEICKAETL

VQARKRKRTSIENRVRGNLENLFLQCPKPTLQQISHIAQQLGLEKDVVRVWFCNRRQ

KGKRSSSDYAQREDFEAAGSPFSGGPVSFPLAPGPHFGTPGYGSPHFTALYSSVPFPE

GEAFPPVSVTTLGSPMHSNASGSGATNFSLLKQAGDVEENPGPACMYNMMETELKP

PGPQQTSGGGGNSTAAAAGGNQKNSPDRVKRPMNAFMVWSRGQRRKMAQENPK

MHNSEISKRLGAEWKLLSETEKRPFIDEAKRLRALHMKEHPDYKYRPRRKTKTLMK

KDKYTLPGGLLAPGGNSMASGVGVGAGLGAGVNQRMDSYAHMNGWSNGSYSMM

QDQLGYPQHPGLNAHGAAQMQPMHRYDVSALQYNSMTSSQTYMNGSPTYSMSYS

QQGTPGMALGSMGSVVKSEASSSPPVVTSSSHSRAPCQAGDLRDMISMYLPGAEVPE

PAAPSRLHMSQHYQSGPVPGTAINGTLPLSHMACGSGEGRGSLLTCGDVEENPGPLE

MAVSDALLPSFSTFASGPAGREKTLRQAGAPNNRWREELSHMKRLPPVLPGRPYDL

AAATVATDLESGGAGAACGGSNLAPLPRRETEEFNDLLDLDFILSNSLTHPPESVAAT

VSSSASASSSSSPSSSGPASAPSTCSFTYPIRAGNDPGVAPGGTGGGLLYGRESAPPPT

APFNLADINDVSPSGGFVAELLRPELDPVYIPPQQPQPPGGGLMGKFVLKASLSAPGS

EYGSPSVISVSKGSPDGSHPVVVAPYNGGPPRTCPKIKQEAVSSCTHLGAGPPLSNGH

RPAAHDFPLGRQLPSRTTPTLGLEEVLSSRDCHPALPLPPGFHPHPGPNYPSFLPDQM

QPQVPPLHYQELMPPGSCMPEEPKPKRGRRSWPRKRTATHTCDYAGCGKTYTKSSH

LKAHLRTHTGEKPYHCDWDGCGWKFARSDELTRHYRKHTGHRPFQCQKCDRAFSR

SDHLALHMKRHF

Human OCT4 nucleic acid sequence (non-limiting example of a nucleic acid
sequence encoding human OCT4) (SEQ ID NO: 40):
ATGGCGGGACACCTGGCTTCGGATTTCGCCTTCTCGCCCCCTCCAGGTGGTGGAG

GTGATGGGCCAGGGGGGCCGGAGCCGGGCTGGGTTGATCCTCGGACCTGGCTAA

GCTTCCAAGGCCCTCCTGGAGGGCCAGGAATCGGGCCGGGGGTTGGGCCAGGCT

CTGAGGTGTGGGGGATTCCCCCATGCCCCCCGCCGTATGAGTTCTGTGGGGGGAT

GGCGTACTGTGGGCCCCAGGTTGGAGTGGGGCTAGTGCCCCAAGGCGGCTTGGA

GACCTCTCAGCCTGAGGGCGAAGCAGGAGTCGGGGTGGAGAGCAACTCCGATGG

GGCCTCCCCGGAGCCCTGCACCGTCACCCCTGGTGCCGTGAAGCTGGAGAAGGA

GAAGCTGGAGCAAAACCCGGAGGAGTCCCAGGACATCAAAGCTCTGCAGAAAG

AACTCGAGCAATTTGCCAAGCTCCTGAAGCAGAAGAGGATCACCCTGGGATATA

CACAGGCCGATGTGGGGCTCACCCTGGGGGTTCTATTTGGGAAGGTATTCAGCCA

AACGACCATCTGCCGCTTTGAGGCTCTGCAGCTTAGCTTCAAGAACATGTGTAAG

CTGCGGCCCTTGCTGCAGAAGTGGGTGGAGGAAGCTGACAACAATGAAAATCTT

CAGGAGATATGCAAAGCAGAAACCCTCGTGCAGGCCCGAAAGAGAAAGCGAAC

CAGTATCGAGAACCGAGTGAGAGGCAACCTGGAGAATTTGTTCCTGCAGTGCCC

-continued

```
GAAACCCACACTGCAGCAGATCAGCCACATCGCCCAGCAGCTTGGGCTCGAGAA

GGATGTGGTCCGAGTGTGGTTCTGTAACCGGCGCCAGAAGGGCAAGCGATCAAG

CAGCGACTATGCACAACGAGAGGATTTTGAGGCTGCTGGGTCTCCTTTCTCAGGG

GGACCAGTGTCCTTTCCTCTGGCCCCAGGGCCCCATTTTGGTACCCCAGGCTATG

GGAGCCCTCACTTCACTGCACTGTACTCCTCGGTCCCTTTCCCTGAGGGGGAAGC

CTTTCCCCCTGTCTCTGTCACCACTCTGGGCTCTCCCATGCATTCAAAC
```

Human OCT4 amino acid sequence (non-limiting example of an amino acid sequence encoding human OCT4) (SEQ ID NO: 41):
```
MAGHLASDFAFSPPPGGGGDGPGGPEPGWVDPRTWLSFQGPPGGPGIGPGVGPGSE

VWGIPPCPPPYEFCGGMAYCGPQVGVGLVPQGGLETSQPEGEAGVGVESNSDGASP

EPCTVTPGAVKLEKEKLEQNPEESQDIKALQKELEQFAKLLKQKRITLGYTQADVGL

TLGVLFGKVFSQTTICRFEALQLSFKNMCKLRPLLQKWVEEADNNENLQEICKAETL

VQARKRKRTSIENRVRGNLENLFLQCPKPTLQQISHIAQQLGLEKDVVRVWFCNRRQ

KGKRSSSDYAQREDFEAAGSPFSGGPVSFPLAPGPHFGTPGYGSPHFTALYSSVPFPE

GEAFPPVSVTTLGSPMHSN
```

Human SOX2 nucleic acid sequence (non-limiting example of a nucleic acid sequence encoding human SOX2) (SEQ ID NO: 42):
```
ATGTACAACATGATGGAGACGGAGCTGAAGCCGCCGGGCCCGCAGCAAACTTCG

GGGGGCGGCGGCGGCAACTCCACCGCGGCGGCGGCCGGCGGCAACCAGAAAAA

CAGCCCGGACCGCGTCAAGCGGCCCATGAATGCCTTCATGGTGTGGTCCCGCGG

GCAGCGGCGCAAGATGGCCCAGGAGAACCCCAAGATGCACAACTCGGAGATCA

GCAAGCGCCTGGGCGCCGAGTGGAAACTTTTGTCGGAGACGGAGAAGCGGCCGT

TCATCGACGAGGCTAAGCGGCTGCGAGCGCTGCACATGAAGGAGCACCCGGATT

ATAAATACCGGCCCCGGCGGAAAACCAAGACGCTCATGAAGAAGGATAAGTACA

CGCTGCCCGGCGGGCTGCTGGCCCCCGGCGGCAATAGCATGGCGAGCGGGGTCG

GGGTGGGCGCCGGCCTGGGCGCGGGCGTGAACCAGCGCATGGACAGTTACGCGC

ACATGAACGGCTGGAGCAACGGCAGCTACAGCATGATGCAGGACCAGCTGGGCT

ACCCGCAGCACCCGGGCCTCAATGCGCACGGCGCAGCGCAGATGCAGCCCATGC

ACCGCTACGACGTGAGCGCCCTGCAGTACAACTCCATGACCAGCTCGCAGACCT

ACATGAACGGCTCGCCCACCTACAGCATGTCCTACTCGCAGCAGGGCACCCCTG

GCATGGCTCTTGGCTCCATGGGTTCGGTGGTCAAGTCCGAGGCCAGCTCCAGCCC

CCCTGTGGTTACCTCTTCCTCCCACTCCAGGGCGCCCTGCCAGGCCGGGGACCTC

CGGGACATGATCAGCATGTATCTCCCCGGCGCCGAGGTGCCGGAACCCGCCGCC

CCCAGCAGACTTCACATGTCCCAGCACTACCAGAGCGGCCCGGTGCCCGGCACG

GCCATTAACGGCACACTGCCCCTCTCACACATG
```

Human SOX2 amino acid sequence (non-limiting example of an amino acid sequence encoding human SOX2) (SEQ ID NO: 43):
```
MYNMMETELKPPGPQQTSGGGGGNSTAAAAGGNQKNSPDRVKRPMNAFMVWSRG

QRRKMAQENPKMHNSEISKRLGAEWKLLSETEKRPFIDEAKRLRALHMKEHPDYKY

RPRRKTKTLMKKDKYTLPGGLLAPGGNSMASGVGVGAGLGAGVNQRMDSYAHMN

GWSNGSYSMMQDQLGYPQHPGLNAHGAAQMQPMHRYDVSALQYNSMTSSQTYM

NGSPTYSMSYSQQGTPGMALGSMGSVVKSEASSSPPVVTSSSHSRAPCQAGDLRDMI

SMYLPGAEVPEPAAPSRLHMSQHYQSGPVPGTAINGTLPLSHM
```

Human KLF4 (non-limiting example of a nucleotide sequence encoding human
KLF4) (SEQ ID NO: 44):
ATGGCTGTCAGCGACGCGCTGCTCCCATCTTTCTCCACGTTCGCGTCTGGCCCGG

CGGGAAGGGAGAAGACACTGCGTCAAGCAGGTGCCCCGAATAACCGCTGGCGG

GAGGAGCTCTCCCACATGAAGCGACTTCCCCCAGTGCTTCCCGGCCGCCCCTATG

ACCTGGCGGCGGCGACCGTGGCCACAGACCTGGAGAGCGGCGGAGCCGGTGCG

GCTTGCGGCGGTAGCAACCTGGCGCCCCTACCTCGGAGAGAGACCGAGGAGTTC

AACGATCTCCTGGACCTGGACTTTATTCTCTCCAATTCGCTGACCCATCCTCCGGA

GTCAGTGGCCGCCACCGTGTCCTCGTCAGCGTCAGCCTCCTCTTCGTCGTCGCCG

TCGAGCAGCGGCCCTGCCAGCGCGCCCTCCACCTGCAGCTTCACCTATCCGATCC

GGGCCGGGAACGACCCGGGCGTGGCGCCGGGCGGCACGGGCGGAGGCCTCCTCT

ATGGCAGGGAGTCCGCTCCCCCTCCGACGGCTCCCTTCAACCTGGCGGACATCAA

CGACGTGAGCCCCTCGGGCGGCTTCGTGGCCGAGCTCCTGCGGCCAGAATTGGA

CCCGGTGTACATTCCGCCGCAGCAGCCGCAGCCGCCAGGTGGCGGGCTGATGGG

CAAGTTCGTGCTGAAGGCGTCGCTGAGCGCCCCTGGCAGCGAGTACGGCAGCCC

GTCGGTCATCAGCGTCAGCAAAGGCAGCCCTGACGGCAGCCACCCGGTGGTGGT

GGCGCCCTACAACGGCGGGCCGCCGCGCACGTGCCCCAAGATCAAGCAGGAGGC

GGTCTCTTCGTGCACCCACTTGGGCGCTGGACCCCCTCTCAGCAATGGCCACCGG

CCGGCTGCACACGACTTCCCCCTGGGGCGGCAGCTCCCCAGCAGGACTACCCCG

ACCCTGGGTCTTGAGGAAGTGCTGAGCAGCAGGGACTGTCACCCTGCCCTGCCG

CTTCCTCCCGGCTTCCATCCCCACCCGGGGCCCAATTACCCATCCTTCCTGCCCGA

TCAGATGCAGCCGCAAGTCCCGCCGCTCCATTACCAAGAGCTCATGCCACCCGGT

TCCTGCATGCCAGAGGAGCCCAAGCCAAAGAGGGGAAGACGATCGTGGCCCCGG

AAAAGGACCGCCACCCACACTTGTGATTACGCGGGCTGCGGCAAAACCTACACA

AAGAGTTCCCATCTCAAGGCACACCTGCGAACCCACACAGGTGAGAAACCTTAC

CACTGTGACTGGGACGGCTGTGGATGGAAATTCGCCCGCTCAGATGAACTGACC

AGGCACTACCGTAAACACACGGGGCACCGCCCGTTCCAGTGCCAAAAATGCGAC

CGAGCATTTTCCAGGTCGGACCACCTCGCCTTACACATGAAGAGGCATTTT

Human KLF4 (non-limiting example of an amino acid sequence encoding human
KLF4) (SEQ ID NO: 45):
MAVSDALLPSFSTFASGPAGREKTLRQAGAPNNRWREELSHMKRLPPVLPGRPYDL

AAATVATDLESGGAGNGGSNLAPLPRRETEEFNDLLDLDFILSNSLTHPPESVAAT

VSSSASASSSSSPSSSGPASAPSTCSFTYPIRAGNDPGVAPGGTGGGLLYGRESAPPPT

APFNLADINDVSPSGGFVAELLRPELDPVYIPPQQPQPPGGGLMGKFVLKASLSAPGS

EYGSPSVISVSKGSPDGSHPVVVAPYNGGPPRTCPKIKQEAVSSCTHLGAGPPLSNGH

RPAAHDFPLGRQLPSRTTPTLGLEEVLSSRDCHPALPLPPGFHPHPGPNYPSFLPDQM

QPQVPPLHYQELMPPGSCMPEEPKPKRGRRSWPRKRTATHTCDYAGCGKTYTKSSH

LKAHLRTHTGEKPYHCDWDGCGWKFARSDELTRHYRKHTGHRPFQCQKCDRAFSR

SDHLALHMKRHF

Human RCVRN (recoverin) promoter (non-limiting example of a human RCVRN
(recoverin) promoter) (SEQ ID NO: 46):
ATTTTAATCTCACTAGGGTTCTGGGAGCACCCCCCCCCACCGCTCCCGCCCTCCA

CAAAGCTCCTGGGCCCCTCCTCCCTTCAAGGATTGCGAAGAGCTGGTCGCAAATC

CTCCTAAGCCACCAGCATCTCGGTCTTCAGCTCACACCAGCCTTGAGCCCAGCCT

GCGGCCAGGGGACCACGCACGTCCCACCCACCCAGCGACTCCCCAGCCGCTGCC

CACTCTTCCTCACTCA

RSV promoter (non-limiting example of a RSV promoter) (SEQ ID NO: 47):
AATGTAGTCTTATGCAATACTCTTGTAGTCTTGCAACATGGTAACGATGAGTTAG

CAACATGCCTTACAAGGAGAGAAAAAGCACCGTGCATGCCGATTGGTGGAAGTA

AGGTGGTACGATCGTGCCTTATTAGGAAGGCAACAGACGGGTCTGACATGGATT

GGACGAACCACTGAATTGCCGCATTGCAGAGATATTGTATTTAAGTGCCTAGCTC

GATACATAAAC

CMV promoter (non-limiting example of a CMV promoter) (SEQ ID NO: 48):
CATTGATTATTGACTAGTTATTAATAGTAATCAATTACGGGGTCATTAGTTCATA

GCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTA

ACGCCAATAGGGACTTTCCATTGACGTCAATGGGTGGACTATTTACGGTAAACTG

CCCACTTGGCAGTACATCAAGTGTATCATATGCCAAGTACGCCCCCTATTGACGT

CAATGACGGTAAATGGCCCGCCTGGCATTATGCCCAGTACATGACCTTATGGGAC

TTTCCTACTTGGCAGTACATCTACGTATTAGTCATCGCTATTACCATGGTGATGCG

GTTTTGGCAGTACATCAATGGGCGTGGATAGCGGTTTGACTCACGGGGATTTCCA

AGTCTCCACCCCATTGACGTCAATGGGAGTTTGTTTTGGCACCAAAATCAACGGG

ACTTTCCAAAATGTCGTAACAACTCCGCCCCATTGACGCAAATGGGCGGTAGGCG

TGTACGGTGGGAGGTCTATATAAGCAGAGCTGGTTTAGTGAACCGTCAGATCCGC

TAGAGATCCGC

EFS promoter (non-limiting example of an EFS promoter) (SEQ ID NO: 49):
TCGAGTGGCTCCGGTGCCCGTCAGTGGGCAGAGCGCACATCGCCCACAGTCCCC

GAGAAGTTGGGGGGAGGGGTCGGCAATTGAACCGGTGCCTAGAGAAGGTGGCG

CGGGGTAAACTGGGAAAGTGATGTCGTGTACTGGCTCCGCCTTTTTCCCGAGGGT

GGGGGAGAACCGTATATAAGTGCAGTAGTCGCCGTGAACGTTCTTTTTCGCAACG

GGTTTGCCGCCAGAACACAGGTGTCGTGACCGCGG

Human GRK1 (rhodopsin kinase) promoter (non-limiting example of a human promoter) (SEQ ID NO: 50):
Gggcccagaagcctggggttgtttgtccttctcaggggaaaagtgaggcggccccttggaggaaggggccgg gcagaatgatctaatcggattccaagcagctcaggggattgtctttttctagcaccttcttgccactcctaagcgtcctccgtgacccc ggctgggatttcgcctggtgctgtgtcagcccggtctcccaggggcttcccagtggtccccaggaaccctcgacagggcccggtctct ctcgtccagcaagggcagggacgggccacaggccaagggc Human CRX (cone rod homeobox transcription factor) promoter (non-limiting example of a human CRX promoter) (SEQ ID NO: 51):
Gcctgtagccttaatctctcctagcaggggtttgggggagggaggaggagaaagaaagggccccttatggctga gacacaatgacccagccacaaggagggattaccgggcg Human NRL promoter (neural retina leucine zipper transcription factor enhancer upstream of the human TK terminal promoter) (non-limiting example of a human NRL promoter) (SEQ ID NO: 52):
Aggtaggaagtggcctttaactccatagaccctatttaaacagcttcggacaggtttaaacatctccttggataattcct agtatccctgttcccactcctactcagggatgatagctctaagaggtgttaggggattaggctgaaaatgtaggtcacccctcagcca tctcggaactagaatgagtgagagaggagagagggggcagagacacacacattcgcatattaaggtgacgcgtgtggcctcgaacacc gagcgaccctgcagcgacccgcttaa Human red opsin promoter (hred promoter) (SEQ ID NO: 101):
Gatccggttccaggcctcggccctaaatagtctccctgggctttcaagagaaccacatgagaaaggaggattcggg ctctgagcagtttcaccacccaccccccagtctgcaaatcctgaccgtgggtccacctgccccaaaggcggacgcaggacagtaga agggaacagagaacacataaacacagagagggccacagcggctcccacagtcaccgccaccttcctggcggggatgggtgggc gtctgagtttggttcccagcaaatccctctgagccgcccttgcgggctcgcctcaggagcaggggagcaagaggtgggaggaggag gtctaagtcccaggcccaattaagagatcaggtagtgtagggtttgggagcttttaaggtgaagaggcccgggctgatcccacaggcc agtataaagcgccgtgaccctcaggtgatgcgccagggccggctgccgtcggggacagggctttccatagc Human rhodopsin promoter (rho promoter) (SEQ ID NO: 102):
Agttaatgattaacccgccatgctacttatctacgtagccatgctctaggaagatcggaattcgcccttaagctagcag atcttccccacctagccacctggcaaactgctccttctctcaaaggcccaaacatggcctcccagactgcaaccccaggcagtcagg ccctgtctccacaacctcacagccaccctggacggaatctgcttcttcccacatttgagtcctcctcagccctgagctcctctgggca gggctgtttctttccatctttgtattcccaggggcctgcaaataaatgtttaatgaacgaacaagagagtgaattccaattccatgcaa caaggatttgggctcctgggccctaggctatgtgtctggcaccagaaacggaagctgcaggttgcagcccctgccctcatggagctcct cctgtcagaggagtgtgggggactggatgactccagaggtaacttgtgggggaacgaacaggtaaggggctgtgtgacgagatgagagact gggagaataaaccagaaagtctctagctgttccagaggacatagcacagaggcccatggtccctatttcaaacccaggccaaccagact gagctgggaccttgggacagacaagtcatgcagaagttagggggaccttctcctcccttttcctggatggatcctgagtaccttctcctcc ctgacctcaggcttcctcctagtgtcaccttggcccctcttagaagccaattaggccctcagtttctgcagcggggattaatatgatta tgaacaccccccaatctcccagatgctgattcagccaggagcttaggaggggggaggtcactttataagggtctgggggggtcagaacccag agtcatccctgaattctgca Mouse cone arrestin promoter (mcar promoter) (SEQ ID NO: 103):
Ggttcttcccatttggctacatggtcttttttttacctttttggttccttggcctttggctttgggcttccagggcttctgga tcccccccaaccctcccatacacatacacatgtgcactcgtgcactcaacccagcacaggataatgttcattcttgaccttttccacat acatctggctatgttctctctcttatctacaataaatctcctccactatacttaggagcagttatgttcttcttctttctttctttt ttttttttcattcagtaacatcatcagaatcccctagctctggcctacctcctcagtaacaatcagctgatccctggccactaatct gtactcactaatctgttttccaaactcttggcccctgagctaattatagcagtgcttcatgccacccaccccaaccctattcttgtt ctctgactcccactaatctacacattcagaggattgtggatataagaggctgggaggccagcttagcaaccagagctggagg Human rhodopsin kinase promoter (hrk promoter) (SEQ ID NO: 104):
Gggccccagaagcctggtggttgtttgtccttctcaggggaaaagtgaggcggcccttggaggaaggggccgg gcagaatgatctaatcggattccaagcagctcaggggattgtcttttttctagcaccttcttgccactcctaagcgtcctccgtgaccc cggctgggatttagcctggtgctgtgtcagccccggtctcccaggggcttcccagtggtccccaggaaccctcgacagggcccggtct ctctcgtccagcaagggcagggacgggccacaggccaagggc TRE-human OSK-SV40 (SEQ ID NO: 105):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

```
TCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAA
TACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGC
AGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTC
CCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGC
GGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAGC
GGATAACAATTTCACACAGGAAACAGCTATGACCATGATTACGCCAGATTTAATT
AAGGCCTTAATTAGGCTGCGCGCTCGCTCGCTCACTGAGGCCGCCCGGGCAAAG
CCCGGGCGTCGGGCGACCTTTGGTCGCCCGGCCTCAGTGAGCGAGCGAGCGCGC
AGAGAGGGAGTGGCCAACTCCATCACTAGGGGTTCCTTGTAGTTAATGATTAACC
CGCCATGCTACTTATCTACGTAGCCATGCTCTAGGAAGATCGGAATTCTTTACTC
CCTATCAGTGATAGAGAACGTATGAAGAGTTTACTCCCTATCAGTGATAGAGAAC
GTATGCAGACTTTACTCCCTATCAGTGATAGAGAACGTATAAGGAGTTTACTCCC
TATCAGTGATAGAGAACGTATGACCAGTTTACTCCCTATCAGTGATAGAGAACGT
ATCTACAGTTTACTCCCTATCAGTGATAGAGAACGTATATCCAGTTTACTCCCTAT
CAGTGATAGAGAACGTATAAGCTTTAGGCGTGTACGGTGGGCGCCTATAAAAGC
AGAGCTCGTTTAGTGAACCGTCAGATCGCCTGGAGCAATTCCACAACACTTTTGT
CTTATACCAACTTTCCGTACCACTTCCTACCCTCGTAAAGCGGCCGCGCCACCAT
GGCGGGACACCTGGCTTCGGATTTCGCCTTCTCGCCCCCTCCAGGTGGTGGAGGT
GATGGGCCAGGGGGCCGGAGCCGGGCTGGGTTGATCCTCGGACCTGGCTAAGC
TTCCAAGGCCCTCCTGGAGGGCCAGGAATCGGGCCGGGGGTTGGGCCAGGCTCT
GAGGTGTGGGGGATTCCCCCATGCCCCCCGCCGTATGAGTTCTGTGGGGGGATGG
CGTACTGTGGGCCCCAGGTTGGAGTGGGGCTAGTGCCCCAAGGCGGCTTGGAGA
CCTCTCAGCCTGAGGGCGAAGCAGGAGTCGGGGTGGAGAGCAACTCCGATGGGG
CCTCCCCGGAGCCCTGCACCGTCACCCCTGGTGCCGTGAAGCTGGAGAAGGAGA
AGCTGGAGCAAAACCCGGAGGAGTCCCAGGACATCAAAGCTCTGCAGAAAGAA
CTCGAGCAATTTGCCAAGCTCCTGAAGCAGAAGAGGATCACCCTGGGATATACA
```

-continued

```
CAGGCCGATGTGGGGCTCACCCTGGGGGTTCTATTTGGGAAGGTATTCAGCCAAA

CGACCATCTGCCGCTTTGAGGCTCTGCAGCTTAGCTTCAAGAACATGTGTAAGCT

GCGGCCCTTGCTGCAGAAGTGGGTGGAGGAAGCTGACAACAATGAAATCTTCA

GGAGATATGCAAAGCAGAAACCCTCGTGCAGGCCCGAAAGAGAAAGCGAACCA

GTATCGAGAACCGAGTGAGAGGCAACCTGGAGAATTTGTTCCTGCAGTGCCCGA

AACCCACACTGCAGCAGATCAGCCACATCGCCCAGCAGCTTGGGCTCGAGAAGG

ATGTGGTCCGAGTGTGGTTCTGTAACCGGCGCCAGAAGGGCAAGCGATCAAGCA

GCGACTATGCACAACGAGAGGATTTTGAGGCTGCTGGGTCTCCTTTCTCAGGGGG

ACCAGTGTCCTTTCCTCTGGCCCCAGGGCCCCATTTTGGTACCCCAGGCTATGGG

AGCCCTCACTTCACTGCACTGTACTCCTCGGTCCCTTTCCCTGAGGGGGAAGCCT

TTCCCCCTGTCTCTGTCACCACTCTGGGCTCTCCCATGCATTCAAACGCTAGCGGC

AGCGGCGCCACGAACTTCTCTCTGTTAAAGCAAGCAGGAGATGTTGAAGAAAAC

CCCGGGCCTGCATGCATGTACAACATGATGGAGACGGAGCTGAAGCCGCCGGGC

CCGCAGCAAACTTCGGGGGCGGCGGCGGCAACTCCACCGCGGCGGCGGCCGGC

GGCAACCAGAAAAACAGCCCGGACCGCGTCAAGCGGCCCATGAATGCCTTCATG

GTGTGGTCCCGCGGGCAGCGGCGCAAGATGGCCCAGGAGAACCCCAAGATGCAC

AACTCGGAGATCAGCAAGCGCCTGGGCGCCGAGTGGAAACTTTTGTCGGAGACG

GAGAAGCGGCCGTTCATCGACGAGGCTAAGCGGCTGCGAGCGCTGCACATGAAG

GAGCACCCGGATTATAAATACCGGCCCCGGCGGAAAACCAAGACGCTCATGAAG

AAGGATAAGTACACGCTGCCCGGCGGGCTGCTGGCCCCCGGCGGCAATAGCATG

GCGAGCGGGTCGGGTGGGCGCCGGCCTGGGCGCGGGCGTGAACCAGCGCAT

GGACAGTTACGCGCACATGAACGGCTGGAGCAACGGCAGCTACAGCATGATGCA

GGACCAGCTGGGCTACCCGCAGCACCCGGGCCTCAATGCGCACGGCGCAGCGCA

GATGCAGCCCATGCACCGCTACGACGTGAGCGCCCTGCAGTACAACTCCATGAC

CAGCTCGCAGACCTACATGAACGGCTCGCCCACCTACAGCATGTCCTACTCGCAG

CAGGGCACCCCTGGCATGGCTCTTGGCTCCATGGGTTCGGTGGTCAAGTCCGAGG

CCAGCTCCAGCCCCCCTGTGGTTACCTCTTCCTCCCACTCCAGGGCGCCCTGCCA

GGCCGGGACCTCCGGGACATGATCAGCATGTATCTCCCCGGCGCCGAGGTGCC

GGAACCCGCCGCCCCCAGCAGACTTCACATGTCCCAGCACTACCAGAGCGGCCC

GGTGCCCGGCACGGCCATTAACGGCACACTGCCCCTCTCACACATGGCATGCGG

CTCCGGCGAGGGCAGGGAAGTCTTCTAACATGCGGGACGTGGAGGAAAATCC

CGGCCCACTCGAGATGGCTGTCAGCGACGCGCTGCTCCCATCTTTCTCCACGTTC

GCGTCTGGCCCGGCGGGAAGGGAGAAGACACTGCGTCAAGCAGGTGCCCCGAAT

AACCGCTGGCGGAGGAGCTCTCCCACATGAAGCGACTTCCCCCAGTGCTTCCCG

GCCGCCCCTATGACCTGGCGGCGGCGACCGTGGCCACAGACCTGGAGAGCGGCG

GAGCCGGTGCGGCTTGCGGCGGTAGCAACCTGGCGCCCCTACCTCGGAGAGAGA

CCGAGGAGTTCAACGATCTCCTGGACCTGGACTTTATTCTCTCCAATTCGCTGAC

CCATCCTCCGGAGTCAGTGGCCGCCACCGTGTCCTCGTCAGCGTCAGCCTCCTCT

TCGTCGTCGCCGTCGAGCAGCGGCCCTGCCAGCGCGCCCTCCACCTGCAGCTTCA

CCTATCCGATCCGGGCCGGGAACGACCCGGGCGTGGCGCGGGCGGCACGGGCG

GAGGCCTCCTCTATGGCAGGGAGTCCGCTCCCCCTCCGACGGCTCCCTTCAACCT
```

```
GGCGGACATCAACGACGTGAGCCCCTCGGGCGGCTTCGTGGCCGAGCTCCTGCG

GCCAGAATTGGACCCGGTGTACATTCCGCCGCAGCAGCCGCAGCCGCCAGGTGG

CGGGCTGATGGGCAAGTTCGTGCTGAAGGCGTCGCTGAGCGCCCCTGGCAGCGA

GTACGGCAGCCCGTCGGTCATCAGCGTCAGCAAAGGCAGCCCTGACGGCAGCCA

CCCGGTGGTGGTGGCGCCCTACAACGGCGGGCCGCCGCGCACGTGCCCCAAGAT

CAAGCAGGAGGCGGTCTCTTCGTGCACCCACTTGGGCGCTGGACCCCCTCTCAGC

AATGGCCACCGGCCGGCTGCACACGACTTCCCCCTGGGGCGGCAGCTCCCCAGC

AGGACTACCCCGACCCTGGGTCTTGAGGAAGTGCTGAGCAGCAGGGACTGTCAC

CCTGCCCTGCCGCTTCCTCCCGGCTTCCATCCCCACCCGGGGCCCAATTACCCATC

CTTCCTGCCCGATCAGATGCAGCCGCAAGTCCCGCCGCTCCATTACCAAGAGCTC

ATGCCACCCGGTTCCTGCATGCCAGAGGAGCCCAAGCCAAAGAGGGGAAGACGA

TCGTGGCCCCGGAAAAGGACCGCCACCCACACTTGTGATTACGCGGGCTGCGGC

AAAACCTACACAAAGAGTTCCCATCTCAAGGCACACCTGCGAACCCACACAGGT

GAGAAACCTTACCACTGTGACTGGGACGGCTGTGGATGGAAATTCGCCCGCTCA

GATGAACTGACCAGGCACTACCGTAAACACACGGGGCACCGCCCGTTCCAGTGC

CAAAAATGCGACCGAGCATTTTCCAGGTCGGACCACCTCGCCTTACACATGAAG

AGGCATTTTTAAATGACTAGTGCGCGCAGCGGCCGACCATGGCCCAACTTGTTTA

TTGCAGCTTATAATGGTTACAAATAAAGCAATAGCATCACAAATTTCACAAATAA

AGCATTTTTTTCACTGCATTCTAGTTGTGGTTTGTCCAAACTCATCAATGTATCTT

ATCATGTCTGGATCTCGGTACCGGATCCAAATTCCCGATAAGGATCTTCCTAGAG

CATGGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCG

AGCGAGCGCGCAGCCTTAATTAACCTAATTCACTGGCCGTCGTTTTACAACGTCG

TGACTGGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCAACAG

TTGCGCAGCCTGAATGGCGAATGGGACGCGCCCTGTAGCGGCGCATTAAGCGCG

GCGGGTGTGGTGGTTACGCGCAGCGTGACCGCTACACTTGCCAGCGCCCTAGCG

CCCGCTCCTTTCGCTTTCTTCCCTTCCTTTCTCGCCACGTTCGCCGGCTTTCCCCGT

CAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAAT

TTAACGCGAATTTTAACAAAATATTAACGTTTATAATTTCAGGTGGCATCTTTCG

GGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGA

AGAGTATGAGTATTCAACATTTCCGTGTCGCCCTTATTCCCTTTTTTGCGGCATT

TGCCTTCCTGTTTTTGCTCACCCAGAAACGCTGGTGAAAGTAAAAGATGCTGAAG

ATCAGTTGGGTGCACGAGTGGGTTACATCGAACTGGATCTCAATAGTGGTAAGAT
```

-continued

CCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTC

GCCGCATACACTATTCTCAGAATGACTTCGTTGAGTACTCACCAGTCACAGAAAA

GCATCTTACGGATGGCATGACAGTAAGAGAA

EFS-human OSK-SV40 (SEQ ID NO: 106):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACCTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGC

GGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACC

GTATTACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCGCCT

CTCCCCGCGCGTTGGCCGATTCATTAATGCAGCTGGCACGACAGGTTTCCCGACT

GGAAAGCGGGCAGTGAGCGCAACGCAATTAATGTGAGTTAGCTCACTCATTAGG

CACCCCAGGCTTTACACTTTATGCTTCCGGCTCGTATGTTGTGTGGAATTGTGAGC

GGATAACAATTTCACACAGGAAACAGCTATGACCATGATTACGCCAGATTTAATT

AAGGCCTTAATTAGGCTGCGCGCTCGCTCGCTCACTGAGGCCGCCCGGGCAAAG

CCCGGGCGTCGGGCGACCTTTGGTCGCCCGGCCTCAGTGAGCGAGCGAGCGCGC

AGAGAGGGAGTGGCCAACTCCATCACTAGGGGTTCCTTGTAGTTAATGATTAACC

CGCCATGCTACTTATCTACGTAGCCATGCTCTAGGAAGATCGGAATTCTCGAGTG

GCTCCGGTGCCCGTCAGTGGGCAGAGCGCACATCGCCCACAGTCCCCGAGAAGT

-continued

```
TGGGGGGAGGGGTCGGCAATTGAACCGGTGCCTAGAGAAGGTGGCGCGGGGTA

AACTGGGAAAGTGATGTCGTGTACTGGCTCCGCCTTTTTCCCGAGGGTGGGGGAG

AACCGTATATAAGTGCAGTAGTCGCCGTGAACGTTCTTTTTCGCAACGGGTTTGC

CGCCAGAACACAGGTGTCGTGACGCGGGCGGCCGCGCCACCATGGCGGGACACC

TGGCTTCGGATTTCGCCTTCTCGCCCCCTCCAGGTGGTGGAGGTGATGGGCCAGG

GGGGCCGGAGCCGGGCTGGGTTGATCCTCGGACCTGGCTAAGCTTCCAAGGCCC

TCCTGGAGGGCCAGGAATCGGGCCGGGGGTTGGGCCAGGCTCTGAGGTGTGGGG

GATTCCCCCATGCCCCCCGCCGTATGAGTTCTGTGGGGGATGGCGTACTGTGGG

CCCCAGGTTGGAGTGGGGCTAGTGCCCCAAGGCGGCTTGGAGACCTCTCAGCCT

GAGGGCGAAGCAGGAGTCGGGGTGGAGAGCAACTCCGATGGGGCCTCCCCGGA

GCCCTGCACCGTCACCCCTGGTGCCGTGAAGCTGGAGAAGGAGAAGCTGGAGCA

AAACCCGGAGGAGTCCCAGGACATCAAAGCTCTGCAGAAAGAACTCGAGCAATT

TGCCAAGCTCCTGAAGCAGAAGAGGATCACCCTGGGATATACACAGGCCGATGT

GGGGCTCACCCTGGGGGTTCTATTTGGGAAGGTATTCAGCCAAACGACCATCTGC

CGCTTTGAGGCTCTGCAGCTTAGCTTCAAGAACATGTGTAAGCTGCGGCCCTTGC

TGCAGAAGTGGGTGGAGGAAGCTGACAACAATGAAAATCTTCAGGAGATATGCA

AAGCAGAAACCCTCGTGCAGGCCCGAAAGAGAAAGCGAACCAGTATCGAGAAC

CGAGTGAGAGGCAACCTGGAGAATTTGTTCCTGCAGTGCCCGAAACCCACACTG

CAGCAGATCAGCCACATCGCCCAGCAGCTTGGGCTCGAGAAGGATGTGGTCCGA

GTGTGGTTCTGTAACCGGCGCCAGAAGGGCAAGCGATCAAGCAGCGACTATGCA

CAACGAGAGGATTTTGAGGCTGCTGGGTCTCCTTTCTCAGGGGGACCAGTGTCCT

TTCCTCTGGCCCCAGGGCCCCATTTTGGTACCCCAGGCTATGGGAGCCCTCACTT

CACTGCACTGTACTCCTCGGTCCCTTTCCCTGAGGGGGAAGCCTTTCCCCCTGTCT

CTGTCACCACTCTGGGCTCTCCCATGCATTCAAACGCTAGCGGCAGCGGCGCCAC

GAACTTCTCTCTGTTAAAGCAAGCAGGAGATGTTGAAGAAAACCCCGGGCCTGC

ATGCATGTACAACATGATGGAGACGGAGCTGAAGCCGCCGGGCCCGCAGCAAAC

TTCGGGGGGCGGCGGCGGCAACTCCACCGCGGCGGCGGCCGGCGGCAACCAGA

AAAACAGCCCGGACCGCGTCAAGCGGCCCATGAATGCCTTCATGGTGTGGTCCC

GCGGGCAGCGGCGCAAGATGGCCCAGGAGAACCCCAAGATGCACAACTCGGAG

ATCAGCAAGCGCCTGGGCGCCGAGTGGAAACTTTTGTCGGAGACGGAGAAGCGG

CCGTTCATCGACGAGGCTAAGCGGCTGCGAGCGCTGCACATGAAGGAGCACCCG

GATTATAAATACCGGCCCCGGCGGAAAACCAAGACGCTCATGAAGAAGGATAAG

TACACGCTGCCCGGCGGGCTGCTGGCCCCCGGCGGCAATAGCATGGCGAGCGGG

GTCGGGGTGGGCGCCGGCCTGGGCGCGGGCGTGAACCAGCGCATGGACAGTTAC

GCGCACATGAACGGCTGGAGCAACGGCAGCTACAGCATGATGCAGGACCAGCTG

GGCTACCCGCAGCACCCGGGCCTCAATGCGCACGGCGCAGCGCAGATGCAGCCC

ATGCACCGCTACGACGTGAGCGCCCTGCAGTACAACTCCATGACCAGCTCGCAG

ACCTACATGAACGGCTCGCCCACCTACAGCATGTCCTACTCGCAGCAGGGCACCC

CTGGCATGGCTCTTGGCTCCATGGGTTCGGTGGTCAAGTCCGAGGCCAGCTCCAG

CCCCCCTGTGGTTACCTCTTCCTCCCACTCCAGGGCGCCCTGCCAGGCCGGGAC

CTCCGGGACATGATCAGCATGTATCTCCCCGGCGCCGAGGTGCCGGAACCCGCC
```

```
GCCCCCAGCAGACTTCACATGTCCCAGCACTACCAGAGCGGCCCGGTGCCCGGC

ACGGCCATTAACGGCACACTGCCCCTCTCACACATGGCATGCGGCTCCGGCGAG

GGCAGGGGAAGTCTTCTAACATGCGGGACGTGGAGGAAAATCCCGGCCCACTC

GAGATGGCTGTCAGCGACGCGCTGCTCCCATCTTTCTCCACGTTCGCGTCTGGCC

CGGCGGGAAGGGAGAAGACACTGCGTCAAGCAGGTGCCCCGAATAACCGCTGG

CGGGAGGAGCTCTCCCACATGAAGCGACTTCCCCCAGTGCTTCCCGGCCGCCCCT

ATGACCTGGCGGCGGCGACCGTGGCCACAGACCTGGAGAGCGGCGGAGCCGGTG

CGGCTTGCGGCGGTAGCAACCTGGCGCCCCTACCTCGGAGAGAGACCGAGGAGT

TCAACGATCTCCTGGACCTGGACTTTATTCTCTCCAATTCGCTGACCCATCCTCCG

GAGTCAGTGGCCGCCACCGTGTCCTCGTCAGCGTCAGCCTCCTCTTCGTCGTCGC

CGTCGAGCAGCGGCCCTGCCAGCGCGCCCTCCACCTGCAGCTTCACCTATCCGAT

CCGGGCCGGGAACGACCCGGGCGTGGCGCCGGGCGGCACGGGCGGAGGCCTCCT

CTATGGCAGGGAGTCCGCTCCCCCTCCGACGGCTCCCTTCAACCTGGCGGACATC

AACGACGTGAGCCCCTCGGGCGGCTTCGTGGCCGAGCTCCTGCGGCCAGAATTG

GACCCGGTGTACATTCCGCCGCAGCAGCCGCAGCCGCCAGGTGGCGGGCTGATG

GGCAAGTTCGTGCTGAAGGCGTCGCTGAGCGCCCCTGGCAGCGAGTACGGCAGC

CCGTCGGTCATCAGCGTCAGCAAAGGCAGCCCTGACGGCAGCCACCCGGTGGTG

GTGGCGCCCTACAACGGCGGGCCGCCGCGCACGTGCCCCAAGATCAAGCAGGAG

GCGGTCTCTTCGTGCACCCACTTGGGCGCTGGACCCCCTCTCAGCAATGGCCACC

GGCCGGCTGCACACGACTTCCCCCTGGGGCGGCAGCTCCCCAGCAGGACTACCC

CGACCCTGGGTCTTGAGGAAGTGCTGAGCAGCAGGGACTGTCACCCTGCCCTGC

CGCTTCCTCCCGGCTTCCATCCCCACCCGGGGCCCAATTACCCATCCTTCCTGCCC

GATCAGATGCAGCCGCAAGTCCCGCCGCTCCATTACCAAGAGCTCATGCCACCC

GGTTCCTGCATGCCAGAGGAGCCCAAGCCAAAGAGGGGAAGACGATCGTGGCCC

CGGAAAAGGACCGCCACCCACACTTGTGATTACGCGGGCTGCGGCAAAACCTAC

ACAAAGAGTTCCCATCTCAAGGCACACCTGCGAACCCACACAGGTGAGAAACCT

TACCACTGTGACTGGGACGGCTGTGGATGGAAATTCGCCCGCTCAGATGAACTG

ACCAGGCACTACCGTAAACACACGGGGCACCGCCCGTTCCAGTGCCAAAAATGC

GACCGAGCATTTTCCAGGTCGGACCACCTCGCCTTACACATGAAGAGGCATTTTT

AAATGACTAGTGCGCGCAGCGGCCGACCATGGCCCAACTTGTTTATTGCAGCTTA

TAATGGTTACAAATAAAGCAATAGCATCACAAATTTCACAAATAAAGCATTTTTT

TCACTGCATTCTAGTTGTGGTTTGTCCAAACTCATCAATGTATCTTATCATGTCTG

GATCTCGGTACCGGATCCAAATTCCCGATAAGGATCTTCCTAGAGCATGGCTACG

TAGATAAGTAGCATGGCGGGTTAATCATTAACTACAAGGAACCCCTAGTGATGG

AGTTGGCCACTCCCTCTCTGCGCGCTCGCTCGCTCACTGAGGCCGGGCGACCAAA

GGTCGCCCGACGCCCGGGCTTTGCCCGGGCGGCCTCAGTGAGCGAGCGAGCGCG

CAGCCTTAATTAACCTAATTCACTGGCCGTCGTTTTACAACGTCGTGACTGGGAA

AACCCTGGCGTTACCCAACTTAATCGCCTTGCAGCACATCCCCCTTTCGCCAGCT

GGCGTAATAGCGAAGAGGCCCGCACCGATCGCCCTTCCCAACAGTTGCGCAGCC

TGAATGGCGAATGGGACGCGCCCTGTAGCGGCGCATTAAGCGCGGCGGGTGTGG
```

-continued

TGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAA

ATCGGGGGCTCCCTTTAGGGTTCCGATTTAGTGCTTTACGGCACCTCGACCCCAA

AAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAAC

TGGAACAACACTCAACCCTATCTCGGTCTATTCTTTTGATTTATAAGGGATTTTGC

CGATTTCGGCCTATTGGTTAAAAAATGAGCTGATTTAACAAAAATTTAACGCGAA

TTTTAACAAAATATTAACGTTTATAATTTCAGGTGGCATCTTTCGGGGAAATGTG

CGCGGAACCCCTATTTGTTTATTTTTCTAAATACATTCAAATATGTATCCGCTCAT

GAGACAATAACCCTGATAAATGCTTCAATAATATTGAAAAAGGAAGAGTATGAG

TATTCAACATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGTTGGG

TGCACGAGTGGGTTACATCGAACTGGATCTCAATAGTGGTAAGATCCTTGAGAGT

TTTCGCCCCGAAGAACGTTTTCCAATGATGAGCACTTTTAAAGTTCTGCTATGTG

GCGCGGTATTATCCCGTATTGACGCCGGGCAAGAGCAACTCGGTCGCCGCATAC

ACTATTCTCAGAATGACTTGGTTGAGTACTCACCAGTCACAGAAAAGCATCTTAC

GGATGGCATGACAGTAAGAGAA

TRE-Fluc-SV40 (SEQ ID NO: 107):
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGC

-continued

```
GGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAGC
GGATAACAATTTCACACAGGAAACAGCTATGACCATGATTACGCCAGATTTAATT
AAGGCCTTAATTAGGCTGCGCGCTCGCTCGCTCACTGAGGCCGCCCGGGCAAAG
CCCGGGCGTCGGGCGACCTTTGGTCGCCCGGCCTCAGTGAGCGAGCGAGCGCGC
AGAGAGGGAGTGGCCAACTCCATCACTAGGGGTTCCTTGTAGTTAATGATTAACC
CGCCATGCTACTTATCTACGTAGCCATGCTCTAGGAAGATCGGAATTCTTTACTC
CCTATCAGTGATAGAGAACGTATGAAGAGTTTACTCCCTATCAGTGATAGAGAAC
GTATGCAGACTTTACTCCCTATCAGTGATAGAGAACGTATAAGGAGTTTACTCCC
TATCAGTGATAGAGAACGTATGACCAGTTTACTCCCTATCAGTGATAGAGAACGT
ATCTACAGTTTACTCCCTATCAGTGATAGAGAACGTATATCCAGTTTACTCCCTAT
CAGTGATAGAGAACGTATAAGCTTTAGGCGTGTACGGTGGGCGCCTATAAAAGC
AGAGCTCGTTTAGTGAACCGTCAGATCGCCTGGAGCAATTCCACAACACTTTTGT
CTTATACCAACTTTCCGTACCACTTCCTACCCTCGTAAAGCGGCCGCATGGAAGA
CGCCAAAAACATAAAGAAAGGCCCGGCGCCATTCTATCCGCTGGAAGATGGAAC
CGCTGGAGAGCAACTGCATAAGGCTATGAAGAGATACGCCCTGGTTCCTGGAAC
AATTGCTTTTACAGATGCACATATCGAGGTGGACATCACTTACGCTGAGTACTTC
GAAATGTCCGTTCGGTTGGCAGAAGCTATGAAACGATATGGGCTGAATACAAAT
CACAGAATCGTCGTATGCAGTGAAAACTCTCTTCAATTCTTTATGCCGGTGTTGG
GCGCGTTATTTATCGGAGTTGCAGTTGCGCCCGCGAACGACATTTATAATGAACG
TGAATTGCTCAACAGTATGGGCATTTCGCAGCCTACCGTGGTGTTCGTTTCCAAA
AAGGGGTTGCAAAAAATTTTGAACGTGCAAAAAAAGCTCCCAATCATCCAAAA
ATTATTATCATGGATTCTAAAACGGATTACCAGGGATTTCAGTCGATGTACACGT
TCGTCACATCTCATCTACCTCCCGGTTTTAATGAATACGATTTTGTGCCAGAGTCC
TTCGATAGGGACAAGACAATTGCACTGATCATGAACTCCTCTGGATCTACTGGTC
TGCCTAAAGGTGTCGCTCTGCCTCATAGAACTGCCTGCGTGAGATTCTCGCATGC
CAGAGATCCTATTTTTGGCAATCAAATCATTCCGGATACTGCGATTTTAAGTGTT
GTTCCATTCCATCACGGTTTTGGAATGTTTACTACACTCGGATATTTGATATGTGG
ATTTCGAGTCGTCTTAATGTATAGATTTGAAGAAGAGCTGTTTCTGAGGAGCCTT
CAGGATTACAAGATTCAAAGTGCGCTGCTGGTGCCAACCCTATTCTCCTTCTTCG
CCAAAAGCACTCTGATTGACAAATACGATTTATCTAATTTACACGAAATTGCTTC
TGGTGGCGCTCCCCTCTCTAAGGAAGTCGGGGAAGCGGTTGCCAAGAGGTTCCAT
CTGCCAGGTATCAGGCAAGGATATGGGCTCACTGAGACTACATCAGCTATTCTGA
TTACACCCGAGGGGGATGATAAACCGGGCGCGGTCGGTAAAGTTGTTCCATTTTT
TGAAGCGAAGGTTGTGGATCTGGATACCGGGAAAACGCTGGGCGTTAATCAAAG
AGGCGAACTGTGTGTGAGAGGTCCTATGATTATGTCCGGTTATGTAAACAATCCG
```

-continued

```
GAAGCGACCAACGCCTTGATTGACAAGGATGGATGGCTACATTCTGGAGACATA
GCTTACTGGGACGAAGACGAACACTTCTTCATCGTTGACCGCCTGAAGTCTCTGA
TTAAGTACAAAGGCTATCAGGTGGCTCCCGCTGAATTGGAATCCATCTTGCTCCA
ACACCCCAACATCTTCGACGCAGGTGTCGCAGGTCTTCCCGACGATGACGCCGGT
GAACTTCCCGCCGCCGTTGTTGTTTTGGAGCACGGAAAGACGATGACGGAAAAA
GAGATCGTGGATTACGTCGCCAGTCAAGTAACAACCGCGAAAAAGTTGCGCGGA
GGAGTTGTGTTTGTGGACGAAGTACCGAAAGGTCTTACCGGAAAACTCGACGCA
AGAAAAATCAGAGAGATCCTCATAAAGGCCAAGAAGGGCGGAAAGATCGCCGT
GTAAACTAGTGCGCGCAGCGGCCGACCATGGCCCAACTTGTTTATTGCAGCTTAT
AATGGTTACAAATAAAGCAATAGCATCACAAATTTCACAAATAAAGCATTTTTTT
CACTGCATTCTAGTTGTGGTTTGTCCAAACTCATCAATGTATCTTATCATGTCTGG
ATCTCGGTACCGGATCCAAATTCCCGATAAGGATCTTCCTAGAGCATGGCTACGT
AGATAAGTAGCATGGCGGGTTAATCATTAACTACAAGGAACCCCTAGTGATGGA
GTTGGCCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGCGCGC
AGCCTTAATTAACCTAATTCACTGGCCGTCGTTTTACAACGTCGTGACTGGGAAA
ACCCTGGCGTTACCCAACTTAATCGCCTTGCAGCACATCCCCCTTTCGCCAGCTG
GCGTAATAGCGAAGAGGCCCGCACCGATCGCCCTTCCCAACAGTTGCGCAGCCT
GAATGGCGAATGGGACGCGCCCTGTAGCGGCGCATTAAGCGCGGCGGGTGTGGT
GGTTACGCGCAGCGTGACCGCTACACTTGCCAGCGCCCTAGCGCCCGCTCCTTTC
GCTTTCTTCCCTTCCTTTCTCGCCACGTTCGCCGGCTTTCCCCGTCAAGCTCTAAA
TCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAACT
GGAACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGAAT
TTTAACAAAATATTAACGTTTATAATTTCAGGTGGCATCTTTCGGGGAAATGTGC
GCGGAACCCCTATTTGTTTATTTTTCTAAATACATTCAAATATGTATCCGCTCATG
AGACAATAACCCTGATAAATGCTTCAATAATATTGAAAAAGGAAGAGTATGAGT
ATTCAACATTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGTTGGGT
GCACGAGTGGGTTACATCGAACTGGATCTCAATAGTGGTAAGATCCTTGAGAGTT
TTCGCCCCGAAGAACGTTTTCCAATGATGAGCACTTTTAAAGTTCTGCTATGTGG
CGCGGTATTATCCCGTATTGACGCCGGGCAAGAGCAACTCGGTCGCCGCATACA
CTATTCTCAGAATGACTTGGTTGAGTACTCACCAGTCACAGAAAAGCATCTTACG
GATGGCATGACAGTAAGAGAA
``` shRNA against mouse KDM1a (SEQ ID NO: 108):
CACAAGTCAAACCTTTAT shRNA against human Tet1-1 (SEQ ID NO: 109):
GGACGTAATCCAGAAAGAAGA shRNA against human Tet1-2 (SEQ ID NO: 110):
TTGTGCCTCTGGAGGTTATAA -continued shRNA against human Tet3-1 (SEQ ID NO: 111):
GGAAATAAAGGCTGGTGAAGG shRNA against human Tet3-2 (SEQ ID NO: 112):
GAAAGATGAAGGTCCATATTA shRNA against mouse Tet1-2 (SEQ ID NO: 113):
GCAGATGGCCGTGACACAAAT shRNA against mouse Tet1-1 (SEQ ID NO: 114):
GCTCATGGAGACTAGGTTTGG shRNA against both mouse and human Tet2 (SEQ ID NO: 115):
GGATGTAAGTTTGCCAGAAGC shRNA against mouse Tet3 (SEQ ID NO: 116):
GCTCCAACGAGAAGCTATTTG shRNA against scramble sequence (no target in genome) (SEQ ID NO: 117):
GTTCAGATGTGCGGCGAGT Amino acid sequence encoding P2A (SEQ ID NO: 118):
GSGATNFSLLKQAGDVEENPGP Nucleic acid sequence encoding P2A (SEQ ID NO: 119):
GGCAGCGGCGCCACGAACTTCTCTCTGTTAAAGCAAGCAGGAGATGTT

GAAGAAAACCCCGGGCCT

Nucleic acid sequence encoding T2A (SEQ ID NO: 120)
GGCTCCGGCGAGGGCAGGGGAAGTCTTCTAACATGCGGGGACGTGGA

GGAAAATCCCGGCCCA (SEQ ID NO: 120).

SEQ ID NO: 121:
TTATGCAGTGCTGCCATAACCATGAGTGATAACACTGCGGCCAACTTA

CTTCTGACAACGATCGGAGGACCGAAGGAGCTAACCGCTTTTTTGCACAACATGG

GGGATCATGTAACTCGCCTTGATCGTTGGGAACCGGAGCTGAATGAAGCCATAC

CAAACGACGAGCGTGACACCACGATGCCTGTAGTAATGGTAACAACGTTGCGCA

AACTATTAACTGGCGAACTACTTACTCTAGCTTCCCGGCAACAATTAATAGACTG

GATGGAGGCGGATAAAGTTGCAGGACCACTTCTGCGCTCGGCCCTTCCGGCTGGC

TGGTTTATTGCTGATAAATCTGGAGCCGGTGAGCGTGGGTCTCGCGGTATCATTG

CAGCACTGGGGCCAGATGGTAAGCCCTCCCGTATCGTAGTTATCTACACGACGGG

GAGTCAGGCAACTATGGATGAACGAAATAGACAGATCGCTGAGATAGGTGCCTC

ACTGATTAAGCATTGGTAACTGTCAGACCAAGTTTACTCATATATACTTTAGATT

GATTTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCT

GCTTGCAAACAAAAAAACCACCGCTACCAGCGGTGGTTTGTTTGCCGGATCAAG

AGCTACCAACTCTTTTTCCGAAGGTAACTGGCTTCAGCAGAGCGCAGATACCAAA

TACTGTCCTTCTAGTGTAGCCGTAGTTAGGCCACCACTTCAAGAACTCTGTAGCA

CCGCCTACATACCTCGCTCTGCTAATCCTGTTACCAGTGGCTGCTGCCAGTGGCG

ATAAGTCGTGTCTTACCGGGTTGGACTCAAGACGATAGTTACCGGATAAGGCGC

AGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTC

CCGAAGGGAGAAAGGCGGACAGGTATCCGGTAAGCGGCAGGGTCGGAACAGGA

GAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGGC

-continued

```
GGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCT
CTCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAGC
GGATAACAATTTCACACAGGAAACAGCTATGACCATGATTACGCCAGATTTAATT
AAGGCCTTAATTAGGCTGCGCGCTCGCTCGCTCACTGAGGCCGCCCGGGCAAAG
CCCGGGCGTCGGGCGACCTTTGGTCGCCCGGCCTCAGTGAGCGAGCGAGCGCGC
AGAGAGGGAGTGGCCAACTCCATCACTAGGGGTTCCTTGTAGTTAATGATTAACC
CGCCATGCTACTTATCTACGTAGCCATGCTCTAGGAAGATCGGAATTCTTTACTC
CCTATCAGTGATAGAGAACGTATGAAGAGTTTACTCCCTATCAGTGATAGAGAAC
GTATGCAGACTTTACTCCCTATCAGTGATAGAGAACGTATAAGGAGTTTACTCCC
TATCAGTGATAGAGAACGTATGACCAGTTTACTCCCTATCAGTGATAGAGAACGT
ATCTACAGTTTACTCCCTATCAGTGATAGAGAACGTATATCCAGTTTACTCCCTAT
CAGTGATAGAGAACGTATAAGCTTTAGGCGTGTACGGTGGGCGCCTATAAAAGC
AGAGCTCGTTTAGTGAACCGTCAGATCGCCTGGAGCAATTCCACAACACTTTTGT
CTTATACCAACTTTCCGTACCACTTCCTACCCTCGTAAAGCGGCCGCGCCACCAT
GGCGGGACACCTGGCTTCGGATTTCGCCTTCTCGCCCCCTCCAGGTGGTGGAGGT
GATGGGCCAGGGGGCCGGAGCCGGGCTGGGTTGATCCTCGGACCTGGCTAAGC
TTCCAAGGCCCTCCTGGAGGGCCAGGAATCGGGCCGGGGGTTGGGCCAGGCTCT
GAGGTGTGGGGGATTCCCCCATGCCCCCCGCCGTATGAGTTCTGTGGGGGGATGG
CGTACTGTGGGCCCCAGGTTGGAGTGGGGCTAGTGCCCCAAGGCGGCTTGGAGA
CCTCTCAGCCTGAGGGCGAAGCAGGAGTCGGGGTGGAGAGCAACTCCGATGGGG
CCTCCCCGGAGCCCTGCACCGTCACCCCTGGTGCCGTGAAGCTGGAGAAGGAGA
AGCTGGAGCAAAACCCGGAGGAGTCCCAGGACATCAAAGCTCTGCAGAAAGAA
CTCGAGCAATTTGCCAAGCTCCTGAAGCAGAAGAGGATCACCCTGGGATATACA
CAGGCCGATGTGGGGCTCACCCTGGGGGTTCTATTTGGGAAGGTATTCAGCCAAA
CGACCATCTGCCGCTTTGAGGCTCTGCAGCTTAGCTTCAAGAACATGTGTAAGCT
GCGGCCCTTGCTGCAGAAGTGGGTGGAGGAAGCTGACAACAATGAAAATCTTCA
GGAGATATGCAAAGCAGAAACCCTCGTGCAGGCCCGAAAGAGAAAGCGAACCA
GTATCGAGAACCGAGTGAGAGGCAACCTGGAGAATTTGTTCCTGCAGTGCCCGA
AACCCACACTGCAGCAGATCAGCCACATCGCCCAGCAGCTTGGGCTCGAGAAGG
ATGTGGTCCGAGTGTGGTTCTGTAACCGGCGCCAGAAGGGCAAGCGATCAAGCA
GCGACTATGCACAACGAGAGGATTTTGAGGCTGCTGGGTCTCCTTTCTCAGGGGG
ACCAGTGTCCTTTCCTCTGGCCCCAGGGCCCCATTTTGGTACCCCAGGCTATGGG
AGCCCTCACTTCACTGCACTGTACTCCTCGGTCCCTTTCCCTGAGGGGGAAGCCT
TTCCCCCTGTCTCTGTCACCACTCTGGGCTCTCCCATGCATTCAAACGCTAGCGGC
AGCGGCGCCACGAACTTCTCTCTGTTAAAGCAAGCAGGAGATGTTGAAGAAAAC
```

-continued
```
CCCGGGCCTGCATGCATGTACAACATGATGGAGACGGAGCTGAAGCCGCCGGGC
CCAGCAAACTTCGGGGGCGGCGGCGGCAACTCCACCGCGGCGGCGGCCGGC
GGCAACCAGAAAAACAGCCCGGACCGCGTCAAGCGGCCCATGAATGCCTTCATG
GTGTGGTCCCGCGGGCAGCGGCGCAAGATGGCCCAGGAGAACCCCAAGATGCAC
AACTCGGAGATCAGCAAGCGCCTGGGCGCCGAGTGGAAACTTTTGTCGGAGACG
GAGAAGCGGCCGTTCATCGACGAGGCTAAGCGGCTGCGAGCGCTGCACATGAAG
GAGCACCCGGATTATAAATACCGGCCCCGGCGGAAAACCAAGACGCTCATGAAG
AAGGATAAGTACACGCTGCCCGGCGGGCTGCTGGCCCCCGGCGGCAATAGCATG
GCGAGCGGGGTCGGGGTGGGCGCCGGCCTGGGCGCGGGCGTGAACCAGCGCAT
GGACAGTTACGCGCACATGAACGGCTGGAGCAACGGCAGCTACAGCATGATGCA
GGACCAGCTGGGCTACCCGCAGCACCCGGGCCTCAATGCGCACGGCGCAGCGCA
GATGCAGCCCATGCACCGCTACGACGTGAGCGCCCTGCAGTACAACTCCATGAC
CAGCTCGCAGACCTACATGAACGGCTCGCCCACCTACAGCATGTCCTACTCGCAG
CAGGGCACCCCTGGCATGGCTCTTGGCTCCATGGGTTCGGTGGTCAAGTCCGAGG
CCAGCTCCAGCCCCCCTGTGGTTACCTCTTCCTCCCACTCCAGGGCGCCCTGCCA
GGCCGGGGACCTCCGGGACATGATCAGCATGTATCTCCCCGGCGCCGAGGTGCC
GGAACCCGCCGCCCCAGCAGACTTCACATGTCCCAGCACTACCAGAGCGGCCC
GGTGCCCGGCACGGCCATTAACGGCACACTGCCCCTCTCACACATGGCATGCGG
CTCCGGCGAGGGCAGGGGAAGTCTTCTAACATGCGGGGACGTGGAGGAAAATCC
CGGCCCACTCGAGATGGCTGTCAGCGACGCGCTGCTCCCATCTTTCTCCACGTTC
GCGTCTGGCCCGGCGGGAAGGGAGAAGACACTGCGTCAAGCAGGTGCCCCGAAT
AACCGCTGGCGGGAGGAGCTCTCCCACATGAAGCGACTTCCCCCAGTGCTTCCCG
GCCGCCCCTATGACCTGGCGGCGGCGACCGTGGCCACAGACCTGGAGAGCGGCG
GAGCCGGTGCGGCTTGCGGCGGTAGCAACCTGGCGCCCCTACCTCGGAGAGAGA
CCGAGGAGTTCAACGATCTCCTGGACCTGGACTTTATTCTCTCCAATTCGCTGAC
CCATCCTCCGGAGTCAGTGGCCGCCACCGTGTCCTCGTCAGCGTCAGCCTCCTCT
TCGTCGTCGCCGTCGAGCAGCGGCCCTGCCAGCGCGCCCTCCACCTGCAGCTTCA
CCTATCCGATCCGGGCCGGGAACGACCCGGGCGTGGCGCCGGGCGGCACGGGCG
GAGGCCTCCTCTATGGCAGGGAGTCCGCTCCCCCTCCGACGGCTCCCTTCAACCT
GGCGGACATCAACGACGTGAGCCCCTCGGGCGGCTTCGTGGCCGAGCTCCTGCG
GCCAGAATTGGACCCGGTGTACATTCCGCCGCAGCAGCCGCAGCCGCCAGGTGG
CGGGCTGATGGGCAAGTTCGTGCTGAAGGCGTCGCTGAGCGCCCCTGGCAGCGA
GTACGGCAGCCCGTCGGTCATCAGCGTCAGCAAAGGCAGCCCTGACGGCAGCCA
CCCGGTGGTGGTGGCGCCCTACAACGGCGGGCCGCCGCGCACGTGCCCCAAGAT
CAAGCAGGAGGCGGTCTCTTCGTGCACCCACTTGGGCGCTGGACCCCCTCTCAGC
AATGGCCACCGGCCGGCTGCACACGACTTCCCCCTGGGGCGGCAGCTCCCCAGC
AGGACTACCCCGACCCTGGGTCTTGAGGAAGTGCTGAGCAGCAGGGACTGTCAC
CCTGCCCTGCCGCTTCCTCCCGGCTTCCATCCCCACCCGGGGCCCAATTACCCATC
CTTCCTGCCCGATCAGATGCAGCCGCAAGTCCCGCCGCTCCATTACCAAGAGCTC
ATGCCACCCGGTTCCTGCATGCCAGAGGAGCCCAAGCCAAAGAGGGGAAGACGA
TCGTGGCCCCGGAAAAGGACCGCCACCCACACTTGTGATTACGCGGGCTGCGGC
```

```
AAAACCTACACAAAGAGTTCCCATCTCAAGGCACACCTGCGAACCCACACAGGT

GAGAAACCTTACCACTGTGACTGGGACGGCTGTGGATGGAAATTCGCCCGCTCA

GATGAACTGACCAGGCACTACCGTAAACACACGGGGCACCGCCCGTTCCAGTGC

CAAAAATGCGACCGAGCATTTTCCAGGTCGGACCACCTCGCCTTACACATGAAG

AGGCATTTTTAAATGACTAGTGCGCGCAGCGGCCGACCATGGCCCAACTTGTTTA

TTGCAGCTTATAATGGTTACAAATAAAGCAATAGCATCACAAATTTCACAAATAA

AGCATTTTTTTCACTGCATTCTAGTTGTGGTTTGTCCAAACTCATCAATGTATCTT

ATCATGTCTGGATCTCGGTACCGGATCCAAATTCCCGATAAGGATCTTCCTAGAG

CATGGCTACGTAGATAAGTAGCATGGCGGGTTAATCATTAACTACAAGGAACCC

CTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCG

AGCGAGCGCGCAGCCTTAATTAACCTAATTCACTGGCCGTCGTTTTACAACGTCG

TGACTGGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCAACAG

TTGCGCAGCCTGAATGGCGAATGGGACGCGCCCTGTAGCGGCGCATTAAGCGCG

GCGGGTGTGGTGGTTACGCGCAGCGTGACCGCTACACTTGCCAGCGCCCTAGCG

CCCGCTCCTTTCGCTTTCTTCCCTTCCTTTCTCGCCACGTTCGCCGGCTTTCCCCGT

CAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTG

ATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAAT

TTAACGCGAATTTTAACAAAATATTAACGTTTATAATTTCAGGTGGCATCTTTCG

GGGAAATGTGCGCGGAACCCCTATTTGTTTATTTTTCTAAATACATTCAAATATGT

ATCCGCTCATGAGACAATAACCCTGATAAATGCTTCAATAATATTGAAAAGGA

AGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAG

ATCAGTTGGGTGCACGAGTGGGTTACATCGAACTGGATCTCAATAGTGGTAAGAT

CCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTC

GCCGCATACACTATTCTCAGAATGACTTGGTTGAGTACTCACCAGTCACAGAAAA

GCATCTTACGGATGGCATGACAGTAAGAGAA

Thy 1.2 promoter (RGC-specific) (SEQ ID NO: 122):
AATTCAGAGACCGGGAACCAAACTAGCCTTTAAAAAACATAAGTACA

GGAGCCAGCAAGATGGCTCAGTGGGTAAAGGTGCCTACCAGCAAGCCTGACAGC

CTGAGTTCAGTCCCCACGAACTACGTGGTAGGAGAGGACCAACCAACTCTGGAA

ATCTGTTCTGCAAACACATGCTCACACACACACACACAAATAGTATAAACAATTT

TAAATTTCATTTAAAAATAATTTGTAAACAAAATCATTAGCACAGGTTTTAGAAA

GAGCCTCTTGGTGACATCAAGTTGATGCTGTAGATGGGGTATCATTCCTGAGGAC

CCAAAACCGGGTCTCAGCCTTTCCCCATTCTGAGAGTTCTCTCTTTTCTCAGCCAC

TAGCTGAAGAGTAGAGTGGCTCAGCACTGGGCTCTTGAGTTCCCAAGTCCTACAA
```

```
CTGGTCAGCCTGACTACTAACCAGCCATGAAGAAACAAGGAGTGGATGGGCTGA

GTCTGCTGGGATGGGAGTGGAGTTAGTAAGTGGCCATGGATGTAATGACCCCAG

CAATGCTGGCTAGAAGGCATGCCTCCTTTCCTTGTCTGGAGACGGAACGGGAGG

GATCATCTTGTACTCACAGAAGGGAGAACATTCTAGCTGGTTGGGCCAAAATGTG

CAAGTTCACCTGGAGGTGGTGGTGCATGCTTTTAACTCCAGTACTCAGGAGGCAG

GGCCAGGTGGATCTCTGTGAGTTCAAGACCAGCCTGCACTATGGAGAGAGTTTTG

GGACAGCCAGAGTTACACAGAAAAATCCTGGTGGAAAATCTGAAAGAAAGAGA

GAAAGAAAGAAAGAAAGAAAGGAAGAAAGAAAGAAAGAGTGGCAGGCAGGCA

GGCAGGAGGAAGGAAGGAAGGAAGGAAGGAAGGAAGGAAGGAAGGAAGGAAA

ATAGGTGCGACTTCAAGATCCGGAGTTACAAGCAGAATGCACTGTTTCCCTAACA

GGGCCAAGTGTTTTGAGTAACTGAAGGTGGGCATGATGCCTGGGAAGCAGAAAC

AAGCCAGGCAGATGCACCCCTTGCCTTGCTTCCGAAGGGCTGCAGTAGCATGGA

AAACATGGAAAACAACCAATCCATTCCCTTTGCTGATATAACAGGCTCCAAAGCC

AAAACCTGTCACTGGAGGCTCAAGAGCAGATCTCCAGCCAAGAGGCAAAGGAAT

GGGGGAAGCTGGAGGGCCTCCCTCTGGTTATCCAGGCTTCTGAAGGTTCAAGCA

AAGAAAGGGTTACAACCTTAAAAGGAGAGCGTCCCGGGGTATGGGTAGAAGACT

GCTCCACCCCGACCCCCAGGGTCCCTAACCGTCTTTTCCCTGGGCGAGTCAGCCC

AATCACAGGACTGAGAGTGCCTCTTTAGTAGCAGCAAGCCACTTCGGACACCCA

AATGGAACACCTCCAGTCAGCCCTCGCCGACCACCCCACCCCCTCCATCCTTTTC

CCTCAGCCTCCGATTGGCTGAATCTAGAGTCCCTCCCTGCTCCCCCCTCTCTCCCC

ACCCCTGGTGAAAACTGCGGGCTTCAGCGCTGGGTGCAGCAACTGGAGGCGTTG

GCGCACCAGGAGGAGGCTGCAGCTAGGGGAGTCCAGGTGAGAGCAGGCCGACG

GGAGGGACCCGCACATGCAAGGACCGCCGCAGGGCGAGGATGCAAGCCTTCCCC

AGCTACAGTTTTGGGAAAGGATACCAGGGCGCTCCTATATGGGGCGCGGGAAC

TGGGGAAAGAAGGTGCTCCCAGGTCGAGGTGGGAGAGGAAGGCAGTGCGGGGT

CACGGGCTTTCTCCCTGCTAACGGACGCTTTCGAAGAGTGGGTGCCGGAGGAGA

ACCATGAGGAAGGACATCAAGGACAGCCTTTGGTCCCCAAGCTCAAATCGCTTT

AGTGGTGCGAATAGAGGGAGGAGGTGGGTGGCAAACTGGAGGGAGTCCCCAGC

GGGTGACCTCGTGGCTGGCTGGGTGCGGGCACCGCAGGTAAGAAAACCGCAAT

GTTGCGGGAGGGGACTGGGTGGCAGGCGCGGGGGAGGGGAAAGCTAGAAAGGA

TGCGAGGGAGCGGAGGGGGGAGGGAGCGGGAGAATCTCAACTGGTAGAGGAAG

ATTAAAATGAGGAAATAGCATCAGGGTGGGGTTAGCCAAGCCGGGCCTCAGGGA

AAGGGCGCAAAGTTTGTCTGGGTGTGGGCTTAGGTGGGCTGGGTATGAGATTCG

GGGCGCCGAAAACACTGCTGCGCCTCTGCCAAATCACGCTACCCCTGTATCTAGT

TCTGCCAGGCTTCTCCAGCCCCAGCCCCAATTCTTTTCTCTAGTGTTCCCCCTTCC

CTCCCCTGAATCTCAAGCCCACACTCCCTCCTCCATAACCCACTGTTATCAAATCT

AAGTCATTTGCCACCCAACAACCATCAGGAGGCGGAAGCAGACGGGAGGAGTTT

GAGATCAACTTGGGCTACATCACGAGTTCCAGGCTCACCAAGGCTTCTTAAGGAG

ACCTTGTCTCTAAAATTAATTAATTAATTAATAGTCCCCTTTCTCTGCCACA

GAACCTTGGGATCTGGCTCCTGGTCGCAGCTCCCCCACCCCAGGCTGACATTCA
```

-continued

```
CTGCCATAGCCCATCCGGAAATCCTAGTCTATTTCCCCATGGATCTTGAACTGCA
GAGAGAATGGCAGAGTGGCCCGCCCTGTGCAAAGGATGTTCCTAGCCTAGGTGG
AGCTCGCGAACTCGCAGACTGTGCCTCTCTTGGGCAAGGACAGGCTAGACAGCC
TGCCGGTGTGTTGAGCTAGGGCACTGTGGGGAAGGCAGAGAACCTGTGCAGGGC
AGCAATGAACACAGGACCAGAAAACTGCAGCCCTAGGAACACTCAAGAGCTGG
CCATTTGCAAGCATCTCTGGCCTCCGTGCTTCTCACTCATGTCCCATGTCTTATAC
AGGCCTCTGTGGCACCTCGCTTGCCTGATCTCATCCCTAGCCGTTAAGCTTTCTGC
ATGACTTATCACTTGGGGCATAATGCTGGATACCTACCATTTTCTTAGACCCCATC
AAAATCCTATTTGAGTGTACGGTTCGGAGAACCTCATTTATCCGGTAAATGTCTT
TTACTCTGCTCTCAGGGAGCTGAGGCAGGACATCCTGAGATACATTGGGAGAGG
AGATACAGTTTCAATAAAATAATAGGTTGGGTGGAGGTACATGCCTATAATGCC
ACCACTCAGGAAATGGTGGCAGCTTCGTGAGTTTGAGGCCAACCCAAGAAACAT
AGTGAAACCCTGTCAGTAAATAAGTAAGCAAGTATTTGAGTATCTACTATATGCT
AGGGCTGACCTGGACATTAGGGGTCATCTTCTGAACAAACTAGTGCTTGAGGGA
GGTATTTGGGGTTTTTGTTTGTTTAATGGATCTGAATGAGTTCCAGAGACTGGCTA
CACAGCGATATGACTGAGCTTAACACCCCTAAAGCATACAGTCAGACCAATTAG
ACAATAAAAGGTATGTATAGCTTACCAAATAAAAAAATTGTATTTTCAAGAGAG
TGTCTGTCTGTGTAGCCCTGGCTGTTCTTGAACTCACTCTGTAGACCAGGCTGGCC
TGGAAATCCATCTGCCTGCCTCTGCCTCTCTGCCTCTCTGCCTCTCTGCCTCTCT
CTGCCTCTCTCTGCCTCTCTCTGCCCCTCTCTGCCCCTCTCTGCCCCTCTCTGCCGC
CCTCTGCCTTTTGCCCTCTGCCCTCTGTTCTCTGGCCTCTGCCCTCTGCCCTCTGGC
CTCTGGCCTCTGCCTCTGCCTCTTGAGTGCTGGAATCAAAGGTGTGAGCTCTGTA
GGTCTTAAGTTCCAGAAGAAAGTAATGAAGTCACCCAGCAGGGAGGTGCTCAGG
GACAGCACAGACACACACCCAGGACATAGGCTCCCACTTCCTTGGCTTTCTCTGA
GTGGCAAAGGACCTTAGGCAGTGTCACTCCCTAAGAGAAGGGGATAAAGAGAGG
GGCTGAGGTATTCATCATGTGCTCCGTGGATCTCAAGCCCTCAAGGTAAATGGGG
ACCCACCTGTCCTACCAGCTGGCTGACCTGTAGCTTTCCCCACCACAGAATCCAA
GTCGGAACTCTTGGCACCTAGAGGATCTCGAGGTCCTTCCTCTGCAGAGGTCTTG
CTTCTCCCGGTCAGCTGACTCCCTCCCCAAGTCCTTCAAATATCTCAGAACATGG
GGAGAAACGGGGACCTTGTCCCTCCTAAGGAACCCCAGTGCTGCATGCCATCAT
CCCCCCCACCCTCGCCCCCACCCCCGCCACTTCTCCCTCCATGCATACCACTAGCT
GTCATTTTGTACTCTGTATTTATTCCAGGGCTGCTTCTGATTATTTAGTTTGTTCTT
TCCCTGGAGACCTGTTAGAACATAAGGGCGTATGGTGGGTAGGGGAGGCAGGAT
ATCAGTCCCTGGGGCGAGTTCCTCCCTGCCAACCAAGCCAGATGCCTGAAAGAG
ATATGGATGAGGGAAGTTGGACTGTGCCTGTACCTGGTACAGTCATACTCTGTTG
AAAGAATCATCGGGGAGGGGGGGGGCTCAAGAGGGGAGAGCTCTGCTGAGCC
TTTGTGGACCATCCAATGAGGATGAGGGCTTAGATTCTACCAGGTCATTCTCAGC
CACCACACACAAGCGCTCTGCCATCACTGAAGAAGCCCCCTAGGGCTCTTGGGC
CAGGGCACACTCAGTAAAGATGCAGGTTCAGTCAGGGAATGATGGGGAAAGGG
GTAGGAGGTGGGGAGGGATCACCCCCTCCTCTAAAACACGAGCTGCTGTCTC
CAAAGGCCTCTGCCTGTAGTGAGGGTGGCAGAAGAAGACAAGGAGCCAGAACTC
```

-continued

```
TGACTCCAGGATCTAAGTCCGTGCAGGAAGGGGATCCTAGAACCATCTGGTTGG

ACCCAGCTTACCAAGGGAGAGCCTTTATTCTTCTTTCCCTTGCCCCTCTGTGCCAG

CCCCTCTTGCTGTCCCTGATCCCCCAGACAGCGAGAGTCTTGCAACCTGCCTCTTC

CAAGACCTCCTAATCTCAGGGGCAGGCGGTGGAGTGAGATCCGGCGTGCACACT

TTTTGGAAGATAGCTTTCCCAAGGATCCTCTCCCCCACTGGCAGCTCTGCCTGTCC

CATCACCATGTATAATACCACCACTGCTACAGCATCTCACCGAGGAAAGAAAAC

TGCACAATAAAACCAAGCCTCTGGAGTGTGTCCTGGTGTCTGTCTCTTCTGTGTCC

TGGCGTCTGTCTCTTCTGTGTTCTTCCAAGGTCAGAAACAAAAACCACACACTTC

AACCTGGATGGCTCGGCTGAGCACTTCTGTGTGCAGAAGGTCCAACCAGACTCTG

GGGTACCCCGGCCCTCCCTATTCCCTTGCCTCCTGTCTCCCGCTTTTTATAGCTCC

CTATGCTGGGCTTCTCTGGAGAGTGAAATCTTTGCCCAAATCAATGCGCATTCTC

TCTGCTGAGTCATCTGGCGACAGCAGTTGAGTTCACCCGCCAACACATGGGCCCA

GCTATGTAGCCGAACCCTGGCTCTGGAAGTGCCAGGGACTTTGTGCATAAGTATG

TACCATGCCCTTTTTTCACAGTCCTAGCTCTGCAGAAGTGCAGCCTGAAGGCCTG

TCTGCTGAGAGGACATGCCCTGGAGCCCTGAAACAGGCACAGTGGGAGGAGGAA

CGGAGGATGACAGGCATCAGGCCCTCAGTCCAAAAGCAACCACTTGAGAATGGG

CTGGAGTACGAAACATGGGGTCCCGTCCCTGGATCCCTCCTCAAAGAGTAATAA

GTAAAATATAAACAGGTACCCCAGGCCGTTCTGGGTTTGGGTTGTAATGGGATCC

ATTTGCAGAGAACTATTGAGACAGCCCAGCCGTACTGTGACAGGCAATGTGGGG

GAGGAGGTTGAATCACTTGGTATTTAGCATGAATAGAATAATTCCCTGAACATTT

TTCTTAAACATCCATATCTAAATTACCACCACTCGCTCCCAGTCTTCCTGCCTTTG

CGCCAGCCTCCTGTCTGGCCATGCCTGAAGAAGGCTGGAGAAGCCACCCACCTC

AGGCCATGACACTGCCAGCCACTTGGCAGGTGCAGCCAAACCTGAGCTGTCCCA

GAAAGGGACATTCTCAAGACCCAGGCACCCTGATCAGCACTGACTTGGAGCTAC

AAGTGTCATGCCAGAAAAGTCTCTAAGAAAACCTTTTCAGGGAAAAGGGGGTGA

CTCAACACCGGGCAAGTTTGGGAAGCCCCACCCTTCGAGTGATGGAAGAGCAGA

TAGGAAGCCTCAGAAGAGAGACACCGGCACCCAGGTAACGTTCCTCATGTGGTC

TCTGTCACACTAGGTGCTCTTCCCTGGACATCTCCGTGACCACACTCTCAGTTCTT

AGGGAGATGCGGGTGCTCTCTGAGGCTATCTCAGAGTTGCAGATTCTGAGGCCTA

GAGTGACTACAGTCAGCCTAGGAAGCCACAGAGGACTGTGGACCAGGAGGGCA

GAAGAGGAGAAGGGAAGAAAAACCATCAGATAGGACTTGCAATGAAACTAACC

CAAGACAATCATAATGCAGACAGGAATGTTAAAGGCGTTCAGCAGC
```

ADDITIONAL EMBODIMENTS

Embodiment 1. A method comprising:
induce in a cell, tissue, organ and/or subject:
(i) OCT4 expression;
(ii) SOX2 expression; and
(iii) KLF4 expression;
in the absence of inducing c-MYC expression.

Embodiment 2. The method of embodiment 1, wherein OCT4 expression is induced by administering:
(i) a first engineered nucleic acid encoding OCT4 or encoding a Cas9 fusion protein (CRISPR activator) and a guide RNA sequence targeting promoter or enhancer at endogenous locus of Oct4, optionally wherein the first nucleic acid (e.g., engineered nucleic acid) comprises RNA and/or DNA;
(ii) a chemical agent that induces OCT4 expression;
(iii) an antibody that induces OCT4 expression; or
(iv) an engineered protein encoding OCT4,
optionally wherein OCT4 comprises a sequence that is at least 70% identical to SEQ ID NO: 2 or SEQ ID NO: 41.

Embodiment 3. The method of any one of embodiments 1-2, wherein SOX2 expression comprises administering:
(v) a second engineered nucleic acid encoding SOX2 encoding a Cas9 fusion protein (CRISPR activator) and a guide RNA sequence targeting promoter or enhancer at endogenous locus of SOX2, wherein the second engineered nucleic acid comprises RNA and/or DNA;
(vi) a chemical agent that induces SOX2 expression;
(vii) an antibody that induces SOX2 expression; or
(viii) an engineered protein encoding SOX2, optionally wherein SOX2 comprises a sequence that is at least 70% identical to SEQ ID NO: 4 or SEQ ID NO: 43.

Embodiment 4. The method of any one of embodiments 1-3, wherein KLF4 expression comprises administering:
(ix) a third engineered nucleic acid encoding KLF4 encoding a Cas9 fusion protein (CRISPR activator) and a guide RNA sequence targeting promoter or enhancer at endogenous locus of KLF4, wherein the third nucleic acid (e.g., engineered nucleic acid) comprises RNA and/or DNA;
(ix) a chemical agent that induces KLF4 expression;
(xi) an antibody that induces KLF4 expression; or
(xii) an engineered protein encoding KLF4, optionally wherein KLF4 comprises a sequence that is at least 70% identical to SEQ ID NO: 6 or SEQ ID NO: 45.

Embodiment 5. The method of any one of embodiments 2-4, wherein said first, second, third engineered nucleic acids, or a combination thereof are present on an expression vector or are not present on an expression vector, optionally wherein the first, second, third engineered nucleic acids are mRNA or plasmid DNA.

Embodiment 6. The method of embodiment 5, wherein two or three of said first, second and third engineered nucleic acids are present in the same expression vector.

Embodiment 7. The method of any one of embodiments 1-5, wherein said first, second and third engineered nucleic acids are present in separate expression vectors.

Embodiment 8. The method of any one of embodiments 5-7, wherein said expression vector(s) include an inducible promoter operably linked to the first, second, third engineered nucleic acids, or a combination thereof, optionally wherein said method further comprises administering an inducing agent.

Embodiment 9. The method of embodiment 8 wherein said promoter comprises a tetracycline response element (TRE).

Embodiment 10. The method of embodiment 9, wherein administration of the inducing agent comprises administering a protein or a fourth engineered nucleic acid encoding the inducing agent, optionally wherein the fourth engineered nucleic acid is introduced simultaneously as the first, second, and third engineered nucleic acids.

Embodiment 11. The method of embodiment 10, wherein the fourth engineered nucleic acid is present on a separate expression vector from the first, second, and third engineered nucleic acids.

Embodiment 12. The method of embodiment 10, wherein the fourth engineered nucleic acid is present on the same expression vector with at least one of the first, second, and third engineered nucleic acids.

Embodiment 13. The method of any one of embodiments 9-12, wherein the inducing agent is capable of inducing expression of the first, second, third engineered nucleic acids, or a combination thereof from the inducible promoter in the presence of a tetracycline and the method further comprises administering tetracycline and/or removing tetracycline, optionally wherein the tetracycline is doxycycline.

Embodiment 14. The method of embodiment 13, wherein the inducing agent is reverse tetracycline-controlled trans-activator (rtTA).

Embodiment 15. The method of embodiment 14, wherein the rtTA is M2-rtTA or rtTA3.

Embodiment 16. The method of embodiment 15, wherein the M2-rtTA comprises an amino acid sequence that is at least 70% identical to SEQ ID NO: 15 or the rtTA3 comprises an amino acid sequence that is at least 70% identical to SEQ ID NO: 11.

Embodiment 17. The method of any one of embodiments 9-12, wherein the inducing agent is capable of inducing expression of the first, second, third engineered nucleic acids, or a combination thereof from the inducible promoter in the absence of a tetracycline, optionally, wherein the tetracycline is doxycycline.

Embodiment 18. The method of embodiment 17, wherein the inducing agent is a temperature, a chemical, a pH, a nucleic acid, a protein, optionally wherein the protein is a tetracycline-controlled transactivator (tTA).

Embodiment 19. The method of any one of embodiments embodiment 11 or 13-18, wherein the first, second, and third engineered nucleic acids are present in a first expression vector and the fourth engineered nucleic acid is present in a second expression vector.

Embodiment 20. The method of any one of embodiments 9-19, wherein the promoter is a TRE3G, a TRE2 promoter, or a P tight promoter, optionally, wherein the promoter comprises a engineered nucleic acid sequence that is at least 70% identical to SEQ ID NO: 7, optionally, wherein the promoter comprises a engineered nucleic acid sequence that is at least 70% identical to SEQ ID NO: 23, and optionally wherein the promoter comprises a sequence that is at least 70% identical to SEQ ID NO: 24.

Embodiment 21. The method of any one of embodiments 1-7 or 10-20, wherein said expression vector(s) comprise a constitutive promoter operably linked to the first, second, third, fourth engineered nucleic acids, or any combination thereof.

Embodiment 22. The method of embodiment 21, wherein the constitutive promoter is operably linked to the fourth engineered nucleic acid but not to the first, second, or third engineered nucleic acids, optionally wherein the constitutive promoter is CP1, CMV, EF1 alpha, SV40, PGK1, Ubc, human beta actin, CAG, Ac5, polyhedrin, TEF1, GDS, CaM3 5S, Ubi, H1, and U6 promoter, or a tissue-specific promoter.

Embodiment 23. The method of embodiment 19-22, wherein the first expression vector comprises the sequence provided in SEQ ID NO: 16, optionally wherein the second expression vector comprises the sequence provided in SEQ ID NO: 31 or SEQ ID NO: 32.

Embodiment 24. The method of any one of embodiments 2-23, wherein at least one of (i)-(xii) is delivered in a viral vector or is delivered without a viral vector, wherein the viral vector is selected from the group consisting of a lentivirus, a retrovirus, an adenovirus, alphavirus, vaccinia virus, and an adeno-associated virus (AAV) vector, optionally wherein delivery without a viral vector comprises administration of a naked nucleic acid, electroporation, use of a nanoparticle, or use of liposomes.

Embodiment 25. The method of any one of embodiments 19-24, wherein the first expression vector is a first viral vector, and the second expression vector is a viral vector, optionally wherein the first and second viral vectors are AAV vectors.

Embodiment 26. The method of any one of embodiments 1-25 wherein at least one engineered nucleic acid comprises an SV40-derived sequence including a sequence that is at least 70% identical to SEQ ID NO: 8.

Embodiment 27. The methods of any one of embodiments 1-26, wherein OCT4, KLF4, or SOX2 is a mammalian protein.

Embodiment 28. The method of any one of embodiments 1-27, wherein the cell or tissue is in a subject, wherein the subject has a condition, is suspected of having a condition, or at risk for a condition, optionally wherein the condition is selected from the group consisting of ocular disease, aging, cancer, musculoskeletal disease, age-related disease, a disease affecting a non-human animal and neurodegenerative disease.

Embodiment 29. The method of any one of embodiments 1-28, wherein the method further comprises regulating: cellular reprogramming, tissue repair, tissue survival, tissue regeneration, tissue growth, tissue function, organ regeneration, organ survival, organ function, disease, or any combination thereof, optionally wherein regulating comprises inducing cellular reprogramming, reversing aging, improving tissue function, improving organ function, tissue repair, tissue survival, tissue regeneration, tissue growth, promoting angiogenesis, treating a disease, reducing scar formation, reducing the appearance of aging, promoting organ regeneration, promoting organ survival, altering the taste and quality of agricultural products derived from animals, treating a disease, or any combination thereof, ex vivo or in vitro and optionally wherein treating a disease comprises inducing expression of OCT4, KLF4, and/or SOX2 prior to the onset of disease or wherein treating a disease a disease comprises inducing expression of OCT4, KLF4, and/or SOX2 after the onset of disease.

Embodiment 30. The method of embodiment 29, wherein the cell or tissue is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine, optionally wherein the tissue is damaged or the tissue may be considered healthy but suboptimal for performance or survival in current or future conditions.

Embodiment 31. The method of any one of embodiments 1-30, wherein the engineered nucleic acid further comprises a self-cleaving peptide, optionally wherein the self-cleaving peptide is a 2A peptide that is at least 70% identical to SEQ ID NO: 9.

Embodiment 32. The method of any one of embodiments 1-31, wherein the engineered nucleic acid further comprises inverted terminal repeats (ITRs) flanking the first nucleic acid, the second nucleic acid, the third nucleic acid, or a combination thereof, optionally, wherein the distance between the ITRs is 4.7 kb or less.

Embodiment 33. An expression vector comprising:
(i) a first engineered nucleic acid encoding OCT4;
(ii) a second engineered nucleic acid encoding SOX2; and
(iii) a third engineered nucleic acid encoding KLF4;
in the absence of an engineered nucleic acid capable of expressing c-MYC.

Embodiment 34. The expression vector of embodiment 33, wherein the OCT4 protein comprises a sequence that is at least 70% identical to SEQ ID NO: 2 or SEQ ID NO: 41.

Embodiment 35. The expression vector of any one of embodiments 33-34, wherein the SOX2 protein comprises a sequence that is at least 70% identical to SEQ ID NO: 4 or SEQ ID NO: 43.

Embodiment 36. The expression vector of any one of embodiments 33-35, wherein the KLF4 protein comprises a sequence that is at least 70% identical to SEQ ID NO: 6 or SEQ ID NO: 45.

Embodiment 37. The expression vector of any one of embodiments 33-36, further comprising an inducible promoter operably linked to the first, second, third engineered nucleic acids, or any combination thereof.

Embodiment 38. The expression vector of embodiment 37, wherein an inducing agent is capable of inducing expression of the first, second, third engineered nucleic acids, or any combination thereof from the inducible promoter in the presence of a tetracycline, optionally wherein the tetracycline is doxycycline.

Embodiment 39. The expression vector of embodiment 38, wherein the inducing agent is reverse tetracycline-controlled transactivator (rtTA).

Embodiment 40. The expression vector of embodiment 39, wherein the rtTA is M2-rtTA or rtTA3.

Embodiment 41. The expression vector of embodiment 40, wherein the M2-rtTA comprises an amino acid sequence that is at least 70% identical to SEQ ID NO: 15 or the rtTA3 comprises an amino acid sequence that is at least 70% identical to SEQ ID NO: 11.

Embodiment 42. The expression vector of any one of embodiments 38-41, wherein the inducing agent is capable of inducing expression of the first, second, third engineered nucleic acids, or any combination thereof from the inducible promoter in the absence of a tetracycline, optionally, wherein the tetracycline is doxycycline.

Embodiment 43. The expression vector of embodiment 42, wherein the inducing agent is a tetracycline-controlled transactivator (tTA).

Embodiment 44. The expression vector of any one of embodiments 37-43, wherein the inducible promoter comprises a tetracycline-responsive element (TRE), optionally, wherein the promoter is a TRE3G promoter comprising a engineered nucleic acid sequence that is at least 70% identical to SEQ ID NO: 7, optionally, wherein the promoter comprises a engineered nucleic acid sequence that is at least 70% identical to SEQ ID NO: 23, and optionally wherein the promoter comprises a sequence that is at least 70% identical to SEQ ID NO: 24.

Embodiment 45. The expression vector of any one of embodiments 33-36, wherein said expression vector(s) comprise a constitutive promoter operably linked to the first, second, third engineered nucleic acids, or a combination thereof.

Embodiment 46. The expression vector of any one of embodiments 33-44, wherein the expression vector comprises the sequence provided in SEQ ID NO: 16.

Embodiment 47. The expression vector of any one of embodiments 33-46, wherein the expression vector is a viral vector, wherein the viral vector is selected from the group consisting of a lentivirus, alphavirus, vaccinia virus, a herpes virus, a retrovirus, an adenovirus, and an adeno-associated virus (AAV) vector.

Embodiment 48. The expression vector of any one of embodiments 33-47, wherein at least one engineered nucleic acid comprises an SV40-derived sequence including a sequence that is at least 70% identical to SEQ ID NO: 8.

Embodiment 49. The expression vectors of any one of embodiments 33-48, wherein OCT4, KLF4, or SOX2 is a mammalian protein.

Embodiment 50. The expression vector of any one of embodiments 33-49, wherein the expression vector further comprises a self-cleaving peptide, optionally wherein the self-cleaving peptide is 2A peptide, optionally wherein the 2A peptide comprises a sequence that is at least 70% identical to SEQ ID NO: 9.

Embodiment 51. The expression vector of any one of embodiments 37-44 and 46-50, wherein the expression vector comprises one inducible promoter.

Embodiment 52. The expression vector of any one of embodiments 45-50, wherein the expression vector comprises one constitutive promoter.

Embodiment 53. The expression vector of any one of embodiments 33-52, wherein the engineered nucleic acid further comprises inverted terminal repeats (ITRs) flanking the first nucleic acid, the second nucleic acid, the third nucleic acid, or a combination thereof.

Embodiment 54. The expression vector of embodiment 32, wherein the distance between the ITRs is 4.7 kb or less.

Embodiment 55. A recombinant virus comprising the expression vector of any one of embodiments 47-54, optionally wherein the recombinant virus is a retrovirus, an adenovirus, an AAV, alphavirus, vaccinia virus, a herpes virus, or a lentivirus.

Embodiment 56. An engineered cell produced by any one of the methods of embodiments 1-32, 63-66, 70-75, 81, and 85-87, optionally wherein the engineered cell comprises the expression vector of any one of embodiments 33-54.

Embodiment 57. A composition comprising the, expression vector of any one of embodiments 33-54, the recombinant virus of embodiment 55, the engineered cell of embodiment 56, a chemical agent that is capable of inducing OCT4, KLF4, and/or SOX2 expression, an engineered protein selected from the group consisting of OCT4, KLF4, and/or SOX2, an antibody capable of inducing expression of OCT4, KLF4, and/or SOX2, optionally wherein the composition comprises a pharmaceutically acceptable carrier.

Embodiment 58. The composition of embodiment 57, further comprising a second expression vector encoding an inducing agent, a second protein encoding an inducing agent, or a second recombinant virus encoding an inducing agent, optionally wherein the second expression vector is an AAV vector and/or the second recombinant virus is an AAV.

Embodiment 59. The composition of embodiment 58, wherein the inducing agent is reverse tetracycline transactivator (rtTA) or tetracycline transactivator (tTA).

Embodiment 60. The composition of any one of embodiments 58-59, wherein the inducing agent is encoded by a viral vector, optionally, wherein the viral vector is selected from the group consisting of a lentiviral vector, an adenoviral vector, an adeno-associated viral vector, and a retroviral vector.

Embodiment 61. The composition of embodiment 60, wherein the viral vector encoding the inducing agent comprises a sequence set forth in SEQ ID NO: 31 or SEQ ID NO: 32.

Embodiment 62. A kit comprising the expression vector of any one of embodiments 33-54, recombinant virus of embodiment 55, the engineered cell of embodiment 56, a chemical agent that is capable of inducing OCT4, KLF4, and/or SOX2 expression, an engineered protein selected from the group consisting of OCT4, KLF4, and/or SOX2, an antibody capable of inducing expression of OCT4, KLF4, and/or SOX2, or the composition of any one of embodiments 56-61.

Embodiment 63. A method of producing an engineered cell comprising the method of any one of embodiments 1-32, thereby producing the engineered cell.

Embodiment 64. The method of embodiment 63, wherein the engineered cell is an induced pluripotent stem cell.

Embodiment 65. The method of any one of embodiments 63-64, wherein the engineered cell is the cell of embodiment 56.

Embodiment 66. A method of producing an engineered cell, comprising the method of any one of embodiments 1-32 and 63-65, wherein the engineered cell is produced ex vivo.

Embodiment 67. The method of any one of embodiments 63-66, further comprising generating an engineered tissue or engineered organ.

Embodiment 68. The method of any one of embodiments 66-67, further comprising administering the engineered cell, engineered tissue, and/or engineered organ to a subject in need thereof, optionally wherein the cell, tissue, and/or organ is from eye, ear, nose, mouth including gum and roots of teeth, bone, lung, breast, udder, pancreas, stomach, oesophagus, muscle including cardiac muscle, liver, blood vessel, skin including hair, heart, brain, nerve tissue, kidney, testis, prostate, penis, cloaca, fin, ovary, or intestine cell.

Embodiment 69. The method of any one of embodiments 63-68, wherein the method further comprises treating a disease, optionally wherein the disease is selected from the group consisting of acute injuries, neurodegenerative diseases, chronic diseases, proliferative diseases, ocular disease, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject, optionally wherein the disease is an ocular disease.

Embodiment 70. A method comprising:
(i) activating OCT4;
(ii) activating SOX2; and
(iii) activating KLF4;
in a cell, tissue, organ, and/or subject and in the absence of activating c-Myc.

Embodiment 71. The method of embodiment 71, wherein the activating in any one of (i)-(iii) comprises administering an antibody, protein, nucleic acid, or chemical agent.

Embodiment 72. The method of any one of embodiments 72, wherein the nucleic acid, antibody, protein, and/or chemical agent replaces OCT4, SOX2, and/or KLF4.

Embodiment 73. The method of embodiment 72, wherein the replacing comprises promoting cellular reprogramming.

Embodiment 74. The method of any one of embodiments 70-73, wherein activating of any one of (i)-(iii) comprises replacing OCT4, SOX2, and/or KLF4, selected from the group consisting of an antibody, a protein, a nucleic acid, and a chemical agent.

Embodiment 75. The method of embodiment 74, wherein the replacing of OCT4, SOX2, and/or KLF4 comprises administering a nucleic acid and/or protein encoding Tet1, NR5A-2, Sal14, E-cadherin, NKX3-1, NANOG, and/or Tet2.

Embodiment 76. The method of any one of embodiments 1-32 and 70-75, wherein the subject is healthy.

Embodiment 77. The method of any one of embodiments 1-32 and 70-76, wherein the subject is a pediatric subject.

Embodiment 78. The method of any one of embodiments 1-32 and 70-76, wherein the subject is an adult subject.

Embodiment 79. The method of any one of embodiments 28-32 and 70-78, wherein the subject has, is suspected of having, or at risk for glaucoma.

Embodiment 80. The method of any one of embodiments 28-32 and 70-79, wherein the subject has, is suspected of having, or at risk for age-related decline in visual acuity, and/or retinal function.

Embodiment 81. A method comprising administering a nucleic acid and/or protein encoding Tet1 or Tet2 to a cell, tissue, organ, and/or subject.

Embodiment 82. The method of embodiment 81, wherein the subject has a disease.

Embodiment 83. The method of embodiment 82, wherein the disease is selected from acute injuries, neurodegenerative diseases, chronic diseases, proliferative diseases, ocular disease, cardiovascular diseases, genetic diseases, inflammatory diseases, autoimmunue diseases, neurological diseases, hematological diseases, painful conditions, psychiatric disorders, metabolic disorders, chronic diseases, cancers, aging, age-related diseases, and diseases affecting any tissue in a subject.

Embodiment 84. The method of embodiment 83, wherein the disease is an ocular disease.

Embodiment 85. The method of any one of embodiments 1-32 and 63-84, further comprising activating an enhancer of reprogramming in the cell, tissue, organ and/or subject.

Embodiment 86. The method of any one of embodiments 1-32 and 63-85, further comprising inhibiting a barrier of reprogramming in the cell, tissue, organ and/or subject.

Embodiment 87. The method of embodiment 86, wherein the barrier of reprogramming is a DNA methyltransferase (DNMT) in the cell, tissue, organ and/or subject.

Embodiment 88. A method comprising:
inducing in a subject:
(i) OCT4 expression;
(ii) SOX2 expression; and
(iii) KLF4 expression;
in the absence of inducing c-MYC expression, wherein the subject has been treated with a chemotherapy drug.

Embodiment 89. The method of embodiment 89, wherein the chemotherapy drug is vincristine (VCS).

Embodiment 90. A method comprising inducing in a cell, tissue, organ, and/or subject:
(i) OCT4 expression;
(ii) SOX2 expression; and
(iii) KLF4 expression;
wherein OCT4, SOX2, and KLF4 is encoded by a nucleic acid and expression of OCT4, SOX2, and/or KLF4 is induced from a single promoter.

Embodiment 91. A method comprising:
inducing in a cell, tissue, organ and/or subject:
(i) OCT4 expression;
(ii) SOX2 expression;
(iii) KLF4 expression; or
(iv) any combination of (i)-(iii),
in the absence of inducing c-MYC expression.

Embodiment 92. The method of embodiment 91, wherein the combination of (i)-(iii) comprises (i) and (ii); (i) and (iii); (ii) and (iii); or (i), (ii), and (iii).

Embodiment 93. An expression vector comprising:
(i) a first engineered nucleic acid encoding OCT4;
(ii) a second engineered nucleic acid encoding SOX2;
(iii) a third engineered nucleic acid encoding KLF4; or
(iv) any combination of (i)-(iii),
in the absence of an engineered nucleic acid capable of inducing c-MYC expression.

Embodiment 94. The expression vector of embodiment 93, wherein the combination of (i)-(iii) comprises (i) and (ii); (i) and (iii); (ii) and (iii); or (i), (ii), and (iii).

Embodiment 95. A recombinant virus comprising the expression vector of any one of embodiments 47-54 and 93-94, optionally wherein the recombinant virus is a retrovirus, an adenovirus, an AAV, alphavirus, vaccinia virus, a herpes virus, or a lentivirus.

Embodiment 96. An engineered cell produced by any one of the methods of embodiments 1-32, 63-66, 70-75, 81, 85-87, and 91-92, optionally wherein the engineered cell comprises the expression vector of any one of embodiments 33-54 and 93-94.

Embodiment 97. A composition comprising the expression vector of any one of embodiments 33-54 and 93-94, the recombinant virus of embodiment 55 or embodiment 95, the engineered cell of embodiment 56 or 96, a chemical agent that is capable of inducing expression of OCT4; KLF4; SOX2; or any combination thereof, an engineered protein selected from the group consisting of OCT4; KLF4; SOX2; or any combination thereof, an antibody capable of inducing expression of OCT4; KLF4; SOX2; or any combination thereof, optionally wherein the composition comprises a pharmaceutically acceptable carrier.

Embodiment 98. A kit comprising the expression vector of any one of embodiments 33-54 and 93-94, recombinant virus of embodiment 55 or 95, the engineered cell of embodiment 56 or 96, a chemical agent that is capable of inducing expression of OCT4; KLF4; SOX2; or any combination thereof, an engineered protein selected from the group consisting of OCT4; KLF4; SOX2; or any combination thereof, an antibody capable of inducing expression of OCT4; KLF4; SOX2; or any combination thereof, or the composition of any one of embodiments 56-61 or 97.

Embodiment 99. A method of producing an engineered cell comprising the method of any one of embodiments 1-32 and 91-92, thereby producing the engineered cell.

Embodiment 100. A method of producing an engineered cell, comprising the method of any one of embodiments 1-32, 63-65, 91-92, and 99, wherein the engineered cell is produced in vivo.

Embodiment 101. A method of producing an engineered cell, comprising the method of any one of embodiments 1-32, 63-65, 91-92, and 99, wherein the engineered cell is produced ex vivo.

Embodiment 102. A method comprising:
(i) activating OCT4;
(ii) activating SOX2;
(iii) activating KLF4; or
(iv) any combination of (i)-(iii),
in a cell, tissue, organ, subject, or any combination thereof, and in the absence of activating c-Myc above endogenous levels.

Embodiment 103. The method of embodiment 102, wherein the combination of (i)-(iii) comprises (i) and (ii); (i) and (iii); (ii) and (iii); or (i), (ii), and (iii).

Embodiment 104. A method comprising:
inducing in a subject:
(i) OCT4 expression;
(ii) SOX2 expression;
(iii) KLF4 expression; or
(iv) any combination of (i)-(iii),
in the absence of inducing c-MYC expression, wherein the subject has been treated with a chemotherapy drug.

Embodiment 105. The method of embodiment 104, wherein the combination of (i)-(iii) comprises (i) and (ii); (i) and (iii); (ii) and (iii); or (i), (ii), and (iii).

Embodiment 106. A method comprising inducing in a cell, tissue, organ, subject, or any combination thereof:
(i) OCT4 expression;
(ii) SOX2 expression;
(iii) KLF4 expression; or
(iv) any combination of (i)-(iii),
wherein OCT4, SOX2, KLF4, or any combination thereof is encoded by a nucleic acid and expression of OCT4, SOX2, KLF4, or any combination thereof is induced from a single promoter.

Embodiment 107. The method of embodiment 106, wherein the combination of (i)-(iii) comprises (i) and (ii); (i) and (iii); (ii) and (iii); or (i), (ii), and (iii).

Embodiment 108. The method of any one of embodiments 1-32, 68-92, or 102-107 wherein the subject is a human.

Embodiment 109. The method of any one of embodiments 1-32, 68-92, or 102-108, wherein the method does not induce teratoma formation.

Embodiment 110. The method of any one of embodiments 1-32, 68-92, or 102-109, wherein the method does not induce tumor formation or tumor growth.

Embodiment 111. The method of embodiment 110, wherein the method reduces tumor formation or tumor growth.

Embodiment 112. The method of any one of embodiments 1-32, 68-92, or 102-111, wherein the method increases visual acuity in the subject.

Embodiment 113. The method of any one of embodiments 1-32, 68-92, or 102-112, wherein the method does not induce cancer.

Embodiment 114. The method of any one of embodiments 1-32, 68-92, or 102-113, wherein the method does not induce glaucoma.

Embodiment 115. The method of any one of embodiments 1-32, 68-92, or 102-114, wherein the method reverses the epigenetic clock of the cell, the tissue, the organ, the subject, or any combination thereof.

Embodiment 116. The method of embodiment 115, wherein the epigenetic clock is determined using a DNA methylation-based (DNAm) age estimator.

Embodiment 117. The method of any one of embodiments 1-32, 68-92, or 102-116, wherein the method alters the expression of one or more genes associated with ageing.

Embodiment 118. The method of embodiment 117, wherein the method reduces expression of one or more genes associated with ageing.

Embodiment 119. The method of embodiment 118, wherein the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Cc19, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galntl5, Galntl8, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4c1, Ltc4s, Manscl, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel113, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 120. The method of embodiment 119, wherein the gene is a sensory gene.

Embodiment 121. The method of any one of embodiments 118-120, wherein the gene is Ace, Kcnk4, Lamc3, Edn1, Syt10, Ngfr, Gprc5c, Cd36, Chrna4, Ednrb, Drd2, or a combination thereof.

Embodiment 122. The method of embodiment 117, wherein the method increases expression of one or more genes associated with ageing.

Embodiment 123. The method of any one of embodiments 1-32, 68-92, 102-122, wherein the method increases expression of 1700031P21Rik, 1810053B23Rik, 2900045O20Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acotl2, Adig, Akr1c1, Ankrd1, Asb15, Atp2c2, AU018091, AW822073, Btn110, C130093G08Rik, C130027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps811, EU599041, Fam90ala, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Muc12, Mug1, Mybl2, Myh15, Nek10, Neurod6, Nrlh5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd111, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Treg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 124. The method of embodiment 123, wherein the method increases expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otog1, Olfr943, Olfr1406, Olfr273, Olfr466, Olfr1043, Olfr427, Olfr890, Rbp4, or any combination thereof.

Embodiment 125. A method of reprogramming comprising rejuvenating the epigenetic clock of a cell, tissue, organ, subject, or any combination thereof.

Embodiment 126. The method of embodiment 125, wherein rejuvenating the epigenetic clock of a cell, tissue, organ, subject, or any combination thereof comprises introducing, activating, and/or expressing OCT4, KLF4, SOX2, or any combination thereof.

Embodiment 127. The method of any one of embodiments 126, wherein the epigenetic clock of a cell, tissue, organ, subject, or any combination thereof is rejuvenated to that of a young cell, tissue, organ, subject, or any combination thereof.

Embodiment 128. The method of any one of embodiments 125-127, wherein rejuvenating the epigenetic clock comprises altering expression of one or more genes associated with ageing in the cell, tissue, organ, subject, or the combination thereof.

Embodiment 129. The method of embodiment 128, wherein the method comprises reducing expression of one or more genes associated with ageing.

Embodiment 130. The method of embodiment 129, wherein the method comprises reducing expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Cc19, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galntl5, Galntl8, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4c1, Ltc4s, Mansc1, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel113, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 131. The method of embodiment 128-130, wherein the one or more genes is one or more sensory genes.

Embodiment 132. The method of any one of embodiments 128-131, wherein the gene is Ace, Kcnk4, Lamc3, Edn1, Syt10, Ngfr, Gprc5c, Cd36, Chrna4, Ednrb, Drd2, or a combination thereof.

Embodiment 133. The method of any one of embodiments 128-132, wherein the method comprises increasing expression of one or more genes associated with ageing.

Embodiment 134. The method of embodiment 133, wherein the method increases expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1c1, Ankrd1, Asb15, Atp2c2, AU018091, AW822073, Btn110, C130093G08Rik, C730027H18Rik, Ccdc162, Chil6, Col26a1, Corin, Crls1, Cybrdl, Cyp2d12, Cyp7a1, D830005E20Rik, Dlx3, Dnah14, Dsc3, Dthd1, Eid2, Eps811, EU599041, Fam90ala, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Muc12, Mug1, Mybl2, Myh15, Nek10, Neurod6, Nrlh5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd1l1, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Treg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 135. The method of any one of embodiments 133-134, wherein the method comprises increasing expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otog1, Olfr943, Olfr1406, Olfr273, Olfr466, Olfr1043, Olfr427, Olfr890, Rbp4, or any combination thereof.

Embodiment 136. A method of reprogramming comprising altering the expression of one or more genes associated with ageing.

Embodiment 137. The method of embodiment 136, comprising increasing expression of OCT4, KLF4, SOX2, or any combination thereof.

Embodiment 138. The method of any one of embodiments 136-137, wherein the method rejuvenates the epigenetic clock of a cell, tissue, organ, subject, or any combination thereof.

Embodiment 139. The method of any one of embodiments embodiment 136-138, wherein the method comprises reducing expression of one or more genes associated with ageing.

Embodiment 140. The method of embodiment 139, wherein the method reduces expression of 0610040J01Rik, 1700080N15Rik, 2900064F13Rik, 4833417C18Rik, 4921522P10Rik, 4930447C04Rik, 4930488N15Rik, Ace, Ackr1, Acot10, Acvr1, Adamts17, Adra1b, AI504432, Best3, Boc, Cadm3, Cand2, Cc19, Cd14, Cd36, Cfh, Chrm3, Chrna4, Cntn4, Cracr2b, Cryaa, CT573017.2, Cyp26a1, Cyp27a1, D330050G23Rik, D930007P13Rik, Ddo, Dgkg, Dlk2, Dnajal-ps, Drd2, Dsel, Dytn, Ecscr, Edn1, Ednrb, Efemp1, Elfn2, Epha10, Ephx1, Erbb4, Fam20a, Fbxw21, Ffar4, Flt4, Fmod, Foxp4, Fzd7, Gabrd, Galntl5, Galntl8, Gfra2, Ggt1, Gm10416, Gm14964, Gm17634, Gm2065, Gm32352, Gm33172, Gm34280, Gm35853, Gm36298, Gm36356, Gm36937, Gm3898, Gm42303, Gm42484, Gm42537, Gm42743, Gm43151, Gm43843, Gm44545, Gm44722, Gm45516, Gm45532, Gm47494, Gm47982, Gm47989, Gm48398, Gm48495, Gm48593, Gm48958, Gm49089, Gm49326, Gm49331, Gm49760, Gm5796, Gm6374, Gm7276, Gm8237, Gm9796, Gm9954, Gpr75, Gprc5c, Grid2ip, Gsg112, Hapln4, Hcn3, Hcn4, Hhat1, Hs6st2, Htr3a, Il1rap, Il1rap12, Inka1, Kbtbd12, Kcnj11, Kcnk4, Kdelc2, Klhl33, Lamc3, Lilra5, Lman11, Lrfn2, Lrrc38, Lrrn4c1, Ltc4s, Manscl, Mir344c, Msr1, Mycbpap, Myoc, Ngfr, Nipal2, Olfr1372-ps1, Otop3, P2rx5, P2ry12, P4ha2, Pcdha12, Pcdha2, Pcdhac2, Pcdhb18, Pcdhb5, Pcsk2os1, Pcsk6, Perp, Pkp1, Plxna4, Prickle2, Qsox1, Rapgef4os2, Rbp4, Rcn3, Sec1415, Sel113, Serpinh1, Sgpp2, Shisa6, Siah3, Siglech, Slc12a4, Slc24a2, Slc2a5, Slc4a4, Slitrk3, Smagp, Smoc2, Speer4b, Spon2, Sstr2, Sstr3, St3gal3, Stc1, Stc2, Syndig1, Syt10, Thsd7a, Tlr8, Tmem132a, Tmem132d, Tmem200a, Tmem44, Trpc4, Trpv4, Unc5b, Vgf, Vmn1r90, Vwc21, Wfikkn2, Wnt11, Wnt6, Zeb2os, Zfp608, Zfp976, or any combination thereof.

Embodiment 141. The method of any one of embodiments 136-140, wherein the one or more genes is one or more sensory genes.

Embodiment 142. The method of any one of embodiments 136-140, wherein the gene is Ace, Kcnk4, Lamc3, Edn1, Syt10, Ngfr, Gprc5c, Cd36, Chrna4, Ednrb, Drd2, or a combination thereof.

Embodiment 143. The method of any one of embodiments embodiment 136-142, wherein the method comprises increasing expression of one or more genes associated with ageing.

Embodiment 144. The method of embodiment 143, wherein the method comprises increasing expression of 1700031P21Rik, 1810053B23Rik, 2900045020Rik, 2900060B14Rik, 4921504E06Rik, 4930402F11Rik, 4930453C13Rik, 4930455B14Rik, 4930500H12Rik, 4930549P19Rik, 4930555B11Rik, 4930556J02Rik, 4932442E05Rik, 4933431K23Rik, 4933438K21Rik, 6720475M21Rik, 9830132P13Rik, A430010J10Rik, A530064D06Rik, A530065N20Rik, Abcb5, Abhd17c, AC116759.2, AC131705.1, AC166779.3, Acot12, Adig, Akr1c1, Ankrd1, Asb15, Atp2c2, AU018091, AW822073, Btn110, C130093G08Rik, C730027H18Rik, Ccdc162, Chil6, Col26a1, Corin, Crls1, Cybrd1, Cyp2d12, Cyp7a1, D830005E20Rik, Dlx3, Dnah14, Dsc3, Dthd1, Eid2, Eps811, EU599041, Fam90ala, Fancf, Fau-ps2, Fezf1, Gja5, Gm10248, Gm10513, Gm10635, Gm10638, Gm10718, Gm10722, Gm10800, Gm10801, Gm11228, Gm11251, Gm11264, Gm11337, Gm11368, Gm11485, Gm11693, Gm12793, Gm13050, Gm13066, Gm13323, Gm13339, Gm13346, Gm13857, Gm14387, Gm14770, Gm15638, Gm16072, Gm16161, Gm16181, Gm17200, Gm17791, Gm18025, Gm18757, Gm18795, Gm18848, Gm19719, Gm20121, Gm20356, Gm2093, Gm21738, Gm21940, Gm22933, Gm24000, Gm24119, Gm25394, Gm26555, Gm27047, Gm28262, Gm28530, Gm29295, Gm29825, Gm29844, Gm3081, Gm32051, Gm32122, Gm33056, Gm33680, Gm34354, Gm34643, Gm3551, Gm36660, Gm36948, Gm37052, Gm37142, Gm37262, Gm37535, Gm37569, Gm37589, Gm37647, Gm37648, Gm37762, Gm38058, Gm38069, Gm38137, Gm38218, Gm39139, Gm42535, Gm42680, Gm42895, Gm42994, Gm43027, Gm43158, Gm43288, Gm43366, Gm44044, Gm44081, Gm44187, Gm44280, Gm44535, Gm45338, Gm45644, Gm45740, Gm46555, Gm46565, Gm4742, Gm47485, Gm47853, Gm47992, Gm48225, Gm48314, Gm48383, Gm48673, Gm48804, Gm48832, Gm4994, Gm5487, Gm5724, Gm595, Gm6012, Gm6024, Gm7669, Gm7730, Gm8043, Gm8953, Gm9348, Gm9369, Gm9495, H2a12a, Ido2, Igfbp1, Kif7, Klhl31, Lrrc31, Mc5r, Mgam, Msh4, Mucl2, Mug1, Mybl2, Myh15, Nek10, Neurod6, Nrlh5, Olfr1042, Olfr1043, Olfr1082, Olfr1090, Olfr1124, Olfr1167, Olfr1205, Olfr1206, Olfr1223, Olfr1263, Olfr1264, Olfr1269, Olfr127, Olfr1291-ps1, Olfr1406, Olfr1469, Olfr215, Olfr273, Olfr328, Olfr355, Olfr372, Olfr390, Olfr427, Olfr456, Olfr466, Olfr481, Olfr522, Olfr6, Olfr601, Olfr603, Olfr706, Olfr727, Olfr728, Olfr741, Olfr801, Olfr812, Olfr816, Olfr822, Olfr860, Olfr890, Olfr923, Olfr943, Otog1, Pi15, Pkhd1, Pkhd111, Platr6, Pou3f4, Prr9, Pvalb, Rhag, Sav1, Serpinb9b, Skint1, Skint3, Skint5, Slc10a5, Slc6a4, Smok2a, Tcaf3, Tomm20l, Trcg1, Trdn, Ugt1a6a, Usp17la, Vmn1r178, Vmn1r179, Vmn1r33, Vmn1r74, Vmn1r87, Vmn2r102, Vmn2r113, Vmn2r17, Vmn2r52, Vmn2r66, Vmn2r68, Vmn2r76, Vmn2r78, Wnt16, or any combination thereof.

Embodiment 145. The method of embodiment 144, wherein the method comprises increasing expression of Olfr816, Olfr812, Olfr1264, Olfr727, Olfr923, Olfr1090, Olfr328, Olfr1124, Olfr522, Olfr1082, Olfr1206, Olfr1167, Olfr706, Olfr6, Pou3f4, Olfr603, Olfr127, Olfr1263, Olfr1269, Olfr1205, Olfr390, Olfr601, Olfr860, Olfr215, Olfr741, Olfr1469, Olfr355, Olfr481, Olfr456, Olfr1042, Olfr728, Olfr372, Olfr801, Olfr1223, Olfr822, Otog1, Olfr943, Olfr1406, Olfr273, Olfr466, Olfr1043, Olfr427, Olfr890, Rbp4, or any combination thereof.

Embodiment 146. A method comprising resetting the transcriptional profile of old cells in vitro.

Embodiment 147. A method comprising resetting the transcriptional profile of old cells in vivo.

Embodiment 148. A method comprising inducing in a subject:
(i) OCT4 expression;
(ii) SOX2 expression; and/or
(iii) KLF4 expression;

in the absence of inducing c-MYC expression, wherein the subject has, is at risk for, or is suspected of having a condition that increases the DNA methylation-based age of a cell, of a tissue, and/or of an organ within the subject, as compared to a control cell, a control tissue, and/or of a control organ of a control subject that does not have the condition.

Embodiment 149. The method of embodiment 148, wherein the method reduces the DNA methylation-based age of the cell, the tissue, the organ, and/or the subject.

Embodiment 150. A method of transdifferentiation comprising inducing in one type of cell:
(i) OCT4 expression;
(ii) SOX2 expression;
(iii) KLF4 expression; and
(iv) expression of a lineage determining factor,
wherein (i)-(iii) are expressed from a single vector, thereby transdifferentiating the cell into another cell type.

Embodiment 151. A method of transdifferentiation comprising inducing in a cell:
(i) OCT4 expression;
(ii) SOX2 expression; and
(iii) KLF4 expression; and
reducing expression of a lineage determining factor, wherein (i)-(iii) are expressed from a single vector.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

SEQUENCE LISTING

```
Sequence total quantity: 123
SEQ ID NO: 1            moltype = DNA   length = 1056
FEATURE                 Location/Qualifiers
source                  1..1056
                        mol_type = genomic DNA
                        organism = Mus musculus
SEQUENCE: 1
atggctggac acctggcttc agacttcgcc ttctcacccc caccaggtgg gggtgatggg   60
tcagcagggc tggagccggg ctgggtggat cctcgaacct ggctaagctt ccaagggcct  120
ccaggtgggc ctggaatcgg accaggctca gaggtattgg ggatctcccc atgtccgccc  180
gcatacgagt tctgcggagg gatggcatac tgtggacctc aggttggact gggcctagtc  240
ccccaagttg gcgtggagac tttgcagcct gagggccagg caggagcacg agtggaaagc  300
aactcagagg gaacctcctc tgagcccgtg gccgaccgcc ccaatgccgt gaagttggag  360
aaggtggaac caactcccga ggagtcccag gacatgaaag ccctgcagaa ggagctagaa  420
cagtttgcca agctgctgaa gcagaagagg atcaccttgg ggtacaccca ggccgacgtg  480
gggctcaccc tgggcgttct ctttggaaag gtgttcagcc agaccaccat ctgtcgcttc  540
gaggccttgc agctcagcct taagaacatg tgtaagctgc ggcccctgct ggagaagtgg  600
gtggaggaag ccgacaacaa tgagaacctt caggagatat gcaaatcgga gaccctggtg  660
caggcccgga agagaaagcg aactagcatt gagaaccgtg tgaggtggag tctggagacc  720
atgtttctga agtgcccgaa gccctcccta cagcagatca ctcacatcgc caatcagctt  780
```

```
gggctagaga aggatgtggt tcgagtatgg ttctgtaacc ggcgccagaa gggcaaaaga 840
tcaagtattg agtattccca acgagaagag tatgaggcta cagggacacc tttcccaggg 900
ggggctgtat cctttcctct gcccccaggt cccactttg gcaccccagg ctatggaagc 960
ccccacttca ccacactcta ctcagtccct tttcctgagg gcgaggcctt tccctctgtt 1020
cccgtcactg ctctgggctc tcccatgcat tcaaac                          1056

SEQ ID NO: 2           moltype = AA  length = 352
FEATURE                Location/Qualifiers
source                 1..352
                       mol_type = protein
                       organism = Mus musculus
SEQUENCE: 2
MAGHLASDFA FSPPPGGGDG SAGLEPGWVD PRTWLSFQGP PGGPGIGPGS EVLGISPCPP   60
AYEFCGGMAY CGPQVGLGLV PQVGVETLQP EGQAGARVES NSEGTSSEPC ADRPNAVKLE  120
KVEPTPEESQ DMKALQKELE QFAKLLKQKR ITLGYTQADV GLTLGVLFGK VFSQTTICRF  180
EALQLSLKNM CKLRPLLEKW VEEADNNENL QEICKSETLV QARKRKRTSI ENRVRWSLET  240
MFLKCPKPSL QQITHIANQL GLEKDVVRVW FCNRRQKGKR SSIEYSQREE YEATGTPFPG  300
GAVSFPLPPG PHFGTPGYGS PHFTTLYSVP FPEGEAFPSV PVTALGSPMH SN          352

SEQ ID NO: 3           moltype = DNA  length = 957
FEATURE                Location/Qualifiers
source                 1..957
                       mol_type = genomic DNA
                       organism = Mus musculus
SEQUENCE: 3
atgtataaca tgatggagac ggagctgaag ccgccgggcc cgcagcaagc ttcgggggc    60
ggcggcggag gaggcaacgc cacggcggcc gcgaccggcg gcaaccagaa gaacagcccg  120
gaccgcgtca gaggcccat gaacgccttc atggtatggt cccgggggca gcggcgtaag  180
atggcccagg agaaccccaa gatgcacaac tcggagatca gcaagcgcct gggcgcggag  240
tggaaacttt tgtccgagac cgagaagcgg ccgttcatcg acgaggccaa gcggctgcgc  300
gctctgcaca tgaaggagca cccggattat aaataccgc gcggcgaa aaccaagacg    360
ctcatgaaga aggataagta cacgcttccc ggaggcttgc tggccccgg cgggaacagc  420
atggcgagcg gggttggggt gggcgccggc ctggtgcgg cgtgaacca gcgcatggac   480
agctacgcgc acatgaacgg ctggagcaac ggcagctaca gcatgatgca ggacagctg   540
ggctacccgc agcaccgg cctcaacgct cacggcgcgg cacagatgca accgatgcac   600
cgctacgacg tcagcgccct gcagtacaac tccatgacca gctcgcagac ctacatgaac  660
ggctcgccca cctacagcat gtcctactcg cagcagggca ccccggtat ggcgctgggc  720
tccatgggct ctgtggtcaa gtccgaggcc agctccagcc ccccgtggt tacctcttcc  780
tcccactcca gggcgccctg ccaggccggg gacctccgga acatgatcag catgtacctc  840
cccggcgccg aggtgccgga gcccgctgcg cccagtagac tgcacatggc ccagcactac  900
cagagcggcc cggtgcccgg cacggccatt aacggcacac tgcccctgtc gcacatg     957

SEQ ID NO: 4           moltype = AA  length = 319
FEATURE                Location/Qualifiers
source                 1..319
                       mol_type = protein
                       organism = Mus musculus
SEQUENCE: 4
MYNMMETELK PPGPQQASGG GGGGGNATAA ATGGNQKNSP DRVKRPMNAF MVWSRGQRRK   60
MAQENPKMHN SEISKRLGAE WKLLSETEKR PFIDEAKRLR ALHMKEHPDY KYRPRRKTKT  120
LMKKDKYTLP GGLLAPGGNS MASGVGVGAG LGAGVNQRMD SYAHMNGWSN GSYSMMQEQL  180
GYPQHPGLNA HGAAQMQPMH RYDVSALQYN SMTSSQTYMN GSPTYSMSYS QQGTPGMALG  240
SMGSVVKSEA SSSPPVVTSS SHSRAPCQAG DLRDMISMYL PGAEVPEPAA PSRLHMAQHY  300
QSGPVPGTAI NGTLPLSHM                                              319

SEQ ID NO: 5           moltype = DNA  length = 1446
FEATURE                Location/Qualifiers
source                 1..1446
                       mol_type = genomic DNA
                       organism = Mus musculus
SEQUENCE: 5
atgaggcagc cacctggcga gtctgacatg gctgtcagcg acgctctgct cccgtccttc   60
tccacgttcg cgtccggccc ggcgggaagg gagaagacac tgcgtccagc aggtgccccg  120
actaaccgtt ggcgtgagga actctctcac gtgaagcgat ttcccccact tcccggccgc  180
ccctacgacc tggcggcgac ggtgccaca gacctggaga gtgcggagc tggtgcagct   240
tgcagcagta acaaccccgg cctcctagcc cggaggggaga ccgaggagtt caacgacctc  300
ctggaccctag acttatcct ttccaactcg ctaacccacc aggaatcggt ggccgccacc   360
gtgaccacct cggcgtcagc ttcatcctcg tcttcccag cgagcagcgg ccctgccagc   420
gcgccctcca cctgcagctt cagctatccg atccggggcg ggggtgacca gggcgtgagt  480
gccagcaaca caggtggagg gctcctctac agccgagaat ctgcgccacc tccacggcc   540
ccttcaacc tggcggacat caatgacgtg agccctcgg gcgcttcgt ggctgagctc    600
ctgcggccg agttggaccc agtatacatt ccgccacagc agcctcagcc gccaggtggc  660
gggctgatgg gcaagtttgt gctgaaggcg tctctgacca cccctggcag cgagtacagc  720
agccttcgg tcatcagtgt tagcaaagga agccagagcc cgcaccccca gctgtagtg    780
gcgcccacca gcgtggccc gccgcgcatg tgcccaaga ttaagcaaga ggcggtcccg    840
tcctgcacgt tcagccggtc cctagaggcc cattgagcg ctggacccca gctcagcaac   900
ggccaccggc caacacaca cgacttcccc ctggggcggc agctcccac caggactacc    960
cctacactga gtcccgagga actgctgaac agcagggact gtcaccctgg cctgcctctt 1020
cccccaggat tccatcccca tccggggccc aactaccctc ctttcctgcc agaccagatg 1080
```

```
cagtcacaag tcccctctct ccattatcaa gagctcatgc caccgggttc ctgcctgcca   1140
gaggagccca agccaaagag gggaagaagg tcgtggcccc ggaaaagaac agccacccac   1200
acttgtgact atgcaggctg tggcaaaacc tataccaaga gttctcatct caaggcacac   1260
ctgcgaactc acacaggcga gaaaccttac cactgtgact gggacggctg tgggtggaaa   1320
ttcgcccgct ccgatgaact gaccaggcac taccgcaaac acacagggca ccggcccttt   1380
cagtgccaga agtgcgacag ggccttttcc aggtcggacc accttgcctt acacatgaag   1440
aggcac                                                              1446

SEQ ID NO: 6             moltype = AA  length = 482
FEATURE                  Location/Qualifiers
source                   1..482
                         mol_type = protein
                         organism = Mus musculus
SEQUENCE: 6
MRQPPGESDM AVSDALLPSF STFASGPAGR EKTLRPAGAP TNRWREELSH MKRLPPLPGR    60
PYDLAATVAT DLESGGAGAA CSSNNPALLA RRETEEFNDL LDLDFILSNS LTHQESVAAT   120
VTTSASASSS SSPASSGPAS APSTCSFSYP IRAGGDPGVA ASNTGGGLLY SRESAPPPTA   180
PFNLADINDV SPSGGFVAEL LRPELDPVYI PPQQPQPPGG GLMGKFVLKA SLTTPGSEYS   240
SPSVISVSKG SPDGSHPVVV APYSGGPPRM CPKIKQEAVP SCTVSRSLEA HLSAGPQLSN   300
GHRPNTHDFP LGRQLPTRTT PTLSPEELLN SRDCHPGLPL PPGFHPHPGP NYPPFLPDQM   360
QSQVPSLHYQ ELMPPGSCLP EEPKPKRGRR SWPRKRTATH TCDYAGCGKT YTKSSHLKAH   420
LRTHTGEKPY HCDWDGCGWK FARSDELTRH YRKHTGHRPF QCQKCDRAFS RSDHLALHMK   480
RH                                                                 482

SEQ ID NO: 7             moltype = DNA  length = 376
FEATURE                  Location/Qualifiers
misc_feature             1..376
                         note = Synthetic Polynucleotide
source                   1..376
                         mol_type = other DNA
                         organism = synthetic construct
SEQUENCE: 7
tttactccct atcagtgata gagaacgtat gaagagttta ctccctatca gtgatagaga    60
acgtatgcag actttactcc ctatcagtga tagagaacgt ataaggagtt tactccctat   120
cagtgataga gaacgtatcg ccagtttact ccctatcatg gatagagaac gtatctacag   180
tttactccct atcagtgata gagaacgtat atccagttta ctccctatca gtgatagaga   240
acgtataagc tttaggcgtg tacggtgggc gcctataaaa gcagagctcg tttagtgaac   300
cgtcagatcg cctggagcaa ttccacaaca cttttgtctt ataccaactt ccgtaccac    360
ttcctaccct cgtaaa                                                   376

SEQ ID NO: 8             moltype = DNA  length = 169
FEATURE                  Location/Qualifiers
misc_feature             1..169
                         note = Synthetic Polynucleotide
source                   1..169
                         mol_type = other DNA
                         organism = synthetic construct
SEQUENCE: 8
tgcgcgcagc ggccgaccat ggcccaactt gtttattgca gcttataatg gttacaaata    60
aagcaatagc atcacaaatt tcacaaataa agcattttt tcactgcatt ctagttgtgg    120
tttgtccaaa ctcatcaatg tatcttatca tgtctggatc tcggtaccg               169

SEQ ID NO: 9             moltype = AA  length = 21
FEATURE                  Location/Qualifiers
REGION                   1..21
                         note = Synthetic Polypeptide
source                   1..21
                         mol_type = protein
                         organism = synthetic construct
SEQUENCE: 9
GSGEGRGSLL TCGDVEENPG P                                              21

SEQ ID NO: 10            moltype = DNA  length = 708
FEATURE                  Location/Qualifiers
misc_feature             1..708
                         note = Synthetic Polynucleotide
source                   1..708
                         mol_type = other DNA
                         organism = synthetic construct
SEQUENCE: 10
atgtctaggc tggacaagag caaagtcata aacggagctc tggaattact caatggtgtc    60
ggtatcgaag gcctgacgac aaggaaactc gctcaaaagc tgggagttga gcagcctacc   120
ctgtactggc acgtgaagaa caagcgggcc ctgctcgatg cctgccaat cgagatgctg   180
gacaggcatc ataccacttt ctgccccctg gaaggcgagt catgcaagga cttctctgcg   240
aacaacgcca agtcataccg ctgtgctctc ctctcacatc gcgacgggc taaagtgcat   300
ctcggcaccc gccaacaga gaaacagtac gaaaccctgg aaaatcagct cgcgttcctg   360
tgtcagcaag gcttctccct ggagaacgca ctgtacgctc tgtccgccgt gggccacttt   420
acactgggct cgcgattgga ggaacaggag catcaagtag caaaagagga aagagagaca   480
cctaccaccg attctatgcc cccacttctg agacaagcaa ttgagctgtt cgaccggcag   540
```

```
ggagccgaac ctgccttcct tttcggcctg gaactaatca tatgtggcct ggagaaacag    600
ctaaagtgcg aaagcggcgg gccgaccgac gcccttgacg attttgactt agacatgctc    660
ccagccgatg cccttgacga ttttgacctt gacatgctcc ccgggtaa                 708

SEQ ID NO: 11              moltype = AA   length = 235
FEATURE                    Location/Qualifiers
REGION                     1..235
                           note = Synthetic Polypeptide
source                     1..235
                           mol_type = protein
                           organism = synthetic construct
SEQUENCE: 11
MSRLDKSKVI NGALELLNGV GIEGLTTRKL AQKLGVEQPT LYWHVKNKRA LLDALPIEML     60
DRHHTHFCPL EGESWQDFLR NNAKSYRCAL LSHRDGAKVH LGTRPTEKQY ETLENQLAFL    120
CQQGFSLENA LYALSAVGHF TLGCVLEEQE HQVAKEERET PTTDSMPPLL RQAIELFDRQ    180
GAEPAFLFGL ELIICGLEKQ LKCESGGPTD ALDDFDLDML PADALDDFDL DMLPG          235

SEQ ID NO: 12              moltype = DNA   length = 747
FEATURE                    Location/Qualifiers
misc_feature               1..747
                           note = Synthetic Polynucleotide
source                     1..747
                           mol_type = other DNA
                           organism = synthetic construct
SEQUENCE: 12
atgtcccgct tggataagag caaggtaata aatagcgcac tcgaactcct caacggcgtg     60
ggcatcgaag gtctgactac tcgaaagctc gcccagaaat tgggtgtgga gcaacctaca    120
ttgtattggc atgtcaagaa caaaagagcc ctgctggacg ctcttcctat gaaaatgctt    180
gacaggcatc acactcattc ctgcccccttt gaggtcgaga gttggcaaga tttttctcga    240
aacaatgcaa agtcctaccg ctgcgcactt tgtcccata gggatggagc aaaagtgcac    300
ctgggaacca ggccaacaga gaaacaatac gagactctcg agaaccagtt ggctttcttg    360
tgccaacagg ggttctcact tgaaaatgcc ctttacgcac tgtcagccgt ggacatttt    420
accctggggt gcgttcttga ggagcaagaa catcaggttg ctaaggagga gcgcgagact    480
ccaaccactg attctatgcc accttttgctg aaacaggcca ttgaacttt cgatagacag    540
ggtgctgaac ctgcctttct cttcgggttg gagctgatta tttgtggtct cgaaaaacag    600
ctgaaatgtg aaagtggtgg ccctactgac gccctcgatg atttcgacct ggatatgctg    660
ccagccgatg cacttgatga tttcgatttg gatatgcttc cagccgacgc actggacgac    720
ttcgatttgg acatgcttcc cggttaa                                         747

SEQ ID NO: 13              moltype = AA   length = 248
FEATURE                    Location/Qualifiers
REGION                     1..248
                           note = Synthetic Polypeptide
source                     1..248
                           mol_type = protein
                           organism = synthetic construct
SEQUENCE: 13
MSRLDKSKVI NSALELLNGV GIEGLTTRKL AQKLGVEQPT LYWHVKNKRA LLDALPIEML     60
DRHHTHSCPL EVESWQDFLR NNAKSYRCAL LSHRDGAKVH LGTRPTEKQY ETLENQLAFL    120
CQQGFSLENA LYALSAVGHF TLGCVLEEQE HQVAKEERET PTTDSMPPLL KQAIELFDRQ    180
GAEPAFLFGL ELIICGLEKQ LKCESGGPTD ALDDFDLDML PADALDDFDL DMLPADALDD    240
FDLDMLPG                                                              248

SEQ ID NO: 14              moltype = DNA   length = 1050
FEATURE                    Location/Qualifiers
misc_feature               1..1050
                           note = Synthetic Polynucleotide
source                     1..1050
                           mol_type = other DNA
                           organism = synthetic construct
SEQUENCE: 14
atgcctttgt atcatgctat tgcttcccgt atgctttca ttttctcctc cttgtataaa     60
tcctggttgc tgtctcttta tgaggagttg tggcccgttg tcaggcaacg tggcgtggtg    120
tgcactgtgt ttgctgacgc aacccccact ggttggggca ttgccaccac ctgtcagctc    180
ctttccggga ctttcgcttt ccccctcct attgccacgg cggaactcat cgccgcctgc    240
cttgcccgct gctggacagg ggctcggctt tgggcactg acaattccgt ggtgttgtcg    300
gggaaatcat cgtcctttcc ttggctgctc gcctgtgttg ccacctggat tctgcgcggg    360
acgtccttct gctacgtccc ttcggccctc aatccagcgg accttcctc ccgcggcctg    420
ctgccgctc tgcggcctct tccggctctt cgccttccgc ctcagacgag tcggatctca    480
cttttgggccg cctccccgca tcgataccgt cgacctcgag acctagaaaa acatgggagca    540
atcacaagta gcaatacagc agctaccaat gctgattgtg cctggctaga agcacaagag    600
gaggaggagg tgggttttcc agtcacacct caggtacctt taagaccaat gacttacaag    660
gcagctgtag atcttagcca cttttttaaa gaaaagggg gactggaagg gctaattcac    720
tcccaacgaa gacaagatat ccttgatctg tggatctacc acacacaagg ctacttccct    780
gattggcaga actacacacc agggccaggg atcagatatc cactgacctt tggatggtgc    840
tacaagctag taccagttga gcaagagaag gtagaagaag ccaatgaagg agagaacacc    900
cgcttgttac accctgtgag cctgcatggg atggatgacc cggagagaga agtattagag    960
tggaggtttg acagccgcct agcatttcat cacatggccc gagagctgca tccggactgt   1020
actgggtctc tctggttaga ccagatctga                                     1050
```

-continued

```
SEQ ID NO: 15           moltype = AA  length = 349
FEATURE                 Location/Qualifiers
REGION                  1..349
                        note = Synthetic Polypeptide
source                  1..349
                        mol_type = protein
                        organism = synthetic construct
SEQUENCE: 15
MPLYHAIASR MAFIFSSLYK SWLLSLYEEL WPVVRQRGVV CTVFADATPT GWGIATTCQL  60
LSGTFAFPLP IATAELIAAC LARCWTGARL LGTDNSVVLS GKSSSFPWLL ACVATWILRG 120
TSFCYVPSAL NPADLPSRGL LPALRPLPRL RLRPQTSRIS LWAASPHRYR RPRDLEKHGA 180
ITSSNTAATN ADCAWLEAQE EEEVGFPVTP QVPLRPMTYK AAVDLSHFLK EKGGLEGLIH 240
SQRRQDILDL WIYHTQGYFP DWQNYTPGPG IRYPLTFGWC YKLVPVEQEK VEEANEGENT 300
RLLHPVSLHG MDDPEREVLE WRFDSRLAFH HMARELHPDC TGSLWLDQI           349

SEQ ID NO: 16           moltype = DNA  length = 7408
FEATURE                 Location/Qualifiers
misc_feature            1..7408
                        note = Synthetic Polynucleotide
source                  1..7408
                        mol_type = other DNA
                        organism = synthetic construct
SEQUENCE: 16
ttatgcagtg ctgccataac catgagtgat aacactgcgg ccaacttact tctgacaacg   60
atcggaggac cgaaggagct aaccgctttt ttgcacaaca tggggatca tgtaactcgc  120
cttgatcgtt gggaaccgga gctgaatgaa gccataccaa acgacgagcg tgacaccacg  180
atgcctgtag taatggtaac aacgttgcgc aaactattaa ctggcgaact acttactcta  240
gcttccggc aacaattaat agactggatg gaggcggata agttgcagg accacttctg  300
cgctcggcc ttccggctgg ctggtttatt gctgataaat ctggagccgg tgagcgtgag  360
tctcgcggta tcattgcagc actggggcca gatggtaagc cctcccgtat cgtagttatc  420
tacacgacgg ggagtcaggc aactatggat gaacgaaata gacagatcgc tgagataggt  480
gcctcactga ttaagcattg gtaactgtca gaccaagttt actcatatat actttagatt  540
gatttaaaac ttcatttta atttaaaagg atctaggtga agatcctttt tgataatctc  600
atgaccaaaa tcccttaacg tgagttttcg ttccactgag cgtcagaccc cgtagaaaag  660
atcaaaggat cttcttgaga tcctttttt ctgcgcgtaa tctgctgctt gcaaacaaaa  720
aaaccaccgc taccagcggt ggtttgtttg ccggatcaag agctaccaac tctttttccg  780
aaggtaactg gcttcagcag agcgcagata ccaaatactg tccttctagt gtagccgtag  840
ttaggccacc acttcaagaa ctctgtagca ccgcctacat acctcgctct gctaatcctg  900
ttaccagtgg ctgctgccag tggcgataag tcgtgtctta ccgggttgga ctcaagacga  960
tagttaccgg ataaggcgca gcggtcgggc tgaacggggg gttcgtgcac acagcccagc 1020
ttggagcgaa cgacctacac cgaactgaga tacctacagc gtgagctatg agaaagcgcc 1080
acgcttcccg aagggagaaa ggcggacagg tatccggtaa gcggcagggt cggaacagga 1140
gagcgcacga gggagcttcc agggggaaac gcctggtatc tttatagtcc tgtcgggttt 1200
cgccacctct gacttgagcg tcgatttttt tgatgctcgt caggggggcg gagcctatgg 1260
aaaaacgcca gcaacgcggc cttttacgg ttcctggcct tttgctggcc ttttgctcac 1320
atgttctttc ctgcgttatc ccctgattct gtggataacc gtattaccgc ctttgagtga 1380
gctgataccg ctcgccgcag ccgaacgacc gagcgcagcg agtcagtgag cgaggaagcg 1440
gaagagcgcc caatacgcaa accgcctctc ccgcgcgtt ggccgattca ttaatgcagc 1500
tggcacgaca ggtttcccga ctggaaagcg ggcagtgagc gcaacgcaat taatgtgagt 1560
tagctcactc attaggcacc ccaggcttta cactttatgc ttccggctcg tatgttgtgt 1620
ggaattgtga gcggataaca atttcacaca ggaaacagct atgaccatga ttacgccaga 1680
tttaattaag gccttaatta ggctgcgcgc tcgctcgctc actgaggccg cccgggcaaa 1740
gcccgggcgt cgggcgacct ttggtcgccc ggcctcagtg agcgagcgag cgcgcagaga 1800
gggagtggcc aactccatca ctaggggttc cttgtagtta atgattaacc cgccatgcta 1860
cttatctacg tagccatgct ctaggaagat cggaattctt tactccctat cagtgataga 1920
gaacgtatga agagtttact ccctatcagt gatagagaac gtatgcagac ttactccct 1980
atcagtgata gagaacgtat aaggagttta ctccctatca gtgatagaga acgtatgacc 2040
agtttactcc ctatcagtga tagagaacgt atctacagtt tactcccat cagtgataga 2100
gaacgtatat ccagtttact ccctatcagt gatagagaac gtataagctt taggcgtgta 2160
cggtgggcgc ctataaaagc agagctcgtt tagtgaaccg tcagatcgcc tggagcaatt 2220
ccacaacact tttgtcttat accaacttc cgtaccactt cctaccctcg taaagcggcc 2280
gcgccaccat ggctggacac ctggcttcag acttcgcctt ctcaccccca ccaggtgggg 2340
gtgatgggtc agcagggctg gagcgggct gggtggatcc tcgaacctgg ctaagcttcc 2400
aagggcctcc aagtgggcct ggaatcggac caggctcaga ggtattgggg atctccccat 2460
gtccgcccgc atacgagttc tgcggaggga tggcatactg tggacctcag gttgactggg 2520
gcctagtccc ccaagttggc gtggagactt tgcagcctga ggccaggca ggagcacgag 2580
tggaaagcaa ctcagaggga acctcctctg agccctgtgc cgaccgcccc aatgccgtga 2640
agttggagaa ggtggaacca actcccgagg agtcccagga catgaagcc ctgcagaagg 2700
agctagaaca gtttgccaag ctgctgaagc agaagaggat caccttgggg tacacccagg 2760
ccgacgtggg gctcacccct ggcgttctct ttgaaaggt gttcagccag accaccatct 2820
gtcgcttcga ggccttgcag ctcagcctta gaacatgtg taagctgcgg cccctgctgg 2880
agaagtgggt ggaggaagcc gacaacaatg gaaccttca ggagatatgc aaatcggaga 2940
cctggttgca gccccggaag agaaagcgaa ctagcattga ggatgtg aggtggagtc 3000
tggagaccat gtttctgaag tgcccgaagc cctccctaca gcagatcact cacatcgcca 3060
atcagcttgg gctagagaag gatgtggttc gagtatggtt ctgtaaccgg cgccagaagg 3120
gcaaaagatc aagtattgag tattcccaac gagaagagta tgaggctaca gggacacctt 3180
tcccaggggg ggctgtatcc tttcctctgc ccccaggtcc ccactttggc accccaggct 3240
atggaagccc ccacttcacc acactctact cagtcccttt cctgagggc gaggcctttc 3300
```

```
cctctgttcc cgtcactgct ctgggctctc ccatgcattc aaacgctagc ggcagcggcg   3360
ccacgaactt ctctctgtta aagcaagcag gagatgttga agaaaacccc gggcctgcat   3420
gcatgtataa catgatggag acggagctga agccgccggg cccgcagcaa gcttcggggg   3480
gcggcggcgg aggaggcaac gccacggcgg cggcgaccgg cggcaaccag aagaacagcc   3540
cggaccgcgt caagaggccc atgaacgcct tcatggtatg gtcccggggg cagcggcgta   3600
agatggccca ggagaacccc aagatgcaca actcggagat cagcaagcgc ctgggcgcgg   3660
agtggaaact tttgtccgag accgagaagc ggccgttcat cgacgaggcc aagcggctgc   3720
gcgctctgca catgaaggag cacccggatt ataaataccg gccgcggcgg aaaaccaaga   3780
cgctcatgaa gaaggataag tacacgcttc ccggaggctt gctggccccc ggcgggaaca   3840
gcatggcgag cggggttggg gtgggcgccg gcctggtgc gggcgtgaac cagcgcatgg   3900
acagctacgc gcacatgaac ggctggagca acggcagcta cagcatgatg caggagcagc   3960
tgggctaccc gcagcacccg ggcctcaacg ctcacgcgcg ggcacagatg caaccgatgc   4020
accgctacga cgtcagcgcc ctgcagtaca actccatgac cagctcgcag acctacatga   4080
acggctcgcc cacctacagc atgtcctact cgcagcaggg caccccccgt atggcgtgg   4140
gctccatggg ctctgtggtc aagtccgagg ccagctccag cccccccgtg ttacctctt   4200
cctcccactc cagggcgccc tgccaggccg ggacctccg gacatgatc agcatgtacc   4260
tccccggcgc cgaggtgccg gagcccgctg cgcccagtag actgcacatg gcccagcact   4320
accagagcgg cccggtgccc ggcacggcca ttaacggcac actgccctg tcgcacatgg   4380
catgcggctc cggcgagggc agggggaagtc ttctaacatg cggggacgtg gaggaaaatc   4440
ccggcccact cgagatgagg cagccacctg gcgagtctga catggctgtc agcgacgctc   4500
tgctcccgtc cttctccacg ttcgcgtccg gcccggcggg aagggagaag acactgcgtc   4560
cagcaggtgc cccgactaac cgttggcgtg aggaactctc tcacatgaag cgacttcccc   4620
cacttcccgg ccgccctac gacctggcgg cgacgtggc cacagacctg gagagtggcg   4680
gagctggtgc agcttgcagc agtaacaacc cggccctcct agcccggagg gagaccgagg   4740
agttcaacga cctcctggac ctagactta tcctttccaa ctcgctaacc caccaggaat   4800
cggtgggctga ccacgtgacc acctcggcgt cagcttcatc ctcgtcttcc ccagcgagca   4860
gcggccctgc cagcgcgccc tccacctgca gcttcagcta tccgatccgg gccggggtg   4920
acccgggcgt ggctgccagc aacacaggtg gagggctcct ctacagccga gaatctgcgc   4980
cacctcccac ggcccccttc aacctggcgg acatcaatga cgtgagccc tcgggcggct   5040
tcgtcgctga gctcctgcgg ccggagttgg acccagtata cattcgcca cagcagcctc   5100
agccggccagg tggcgggctg atgggcaagt ttgtgctgaa ggcgtctctg accacccctg   5160
gcagcgagta cagcagccct tcggtcatca gtgttagcaa aggaagccca gacggcagcc   5220
accccgtggt agtggcgccc tacagcgcgg gccccgcgcg catgtgcccc aagattaagc   5280
aagaggcggt cccgtcctgc acggtcagcc ggtccctaga ggcccatttg agcgctggac   5340
cccagctcag caacggcac cggcccaaca cacacgactt cccctgggg cggcagctcc   5400
ccaccaggac tacccctaca ctgagtcccg aggaactgct gaacagcagg gactgtcacc   5460
ctggcctgcc tcttccccca ggattccatc cccatccggg gcccaactac cctccttcc   5520
tgccagacca gatgcagtca caagtcccct ctctccatta tcaagagctc atgccaccgg   5580
gttcctgcct gccagaggag cccaagccaa agaggggaag aagtcgtgg ccccggaaaa   5640
gaacagccac ccacacttgt gactatgcag gctgtggcaa aacctatacc aagagttctc   5700
atctcaaggc acacctgcga actcacacag gcgagaaacc ttaccactgt gactgggacg   5760
gctgtgggtg gaaattcgcc cgctccgatg aactgaccag gcactaccgc aaacacacag   5820
ggcaccgggc ctttcagtgc cagaagtgcg acagggcctt ttccaggtcg gaccaccttg   5880
ccttacacat gaagaggcac taaatgacta gtgcgcgcga cggccgacca tggcccaact   5940
tgtttattgc agcttataat ggttacaaat aaagcaatag catcacaaat ttcacaaata   6000
aagcattttt tcactgcat tctagttgtg gtttgtccaa actcatcaat gtatcttatc   6060
atgtctggat ctcggtaccg gatccaaatt cccgataagg atcttcctag agcatggcta   6120
cgtagataag tagcatggcg ggttaatcat taactacaag gaaccccctag tgatggagtt   6180
ggccactccc tctctgcgcg ctcgctcgct cactgaggcc gggcgaccaa aggtcgcccg   6240
acgcccgggc tttgcccggg cggcctcagt gagcgagcga gcgcgcagcc ttaattaacc   6300
taattcactg gccgtcgttt tacaacgtcg tgactggaa aaccctggcg ttacccaact   6360
taatcgcctt gcagcacatc cccctttcgc cagctggcgt aatagcgaag aggcccgcac   6420
cgatcgccct tcccaacagt tgcgcagcct gaatggcgaa tgggacgcgc cctgtagcgg   6480
cgcattaagc gcggcgggtg tggtggttac gcgcagcgtg accgctacac ttgccagcgc   6540
cctacgccgc gctcctttcg ctttcttccc ttcctttctc gccacgttcg ccggctttcc   6600
ccgtcaagct ctaaatcggg ggctcccttt agggttccga tttagtgctt tacggcacct   6660
cgaccccaaa aaacttgatt agggtgatgg ttcacgtagt gggccatcgc cctgatagac   6720
ggtttttcgc cctttgacgt tggagtccac gttctttaat agtggactct tgttccaaac   6780
tggaacaaca ctcaaccta tctcggtcta ttcttttgat ttataaggga ttttgccgat   6840
ttcggcctat tggttaaaaa atgagctgat ttaacaaaaa tttaacgcga attttaacaa   6900
aatattaacg tttataattt caggtggcat ctttcgggga aatgtgcgcg gaaccccctat   6960
ttgtttattt ttctaaatac attcaaatat gtatccgctc atgagacaat aaccctgata   7020
aatgcttcaa taatattgaa aaaggaagag tatgagtatt caacatttcc gtgtcgccct   7080
tattcccttt tttgcggcat tttgccttcc tgttttttgct caccagaaa cgctggtgaa   7140
agtaaaagat gctgaagatc agttgggtgc acgagtgggt tacatcgaac tggatctcaa   7200
tagtggtaag atccttgaga gttttcgccc cgaagaacgt tttccaatga tgagcacttt   7260
taaagttctg ctatgtggcg cggtattatc ccgtattgac gccgggcaag agcaactcgg   7320
tcgccgcata cactattctc agaatgactt ggttgagtac tcaccagtca cagaaaagca   7380
tcttacggat ggcatgacag taagagaa                                      7408
```

SEQ ID NO: 17  moltype = DNA length = 5657
FEATURE  Location/Qualifiers
misc_feature  1..5657
  note = Synthetic Polynucleotide
source  1..5657
  mol_type = other DNA
  organism = synthetic construct
SEQUENCE: 17
ttatgcagtg ctgccataac catgagtgat aacactgcgg ccaacttact tctgacaacg   60

```
atcggaggac cgaaggagct aaccgctttt ttgcacaaca tgggggatca tgtaactcgc   120
cttgatcgtt gggaaccgga gctgaatgaa gccataccaa acgacgagcg tgacaccacg   180
atgcctgtag taatggtaac aacgttgcgc aaactattaa ctggcgaact acttactcta   240
gcttcccggc aacaattaat agactggatg gaggcggata agttgcagg accacttctg    300
cgctcggccc ttccggctgg ctggtttatt gctgataaat ctggagccgg tgagcgtggg   360
tctcgcggta tcattgcagc actggggcca gatggtaagc cctcccgtat cgtagttatc   420
tacacgacgg ggagtcaggc aactatggat gaacgaaata gacagatcgc tgagataggt   480
gcctcactga ttaagcattg gtaactgtca gaccaagttt actcatatat actttagatt   540
gatttaaaac ttcatttta atttaaaagg atctaggtga agatcctttt tgataatctc    600
atgaccaaaa tcccttaacg tgagttttcg ttccactgag cgtcagaccc cgtagaaaag   660
atcaaaggat cttcttgaga tcctttttt ctgcgcgtaa tctgctgctt gcaaacaaaa    720
aaaccaccgc taccagcggt ggtttgtttg ccggatcaag agctaccaac tcttttccg    780
aaggtaactg gcttcagcag agcgcagata ccaaatactg tccttctagt gtagccgtag   840
ttaggccacc acttcaagaa ctctgtagca ccgcctacat acctcgctct gctaatcctg   900
ttaccagtgg ctgctgccag tggcgataag tcgtgtctta ccgggttgga ctcaagacga   960
tagttaccgg ataaggcgca gcggtcgggc tgaacggggg gttcgtgcac acagcccagc  1020
ttggagcgaa cgacctacac cgaactgaga tacctcacagc gtgagctatg agaaagcgcc 1080
acgcttcccg aagggagaaa ggcggacagg tatccggtaa gcggcagggt cggaacagga  1140
gagcgcacga gggagcttcc aggggggaaac gcctggtatc tttatagtcc tgtcgggttt  1200
cgccacctct gacttgagcg tcgatttttt tgatgctcgt caggggggcg gagcctatgg   1260
aaaaacgcca gcaacgcggc cttttttacgg ttcctggcct tttgctggcc ttttgctcac  1320
atgttctttc ctgcgttatc ccctgattct gtggataacc gtattaccgc ctttgagtga  1380
gctgataccg ctcgccgcag ccgaacgacc gagcgcagcg agtcagtgag cgaggaagcg  1440
gaagagcgcc caatacgcaa accgcctctc ccgcgcgtt ggccgattca ttaatgcagc    1500
tggcacgaca ggtttcccga ctggaaagcg ggcagtgagc gcaacgcaat taatgtgagt  1560
tagctcactc attaggcacc ccaggctta cactttatgc ttccggctcg tatgttgtgt    1620
ggaattgtga gcggataaca atttcacaca ggaaacagct atgaccatga ttacgccaga  1680
tttaattaag gccttaatta ggctgcgcgc tcgctcgctc actgaggccg cccgggcaaa  1740
gcccgggcgt cgggcgacct ttggtcgccc ggcctcagtg agcgagcgag cgcgcagaga  1800
gggagtggcc aactccatca ctagggttc ctttgtagtta atgattaacc cgccatgcta   1860
cttatctacg tagccatgct ctaggaagat cggaattcct gatctggcct ccgcgccggg  1920
ttttggcgcc tcccgcgggc gccccctcc tcacggcgag cgctgccacg tcagacgaag    1980
ggcgcagcga gcgtcctgat ccttccgccc ggacgctcag gacagcggcc cgctgctcat  2040
aagactcggc cttagaaccc cagtatcagc agaaggacag tttaggacgg gacttgggtg  2100
actctagggc actggttttc tttccagaga gcggaacagg cgaggaaaag tagtcccttc  2160
tcggcgattc tgcggaggga tctccgtggg gcggtgaacg ccgatgatta tataaggacg  2220
cgccgggtgt ggcacagcta gttccgtcgc agccgggatt tgggtcgcgg ttcttgtttg  2280
tggatcgctg tgatcgtcac ttggtgagta gcgggctgct gggctggccg gggctttcgt  2340
ggccgcgggg ccgctcggtg ggacggaagc gtgtggagga accgccaagg gctgtagtct  2400
gggtccgcga gcaaggttgc cctgaactgg gggttggggg gagcgcagca aaatggcggc  2460
tgttcccgag tcttgaatgg aagacgcttg tgaggcgggc tgtgaggtcg ttgaaacaag  2520
gtgggggca tggtgggcgg caagaaccca aggtcttgag gccttcgcta atgcgggaaa    2580
gctcttattc gggtgagatg ggctgggggca ccatctgacgt gaagtttgtc             2640
actgactgga gaactcggtt tgtcgtctgt tgcgggggcg gcagttatgc ggtgccgttg   2700
ggcagtgcac ccgtaccttt gggagcgcgc gcctcgtcgt gtcgtgacgt cacccgttct   2760
gttggcttat aatgcaggt ggggccacct gccggtaggt gtgcgtagg ctttctccg     2820
tcgcaggacg cagggttcgg gcctaggtca ggctctcctg aatcgacagg cgccggacct  2880
ctggtgaggg gagggataag tgaggcgtca gtttctttgg tcggttttat gtacctatct  2940
tcttaagtag ctgaagctcc ggttttgaac tatgcgctcg gggttggcga gtgtgttttg  3000
tgaagttttt taggcacctt ttgaaatgta atcatttggg tcaatatgta attttcagtg  3060
ttagactagt aaattgtccg ctaaattctg gccgtttttg gctttttgt tagacgaag    3120
ggccgcatta aacgccacca tgtcccgctt ggataagagc aaggtaataa atagcgcact  3180
cgaactcctc aacggcgtgg gcatcgaagg tctgactact cgaaagctcg cccagaaatt  3240
gggtgtggag caacctacat tgtattgcaa tgtcaagaac aaaagagccc tgctggacgc  3300
tcttcctatt gaaatgcttg acaggcatca cactcattcc tgcccccttg aggtcgagg   3360
ttggcaagat ttctccgaa acaatgcaaa gtcctaccgc tgccgcactt tgtccccatag  3420
ggatggagca aaagtgcacc tgggaaccag gccaacagag aaacaatacg agactctcga  3480
gaaccagttg gcttttcttgt gccaacaggg gttctcactt gaaaatgccc tttacgcact  3540
gtcagccgtt ggacattta ccctggggtg cgttcttgag gagcaagaac atcaggttgc   3600
taaggaggag cgcgagactc caaccactga ttctatgcca cctttgctga aacaggccat  3660
tgaacttttc gatagacagg gtgctgaacc tgccttctc ttcgggttgg agctgattat    3720
ttgtggtctc gaaaaacagc tgaaatgtga aagtggtggc cctactgacg ccctcgatga  3780
tttcgacctg gatatgctgc cagccgatgc acttgatgat ttcgatttgg atatgcttcc  3840
agccgacgct ctgacgact tcgatttgga catgcttccc ggttaaacta gtctgcaat    3900
caacctctgg attacaaaat ttgtgaaaga ttgactggta ttcttaacta tgttgctcct  3960
tttacgctat gtggatacgc tgctttaatg cctttgtatc atgctattgc ttcccgtatg  4020
gctttcattt tctcctcctt gtataaatcc tggttagttc ttgccacggc ggaactcatc  4080
gccgcctgcc ttgcccgctg ctggacaggg gctcggctgt tgggcactgc caattccgtg  4140
gtgttatttt gtgaaatttg tgatgctatt gctttatttg taaccattat aagctgcaat  4200
gtgaaatttg tgatgctatt gctttatttg taaccattat aagctgcaat aaacaagtta  4260
acaacaacaa ttgcattcat tttatgtttc aggttcaggg ggagatgtgg gaggtttttt  4320
aaagcggggg atccaaattc ccgataagga tcttcctaga gcatggctac gtagataagt  4380
agcatggcgg gttaatcatt aactacaagg aacccctagt gatggagttg gccactccct  4440
ctctgcgcgc tcgctcgctc actgaggccg ggcgaccaaa ggtcgcccga cgcccgggct  4500
ttgcccggc ggcctcagtg agcgagcgag cgcgcagcct taattaacct aattcactgg   4560
ccgtcgtttt acaacgtcgt gactgggaaa accctggcgt tacccaactt aatcgccttg  4620
cagcacatcc ccctttcgcc agctggcgta atagcgaaga ggcccgcacc gatcgccctt  4680
cccaacagtt gcgcagcctg aatggcgaat gggacgcgcc ctgtagcggc gcattaagcg  4740
cggcgggtgt ggtggttacg cgcagcgtga ccgctacact tgccagcgcc ctagcgcccg  4800
```

```
ctcctttcgc tttcttccct tcctttctcg ccacgttcgc cggctttccc cgtcaagctc    4860
taaatcgggg gctcccttta ggggttccgat ttagtgcttt acggcacctc gacccccaaaa   4920
aacttgatta gggtgatggt tcacgtagtg ggccatcgcc ctgatagacg gttttttcgcc    4980
cttttgacgtt ggagtccacg ttctttaata gtggactctt gttccaaact ggaacaacac   5040
tcaaccctat ctcggtctat tcttttgatt tataaggagt tttgccgatt tcggcctatt     5100
ggttaaaaaa tgagctgatt taacaaaaat ttaacgcgaa ttttaacaaa atattaacgt    5160
ttataatttc aggtggcatc tttcggggaa atgtgcgcgg aacccctatt tgtttatttt    5220
tctaaatacc ttcaaatatg tatccgctca tgagacaata accctgataa atgcttcaat    5280
aatattgaaa aaggaagagt atgagtattc aacatttccg tgtcgcccttt attccctttt    5340
ttgcggcatt ttgccttcct gttttgctc acccagaaac gctggtgaaa gtaaaagatg     5400
ctgaagatca gttgggtgca cgagtgggtt acatcgaact ggatctcaat agtggtaaga    5460
tccttgagag ttttcgcccc gaagaacgtt ttccaatgat gagcactttt aaagttctgc    5520
tatgtggcgc ggtattatcc cgtattgacg ccgggcaaga gcaactcggt cgccgcatac     5580
actattctca gaatgacttg gttgagtact caccagtcac agaaaagcat cttacggatg    5640
gcatgacagt aagagaa                                                    5657

SEQ ID NO: 18           moltype = DNA    length = 1215
FEATURE                 Location/Qualifiers
misc_feature            1..1215
                        note = Synthetic Polynucleotide
source                  1..1215
                        mol_type = other DNA
                        organism = synthetic construct
SEQUENCE: 18
gatctggcct ccgcgccggg ttttggcgcc tcccgcgggc gccccctcc tcacggcgag      60
cgctgccacg tcagacgaag ggcgcagcga gcgtcctgca ccttccgcgc ggacgctcag    120
gacagcggcc cgctgctcat aagactcggc cttagaaccc cagtatcagc agaaggacat    180
tttaggacgg gacttgggtg actctagggc actggttttc tttccagaga gcggaacagg    240
cgaggaaaag tagtcccttc tcggcgattc tgcggaggga tctccgtggg gcggtgaacg    300
ccgatgatta tataaggacg cgccgggtgt ggcacagtca gttccgtcgc agccgggatt    360
tgggtcgcgg ttcttgtttg tggatcgctg tgatcgtcac ttggtgagta gcgggctgct    420
gggctggccg gggctttcgt ggccgccggg ccgctcggtg ggacggaagc gtgtggagag    480
accgccaagg gctgtagtct gggtccgcga gcaaggttgc cctgaactgg gggttggggg    540
gagcgcagca aaatggcggc tgttcccgag tcttgaatgg aagacgcttg tgaggcgggc    600
tgtgaggtcg ttgaaacaag gtgggggcga tgggggcca caagaaccca aggtcttgag    660
gccttcgcta atgcgggaaa gctccttatc gggtgagatg ggctggggca ccatctgggg   720
accctgacgt gaagtttgtc actgactgga gaactcggtt tgtcgtctgt tgcggggcg     780
gcagttatgc ggtgccgttg ggcagtgcac ccgtacccttt gggagcgcgc gcctcgtcgt   840
gtcgtgacgt caccgttct gttggcttat aatgcagggt ggggccacct gccggtaggt   900
gtgcggtagg cttttctccg tcgcaggacg caggggttcgg gcctaggta ggctctcctg    960
aatcgacagg cgccggacct ctggtgaggg gagggataag tgaggcgtca gtttcttttgg  1020
tcggttttat gtacctatct tcttaagtag ctgaagctcc ggttttgaac tatgcgctcg  1080
gggttgacga gtgtgttttg tgaagttttt taggcaccctt ttgaaattgta atcatttggg 1140
tcaatatgta atttttcagtg ttagactagt aaattgtccg ctaaattctg gccgttttgtg 1200
gcttttttgt tagac                                                   1215

SEQ ID NO: 19           moltype = DNA    length = 19
FEATURE                 Location/Qualifiers
misc_feature            1..19
                        note = Synthetic Polynucleotide
source                  1..19
                        mol_type = other DNA
                        organism = synthetic construct
SEQUENCE: 19
tccctatcag tgatagaga                                                  19

SEQ ID NO: 20           moltype = DNA    length = 68
FEATURE                 Location/Qualifiers
misc_feature            1..68
                        note = Synthetic Polynucleotide
source                  1..68
                        mol_type = other DNA
                        organism = synthetic construct
SEQUENCE: 20
gctttaggcg tgtacggtgg gcgcctataa aagcagagct cgtttagtga accgtcagat     60
cgcctgga                                                              68

SEQ ID NO: 21           moltype = DNA    length = 248
FEATURE                 Location/Qualifiers
misc_feature            1..248
                        note = Synthetic Polynucleotide
source                  1..248
                        mol_type = other DNA
                        organism = synthetic construct
SEQUENCE: 21
aatcaacctc tggattacaa aatttgtgaa agattgactg gtattcttaa ctatgttgct     60
ccttttacgc tatgtggata cgctgcttta atgcctttgt atcatgctat tgcttcccgt   120
atggctttca ttttctcctc cttgtataaa tcctggttag ttcttgccac ggcggaactc   180
atcgccgcct gccttgcccg ctgctggaca ggggctcggc tgttgggcac tgacaattcc   240
```

```
gtggtgtt                                                                      248

SEQ ID NO: 22          moltype = DNA  length = 141
FEATURE                Location/Qualifiers
misc_feature           1..141
                       note = Synthetic Polynucleotide
source                 1..141
                       mol_type = other DNA
                       organism = synthetic construct
SEQUENCE: 22
ccttaattag gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac tagggggttcc t                                           141

SEQ ID NO: 23          moltype = DNA  length = 438
FEATURE                Location/Qualifiers
misc_feature           1..438
                       note = Synthetic Polynucleotide
source                 1..438
                       mol_type = other DNA
                       organism = synthetic construct
SEQUENCE: 23
aattcgtaca cgcctacctc gacccatcaa gtgccacctg acgtctccct atcagtgata   60
gagaagtcga cacgtctcga gctccctatc agtgatagag aaggtacgtc tagaacgtct  120
ccctatcagt gatagagaag tcgacacgtc tcgagctccc tatcagtgat agagaaggta  180
cgtctagaac gtctccctat cagtgataga gaagtcgact gtctcgagc tcctcatcag  240
tgatagagaa ggtacgtcta gaacgtctcc ctatcagtga tagagaagtc gacacgtctc  300
gagctcccta tcagtgatag agaaggtacc cctatataa gcagagctcg tttagtgaac  360
cgtcagatcg cctggagacg ccatccacgc tgttttgacc tccatagaag acaccgggac  420
cgatccagcc tggatcgc                                                438

SEQ ID NO: 24          moltype = DNA  length = 315
FEATURE                Location/Qualifiers
misc_feature           1..315
                       note = Synthetic Polynucleotide
source                 1..315
                       mol_type = other DNA
                       organism = synthetic construct
SEQUENCE: 24
gagtttactc cctatcagtg atagagaacg tatgtcgagt ttactcccta tcagtgatag   60
agaacgatgt cgagtttact ccctatcagt gatagagaac gtatgtcgag tttactccct  120
atcagtgata gagaacgtat gtcgagttta ctccctatca gtgatagaga acgtatgtcg  180
agtttatccc tatcagtgat agagaacgta tgtcgagttt actccctatc agtgatagag  240
aacgtatgtc gaggtaggcg tgtacggtgg gaggcctata aagcagagc tcgtttagtg  300
aaccgtcaga tcgcc                                                   315

SEQ ID NO: 25          moltype = DNA  length = 618
FEATURE                Location/Qualifiers
misc_feature           1..618
                       note = Synthetic Polynucleotide
source                 1..618
                       mol_type = other DNA
                       organism = synthetic construct
SEQUENCE: 25
atggctagat tagataaaag taaagtgatt aacagcgcat tagagctgct taatgaggtc   60
ggaatcgaag gtttaacaac ccgtaaactc gcccagaagc taggtgtaga gcagcctaca  120
ttgtattggc atgtaaaaaa taagcgggct tgctcgacg ccttagccat tgagatgtta  180
gataggcacc atactcactt tgccccttta aagggggaaa gctggcaaga ttttttacgt  240
aataacgcta aaagttttag atgtgctttta ctaagtcatc gcgatggagc aaaagtacat  300
ttaggtacac ggcctacaga aaaacagtat gaaactctcg aaaatcaatt agccttttta  360
tgccaacaag ttttttcact agagaatgca ttatatgcac tcagcgctgt ggggcatttt  420
actttaggtt gcgtattgga agatcaagag catcaagtcg ctaaagaaga agggaaaca  480
cctactactg atagtatgcc gccattatta cgacaagcta tcgaattatt tgatcaccaa  540
ggtgcagagc cagccttctt attcggcctt gaattgatca tatgcggatt agaaaacaa  600
cttaaatgtg aaagtggg                                                618

SEQ ID NO: 26          moltype = AA  length = 206
FEATURE                Location/Qualifiers
REGION                 1..206
                       note = Synthetic Polypeptide
source                 1..206
                       mol_type = protein
                       organism = synthetic construct
SEQUENCE: 26
MARLDKSKVI NSALELLNEV GIEGLTTRKL AQKLGVEQPT LYWHVKNKRA LLDALAIEML   60
DRHHTHFCPL EGESWQDFLR NNAKSFRCAL LSHRDGAKVH LGTRPTEKQY ETLENQLAFL  120
CQQGFSLENA LYALSAVGHF TLGCVLEDQE HQVAKEERET PTTDSMPPLL RQAIELFDHQ  180
GAEPAFLFGL ELIICGLEKQ LKCESG                                       206
```

| SEQ ID NO: 27 | moltype = DNA length = 1008 |
|---|---|
| FEATURE | Location/Qualifiers |
| misc_feature | 1..1008 |
| | note = Synthetic Polynucleotide |
| source | 1..1008 |
| | mol_type = other DNA |
| | organism = synthetic construct |

SEQUENCE: 27
```
atggctagat tagataaaag taaagtgatt aacagcgcat tagagctgct taatgaggtc   60
ggaatcgaag gtttaacaac ccgtaaactc gcccagaagc taggtgtaga gcagcctaca  120
ttgtattggc atgtaaaaaa taagcgggct ttgctcgacg ccttagccat tgagatgtta  180
gataggcacc atactcactt tgcccttta aagggaaa gctggcaaga tttttacgt  240
aataacgcta aaagttttag atgtgctta ctaagtcatc gcgatggagc aaaagtacat  300
ttaggtacac ggcctacaga aaaacagtat gaaactctcg aaaatcaatt agccttta  360
tgccaacaag gttttttcact agagaatgca ttatatgcac tcagcgctgt ggggcatttt  420
actttaggtt gcgtattgga agatcaagag catcaagtcg ctaaagaaga aagggaaaca  480
cctactactg atagtatgcc gccattatta cgacaagcta tcgaattatt tgatcaccaa  540
ggtgcagagc cagccttctt attcggcctt gaattgatca tatgcggatt agaaaaacaa  600
cttaaatgtg aaagtgggtc gccaaaaaag aagagaaagg tcgacggcgg tggtgctttg  660
tctcctcagc actctgctgt cactcaagga agtatcatca agaacaagga gggcatggat  720
gctaagtcac taactgcctg gtcccggaca ctggtgacct tcaaggatgt atttgtggac  780
ttcaccaggg aggagtggaa gctgctggac actgctcagc agatcgtgta cagaaatgtg  840
atgctggaga actataagaa cctggtttcc ttgggttatc agcttactaa gccagatgtg  900
atcctccggt tggagaaggg agaagagccc tggctggtgg agagagaaat tcaccaagag  960
acccatcctg attcagagac tgcatttgaa atcaaatcat cagtttaa         1008
```

| SEQ ID NO: 28 | moltype = AA length = 335 |
|---|---|
| FEATURE | Location/Qualifiers |
| REGION | 1..335 |
| | note = Synthetic Polypeptide |
| source | 1..335 |
| | mol_type = protein |
| | organism = synthetic construct |

SEQUENCE: 28
```
MARLDKSKVI NSALELLNEV GIEGLTTRKL AQKLGVEQPT LYWHVKNKRA LLDALAIEML   60
DRHHTHFCPL EGESWQDFLR NNAKSFRCAL LSHRDGAKVH LGTRPTEKQY ETLENQLAFL  120
CQQGFSLENA LYALSAVGHF TLGCVLEDQE HQVAKEERET PTTDSMPPLL RQAIELFDHQ  180
GAEPAFLFGL ELIICGLEKQ LKCESGSPKK KRKVDGGGAL SPQHSAVTQG SIIKNKEGMD  240
AKSLTAWSRT LVTFKDVFVD FTREEWKLLD TAQQIVYRNV MLENYKNLVS LGYQLTKPDV  300
ILRLEKGEEP WLVEREIHQE THPDSETAFE IKSSV                           335
```

| SEQ ID NO: 29 | moltype = DNA length = 977 |
|---|---|
| FEATURE | Location/Qualifiers |
| misc_feature | 1..977 |
| | note = Synthetic Polynucleotide |
| source | 1..977 |
| | mol_type = other DNA |
| | organism = synthetic construct |

SEQUENCE: 29
```
accttgcttc ctagctgggc cttttccttct cctctataaa taccagctct ggtatttcgc   60
cttggcagct gttgctgcta gggagacggc tggcttgaca tgcatctcct gacaaaacac  120
aaacccgtgg tgtgagtggg tgtgggcggt gtgagtaggg ggatgaatca gagagggggc  180
gagggagaca ggggcgcagg agtcaggcaa aggcgatgcg ggggtgcgac tacacgcagt  240
tggaaacagt cgtcagaaga ttctggaaac tatcttgctg gctataaact tgagggaagc  300
agaaggccaa cattcctccc aagggaaact gaggctcaga gttaaaaccc aggtatcagt  360
gatatgcatg tgccccggcc agggtcactc tctgactaac cggtacctac cctacaggcc  420
tacctagaga ctcttttgaa aggatggtag agacctgtcc gggctttgcc cacagtcgtt  480
ggaaacctca gcattttcta ggcaacttgt gcgaataaaa cacttcgggg gtccttcttg  540
ttcattccaa taacctaaaa cctctcctcg gagaaaatag ggggcctcaa acaaacgaaa  600
ttctctagcc cgctttcccc aggataaggc aggcatccaa atggaaaaaa aggggccggc  660
cgggggtctc ctgtcagctc cttgcccgt gaaacccagc aggcctgcct gtcttcgtc  720
ctcttggggc tgtccagggg cgcaggcctc ttgcggggga gctggcctcc ccgcccctc  780
gcctgtggcc gccctttttcc tggcaggaca gagggatcct gcagctgtca ggggagggc  840
gcgggggggt gatgtcagga gggctacaaa tagtgcagac agctaagggg ctccgtcacc  900
catcttcaca tccactccag ccggctgccc gcccgctgcc tcctctgtgc gtccgcccag  960
ccagcctcgt ccacgcc                                              977
```

| SEQ ID NO: 30 | moltype = DNA length = 5428 |
|---|---|
| FEATURE | Location/Qualifiers |
| misc_feature | 1..5428 |
| | note = Synthetic Polynucleotide |
| source | 1..5428 |
| | mol_type = other DNA |
| | organism = synthetic construct |

SEQUENCE: 30
```
ttatgcagtg ctgccataac catgagtgat aacactgcgg ccaacttact tctgacaacg   60
atcgaggac cgaaggagct aaccgctttt ttgcacaaca tgggggatca tgtaactcgc  120
cttgatcgtt gggaaccgga gctgaatgaa gccataccaa acgacgagcg tgacaccacg  180
atgcctgtag taatggtaac aacgttgcgc aaactattaa ctggcgaact acttactcta  240
```

```
gcttcccggc aacaattaat agactggatg gaggcggata aagttgcagg accacttctg    300
cgctcggccc ttccggctgg ctggtttatt gctgataaat ctggagccgg tgagcgtggg    360
tctcgcggta tcattgcagc actgggggcca gatggtaagc cctcccgtat cgtagttatc   420
tacacgacgg ggagtcaggc aactatggat gaacgaaata gacagatcgc tgagataggt    480
gcctcactga ttaagcattg gtaactgtca gaccaagttt actcatatat actttagatt    540
gatttaaaac ttcattttta atttaaaagg atctaggtga agatccttttt tgataatctc   600
atgaccaaaa tcccttaacg tgagttttcg ttccactgag cgtcagaccc cgtagaaaag    660
atcaaaggat cttcttgaga tcctttttttt ctgcgcgtaa tctgctgctt gcaaacaaaa   720
aaaccaccgc taccaggcgg tggtttgtttg ccggatcaag agctaccaac tctttttccg   780
aaggtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgc tgctgccag tggcgataag tcgtgtctta ccgggttgga ctcaagacga     960
tagttaccgg ataaggcgca gcggtcgggc tgaacggggg gttcgtgcac acagcccagc   1020
ttggagcgaa cgacctacac cgaactgaga tacctacagc gtgagctatg agaaagcgcc   1080
acgcttcccg aagggagaaa ggcggacagg tatccggtaa gcggcagggt cggaacagga   1140
gagcgcacga gggagcttcc agggggaaac gcctggtatc tttatagtcc tgtcggtttt   1200
cgccacctct gacttgagcg tcgatttttgt gatgctcgt caggggggcg gagcctatgg   1260
aaaaacgcca gcaacgcggc cttttttacgg ttcctggcct tttgctggcc ttttgctcac   1320
atgttctttc ctgcgttatc ccctgattct gtggataacc gtattaccgc ctttgagtga   1380
gctgataccg ctcgccgcag ccgaacgacc gagcgcagcg agtcagtgag cgaggaagcg   1440
gaagagcgcc caatacgcaa accgcctctc cccgcgcgtt ggccgattca ttaatgcagc   1500
tggcacgaca ggtttcccga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccggggcgt cgggcgacct ttggtcgccc ggcctcagtg agcgagcgag cgcgcagaga   1800
gggagtggcc aactccatca ctaggggttc cttgtagtta atgattaacc cgccatgcta   1860
cttatctacg tagccatgct ctaggaagat cggaattcct agatctacct tgcttcctag   1920
ctgggccttt ccttctcctc tataaatacc agctctggta tttcgccttg gcagctgttg   1980
ctgctaggga gacggctggc ttgacatgca tctcctgaca aaacacaaac ccgtggtgtg   2040
agtgggtgtg ggcggtgtga gtaggggggat gaatcagaga gggggcgagg gagacagggg   2100
cgcaggagtc aggcaaaggc gatgcggggg tgcgactaca cgcagttgga aacagtcgtc   2160
agaagattct ggaaactatc ttgctggcta taaacttgag ggaagcagaa ggccaacatt   2220
cctcccaagg gaaactgagg ctcagagtta aaacccaggt atcagtgata tgcctgtgct   2280
ccggccaggg tcactctctg actaaccggt acctaccccta caggcctacc tagagactct   2340
tttgaaagga tggtagagac ctgtccggc ttttgcccaca gtcgttggaa acctcagcat    2400
tttctaggca acttgtgcga ataaaacact tcggggtgtcc ttcttgttca ttccaataac   2460
ctaaaacctc tcctcggaga aaatagggggg cctcaaacaa acgaaattct ctagcccgct   2520
ttccccagga taaggcaggc atccaaatgg aaaaaaaggg gccggccggg ggtctcctga   2580
cagctccttg ccctgtgaaa cccagcaggc ctgcctgtct tctgtcctct tggggctgtc   2640
caggggcgca ggcctcttgc gggggagctg gcctccccgc ccctcgcct gtggccgccc    2700
ttttcctggc aggacagagg gatcctgcag ctgtcagggg aggggcgccg gggggtgatg   2760
tcaggagggc tacaaatagt acagacagct aaggggctcc gtcacccatc ttcacatcca   2820
ctccagccgg ctgcccgccc gctgcctcct ctgtgcgtcc gccagccag cctcgtccac    2880
gccaagcttg cggccgcatt aaacgccacc atgtcccgct tggataagag caaggtaata   2940
aatagcgcac tcgaactcct caacggcgtg ggcatcgaag tctgactac tcgaaagctc    3000
gcccagaaat tgggtgtgga gcaacctaca ttgtattggc atgtcaagaa caaaagagcc   3060
ctgctggacg ctcttcctat tgaaatgctt gacaggcatc acactcattc ctgccccctt   3120
gaggtcgaga gttggcaaga ttttctccga aacaatgcaa agtcctaccg ctgcgcactt   3180
ttgtcccata gggatggagc aaaagtgcac ctggaaccag gccaacaga gaaacaatac    3240
gagactctcg agaaccagtt ggctttcttg tgccaacagg ggttctcact tgaaaatgcc   3300
ctttacgcac tgtcagccgt tggacatttt accctggggt gcgttcttga ggagcaagaa   3360
catcaggttg ctaaggagga gcgcgagact ccaaccactg attctatgcc accttttgctg   3420
aaacaggcca ttgaacttt cgatagacag ggtgctgaac ctgcctttct cttcgggttg    3480
gagctgatta tttgtggtct cgaaaaacag ctgaaatgta aagtggttgg ccctactgga   3540
gccctcgatg atttcgacct ggatatgctg ccagccgatg cacttgatga tttcgatttg   3600
gatatgcttc cagccgacgc actgacgac ttcgatttgg acatgcttcc cggttaaact    3660
agtctagcaa tcaacctctg gattacaaaa tttgtgaaag attgactggt attcttaact   3720
atgttgctcc ttttacgcta tgtggatacg ctgctttaat gcctttgtat catgctattg   3780
cttcccgtat ggctttcatt ttctcctcct tgtataaatc ctggttagtt cttgccacgg   3840
cggaactcat cgccgcctgc cttgcccgct gctggacagg ggctcggctg ttgggcactg   3900
acaattccgt ggtgttatt tgtgaaattt gtgatgctat tgctttattt gtaaccattc   3960
tagctttatt tgtgaaattt gtgatgctat tgctttattt gtaaccatta taagctgcaa   4020
taaacaagtt aacaacaaca attgcattca ttttatgttt caggttcagg ggggagatgt   4080
ggaggttttt taaagcgggg gatccaaatt cccgataagg atcttcctag agcatggcta   4140
cgtagataag tagcatggcg ggttaatcat taactacaag gaaccccctag tgatggagtt   4200
ggccactccc tctctgcgcg ctcgctcgct cactgaggcc gggcgaccaa aggtcgcccg   4260
acgcccgggc tttgcccggg cggcctcagt gagcgagcga gcgcgcagcc ttaattaacc   4320
taattcactg gccgtcgttt tacaacgtcg tgactgggaa aaccctggcg ttacccaact   4380
taatcgcctt gcagcacatc cccctttcgc cagctggcgt aatagcgaag aggcccgcac   4440
cgatcgccct tcccaacagt tgcgcagcct gaatggcgaa tgggacgcgc cctgtagcgg   4500
cgcattaagc gcggcgggtg tggtggttac gcgcagcgtg accgctacac ttgccagcgc   4560
cctagcgccc gctcctttcg ctttcttccc ttcctttctc gccacgttcg ccggctttcc   4620
ccgtcaagct ctaaatcggg ggctcccttt agggttccga tttagtgctt tacggcacct   4680
cgaccccaaa aaacttgatt agggtgatgg ttcacgtagt gggccatcgc cctgatagac   4740
ggttttttcgc cctttgacgt tggagtccac gttctttaat agtggactct tgttccaaac   4800
tggaacaaca ctcaaccctca tctcggtcta ttcttttgat ttataaggga ttttgccgat   4860
ttcggcctat tggttaaaaa atgagctgat ttaacaaaaa tttaacgcga attttaacaa   4920
aatattaacg tttataattt caggtggcat ctttcgggga aatgtgcgcg gaaccctat    4980
```

```
ttgtttattt ttctaaatac attcaaatat gtatccgctc atgagacaat aaccctgata  5040
aatgcttcaa taatattgaa aaaggaagag tatgagtatt caacatttcc gtgtcgccct  5100
tattcccttt tttgcggcat tttgccttcc tgtttttgct cacccagaaa cgctggtgaa  5160
agtaaaagat gctgaagatc agttgggtgc acgagtgggt tacatcgaac tggatctcaa  5220
tagtgggtaag atccttgaga gttttcgccc cgaagaagct tttccaatga tgagcacttt  5280
taaagttctg ctatgtggcg cggtattatc ccgtattgac gccgggcaag agcaactcgg  5340
tcgccgcata cactattctc agaatgactt ggttgagtac tcaccagtca cagaaaagca  5400
tcttacggat ggcatgacag taagagaa                                     5428

SEQ ID NO: 31          moltype = DNA   length = 5332
FEATURE                Location/Qualifiers
misc_feature           1..5332
                       note = Synthetic Polynucleotide
source                 1..5332
                       mol_type = other DNA
                       organism = synthetic construct
SEQUENCE: 31
aaattgtaaa cgttaatatt ttgttaaaat tcgcgttaaa ttttttgttaa atcagctcat   60
tttttaacca ataggccgaa atcggcaaaa tcccttataa atcaaaagaa tagcccgaga  120
tagggttgag tgttgttcca gtttggaaca agagtccact attaaagaac gtggactcca  180
acgtcaaagg gcgaaaaacc gtctatcagg gcgatggccc actacgtgaa ccatcaccca  240
aatcaagttt tttggggtcg aggtgccgta aagcactaaa tcggaaccct aaagggagcc  300
cccgatttag agcttgacgg ggaaagccgg cgaacgtggc gagaaaggaa gggaagaaag  360
cgaaaggagc gggcgctagg gcgctggcaa gtgtagcggt cacgctgcgc gtaaccacca  420
cacccgccgc gcttaatgcg ccgctacagg gcgcgtacta tggttgcttt gacgtatgcg  480
gtgtgaaata ccgcacagat gcgtaaggag aaaataccgc atcaggcgcc cctgcaggca  540
gctgcgcgct cgctcgctca ctgaggccgc ccgggcaaag cccgggcgtc gggcgacctt  600
tggtcgcccg gcctcagtga gcgagcgagc gcgcagagag ggagtggcca actccatcac  660
tagggggttcc tgcggccgct cggtccgcac gatctcaatt cggccattac ggccggatcc  720
ggctcgagga gcttggccca ttgcatacgt tgtatccata tcataatatg tacatttata  780
ttggctcatg tccaacatta ccgccatgtt gacattgatt attgactagt tattaatagt  840
aatcaattac ggggtcatta gttcatagcc catatatgga gttccgcgtt acataactta  900
cggtaaatgg cccgcctggc tgaccgccca acgacccccg cccattgacg tcaataatga  960
cgtatgttcc catagtaacg ccaatagggga ctttccattg acgtcaatgg gtggagtatt 1020
tacgctaaac tgcccacttg gcagtacatc aagtgtatca tatgccaagt acgcccccta 1080
ttgacgtcaa tgacggtaaa tggcccgcct ggcattatgc ccagtacatg accttatggg 1140
actttcctac ttggcagtac atctacgtat tagtcatcgc tattaccatg gtgatgcggt 1200
tttggcagta catcaatggg cgtggatagc ggtttgactc acggggattt ccaagtctcc 1260
accccattga cgtcaatggg agtttgtttt ggcaccaaaa tcaacgggac tttccaaaat 1320
gtcgtaacaa ctccgcccca ttgacgcaaa tgggcggtag gcgtgtacgg tgggaggtct 1380
atataagcag agctcgttta gtgaaccgtc agatcgcctg gagacgccat ccacgctgtt 1440
ttgacctcca tagaagacac cgggaccgat ccagcctccg cggccccgaa ttcaccatgt 1500
ctagactgga caagagcaaa atcataaaca gcgctctgga attactcaat ggagtcggta 1560
tcgaaggcct gacgacaagg aaactcgctc aaaagctggg agttgagcag cctaccctgt 1620
actggcacgt gaagaacaag cgggccctc tcgatgccct gccaatcgag atgctggaca 1680
ggcatcatac ccacagctgc cccctggaag gcgagtcatg caagactttt ctgcggaaca 1740
acgccaagtc ataccgctgt gctctcctct cacatcgcga cggggctaaa gtgcatctcg 1800
gcacccgccc aacagagaaa cagtacgaaa ccctggaaaa tcagctcgcg ttcctgtgtc 1860
agcaaggctt ctccctggag aacgcactgt acgctctgtc cgccgtgggc cactttacac 1920
tgggctgcgt attggaggaa caggagcatc aagtagcaaa agaggaaaga gagacaccta 1980
ccaccgattc tatgccccca cttctgaagc aagcaattga gctgttcgac cggcagggaa 2040
ccgaacctgc cttccttttc ggcctggaac taatcatatg tggcctggag aaacagctaa 2100
agtgcgaaag cggcggccg accgacgccc ttgacgattt tgacttagac atgctcccag 2160
ccgatgccct tgacgacttt gaccttgata tgctgcctgc tgacgctctt gacgattttg 2220
accttgacat gctccccggg taactaagta aggatcatct taattaaatc gataaggatc 2280
tggccgcctc ggcctaatca acctctggat tacaaaattt gtgaaagatt gactggtatt 2340
cttaactatg ttgctccttt tacgctatgt ggatacgctg ctttaatgcc tttgtatcat 2400
gctattgctt cccgtatggc tttcattttc tcctccttgt ataaatcctg gttgctgtct 2460
ctttatgagg agttgtggcc cgttgtcagg caacgtggcg tggtgtgcac tgtgtttgct 2520
gacgcaaccc ccactggttg gggcattgcc accacctgtc agctcctttc cgggactttc 2580
gctttccccc tccctattgc cacggcggaa ctcatcgccg cctgccttgc ccgctgctgg 2640
acaggggctc ggctgttggg cactgacaat tccgtggtgt tgtcgggaa atcatcgtcc 2700
tttccttggc tgctcgcctg tgttgccacc tggattctgc gcgggacgtc cttctgctac 2760
gtcccttcgg ccctcaatcc agcggacctt cttcccgcg gcctgctgcc ggctctgcgg 2820
cctcttccgc gtcttcgcct tcgccctcag acgagtcgga tctccctttg ggccgcctcc 2880
ccgccagaca tgataagata cattgatgag tttggacaaa ccacaactag aatgcagtga 2940
aaaaaatgct ttatttgtga aatttgtgat gctattgctt tatttgtaac cattataagc 3000
tgcaataaac aagttaacaa caacaattgc attcattta tgtttcaggt tcaggggag  3060
atgtgggagg tttttttaaag caagtaaaac ctctacaaat gtggtaacta gcgcgtgcgg 3120
ccgcaggaac ccctagtgat ggagttggcc actccctctc tgcgcgctcg ctcgctcact 3180
gaggccgggc gaccaaaggt cgcccgacgc ccgggctttg cccgggcggc ctcagtgagc 3240
gagcgagcgc gcagctgcct gcaggacatg tgagcaaaag gccagcaaaa ggccaggaac 3300
cgtaaaaagg ccgcgttgct ggcgtttttc cataggctcc gccccctga cgagcatcac 3360
aaaaatcgac gctcaagtca gaggtggcga acccgacaga ctataaag atacaggcg 3420
tttccccctg gaagctccct cgtgcgctct cctgttccga ccctgccgct taccggatac 3480
ctgtccgcct ttctcccttc gggaagcgtg gcgctttctc atagctcacg ctgtaggtat 3540
ctcagttcgg tgtaggtcgt tcgctccaag ctgggctgtg tgcacgaacc cccgttcag 3600
cccgaccgct gcgccttatc cggtaactat cgtcttgagt ccaacccggt aagacacgac 3660
ttatcgccac tggcagcagc cactggtaac aggattagca gagcgaggta tgtaggcggt 3720
```

```
gctacagagt tcttgaagtg gtggcctaac tacggctaca ctagaaggac agtatttggt  3780
atctgcgctc tgctgaagcc agttaccttc ggaaaaagag ttggtagctc ttgatccggc  3840
aaacaaacca ccgctggtag cggtggtttt tttgtttgca agcagcagat tacgcgcaga  3900
aaaaaaggat ctcaagaaga tcctttgatc ttttctacgg ggtctgacgc tcagtggaac  3960
gaaaactcac gttaagggat tttggtcatg agattatcaa aaaggatctt cacctagatc  4020
cttttaaatt aaaaatgaag ttttaaatca atctaaagta tatatgagta aacttggtct  4080
gacagttacc aatgcttaat cagtgaggca cctatctcag cgatctgtct atttcgttca  4140
tccatagttg cctgactccc cgtcgtgtag ataactacga tacgggaggg cttaccatct  4200
ggccccagtg ctgcaatgat accgcgagac ccacgctcac cggctccaga tttatcagca  4260
ataaaccagc cagccggaag ggccgagcgc agaagtggtc ctgcaacttt atccgcctcc  4320
atccagtcta ttaattgttg ccgggaagct agagtaagta gttcgccagt taatagtttg  4380
cgcaacgttg ttgccattgc tacaggcatc gtggtgtcac gctcgtcgtt tggtatggct  4440
tcattcagct ccggttccca acgatcaagg cgagttacat gatccccat gttgtgcaaa  4500
aaagcggtta gctccttcgg tcctccgatc gttgtcagaa gtaagttggc cgcagtgtta  4560
tcactcatgg ttatggcagc actgcataat tctcttactg tcatgccatc cgtaagatgc  4620
ttttctgtga ctggtgagta ctcaaccaag tcattctgag aatagtgtat gcggcgaccg  4680
agttgctctt gcccggcgtc aatacgggat aataccgcgc cacatagcag aactttaaaa  4740
gtgctcatca ttggaaaacg ttcttcgggg cgaaaactct caaggatctt accgctgttg  4800
agatccagtt cgatgtaacc cactcgtgca cccaactgat cttcagcatc ttttactttc  4860
accagcgttt ctgggtgagc aaaaacagga aggcaaaatg ccgcaaaaaa gggaataagg  4920
gcgacacgga aatgttgaat actcatactc ttcctttttc aatattattg aagcatttat  4980
cagggttatt gtctcatgag cggatacata tttgaatgta tttagaaaaa taaacaaata  5040
ggggttccgc gcacatttcc ccgaaaagtg ccacctgacg tctaagaaac cattattatc  5100
atgacattaa cctataaaaa taggcgtatc acgaggccct ttcgtctcgc gcgtttcggt  5160
gatgacggtg aaaacctctg acacatgcag ctcccggaga cggtcacagc ttgtctgtaa  5220
gcggatgccg ggagcagaca gcccgtcag ggcgcgtcag cgggtgttgg cgggtgtcgg  5280
ggctggctta actatgcggc atcagagcag attgtactga gagtgcacca ta         5332
```

SEQ ID NO: 32          moltype = DNA   length = 5392
FEATURE                Location/Qualifiers
misc_feature           1..5392
                       note = Synthetic Polynucleotide
source                 1..5392
                       mol_type = other DNA
                       organism = synthetic construct
SEQUENCE: 32

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggtcc tgcggccgca cgcgtgagc tagttattaa tagtaatcaa    180
ttacggggtc attagttcat agcccatata tggagttccg cgttacataa cttacggtaa   240
atggcccgcc tggctgaccg cccaacgacc cccgcccatt gacgtcaata atgacgtatg   300
ttcccatagt aacgtcaata gggactttcc attgacgtca atgggtggag tatttacggt   360
aaactgccca cttggcagta catcaagtgt atcatatgcc aagtacgccc cctattgacg   420
tcaatgacgg taaatggccc gcctggcatt atgcccagta catgacctta tgggactttc   480
ctacttggca gtacatctac gtattagtca tcgctattac catggtgatg cggttttggc   540
agtacatcaa tgggcgtgga tagcggtttg actcacgggg atttccaagt ctccacccca   600
ttgacgtcaa tgggagtttg ttttggcacca aaatcaacgg gactttccaa aatgtcgtaa   660
caactccgcc ccattgacgc aaatgggcgg taggcgtgta cggtgggagg tctatataag   720
cagagctcgt ttagtgaacc gtcagatcgc ctggagacgc catccacgct gttttgacct   780
ccatagaaga caccgggacc gatccagcct ccgcggattc gaatcccggc cgggaacggt   840
gcattggaac gcggattccc cgtgccaaga gtgacgtaag taccgcctat agagtctata   900
ggcccacaaa aaatgctttc ttcttttaat atacttttttt gtttatctta tttctaaatac    960
tttccctaat ctctttcttt cagggcaata atgatacaat gtatcatgcc tctttgcacc  1020
attctaaaga ataacagtga taatttctgg gttaaggcaa tagcaatatt tctgcatata  1080
aatatttctg catataaatt gtaactgatg taagaggttt catattgcta atagcagcta  1140
caatccagct accattctgc ttttatttta tggttgggat aaggctggat tattctgagt  1200
ccaagctagg cccttttgct aatcatgttc atacctctta tcttcctccc acagctcctg  1260
ggcaacgtgc tggtctgtgt gctggcccat cactttggca aagaattggg attcgaacat  1320
cgattgaatt catgtctaga ctggacaaga gcaaagtcat aaactctgct ctggaattac  1380
tcaatgaagt cggtatcgaa ggcctgacga caaggaaact cgctcaaaag ctggagttg   1440
agcagcctac cctgtactgg cacgtgaaga caagcgggc cctgctcgat gccctggcaa  1500
tcgagatgct ggacaggcat catcccact tctgcccct ggaaggcgag tcatggcaag  1560
actttctgcg gaacaacgcc aagtcattcc gctgtgctct cctctcacat cgcgacgggg  1620
ctaaagtgca tctcggcaca cgcccaacag agaaacagta cgaaaccctg aaaatcgac   1680
tcgcgttcct gtgtcagcaa gcttctccc tggagaacga ctgtacgct ctgtccgccg   1740
tgggccactt tacactgggc tgcgtattgg aggatcagga gcatcaagta gcaaagagg   1800
aaagagagac acctaccacc gattctatgc ccccacttct gagacaagca attgagctgt  1860
tcgaccatca gggagccgaa cctgccttcc ttttcggcct ggaactaatc atatgtggcc  1920
tggagaaaca gctaaagtgc gaaagcggcg ggccggccga cgcccttgac gattttgact  1980
tagacatgct cccagccgat gcccttgacg actttgacct tgatatgctg cctgctgacg  2040
ctcttgacga ttttgacctt gacatgctcc ccggatgagg atcctctaga gtcgacctgc  2100
agaagcttgc ctcgagcagc gctgctcgag agatctacgg gtggcatccc tgtgacccct  2160
ccccagtgcc tctcctggcc ctggaagttg ccactccagt gcccaccagc cttgtcctaa  2220
taaaattaag ttgcatcatt ttgtctgact aggtgtcctt ctataatatt atggggtgga  2280
ggggggtgg atgagcaag ggcaagttg ggaagacaac ctgtagggcc tgcggggtct   2340
attgggaacc aagctggagt gcagtggcac aatcttggct cactgcaatc tccgcctcct  2400
gggttcaagc gattctcctg cctcagcctc ccgagttgtt gggattccag gcatgcatga  2460
ccaggctcag ctaatttttg ttttttttggt agagacgggg ttcaccata ttggccaggc  2520
tggtctccaa ctcctaatct caggtgatct acccaccttg gcctcccaaa ttgctgggat  2580
```

```
tacaggcgtg aaccactgct cccttccctg tccttctgat tttgtaggta accacgtgcg   2640
gaccgagcgg ccgcaggaac ccctagtgat ggagttggcc actccctctc tgcgcgctcg   2700
ctcgctcact gaggccgggc gaccaaaggt cgcccgacgc ccgggctttg cccgggcggc   2760
ctcagtgagc gagcgagcgc gcagctgcct gcaggggcgc ctgatgcggt attttctcct   2820
tacgcatctg tgcggtattt cacaccgcat acgtcaaagc aaccatagta cgccctgt     2880
agcggcgcat taagcgcggc gggtgtggtg gttacgcgca gcgtgaccgc tacacttgcc   2940
agcgccctag cgcccgctcc tttcgctttc ttcccttcct ttctcgccac gttcgccggc   3000
tttccccgtc aagctctaaa tcgggggctc cctttagggt tccgatttag tgctttacgg   3060
cacctcgacc ccaaaaaact tgatttgggt gatggttcac gtagtgggcc atcgccctga   3120
tagacggttt ttcgcccttt gacgttggag tccacgttct ttaatagtgg actcttgttc   3180
caaactggaa caacactcaa ccctatctcg ggctattctt ttgatttata agggattttg   3240
ccgatttcgg cctattggtt aaaaaatgag ctgatttaac aaaaatttaa cgcgaatttt   3300
aacaaaatat taacgtttac aattttatgg tgcactctca gtacaatctg ctctgatgcc   3360
gcatagttaa gccagccccg acacccgcca cacccgctg acgcgccctg acgggcttgt   3420
ctgctcccgg catccgctta cagacaagct gtgaccgtct ccgggagctg catgtgtcag   3480
aggttttcac cgtcatcacc gaaacgcgcg agacgaaagg gcctcgtgat acgcctattt   3540
ttataggtta atgtcatgat aataatggtt tcttagacgt caggtggcac ttttcgggga   3600
aatgtgcgcg gaaccctat ttgttatt ttctaaatac attcaaatat gtatccgctc     3660
atgagacaat aaccctgata aatgcttcaa taatattgaa aaaggaagag tatgagtatt   3720
caacatttcc gtgtcgccct tattccctt tttgcggcat tttgccttcc tgttttgct    3780
cacccagaaa cgctggtgaa agtaaaagat gctgaagatc agttgggtgc acgagtgggt   3840
tacatcgaac tggatctcaa cagcggtaag atccttgaga gttttcgccc cgaagaacgt   3900
tttccaatga tgagcacttt taaagttctg ctatgtggcg cggtattatc ccgtattgac   3960
gccgggcaag agcaactcgg tcgccgcata cactattctc agaatgactt ggttgagtac   4020
tcaccagtca cagaaaagca tcttacggat ggcatgacag taagagaatt atgcagtgct   4080
gccataacca tgagtgataa cactgcggcc aacttacttc tgacaacgat cggaggaccg   4140
aaggagctaa ccgcttttt gcacaacatg ggggatcatg taactcgcct tgatcgttg     4200
gaaccggagc tgaatgaagc cataccaaac gacgagcgtg acaccacgat gcctgtagca   4260
atggcaacaa cgttgcgcaa actattaact ggcgaactac ttactctagc ttcccggcaa   4320
caattaatag actggatgga ggcggataaa gttgcaggac cacttctgcg ctcggccctt   4380
ccggctggct ggtttattgc tgataaatct ggagccggtg agcgtgggtc tcgcggtatc   4440
attgcagcac tggggccaga tggtaagccc tcccgtatcg tagttatcta cacgacgggg   4500
agtcaggcaa ctatggatga acgaaataga cagatcgctg agataggtgc ctcactgatt   4560
aagcattggt aactgtcaga ccaagtttac tcatatatac tttagattga tttaaaactt   4620
catttttaat ttaaaaggat ctaggtgaag atcctttttg ataatctcat gaccaaaatc   4680
ccttaacgtg agttttcgtt ccactgagcg tcagacccg tagaaaagat caaaggatct   4740
tcttgagatc ctttttttct gcgcgtaatc tgctgcttgc aaacaaaaaa accaccgcta   4800
ccagcggtgg tttgtttgcc ggatcaagag ctaccaactc tttttccgaa ggtaactggc   4860
ttcagcagag cgcagatacc aaatactgtc cttctagtgt agccgtagtt aggccaccac   4920
ttcaagaact ctgtagcacc gcctacatac ctcgctctgc taatcctgtt accagtggct   4980
gctgccagtg gcgataagtc gtgtcttacc gggttggact caagacgata gttaccggat   5040
aaggcgcagc ggtcgggctg aacggggggt tcgtgcacac agcccagctt ggagcgaacg   5100
acctacaccg aactgagata cctacagcgt gagctatgag aaagcgccac gcttcccgaa   5160
gggagaaagg cggacaggta tccggtaagc ggcagggtcg aacaggagag cgcacgagg    5220
gagcttccag ggggaaacgc ctggtatctt tatagtcctg tcgggtttcg ccacctctga   5280
cttgagcgtc gatttttgtg atgctcgtca ggggggcgga gcctatgaa aaacgccagc    5340
aacgcggcct ttttacggtt cctggccttt tgctggcctt tgctcacat gt            5392
```

SEQ ID NO: 33          moltype = DNA   length = 7732
FEATURE                Location/Qualifiers
misc_feature           1..7732
                       note = Synthetic Polynucleotide
source                 1..7732
                       mol_type = other DNA
                       organism = synthetic construct
SEQUENCE: 33

```
ttatgcagtg ctgccataac catgagtgat aacactgcgg ccaacttact tctgacaacg    60
atcggaggac cgaaggagct aaccgctttt ttgcacaaca tggggatca tgtaactcgc    120
cttgatcgtt gggaaccgga gctgaatgaa gccataccaa acgacgagcg tgacaccacg   180
atgcctgtag taatggtaac aacgttgcgc aaactattaa ctggcgaact acttactcta   240
gcttcccggc aacaattaat agactggatg gaggcggata agttgcagg accacttctg    300
cgctcggccc ttccggctgg ctggtttatt gctgataaat ctggagccgg tgagcgtggg   360
tctcgcggta tcattgcagc actggggcca gatggtaagc cctcccgtat cgtagttatc   420
tacacgacgg ggagtcaggc aactatggat gaacgaaata cagatcgctg tgagataggt   480
gcctcactga ttaagcattg gtaactgtca gaccaagttt actcatatat actttagatt   540
gatttaaaac ttcatttta atttaaaagg atctaggtga agatcctttt tgataatctc   600
atgaccaaaa tcccttaacg tgagttttcg ttccactgag cgtcagaccc cgtagaaaag   660
atcaaaggat cttcttgaga tcctttttt ctgcgcgtaa tctgctgctt gcaaacaaaa    720
aaaccaccgc taccagcggt ggtttgtttg ccggatcaag agctaccaac tctttttccg   780
aaggtaactg gcttcagcag agcgcagata ccaaatactg tccttctagt gtagccgtag   840
ttaggccacc acttcaagaa ctctgtagca ccgcctacat acctcgctct gctaatcctg   900
ttaccagtgg ctgctgccag tggcgataag tcgtgtctta ccgggttgga ctcaagacga   960
tagttaccgg ataaggcgca gcggtcgggc tgaacggggg gttcgtgcac acagcccagc  1020
ttggagcgaa cgacctacac cgaactgaga tacctacagc gtgagctatg agaaagcgcc  1080
acgcttcccg aagggagaaa ggcggacagg tatccggtaa gcggcagggt cggaacagga  1140
gagcgcacga gggagcttcc agggggaaac gcctggtatc tttatagtcc tgtcgggttt  1200
cgccacctct gacttgagcg tcgatttttg tgatgctcgt caggggggcg gagcctatgg  1260
aaaaacgcca gcaacgcggc cttttacgg ttcctggcct tttgctggcc ttttgctcac   1320
atgttctttc ctgcgttatc ccctgattct gtggataacc gtattaccgc ctttgagtga  1380
```

```
gctgataccg ctcgccgcag ccgaacgacc gagcgcagcg agtcagtgag cgaggaagcg   1440
gaagagcgcc caatacgcaa accgcctctc cccgcgcgtt ggccgattca ttaatgcagc   1500
tggcacgaca ggtttccgga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccgggcgt cgggcgacct ttggtcgccc ggcctcagtg agcgagcgag cgcgcagaga   1800
gggagtggcc aactccatca ctaggggttc cttgtagtta atgattaacc cgccatgcta   1860
cttatctacg tagccatgct ctaggaagat cggaattcgt acacgcctac ctcgacccat   1920
caagtgccac ctgacgtctc cctatcagtg atagagaagt cgacacgtct cgagctccct   1980
atcagtgata gagaaggtac gtctagaacg tctccctatc agtgatagag aagtcgacac   2040
gtctcgagct ccctatcagt gatagagaag gtacgtctag aacgtctccc tatcagtgat   2100
agagaagtcg acacgtctcg agctccctat cagtgataga gaaggtacgt ctagaacgtc   2160
tccctatcag tgatagagaa gtcgacacgt ctcgagctcc ctatcagtga tagagaaggt   2220
accccctata taagcagagc tcgtttagtg aaccgtcaga tcgcctggag acgccatcca   2280
cgctgttttg acctccatag aagacaccgg gaccgatcca gcctggatcg cggccgcgcc   2340
accatggctg acacctggcc ttcagacttc gccttctcac ccccaccagg tggggtgat   2400
gggtcagcag ggctggagcc ggctgggtg gatcctcgaa cctggctaag cttccaagg   2460
cctccaggtg ggcctggaat cggaccaggc tcagaggtat tggggatctc ccatgtccg   2520
cccgcatacg agttctgcgg agggatggca tactgtggac ctcaggttgg actgggccta   2580
gtcccccaag ttggcgtgga gactttgcag cctgagggcc aggcaggagc acgagtggaa   2640
agcaactcag agggaacctc ctctgaaccc tgtgccgaac ccccaatgc cgtgaagttg   2700
gagaaggtgg aaccaactcc cgaggagtcc caggacatga aagccctgca gaaggagcta   2760
gaacagtttg ccaagctgct gaagcagaag aggatcacct tggggtacac ccaggccgac   2820
gtggggctca ccctgggcgt tctctttgga aaggtgttca gccagaccac catctgtcgc   2880
ttcgaggcct tgcagctcag ccttaagaac atgtgtaagc tgcgccccct gctggagaag   2940
tgggtggagg aagccgacaa caatgagaac cttcaggaga tatgcaaatc ggagaccctg   3000
gtgcaggccc ggaagagaaa gcgaactagc attgagaacc gtgtgaggtg gagtctggag   3060
accatgtttc tgaagtgccc gaagccctcc ctacagcaga tcactcacat cgccaatcag   3120
cttggctag agaaggatgt ggttcgagta tggttctgta accggcgcca gaagggcaaa   3180
agatcaagta ttgagtattc ccaacgagaa gagtatgagg ctacagggac acctttccca   3240
ggggggggctg tatcctttcc tctgccccca ggtcccact ttggcacccc aggctatgga   3300
agcccccact tcaccacact ctactcagtc ccttttcctg agggcgaggc cttccctct   3360
gttccgtca ctgctctggg ctctcccatg cattcaaacg ctagcggcag cggcgccacg   3420
aacttctctc tgttaaagca agcaggagat gttgaagaaa accccgggcc tgcatgcatg   3480
tataacatga tggagacgga gctgaagccg ccgggcccgc agcaagcttc gggggcggc   3540
ggcggaggag gcaacgccac ggcggcgcg accggcggca accagaagaa cagcccggac   3600
cgcgtcaaga ggcccatgaa cgccttcatg gtatggtccc gggggcagcg gcgtaagatg   3660
gcccaggaga acccccaagat gcacaactcg gagatcagca agcgcctggg cgcggagtgg   3720
aaacttttgt ccgagaccga gaagcggccg ttcatcgacg aggccaagcg gctgcgcgct   3780
ctgcacatga aggagcaccc ggattataaa taccggccgc ggcggaaaac caagacgctc   3840
atgaagaagg ataagtacac gcttcccgga ggcttgctgg ccccgggcgg aacagcatg   3900
gcgagcgggg ttggggtggg cgccggcctg ggtgcggcg tgaaccagcg catggacagc   3960
tacgcgcaca tgaacggctg gagcaacggc agctacagca tgatgcagga gcagctgggc   4020
tacccgcagc acccgggcct caacgctcac ggcgcggcac agatgcaacc gatgcaccgc   4080
tacgacgtca gcgccctgca gtacaactcc atgaccagct cgcagaccta catgaacggc   4140
tcgcccacct acagcatgtc ctactcgcag cagggcaccc ccggtatggc gctgggctcc   4200
atgggctctg tggtcaagtc cgaggccagc tccagccccc ccgtggttac ctcttcctcc   4260
cactccaggg cgccctgcca ggcggggac ctccgggaca tgatcagcat gtaccctccc   4320
ggcgccgagg tgccggagcc cgctgcgccc agtagactgc acatgcccca gcactaccag   4380
agcggcccgg tgcccggcac ggccattaac ggcacactgc ccctgtcgca catggcatgg   4440
ggctccggcg agggcagggg aagtcttcta acatgcgggg acgtggagga aaatcccggc   4500
ccactcgaga tgaggcagcc acctggcgag tctgacatgg ctgtcagcga cgtctctctc   4560
ccgtccttct ccacgttcgc gtccggcccg gcgggaaggg agaagacact gcgtccagca   4620
ggtgccccga ctaaccgttg gcgtgaggaa ctctctcaca tgaagcgact tccccactt   4680
cccggccgcc cctacgacct ggcggcgacg gtgccacag acctggagag tggcggagct   4740
ggtgcagctt gcagcagtaa caacccggcc ctcctagccc ggagggagac cgaggagttc   4800
aacgacctcc tggacctaga ctttatcctt tccaactcgc taaccaccca ggaatcggtg   4860
gccgccaacg tgaccacctc ggcgtcagct tcatcctcgt cttccccagc gagcagggc   4920
cctgccagcg cgccctccac ctgcagcttc agctatccga tccgggccgg gggtgacccg   4980
ggcgtggctg ccagcaacac aggtggagg ctcctctaca gccgagaatc tgcgccacct   5040
cccacgcgcc ccttcaacct ggcggacatc aatgacgtga gccctcggg cggcttcgtg   5100
gctgagctcc tgcggccgga gttggaccca gtatacattc gccacagca gcctcagccg   5160
ccaggtgggc ggctgatggg caagtttgtg ctgaaggcgt ctctgaccac ctgctggcagc   5220
gagtacagca gcccttcggt catcagtgtt agcaaaggaa gcccagacgg cagccacccc   5280
gtggtagtgg cgccctacag cggtggcccg ccgcgcatgt gccccaagat taagcaagag   5340
gcggtcccgt cctgcacggt cagccggtcc ctagaggccc atttgagcgc tggacccag   5400
ctcagcaacg gccaccggcc caacacacac gacttcccc tggggcggca gctccccacc   5460
aggactaccc ctacactgag tcccgaggaa ctgctgaaca gcagggactg tcaccctggc   5520
ctgcctcttc ccccaggatt ccatcccat ccggggccca actaccctcc tttcctgcca   5580
gaccagatgc agtcacaagt cccctctctc cattatcaag agctcatgcc accgggttcc   5640
tgcctgccaa aggagcccaa gccaagagag ggaagaaggt cgtggcccg gaaaagaaca   5700
gccacccaca cttgtgacta tgcaggctgt ggcaaaacct ataagagag ttctcatctc   5760
aaggcacacc tgcgaactca cacaggcgag aaacttacc actgtgactg ggacggctgt   5820
gggtggaaat tcgcccgctc cgatgaactg accaggcact accgcaaaca cacagggcac   5880
cggcccttc agtgccagaa gtgcgacagg gccttttcca ggtcggacca ccttgcctta   5940
cacatgaaga ggcactaaat gactagtcta gcaatcaacc tctggattac aaaatttgtg   6000
aaagattgac tggtattctt aactatgttg ctccttttac gctatgtgga tacgctgctt   6060
taatgccttt gtatcatgct attgcttccc gtatggcttt cattttctcc tccttgtata   6120
```

```
aatcctggtt agttcttgcc acggcgaaac tcatcgccgc ctgccttgcc cgctgctgga   6180
caggggctcg gctgttgggc actgacaatt ccgtggtgtt tatttgtgaa atttgtgatg   6240
ctattgcttt atttgtaacc attctagctt tatttgtgaa atttgtgatg ctattgcttt   6300
atttgtaacc attataagct gcaataaaca agttaacaac aacaattgca ttcattttat   6360
gtttcaggtt caggggggaga tgtgggaggt ttttaaagc cggggatcca aattcccgat   6420
aaggatcttc ctagagcatg gctacgtaga taagtagcat ggcgggttaa tcattaacta   6480
caaggaaccc ctagtgatgg agttggccac tccctctctg cgcgctcgct cgctcactga   6540
ggccgggcga ccaaaggtcg cccgacgccc gggctttgcc cgggcggcct cagtgagcga   6600
gcgagcgcgc agccttaatt aacctaattc actggccgtc gttttacaac gtcgtgactg   6660
ggaaaaccct ggcgttaccc aacttaatcg ccttgcagca catccccctt tcgccagctg   6720
gcgtaatagc gaagaggccc gcaccgatcg cccttcccaa cagttgcgca gcctgaatgg   6780
cgaatgggac gcgccctgta gcggcgcatt aagcgcggcg ggtgtggtgg ttacgcgcag   6840
cgtgaccgct acacttgcca gcgccctagc gcccgctcct ttcgctttct tcccttcctt   6900
tctcgccacg ttcgccggct ttccccgtca agctctaaat cggggggctcc ctttagggtt   6960
ccgatttagt gctttacggc acctcgaccc caaaaaactt gattagggtg atggttcacg   7020
tagtgggcca tcgccctgat agacggtttt tcgccctttg acgttggagt ccacgttctt   7080
taatagtgga ctcttgttcc aaactggaac aacactcaac cctatctcgg tctattcttt   7140
tgatttataa gggattttgc cgatttcggc ctattgtta aaaaatgagc tgatttaaca   7200
aaaatttaac gcgaatttta acaaaatatt aacgtttata atttcaggtg gcatctttcg   7260
gggaaatgtg cgcggaaccc ctatttgttt atttttctaa atacattcaa atatgtatcc   7320
gctcatgaga caataaccct gataaatgct tcaataatat tgaaaaagga agagtatgag   7380
tattcaacat ttccgtgtcg cccttattcc cttttttgcg gcattttgcc ttcctgtttt   7440
tgctcaccca gaaacgctgg tgaaagtaaa agatgctgaa gatcagttgg gtgcacgagt   7500
gggttacatc gaactggatc tcaatagtgg taagatcctt gagagttttc gccccgaaga   7560
acgttttcca atgatgagca cttttaaagt tctgctatgt ggcgcggtat tatcccgtat   7620
tgacgccggg caagagcaac tcggtcgccg catacactat tctcagaatg acttggttga   7680
gtactcacca gtcacagaaa agcatcttac ggatggcatg acagtaagag aa            7732

SEQ ID NO: 34         moltype = DNA   length = 186
FEATURE               Location/Qualifiers
misc_feature          1..186
                      note = Synthetic Polynucleotide
source                1..186
                      mol_type = other DNA
                      organism = synthetic construct
SEQUENCE: 34
gaggccagcg gttccggacg ggctgacgca ttggacgatt ttgatctgga tatgctggga   60
agtgacgccc tcgatgattt tgaccttgac atgcttggtt cggatgccct tgatgacttt   120
gacctcgaca tgctcggcag tgacgccctt gatgatttcg acctggacat gctgattaac   180
tctaga                                                               186

SEQ ID NO: 35         moltype = DNA   length = 783
FEATURE               Location/Qualifiers
misc_feature          1..783
                      note = Synthetic Polynucleotide
source                1..783
                      mol_type = other DNA
                      organism = synthetic construct
SEQUENCE: 35
agccagtacc tgcccgacac cgacgaccgg caccggatcg aggaaaagcg gaagcggacc   60
tacgagacat tcaagagcat catgaagaag tcccccttca gcggcccccac cgaccctgga   120
cctccaccta gaagaatcgc cgtgcccagc agatccagcg ccagcgtgcc aaaacctgcc   180
ccccagcctt accccttcac cagcagcctg agcaccatca actacgacga gttccctacc   240
atggtgttcc ccagcggcca gatctctcag gcctctgctc tggctccagc ccctcctcag   300
gtgctgcctc aggctcctgc tcctgcacca gtccagcaca tggtctctgc actggctcag   360
gcaccagcac ccgtgcctgt gctggctcct ggacctccac aggctgtggc tccaccagcc   420
cctaaaccta cacaggccgg cgagggcaca ctgtctgaag ctgctgctgca gctgcagttc   480
gacgacgagg atcgggagc cctgctggga aacagcaccg atcctgccgt gttcaccgac   540
ctggccagcg tggacaacag cgagttccag cagctgctga accagggcat cctgtgtgcc   600
cctcacacca ccgagcccat gctgatggaa taccccgagg ccatcacccg gctcgtgaca   660
ggcgctcaga ggcctcctga tccagctcct gcccctctgg gagcaccagg cctgcctaat   720
ggactgctgt ctggcgacga ggacttcagc tctatcgccg atatggattt ctcagccttg   780
ctg                                                                 783

SEQ ID NO: 36         moltype = DNA   length = 570
FEATURE               Location/Qualifiers
misc_feature          1..570
                      note = Synthetic Polynucleotide
source                1..570
                      mol_type = other DNA
                      organism = synthetic construct
SEQUENCE: 36
cgggattcca gggaagggat gttttttgccg aagcctgagg ccggctccgc tattagtgac   60
gtgttttgagg gccgcgaggt gtgccagcca aaacgaatcc ggcattttca tcctccagga   120
agtccatggg ccaaccgccc actccccgcc agcctcgcac caacaccaac cggtccagta   180
catgagccag tcgggtcact gaccccggca ccagtccctc agccactgga tccagcgccc   240
gcagtgactc ccgaggccag tcacctgttg gaggatcccg atgaagagac gagccaggct   300
gtcaaagccc ttcgggagat ggccgatact gtgattcccc agaaggaaga ggctgcaatc   360
tgtggccaaa tggacctttc ccatccgccc ccaagggggc atctgatga gctgacaacc   420
```

```
acacttgagt ccatgaccga ggatctgaac ctggactcac ccctgacccc ggaattgaac    480
gagattctgg ataccttcct gaacgacgag tgcctcttgc atgccatgca tatcagcaca    540
ggactgtcca tcttcgacac atctctgttt                                     570

SEQ ID NO: 37         moltype = DNA   length = 1416
FEATURE               Location/Qualifiers
misc_feature          1..1416
                      note = Synthetic Polynucleotide
source                1..1416
                      mol_type = other DNA
                      organism = synthetic construct
SEQUENCE: 37
gcttcaaact ttactcagtt cgtgctcgtg gacaatggtg ggacagggga tgtgacagtg     60
gctccttcta atttcgctaa tggggtggca gagtggatca gctccaactc acggagccag    120
gcctacaagg tgacatgcag cgtcaggcag tctagtgccc agaagagaaa gtataccatc    180
aaggtggagg tccccaaagt ggctacccag acagtgggcg gagtcgaact gcctgtcgcc    240
gcttggaggt cctacctgaa catggagctc actatcccaa ttttcgctac caattctgac    300
tgtgaactca tcgtgaaggc aatgcagggg ctcctcaaag acggtaatcc tatccctcc    360
gccatcgccg ctaactcagg tatctacagc gctggaggag gtggaagcgg aggaggagga    420
agcggaggag gaggtagcgg acctaagaaa aagaggaagg tggcggccgc tggatcccct    480
tcagggcaga tcagcaacca ggccctggct ctggccccta gctccgctcc agtgctggcc    540
cagactatgg tgcctctag tgctatggtg cctctgtgc agccacctgc tccagcccct    600
gtgctgaccc caggaccacc ccagtcactg agcgctccag tgcccaagtc tacacaggcc    660
ggcgagggga ctctgagtga agctctgctg cacctgcagt tcgacgctga tgaggacctg    720
ggagctctgc tggggaacag caccgatccc ggagtgttca cagatctggc ctccgtggac    780
aactcagagt ttcagcagct gctgaatcag ggcgtgtcca tgtctcatag tacagccgaa    840
ccaatgctga tggagtaccc cgaagccatt accggctgg tgaccggcag ccagcgggcc    900
cccgacccg ctccaactcc cctgggaacc agccggcctgc ctaatgggct gtccggagat    960
gaagacttct caagcatcgc tgatatggac tttagtgccc tgctgtcaca gatttcctct   1020
agtgggcagg gaggaggtgg aagcggcttc agcgtggaca ccagtgccct gctggacctg   1080
ttcagcccct cggtgaccgt gcccgacatg agcctgcctg accttgacag cagcctggcc   1140
agtatccaag agctcctgtc tccccaggag ccccccaggc ctcccgaggc agagaacagc   1200
agcccggatt cagggaagca gctggtgcac tacacagcgc agccgctgtt cctgctggac   1260
cccggctccg tggacaccgg gagcaacgac ctgccggtgc tgtttgagct gggagagggc   1320
tcctacttct ccgaagggga cggcttcgcc gaggacccca ccatctccct gctgacaggc   1380
tcggagcctc caaagccaa ggaccccact gtctcc                              1416

SEQ ID NO: 38         moltype = DNA   length = 3594
FEATURE               Location/Qualifiers
misc_feature          1..3594
                      note = Synthetic Polynucleotide
source                1..3594
                      mol_type = other DNA
                      organism = synthetic construct
SEQUENCE: 38
atggcgggac acctggcttc ggatttcgcc ttctcgcccc ctccaggtgg tggaggtgat     60
gggccagggg ggccggagcc gggctgggtt gatcctcgga cctggctaag cttccaaggc    120
cctcctggag ggccaggaat cgggccgggg gttgggccag gctctgaggt gtgggggatt    180
cccccatgcc ccccgccgta tgagttctgt gggggatgg cgtactgtgg ccccaggtt    240
ggagtgggc tagtgcccca aggcggcttg agagacctctc agcctgaggg cgaagcagga    300
gtcgggggtgg agagcaactc cgatgggcc tccccggagc cctgcaccgt caccccctgg    360
gccgtgaagc tggagaagga gaagctggag caaaacccgg aggagtccca ggacatcaaa    420
gctctgcaga agaactcga gcaatttgcc aagctcctga gcagaagag gatcaccctg    480
ggatataca aggccgatgt gggctcacc ctggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga aagagaaagc gaaccagtat cgagaaccga    720
gtgagaggca acctggagaa tttgttcctg cagtgcccga accacact gcagcagatc    780
agccacatcg cccagcagct tgggctcgag aaggatgtgg tccgagtgtg gttctgtaac    840
cggcgccaga agggcaagcg atcaagcagc gactatgcac aacgaggaga ttttgaggct    900
gctgggtctc ctttctcagg gggaccagtg tcctttcctc tggccccagg ccccatttt    960
ggtacccag gctatgggag ccctcacttc actgcactgt actcctcggt ccctttcct   1020
gaggggggaag ccttcccccc tgtctctgtc accactctgg gctctcccat gcattcaaac   1080
gctagcggca gggcgccac gaacttctct ctgttaaagc aagcaggaga tgttgaagaa   1140
aaccccggc ctgcatgcat gtacaacatg atggagacgg agctgaagcc gccgggcccg   1200
cagcaaactt cggggggcgg cggcggcaac tccaccgcgg cggcggccgg cggcaaccag   1260
aaaaacagcc cggaccgcgt caagcggccc atgaatgcct tcatggtgtg gtcccgcggg   1320
cagcggcgca gatggcccca ggagaaccac aagatgcaca actcggagat cagcaagcgc   1380
ctgggcgccg agtggaaact tttgtcggag acggagaagc ggcgtttcat cgacgaggct   1440
aagcggctgc gagcgctgca catgaaggag caccgggatt ataaataccg gccccggcgg   1500
aaaaccaaga cgctcatgaa gaaggataag tacacgctgc ccggcgggct gctggccccc   1560
ggcggcaata gcatggcgag cggggtcggg gtgggcgccg gctgggcgc gggcgtgaac   1620
cagcgcatgg acagttacgc gcacatgaac ggctgggca acggcagcta cagcatgatg   1680
caggaccagc tgggctaccc gcagcacccg ggcctcaatg cgcacggcgc agcgcagatg   1740
cagcccatgc accgctacga cgtgagcgcc ctgcagtaca actccatgac cagctcgcag   1800
acctacatga acggctcgcc cacctacagc atgtcctact cgcagcaggg caccccctgc   1860
atggctcttg gctccatggg ttcggtggtc aagtccgagg ccagtccag ccccctgtg   1920
gttacctctt cctcccactc cagggcgccc tgccaggccg ggaccctcgg gacatgatc   1980
agcatgtatc tccccggcgc cgaggtgccg gaacccgccg ccccagcag acttcacatg   2040
```

```
tcccagcact accagagcgg cccggtgccc ggcacggcca ttaacggcac actgcccctc   2100
tcacacatgg catgcggctc cggcgagggc aggggaagtc ttctaacatg cggggacgtg   2160
gaggaaaatc ccggcccact cgagatggct gtcagcgacg cgctgctccc atctttctcc   2220
acgttcgcgt ctgccccggc gggaaggag aagacactgc gtcaagcagg tgccccgaat   2280
aaccgctggc gggaggagct ctcccacatg aagcgacttc cccagtgct tcccggccgc   2340
ccctatgacc tggcggcggc gaccgtggcc acagacctgg agagcggcgg agccggtgcg   2400
gcttgcggcg gtagcaacct ggcgccccta cctcggagag agaccgagga gttcaacgat   2460
ctcctgacc tggactttat tctctccaat tcgctgaccc atcctccgga gtcagtggcc   2520
gccaccgtgt cctcgtcagc gtcagcctcc tcttcgtcgt cgccgtcgag cagcggccct   2580
gccagcgcc cctccacctg cagcttcacc tatccgatcc gggccgggaa cgacccgggc   2640
gtggcgccgg gcggcacggg cggaggcctc tctatggca gggagtccgc tccccctccg   2700
acggctccct caacctggc ggacatcaac gacgtgagcc cctcgggcgg cttcgtggcc   2760
gagctcctgc ggccagaatt ggaccccgtg tacattccgc cgcagcagcc gcagccgcca   2820
ggtggccggg tgatgggcaa gttcgtgctg aaggcgtgc tgagcgcccc tggcagcgag   2880
tacggcagcc cgtcggtcat cagcgtcagc aaaggcagcc ctgacggcag ccaccccggtg   2940
gtggtggcgc cctacaacgg cgggccgccg cgcacgtgcc caagatcaa gcaggaggcg   3000
gtctcttcgt gcacccactt gggcgctgga cccctcta gcaatggcca ccggccggct   3060
gcacacgact tcccctggg gcggcacgtc cccagcagga ctaccccgac cctgggtctt   3120
gaggaagtgc tgagcagcag ggactgtcac cctgccctgc cgcttcctcc cggcttccat   3180
ccccacccgg ggcccaatta cccatccttc ctgcccgatc agatgcagcc gcaagtcccg   3240
ccgctccatt accaagagct catgccaccc ggttcctgca tgccagagga gcccaagcca   3300
aagaggggaa gacgatcgtg gccccggaaa aggaccgcca cccacacttg tgattacgcg   3360
ggctgcggca aaacctacac aaagagttcc catctcaagg cacacctgcg aacccacaca   3420
ggtgagaaac cttaccactg tgactgggac ggctgtggat ggaaattcgc ccgctcagat   3480
gaactgacca ggcactaccg taaacacacg ggcaccgcc cgttccagtg ccaaaaatgc   3540
gaccgagcat tttccaggtc ggaccacctc gccttacaca tgaagaggca tttt          3594

SEQ ID NO: 39       moltype = AA   length = 1198
FEATURE             Location/Qualifiers
REGION              1..1198
                    note = Synthetic Polypeptide
source              1..1198
                    mol_type = protein
                    organism = synthetic construct
SEQUENCE: 39
MAGHLASDFA FSPPPGGGGD GPGGPEPGWV DPRTWLSFQG PPGGPGIGPG VGPGSEVWGI    60
PPCPPPYEFC GGMAYCGPQV GVGLVPQGGL ETSQPEGEAG VGVESNSDGA SPEPCTVTPG   120
AVKLEKEKLE QNPEESQDIK ALQKELEQFA KLLKQKRITL GYTQADVGLT LGVLFGKVFS   180
QTTICRFEAL QLSFKNMCKL RPLLQKWVEE ADNNENLQEI CKAETLVQAR KRKRTSIENR   240
VRGNLENLFL QCPKPTLQQI SHIAQQLGLE KDVVRVWFCN RRQKGKRSSS DYAQREDFEA   300
AGSPFSGGPV SFPLAPGPHF GTPGYGSPHF TALYSSVPFP EGEAFPPVSV TTLGSPMHSN   360
ASGSGATNFS LLKQAGDVEE NPGPACMYNM METELKPPGP QQTSGGGGGN STAAAAGGNQ   420
KNSPDRVKRP MNAFMVWSRG QRRKMAQENP KMHNSEISKR LGAEWKLLSE TEKRPFIDEA   480
KRLRALHMKE HPDYKYRPRR KTKTLMKKDK YTLPGGLLAP GGNSMASGVG VGAGLGAGVN   540
QRMDSYAHMN GWSNGSYSMM QDQLGYPQHP GLNAHGAAQM QPMHRYDVSA LQYNSMTSSQ   600
TYMNGSPTYS MSYSQQGTPG MALGSMGSVV KSEASSSPPV VTSSSHSRAP CQAGDLRDMI   660
SMYLPGAEVP EPAAPSRLHM SQHYQSGPVP GTAINGTLPL SHMACGSGEG RGSLLTCGDV   720
EENPGPLEMA VSDALLPSFS TFASGPAGRE KTLRQAGAPN NRWREELSHM KRLPPVLPGR   780
PYDLAAATVA TDLESGGAGA ACGGSNLAPL PRRETEEFND LLDLDFILSN SLTHPPESVA   840
ATVSSSASAS SSSSPSSSGP ASAPSTCSFT YPIRAGNDPG VAPGGTGGGL LYGRESAPPP   900
TAPFNLADIN DVSPSGGFVA ELLRPELDPV YIPPQQPQPP GGGLMGKFVL KASLSAPGSE   960
YGSPSVISVS KGSPDGSHPV VVAPYNGGPP RTCPKIKQEA VSSCTHLGAG PPLSNGHRPA  1020
AHDFPLGRQL PSRTTPTLGL EEVLSSRDCH PALPLPPGFH PHPGPNYPSF LPDQMQPQVP  1080
PLHYQELMPP GSCMPEEPKP KRGRRSWPRK RTATHTCDYA GCGKTYTKSS HLKAHLRTHT  1140
GEKPYHCDWD GCGWKFARSD ELTRHYRKHT GHRPFQCQKC DRAFSRSDHL ALHMKRHF    1198

SEQ ID NO: 40       moltype = DNA   length = 1080
FEATURE             Location/Qualifiers
source              1..1080
                    mol_type = genomic DNA
                    organism = Homo sapiens
SEQUENCE: 40
atggcgggac acctggcttc ggatttcgcc ttctcgcccc ctccaggtgg tggaggtgat     60
gggccagggg ggccggagcc gggctgggtt gatcctcgga cctggctaag cttccaaggc    120
cctcctggag ggcaggaat cgggccgggg gttgggccag gctctgaggt gtggggatt     180
ccccccatgcc ccccgccgta tgagttctgt ggggggatgg cgtactgtgg gccccaggtt    240
ggagtggggc tagtgcccca aggcggcttg agacctctc agcctgaggg cgaagcagga    300
gtcggggtgg agagcaactc cgatgggcc tcccccggagc cctgcaccgt caccccctggt    360
gccgtgaagc tggagaagga gaagctggag caaaaccccgg aggagtccca ggacatcaaa    420
gctctgcaga agaaactcga gcaatttgcc aagctcctga gcagaagag gatcaccctg    480
ggatatacac aggccgatgt ggggctcacc ctggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcgt aaaaccctcgt gcaggcccga aagagaagaa ccacagtat cgagaaccga    720
gtgagaggca acctgagaa tttgttcctg cagtgcccga aacccacact gcagcagatc    780
agccacatcg cccagcagct ggctctgag aaggatgtgg tccgagtgtg gttctgtaac    840
cggcgccaga aggcaagcg atcaagcagc gactatgcac aacgagagga ttttgaggct    900
gctgggtctc ctttctcagg ggaccagtg tcctttcctc tggccccagg gccccatttt    960
ggtacccag gctatgggag cctcacttc actgcactgt actcctcggt cccttttcct   1020
```

```
                 gaggggggaag cctttccccc tgtctctgtc accactctgg gctctcccat gcattcaaac    1080

SEQ ID NO: 41           moltype = AA   length = 360
FEATURE                 Location/Qualifiers
source                  1..360
                        mol_type = protein
                        organism = Homo sapiens
SEQUENCE: 41
MAGHLASDFA FSPPPGGGGD GPGGPEPGWV DPRTWLSFQG PPGGPGIGPG VGPGSEVWGI      60
PPCPPPYEFC GGMAYCGPQV GVGLVPQGGL ETSQPEGEAG VGVESNSDGA SPEPCTVTPG     120
AVKLEKEKLE QNPEESQDIK ALQKELEQFA KLLKQKRITL GYTQADVGLT LGVLFGKVFS     180
QTTICRFEAL QLSFKNMCKL RPLLQKWVEE ADNNENLQEI CKAETLVQAR KRKRTSIENR     240
VRGNLENLFL QCPKPTLQQI SHIAQQLGLE KDVVRVWFCN RRQKGKRSSS DYAQREDFEA     300
AGSPFSGGPV SFPLAPGPHF GTPGYGSPHF TALYSSVPFP EGEAFPPVSV TTLGSPMHSN     360

SEQ ID NO: 42           moltype = DNA   length = 951
FEATURE                 Location/Qualifiers
source                  1..951
                        mol_type = genomic DNA
                        organism = Homo sapiens
SEQUENCE: 42
atgtacaaca tgatggagac ggagctgaag ccgccgggcc cgcagcaaac ttcggggggc       60
ggcggcggca actccaccgc ggcggcggcc ggcggcaacc agaaaaacag cccgaccgc      120
gtcaagcggc ccatgaatgc cttcatggtg tggtcccgcg gcagcggcg caagatggcc      180
caggagaacc ccaagatgca caactcggag atcagcaagc gcctgggcgc cgagtggaaa     240
cttttgtcgg agacggagaa gcggccgttc atcgacgagg ctaagcggct gcgagcgctg     300
cacatgaagg agcacccgga ttataaatac cggccccggc ggaaaaccaa gacgctcatg     360
aagaaggata gtacacgct gcccggcggg ctgctggccc ccggcggcaa tagcatggcg      420
agcggggtcg ggtgggcgc cggcctgggc gcgggcgtga accagcgcat ggacagttac      480
gcgcacatga acggctggag caactcgcag tacagcatga tgcaggacca gctgggctac     540
ccgcagcacc cgggcctcaa tgcgcacggc gcagcgcaga tgcagcccat gcaccgctac     600
gacgtgagcg ccctgcagta caactccatg accagctcgc agacctacat gaacggctcg     660
cccacctaca gcatgtccta ctcgcagcag ggcacccctg gcatggctct tggctccatg     720
ggttcggtgg tcaagtccga ggccagctcc agcccccctg tggttacctc ttcctcccac     780
tccagggcgc cctgccaggc cggggacctc cgggacatga tcagcatgta tctccccggc     840
gccgaggtgc cggaaccccgc cgcccccagc agacttcaca tgtcccagca ctaccagagc     900
ggcccggtgc ccggcacggc cattaacggc acactgcccc tctcacacat g              951

SEQ ID NO: 43           moltype = AA   length = 317
FEATURE                 Location/Qualifiers
source                  1..317
                        mol_type = protein
                        organism = Homo sapiens
SEQUENCE: 43
MYNMMETELK PPGPQQTSGG GGGNSTAAAA GGNQKNSPDR VKRPMNAFMV WSRGQRRKMA       60
QENPKMHNSE ISKRLGAEWK LLSETEKRPF IDEAKRLRAL HMKEHPDYKY RPRRKTKTLM      120
KKDKYTLPGG LLAPGGNSMA SGVGVGAGLG AGVNQRMDSY AHMNGWSNGS YSMMQDQLGY      180
PQHPGLNAHG AAQMQPMHRY DVSALQYNSM TSSQTYMNGS PTYSMSYSQQ GTPGMALGSM      240
GSVVKSEASS SPPVVTSSSH SRAPCQAGDL RDMISMYLPG AEVPEPAAPS RLHMSQHYQS      300
GPVPGTAING TLPLSHM                                                    317

SEQ ID NO: 44           moltype = DNA   length = 1410
FEATURE                 Location/Qualifiers
source                  1..1410
                        mol_type = genomic DNA
                        organism = Homo sapiens
SEQUENCE: 44
atggctgtca gcgacgcgct gctcccatct ttctccacgt tcgcgtctgg cccggcggga       60
agggagaaga cactgcgtca agcaggtgcc ccgaataacc gcgcgccct gctgcgggga      120
cacatgaagc gacttccccc agtgcttccc ggcgcttcc atgacctggc ggcggcgacc      180
gtggccacag acctgagag cggcggagcc ggtgcggctt gcgcggtag caacctggcg      240
cccctacctc ggagagagac cgaggagttc aacgatctcc tggacctgga cttatattctc     300
tccaattcgc tgacccatcc tccggagtca gtggccgcca ccgtgtcctc gtcagcgtca     360
gcctcctctt cgtcgtcgcc gtcgagcagc ggccctgcca gcgcccctc cacctgcagc     420
ttcacctatc cgatccgggc cggaaccgac ccgggcgtgg cgccgggcgg cacgggcgga     480
ggcctcctct atggcaggga gtccgctccc cctccgacgg ctcccttcaa cctggcggac     540
atcaacgacg tgagccctc gggcggcttc gtggccgagc cctgcgcc agaattggac       600
ccggtgtaca ttccgccgca gcagccgcag ccgcaggtg gcgggctgat gggcaagttc     660
gtgctgaagg cgtcgctgag cgccccctggc agcgagtacg gccgcgtc ggtcatcgc       720
gtcagcaaag gcagccctga cggcagccac ccggtggtgg tggcgcccta caacggcggg     780
ccgccgcgca cgtgccccaa gatcaagcag gaggcggtct cttcgtgcac ccacttgggc     840
gctgaccccc ctctcagcaa tggccaccgg ccggctgcac acgacttccc cctggggcgg     900
cagctcccca gcaggactac cccgaccctg ggtcttgagg aagtgctgag cagcagggac     960
tgtcacctg ccctgccgct tcctcccggg ttccatccca acccggggcc caattaccca     1020
tccttcctgc ccgatcagat gcagccgcaa gtcccgccgc tccattacca agagctcatg     1080
ccacccggtt cctgcatgcc agaggagccc aagccaaaga ggggaagacg atcgtggccc     1140
cggaaaagga ccgccacca cacttgtgat tacgcgggct gcggcaaaac ctacacaaag     1200
agttcccatc tcaaggcaca cctgcgaacc cacacaggtg agaaaccta ccactgtgac     1260
tgggacggct gtggatggaa attcgcccgc tcagatgaac tgaccaggca ctaccgtaaa     1320
```

```
cacacggggc accgcccgtt ccagtgccaa aaatgcgacc gagcattttc caggtcggac  1380
cacctcgcct tacacatgaa gaggcatttt                                    1410

SEQ ID NO: 45            moltype = AA  length = 470
FEATURE                  Location/Qualifiers
source                   1..470
                         mol_type = protein
                         organism = Homo sapiens
SEQUENCE: 45
MAVSDALLPS FSTFASGPAG REKTLRQAGA PNNRWREELS HMKRLPPVLP GRPYDLAAAT   60
VATDLESGGA GAACGGSNLA PLPRRETEEF NDLLDLDFIL SNSLTHPPES VAATVSSSAS  120
ASSSSSPSSS GPASAPSTCS FTYPIRAGND PGVAPGGTGG GLLYGRESAP PPTAPFNLAD  180
INDVSPSGGF VAELLRPELD PVYIPPQQPQ PPGGGLMGKF VLKASLSAPG SEYGSPSVIS  240
VSKGSPDGSH PVVVAPYNGG PPRTCPKIKQ EAVSSCTHLG AGPPLSNGHR PAAHDFPLGR  300
QLPSRTTPTL GLEEVLSSRD CHPALPLPPG FHPHPGPNYP SFLPDQMQPQ VPPLHYQELM  360
PPGSCMPEEP KPKRGRRSWP RKRTATHTCD YAGCGKTYTK SSHLKAHLRT HTGEKPYHCD  420
WDGCGWKFAR SDELTRHYRK HTGHRPFQCQ KCDRAFSRSD HLALHMKRHF             470

SEQ ID NO: 46            moltype = DNA  length = 235
FEATURE                  Location/Qualifiers
misc_feature             1..235
                         note = Synthetic Polynucleotide
source                   1..235
                         mol_type = other DNA
                         organism = synthetic construct
SEQUENCE: 46
attttaatct cactagggtt ctgggagcac cccccccac cgctcccgcc ctccacaaag    60
ctcctgggcc cctcctccct tcaaggattg cgaagagctg gtcgcaaatc ctcctaagcc  120
accagcatct cggtcttcag ctcacaccag ccttgagccc agcctgcggc caggggacca  180
cgcacgtccc acccacccag cgactcccca gccgctgccc actcttcctc actca       235

SEQ ID NO: 47            moltype = DNA  length = 229
FEATURE                  Location/Qualifiers
misc_feature             1..229
                         note = Synthetic Polynucleotide
source                   1..229
                         mol_type = other DNA
                         organism = synthetic construct
SEQUENCE: 47
aatgtagtct tatgcaatac tcttgtagtc ttgcaacatg gtaacgatga gttagcaaca   60
tgccttacaa ggagagaaaa agcaccgtgc atgccgattg gtggaagtaa ggtggtacga  120
tcgtgcctta ttaggaaggc aacagacggg tctgacatgg attggacgaa ccactgaatt  180
gccgcattgc agagatattg tatttaagtg cctagctcga tacataaac               229

SEQ ID NO: 48            moltype = DNA  length = 617
FEATURE                  Location/Qualifiers
misc_feature             1..617
                         note = Synthetic Polynucleotide
source                   1..617
                         mol_type = other DNA
                         organism = synthetic construct
SEQUENCE: 48
cattgattat tgactagtta ttaatagtaa tcaattacgg ggtcattagt tcatagccca   60
tatatggagt tccgcgttac ataacttacg gtaaatggcc cgcctggctg accgcccaac  120
gacccccgcc cattgacgtc aataatgacg tatgttccca tagtaacgcc aatagggact  180
ttccattgac gtcaatgggt ggactattta cggtaaactg cccacttggc agtacatcaa  240
gtgtatcata tgccaagtac gccccctatt gacgtcaatg acggtaaatg gcccgcctgg  300
cattatgccc agtacatgac cttatgggac tttcctactt ggcagtacat ctacgtatta  360
gtcatcgcta ttaccatggt gatgcggttt tggcagtaca caatgggcg tggatagcgg  420
tttgactcac ggggatttcc aagtctccac cccattgacg tcaatgggag tttgttttgg  480
caccaaaatc aacgggactt tccaaaatgt cgtaacaact ccgccccatt gacgcaaatg  540
ggcggtaggc gtgtacggtg ggaggtctat ataagcagag ctggtttagt gaaccgtcag  600
atccgctaga gatccgc                                                  617

SEQ ID NO: 49            moltype = DNA  length = 252
FEATURE                  Location/Qualifiers
misc_feature             1..252
                         note = Synthetic Polynucleotide
source                   1..252
                         mol_type = other DNA
                         organism = synthetic construct
SEQUENCE: 49
tcgagtggct ccggtgcccg tcagtgggca gagcgcacat cgcccacagt ccccgagaag   60
ttgggggag gggtcggcaa ttgaaccggt gcctagagaa ggtggcgcgg ggtaaactgg   120
gaaagtgatg tcgtgtactg gctccgcctt tttcccgagg gtgggggaga accgtatata  180
agtgcagtag tcgccgtgaa cgttcttttt cgcaacgggt ttgccgccag aacacaggtg  240
tcgtgaccgc gg                                                       252

SEQ ID NO: 50            moltype = DNA  length = 292
```

```
FEATURE                 Location/Qualifiers
misc_feature            1..292
                        note = Synthetic Polynucleotide
source                  1..292
                        mol_type = other DNA
                        organism = synthetic construct
SEQUENCE: 50
gggccccaga agcctggtgg ttgtttgtcc ttctcagggg aaaagtgagg cggccccttg    60
gaggaagggg ccgggcagaa tgatctaatc ggattccaag cagctcaggg gattgtcttt   120
ttctagcacc ttcttgccac tcctaagcgt cctccgtgac cccggctggg atttcgcctg   180
gtgctgtgtc agccccggtc tcccaggggc ttcccagtgg tccccaggaa ccctcgacag   240
ggcccggtct ctctcgtcca gcaagggcag ggacgggcca caggccaagg gc           292

SEQ ID NO: 51           moltype = DNA  length = 113
FEATURE                 Location/Qualifiers
misc_feature            1..113
                        note = Synthetic Polynucleotide
source                  1..113
                        mol_type = other DNA
                        organism = synthetic construct
SEQUENCE: 51
gcctgtagcc ttaatctctc ctagcagggg gtttgggga gggaggagga gaaagaaagg    60
gccccttatg gctgagacac aatgacccag ccacaaggag ggattaccgg gcg          113

SEQ ID NO: 52           moltype = DNA  length = 281
FEATURE                 Location/Qualifiers
misc_feature            1..281
                        note = Synthetic Polynucleotide
source                  1..281
                        mol_type = other DNA
                        organism = synthetic construct
SEQUENCE: 52
aggtaggaag tggcctttaa ctccatagac cctatttaaa cagcttcgga caggtttaaa    60
catctccttg gataattcct agtatccctg ttcccactcc tactcaggga tgatagctct   120
aagaggtgtt aggggattag gctgaaaatg taggtcaccc ctcagccatc tgggaactag   180
aatgagtgag agaggagaga ggggcagaga cacacacatt cgcatattaa ggtgacgcgt   240
gtggcctcga acaccgagcg accctgcagc gacccgctta a                      281

SEQ ID NO: 53           moltype = DNA  length = 26
FEATURE                 Location/Qualifiers
misc_feature            1..26
                        note = Synthetic Polynucleotide
source                  1..26
                        mol_type = other DNA
                        organism = synthetic construct
SEQUENCE: 53
aacgtatcta cagtttactc cctatc                                        26

SEQ ID NO: 54           moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 54
ggtaggaagt ggtacggaaa g                                             21

SEQ ID NO: 55           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 55
cactgacaat tccgtggtgt                                               20

SEQ ID NO: 56           moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 56
gagatccgac tcgtctgagg                                               20

SEQ ID NO: 57           moltype = DNA  length = 20
```

```
FEATURE               Location/Qualifiers
misc_feature          1..20
                      note = Synthetic Polynucleotide
source                1..20
                      mol_type = other DNA
                      organism = synthetic construct
SEQUENCE: 57
tgggaagaca acctgtaggg                                                   20

SEQ ID NO: 58         moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 58
tgaaccccg tctctaccaa                                                    20

SEQ ID NO: 59         moltype = DNA   length = 19
FEATURE               Location/Qualifiers
misc_feature          1..19
                      note = Synthetic Polynucleotide
source                1..19
                      mol_type = other DNA
                      organism = synthetic construct
SEQUENCE: 59
acatcgccaa tcagcttgg                                                    19

SEQ ID NO: 60         moltype = DNA   length = 23
FEATURE               Location/Qualifiers
misc_feature          1..23
                      note = Synthetic Polynucleotide
source                1..23
                      mol_type = other DNA
                      organism = synthetic construct
SEQUENCE: 60
agaaccatac tcgaaccaca tcc                                               23

SEQ ID NO: 61         moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 61
acagatgcaa ccgatgcacc                                                   20

SEQ ID NO: 62         moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 62
tggagttgta ctgcagggcg                                                   20

SEQ ID NO: 63         moltype = DNA   length = 19
FEATURE               Location/Qualifiers
misc_feature          1..19
                      note = Synthetic Polynucleotide
source                1..19
                      mol_type = other DNA
                      organism = synthetic construct
SEQUENCE: 63
gtgccccgac taaccgttg                                                    19

SEQ ID NO: 64         moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 64
gtcgttgaac tcctcggtct                                                   20
```

```
SEQ ID NO: 65              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 65
atgcccctca acgtgaactt c                                                    21

SEQ ID NO: 66              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 66
cgcaacatag gatggagagc a                                                    21

SEQ ID NO: 67              moltype = DNA   length = 22
FEATURE                    Location/Qualifiers
misc_feature               1..22
                           note = Synthetic Polynucleotide
source                     1..22
                           mol_type = other DNA
                           organism = synthetic construct
SEQUENCE: 67
gcgacaacaa gaagacgcgc at                                                   22

SEQ ID NO: 68              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 68
ctggatgttg ggcaggacgc c                                                    21

SEQ ID NO: 69              moltype = DNA   length = 22
FEATURE                    Location/Qualifiers
misc_feature               1..22
                           note = Synthetic Polynucleotide
source                     1..22
                           mol_type = other DNA
                           organism = synthetic construct
SEQUENCE: 69
aagaaggacg gcaagaagcg ca                                                   22

SEQ ID NO: 70              moltype = DNA   length = 22
FEATURE                    Location/Qualifiers
misc_feature               1..22
                           note = Synthetic Polynucleotide
source                     1..22
                           mol_type = other DNA
                           organism = synthetic construct
SEQUENCE: 70
cgctcgaaga tgtcgttcac ga                                                   22

SEQ ID NO: 71              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 71
gaagaagcct caccgctacc g                                                    21

SEQ ID NO: 72              moltype = DNA   length = 23
FEATURE                    Location/Qualifiers
misc_feature               1..23
                           note = Synthetic Polynucleotide
source                     1..23
                           mol_type = other DNA
                           organism = synthetic construct
SEQUENCE: 72
ggttggtgtc ctcaaacaga ccc                                                  23
```

```
SEQ ID NO: 73          moltype = DNA   length = 22
FEATURE                Location/Qualifiers
misc_feature           1..22
                       note = Synthetic Polynucleotide
source                 1..22
                       mol_type = other DNA
                       organism = synthetic construct
SEQUENCE: 73
aacatccagg gcatcaccaa gc                                              22

SEQ ID NO: 74          moltype = DNA   length = 22
FEATURE                Location/Qualifiers
misc_feature           1..22
                       note = Synthetic Polynucleotide
source                 1..22
                       mol_type = other DNA
                       organism = synthetic construct
SEQUENCE: 74
gttctccagg aacaccttca gc                                              22

SEQ ID NO: 75          moltype = DNA   length = 19
FEATURE                Location/Qualifiers
misc_feature           1..19
                       note = Synthetic Polynucleotide
source                 1..19
                       mol_type = other DNA
                       organism = synthetic construct
SEQUENCE: 75
ccggcctcaa ggctctcta                                                  19

SEQ ID NO: 76          moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 76
tgccgcctca tactctcgaa                                                 20

SEQ ID NO: 77          moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 77
agtgtgacgt tgacatccgt                                                 20

SEQ ID NO: 78          moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 78
tgctaggagc cagagcagta                                                 20

SEQ ID NO: 79          moltype = DNA   length = 21
FEATURE                Location/Qualifiers
misc_feature           1..21
                       note = Synthetic Polynucleotide
source                 1..21
                       mol_type = other DNA
                       organism = synthetic construct
SEQUENCE: 79
tcttcctggt ccccacagtt t                                               21

SEQ ID NO: 80          moltype = DNA   length = 23
FEATURE                Location/Qualifiers
misc_feature           1..23
                       note = Synthetic Polynucleotide
source                 1..23
                       mol_type = other DNA
                       organism = synthetic construct
SEQUENCE: 80
```

```
gcaagaatag ttctcgggat gaa                                          23

SEQ ID NO: 81          moltype = DNA   length = 25
FEATURE                Location/Qualifiers
misc_feature           1..25
                       note = Synthetic Polynucleotide
source                 1..25
                       mol_type = other DNA
                       organism = synthetic construct
SEQUENCE: 81
gtgtcttcct caactttctc cttgg                                        25

SEQ ID NO: 82          moltype = DNA   length = 26
FEATURE                Location/Qualifiers
misc_feature           1..26
                       note = Synthetic Polynucleotide
source                 1..26
                       mol_type = other DNA
                       organism = synthetic construct
SEQUENCE: 82
cgcggacagc cgcggccgtg gattgc                                       26

SEQ ID NO: 83          moltype = DNA   length = 27
FEATURE                Location/Qualifiers
misc_feature           1..27
                       note = Synthetic Polynucleotide
source                 1..27
                       mol_type = other DNA
                       organism = synthetic construct
SEQUENCE: 83
ggctccttgc tgtcattcat cttccac                                      27

SEQ ID NO: 84          moltype = DNA   length = 26
FEATURE                Location/Qualifiers
misc_feature           1..26
                       note = Synthetic Polynucleotide
source                 1..26
                       mol_type = other DNA
                       organism = synthetic construct
SEQUENCE: 84
caccgccgtc aggatctgga agttgg                                       26

SEQ ID NO: 85          moltype = DNA   length = 19
FEATURE                Location/Qualifiers
misc_feature           1..19
                       note = Synthetic Polynucleotide
source                 1..19
                       mol_type = other DNA
                       organism = synthetic construct
SEQUENCE: 85
ccggcctcaa ggctctcta                                               19

SEQ ID NO: 86          moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 86
tgccgcctca tactctcgaa                                              20

SEQ ID NO: 87          moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 87
tcaagcaatg gaccactggg                                              20

SEQ ID NO: 88          moltype = DNA   length = 20
FEATURE                Location/Qualifiers
misc_feature           1..20
                       note = Synthetic Polynucleotide
source                 1..20
                       mol_type = other DNA
                       organism = synthetic construct
```

```
SEQUENCE: 88
tctccatgag ctccctgaca                                                   20

SEQ ID NO: 89         moltype = DNA  length = 22
FEATURE               Location/Qualifiers
misc_feature          1..22
                      note = Synthetic Polynucleotide
source                1..22
                      mol_type = other DNA
                      organism = synthetic construct
SEQUENCE: 89
actcctggtg aacaaagtca ga                                                22

SEQ ID NO: 90         moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 90
catccctgag agctcttgcc                                                   20

SEQ ID NO: 91         moltype = DNA  length = 22
FEATURE               Location/Qualifiers
misc_feature          1..22
                      note = Synthetic Polynucleotide
source                1..22
                      mol_type = other DNA
                      organism = synthetic construct
SEQUENCE: 91
ccaatgtgtc cgtcgtggat ct                                                22

SEQ ID NO: 92         moltype = DNA  length = 22
FEATURE               Location/Qualifiers
misc_feature          1..22
                      note = Synthetic Polynucleotide
source                1..22
                      mol_type = other DNA
                      organism = synthetic construct
SEQUENCE: 92
gttgaagtcg caggagacaa cc                                                22

SEQ ID NO: 93         moltype = DNA  length = 23
FEATURE               Location/Qualifiers
misc_feature          1..23
                      note = Synthetic Polynucleotide
source                1..23
                      mol_type = other DNA
                      organism = synthetic construct
SEQUENCE: 93
acatcaagac atcgtgcgat att                                               23

SEQ ID NO: 94         moltype = DNA  length = 20
FEATURE               Location/Qualifiers
misc_feature          1..20
                      note = Synthetic Polynucleotide
source                1..20
                      mol_type = other DNA
                      organism = synthetic construct
SEQUENCE: 94
ccagcggtac acaaagacca                                                   20

SEQ ID NO: 95         moltype = DNA  length = 21
FEATURE               Location/Qualifiers
misc_feature          1..21
                      note = Synthetic Polynucleotide
source                1..21
                      mol_type = other DNA
                      organism = synthetic construct
SEQUENCE: 95
aagcacctcc gaaagtacgt g                                                 21

SEQ ID NO: 96         moltype = DNA  length = 23
FEATURE               Location/Qualifiers
misc_feature          1..23
                      note = Synthetic Polynucleotide
source                1..23
                      mol_type = other DNA
```

```
                        organism = synthetic construct
SEQUENCE: 96
ctccagctct accttacagt tga                                                  23

SEQ ID NO: 97           moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 97
gatagaacca accatgttga ggg                                                  23

SEQ ID NO: 98           moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 98
tggagctttg tagccagagg t                                                    21

SEQ ID NO: 99           moltype = DNA  length = 22
FEATURE                 Location/Qualifiers
misc_feature            1..22
                        note = Synthetic Polynucleotide
source                  1..22
                        mol_type = other DNA
                        organism = synthetic construct
SEQUENCE: 99
caccattggc aatgagcggt tc                                                   22

SEQ ID NO: 100          moltype = DNA  length = 22
FEATURE                 Location/Qualifiers
misc_feature            1..22
                        note = Synthetic Polynucleotide
source                  1..22
                        mol_type = other DNA
                        organism = synthetic construct
SEQUENCE: 100
aggtctttgc ggatgtccac gt                                                   22

SEQ ID NO: 101          moltype = DNA  length = 492
FEATURE                 Location/Qualifiers
source                  1..492
                        mol_type = genomic DNA
                        organism = Homo sapiens
SEQUENCE: 101
gatccggttc caggcctcgg ccctaaatag tctccctggg ctttcaagag aaccacatga           60
gaaaggagga ttcgggctct gagcagtttc accacccacc ccccagtctg caaatcctga          120
cccgtgggtc cacctgcccc aaaggcggac gcaggacagt agaagggaac agagaacaca          180
taaacacaga gagggccaca gcggctccca cagtcaccgc caccttcctg gcggggatgg          240
gtggggcgtc tgagtttggt tcccagcaaa tccctctgag ccgcccttgc gggctcgcct          300
caggcagg ggagcaagag gtgggaggag gaggtctaag tcccaggccc aattaagaga           360
tcaggtagtg tagggtttgg gagcttttaa ggtgaagagg cccgggctga tcccacaggc          420
cagtataaag cgccgtgacc ctcaggtgat gcgccagggc cggctgccgt cggggacagg          480
gctttccata gc                                                             492

SEQ ID NO: 102          moltype = DNA  length = 900
FEATURE                 Location/Qualifiers
source                  1..900
                        mol_type = genomic DNA
                        organism = Homo sapiens
SEQUENCE: 102
agttaatgat taacccgcca tgctactat ctacgtagcc atgctctagg aagatcggaa            60
ttcgcccta agctagcaga tcttccccac ctagccacct ggcaaactgc tcctttctc           120
aaaggcccaa acatggcctc ccagactgca accccaggc agtcaggcc tgtctccaca           180
acctcacagc caccctggac ggaatctgct tcttcccaca tttgagtcct cctcagcccc          240
tgagctcctc tgggcagggc tgtttctttc catctttgta ttcccagggg cctgcaaata          300
aatgtttaat gaacgaacaa gagagtgaat tccaattcca tgcaacaagg attgggctcc          360
tgggccctag gctatgtgtc tggcaccaga aacggaagct gcaggttgca gccctgccc          420
tcatggagct cctcctgtca gaggagtgtg gggactggat gactccagag gtaacttgtg          480
ggggaacgaa caggtaaggg gctgtgtgac gagatgagag actgggagaa taaaccagaa          540
agtctctagc tgtccagagg acatagcaca gaggcccatg gtcccctattt caaacccagg         600
ccaccagact gagctgggac cttgggacag acaagtcatg cagaagttag gggaccttct          660
cctccctttt cctggatgga tcctgagtac cttctcctcc ctgacctcag gcttcctcct          720
agtgtcacct tggcccctct tagaagccaa ttaggccctc agtttctgca gcggggatta          780
```

-continued

```
atatgattat gaacacccccc aatctcccag atgctgattc agccaggagc ttaggagggg  840
gaggtcactt tataagggtc tgggggggtc agaacccaga gtcatcccct gaattctgca  900

SEQ ID NO: 103         moltype = DNA   length = 521
FEATURE                Location/Qualifiers
source                 1..521
                       mol_type = genomic DNA
                       organism = Mus musculus
SEQUENCE: 103
ggttcttccc attttggcta catggtcttt ttttttacct ttttggttcc tttggcctt  60
tggcttttgg cttccagggc ttctggatcc cccccaaccc ctcccataca catacacatg  120
tgcactcgtg cactcaaccc agcacaggat aatgttcatt cttgaccttt ccacatacat  180
ctggctatgt tctctctctt atctacaata aatctcctcc actatactta ggagcagtta  240
tgttcttctt cttttcttct ttttttttt tttcattcag taacatcatc agaatcctct  300
agctctggcc tacctcctca gtaacaatca gctgatccct ggccactaat ctgtactcac  360
taatctgttt tccaaactct tggcccctga gctaattata gcagtgcttc atgccaccca  420
ccccaacct attcttgttc tctgactccc actaatctac acattcagag gattgtggat  480
ataagaggct gggaggccag cttagcaacc agagctggag g                       521

SEQ ID NO: 104         moltype = DNA   length = 292
FEATURE                Location/Qualifiers
source                 1..292
                       mol_type = genomic DNA
                       organism = Homo sapiens
SEQUENCE: 104
gggcccccaga agcctggtgg ttgtttgtcc ttctcagggg aaaagtgagg cggccccttg  60
gaggaagggg ccgggcagaa tgatctaatc ggattccaag cagctcaggg gattgtcttt  120
ttctagcacc ttcttgccac tcctaagcgt cctccgtgac cccggctggg atttagcctg  180
gtgctgtgtc agcccggtc tcccagggc ttcccagtgg tccccaggaa ccctcgacag  240
ggcccggtct ctctcgtcca gcaagggcag ggacgggcca caggccaagg gc           292

SEQ ID NO: 105         moltype = DNA   length = 7390
FEATURE                Location/Qualifiers
source                 1..7390
                       mol_type = genomic DNA
                       organism = Homo sapiens
SEQUENCE: 105
ttatgcagtg ctgccataac catgagtgat aacactgcgg ccaacttact tctgacaacg  60
atcggaggac cgaaggagct aaccgctttt ttgcacaaca tggggggatca tgtaactcgc  120
cttgatcgtt gggaaccgga gctgaatgaa gccataccaa acgacgagcg tgacaccacg  180
atgcctgtag taatggtaac aacgttgcgc aaactattaa ctggcgaact acttactcta  240
gcttcccggc aacaattaat agactggatg gaggcggata agttgcagg accacttctg  300
cgctcggccc ttccggctgg ctggtttatt gctgataaat ctggagccgg tgagcgtgg  360
tctcgcggta tcattgcagc actggggcca gatggtaagc cctcccgtat cgtagttatc  420
tacacgacgg ggagtcaggc aactatggat gaacgaaata gacagatcgc tgagataggt  480
gcctcactga ttaagcattg gtaactgtca gaccaagttt actcatatat actttagatt  540
gatttaaaac ttcatttta atttaaaagg atctaggtga atatcccttttt tgataatctc  600
atgaccaaaa tcccttaacg tgagttttcg ttccactgag cgtcagaccc cgtagaaaag  660
atcaaaggat cttcttgaga tcctttttt ctgcgcgtaa tctgctgctt gcaaacaaaa  720
aaaccaccgc taccagcggt ggtttgtttg ccggatcaag agctaccaac tcttttttccg  780
aaggtaactg gcttcagcag agcgcagata ccaaatactg tccttctagt gtagccgtag  840
ttaggccacc acttcaagaa ctctgtagca ccgcctacat acctcgctct gctaatcctg  900
ttaccagtgg ctgctgccag tggcgataag tcgtgtctta ccgggttgga ctcaagacga  960
tagttaccgg ataaggcgca gcggtcgggc tgaacggggg gttcgtgcac acagcccagc  1020
ttggacgcgaa cgacctacac cgaactgaga tacctacagc gtgagctatg agaaagcgcc  1080
acgcttcccg aagggagaaa ggcggacagg tatccggtaa gcggcagggt cggaacagga  1140
gagcgcacga gggagcttcc aggggaaac gcctggtatc tttatagtcc tgtcgggttt  1200
cgccacctct gacttgagcg tcgattttg tgatgctcgt caggggggcg gagcctatgg  1260
aaaaacgcca gcaacgcggc cttttacgg ttcctggcct tttgctggcc ttttgctcac  1320
atgttctttc ctgcgttatc ccctgattct gtggataacc gtattaccgc ctttgagtga  1380
gctgataccg ctcgccgcag ccgaacgacc gagcgcagcg agtcagtgag cgaggaagcg  1440
gaagagcgcc caatacgcaa accgcctctc ccgcgcgtt ggcgattca ttaatgcagc  1500
tggcacgaca ggtttcccga ctggaaagcg ggcagtgagc gcaacgcaat taatgtgagt  1560
tagctcactc attaggcacc ccaggcttta cactttatgc ttccggctcg tatgttgtgg  1620
ggaattgtga gcggataaca atttcacaca ggaaacagct atgaccatga ttacgccaga  1680
tttaattaag gccttaatta ggctgcgcgc tcgctcgctc actgaggccg cccgggcaaa  1740
gcccgggcgt cgggcgacct ttggtcgccc ggcctcagtg agcgagcgag cgcgcagaga  1800
gggagtggcc aactccatca ctaggggttc cttgtagtta atgattaacc cgcatgcta  1860
cttatctacg tagcctgct ctaggaagat cgaattctt tactcctat cagtgataga  1920
gaacgtatga agagtttact ccctatcagt gatagagaac gtatgcagac tttactccct  1980
atcagtgata gagaacgtat aaggagttta ctccctatca gtgatagaga acgtatgacc  2040
agtttactcc ctatcagtga tagagaacgt atctacagtt tactccctat cagtgataga  2100
gaacgtatat ccagttttact ccctatcagt gatagagaac gtataagctt taggcgtgta  2160
cggtgggcgc ctataaaagc agagctcgtt tagtgaaccg tcagatcgcc tggagcaatt  2220
ccacaacact tttgtcttat accaactttc cgtaccactt cctaccctcg taaagcggcc  2280
gcgccaccat ggcgggacac ctggcttcgg atttcgcctt ctcgcccct ccaggtggtg  2340
gaggtgatgg gccaggggg ccggagccgg gctgggttga tcctcggacc tggctaagct  2400
tccaaggccc tcctggaggg ccaggaatcg ggccgggggt tgggccaggc tctgaggtgt  2460
gggggattcc cccatgcccc ccgccgtatg agttctgtgg ggggatggcg tactgtgggc  2520
```

```
cccaggttgg agtggggcta gtgcccaag gcggcttgga gacctctcag cctgagggcg   2580
aagcaggagt cggggtggag agcaactccg atggggcctc cccggagccc tgcaccgtca   2640
cccctggtgc cgtgaagctg gagaaggaga agctggagca aaacccggag gagtcccagg   2700
acatcaaagc tctgcagaaa gaactcgagc aatttgccaa gctcctgaag cagaagagga   2760
tcaccctggg atatacacag gccgatgtgg ggctcaccct gggggttcta tttgggaagg   2820
tattcagcca aacgaccatc tgccgctttg aggctctgca gcttagcttt aagaacatgt   2880
gtaagctgcg gcccttgctg cagaagtggg tggaggaagc tgacaacaat gaaaatcttc   2940
aggagatatg caaagcagaa accctcgtgc aggcccgaaa gagaaagcga accagtatcg   3000
agaaccgagt gagaggcaac ctggagaatt tgttcctgca gtgcccgaaa cccacactgc   3060
agcagatcag ccacatcgcc cagcagcttg ggctcgagaa ggatgtggtc cgagtgtggt   3120
tctgtaaccg gcgccagaag ggcaagcgat caagcagcga ctatgcacaa cgagaggatt   3180
ttgaggctgc tgggtctcct ttctcagggg gaccagtgtc ctttcctctg gcccagggc    3240
cccatttttgg taccccaggc tatgggagcc ctcacttcac tgcactgtac tcctcggtcc   3300
ctttccctga ggggggaagcc tttccccctg tctctgtcac cactctgggc tctcccatgc   3360
attcaaacgc tagcggcagc ggcgccacga acttctctct gttaaagcaa gcaggagatg   3420
ttgaagaaaa ccccgggcct gcatgcatgt acaacatgat ggagacggag ctgaagccgc   3480
cgggccccgca gcaaacttcg gggggcggcg gcggcaactc caccgcggcg gcggccggcg   3540
gcaaccagaa aaacagcccg gaccgcgtca agcggcccat gaatgccttc atggtgtggt   3600
cccgcgggca gcggcgcaag atggcccagg agaaccccaa gatgcacaac tcggagatca   3660
gcaagcgcct gggcgccgag tggaaacttt tgtcggagac ggagaagcgg ccgttcatcg   3720
acgaggctaa gcggctgcga gcgctgcaca tgaaggagca cccggattat aaataccggc   3780
cccggcggaa aaccaagacg ctcatgaaga aggataagta cagctgccc ggcgggctgc    3840
tggccccggg cggcaatagc atggcgagcg gggtcggggt gggcgccggc ctgggcgcgg   3900
gcgtgaacca gcgcatggac agttacgcgc acatgaacgg ctggagcaac ggcagctaca   3960
gcatgatgca ggaccagctg ggctaccgcg cagcccggg cctcaatgcg cacggcgcag    4020
cgcagatgca gcccatgcac cgtgacacg tgagcgccct gcagtacaac tccatgacca   4080
gctcgcagac ctacatgaac ggctcgccca cctacagcat gtcctactcg cagcagggca   4140
cccctggcat ggctcttggc tccatgggtt cggtggtcaa gtccgaggcc agctccagcc   4200
cccctgtggt tacctcttcc tcccactcca gggcgccctg ccaggccggg gacctccggg   4260
acatgatcag catgtatctc cccggccgcg aggtgccgga aggccccgcc ccagcagcag   4320
ttcacatgtc ccagcactac cagagcggcc cggtgcccgg cacggccatt aacggcacac   4380
tgcccctctc acacatggca tgcggctccg gcgagggcag gggaagtctt ctaacatgcg   4440
gggacgtgga ggaaaatccc ggcccactcg agatggctgt cagcgacgcg ctgctcccat   4500
ctttctccac gttcgcgtct ggcccggcgg aagggagaa gcgacttcgt caagcaggtg    4560
ccccgaataa ccgctggcgg gaggagctct cccacatgaa gcgacttccc ccagtgcttc   4620
ccggccgccc ctatgacctg gcggcggcga ccgtggccac agacctggag agcggcggag   4680
ccggtgcggc ttgcggcgt agcaacctgg cgccctacc tcggagagag accgaggagt    4740
tcaacgatct cctggacctg gactttattc tctccaattc gctgacccat cctccggagt   4800
cagtggccgc caccgtgtcc tcgtcagcgt cagcctcctc ttcgtcgtcg ccgtcgagca   4860
gcggccctgc cagcgcgccc tccacctgca gcttcaccta tccgatccgg ccgggaacgc   4920
acccgggcgt ggcgccgggc ggcacgggcg gaggcctcct ctatggcagg gagtccgctc   4980
cccctccgac ggctcccttc aacctggcgg acatcaacga cgtgagcccc tcgggcgggt    5040
tgtcgggcga gctcctgcgg ccagaattgg acccggttga cattccgcgc cagcagccgc   5100
agccgccagg tggcgggctg atgggcaagt tcgtgctgaa ggcgtcgctg agcgcccctg   5160
gcagcgagta cggcagcccg tcggtcatca gcgtcagcaa aggcagccct gacggcagcc   5220
acccggtggt ggtggcgccc tacaacgcg ggccgccgcg cacgtgccccc aagatcaagc    5280
aggaggcggt ctcttcgtgc acccacttgg gcgctggacc ccctctcagc aatggccacc   5340
ggccggctgc acacgacttc cccctggggc ggcagctccc cagcaggact accccgaccc   5400
tgggtcttga ggaagtgctg agcagcaggg actgtcaccc tgccctgccg cttcctcccg   5460
gcttccatcc ccaccggggg cccaattacc catccttcct gcccgatcag atgcagccgc   5520
aagtcccgcc gctccattac caagagctca gccaccccgg ttcctgcatg ccagaggagc   5580
ccaagccaaa gaggggaaga cgatcgtggc cccggaaaag gaccgccacc cacacttgtg   5640
attacgcggg ctgcggcaaa acctacacaa agagttccca tctcaaggca cacctgcgaa   5700
cccacacagg tgagaaacct taccactgtg actgggacgg ctgtggatgg aaattcgccc   5760
gctcagatga actgaccagg cactacgta aacacgcgga gcaccgcccg ttccagtgca    5820
aaaaatgcga ccgagcattt tccaggtcgg accacctcgc cttacacatg aagaggcatt   5880
tttaaatgac tagtgcgcgc agcggccgac catgcccaa cttgtttatt gcagcttata    5940
atggttacaa ataaagcaat agcatcacaa atttcacaaa taaagcattt ttttcactgc   6000
attctagttg tggttttgtcc aaactcatca atgtatctta tcatgtctgg atctcggtac   6060
cggatccaaa ttcccgataa ggatcttcct agagcatgac tacgtagata agtagcatgg   6120
cgggttaatc attaactaca aggaacccct agtgatggag ttggcactc cctctctgcg    6180
cgctcgctcg ctcactgagg ccgggcgacc aaagtcgcc cgacgcccgg gctttgcccg    6240
ggcggcctca gtgagcgagc gagcgcgcag ccttaattaa cctaattcac tggccgtcgt   6300
tttacaacgt cgtgactggg aaaaccctgg cgttacccaa cttaatcgcc ttgcagcaca   6360
tccccctttc gccagctggc gtaatagcga agaggcccgc accgatcgcc cttcccaaca   6420
gttgcgcagc ctgaatggcg aatgggacgc gccctgtagc ggcgcattaa gcgcggcggg   6480
tgtggtggtt acgcgcagcg tgaccgctac acttgccagc gccctagcgc ccgctccttt   6540
cgctttcttc ccttccttc tcgccacgtt cgccggcttt ccccgtcaag ctctaaatcg   6600
ggggctccct ttagggttcc gatttagtgc tttacggcac ctcgacccca aaaaacttga   6660
ttagggtgat ggttcacgta gtgggccatc gccctgatag acggttttc gccctttgac   6720
gttggagtcc acgttcttta atagtggact cttgttccaa actggaacaa cactcaaccc   6780
tatctcggtc tattctttg atttataagg gattttgccg atttcggcct attggttaaa   6840
aaatgagctg atttaacaaa aatttaacgc gaattttaac aaaatattaa cgtttataat   6900
ttcaggtggc atctttcggg gaaatgtgcg cggaacccct atttgtttat ttttctaaat   6960
acattcaaat atgtatccgc tcatgagaca ataaccctga taaatgcttc aataatattg   7020
aaaaaggaag agtatgagta ttcaacattt ccgtgtcgcc cttattccct ttttgcggc    7080
attttgcctt cctgttttg ctcacccaga aacgctggtg aaagtaaaag atgctgaaga   7140
tcagttgggt gcacgagtgg gttacatcga actggatctc aatagtggta agatccttga   7200
gagttttcgc cccgaagaac gttttccaat gatgagcact tttaaagttc tgctatgtgg   7260
```

```
cgcggtatta tcccgtattg acgccgggca agagcaactc ggtcgccgca tacactattc   7320
tcagaatgac ttggttgagt actcaccagt cacagaaaag catcttacgg atggcatgac   7380
agtaagagaa                                                          7390

SEQ ID NO: 106          moltype = DNA   length = 7265
FEATURE                 Location/Qualifiers
source                  1..7265
                        mol_type = genomic DNA
                        organism = Homo sapiens
SEQUENCE: 106
ttatgcagtg ctgccataac catgagtgat aacactgcgg ccaacttact tctgacaacg    60
atcggaggac cgaaggagct aaccgctttt ttgcacaaca tggggggatca tgtaactcgc   120
cttgatcgtt gggaaccgga gctgaatgaa gccataccaa acgacgagcg tgacaccacg   180
atgcctgtag taatggtaac aacgttgcgc aaactattaa ctggcgaact acttactcta   240
gcttcccggc aacaattaat agactggatg gaggcggata aagttgcagg accacttctg   300
cgctcggccc ttccggctgg ctggtttatt gctgataaat ctggagccgg tgagcgtggg   360
tctcgcggta tcattgcagc actggggcca gatggtaagc cctcccgtat cgtagttatc   420
tacacgacgg ggagtcaggc aactatggat gaacgaaata gacagatcgc tgagataggt   480
gcctcactga ttaagcattg gtaactgtca gaccaagttt actcatatat actttagatt   540
gatttaaaac ttcattttta atttaaaagg atctaggtga agatcctttt tgataatctc   600
atgaccaaaa tcccttaacg tgagttttcg ttccactgag cgtcagaccc cgtagaaaag   660
atcaaaggat cttcttgaga tccttttttt ctgcgcgtaa tctgctgctt gcaaacaaaa   720
aaaccaccgc taccagcggt ggtttgtttg ccggatcaag agctaccaac tcttttttccg   780
aaggtaactg gcttcagcag agcgcagata ccaaatactg tccttctagt gtagccgtag   840
ttaggccacc acttcaagaa ctctgtagca ccgcctacat acctcgctct gctaatcctg   900
ttaccagtgg ctgctgccag tggcgataag tcgtgtctta ccgggttgga ctcaagacga   960
tagttaccgg ataaggcgca gcggtcgggc tgaacggggg gttcgtgcac acagcccagc  1020
ttggagcgaa cgacctacac cgaactgaga tacctacagc gtgagctatg agaaagcgcc  1080
acgcttcccg aagggagaaa ggcggacagg tatccggtaa gcggcagggt cggaacagga  1140
gagcgcacga gggagcttcc agggggaaac gcctggtatc tttatagtcc tgtcgggttt  1200
cgccacctct gacttgagcg tcgatttttg tgatgctcgt caggggggcg gagcctatgg  1260
aaaaacgcca gcaacgcggc cttttacgg ttcctggcct tttgctgcc tttgctcac    1320
atgttctttc ctgcgttatc ccctgattct gtggataacc gtattaccgc ctttgagtga  1380
gctgataccg ctcgccgcag ccgaacgacc gagcgcagcg agtcagtgag cgaggaagcg  1440
gaagagcgcc caatacgcaa accgcctctc cccgcgcgtt ggccgattca ttaatgcagc  1500
tggcacgaca ggtttcccga ctggaaagcg ggcagtgagc gcaacgcaat taatgtgagt  1560
tagctcactc attaggcacc ccaggcttta cactttatgc ttccggctcg tatgttgtgt  1620
ggaattgtga gcggataaca atttcacaca ggaaacagct atgaccatga ttacgccaga  1680
tttaattaag gccttaatta ggctgcgcgc tcgctcgctc actgaggccg cccgggcaaa  1740
gcccgggcgt cgggcgacct ttggtcgccc ggcctcagtg agcgagcgag cgcgcagaga  1800
gggagtggcc aactccatca ctaggggttc cttgtagtta atgattaacc cgccatgcta  1860
cttatctacg tagccatgct ctaggaagat cggaattctc gagtggctcc ggtgccgtc   1920
agtggtgcaga gcgcacatcg cccacagtcc ccgagaagtt gggggaggg gtcggcaatt  1980
gaaccggtgc ctagagaagg tggcgcgggg taaactggga aagtgatgtc gtgtactggc  2040
tccgcctttt tcccgagggt gggggagaac cgtatataag tgcagtagtc gccgtgaacg  2100
ttcttttttcg caacgggttt gccgccagaa cacaggtgtc gtgacgcggg cggccgcgcc  2160
accatgacgg gacacctggc ttcggatttc gccttctcga ccctccagg tggtggaggt  2220
gatgggccag gggggccgga gccgggctgg gttgatcctc ggacctggct aagcttccaa  2280
ggccctcctg gagggccagg aatcggggcg ggggttgggc caggctctga ggtgtggggg  2340
attccccccat gccccccgcc gtatgagttc tgtggggga tggcgtactg tgggcccag   2400
gttggagtgg ggctagtgcc ccaaggcgtg ttggagacct ctcagcctga gggcgaagca  2460
ggagtcgggg tggagagcaa ctccgatggg gcctccccgg agccctgcac cgtcacccct  2520
ggtgccgtga agctggagaa ggagaagctg gagcaaaacc cggaggagtc ccaggacatc  2580
aaagctctgc agaaagaact cgagcaattt gccaagctcc tgaagcagaa gaggatcacc  2640
ctgggatata cacaggccga tgtggggctc accctgggga ttctatttgg gaaggtattc  2700
agccaaacga ccatctgccg ctttgaggct ctgcagcttta gcttcaagaa catgtgtaag  2760
ctgcggccct tgctgcagaa gtgggtggag gaagctgaca caatgaaaaa tcttcaggag  2820
atatgcaaag cagaaacccct cgtgcaggcc cgaaagagaa agcgaaccag tatcgagaac  2880
cgagtgagag gcaacctgga gaatttgttc ctgcagtgcc cgaaacccac actgcagcag  2940
atcagccaca tcgcccagca gcttgggctc gagaaggatg tggtccgagt gtggttctgt  3000
aaccggcgcc agaagggcaa gcgatcaagc agcgactatg cacaacgaga ggattttgag  3060
gctgctgggt ctccttttctc aggggggacca gtgtccttc ctctggcccc agggccccat  3120
tttggtaccc caggctatgg gagccctcac ttcactgcac tgtactcctc ggtcccttc   3180
cctgagggg aagccttttcc cctgtctct gtcaccactc tgggctctcc catgcattca  3240
aacgctagcg gcagcggcgc cacgaacttc tctctgttaa agcaagcagg agatgttgaa  3300
gaaaacccg gcctgcatg catgtacaac atgatggaga cggagctgaa gccgccgggc  3360
ccgcagcaaa cttcggggg cggcggcggc aactccaccg cggcggcggc cggcggcaac  3420
cagaaaaaca gcccggaccg cgtcaagcgg cccatgaatg ccttcatggt gtggtcccgc  3480
gggcagcgc gcaagatggc ccaggagaac cccaagatga ccaactcgga gatcagcaag  3540
cgcctgggcg ccgagtggaa actttttgtcg gagacggaga gcggccgtt catcgacagg  3600
gctaagcggc tgcgagcgct gcacatgaag gagcacccgg attataaaata ccggccccgg  3660
cggaaaacca gacgctcat gaagaaggat aagtacacgc tgcccggcgg gctgctggcc  3720
cccggcggca atagcatggc gagcgggtc ggggtgggcg ccggcctggg cgcgggcgtg  3780
aaccggtga tggacagtta cgcgcacatg aacggccacg gcaacgggc ctacagcagg  3840
atgcaggacc agctgggcta cccgcagcac ccgggcctca atgcgcacgg cgcagcgcag  3900
atgcagccca tgcaccgcta cgacgtgagc gccctgcagt acaactccat gaccagctcg  3960
cagacctaca tgaacggctc gcccacctac agcatgtcct actcgcagca gggcaccccc  4020
ggcatggctc ttgggctccat gggttcggtg gtcaagtccg aggccagctc cagcccccct  4080
gtggttacct cttcctccca ctccagggcg cccctgcagg ccggggaccct ccgggacatg  4140
```

```
atcagcatgt atctcccegg cgccgaggtg ccggaacccg ccgccccag cagacttcac  4200
atgtcccagc actaccagag cggcccggtg cccggcacgg ccattaacgg cacactgccc  4260
ctctcacaca tggcatgcgg ctccggcgag ggcaggggaa gtcttctaac atgcggggac  4320
gtggaggaaa atcccggccc actcgagatg gctgtcagcg acgcgctgct cccatctttc  4380
tccacgttcg cgtctggccc ggcgggaagg gagaagacac tgcgtcaagc aggtgccccg  4440
aataaccgct ggcgggagga gctctcccac atgaagcgac ttcccccagt gcttcccggc  4500
cgccccatg  acctggcggc ggcgaccgtg gccacagacc tggagagcgg cggagccggt  4560
gcggcttgcg gcggtagcaa cctggcgccc taccgtcgga gagagaccga ggagttcaac  4620
gatctcctgg acctggactt tattctctcc aattcgctga cccatcctcc ggagtcagtg  4680
gccgccaccg tgtcctcgtc agcgtcagcc tcctcttcgt cgtcgccgtc gagcagcgag  4740
cctgccagcg cgccctccac ctgcagcttc acctatccga tccgggcgg  gaacgacccg  4800
ggcgtggcgc cgggcggcac gggcggaggc ctcctctatg gcaggagtc cgctccccct  4860
ccgacggctc ccttcaacct ggcggacatc aacgacgtga gccctcggg cggcttcgtg  4920
gccgagctcc tgcgggccaga attggacccg gtgtacattc cgccgcagca gccgcagccg  4980
ccaggtggcg ggctgatggg caagttcgtg ctgaaggcgc cgctgagcgc ccctggcagc  5040
gagtacggca gcccgtcggt catcagcgtc agcaaaggca gccctgacgg cagccacccg  5100
gtggtggtgg cgccctacaa cggcgggccg ccgcgcacgt gccccaagat caagcaggag  5160
gcggtctctt cgtgcaccca cttgggcgct ggaccccctc tcagcaatgg ccaccggccg  5220
gctgcacacg acttcccccct ggggcggcag ctccccagca ggactacccc gaccctgggt  5280
cttgaggaag tgctgagcag cagggactgt caccctgccc tgccgcttcc tcccggcttc  5340
catcccacc cggggcccaa ttacccatcc ttcctgcccg atcagatgca gccgcaagtc  5400
ccgccgctcc attaccaaga gctcatgcca cccggttcct gcatgccaga ggagcccaag  5460
ccaaagaggg gaagacgatc gtggcccggg aaaaggaccc ccaccacac ttgtgattac  5520
gcgggctgcg gcaaaaccta cacaaagagt tcccatctca aggcacacct gcgaaccac  5580
acaggtgaga aaccttacca ctgtgactgg gacggctgtg gatggaaatt cgcccgctca  5640
gatgaactga ccaggcacta ccgtaaacac acggggcacc gcccgttcca gtgccaaaaa  5700
tgcgaccgag cattttccag gtcggaccac ctcgccttac acatgaagga gcattttttaa  5760
atgactagtg cgcgcagcgg ccgaccatgg cccaacttgt ttattgcagc ttataatggt  5820
tacaaataaa gcaatagcat cacaaatttc acaaataaag cattttttttc actgcattct  5880
agttgtggtt tgtccaaact catcaatgta tcttatcatg tctggatctc ggtaccggat  5940
ccaaattccc gataaggatc ttcctagagc atggctacgt agataagtag catgcgggt  6000
taatcattaa ctacaaggaa ccccctagtga tggagttggc cactccctct ctgcgcgctc  6060
gctcgctcac tgaggccggg cgaccaaagg tcgcccgacg cccgggcttt gcccgggcgg  6120
cctcagtgag cgagcgagcg cgcagcctta attaacctaa ttcactggcc gtcgttttac  6180
aacgtcgtga ctgggaaaac cctggcgtta cccaacttaa tcgccttgca gcacatcccc  6240
ctttcgccag ctggcgtaat agcgaagagg cccgcaccga tcgcccttcc caacagttgc  6300
gcagcctgaa tggcgaatgg gacgcgccct gtagcggcgc attaagcgcg gcgggtgtgg  6360
tggttacgcg cagcgtgacc gctacacttg ccagcgcct agcgcccgct cctttcgctt  6420
tcttcccttc ctttctcgcc acgttcgccg gcttccccg tcaagctcta aatcggggc  6480
tccctttagg gttccgattt agtgctttac ggcacctcga ccccaaaaaa cttgattagg  6540
gtgatggttc acgtagtggg ccatcgccct gatagacggt ttttcgccct ttgacgttgg  6600
agtccacgtt ctttaatagt ggactcttgt tccaaactgg aacaacactc aaccctatct  6660
cggtctattc ttttgattta agggatttt tgccgatttc ggcctattgg ttaaaaatg  6720
agctgattta acaaaattt aacgcgaatt ttaacaaaat attaacgttt ataattcag  6780
gtggcatctt tcggggaaat gtgcgcggaa ccccctatttg ttttatttc taaatacatt  6840
caaatatgta tccgctcatg agacaataac cctgataaat gcttcaataa tattgaaaaa  6900
ggaagagtat gagtattcaa catttccgtg tcgcccttat tcccttttttt gcggcattt  6960
gccttcctgt ttttgctcac ccagaaacgc tggtgaaagt aaaagatgct gaagatcagt  7020
tgggtgcacg agtgggttac atcgaactgg atctcaatag tggtaagatc cttgagagtt  7080
ttcgccccga agaacgtttt ccaatgatga gcactttaa agttctgcta tgtggcgcgg  7140
tattatcccg tattgacgcc gggcaagagc aactcggtcg ccgcatacac tattctcaga  7200
atgacttggt tgagtactca ccagtcacag aaaagcatct tacggatggc atgacagtaa  7260
gagaa                                                            7265
```

```
SEQ ID NO: 107        moltype = DNA   length = 5437
FEATURE               Location/Qualifiers
misc_feature          1..5437
                      note = Synthetic Polynucleotide
source                1..5437
                      mol_type = other DNA
                      organism = synthetic construct
SEQUENCE: 107
ttatgcagtg ctgccataac catgagtgat aacactgcgg ccaacttact tctgacaacg   60
atcggaggac cgaaggagct aaccgctttt ttgcacaaca tgggggatca tgtaactcgc  120
cttgatcgtt gggaaccgga gctgaatgaa gccataccaa acgacgagcg tgacaccacg  180
atgcctgtag taatggtaac aacgttgcgc aaactattaa ctggcgaact acttactcta  240
gcttcccggc aacaattaat agactggatg gaggcggata agttgcagg accacttctg  300
cgctcggccc ttccggctgg ctggtttatt gctgataaat ctggagccgg tgagcgtggg  360
tctcgcggta tcattgcagc actggggcca gatggtaagc cctcccgta cgtagttatc  420
tacacgacgg ggagtcaggc aactatggat gaacgaaata gacagatcgc tgagataggt  480
gcctcactga ttaagcattg gtaactgtca gaccaagttt actcatatat actttagatt  540
gatttaaaac ttcatttta atttaaaagg atctaggtga agatccttttt tgataatctc  600
atgaccaaaa tcccttaacg tgagttttcg ttccactgag cgtcagaccc cgtagaaaag  660
atcaaaggat cttcttgaga tcctttttt ctgcgcgtaa tctgctgctt gcaaacaaaa  720
aaaccaccgc taccagcggt ggtttgtttg ccggatcaag agctaccaac tctttttccg  780
aaggtaactg gcttcagcag agcgcagata ccaaatactg tccttctagt gtagccgtag  840
ttaggccacc acttcaagaa ctctgtagca ccgcctacat acctcgctct gctaatcctg  900
ttaccagtgg ctgctgccag tggcgataag tcgtgtctta ccgggttgga ctcaagacga  960
tagttaccgg ataaggcgca gcggtcgggc tgaacggggg gttcgtgcac acagcccagc 1020
```

```
ttggagcgaa cgacctacac cgaactgaga tacctacagc gtgagctatg agaaagcgcc  1080
acgcttccg aagggagaaa ggcggacagg tatccggtaa gcggcagggt cggaacagga   1140
gagcgcacga gggagcttcc agggggaaac gcctggtatc tttatagtcc tgtcggtttt   1200
cgccacctct gacttgagcg tcgattttg tgatgctcgt caggggggcg gagcctatgg    1260
aaaaacgcca gcaacgcggc cttttacgg ttcctggcct tttgctgagc ttttgctcac    1320
atgttctttc ctgcgttatc ccctgattct gtggataacc gtattaccgc ctttgagtga   1380
gctgataccg ctcgccgcag ccgaacgacc gagcgcagcg agtcagtgag cgaggaagcg   1440
gaagagcgcc caatacgcaa accgcctctc cccgcgcgtt ggccgattca ttaatgcagc   1500
tggcacgaca ggtttcccga ctggaaagcg ggcagtgagc gcaacgcaat taatgtgagt   1560
tagctcactc attaggcacc ccaggcttta cactttatgc ttccggctcg tatgttgtgt   1620
ggaattgtga gcggataaca atttcacaca ggaaacagct atgaccatga ttacgccaga   1680
tttaattaag gccttaatta ggctgcgcgc tcgctcgctc actgaggccg cccgggcaaa   1740
gcccgggcgt cgggcgacct ttggtcgccc ggcctcagtg agcgagcgag cgcgcagaga   1800
gggagtggcc aactccatca ctaggggttc cttgtagtta atgattaacc cgcatgcta   1860
cttatctacg tagccatgct ctaggaagat cggaattctt tactccctat cagtgataga   1920
gaacgtatga agagtttact ccctatcagt gatagagaac gtatgcagac tttactccct   1980
atcagtgata gagaacgtat aaggagttta ctccctatca gtgatagaga acgtatgacc   2040
agtttactcc ctatcagtga tagagaacgt atctacagtt tactccctat cagtgataga   2100
gaacgtatat ccagtttact ccctatcagt gatagagaac gtataagctt taggcgtgta   2160
cggtgggcgc ctataaaagc agagctcgtt tagtgaaccg tcagatcgcc tggagcaatt   2220
ccacaacact tttgtcttat accaactttc cgtaccactt cctaccctcg taaagcggcc   2280
gcatggaaga cgccaaaaac ataaagaaag gcccggccgc attctatccg ctggaagatg   2340
gaaccgctgg agagcaactg cataaggcta tgaagagata cgccctggtt cctggaacaa   2400
ttgcttttac agatgcacat atcgaggtgg acatcactta cgctgagtac ttcgaaatgt   2460
ccgttcggtt ggcagaagct atgaaacgat atgggctgaa tacaaatcac agaatcgtcg   2520
tatgcagtga aaactctctt caattctttta tgccggtgtt gggcgcgtta tttatcgaag   2580
ttgcagttgc gcccgcgaac gacatttata tgaacgtga attgctcaac agtatgggca   2640
tttcgcagcc taccgtggtg ttcgtttcca aaaggggtt gcaaaaaatt ttgaacgtgc    2700
aaaaaaagct cccaatcatc caaaaaatta ttatcatgga ttctaaaacg gattaccagg   2760
gatttcagtc gatgtacacg ttcgtcacat ctcatctacc tcccggtttt aatgaatacg   2820
attttgtgcc agagtccttc gatagggaca agacaattgc actgatcatg aactcctctg   2880
gatctactgg tctgcctaaa ggtgtcgctc tgcctcatag aactgcctgc gtgagattct   2940
cgcatgccag agatcctatt tttggcaatc aaatcattcc ggatactgcg attttaagtg   3000
ttgttccatt ccatcacggt tttggaatgt ttactacact cggatatttg atatgtggat   3060
ttcgagtcgt cttaatgtat agatttgaag aagagctgtt tctgaggagc cttcaggatt   3120
acaagattca aagtgcgctg ctggtgccaa cccctattct ccttcttcgcc aaaagcactc   3180
tgattgacaa atacgattta tctaatttac acgaaattgc ttctggtggc gctcccctct   3240
ctaaggaagt cggggaagcg gttgccaaga ggttccatct gccaggtatc aggcaaggat   3300
atgggctcac tgagactaca tcagctattc tgattacacc cgagggggat gataaaccgg   3360
gcgcggtcgg taaagttgtt ccattttttg aagcgaaggt tgtggatctg gataccggga   3420
aaacgctggg cgttaatcaa agaggcgaac tgtgtgtgag aggtcctatg attatgtccg   3480
gttatgtaaa caatccggaa gcgaccaacg ccttgattga caaggatgga tggctacatt   3540
ctggagacat agcttactgg gacgaagacg aacacttctt catcgttgac cgcctgaagt   3600
ctctgattaa gtacaaaggc tatcaggtgg ctcccgctga attggaatcc atcttgctcc   3660
aacaccccaa catcttcgac gcaggtgtcg caggtcttcc cgacgatgac gccggtgaac   3720
ttcccgccgc cgttgttgtt ttggagcacg gaaagacgat gacggaaaaa gagatcgtgg   3780
attacgtcgc cagtcaagta acaaccgcga aaaagttgcg cggaggagtt gtgtttgtgg   3840
acgaagtacc gaaaggtctt accggaaaac tcgacgcaag aaaaatcaga gagatcctca   3900
taaaggccaa gaagggcgga aagatcgccg tgtaaactag tgcgcgcagc ggccgaccat   3960
ggcccaactt gtttattgca gcttataatg gttacaaata aagcaatagc atcacaaatt   4020
tcacaaataa agcatttttt tcactgcatt ctagttgtgg tttgtccaaa ctcatcaatg   4080
tatcttatca tgtctggatc tcggtaccgg atccaaattc ccgataagga tcttcctaga   4140
gcatggctac gtagataagt agcatggcgg gttaatcatt aactacaagg aaccccctagt  4200
gatggagttg gccactccct ctctgcgcgc tcgctcgctc actgaggccg ggcgaccaaa   4260
ggtcgcccga gcccgggct tgcccgggc ggcctcagtg agcgaggag cgcgcagcct     4320
taattaacct aattcactgg ccgtcgtttt acaacgtcgt gactgggaaa acctggcgt    4380
tacccaactt aatcgccttg cagcacatcc ccctttcgcc agctggcgta atagcgaaga   4440
ggcccgcacc gatcgccctt cccaacagtt gcgcagcctg aatggcgaat gggacgcgcc   4500
ctgtagcggc gcattaagcg cggcgggtgt ggtggttacg cgcagcgtga ccgctacact   4560
tgccagcgcc ctagcgcccg ctcctttcgc tttcttccct tcctttctcg ccacgttcgc   4620
cggctttccc cgtcaagctc taaatcgggg gctcccttta gggttccgat ttagtgcttt   4680
acggcacctc gaccccaaaa aacttgatta gggtgatggt tcacgtagtg gccatcgcc    4740
ctgatagacg gtttttcgcc ctttgacgtt ggagtccacg ttctttaata gtggactctt   4800
gttccaaact ggaacaacac tcaaccctat ctcggtctat tcttttgatt tataagggat   4860
tttgccgatt tcggcctatt ggttaaaaaa tgagctgatt taacaaaaat ttaacgcgaa   4920
ttttaacaaa atattaacgt ttataatttc aggtggcatc tttcggggaa atgtgcgcgg   4980
aacccctatt tgtttatttt tctaaataca ttcaaatatg tatccgctca tgagacaata   5040
accctgataa atgcttcaat aatattgaaa aaggaagagt atgagtattc aacatttccg   5100
tgtcgcccct attcccttttt ttgcggcatt ttgccttcct gtttttgctc acccagaaac   5160
gctggtgaaa gtaaaagatg ctgaagatca gttgggtgca cgagtgggtt acatcgaact   5220
ggatctcaat agtggtaaga tccttgagag ttttcgcccc gaagaacgtt ttccaatgat   5280
gagcactttt aaagttctgc tatgtggcgc ggtattatcc cgtattgacg ccgggcaaga   5340
gcaactcggt cgccgcatac actattctca gaatgacttg gttgagtact caccagtcac   5400
agaaaagcat cttacggatg gcatgacagt aagagaa                            5437
```

SEQ ID NO: 108       moltype = DNA  length = 19
FEATURE              Location/Qualifiers
misc_feature      1..19
                       note = Synthetic Polynucleotide

```
source                  1..19
                        mol_type = other DNA
                        organism = synthetic construct
SEQUENCE: 108
cacaagtcaa accttatt                                                  19

SEQ ID NO: 109          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 109
ggacgtaatc cagaaagaag a                                              21

SEQ ID NO: 110          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 110
ttgtgcctct ggaggttata a                                              21

SEQ ID NO: 111          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 111
ggaaataaag gctggtgaag g                                              21

SEQ ID NO: 112          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 112
gaaagatgaa ggtccatatt a                                              21

SEQ ID NO: 113          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 113
gcagatggcc gtgacacaaa t                                              21

SEQ ID NO: 114          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 114
gctcatggag actaggtttg g                                              21

SEQ ID NO: 115          moltype = DNA  length = 21
FEATURE                 Location/Qualifiers
misc_feature            1..21
                        note = Synthetic Polynucleotide
source                  1..21
                        mol_type = other DNA
                        organism = synthetic construct
SEQUENCE: 115
ggatgtaagt ttgccagaag c                                              21

SEQ ID NO: 116          moltype = DNA  length = 21
FEATURE                 Location/Qualifiers
misc_feature            1..21
```

```
                        note = Synthetic Polynucleotide
source                  1..21
                        mol_type = other DNA
                        organism = synthetic construct
SEQUENCE: 116
gctccaacga gaagctattt g                                              21

SEQ ID NO: 117          moltype = DNA  length = 19
FEATURE                 Location/Qualifiers
misc_feature            1..19
                        note = Synthetic Polynucleotide
source                  1..19
                        mol_type = other DNA
                        organism = synthetic construct
SEQUENCE: 117
gttcagatgt gcggcgagt                                                 19

SEQ ID NO: 118          moltype = AA   length = 22
FEATURE                 Location/Qualifiers
REGION                  1..22
                        note = Synthetic Polypeptide
source                  1..22
                        mol_type = protein
                        organism = synthetic construct
SEQUENCE: 118
GSGATNFSLL KQAGDVEENP GP                                             22

SEQ ID NO: 119          moltype = DNA  length = 66
FEATURE                 Location/Qualifiers
misc_feature            1..66
                        note = Synthetic Polynucleotide
source                  1..66
                        mol_type = other DNA
                        organism = synthetic construct
SEQUENCE: 119
ggcagcggcg ccacgaactt ctctctgtta aagcaagcag gagatgttga agaaaacccc    60
gggcct                                                               66

SEQ ID NO: 120          moltype = DNA  length = 63
FEATURE                 Location/Qualifiers
misc_feature            1..63
                        note = Synthetic Polynucleotide
source                  1..63
                        mol_type = other DNA
                        organism = synthetic construct
SEQUENCE: 120
ggctccggcg agggcagggg aagtcttcta acatgcgggg acgtggagga aaatcccggc    60
cca                                                                  63

SEQ ID NO: 121          moltype = DNA  length = 7390
FEATURE                 Location/Qualifiers
misc_feature            1..7390
                        note = Synthetic Polynucleotide
source                  1..7390
                        mol_type = other DNA
                        organism = synthetic construct
SEQUENCE: 121
ttatgcagtg ctgccataac catgagtgat aacactgcgg ccaacttact tctgacaacg    60
atcggaggac cgaaggagct aaccgctttt ttgcacaaca tggggatca tgtaactcgc    120
cttgatcgtt gggaaccgga gctgaatgaa gccataccaa acgacgagcg tgacaccagc    180
atgcctgtag taatggtaac aacgttcgcg aaactattaa ctggcgaact acttactcta    240
gcttcccggc aacaattaat agactggatg gaggcggata agttgcagg accacttctg     300
cgctcggccc ttccggctgg ctggtttatt gctgataaat ctggagccgg tgagcgtggg    360
tctcgcggta tcattgcagc actggggcca gatggtaagc cctcccgtat cgtagttatc    420
tacacgacgg ggagtcaggc aactatggat gaacgaaata gacagatcgc tgagataggt    480
gcctcactga ttaagcattg gtaactgtca gaccaagttt actcatatat actttagatt    540
gatttaaaac ttcatttta atttaaaagg atctaggtga agatcctttt tgataatctc    600
atgaccaaaa tcccttaacg tgagttttcg ttccactgag cgtcagaccc cgtagaaaaa    660
atcaaaggat cttcttgaga tcctttttt ctgcgcgtaa tctgctgctt gcaaacaaaa    720
aaaccaccgc taccagcggt ggtttgtttg ccggatcaag agctaccaac tcttttttccg    780
aagtaactg gcttcagcag agcgcagata ccaaatactg tccttctagt gtagccgtag    840
ttaggccacc acttcaagaa ctctgtagca ccgcctacat acctcgctct gctaatcctg    900
ttaccagtgg ctgctgccag tggcgataag tcgtgtctta ccgggttgga ctcaagacga    960
tagttaccgg ataaggcgca gcggtcgggc tgaacggggg gttcgtgcac acagcccagc    1020
ttggagcgaa cgacctacac cgaactgaga tacctacagc gtgagctatg agaaagcgcc    1080
acgcttcccg aagggagaaa ggcggacagg tatccggtaa gcggcagggt cggaacagga    1140
gagcgcacga gggagcttcc agggggaaac gcctggtatc tttatagtcc tgtcgggttt    1200
cgccacctct gacttgagcg tcgatttttg tgatgctcgt caggggggcg gagcctatgg    1260
aaaaacgcca gcaacgcggc cttttacgg ttcctggcct tttgctggcc ttttgctcac    1320
```

```
atgttctttc ctgcgttatc ccctgattct gtggataacc gtattaccgc ctttgagtga  1380
gctgataccg ctcgccgcag ccgaacgacc gagcgcagcg agtcagtgag cgaggaagcg  1440
gaagagcgcc caatacgcaa accgcctctc cccgcgcgtt ggccgattca ttaatgcagc  1500
tggcacgaca ggtttcccga ctggaaagcg ggcagtgagc gcaacgcaat taatgtgagt  1560
tagctcactc attaggcacc ccaggcttta cactttatgc ttccggctcg tatgttgtgt  1620
ggaattgtga gcggataaca atttcacaca ggaaacagct atgaccatga ttacgccaga  1680
tttaattaag gccttaatta ggctgcgcgc tcgctcgctc actgaggccg cccgggcaaa  1740
gcccgggcgt cgggcgacct ttggtcgccc ggcctcagtg agcgagcgag cgcgcagaga  1800
gggagtggcc aactccatca ctaggggttc cttgtagtta atgattaacc cgccatgcta  1860
cttatctacg tagccatgct ctaggaagat cggaattctt tactccctat cagtgataga  1920
gaacgtatga agagtttact ccctatcagt gatagagaac gtatgcagac tttactccct  1980
atcagtgata gagaacgtat aaggagttta ctccctatca gtgatagaga acgtatgacc  2040
agtttactcc ctatcagtga tagagaacgt atctacagtt tactccctat cagtgataga  2100
gaacgtatat ccagtttact ccctatcagt gatagagaac gtataagctt taggcgtgta  2160
cggtgggcgc ctataaaagc agagctcgtt tagtgaaccg tcagatcgcc tggagcaatt  2220
ccacaacact tttgtcttat accaactttc cgtaccactt cctaccctcg taaagcggcc  2280
gcgccaccat ggcgggacac ctggcttcgg atttcgcctt ctcgcccct ccaggtggtg  2340
gaggtgatgg gccaggtggg gccggagccgg gctgggttga tcctcggacc tggctaagct  2400
tccaaggccc tcctggaggg ccaggaatcg ggccggggggt tgggccaggc tctgaggtgt  2460
gggggattcc cccatgcccc ccgccgtatg agttctgtgg ggggatggcg tactgtgggc  2520
cccaggttgg agtgggcta gtgccccaag gcggcttgga gacctctcag cctgagggcg  2580
aagcaggagt cggggtggag agcaactccg atggggcctc cccggagccc tgcaccgtca  2640
cccctggtgc cgtgaagctg gagaaggaga agctggagca aaaccccgag gagtcccagg  2700
acatcaaagc tctgcagaaa gaactcgagc aatttgccaa gctcctgaag cagaaggaga  2760
tcaccctggg atatacacag gccgatgtgg ggctcaccct gggggttcta tttgggaagg  2820
tattcagcca aacgaccatc tgccgctttg aggctagctt caagaacatg t  2880
gtaagctgcg gcccttgctg cagaagtggg tggaggaagc tgacaacaat gaaaatcttc  2940
aggagatatg caaagcagaa accctcgtgc aggcccgaaa gagaaagcga accagtatcg  3000
agaaccgagt gagaggcaac ctggagaatt tgttcctgca gtgcccgaaa cccacactgc  3060
agcagatcag ccacatcgcc cagcagcttg ggctcgagaa ggatgtggtc cgagtgtggt  3120
tctgtaaccg gcgccagaag ggcaagcgat caagcagcga ctatgcacaa cgagaggatt  3180
ttgaggctgc tgggtctcct ttctcagggg gaccagtgtc ctttcctctg gcccagggc  3240
cccattttgg taccccaggc tatgggagcc ctcacttcac tgcactgtac tcctcggtcc  3300
cttccctga ggggaagcc ttccccctg tctctgtcaa cactctgggc tctcccatgc  3360
attcaaacgc tagcggcagc ggcgccacga acttctctct gttaaagcaa gcaggagatg  3420
ttgaagaaaa ccccgggcct gcatgcatgt acaacatgat ggagacggag ctgaagccgc  3480
cgggcccgca gcaaacttcg ggggcggcg gcggcaactc caccgcggcg gcggccggcg  3540
gcaaccagaa aaacagcccg gaccgcgtca agcggcccat gaatgccttc atggtgtggt  3600
cccgcgggca gcggcgcaag atggcccagg agaacccaa gatgcacaac tcggagatca  3660
gcaagcgcct gggcgccgag tggaaactt tgtcggagac ggagaagcgg ccgttcatcg  3720
acgaggctaa gcggctgcga gcgctgcaca tgaaggagca cccggattat aaataccggc  3780
cccggcgaa aaccaagacg ctcatgaaga aggataagta cacgctgccc ggcgggctgc  3840
tggcccccgg cggcaatagc atggcgagcg gggtcgggt ggggccggc ctgggcgcgg  3900
gcgtgaacca gcgcatggac agttacgcgc acatgaacgg ctggagcaac ggcagctaca  3960
gcatgatgca ggaccagctg ggctaccgc agcacccggg cctcaatgcg cacggcgcag  4020
cgcagatgca gcccatgcac cgctacgacg tgagcgccct gcagtacaac tccatgacca  4080
gctcgcagac ctacatgaac ggctcgccca cctacagcat gtcctactcg cagcagggca  4140
cccctggcat ggctcttggc tccatggtt cggtggtcaa gtccgaggcc agctccagcc  4200
ccctgtggt tacctcttcc tcccactcca gggcgccctg ccaggccggg gacctccggg  4260
acatgatcag catgtatctc cccggcgccg aggtgccgga accgccgcc cccagcgac  4320
ttcacatgtc ccagcactac cagagcggcc cggtgccccg cacggccatt aacggccagc  4380
tgccctctc acacatggca tgcggctccg gcgagggcag gggaagtctt ctaacatgc  4440
gggacgtgga ggaaaatccc ggcccactcg agatggctgt cagcgacgcg ctgctcccat  4500
cttctccac gttcgcgtct ggccggcgg aagggagaa gacactgcgt caagcaggtg  4560
ccccgaataa ccgctggcgg gaggagctct cccacatgaa cgacttccc ccagtgcttc  4620
ccggccgccc ctatgacctg cgggcggcga ccgtgccac agacctggag agcggcggag  4680
ccggtgcggc ttgcggcggt agcaacctgg cgccctacc tcggagagag accgaggagt  4740
tcaacgatct cctggacctg gactttattc tctccaattc gctgacccat cctcggagt  4800
cagtggccgc caccgtgtcc tcgtcagcgt cagcctcctc ttcgtcgtcg ccgtcgagca  4860
gcggccctgc cagcgcgccc tccacctgca gcttcaccta tccgatccgg gccgggaacg  4920
acccgggcgt ggcgccggc ggcacgggcg gaggcctcct ctatggcagg gagtccgctc  4980
cccctccgac ggctcccttc aacctggcgg acatcaacga cgtgagcccc tcgggcgct  5040
tcgtggccga gctcctgcgg ccagaattgg accggtgta cattccgccg cagcagccgc  5100
agccgcaggg tggcgggctg atgggcaagt tcgtgctgaa ggcgtcgctg accgccctg  5160
gcagcgagta cggcagcccg tcggtcatca gcgtcagcaa aggcagccct gacggcagcc  5220
acccggtggt ggtggcgccc tacaacggcg gccgccgcg cacgtgcccc aagatcaagc  5280
aggaggcggt ctcttcgtgc acccacttgg gcgctggacc cctctcagc aatgccacc  5340
ggccggctgc acacgacttc cccctgggc ggcagctcc cagcaggact accccgaccc  5400
tgggtcttga ggaagtgctg agcagcaggg actgtcaccc tgccctgccg cttcctcccg  5460
gcttccatcc ccaccggg cccaattacc catccttcct gcccgatcag atgcagccgc  5520
aagtcccgcc gctccattac caagagctca tgccacccgg ttcctgcatg ccagaggagc  5580
ccaagccaaa gagggaaga cgatcgtggc cccgaaaag accgccacc cacacttgtg  5640
attacgcggg ctgcggcaaa acctacacaa agagttccca tctcaaggca cacctgcgaa  5700
cccacacagg tgaaaacct taccactgtg actgggacgg ctgtggatgg aaattcgcc  5760
gctcagatga actgaccagg cactaccgta aacacacggg gcaccgcccg ttccagtgcc  5820
aaaaatgcga ccgagcattt tccaggtcgg accacctcgc cttacacatg aagaggcatt  5880
tttaaatgac tagtgcgcgc agcggccgac catggcccaa cttgtttatt gcagcttata  5940
atggttacaa ataaagcaat agcatcacaa atttcacaaa taaagcattt ttttcactgc  6000
attctagttg tggtttgtcc aaactcatca atgtatctta tcatgtctgg atctcggtac  6060
```

```
cggatccaaa ttcccgataa ggatcttcct agagcatggc tacgtagata agtagcatgg    6120
cgggttaatc attaactaca aggaacccct agtgatggag ttggccactc cctctctgcg    6180
cgctcgctcg ctcactgagg ccgggcgacc aaaggtcgcc cgacgccggg ctttgcccg     6240
ggcggcctca gtgagcgagc gagcgcgcag ccttaattaa cctaattcac tggccgtcgt    6300
tttacaacgt cgtgactggg aaaaccctgg cgttacccaa cttaatcgcc ttgcagcaca    6360
tccccctttc gccagctggc gtaatagcga agaggcccgc accgatcgcc cttcccaaca    6420
gttgcgcagc ctgaatggcg aatgggacgc gccctgtagc ggcgcattaa gcgcggcggg    6480
tgtggtggtt acgcgcagcg tgaccgctac acttgccagc gccctagcgc ccgctccttt    6540
cgctttcttc ccttcctttc tcgccacgtt cgccggcttt ccccgtcaag ctctaaatcg    6600
ggggctccct ttagggttcc gatttagtgc tttacggcac ctcgacccca aaaaacttga    6660
ttagggtgat ggttcacgta gtgggccatc gccctgatag acggtttttc gccctttgac    6720
gttggagtcc acgttcttta atagtggact cttgttccaa actggaacaa cactcaaccc    6780
tatctcggtc tattctttttg atttataagg gattttgccg atttcggcct attggttaaa    6840
aaatgagctg atttaacaaa aatttaacgc gaattttaac aaaatattaa cgtttataat    6900
ttcaggtggc atctttcggg gaaatgtgcg cggaacccct atttgtttat ttttctaaat    6960
acattcaaat atgtatccgc tcatgagaca ataaccctga taaatgcttc aataatattg    7020
aaaaaggaag agtatgagta ttcaacattt ccgtgtcgcc cttattccct ttttttgcggc    7080
attttgcctt cctgttttttg ctcacccaga aacgctggtg aaagtaaaag atgctgaaga    7140
tcagttgggt gcacgagtgg gttacatcga actggatctc aatagtggta agatccttga    7200
gagttttcgc cccgaagaac gttttccaat gatgagcact tttaaagttc tgctatgtgg    7260
cgcggtatta tcccgtattg acgccgggca agagcaactc ggtcgccgca tacactattc    7320
tcagaatgac ttggttgagt actcaccagt cacagaaaag catcttacgg atggcatgac    7380
agtaagagaa                                                           7390

SEQ ID NO: 122        moltype = DNA   length = 6586
FEATURE               Location/Qualifiers
misc_feature          1..6586
                      note = Synthetic polynucleotide
source                1..6586
                      mol_type = other DNA
                      organism = synthetic construct
SEQUENCE: 122
aattcagaga ccgggaacca aactagcctt taaaaaacat aagtacagga gccagcaaga    60
tggctcagtg ggtaaaggtg cctaccagca agcctagctg gtcccccacga               120
actacgtggt aggagaggac caaccaactc tggaaatctg ttctgcaaac acatgctcac    180
acacacacac acaaatagta taaacaattt taaatttcat ttaaaaataa tttgtaaaca    240
aaatcattag cacaggtttt agaaagagcc tcttggtgac atcaagttga tgctgtagat    300
ggggtatcat tcctgaggac ccaaaaccgg gtctcagcct ttcccattc tgagagttct     360
ctcttttctc agccactagc tgaagagtag agtggctcag cactgggctc ttgagttcca    420
aagtcctaca actggtcagc ctgactacta accagccatg aagaaacaag gagtggatgg    480
gctgagtctg ctgggatggg agtggagtta gtaagtggcc atggatgtaa tgaccccagc    540
aatgctggct agaaggcatg cctcctttcc ttgtctggag acggaacggg agggatcatc    600
ttgtactcac agaagggaga acattctagc tggttgggca aaaatgtgca agttcacctg    660
gaggtggtgg tgcatgcttt taactccagt actcaggagg cagggccagg tggatctctg    720
tgagttcaag accagcctgc actatggaga gagtttttggg acagcagag ttacacagaa     780
aaatcctggt ggaaaatctg aaagaaagag agaaagaaag aaagaaagaa aggaagaaag    840
aaagaaagag tggcaggcag gcaggcagga ggaaggaagg gaaggaagga gggaaggaagg   900
aaggaaggaa ggaaaatagg tgcgacttca agatccggag ttacaagcag aatgcactgt    960
ttccctaaca gggccaagtg ttttgagtaa ctgaaggtgg gcatgatgcc tgggaagcag   1020
aaacaagcca ggcagatgca cccccttgcct tgcttccgaa gggctgcagt agcatggaaa   1080
acatggaaaa caaccaatcc attcccttttg ctgatataac aggctccaaa gccaaaacct   1140
gtcactggag gctcaagagc agatctccag ccaagaggca aaggaatggg ggaagctgga   1200
gggcctccct ctggttatcc aggcttctga aggttcaagc aaagaaaggg ttacaacctt   1260
aaaaggagag cgtcccgggg tatgggtaga agactgctcc accccgaccc ccagggtccc   1320
taaccgtctt ttccctgggc gagtcagccc aatcacagga ctgagagtgc ctctttagta   1380
gcagcaagcc acttcggaca cccaaatgga acacctccag tcagccctcg ccgaccaccc   1440
cacccccctcc atccttttcc ctcagcctcc gattggctga atctagagtc cctccctgct   1500
ccccccctctc tccccacccc tggtgaaaac tgcgggcttc agcgctgggt gcagcaactg   1560
gaggcgttgg cgcaccagga ggaggctgca gctagggagg tccaggtgag agcaggccgg   1620
cgggagggac ccgcacatgc aaggaccgcc gcagggcgga gatgcaagcc ttcccagct    1680
acagttttgg gaaaggatac cagggcgctc tatatgggg gcgcgggaac tggggaaaga    1740
aggtgctccc aggtcgaggt gggagaggaa ggcagtgcgg ggtcacgggc tttctccctg   1800
ctaacgacg ctttcgaaga gtgggtgccg gaggagaacc atgaggaagg acatcaagga    1860
cagccttttgg tccccaagct caaatgcttt tagtggtggg aatagaggga ggaggtgggt   1920
ggcaaactgg agggagtccc cagcgggtga cctcgtggct ggctgggtgc ggggcaccgc   1980
aggtaagaaa accgcaatgt tgcgggaggg gactgggtgg caggcgcggg ggaggggaaa    2040
gctagaaaag atgcgaggga gcggaggggg gagggagcgg gagaatctca actggtagag   2100
gaagattaaa atgaggaaat agcatcaggg tggggttagc caagccggc ctcgggaga     2160
gggcgcaaag ttgtctggg tgtgggctta ggtgggctgg gtatgatgatt cggggcgcg    2220
aaaacactgc tgcgcctctg ccaaatcacg ctacccctgt atctagttct gccaggcttc   2280
tccagcccca gccccaattc ttttttctag tgttcccctt tccctcccct gaatctcaag    2340
cccacactcc ctcctccata acccactgtt atcaaatcta agtcattgc cacccaacaa     2400
ccatcaggag gcggaagcag acgggaggag tttgagatca acttgggcta catcacgagt    2460
tccaggctca ccaaggcttc ttaaggagaa ccttgtctct aaaattaatta attaattaat   2520
taatagtccc ctttctctgc cacagaacct tgggatctgg ctcctggtcg cagctccccc   2580
cacccccaggc tgacattcac tgccatagcc catccgaaa tcctagtcta tttcccatg    2640
gatcttgaac tgcagagaga atggcagagt ggcccgccct gtgcaaagga tgttcctagc   2700
ctaggtggag ctcgcgaact cgcagactgt gcctctcttg gcaaggaca ggctagacag    2760
cctgccggtg tgttgagcta gggcactgtg gggaaggcag agaacctgtg cagggcagca   2820
```

```
atgaacacag gaccagaaaa ctgcagccct aggaacactc aagagctggc catttgcaag   2880
catctctggc ctccgtgctt ctcactcatg tcccatgtct tatacaggcc tctgtgcac   2940
ctcgcttgcc tgatctcatc cctagccgtt aagctttctg catgacttat cactttgggc   3000
ataatgctgg atacctacca ttttcttaga ccccatcaaa atcctatttg agtgtacggt   3060
tcggagaacc tcatttatcc ggtaaatgtc ttttactctg ctctcaggga gctgaggcag   3120
gacatcctga gatacattgg gagaggagat acagtttcaa taaaataata ggttgggtgg   3180
aggtacatgc ctataatgcc accactcagg aaatggtggc agcttcgtga gtttgaggcc   3240
aacccaagaa acatagtgaa accctgtcag taaataagta agcaagtatt tgagtatcta   3300
ctatatgcta gggctgacct ggacattagg ggtcatcttc tgaacaaact agtgcttgag   3360
ggaggtattt gggtttttg tttgtttaat ggatctgaat gagttccaga gactggctac   3420
acagcgatat gactgagctt aacaccccta aagcatacag tcagaccaat tagacaataa   3480
aagtatgta tagcttacca aataaaaaaa ttgtattttc aagagagtgt ctgtctgtgt   3540
agccctggct gttcttgaac tcactctgta gaccaggctg gcctggaaat ccatctgcct   3600
gcctctgcct ctctgcctct ctgcctctct gcctctctct ctgcctctct ctgcctctct   3660
ctgcccctct ctgcccctct ctgcccctct ctgccgcctct ctgccttttg ccctctgccc   3720
tctgttctct ggcctctgcc ctctgccctc tggcctctgg cctctgcctc tgcctcttga   3780
gtgctggaat caaaggtgtg agctctgtag gtcttaagtt ccagaagaaa gtaatgaagt   3840
cacccagcag ggaggtgctc agggacagca cagacacaca cccaggacat aggctccgac   3900
ttccttggct ttctctgagt ggcaaaggac cttaggcagt gtcactccct aagagaaggg   3960
gataaagaga ggggctgagg tattcatcat gtgctccgtg gatctcaagc cctcaaggta   4020
aatgggacc cacctgtcct accagctggc tgacctgtag ctttcccac cacagaatcc   4080
aagtcggaac tcttggcacc tagaggatct cgaggtcctc ctctgcgaga ggtcttgctt   4140
ctcccggtca gctgactccc tccccaagtc cttcaaatat ctcagaacat ggggagaaac   4200
ggggaccttg tccctcctaa ggaacccag tgctgcatgc catcatcccc ccacccctcg   4260
cccccacccc cgccacttct ccctccatgc ataccactag ctgtcatttt gtactctgta   4320
tttattccag ggctgcttct gattatttag tttgttcttt ccctggagac ctgttagaac   4380
ataagggcgt atggtgggta ggggaggcag gatatcagtc cctggggcga gttcctccct   4440
gccaaccaag ccagatgcct gaaagagata tggatgaggg aagttggact gtgcctgtac   4500
ctggtacagt catactctgt tgaaagaatc atcggggagg gggggggggct caagaggga   4560
gagctctgct gagccttgt ggaccatcca atgaggatgg gggcttagat tctaccaggt   4620
cattctcagc caccacacac aagcgctctg ccatcactga agaagccccc tagggctctt   4680
gggcagggc acactcagta aagatgcagg ttcagtcagg gaatgatggg gaaggggta   4740
ggaggtgggg gagggatcac cccctcctct aaaacacgag cctgctgtct ccaaaggcct   4800
ctgcctgtag tgagggtggc agaagaagac aaggagccag aactctgact ccaggatcta   4860
agtccgtgca ggaaggggat cctagaacca tctggttgga cccagcttac caaggggagag   4920
cctttattct tctttccctt gcccctctgt gccagcccct cttgctgcc ctgatccccc   4980
agacagcgag agtcttgcaa cctgcctctt ccaagacctc ctaatctcag gggcaggcgg   5040
tggagtgaga tccggcgtgc acacttttg gaagatagct ttccaagga tcctctcccc   5100
cactgcgcag tctgcctgtc ccatcaccat gtataataac accactgcta cagcatctca   5160
ccgaggaaag aaaactgcac aataaaaacca agcctctgga gtgtgtcctg gtgtctgtct   5220
cttctgtgtc ctgccgtctg tcttctctgt gttcttccaa ggtcagaaac aaaaaccaca   5280
cacttcaacc tggatggctc ggctgagcac ttctgtgtgc agaaggtcca accagactct   5340
ggggtacccc ggccctccct attcctttgc ctcctgtcta ccgcttttta tagctcccta   5400
tgctgggctt ctctggagag tgaaatcttt gcccaaatca atgcgcattc tctctgctga   5460
gtcatctggc gacagcagtt gagttcaccc gccaacacat gggcccagct atgtagccga   5520
accctggctc tggaagtgcc agggactttg tgcataagta tgtaccatgc ccttttttca   5580
cagtcctagc tctgcagaag tgcagcctga aggcctgct ctgagagga catgccctgg   5640
agccctgaaa caggcacagt gggaggagga acgaggatg acaggcatca ggccctcagt   5700
ccaaaagcaa ccacttgaga atgggctgga gtacgaaaca tggggtcccg tccctggatc   5760
cctcctcaaa gagtaataag taaaatataa acaggtaccc caggccgttc tgggtttggg   5820
ttgtaatggg atccatttgc agagaactat tgagacagcc cagccgtact agтgacaggca   5880
atgtgggga ggaggttgaa tcacttggta tttagcatga atagaataat tccctgaaca   5940
tttttcttaa acatccatat ctaaattacc accactcgct cccagtcttc ctgcсттттgc   6000
gccagcctcc tgtctggcca tgcctgaaga aggctggaga agccacccac ctcaggccat   6060
gacactgcca gccacttggc aggtgcagcc aaacctggcc tgtcccagaa agggacattc   6120
tcaagaccca ggcaccctga tcagcactga cttggagtca caagtgtcat gccagaaaag   6180
tctctaagaa aaccttttca gggaaaaggg ggtgactcaa caccgggcaa gtttgggaag   6240
ccccacccct cgagtgatgg aagagcagat aggaagcctc agaagagaga caccggcacc   6300
cagttaacgt tcctcatgtg gtctctgtca cactaggtgc тcтттcсстgg acatctccgt   6360
gaccacactc tcagttctta gggagatgcg ggtgctctct gaggctatct cagagтттgca   6420
gattctgagg ccтagaгтga ctacagtcag cctaggaagc cacagaggac tgtgaccag   6480
gagggcagaa gaggagaagg gaagaaaaac catcagatag gacttgcaat gaaactaacc   6540
caagacaatc ataatgcaga caggaatgtt aaaggcgttc agcagc            6586
```

SEQ ID NO: 123          moltype = AA   length = 1203
FEATURE                 Location/Qualifiers
source                  1..1203
                        mol_type = protein
                        organism = synthetic construct
SEQUENCE: 123
AGHLASDFAF SPPPGGGDGS AGLEPGWVDP RTWLSFQGPP GGPGIGPGSE VLGISPCPPA   60
YEFCGGMAYC GPQVGLGLVP QVGVETLQPE GQAGARVESN SEGTSSEPCA DRPNAVKLEK  120
VEPTPEESQD MKALQKELEQ FAKLLKQKRI TLGYTQADVG LTLGVLFGKV FSQTTICRFE  180
ALQLSLKNMC KLRPLLEKWV EEADNNENLQ EICKSETLVQ ARKRKRTSIE NRVRWSLETM  240
FLKCPKPSLQ QITHIANQLG LEKDVVRVWF CNRRQKGKRS SIEYSQREEY EATGTPFPGG  300
AVSFPLPPGP HFGTPYGSP HFTTLYSVPF PEGEAFPSVP VTALGSPMHS NASGSGATNF  360
SLLKQAGDVE ENPGPACMYN MMETELKPPG PQQASGGGGG GGNATAAATG GNQKNSPDRV  420
KRPMNAFMVW SRGQRRKMAQ ENPKMHNSEI SKRLGAEWKL LSETEKRPFI DEAKRLRALH  480
MKEHPDYKYR PRRKTKTLMK KDKYTLPGGL LAPGGNSMAS GVGVGAGLGA GVNQRMDSYA  540

-continued

```
HMNGWSNGSY SMMQEQLGYP QHPGLNAHGA AQMQPMHRYD VSALQYNSMT SSQTYMNGSP  600
TYSMSYSQQG TPGMALGSMG SVVKSEASSS PPVVTSSSHS RAPCQAGDLR DMISMYLPGA  660
EVPEPAAPSR LHMAQHYQSG PVPGTAINGT LPLSHMACGS GEGRGSLLTC GDVEENPGPL  720
EMRQPPGESD MAVSDALLPS FSTFASGPAG REKTLRPAGA PTNRWREELS HMKRLPPLPG  780
RPYDLAATVA TDLESGGAGA ACSSNNPALL ARRETEEFND LLDLDFILSN SLTHQESVAA  840
TVTTSASASS SSSPASSGPA SAPSTCSFSY PIRAGGDPGV AASNTGGGLL YSRESAPPPT  900
APFNLADIND VSPSGGFVAE LLRPELDPVY IPPQQPQPPG GGLMGKFVLK ASLTTPGSEY  960
SSPSVISVSK GSPDGSHPVV VAPYSGGPPR MCPKIKQEAV PSCTVSRSLE AHLSAGPQLS  1020
NGHRPNTHDF PLGRQLPTRT TPTLSPEELL NSRDCHPGLP LPPGFHPHPG PNYPPFLPDQ  1080
MQSQVPSLHY QELMPPGSCL PEEPKPKRGR RSWPRKRTAT HTCDYAGCGK TYTKSSHLKA  1140
HLRTHTGEKP YHCDWDGCGW KFARSDELTR HYRKHTGHRP FQCQKCDRAF SRSDHLALHM  1200
KRH                                                              1203
```

What is claimed is:

1. A method of increasing survival and/or regeneration of neuronal cells, the method comprising:
    contacting the neuronal cells with one or more polynucleotides encoding OCT4, SOX2, and KLF4, but not c-Myc, operably linked to one or more promoters, or an expression vector comprising the one or more polynucleotides,
    wherein the method maintains the neuronal cells as neuronal cells without loss of cellular identity.

2. The method of claim 1, wherein the one or more promoters are inducible promoters.

3. The method of claim 2, wherein the one or more inducible promoters comprise:
    a mifepristone-responsive promoter, or
    a coumermycin-responsive promoter.

4. The method of claim 2, wherein the one or more inducible promoters comprise one or more tetracycline-responsive elements (TREs).

5. The method of claim 4, wherein the method comprises introducing into the neuronal cells a polynucleotide encoding a reverse tetracycline-controlled transactivator (rtTA).

6. The method of claim 5, wherein the expression vector comprises the polynucleotide encoding the rtTA.

7. The method of claim 2, wherein the inducible promoter is a TRE3G promoter.

8. The method of claim 2, wherein the method comprises administering an inducing agent for the one or more inducible promoters.

9. The method of claim 8, wherein the inducing agent is a tetracycline-class antibiotic.

10. The method of claim 8, wherein the inducing agent is tetracycline.

11. The method of claim 8, wherein the inducing agent is doxycycline.

12. The method of claim 1, wherein the method further comprises measuring expression of one or more of Esrrb, Nanog, Lin28, TRA-1-3/TRA-1-81/TRA-2-54, SSEA1, or SSEA4.

13. The method of claim 1, wherein the method further comprises measuring DNA methylation-based age (DNAmAge) in the neuronal cells.

14. The method of claim 1, wherein the method further comprises measuring expression of Nanog.

15. The method of claim 1, wherein the expression vector is an adeno-associated virus (AAV) vector.

16. The method of claim 1, wherein the expression vector is a lentiviral vector.

17. The method of claim 1, wherein the expression vector comprises a polynucleotide sequence encoding a self-cleaving peptide.

18. The method of claim 1, wherein:
    i) OCT4 comprises an amino acid sequence having at least 90% identity to SEQ ID NO: 41;
    ii) SOX2 comprises an amino acid sequence having at least 90% identity to SEQ ID NO: 43; and
    iii) KLF4 comprises an amino acid sequence having at least 90% identity to SEQ ID NO: 45.

19. The method of claim 1, wherein:
    i) OCT4 comprises an amino acid sequence having at least 95% identity to SEQ ID NO: 41;
    ii) SOX2 comprises an amino acid sequence having at least 95% identity to SEQ ID NO: 43; and
    iii) KLF4 comprises an amino acid sequence having at least 95% identity to SEQ ID NO: 45.

20. The method of claim 1, wherein:
    i) OCT4 comprises the amino acid sequence of SEQ ID NO: 41;
    ii) SOX2 comprises the amino acid sequence of SEQ ID NO: 43; and
    iii) KLF4 comprises the amino acid sequence of SEQ ID NO: 45.

21. The method of claim 1, wherein the expression vector does not encode other transcription factors besides OCT4, SOX2, and KLF4.

22. The method of claim 1, wherein after the contacting step, the neuronal cells do not express at least one stem cell marker.

23. The method of claim 22, wherein the at least one stem cell marker is Esrrb, Nanog, Lin28, TRA-1-60/TRA-1-81/TRA-2-54, SSEA1, SSEA4, or any combination thereof.

* * * * *